(12) United States Patent
Capet et al.

(10) Patent No.: US 8,802,678 B2
(45) Date of Patent: Aug. 12, 2014

(54) CARBONYLATED (AZA) CYCLOHEXANES AS DOPAMINE $D_3$ RECEPTOR LIGANDS

(75) Inventors: Marc Capet, Melesse (FR); Denis Danvy, Yvetot (FR); Nicolas Levoin, Mordelles (FR); Isabelle Berrebi-Bertrand, Pace (FR); Thierry Calmels, Melesse (FR); Philippe Robert, Pace (FR); Jeanne-Marie Lecomte, Paris (FR); Jean-Charles Schwartz, Paris (FR); Xavier Ligneau, Saint Gregoire (FR)

(73) Assignee: Bioprojet, Paris (FR)

( * ) Notice: Subject to any disclaimer, the term of this patent is extended or adjusted under 35 U.S.C. 154(b) by 16 days.

(21) Appl. No.: 12/306,044

(22) PCT Filed: Jun. 21, 2007

(86) PCT No.: PCT/IB2007/001673
§ 371 (c)(1),
(2), (4) Date: Dec. 22, 2008

(87) PCT Pub. No.: WO2007/148208
PCT Pub. Date: Dec. 27, 2007

(65) Prior Publication Data
US 2009/0286801 A1 Nov. 19, 2009

Related U.S. Application Data

(60) Provisional application No. 60/815,563, filed on Jun. 22, 2006.

(30) Foreign Application Priority Data

Jun. 22, 2006 (EP) .................................. 06291027

(51) Int. Cl.
*A61K 31/497* (2006.01)
*A61K 31/4965* (2006.01)
*C07D 401/06* (2006.01)
*C07D 413/06* (2006.01)
*C07D 403/06* (2006.01)

(52) U.S. Cl.
USPC ............ 514/252.14; 514/253.06; 514/253.13; 514/255.03; 544/360; 544/363; 544/369; 544/372

(58) Field of Classification Search
USPC .......................... 544/360, 363, 369, 372, 393; 514/253.06, 253.13, 255.03
See application file for complete search history.

(56) References Cited

U.S. PATENT DOCUMENTS

| 5,047,406 A | 9/1991 | Caprathe et al. |
|---|---|---|
| 6,465,485 B1 | 10/2002 | Branch et al. |
| 7,074,796 B2 | 7/2006 | Bang-Andersen et al. |
| 7,875,610 B2 * | 1/2011 | Szalai et al. ............... 514/235.8 |
| 2005/0107397 A1 * | 5/2005 | Galambos et al. ........ 514/255.03 |
| 2006/0229297 A1 | 10/2006 | Csongor et al. |
| 2008/0103140 A1 | 5/2008 | Againe Csongor et al. |
| 2008/0214542 A1 | 9/2008 | Capet et al. |

FOREIGN PATENT DOCUMENTS

| WO | 2005/012266 | * | 2/2005 |
|---|---|---|---|
| WO | 2006/082456 | * | 8/2006 |

OTHER PUBLICATIONS

Wermuth C.G. Chapter 13, "Molecular Variations Based on Isosteric Replacements" in The Practice of Medicinal Chemistry (1996), pp. 203-237.*
Vippagunta et al. Advanced Drug Delivery Reviews, vol. 48, p. 3-26 (2001).*
Joyce, Pharmacology & Therapeutics, vol. 90,pp. 231-259 (2001).*
Heidbreder et al. Brain Research Reviews, vol. 49,pp. 77-105 (2005).*
Luippold et al. Arch.Pharmacology, vol. 371,pp. 420-427 (2005).*

* cited by examiner

*Primary Examiner* — Kamal Saeed
*Assistant Examiner* — Ebenezer O Sackey
(74) *Attorney, Agent, or Firm* — B. Aaron Schulman, Esq.; Stites & Harbison, PLLC

(57) ABSTRACT

The invention relates to compounds of the general formula (I): to the process for preparing them, and to the use thereof as a therapeutic agent.

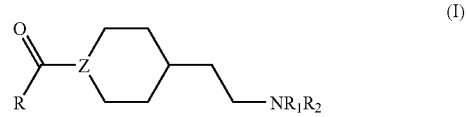

14 Claims, No Drawings

CARBONYLATED (AZA) CYCLOHEXANES AS DOPAMINE $D_3$ RECEPTOR LIGANDS

CROSS REFERENCE TO RELATED APPLICATIONS

This application claims benefit of U.S. Provisional Application No. 60/815,563, filed Jun. 22, 2006.

The present patent application concerns new ligands of the $D_3$ receptor, their process of preparation and their therapeutic use.

These ligands of the human $D_3$ receptor behave as antagonists, or inverse agonists or partial agonists or full agonists.

BACKGROUND

The invention relates to novel carbonylated (aza)cyclohexane derivatives that potently bind to the dopamine $D_3$ receptor as partial, full or inverse agonists and antagonists. This receptor, a $D_2$-like receptor, is discretely expressed in only but a few brain projections areas of dopamine neurons, within dopamine neurons themselves (auto-receptors) and in discrete peripheral organs, e.g. the kidney (Schwartz et al. *Clinical NeuroPharmacol*, 1993, 16, 295). It has been suggested, or even demonstrated that such brain localisations imply a role of this receptor subtype in a number of physiological or pathological processes such as cognition, dementia, psychosis, substance abuse and dependence, mood regulation and disorders (e.g. depression or anxiety), motor regulation and disorders (e.g. Parkinson disease, dyskinesias or equilibration disorders).

In addition, peripheral $D_3$ receptors, namely in kidney, seem involved in the control of hormone secretion, diabetic disorders or blood pressure (Jose et al., *Curr. Opin. Nephrol. Hypertens.*, 2002, 11, 87; Gross et al *Lab. Invest.*, 2006, 86, 862). These considerations indicate that modulation (via partial, full or inverse agonism or antagonism) of dopamine $D_3$ receptors represents a potentially novel approach to treating diseases of the central nervous system in neurology and psychiatry as well as diseases of the cardiovascular or hormonal systems.

The international patent application WO 01/49679 discloses arylpiperazine derivatives that display dopamine antagonist properties on its receptors $D_3$ and $D_4$; however, these compounds have a phenyl group on the position 4 of the piperazine substituted by an halogen atom, and, on the other hand, on the position 1 of the piperazine, an alkylene group optionally substituted by a carbonyl group, and then a 5- or 6-membered aza heterocycle fused with a phenyl group, such as indoline or isoquinoleine.

The international patent application PCT/FR05/02964 discloses arylpiperazine derivatives having an alkylene group and an indoline cycle. These compounds are selective ligands of $D_3$ receptor.

Unexpectedly, it has now been discovered that the compounds according to the invention, which represent a new family of arylpiperazine derivatives, display a high affinity for the $D_3$ receptor of dopamine. By contrast to the compounds disclosed in WO 01/49769 and in PCT/FR05/02964, the compounds according to the invention have an aza heterocycle, such as an arylpiperazine, and an alkylene group substituted by an (aza)cyclohexyl group. Further, they are selective ligands of $D_3$ receptor.

These compounds are useful as medicaments, notably in neurology and psychiatry, particularly in Parkinson's disease, schizophrenia, dementia, depression, mania, anxiety, dyskinesias, equilibration disorders, Gilles de la Tourette's disease. Further, these compounds are useful for treating drug and tobacco dependency.

They are also useful for preventing or treating cardiovascular disorders implying the peripheral dopamine receptors, particularly in kidneys, such as hypertension, cardiac failure, and other disorders such as renal insufficiency or diabetes.

These compounds are also useful for preventing or treating hormonal disorders implying dopamine receptors in the hypothalamus pituitary complex, such as menopausal disorders or growth disorders.

According to a first object, the present invention concerns new compounds of formula (I):

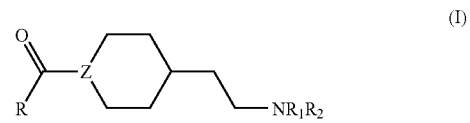

with $NR_1R_2$ chosen from the group selected within:

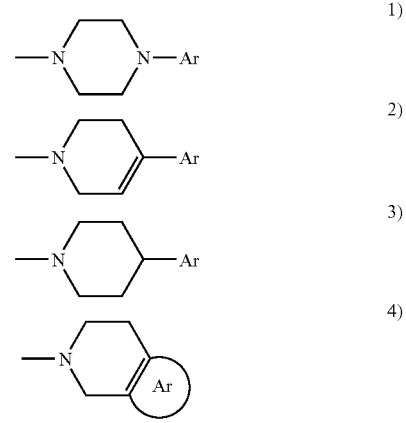

Z chosen from the group selected within:

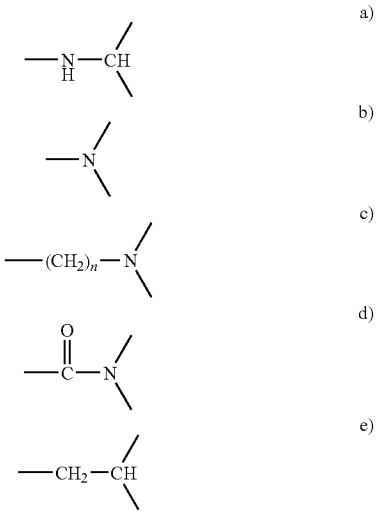

f)

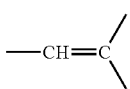

R representing alkyl; cyanoalkyl monohalogenocyanoalkyl; polyhalogenocyanoalkyl; hydroxyalkyl monohalogenoalkyl; polyhalogenoalkyl; cycloalkyl; monhalogenocycloalkyl; polyhalogenocycloalkyl; cyanocycloalkyl; alkoxy; monohalogenoalkoxy; polyhalogenoalkoxy; alkoxyalkyl; monohalogeno-alkoxyalkyl polyhalogenoalkoxyalkyl; alkoxyalkoxyalkyl monohalogeno-alkoxyalkoxyalkyl; polyhalogenoalkoxyalkoxyalkyl; alkylcarbonyl aryl; mono- or polyhalogenoaryl; aryloxy; aryloxyalkyl; mono- or polyhalogenoaryloxyalkyl; arylalkoxy; alkenyl cycloalkenyl; cycloalkenylalkyl; cyclalkenyl fused with benzene; alkynyl, amino; alkylamino; dialkylamino; dialkylaminoalkyl; monohalogenoalkylamino; monohalogenodialkylamino; halodialkylaminoalkyl; polyhalogenoalkylamino; polyhalogenodialkylamino; polyhalogenodialkylaminoalkyl;

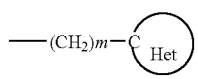

where

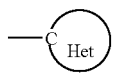

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl aminocarbonylalkyl; alkylsulfanylalkyl; alkylsulfinylalkyl; alkylsulfonylalkyl;

n being an integer from 1 to 3;

m being an integer from 0 to 4;

Ar representing an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxy-carbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

with the proviso that:

when Z is a) NHCH and NR1R2 is 1) with Ar representing a phenyl fused with a carbocycle and R is non aromatic heterocyclyl(CH2)m with m=0, then the heterocycle is linked to the carbonyl by a carbon atom, when Z is a) NHCH, then R is not alkyl, unsubstituted cycloalkyl, aryl, heteroaryl or heteroarlyalkyl;

when Z is a) NHCH and NR1R2 is 1) with Ar representing a phenyl substituted with two chlorine atoms or fused with a carbocycle, then R is not amino, alkylamino, dialkylamino, monohalogenoalkylamino, monohalogenodialkylamino, polyhalogenoalkylamino, polyhalogenodialkylamino, alkyl, alkenyl, aryl or unsubstituted cycloalkyl;

when Z is a) NHCH and NR1R2 is 1) with Ar representing an unsubstituted phenyl, then R is not alkyl, aryl or unsubstituted cycloalkyl;

when Z is a) NHCH and NR1R2 is 4), then R is not aryl, aralkyl, aralkoxyalkyl, aralkylsulfanylalkyl; and when Z is b) N, then R is not amino, alkylamino, dialkylamino or halogenoderivative thereof, or their pharmaceutically acceptable salts, hydrates, or hydrated salts, or the polymorphic, cristalline structures of these compounds or their optical isomers, racemates, diastereomers or enantiomers.

Preferably, $NR_1R_2$ is 1):

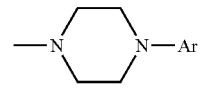

Preferably, Z is a).

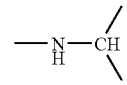

Preferably, R is cyanoalkyl, polyhalogenocyanoalkyl, hydroxyalkyl, polyhalogenoalkyl, cyanocycloalkyl, alkoxy, alkoxyalkyl, alkoxyalkoxyalkyl, alkylcarbonyl, aryloxyalkyl, mono- or polyhalogenoaryloxyalkyl, arylalkoxy, alkenyl, cycloalkenyl, non aromatic heterocyclyl(CH2)m wherein the non aromatic heterocycle is optionally fused with aryl or optionally substituted with one or more acyl, alkyl or halogen, alkylcarbonylalkyl, acylaminoalkyl, aminocarbonylalkyl, alkylsulfanylalkyl, alkylsulfonylalkyl, m being an integer from 0 to 4, notably 0 or 2.

Preferably, Ar represents an aryl, more preferably phenyl.

Preferably, Ar is substituted with one or more alkyl, cyano, halogeno, alkoxy, polyhalogenoalkoxy, alcanediyl, dialkylamino, alkylsulfanyl, aryl, aralkyl, aryloxy, alkoxycarbonylamino, acyl, alkylsulfonylamino, polyhalogenoalkyl, hydroxy, hydroxyalkyl, oxoalkyl.

Preferably, Ar is unsubstituted or substituted with one or more alkyl, polyhalogenoalkyl, halogen or cyano, more preferably with alkyl or polyhalogenoalkyl.

The present invention encompasses the following embodiments:

NR1R2 is a group of formula 1) and Z is a group a);

NR1R2 is a group of formula 1) and Z is a group b), c) or d), more preferably those where NR1R2 is 1) and Z is c);

NR1R2 is a group of formula 1) and Z is a group e) or f);

NR1R2 is a group of formula 2) or 3), more preferably those where NR1R2 is 2) and Z is a), those where NR1R2 is 2) and Z is c) and those where NR1R2 is 3) and Z is c);

NR1R2 is a group of formula 4) and Z is a group a);

NR1R2 is a group of formula 4) and Z is a group b), c) or d), more preferably where NR1R2 is 4) and Z is c);

NR1R2 is a group of formula 4) and Z is a group e) or f) wherein R, Ar, m, n are defined as above.

Preferably, the compounds of the invention are those of formula (A):

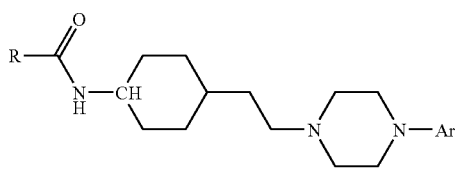
(A)

where:
R is chosen from cyanoalkyl; monohalogenoalkyl; polyhalogenoalkyl; monohalogenocycloalkyl; polyhalogeno-cycloalkyl; alkoxy; monohalogenoalkoxy; polyhalogenoalkoxy; alkoxyalkyl; monohalogenoalkoxyalkyl; polyhalogenoalkoxyalkyl; alkoxyalkoxyalkyl; monohalogenoalkoxyalkoxyalkyl; polyhalogenoalkoxyalkoxyalkyl; monohalogenocyanoalkyl; polyhalogenocyanoalkyl; cyanocycloalkyl; aryloxy; aryloxyalkyl; arylalkoxy; cycloalkenyl; cycloalkenylalkyl; cycloalkenyl fused with benzene; alkynyl; dialkylaminoalkyl; hydroxyalkyl; polyhalogenodialkylaminoalkyl;

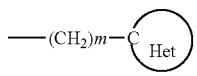

where

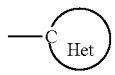

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl; aminocarbonylalkyl; alkylsulfanylalkyl; alkylsulfinylalkyl; alkylsulfonylalkyl; alkylcarbonyl; mono- or polyhalogenoaryl; mono- or polyhalogenoaryloxyalkyl;

m being an integer from 0 to 4,

Ar represents an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxy-carbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, hydrates, or hydrated salts, or the polymorphic, cristalline structures of these compounds or their optical isomers, racemates, diastereomers or enantiomers.

Preferably, in formula (A):
R is chosen from cyanoalkyl; polyhalogenoalkyl; alkoxy; alkoxyalkyl; polyhalogenocyanoalkyl; cyanocycloalkyl; aryloxyalkyl; arylalkoxy; cycloalkenyl; cycloalkenylalkyl; cycloalkenyl fused with benzene; dialkylaminoalkyl; hydroxyalkyl; alkylcarbonylalkyl; acylaminoalkyl; aminocarbonylalkyl; alkylsulfinylalkyl; alkylsulfonylalkyl; alkylcarbonyl;

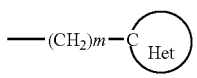

where

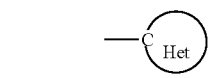

is a non aromatic heterocycle optionally fused with aryl or optionally substituted with one or more acyl, alkyl or halogen;

Ar represents an aryl optionally fused with a cycloalkyl or an heterocycle and/or Ar being optionally substituted with one or more alkyl; cyano; halogeno; alkoxy; polyhalogenoalkoxy; alkoxyalkyl; dialkylamino; alkylsulfanyl; alkylsulfonyl; polyhalogenoalkylsulfanyl; heteroaryl; aryloxy; alkoxy-carbonylamino; acyl; aminocarbonyl; alkylsulfonylamino; polyhalogenoalkyl; hydroxyl; hydroxyalkyl;

or their pharmaceutically acceptable salts, hydrates, or hydrated salts, or the polymorphic, cristalline structures of these compounds or their optical isomers, racemates, diastereomers or enantiomers.

According to a further aspect, the compounds of the invention are those of formula (1c):

(1c)

R is chosen from alkyl; cyanoalkyl; monohalogenocyanoalkyl; polyhalogenocyanoalkyl; hydroxyalkyl; monohalogenoalkyl; polyhalogenoalkyl; cycloalkyl; monhalogenocycloalkyl; polyhalogenocycloalkyl; cyanocycloalkyl; alkoxy; monohalogenoalkoxy; polyhalogenoalkoxy; alkoxyalkyl; monohalogeno-alkoxyalkyl; polyhalogenoalkoxyalkyl; alkoxyalkoxyalkyl; monohalogeno-alkoxyalkoxyalkyl; polyhalogenoalkoxyalkoxyalkyl; alkylcarbonyl; aryl; mono- or polyhalogenoaryl aryloxy; aryloxyalkyl; mono- or polyhalogenoaryloxyalkyl; arylalkoxy; alkenyl; cycloalkenyl; cycloalkenylalkyl; benzofusedcyclalkenyl; alkynyl; amino; alkylamino; dialkylamino; dialkylaminoalkyl; monohalogenoalkylamino; monohalogenodialkylamino; halodialkylaminoalkyl; polyhalogenoalkylamino; polyhalogenodialkylamino; polyhalogenodialkylaminoalkyl;

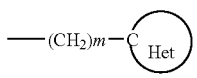

where

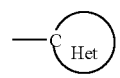

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl aminocarbonylalkyl; alkylsulfanylalkyl; alkylsulfinylalkyl; alkylsulfonylalkyl n is an integer from 1 to 3;
m is an integer from 0 to 4;
Ar is chosen from an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxycarbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, hydrates, or hydrated salts, or the polymorphic, cristalline structures of these compounds or their optical isomers, racemates, diastereomers or enantiomers.

Preferably, in formula (1c)
R is chosen from alkyl; cyanoalkyl; alkoxy; alkoxyalkyl; aryl; amino; alkoxy(alkyl)amino;
n is 1;
Ar is chosen from aryl optionally fused with a cycloalkyl or an heterocycle; and/or optionally substituted with one or more alkyl; cyano; halogeno; alkoxy; polyhalogenoalkoxy; alkylsulfonyl; polyhalogenoalkylsulfanyl; aralkyl; aryloxy; acyl; polyhalogenoalkyl; hydroxyalkyl;

or their pharmaceutically acceptable salts, hydrates, or hydrated salts, or the polymorphic, cristalline structures of these compounds or their optical isomers, racemates, diastereomers or enantiomers.

According to a still further aspect, the compounds of the invention are those of formula (2a):

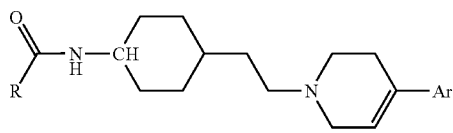

(2a)

with
R chosen from cyanoalkyl; monohalogenocyanoalkyl; polyhalogenocyanoalkyl; hydroxyalkyl; monohalogenoalkyl; polyhalogenoalkyl monhalogenocycloalkyl polyhalogenocycloalkyl cyanocycloalkyl; alkoxy; monohalogenoalkoxy; polyhalogenoalkoxy; alkoxyalkyl monohalogeno-alkoxyalkyl; polyhalogenoalkoxyalkyl alkoxyalkoxyalkyl monohalogeno-alkoxyalkoxyalkyl polyhalogenoalkoxyalkoxyalkyl; alkylcarbonyl; aryloxy; aryloxyalkyl; mono- or polyhalogenoaryloxyalkyl; arylalkoxy; alkenyl; cycloalkenyl; cycloalkenylalkyl benzofusedcyclkenyl; alkynyl, amino; alkylamino; dialkylamino; dialkylaminoalkyl monohalogenoalkylamino; monohalogenodialkylamino; halodialkylaminoalkyl polyhalogenoalkylamino; polyhalogenodialkylamino; polyhalogenodialkylaminoalkyl

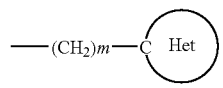

where

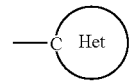

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl; aminocarbonylalkyl; alkylsulfanylalkyl alkylsulfinylalkyl; alkylsulfonylalkyl m being an integer from 0 to 4;
Ar representing an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxy-carbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, hydrates, or hydrated salts, or the polymorphic, cristalline structures of these compounds or their optical isomers, racemates, diastereomers or enantiomers.

Preferably in formula (2a):
R is chosen from cyanoalkyl; polyhalogenoalkyl; alkoxyalkyl; cycloalkenyl
Ar is chosen from an aryl optionally substituted with one or more alkyl; cyano; halogeno; polyhalogenoalkyl;

or their pharmaceutically acceptable salts, hydrates, or hydrated salts, or the polymorphic, cristalline structures of these compounds or their optical isomers, racemates, diastereomers or enantiomers.

According to a still further aspect, the compounds of the invention are those of formula (2c):

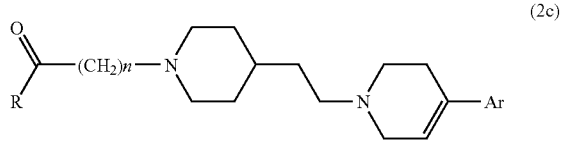

(2c)

R is chosen from alkyl; cyanoalkyl; monohalogenocyanoalkyl polyhalogenocyanoalkyl; hydroxyalkyl; monohalogenoalkyl; polyhalogenoalkyl; cycloalkyl; monhalogenocycloalkyl; polyhalogenocycloalkyl; cyanocycloalkyl; alkoxy; monohalogenoalkoxy; polyhalogenoalkoxy; alkoxyalkyl; monohalogeno-alkoxyalkyl polyhalogenoalkoxyalkyl; alkoxyalkoxyalkyl monohalogeno-alkoxyalkoxyalkyl polyhalogenoalkoxyalkoxyalkyl; alkylcarbonyl; aryl; mono- or polyhalogenoaryl; aryloxy; aryloxyalkyl; mono- or polyhalogenoaryloxyalkyl; arylalkoxy; alkenyl; cycloalkenyl; cycloalkenylalkyl; benzofusedcyclalkenyl; alkynyl, amino; alkylamino; dialkylamino; dialkylaminoalkyl; monohalogenoalkylamino; monohalogenodialkylamino; halodialkylaminoalkyl; polyhalogenoalkylamino; polyhalogenodialkylamino; polyhalogenodialkylaminoalkyl;

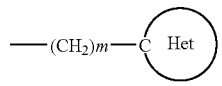

where

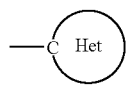

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl aminocarbonylalkyl; alkylsulfanylalkyl; alkylsulfinylalkyl; alkylsulfonylalkyl n is an integer from 1 to 3;

m is an integer from 0 to 4;

Ar is chosen from an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxycarbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, hydrates, or hydrated salts, or the polymorphic, cristalline structures of these compounds or their optical isomers, racemates, diastereomers or enantiomers.

Preferably, in formula (2c):

R is chosen from alkyl n is 1;

Ar represents an aryl optionally fused with a cycloalkyl and/or optionally substituted with one or more alkyl; cyano; halogeno; polyhalogenoalkyl;

or their pharmaceutically acceptable salts, hydrates, or hydrated salts, or the polymorphic, cristalline structures of these compounds or their optical isomers, racemates, diastereomers or enantiomers.

According to a still further aspect, the compounds of the invention are those of formula (3c):

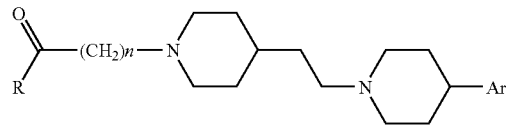

R is chosen from alkyl cyanoalkyl monohalogenocyanoalkyl; polyhalogenocyanoalkyl; hydroxyalkyl; monohalogenoalkyl; polyhalogenoalkyl; cycloalkyl; monhalogenocycloalkyl; polyhalogenocycloalkyl; cyanocycloalkyl; alkoxy; monohalogenoalkoxy; polyhalogenoalkoxy; alkoxyalkyl; monohalogeno-alkoxyalkyl polyhalogenoalkoxyalkyl; alkoxyalkoxyalkyl; monohalogeno-alkoxyalkoxyalkyl polyhalogenoalkoxyalkoxyalkyl; alkylcarbonyl aryl; mono- or polyhalogenoaryl aryloxy; aryloxyalkyl; mono- or polyhalogenoaryloxyalkyl; arylalkoxy; alkenyl; cycloalkenyl; cycloalkenylalkyl; benzofusedcyclalkenyl; alkynyl, amino; alkylamino; dialkylamino; dialkylaminoalkyl; monohalogenoalkylamino; monohalogenodialkylamino; halodialkylaminoalkyl; polyhalogenoalkylamino; polyhalogenodialkylamino; polyhalogenodialkylaminoalkyl;

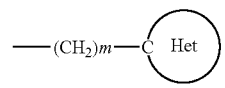

where

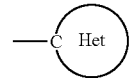

is a non aromatic heterocycle optionally fused with aryl or optionally substituted with one or more acyl, alkyl or halogen; arylaminoalkyl; alkoxyalkylamino; alkoxy(alkyl)amino; cyanoalkylamino; alkylcarbonylalkyl; acylaminoalkyl; aminocarbonylalkyl; alkylsulfanylalkyl; alkylsulfinylalkyl; alkylsulfonylalkyl n is an integer from 1 to 3;

m is an integer from 0 to 4;

Ar is chosen from an aryl; an heteroaryl or an aryl fused with a cycloalkyl or an heterocycle; Ar being optionally substituted with one or more alkyl; alkenyl; alkynyl; cyano; halogeno; alkoxy; monohalogenoalkoxy; polyhalogenoalkoxy; alkoxyalkyl; dialkylamino; non aromatic heterocyclyl attached by a nitrogen; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; heteroaryl; aryl; aralkyl; aryloxy; alkoxycarbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, hydrates, or hydrated salts, or the polymorphic, cristalline structures of these compounds or their optical isomers, racemates, diastereomers or enantiomers.

Preferably, in formula (3c);

R is chosen from alkyl;

n is 1;

Ar is an aryl optionally fused with a cycloalkyl and/or optionally substituted with one or more halogeno;

or their pharmaceutically acceptable salts, hydrates, or hydrated salts, or the polymorphic, crystalline structures of these compounds or their optical isomers, racemates, diastereomers or enantiomers.

Preferred compounds of formula (1) can be chosen from:
2-cyano-N-(4-{2-[4-(3-trifluoromethylphenyl)piperazin-1-yl]ethyl}cyclohexyl)acetamide,
1-(4-{2-[4-(3-trifluoromethylphenyl)piperazin-1-yl]ethyl}piperidin-1-yl)propane-1,2-dione, hydrochloride,
1-(4-{2-[4-(3-trifluoromethylphenyl)piperazin-1-yl]ethyl}piperidin-1-yl)propan-2-one,
N-methoxy-N-methyl-2-(4-{2-[4-(3-trifluoromethylphenyl)piperazin-1-yl]ethyl}cyclohexylidene)acetamide,
1-(4-{2-[4-(3-trifluoromethylphenyl)piperazin-1-yl]ethyl}cyclo-hexylidene)propan-2-one,
1-(4-{2-[4-(3-trifluoromethylphenyl)piperazin-1-yl]ethyl}cyclohexyl)propan-2-one, hydrochloride,
N-(4-{2-[4-(3-acetylphenyl)piperazin-1-yl]ethyl}cyclohexyl)-2-cyanoacetamide,
4-{2-[4-(3-Trifluoromethylphenyl)piperazin-1-yl]ethyl}piperidine-1-carboxylic acid tert-butyl ester, hydrochloride,
1-(4-{2-[4-(2-Fluorophenyl)piperazin-1-yl]ethyl}piperidin-1-yl)propan-2-one, dihydrochloride,
(4-{2-[4-(3-Trifluoromethylphenyl)piperazin-1-yl]ethyl}piperidin-1-yl)acetic acid tert-butyl ester, dihydrochloride,
1-Phenyl-2-(4-{2-[4-(3-trifluoromethylphenyl)piperazin-1-yl]ethyl}piperidin-1-yl)ethanone, dihydrochloride,
1-(4-{2-[4-(3-Trifluoromethylphenyl)piperazin-1-yl]ethyl}piperidin-1-yl)butane-1,2-dione, hydrochloride,
3,3-Dimethyl-1-(4-{2-[4-(3-trifluoromethylphenyl)piperazin-1-yl]ethyl}piperidin-1-yl)butan-2-one,
N-[2-Oxo-2-(4-{2-[4-(3-trifluoromethylphenyl)piperazin-1-yl]ethyl}piperidin-1-yl)ethyl]acetamide,
3-Oxo-3-(4-{2-[4-(3-trifluoromethylphenyl)piperazin-1-yl]ethyl}piperidin-1-yl)propanenitrile, hydrochloride,
2-Methoxy-1-(4-{2-[4-(3-trifluoromethylphenyl)piperazin-1-yl]ethyl}piperidin-1-yl)ethanone, hydrochloride,
2-Ethoxy-1-(4-{2-[4-(3-trifluoromethylphenyl)piperazin-1-yl]ethyl}piperidin-1-yl)ethanone, hydrochloride,
5-Oxo-5-(4-{2-[4-(3-trifluoromethylphenyl)piperazin-1-yl]ethyl}piperidin-1-yl)pentanenitrile, hydrochloride,
3-(4-{2-[1-(2-Oxopropyl)piperidin-4-yl]ethyl}piperazin-1-yl)-5-trifluoromethylbenzonitrile, dihydrochloride,
1-(4-{2-[4-(2-Methoxyphenyl)piperazin-1-yl]ethyl}piperidin-1-yl)propan-2-one, dihydrochloride,
1-(4-{2-[4-(2,3-Dichlorophenyl)piperazin-1-yl]ethyl}piperidin-1-yl)propan-2-one,
2-Methyl-6-(4-{2-[1-(2-oxopropyl)piperidin-4-yl]ethyl}piperazin-1-yl)benzonitrile, dihydrochloride,
2-(4-{2-[4-(3-Trifluoromethylphenyl)piperazin-1-yl]ethyl}piperidin-1-yl)acetamide, dihydrochloride,
1-(4-{2-[4-(2-Chlorophenyl)piperazin-1-yl]ethyl}piperidin-1-yl)propan-2-one, dihydrochloride,
3-(4-{2-[1-(2-Oxopropyl)piperidin-4-yl]ethyl}piperazin-1-yl)benzonitrile, dihydrochloride,
(4-{2-[4-(3-Trifluoromethylphenyl)piperazin-1-yl]ethyl}piperidin-1-yl)acetic acid ethyl ester, dihydrochloride,
1-(4-{2-[4-(3,5-Difluorophenyl)piperazin-1-yl]ethyl}piperidin-1-yl)propan-2-one, dihydrochloride,
1-(4-{2-[4-(2,3-Dimethylphenyl)piperazin-1-yl]ethyl}piperidin-1-yl)propan-2-one, dihydrochloride,
1-(4-{2-[4-(3-Chlorophenyl)piperazin-1-yl]ethyl}piperidin-1-yl)propan-2-one,
1-{4-[2-(4-o-Tolylpiperazin-1-yl)-thyl]piperidin-1-yl}propan-2-one, dihydrochloride,
1-(4-{2-[4-(2-Chloro-5-methylphenyl)piperazin-1-yl]ethyl}piperidin-1-yl)propan-2-one, dihydrochloride,
1-(4-{2-[4-(5-Fluoro-2-methylphenyl)piperazin-1-yl]ethyl}piperidin-1-yl)propan-2-one, dihydrochloride,
1-(3,4-Difluorophenyl)-2-(4-{2-[4-(3-trifluoromethylphenyl)piperazin-1-yl]ethyl}piperidin-1-yl)ethanone,
1-(4-{2-[4-(3,5-Bistrifluoromethylphenyl)piperazin-1-yl]ethyl}piperidin-1-yl)propan-2-one,
1-(4-{2-[4-(2,3-Difluorophenyl)piperazin-1-yl]ethyl}piperidin-1-yl)propan-2-one,
1-{4-[2-(4-Naphthalen-1-ylpiperazin-1-yl)ethyl]piperidin-1-yl}propan-2-one,
(4-{2-[4-(3-Trifluoromethylphenyl)piperazin-1-yl]ethyl}cyclohexyl)carbamic acid benzyl ester,
2,2,2-Trifluoro-N-(4-{2-[4-(3-trifluoromethylphenyl)piperazin-1-yl]ethyl}cyclohexyl)acetamide,
(4-{2-[4-(3-Trifluoromethylphenyl)piperazin-1-yl]ethyl}cyclohexyl)carbamic acid methyl ester,
Tetrahydrofuran-2-carboxylic acid (4-{2-[4-(3-trifluoromethyl-phenyl)piperazin-1-yl]ethyl}cyclohexyl)amide,
2-Methoxy-N-(4-{2-[4-(3-trifluoromethylphenyl)piperazin-1-yl]ethyl}cyclohexyl)acetamide,
2-Methoxy-N-(4-{2-[4-(3-trifluoromethylphenyl)piperazin-1-yl]ethyl}cyclohexyl)acetamide, hydrochloride,
2,2-Difluoro-N-(4-{2-[4-(3-trifluoromethylphenyl)piperazin-1-yl]ethyl}cyclohexyl)acetamide,
Cyclopent-1-enecarboxylic acid (4-{2-[4-(3-trifluoromethyl-phenyl)piperazin-1-yl]ethyl}cyclohexyl)amide,
2-Hydroxy-N-(4-{2-[4-(3-trifluoromethylphenyl)piperazin-1-yl]ethyl}cyclohexyl)acetamide, hydrochloride,
3-Methoxy-N-(4-{2-[4-(3-trifluoromethylphenyl)piperazin-1-yl]ethyl}cyclohexyl)propanamide,
N-(4-{2-[4-(2,4-Difluorophenyl)piperazin-1-yl]ethyl}cyclohexyl)-2-methoxyacetamide,
N-(4-{2-[4-(2-Cyano-3-methylphenyl)piperazin-1-yl]ethyl}cyclohexyl)-2-methoxyacetamide,
N-(4-{2-[4-(2-Fluorophenyl)piperazin-1-yl]ethyl}cyclohexyl)-2-methoxyacetamide,
2-Ethoxy-N-(4-{2-[4-(3-trifluoromethylphenyl)piperazin-1-yl]ethyl}cyclohexyl)acetamide, hydrochloride,
Cyclopent-3-enecarboxylic acid (4-{2-[4-(3-trifluoromethyl-phenyl)piperazin-1-yl]ethyl}cyclohexyl)amide,
Cyclohex-1-enecarboxylic acid (4-{2-[4-(3-trifluoromethyl-phenyl)piperazin-1-yl]ethyl}cyclohexyl)-amide,
N-(4-{2-[4-(2-Cyano-3-methylphenyl)-3,6-dihydro-2H-pyridin-1-yl]ethyl}cyclohexyl)-2-methoxyacetamide,
N-(4-{2-[4-(2-Cyano-3-methylphenyl)piperidin-1-yl]ethyl}cyclohexyl)-2-methoxyacetamide,
2-Ethoxy-N-(4-{2-[4-(2-fluorophenyl)piperazin-1-yl]ethyl}cyclo-hexyl)acetamide,
Tetrahydrofuran-2-carboxylic acid (4-{2-[4-(2-fluorophenyl)piperazin-1-yl]ethyl}cyclohexyl)amide,
N-(4-{2-[4-(2-Cyanophenyl)piperazin-1-yl]ethyl}cyclohexyl)-2-methoxyacetamide,
2-Methoxy-N-(4-{2-[4-(3-trifluoromethylphenyl)-3,6-dihydro-2H-pyridin-1-yl]ethyl}cyclohexyl)acetamide,
2-Methoxy-N-{4-[2-(4-phenylpiperazin-1-yl)ethyl]cyclohexyl}acetamide,
2-Methoxy-N-(4-{2-[4-(3-trifluoromethylphenyl)piperidin-1-yl]ethyl}cyclohexyl)acetamide,
2-Phenoxy-N-(4-{2-[4-(3-trifluoromethylphenyl)piperazin-1-yl]ethyl}cyclohexyl)acetamide, 3,3,3-Trifluoro-N-(4-{2-[4-(3-trifluoromethylphenyl)piperazin-1-yl]ethyl}cyclohexyl)propanamide,
4-Methoxy-N-(4-{2-[4-(3-trifluoromethylphenyl)piperazin-1-yl]ethyl}cyclohexyl)butanamide,
Cyclopent-3-enecarboxylic acid {4-[2-(4-pyridin-2-ylpiperazin-1-yl)ethyl]cyclohexyl}amide,
Cyclohex-1-enecarboxylic acid {4-[2-(4-phenylpiperazin-1-yl)ethyl]cyclohexyl}amide,
Cyclohex-1-enecarboxylic acid (4-{2-[4-(2-fluorophenyl)piperazin-1-yl]ethyl}cyclohexyl)amide,
Cyclopent-1-enecarboxylic acid (4-{2-[4-(2-fluorophenyl)piperazin-1-yl]ethyl}cyclohexyl)amide,
N-(4-{2-[4-(2-Fluorophenyl)piperazin-1-yl]ethyl}cyclohexyl)-2-methoxypropanamide,
Cyclopent-3-enecarboxylic acid (4-{2-[4-(2-fluorophenyl)piperazin-1-yl]ethyl}cyclohexyl)amide,
Cyclohex-1-enecarboxylic acid (4-{2-[4-(2,4-difluorophenyl)piperazin-1-yl]ethyl}cyclohexyl)amide,
Cyclopent-1-enecarboxylic acid (4-{2-[4-(2-cyano-3-methylphenyl)-3,6-dihydro-2H-pyridin-1-yl]ethyl}cyclohexyl)amide,
N-(4-{2-[4-(2-Cyanophenyl)piperazin-1-yl]ethyl}cyclohexyl)-2-ethoxyacetamide,
Cyclopent-1-enecarboxylic acid (4-{2-[4-(2-cyanophenyl)piperazin-1-yl]ethyl}cyclohexyl)amide,
N-(4-{2-[4-(2-Fluorophenyl)piperazin-1-yl]ethyl}cyclohexyl)-2-methoxypropanamide,
N-(4-{2-[4-(2-Fluorophenyl)piperazin-1-yl]ethyl}cyclohexyl)-4-methoxybutanamide,
2-Methoxy-2-methyl-N-(4-{2-[4-(3-trifluoromethylphenyl)piperazin-1-yl]ethyl}cyclohexyl)propanamide,
N-(4-{2-[4-(3-Cyanophenyl)piperazin-1-yl]ethyl}cyclohexyl)-2-ethoxyacetamide,
2-Cyano-N-(4-{2-[4-(2-fluorophenyl)piperazin-1-yl]ethyl}cyclohexyl)acetamide,
2-Methylsulfanyl-N-(4-{2-[4-(3-trifluoromethylphenyl)piperazin-1-yl]ethyl}cyclohexyl)acetamide,
4-Methoxy-N-(4-{2-[4-(3-trifluoromethylphenyl)-3,6-dihydro-2H-pyridin-1-yl]ethyl}cyclohexyl)butanamide,
2-Ethoxy-N-(4-{2-[4-(3-trifluoromethylphenyl)-3,6-dihydro-2H-pyridin-1-yl]ethyl}cyclohexyl)acetamide,
2-Ethoxy-N-(4-{2-[4-(3-trifluoromethylphenyl)piperidin-1-yl]ethyl}cyclohexyl)acetamide,
4-Methoxy-N-(4-{2-[4-(3-trifluoromethylphenyl)piperidin-1-yl]ethyl}cyclohexyl)butanamide,
2-(2-Methoxyethoxy)-N-(4-{2-[4-(3-trifluoromethylphenyl)piperazin-1-yl]ethyl}cyclohexyl)acetamide, hydrochloride,
N-(4-{2-[4-(3-Cyanophenyl)piperazin-1-yl]ethyl}cyclohexyl)-2-methoxyacetamide,
3,3,3-Trifluoro-N-(4-{2-[4-(2-fluorophenyl)piperazin-1-yl]ethyl}cyclohexyl)propanamide,
N-(4-{2-[4-(2-Fluorophenyl)piperazin-1-yl]ethyl}cyclohexyl)-2-phenoxyacetamide,
N-(4-{2-[4-(2-Fluorophenyl)piperazin-1-yl]ethyl}cyclohexyl)-2-oxobutanamide,
2-Cyano-N-(4-{2-[4-(3-cyanophenyl)piperazin-1-yl]ethyl}cyclohexyl)acetamide,
N-(4-{2-[4-(2,3-Difluorophenyl)piperazin-1-yl]ethyl}cyclohexyl)-2-methoxyacetamide,
2-Cyano-N-(4-{2-[4-(3-trifluoromethylphenyl)-3,6-dihydro-2H-pyridin-1-yl]ethyl}cyclohexyl)acetamide,
2-Oxo-N-(4-{2-[4-(3-trifluoromethylphenyl)piperazin-1-yl]ethyl}cyclohexyl)butanamide,hydrochloride,
2-Oxo-N-(4-{2-[4-(3-trifluoromethylphenyl)piperazin-1-yl]ethyl}cyclohexyl)propanamide, hydrochloride,
2-Dimethylamino-N-(4-{2-[4-(3-trifluoromethylphenyl)piperazin-1-yl]ethyl}cyclohexyl)acetamide,
N-(4-{2-[4-(2-Fluorophenyl)piperazin-1-yl]ethyl}cyclohexyl)-2-isopropoxyacetamide,
4-Methoxy-N-{4-[2-(4-phenylpiperazin-1-yl)ethyl]cyclohexyl}butanamide,
2-Isopropoxy-N-(4-{2-[4-(3-trifluoromethylphenyl)piperazin-1-yl]ethyl}cyclohexyl)acetamide,
N-(4-{2-[4-(2-Cyano-3-trifluoromethylphenyl)piperazin-1-yl]ethyl}cyclohexyl)-2-isopropoxyacetamide,
N-(4-{2-[4-(2-Cyano-3-trifluoromethylphenyl)piperazin-1-yl]ethyl}cyclohexyl)-2-ethoxyacetamide,
2-Cyano-N-(4-{2-[4-(2-cyano-3-trifluoromethylphenyl)piperazin-1-yl]ethyl}cyclohexyl)acetamide,
2-Cyano-N-{4-[2-(4-phenylpiperazin-1-yl)ethyl]cyclohexyl}acetamide, hydrochloride,
2-Acetylamino-N-(4-{2-[4-(3-trifluoromethylphenyl)piperazin-1-yl]ethyl}cyclohexyl)acetamide,
N-(4-{2-[4-(3,5-Bistrifluoromethylphenyl)piperazin-1-yl]ethyl}cyclohexyl)-2-cyanoacetamide,
N-(4-{2-[4-(3,5-Bistrifluoromethylphenyl)piperazin-1-yl]ethyl}cyclohexyl)-2-ethoxyacetamide,
3-Oxo-N-(4-{2-[4-(3-trifluoromethylphenyl)piperazin-1-yl]ethyl}cyclohexyl)butanamide,
N-{4-[2-(6-Cyano-3,4-dihydro-1H-isoquinolin-2-yl)ethyl]cyclohexyl}-3,3,3-trifluoropropanamide,
2-Cyano-N-(4-{2-[4-(2,6-di-tert-butylpyrimidin-4-yl)piperazin-1-yl]ethyl}cyclohexyl)acetamide,
N-(4-{2-[4-(2,3-Difluorophenyl)piperazin-1-yl]ethyl}cyclohexyl)-2-ethoxyacetamide,
2-Cyano-N-(4-{2-[4-(2,3-difluorophenyl)piperazin-1-yl]ethyl}cyclohexyl)acetamide,
2-Cyano-N-(4-{2-[4-(2-cyano-3-methylphenyl)piperazin-1-yl]ethyl}cyclohexyl)acetamide,
N-(4-{2-[4-(2-Cyano-3-methylphenyl)piperazin-1-yl]ethyl}cyclohexyl)-3,3,3-trifluoropropanamide,
2-Cyano-N-(4-{2-[4-(5,6,7,8-tetrahydronaphthalen-1-yl)piperazin-1-yl]ethyl}cyclohexyl)acetamide,
2-Ethoxy-N-(4-{2-[4-(5,6,7,8-tetrahydronaphthalen-1-yl)piperazin-1-yl]ethyl}cyclohexyl)acetamide,
N-(4-{2-[4-(3,5-Bistrifluoromethylphenyl)piperazin-1-yl]ethyl}cyclohexyl)-2-methoxyacetamide,
N-(4-{2-[4-(2-Cyano-3-trifluoromethylphenyl)piperazin-1-yl]ethyl}cyclohexyl)-2-methoxyacetamide,
2-Cyano-N-{4-[2-(4-pyridin-4-ylpiperazin-1-yl)ethyl]cyclohexyl}acetamide,
N-(4-{2-[4-(2,6-Di-tert-butylpyrimidin-4-yl)piperazin-1-yl]ethyl}cyclohexyl)-2-ethoxyacetamide,
N-(4-{2-[4-(2,6-Di-tert-butylpyrimidin-4-yl)piperazin-1-yl]ethyl}cyclohexyl)-2-methoxyacetamide,
2-Ethoxy-N-(4-{2-[4-(2-methoxyphenyl)piperazin-1-yl]ethyl}cyclohexyl)acetamide,
2-Cyano-N-(4-{2-[4-(2-methoxyphenyl)piperazin-1-yl]ethyl}cyclohexyl)acetamide,
2-Methoxy-N-(4-{2-[4-(2-methoxyphenyl)piperazin-1-yl]ethyl}cyclohexyl)acetamide,
2-Cyano-N-(4-{2-[4-(2-fluorophenyl)piperazin-1-yl]ethyl}cyclohexyl)acetamide, hydrochloride,
2-Cyano-N-(4-{2-[4-(2-fluorophenyl)-3,6-dihydro-2H-pyridin-1-yl]ethyl}cyclohexyl)acetamide,
2-Acetylamino-N-{4-[2-(4-phenylpiperazin-1-yl)ethyl]cyclohexyl}acetamide,
N-(4-{2-[4-(2-Chlorophenyl)piperazin-1-yl]ethyl}cyclohexyl)-2-methoxyacetamide,
2-Methoxy-N-(4-{2-[4-(5,6,7,8-tetrahydronaphthalen-1-yl)piperazin-1-yl]ethyl}cyclohexyl)acetamide, N-(4-{2-[4-(2-Chlorophenyl)piperazin-1-yl]ethyl}cyclohexyl)-2-cyanoacetamide,
N-(4-{2-[4-(2-Chlorophenyl)piperazin-1-yl]ethyl}cyclohexyl)-2-ethoxyacetamide,
2-Cyano-N-(4-{2-[4-(3-fluorophenyl-piperazin-1-yl]ethyl}cyclohexyl)acetamide,
2-Acetylamino-N-(4-{2-[4-(2-fluorophenyl)piperazin-1-yl]ethyl}cyclohexyl)acetamide,
2-tert-Butoxy-N-(4-{2-[4-(3-trifluoromethylphenyl)piperazin-1-yl]ethyl}cyclohexyl)acetamide,
N-(4-{2-[4-(3-Chloro-2-methylphenyl)piperazin-1-yl]ethyl}cyclohexyl)-2-cyanoacetamide,
N-(4-{2-[4-(3-Chloro-2-methylphenyl)piperazin-1-yl]ethyl}cyclohexyl)-2-ethoxyacetamide,
2-Cyano-N-(4-{2-[4-(3-cyano-5-trifluoromethylphenyl)piperazin-1-yl]ethyl}cyclohexyl)acetamide,
N-(4-{2-[4-(3-Cyano-5-trifluoromethylphenyl)piperazin-1-yl]ethyl}cyclohexyl)-2-methoxyacetamide,
N-(4-{2-[4-(3-Cyano-5-trifluoromethylphenyl)piperazin-1-yl]ethyl}cyclohexyl)-2-ethoxyacetamide,
2-Cyano-N-{4-[2-(4-phenyl-3,6-dihydro-2H-pyridin-1-yl)ethyl]cyclohexyl}acetamide,
N-(4-{2-[4-(2,3-Dichlorophenyl)piperazin-1-yl]ethyl}cyclohexyl)-2-methoxyacetamide,
2-Cyano-N-(4-{2-[4-(2,3-dichlorophenyl)piperazin-1-yl]ethyl}cyclohexyl)acetamide,
N-(4-{2-[4-(2,3-Dichlorophenyl)piperazin-1-yl]ethyl}cyclohexyl)-2-ethoxyacetamide,
2-Acetylamino-N-(4-{2-[4-(2,3-difluorophenyl)piperazin-1-yl]ethyl}cyclohexyl)acetamide,
N-(4-{2-[4-(2,3-Difluorophenyl)piperazin-1-yl]ethyl}cyclohexyl)-2-isopropoxyacetamide, hydrochloride,
2-Cyano-N-(4-{2-[4-(3,5-dimethylphenyl)piperazin-1-yl]ethyl}cyclohexyl)acetamide,
2-Cyano-N-(4-{2-[4-(3-ethylphenyl)piperazin-1-yl]ethyl}cyclohexyl)acetamide,
2-Cyano-N-(4-{2-[4-(3-dimethylaminophenyl)piperazin-1-yl]ethyl}cyclohexyl)acetamide,
2-Cyano-N-(4-{2-[4-(3,5-dichlorophenyl)piperazin-1-yl]ethyl}cyclohexyl)acetamide,
2-Cyano-N-(4-{2-[4-(2,5-dimethylphenyl)piperazin-1-yl]ethyl}cyclohexyl)acetamide,
1-Acetylpiperidine-4-carboxylic acid (4-{2-[4-(3-trifluoromethyl-phenyl)piperazin-1-yl]ethyl}cyclohexyl)amide,
N-(4-{2-[4-(3-Trifluoromethylphenyl)piperazin-1-yl]ethyl}cyclo-hexyl)succinamide,
N-(4-{2-[4-(5-Chloro-2-methylphenyl)piperazin-1-yl]ethyl}cyclohexyl)-2-cyanoacetamide,
N-(4-{2-[4-(3-Chlorophenyl)piperazin-1-yl]ethyl}cyclohexyl)-2-cyanoacetamide,
2-Cyano-N-(4-{2-[4-(3-trifluoromethoxyphenyl)piperazin-1-yl]ethyl}cyclohexyl)acetamide,
2-Cyano-N-(4-{2-[4-(2-fluoro-3-trifluoromethylphenyl)piperazin-1-yl]ethyl}cyclohexyl)acetamide,
2-Cyano-N-(4-{2-[4-(3,5-difluorophenyl)piperazin-1-yl]ethyl}cyclohexyl)acetamide,
2-Cyano-N-(4-{2-[4-(3-methoxy-5-trifluoromethylphenyl)piperazin-1-yl]ethyl}cyclohexyl)acetamide,
4-Cyano-N-(4-{2-[4-(3-trifluoromethylphenyl)piperazin-1-yl]ethyl}cyclohexyl)butanamide,
2-Cyano-N-(4-{2-[4-(2,4-difluorophenyl)piperazin-1-yl]ethyl}cyclohexyl)acetamide,
2-Cyano-N-(4-{2-[4-(3-isopropoxyphenyl)piperazin-1-yl]ethyl}cyclohexyl)acetamide, hydrochloride,
2-Cyano-N-(4-{2-[4-(3-methoxyphenyl)piperazin-1-yl]ethyl}cyclohexyl)acetamide, hydrochloride,
2-Cyano-N-(4-{2-[4-(2-methoxy-5-trifluoromethylphenyl)piperazin-1-yl]ethyl}cyclohexyl)acetamide,
2-Cyano-N-{4-[2-(4-m-tolylpiperazin-1-yl)ethyl]cyclohexyl}acetamide,
3-Diethylamino-N-(4-{2-[4-(3-trifluoromethylphenyl)piperazin-1-yl]ethyl}cyclohexyl)propanamide,
3-Cyano-N-(4-{2-[4-(3-trifluoromethylphenyl)piperazin-1-yl]ethyl}cyclohexyl)propanamide, hydrochloride,
N-(4-{2-[4-(3-tert-Butylphenyl)piperazin-1-yl]ethyl}cyclohexyl)-2-cyanoacetamide,
2-Cyano-N-(4-{2-[4-(3-ethoxyphenyl)piperazin-1-yl]ethyl}cyclohexyl)acetamide,
N-(4-{2-[4-(5-Chloro-2-fluorophenyl)piperazin-1-yl]ethyl}cyclohexyl)-2-cyanoacetamide,
4-Cyano-N-(4-{2-[4-(2-fluoro-3-trifluoromethylphenyl)piperazin-1-yl]ethyl}cyclohexyl)butanamide,
2-Cyano-N-(4-{2-[4-(6-trifluoromethylbenzo[b]thiophen-3-yl)piperazin-1-yl]ethyl}cyclohexyl)acetamide,
2-Cyano-N-(4-{2-[4-(2-fluoro-5-trifluoromethylphenyl)piperazin-1-yl]ethyl}cyclohexyl)acetamide,
2-Cyano-N-(4-{2-[4-(3-hydroxyphenyl)piperazin-1-yl]ethyl}cyclo-hexyl)acetamide, hydrochloride,
N-(4-{2-[4-(5-Chloro-2-methoxyphenyl)piperazin-1-yl]ethyl}cyclohexyl)-2-cyanoacetamide,
N-(4-{2-[4-(2-tert-Butyl-6-trifluoromethylpyrimidin-4-yl)piperazin-1-yl]ethyl}cyclohexyl)-2-cyanoacetamide,
2-Cyano-N-(4-{2-[4-(2-methyl-3-trifluoromethylphenyl)piperazin-1-yl]ethyl}cyclohexyl)acetamide,
N-(4-{2-[4-(5-Chloro-2-methylphenyl)piperazin-1-yl]ethyl}cyclohexyl)-3,3,3-trifluoropropanamide,
2-Cyano-N-(4-{2-[4-(3,5-dimethoxyphenyl)piperazin-1-yl]ethyl}cyclohexyl)acetamide,
N-(4-{2-[4-(3-Chloro-5-fluorophenyl)piperazin-1-yl]ethyl}cyclohexyl)-2-cyanoacetamide,
2-Cyano-N-(4-{2-[4-(3-methylsulfanylphenyl)piperazin-1-yl]ethyl}cyclohexyl)acetamide,
2-Cyano-N-{4-[2-(4-naphthalen-1-ylpiperazin-1-yl)ethyl]cyclohexyl}acetamide,
N-(4-{2-[4-(3,5-Bistrifluoromethylphenyl)piperazin-1-yl]ethyl}cyclohexyl)-4-cyanobutanamide,
N-(4-{2-[4-(3-Chloro-2-fluorophenyl)piperazin-1-yl]ethyl}cyclohexyl)-2-cyanoacetamide,
N-(4-{2-[4-(2-Fluorophenyl)piperazin-1-yl]ethyl}cyclohexyl)succinamide,
N-{4-[2-(4-Phenylpiperazin-1-yl)ethyl]cyclohexyl}succinamide,
3,3,3-Trifluoro-N-{4-[2-(4-phenylpiperazin-1-yl)ethyl]cyclohexyl}propanamide,
N-(4-{2-[4-(2-Chloro-5-trifluoromethylphenyl)piperazin-1-yl]ethyl}cyclohexyl)-2-cyanoacetamide,
N-(4-{2-[4-(5-Chloro-2-methylphenyl)piperazin-1-yl]ethyl}cyclohexyl)succinamide,
4-Oxopentanoic acid (4-{2-[4-(3-trifluoromethylphenyl)piperazin-1-yl]ethyl}cyclohexyl)amide,
2-Cyano-N-(4-{2-[4-(2-fluoro-5-methylphenyl)piperazin-1-yl]ethyl}cyclohexyl)acetamide,
N-(4-{2-[4-(2-Chloro-5-methoxyphenyl)piperazin-1-yl]ethyl}cyclohexyl)-2-cyanoacetamide,
2-Cyano-N-(4-{2-[4-(2-methylsulfanylphenyl)piperazin-1-yl]ethyl}cyclohexyl)acetamide,
2-Cyano-N-(4-{2-[4-(2-methoxy-5-methylphenyl)piperazin-1-yl]ethyl}cyclohexyl)acetamide,
2-Cyano-N-(4-{2-[4-(5-fluoro-2-methylphenyl)piperazin-1-yl]ethyl}cyclohexyl)acetamide,
N-(4-{2-[4-(5-tert-Butyl-2-methoxyphenyl)piperazin-1-yl]ethyl}cyclohexyl)-2-cyanoacetamide, 2-Cyano-N-(4-{2-[4-(5-methoxy-2-methylphenyl)piperazin-1-yl]ethyl}cyclohexyl)acetamide,
N-(4-{2-[4-(3,5-Bistrifluoromethylphenyl)-3,6-dihydro-2H-pyridin-1-yl]ethyl}cyclohexyl)-2-cyanoacetamide,
N-(4-{2-[4-(3,5-Bis-trifluoromethylphenyl)piperidin-1-yl]ethyl}cyclohexyl)-2-cyanoacetamide,
5-Oxohexanoic acid (4-{2-[4-(3-trifluoromethylphenyl)piperazin-1-yl]ethyl}cyclohexyl)amide,
4-Cyano-N-(4-{2-[4-(3-ethylphenyl)piperazin-1-yl]ethyl}cyclohexyl)butanamide, hydrochloride,
4-Cyano-N-(4-{2-[4-(2-fluorophenyl)piperazin-1-yl]ethyl}cyclohexyl)butanamide,
20-N-(4-{2-[4-(3-Chloro-2-fluorophenyl)piperazin-1-yl]ethyl}cyclohexyl)-4-cyanobutanamide,
4-Cyano-N-(4-{2-[4-(3-trifluoromethoxyphenyl)piperazin-1-yl]ethyl}cyclohexyl)butanamide,
4-Cyano-N-(4-{2-[4-(2-fluoro-5-trifluoromethylphenyl)piperazin-1-yl]ethyl}cyclohexyl)butanamide,
2-Cyano-N-(4-{2-[4-(2-cyano-3-fluorophenyl-piperazin-1-yl]ethyl}cyclohexyl)acetamide,
4-Cyano-N-(4-{2-[4-(5,6,7,8-tetrahydronaphthalen-1-yl)piperazin-1-yl]ethyl}cyclohexyl)butanamide,
4-Cyano-N-(4-{2-[4-(2,3-dichlorophenyl)piperazin-1-yl]ethyl}cyclohexyl)butanamide,
2-Cyano-N-(4-{2-[4-(5,6,7,8-tetrahydronaphthalen-2-yl)piperazin-1-yl]ethyl}cyclohexyl)acetamide,
2-Cyano-N-{4-[2-(4-indan-5-ylpiperazin-1-yl)ethyl]cyclohexyl}acetamide,
N-(4-{2-[4-(3,5-Bistrifluoromethylphenyl)piperazin-1-yl]ethyl}cyclohexyl)-3-cyanopropanamide,
3-Cyano-N-(4-{2-[4-(2-fluoro-3-trifluoromethylphenyl)piperazin-1-yl]ethyl}cyclohexyl)propanamide,
N-(4-{2-[4-(3-Chloro-2-methoxyphenyl)piperazin-1-yl]ethyl}cyclohexyl)-2-cyanoacetamide,
N-(4-{2-[4-(3-Benzylphenyl)piperazin-1-yl]ethyl}cyclohexyl)-2-cyanoacetamide,
[3-(4-{2-[4-(2-Cyanoacetylamino)cyclohexyl]ethyl}piperazin-1-yl)phenyl]carbamic acid ethyl ester,
2-Cyano-N-(4-{2-[4-(3-trifluoromethylphenyl)piperidin-1-yl]ethyl}cyclohexyl)acetamide,
2-Cyano-N-(4-{2-[4-(2,3-dimethylphenyl)piperazin-1-yl]ethyl}cyclohexyl)acetamide,
2-Cyano-N-{4-[2-(4-o-tolylpiperazin-1-yl)ethyl]cyclohexyl}acetamide,
2-Cyano-N-(4-{2-[4-(2,5-dimethoxyphenyl)piperazin-1-yl]ethyl}cyclohexyl)acetamide,
4-Oxopentanoic acid (4-{2-[4-(3,5-bis-trifluoromethylphenyl)piperazin-1-yl]ethyl}cyclohexyl)amide,
4-Dimethylamino-N-(4-{2-[4-(3-trifluoromethylphenyl)piperazin-1-yl]ethyl}cyclohexyl)butanamide,
2-(4-Fluorophenoxy)-N-(4-{2-[4-(3-trifluoromethylphenyl)piperazin-1-yl]ethyl}cyclohexyl)acetamide,
2-Cyano-N-(4-{2-[4-(2-trifluoromethylphenyl)piperazin-1-yl]ethyl}cyclohexyl)acetamide, hydrochloride,
2-Cyano-N-(4-{2-[4-(2,5-difluorophenyl)piperazin-1-yl]ethyl}cyclohexyl)acetamide,
N-(4-{2-[4-(2-Chloro-5-methylphenyl)piperazin-1-yl]ethyl}cyclohexyl)-2-cyanoacetamide,
2-Cyano-N-(4-{2-[4-(2,5-dichlorophenyl)piperazin-1-yl]ethyl}cyclohexyl)acetamide,
N-(4-{2-[4-(3-Chlorophenyl)piperazin-1-yl]ethyl}cyclohexyl)-4-cyanobutanamide,
4-Cyano-N-(4-{2-[4-(2-methyl-3-trifluoromethylphenyl)piperazin-1-yl]ethyl}cyclohexyl)butanamide,
4-Oxopentanoic acid (4-{2-[4-(2-fluoro-3-trifluoromethylphenyl)piperazin-1-yl]ethyl}cyclohexyl)amide,
2-Cyano-N-(4-{2-[4-(3,5-di-tert-butylphenyl)piperazin-1-yl]ethyl}cyclohexyl)acetamide,
N-(4-{2-[4-(2-Chlorophenyl)piperazin-1-yl]ethyl}cyclohexyl)-4-cyanobutanamide,
4-Cyano-N-{4-[2-(4-m-tolylpiperazin-1-yl)ethyl]cyclohexyl}butanamide,
3,3,3-Trifluoro-N-{4-[2-(4-m-tolylpiperazin-1-yl)ethyl]cyclohexyl}propanamide,
4-Cyano-N-(4-{2-[4-(2-methylsulfanylphenyl)piperazin-1-yl]ethyl}cyclohexyl)butanamide,
2-Cyano-N-{4-[2-(4-quinolin-8-ylpiperazin-1-yl)ethyl]cyclohexyl}acetamide,
4-Cyano-N-(4-{2-[4-(3-methylsulfanylphenyl)piperazin-1-yl]ethyl}cyclohexyl)butanamide,
2-Cyano-N-{4-[2-(4-quinolin-5-ylpiperazin-1-yl)ethyl]cyclohexyl}acetamide,
2-Cyano-N-(4-{2-[4-(3-methanesulfonylaminophenyl)piperazin-1-yl]ethyl}cyclohexyl)acetamide,
2-Cyano-N-(4-{2-[4-(4-fluoro-phenyl)piperazin-1-yl]ethyl}cyclohexyl)acetamide,
2-Cyano-N-{4-[2-(4-p-tolylpiperazin-1-yl)ethyl]cyclohexyl}acetamide,
2-Cyano-N-(4-{2-[4-(2-ethoxyphenyl)piperazin-1-yl]ethyl}cyclohexyl)acetamide,
N-(4-{2-[4-(2-tert-Butyl-6-trifluoromethylpyrimidin-4-yl)piperazin-1-yl]ethyl}cyclohexyl)-3-cyanopropanamide,
2-Cyano-N-(4-{2-[4-(2-phenoxyphenyl)piperazin-1-yl]ethyl}cyclohexyl)acetamide,
N-(4-{2-[4-(3-Chloro-2-cyanophenyl)piperazin-1-yl]ethyl}cyclohexyl)-2-cyanoacetamide,
2-Cyano-N-(4-{2-[4-(2-ethylphenyl)piperazin-1-yl]ethyl}cyclohexyl)acetamide,
N-(4-{2-[4-(5-Chloro-2-methylphenyl)piperazin-1-yl]ethyl}cyclohexyl)-4-cyanobutanamide,
4-Cyano-N-(4-{2-[4-(3,5-dimethylphenyl)piperazin-1-yl]ethyl}cyclohexyl)butanamide,
N-(4-{2-[4-(3-Ethylphenyl)piperazin-1-yl]ethyl}cyclohexyl)-3,3,3-trifluoropropanamide,
3-Cyano-N-(4-{2-[4-(3-ethylphenyl)piperazin-1-yl]ethyl}cyclohexyl)propanamide,
4-Cyano-N-(4-{2-[4-(6-trifluoromethylbenzo[b]thiophen-3-yl)piperazin-1-yl]ethyl}cyclohexyl)butanamide,
4-Cyano-N-(4-{2-[4-(3,5-difluorophenyl)piperazin-1-yl]ethyl}cyclohexyl)butanamide,
2-Cyano-N-(4-{2-[4-(2,4-diethylphenyl)piperazin-1-yl]ethyl}cyclohexyl)acetamide,
3,3,3-Trifluoro-N-(4-{2-[4-(2-fluoro-3-trifluoromethylphenyl)piperazin-1-yl]ethyl}cyclohexyl)propanamide,
N-(4-{2-[4-(5-Chloro-2-methylphenyl)piperazin-1-yl]ethyl}cyclohexyl)-3-cyanopropanamide,
5-N-(4-{2-[4-(3-Chloro-2-methylphenyl)piperazin-1-yl]ethyl}cyclohexyl)-4-cyanobutanamide,
N-(4-{2-[4-(3-Chloro-5-fluorophenyl)piperazin-1-yl]ethyl}cyclohexyl)-4-cyanobutanamide,
N-(4-{2-[4-(2-Fluoro-3-trifluoromethylphenyl)piperazin-1-yl]ethyl}cyclohexyl)-2-methoxyacetamide,
4-Cyano-N-(4-{2-[4-(3,5-dichlorophenyl)piperazin-1-yl]ethyl}cyclohexyl)butanamide,
4-Cyano-N-{4-[2-(4-quinolin-8-ylpiperazin-1-yl)ethyl]cyclohexyl}butanamide,
4,4,4-Trifluoro-N-(4-{2-[4-(3-trifluoromethylphenyl)piperazin-1-yl]ethyl}cyclohexyl)butanamide,
3-Cyano-N-(4-{2-[4-(2-fluorophenyl)piperazin-1-yl]ethyl}cyclohexyl)propanamide,
2-Cyano-N-(4-{2-[4-(2,6-dimethylphenyl)piperazin-1-yl]ethyl}cyclohexyl)acetamide, 2-Cyano-N-(4-{2-[4-(3-hydroxymethylphenyl)piperazin-1-yl]ethyl}cyclohexyl)acetamide,
3-Cyano-N-(4-{2-[4-(3-methylsulfanylphenyl)piperazin-1-yl]ethyl}cyclohexyl)propanamide,
2-Cyano-N-(4-{2-[4-(3-methoxymethylphenyl)piperazin-1-yl]ethyl}cyclohexyl)acetamide,
2-Cyano-N-(4-{2-[4-(3-propylphenyl)piperazin-1-yl]ethyl}cyclohexyl)acetamide,
2-Cyano-N-(4-{2-[4-(3,4-dichlorophenyl)piperazin-1-yl]ethyl}cyclohexyl)acetamide,
2-Cyano-N-[4-(2-{4-[3-(1-hydroxyethyl)phenyl]piperazin-1-yl}ethyl)cyclohexyl]acetamide,
2-Cyano-N-(4-{2-[4-(4-trifluoromethylphenyl)piperazin-1-yl]ethyl}cyclohexyl)acetamide,
N-(4-{2-[4-(4-Chlorophenyl)piperazin-1-yl]ethyl}cyclohexyl)-2-cyanoacetamide,
N-{4-[2-(4-Biphenyl-3-yl-piperazin-1-yl)ethyl]cyclohexyl}-2-cyanoacetamide,
2-Cyano-N-(4-{2-[4-(4-fluoro-3-trifluoromethylphenyl)piperazin-1-yl]ethyl}cyclohexyl)acetamide,
3-Cyano-N-(4-{2-[4-(5-fluoro-2-methylphenyl)piperazin-1-yl]ethyl}cyclohexyl)propanamide,
4-Cyano-N-(4-{2-[4-(5-fluoro-2-methylphenyl)piperazin-1-yl]ethyl}cyclohexyl)butanamide,
N-(4-{2-[4-(3-Bromophenyl)piperazin-1-yl]ethyl}cyclohexyl)-2-cyanoacetamide,
2-Cyano-N-[4-(2-{4-[3-(1,1-difluoroethyl)phenyl]piperazin-1-yl}ethyl)cyclohexyl]acetamide,
2-Cyano-2,2-dimethyl-N-(4-{2-[4-(3-trifluoromethylphenyl)piperazin-1-yl]ethyl}cyclohexyl)acetamide,
4-Cyano-N-(4-{2-[4-(4-fluorophenyl)piperazin-1-yl]ethyl}cyclohexyl)butanamide,
3,3,3-Trifluoro-N-(4-{2-[4-(4-fluorophenyl)piperazin-1-yl]ethyl}cyclohexyl)propanamide,
2-Cyano-N-(4-{2-[4-(4-ethylphenyl)piperazin-1-yl]ethyl}cyclohexyl)acetamide,
4-Cyano-N-(4-{2-[4-(2-ethylphenyl)piperazin-1-yl]ethyl}cyclohexyl)butanamide,
1-(4-{2-[4-(2-Fluorophenyl)piperazin-1-yl]ethyl}cyclohexylidene)propan-2-one, hydrochloride,
1-(4-{2-[4-(2-Fluorophenyl)piperazin-1-yl]ethyl}cyclohexyl)propan-2-one, hydrochloride,
1-(1,3-Dihydroisoindol-2-yl)-2-(4-{2-[4-(3-trifluoromethylphenyl)piperazin-1-yl]ethyl}cyclohexylidene)ethanone, hydrochloride,
1-(1,3-Dihydroisoindol-2-yl)-2-(4-{2-[4-(3-trifluoromethylphenyl)piperazin-1-yl]ethyl}cyclohexyl)ethanone, hydrochloride 60/40 mixture of isomers,
1-Pyrrolidin-1-yl-2-(4-{2-[4-(3-trifluoromethylphenyl)piperazin-1-yl]ethyl}cyclohexylidene)ethanone,
N,N-Dimethyl-2-(4-{2-[4-(3-trifluoromethylphenyl)piperazin-1-yl]ethyl}cyclohexylidene)acetamide,
N,N-Dimethyl-2-(4-{2-[4-(3-trifluoromethylphenyl)piperazin-1-yl]ethyl}cyclohexyl)acetamide,
1-Pyrrolidin-1-yl-2-(4-{2-[4-(3-trifluoromethylphenyl)piperazin-1-yl]ethyl}cyclohexyl)ethanone,
N-Methyl-2-(4-{2-[4-(3-trifluoromethylphenyl)piperazin-1-yl]ethyl}cyclohexyl)acetamide,
N-(2-Methoxyethyl)-2-(4-{2-[4-(3-trifluoromethylphenyl)piperazin-1-yl]ethyl}cyclohexyl)acetamide,
N-(2-Methoxyethyl)-2-(4-{2-[4-(3-trifluoromethylphenyl)piperazin-1-yl]ethyl}cyclohexylidene)acetamide,
N-(2-Methoxyethyl)-2-(4-{2-[4-(3-trifluoromethylphenyl)piperazin-1-yl]ethyl}cyclohexyl)acetamide, hydrochloride,
2-(4-{2-[4-(2-Fluorophenyl)piperazin-1-yl]ethyl}cyclohexylidene)-N-methylacetamide,
2-(4-{2-[4-(2-Fluorophenyl)piperazin-1-yl]ethyl}cyclohexyl)-N-methylacetamide,
2-(4-{2-[4-(2-Fluorophenyl)piperazin-1-yl]ethyl}cyclohexylidene)-1-pyrrolidin-1-ylethanone,
2-(4-{2-[4-(2-Fluorophenyl)piperazin-1-yl]ethyl}cyclohexyl)-1-pyrrolidin-1-ylethanone,
2-(4-{2-[4-(2-Fluorophenyl)piperazin-1-yl]ethyl}cyclohexylidene)-N-(2,2,2-trifluoroethyl)acetamide,
2-(4-{2-[4-(2-Fluorophenyl)piperazin-1-yl]ethyl}cyclohexyl)-N-(2,2,2-trifluoroethyl)acetamide,
2-(4-{2-[4-(2-Fluorophenyl)piperazin-1-yl]ethyl}cyclohexylidene)-N-propylacetamide,
2-(4-{2-[4-(2-Fluorophenyl)piperazin-1-yl]ethyl}cyclohexyl)-N-propylacetamide,
N-Cyanomethyl-2-(4-{2-[4-(2-fluorophenyl)piperazin-1-yl]ethyl}cyclohexylidene)acetamide,
N-Cyanomethyl-2-(4-{2-[4-(2-fluorophenyl)piperazin-1-yl]ethyl}cyclohexyl)acetamide,
1-(4-fluorophenyl)-2-(4-{2-[4-(3-trifluoromethylphenyl)piperazin-1-yl]ethyl}piperidin-1-yl)ethanone, dihydrochloride
1-{4-[2-(4-p-tolylpiperazin-1-yl)ethyl]piperidin-1-yl}propan-2-one
1-(4-{2-[4-(3,5-dichlorophenyl)piperazin-1-yl]ethyl}piperidin-1-yl)propan-2-one
4-cyano-N-(4-{2-[4-(3-propylphenyl)piperazin-1-yl]ethyl}cyclohexyl)butanamide
2-cyano-N-(4-{2-[4-(3-fluoro-2-methylphenyl)piperazin-1-yl]ethyl}cyclohexyl)acetamide
4-cyano-N-[4-(2-{4-[3-(1,1-difluoroethyl)phenyl]piperazin-1-yl}ethyl)cyclohexyl]butanamide
N-{4-[2-(4-benzo[1,3]dioxol-5-ylpiperazin-1-yl)ethyl]cyclohexyl}-2-cyanoacetamide
2-cyano-N-(4-{2-[4-(2,3-dihydrobenzo[1,4]dioxin-6-yl)piperazin-1-yl]ethyl}cyclohexyl)acetamide
1-(4-{2-[4-(5,6,7,8-tetrahydronaphthalen-1-yl)piperazin-1-yl]ethyl}piperidin-1-yl)propan-2-one
1-(4-{2-[4-(2-fluoro-3-trifluoromethylphenyl)piperazin-1-yl]ethyl}piperidin-1-yl)propan-2-one, dihydrochloride
1-(4-{2-[4-(2-methyl-3-trifluoromethylphenyl)piperazin-1-yl]ethyl}piperidin-1-yl)propan-2-one, dihydrochloride
3,3,3-trifluoro-N-{4-[2-(4-quinolin-5-ylpiperazin-1-yl)ethyl]cyclohexyl}propanamide
4-cyano-N-{4-[2-(4-quinolin-5-ylpiperazin-1-yl)ethyl]cyclohexyl}butanamide
2-cyano-N-(4-{2-[4-(4-fluoro-3-methylphenyl)piperazin-1-yl]ethyl}cyclohexyl)acetamide
1-(4-{2-[4-(3-trifluoromethylphenyl)-3,6-dihydro-2H-pyridin-1-yl]ethyl}piperidin-1-yl)propan-2-one, dihydrochloride
2-cyano-cyclopropanecarboxylic acid (4-{2-[4-(3-trifluoromethylphenyl)piperazin-1-yl]ethyl}cyclohexyl)amide
2-cyano-N-(4-{2-[4-(3,4-difluorophenyl)piperazin-1-yl]ethyl}cyclohexyl)acetamide
2-cyano-N-(4-{2-[4-(3-ethylphenyl)-3,6-dihydro-2H-pyridin-1-yl]ethyl}cyclohexyl)acetamide
4-cyano-N-(4-{2-[4-(3-ethylphenyl)-3,6-dihydro-2H-pyridin-1-yl]ethyl}cyclohexyl)butanamide
2-cyano-N-(4-{2-[4-(3-ethylphenyl)piperazin-1-yl]ethyl}cyclohexyl)acetamide
1-(4-{2-[4-(3-ethylphenyl)piperazin-1-yl]ethyl}piperidin-1-yl)propan-2-one, dihydrochloride
5-(4-{2-[4-(3-trifluoromethylphenyl)piperazin-1-yl]ethyl}piperidin-1-yl)pentan-2-one, dihydrochloride
1-(4-{2-[4-(3-chloro-2-fluorophenyl)piperazin-1-yl]ethyl}piperidin-1-yl)propan-2-one, dihydrochloride 1-{4-[2-(4-m-tolylpiperazin-1-yl)ethyl]piperidin-1-yl}propan-2-one, dihydrochloride
1-(4-{2-[4-(3-fluoro-2-methylphenyl)piperazin-1-yl]ethyl}piperidin-1-yl)propan-2-one, dihydrochloride
2-methanesulfinyl-N-(4-{2-[4-(3-trifluoromethylphenyl)piperazin-1-yl]ethyl}cyclohexyl)acetamide
2-cyano-N-(4-{2-[4-(3-isopropylphenyl)piperazin-1-yl]ethyl}cyclohexyl)acetamide
2-cyano-N-(4-{2-[4-(3,5-dimethylphenyl)piperazin-1-yl]ethyl}cyclohexyl)acetamide
2-methanesulfonyl-N-(4-{2-[4-(3-trifluoromethylphenyl)piperazin-1-yl]ethyl}cyclohexyl)acetamide
1-{4-[2-(4-quinolin-8-ylpiperazin-1-yl)ethyl]piperidin-1-yl}propan-2-one, dihydrochloride
2-cyano-N-(4-{2-[4-(3-fluoro-4-methylphenyl)piperazin-1-yl]ethyl}cyclohexyl)acetamide
2-cyano-N-(4-{2-[4-(3,4-dimethylphenyl)piperazin-1-yl]ethyl}cyclohexyl)acetamide
2-cyano-N-(4-{2-[4-(3,4,5-trifluorophenyl)piperazin-1-yl]ethyl}cyclohexyl)acetamide
2-cyano-N-(4-{2-[4-(2-fluoro-3-trifluoromethylphenyl)-3,6-dihydro-2H-pyridin-1-yl]ethyl}cyclohexyl)acetamide
2-cyano-N-(4-{2-[4-(3-trifluoromethylsulfanylphenyl)piperazin-1-yl]ethyl}cyclohexyl)acetamide
1-(4-{2-[4-(3,5-dimethylphenyl)piperazin-1-yl]ethyl}piperidin-1-yl)propan-2-one, dihydrochloride
1-(4-{2-[4-(3-methoxyphenyl)piperazin-1-yl]ethyl}piperidin-1-yl)propan-2-one, dihydrochloride
2-(4-{2-[1-(2-oxopropyl)piperidin-4-yl]ethyl}piperazin-1-yl)benzonitrile, dihydrochloride
1-(4-{2-[4-(3-propylphenyl)piperazin-1-yl]ethyl}piperidin-1-yl)propan-2-one, dihydrochloride
1-(4-{2-[4-(3-trifluoromethoxyphenyl)piperazin-1-yl]ethyl}piperidin-1-yl)propan-2-one, dihydrochloride
1-(4-{2-[4-(2-ethylphenyl)piperazin-1-yl]ethyl}piperidin-1-yl)propan-2-one, dihydrochloride
1-{4-[2-(4-quinolin-5-ylpiperazin-1-yl)ethyl]piperidin-1-yl}propan-2-one, dihydrochloride
2-cyano-N-(4-{2-[4-(3-methanesulfonylphenyl)piperazin-1-yl]ethyl}cyclohexyl)acetamide
4-(4-{2-[4-(3-trifluoromethylphenyl)piperazin-1-yl]ethyl}piperidin-1-yl)butan-2-one, dihydrochloride
1-{4-[2-(4-indan-4-ylpiperazin-1-yl)ethyl]piperidin-1-yl}propan-2-one, dihydrochloride
2-cyano-N-(4-{2-[4-(3-difluoromethylphenyl)piperazin-1-yl]ethyl}cyclohexyl)acetamide
4-cyano-N-(4-{2-[4-(2-fluoro-3-trifluoromethylphenyl)-3,6-dihydro-2H-pyridin-1-yl]ethyl}cyclohexyl)butanamide
4-cyano-N-(4-{2-[4-(3-fluoro-2-methylphenyl)piperazin-1-yl]ethyl}cyclohexyl)butanamide
4-cyano-N-(4-{2-[4-(3,4-difluorophenyl)piperazin-1-yl]ethyl}cyclohexyl)butanamide
4-cyano-N-(4-{2-[4-(4-fluoro-3-methylphenyl)piperazin-1-yl]ethyl}cyclohexylbutanamide
N-(4-{2-[4-(4-chloro-2-fluorophenyl)piperazin-1-yl]ethyl}cyclohexyl)-2-cyanoacetamide
N-(4-{2-[4-(4-chloro-3-trifluoromethylphenyl)piperazin-1-yl]ethyl}cyclohexyl)-2-cyanoacetamide
2-cyano-N-(4-{2-[4-(4-fluorophenyl)-3,6-dihydro-2H-pyridin-1-yl]ethyl}cyclohexyl)acetamide
N-(4-{2-[4-(4-chlorophenyl)-3,6-dihydro-2H-pyridin-1-yl]ethyl}cyclohexyl)-2-cyanoacetamide
4-cyano-N-(4-{2-[4-(2-trifluoromethylsulfanylphenyl)piperazin-1-yl]ethyl}cyclohexyl)butanamide
4-cyano-N-(4-{2-[4-(3-difluoromethylphenyl)piperazin-1-yl]ethyl}cyclohexyl)butanamide
N-{4-[2-(4-benzo[1,3]dioxol-5-ylpiperazin-1-yl)ethyl]cyclohexyl}-4-cyanobutanamide
4-cyano-N-(4-{2-[4-(2-fluoro-3-trifluoromethylphenyl)piperazin-1-yl]ethyl}cyclohexyl)butanamide
4-cyano-N-(4-{2-[4-(4-fluoro-3-methylphenyl)piperazin-1-yl]ethyl}cyclohexyl)butanamide, hydrochloride
4-cyano-N-(4-{2-[4-(3,4-dichlorophenyl)piperazin-1-yl]ethyl}cyclohexyl)butanamide
N-(4-{2-[4-(3-chloro-4-methylphenyl)piperazin-1-yl]ethyl}cyclohexyl)-2-cyanoacetamide
2-cyano-N-(4-{2-[4-(4-cyanophenyl)piperazin-1-yl]ethyl}cyclohexyl)acetamide
4-cyano-N-(4-{2-[4-(2,5-dichlorophenyl)piperazin-1-yl]ethyl}cyclohexyl)butanamide
cyclopent-3-enecarboxylic acid (4-{2-[4-(2-methoxyphenyl)piperazin-1-yl]ethyl}cyclohexyl)amide
2-cyclopent-2-enyl-N-(4-{2-[4-(3-trifluoromethylphenyl)piperazin-1-yl]ethyl}cyclohexyl)acetamide
4-cyano-N-(4-{2-[4-(3,4,5-trifluorophenyl)piperazin-1-yl]ethyl}cyclohexyl)butanamide
N-(4-{2-[4-(3-acetylphenyl)piperazin-1-yl]ethyl}cyclohexyl)-4-cyanobutanamide
2-cyano-N-(4-{2-[4-(2-cyanophenyl)piperazin-1-yl]ethyl}cyclohexyl)acetamide
4-cyano-N-(4-{2-[4-(2-cyanophenyl)piperazin-1-yl]ethyl}cyclohexyl)butanamide
cyclopent-3-enecarboxylic acid (4-{2-[4-(3-ethylphenyl)piperazin-1-yl]ethyl}cyclohexyl)amide
cyclopent-3-enecarboxylic acid {4-[2-(4-m-tolylpiperazin-1-yl)ethyl]cyclohexyl}-cyclopent-1-enecarboxylic acid {4-[2-(4-m-tolylpiperazin-1-yl)ethyl]cyclohexyl}amide
N-(4-{2-[4-(3-chloro-4-methylphenyl)piperazin-1-yl]ethyl}cyclohexyl)-4-cyanobutanamide
4-cyano-N-(4-{2-[4-(2-methoxyphenyl)piperazin-1-yl]ethyl}cyclohexyl)butanamide
cyclopent-1-enecarboxylic acid (4-{2-[4-(2,4-difluorophenyl)piperazin-1-yl]ethyl}cyclohexyl)amide
N-(4-{2-[4-(2,4-difluorophenyl)piperazin-1-yl]ethyl}cyclohexyl)-2-(4-fluorophenoxy)acetamide
N-(4-{2-[4-(2,4-difluorophenyl)piperazin-1-yl]ethyl}cyclohexyl)-3,3,3-trifluoropropanamide
2-cyclopent-3-enyl-N-(4-{2-[4-(2-fluorophenylpiperazin-1-yl]ethyl}cyclohexyl)acetamide
N-(4-{2-[4-(2-chloro-4-fluoro-5-methylphenyl)piperazin-1-yl]ethyl}cyclohexyl)-2-cyanoacetamide
N-(4-{2-[4-(2-chloro-4-fluoro-5-methylphenylpiperazin-1-yl]ethyl}cyclohexyl)-4-cyanobutanamide
4-cyano-N-(4-{2-[4-(5-methoxy-2-methylphenyl)piperazin-1-yl]ethyl}cyclohexyl)butanamide
4-cyano-N-(4-{2-[4-(3,5-dimethoxyphenyl)piperazin-1-yl]ethyl}cyclohexyl)butanamide
N-(4-{2-[4-(3-chloro-2-cyanophenyl)piperazin-1-yl]ethyl}cyclohexyl)-4-cyanobutanamide
cyclohex-1-enecarboxylic acid (4-{2-[4-(3-fluorophenyl)piperazin-1-yl]ethyl}cyclohexylamide
4-cyano-N-(4-{2-[4-(3-fluorophenyl)piperazin-1-yl]ethyl}cyclohexyl)butanamide
N-(4-{2-[4-(3-fluorophenyl)piperazin-1-yl]ethyl}cyclohexyl)-2-phenoxyacetamide
N-(4-{2-[4-(3-fluorophenyl)piperazin-1-yl]ethyl}cyclohexyl)succinamide
N-(4-{2-[4-(3-fluorophenyl)piperazin-1-yl]ethyl}cyclohexyl)succinamide
2-cyano-N-(4-{2-[4-(3,5-dimethylphenyl)-3,6-dihydro-2H-pyridin-1-yl]ethyl}cyclohexyl)acetamide
cyclopent-1-enecarboxylic acid (4-{2-[4-(3-fluorophenyl)piperazin-1-yl]ethyl}cyclohexyl)amide 4-cyano-N-(4-{2-[4-(2,4-difluorophenyl)piperazin-1-yl]
    ethyl}cyclohexyl)butanamide
3-cyano-N-(4-{2-[4-(2,4-difluorophenyl)piperazin-1-yl]
    ethyl}cyclohexyl)propanamide
N-(4-{2-[4-(2-chloro-5-trifluoromethylphenyl)piperazin-1-
    yl]ethyl}cyclohexyl)-4-cyanobutanamide
4-cyano-N-(4-{2-[4-(2-methoxy-5-trifluoromethylphenyl)
    piperazin-1-yl]ethyl}cyclohexyl)butanamide
4-cyano-N-(4-{2-[4-(3,5-dimethylphenyl)-3,6-dihydro-2H-
    pyridin-1-yl]ethyl}cyclohexyl)butanamide
1H-indene-2-carboxylic acid (4-{2-[4-(3-fluorophenyl)pip-
    erazin-1-yl]ethyl}cyclohexyl)amide
cyclopent-3-enecarboxylic acid (4-{2-[4-(3-fluorophenyl)
    piperazin-1-yl]ethyl}cyclohexyl)amide
3,3,3-trifluoro-N-(4-{2-[4-(3-fluorophenyl)piperazin-1-yl]
    ethyl}cyclohexyl)propanamide
3-diethylamino-N-(4-{2-[4-(3-fluorophenyl)piperazin-1-yl]
    ethyl}cyclohexyl)propanamide
3-cyano-N-(4-{2-[4-(3-fluorophenyl)piperazin-1-yl]
    ethyl}cyclohexyl)propanamide
4-cyano-N-(4-{2-[4-(2,5-dimethylphenyl)piperazin-1-yl]
    ethyl}cyclohexyl)butanamide
N-(4-{2-[4-(5-chloro-2-fluorophenyl)piperazin-1-yl]
    ethyl}cyclohexyl)-4-cyanobutanamide
N-(4-{2-[4-(5-chloro-2-methoxyphenyl)piperazin-1-yl]
    ethyl}cyclohexyl)-4-cyanobutanamide
4-cyano-N-(4-{2-[4-(3-methoxyphenyl)piperazin-1-yl]
    ethyl}cyclohexyl)butanamide
cyclopent-1-enecarboxylic acid (4-{2-[4-(3-methoxyphenyl)
    piperazin-1-yl]ethyl}cyclohexyl)amide
3-cyano-N-(4-{2-[4-(3-methoxyphenyl)piperazin-1-yl]
    ethyl}cyclohexyl)propanamide
N-(4-{2-[4-(3-fluorophenyl)piperazin-1-yl]
    ethyl}cyclohexyl)-4-methoxybutanamide
2-cyclopent-2-enyl-N-(4-{2-[4-(3-fluorophenyl)piperazin-
    1-yl]ethyl}cyclohexyl)acetamide
4-cyano-N-(4-{2-[4-(3-methoxy-5-trifluoromethylphenyl)
    piperazin-1-yl]ethyl}cyclohexyl)butanamide
N-(4-{2-[4-(2-ethylphenyl)piperazin-1-yl]
    ethyl}cyclohexyl)-3,3,3-trifluoropropanamide
2-cyano-N-(4-{2-[4-(2,4-dichloro-5-trifluoromethylphenyl)
    piperazin-1-yl]ethyl}cyclohexyl)acetamide
4-cyano-N-(4-{2-[4-(2,4-dichloro-5-trifluoromethylphenyl)
    piperazin-1-yl]ethyl}cyclohexyl)butanamide
N-(4-{2-[4-(3-ethylphenyl)piperazin-1-yl]
    ethyl}cyclohexyl)-2-methanesulfonylacetamide
N-(4-{2-[4-(2,3-difluorophenyl)piperazin-1-yl]
    ethyl}cyclohexyl)-2-methanesulfonylacetamide
N-(4-{2-[4-(4-chlorophenyl)piperazin-1-yl]
    ethyl}cyclohexyl)-2-methanesulfonylacetamide
4-cyano-N-{4-[2-(4-o-tolylpiperazin-1-yl)ethyl]
    cyclohexyl}butanamide
4-cyano-N-(4-{2-[4-(2,3-dimethylphenyl)piperazin-1-yl]
    ethyl}cyclohexyl)butanamide
4-cyano-N-(4-{2-[4-(4-fluoro-3-trifluoromethylphenyl)pip-
    erazin-1-yl]ethyl}cyclohexyl)butanamide
cyclopent-1-enecarboxylic acid (4-{2-[4-(4-fluorophenyl)
    piperazin-1-yl]ethyl}cyclohexyl)amide
4-cyano-N-(4-{2-[4-(3-cyano-5-trifluoromethylphenyl)pip-
    erazin-1-yl]ethyl}cyclohexyl)butanamide
1-(4-{2-[4-(2-chloro-4-fluoro-5-methylphenyl)piperazin-1-
    yl]ethyl}piperidin-1-yl)propan-2-one, dihydrochloride
1-(4-{2-[4-(3-chloro-5-methylphenyl)piperazin-1-yl]
    ethyl}piperidin-1-yl)propan-2-one, dihydrochloride
4-cyano-N-{4-[2-(4-phenyl-3,6-dihydro-2H-pyridin-1-yl)
    ethyl]cyclohexyl}butanamide
4-cyano-N-(4-{2-[4-(2-trifluoromethylphenyl)piperazin-1-
    yl]ethyl}cyclohexyl)butanamide, hydrochloride
N-(4-{2-[4-(3-chloro-5-methylphenyl)piperazin-1-yl]
    ethyl}cyclohexyl)-2-cyanoacetamide
N-(4-{2-[4-(3-chloro-5-methylphenyl)piperazin-1-yl]
    ethyl}cyclohexyl)-4-cyanobutanamide
4-cyano-N-(4-{2-[4-(2-ethoxyphenyl)piperazin-1-yl]
    ethyl}cyclohexyl)butanamide
4-cyano-N-(4-{2-[4-(2-fluoro-5-methylphenyl)piperazin-1-
    yl]ethyl}cyclohexyl)butanamide
cyclopent-1-enecarboxylic acid (4-{2-[4-(2,5-difluorophe-
    nyl)piperazin-1-yl]ethyl}cyclohexyl)amide
4-cyano-N-(4-{2-[4-(2,5-difluorophenyl)piperazin-1-yl]
    ethyl}cyclohexyl)butanamide
2,2-difluoro-N-(4-{2-[4-(2-fluoro-3-trifluoromethylphenyl)
    piperazin-1-yl]ethyl}cyclohexyl)acetamide
4-cyano-N-(4-{2-[4-(2,3-difluorophenyl)piperazin-1-yl]
    ethyl}cyclohexyl)butanamide
N-(4-{2-[4-(2,3-difluorophenyl)piperazin-1-yl]
    ethyl}cyclohexyl)-3,3,3-trifluoropropanamide
cyclopent-1-enecarboxylic acid (4-{2-[4-(2,3-difluorophe-
    nyl)piperazin-1-yl]ethyl}cyclohexyl)amide
4-cyano-N-(4-{2-[4-(3-cyanophenyl)piperazin-1-yl]
    ethyl}cyclohexyl)butanamide
N-(4-{2-[4-(3-chloro-2-methoxyphenyl)piperazin-1-yl]
    ethyl}cyclohexyl)-4-cyanobutanamide
2-cyano-N-(4-{2-[4-(2,3,4-trifluorophenyl)piperazin-1-yl]
    ethyl}cyclohexyl)acetamide
4-cyano-N-(4-{2-[4-(2,3,4-trifluorophenyl)piperazin-1-yl]
    ethyl}cyclohexyl)butanamide
3,3,3-trifluoro-N-(4-{2-[4-(3-methanesulfonylphenyl)piper-
    azin-1-yl]ethyl}cyclohexyl)propanamide
1-(4-{2-[4-(3-fluorophenyl)piperazin-1-yl]ethyl}piperidin-
    1-yl)propan-2-one, dihydrochloride
1-(4-{2-[4-(3-ethoxyphenyl)piperazin-1-yl]ethyl}piperidin-
    1-yl)propan-2-one, dihydrochloride
1-(4-{2-[4-(2,4-difluorophenyl)piperazin-1-yl]
    ethyl}piperidin-1-yl)propan-2-one, dihydrochloride
2-cyano-N-{4-[2-(4-indan-4-ylpiperazin-1-yl)ethyl]
    cyclohexyl}acetamide
4-cyano-N-{4-[2-(4-indan-4-ylpiperazin-1-yl)ethyl]
    cyclohexyl}butanamide
cyclopent-1-enecarboxylic acid (4-{2-[4-(2-fluoro-3-trifluo-
    romethylphenyl)piperazin-1-yl]ethyl}cyclohexyl)amide
N-(4-{2-[4-(2-fluoro-3-trifluoromethylphenyl)piperazin-1-
    yl]ethyl}cyclohexyl)succinamide
4-cyano-2,2-difluoro-N-(4-{2-[4-(2-fluoro-3-trifluorometh-
    ylphenyl)piperazin-1-yl]ethyl}cyclohexyl)butanamide
2,2,2-trifluoro-N-(4-{2-[4-(3-methanesulfonylphenyl)piper-
    azin-1-yl]ethyl}cyclohexyl)acetamide
N-{4-[2-(4-biphenyl-3-ylpiperazin-1-yl)ethyl]cyclo-
    hexyl}-4-cyanobutanamide
cyclopent-1-enecarboxylic acid (4-{2-[4-(3,4,5-trifluo-
    rophenyl)piperazin-1-yl]ethyl}cyclohexyl)amide
2-ethoxy-N-(4-{2-[4-(3,4,5-trifluorophenyl)piperazin-1-yl]
    ethyl}cyclohexyl)acetamide
cyclopent-3-enecarboxylic acid (4-{2-[4-(3,4,5-trifluo-
    rophenyl)piperazin-1-yl]ethyl}cyclohexyl)amide
4-cyano-N-{4-[2-(4-p-tolylpiperazin-1-yl)ethyl]
    cyclohexyl}butanamide
4,4,4-trifluoro-N-(4-{2-[4-(3-methanesulfonylphenyl)piper-
    azin-1-yl]ethyl}cyclohexyl)butanamide
N-(4-{2-[4-(2-fluoro-3-trifluoromethylphenyl)piperazin-1-
    yl]ethyl}cyclohexyl)-4-methoxybutanamide
N-(4-{2-[4-(4-chloro-2-fluorophenyl)piperazin-1-yl]
    ethyl}cyclohexyl)-4-cyanobutanamide 2-cyano-N-(4-{2-[4-(2,4,5-trifluorophenyl)piperazin-1-yl]
ethyl}cyclohexyl)acetamide
4-cyano-N-(4-{2-[4-(2,4,5-trifluorophenyl)piperazin-1-yl]
ethyl}cyclohexyl)butanamide
2-ethoxy-N-{4-[2-(4-p-tolylpiperazin-1-yl)ethyl]
cyclohexyl}acetamide
cyclopent-1-enecarboxylic acid {4-[2-(4-p-tolylpiperazin-1-
yl)ethyl]cyclohexyl}amide
5,6-dihydro-4H-pyran-3-carboxylic acid (4-{2-[4-(2-fluoro-
3-trifluoromethylphenyl)piperazin-1-yl]ethyl}cyclohexyl
amide
3,3,3-trifluoro-N-[4-(2-{4-[3-(1-hydroxyethyl)phenyl]pip-
erazin-1-yl}ethyl)cyclohexyl]propanamide
2-ethoxy-N-(4-{2-[4-(2-fluoro-3-trifluoromethylphenyl)
piperazin-1-yl]ethyl}cyclohexyl)acetamide
N-(4-{2-[4-(4-chlorophenyl)piperazin-1-yl]
ethyl}cyclohexyl)-4-cyanobutanamide
N-(4-{2-[4-(4-chlorophenyl)piperazin-1-yl]
ethyl}cyclohexyl)-3,3,3-trifluoropropanamide
1-(4-{2-[4-(4-chloro-2-fluorophenyl)piperazin-1-yl]
ethyl}piperidin-1-yl)propan-2-one
1-(4-{2-[4-(2-fluoro-4-methylphenyl)piperazin-1-yl]
ethyl}piperidin-1-yl)propan-2-one
4-cyano-N-(4-{2-[4-(2-methoxy-5-methylphenyl)piperazin-
1-yl]ethyl}cyclohexyl)butanamide
2-cyano-N-(4-{2-[4-(2-fluoro-4-methylphenyl)piperazin-1-
yl]ethyl}cyclohexyl)acetamide
4-cyano-N-(4-{2-[4-(2-fluoro-4-methylphenyl)piperazin-1-
yl]ethyl}cyclohexyl)butanamide
cyclopent-1-enecarboxylic acid (4-{2-[4-(3,4-dichlorophe-
nyl)piperazin-1-yl]ethyl}cyclohexyl)amide
N-(4-{2-[4-(3,4-dichlorophenyl)piperazin-1-yl]
ethyl}cyclohexyl)-2-ethoxyacetamide
cyclopent-1-enecarboxylic acid (4-{2-[4-(4-chlorophenyl)
piperazin-1-yl]ethyl}cyclohexyl)amide
N-(4-{2-[4-(3-chloro-4-methylphenyl)piperazin-1-yl]
ethyl}cyclohexyl)-2-ethoxyacetamide
cyclopent-1-enecarboxylic acid (4-{2-[4-(3-chloro-4-meth-
ylphenyl)piperazin-1-yl]ethyl}cyclohexyl)amide
N-(4-{2-[4-(3-chloro-4-methylphenyl)piperazin-1-yl]
ethyl}cyclohexyl)-3,3,3-trifluoropropanamide
3,3,3-trifluoro-N-{4-[2-(4-p-tolylpiperazin-1-yl)ethyl]
cyclohexyl}propanamide
cyclopent-3-enecarboxylic acid (4-{2-[4-(2,4-difluorophe-
nyl)piperazin-1-yl]ethyl}cyclohexyl)amide
1-(4-{2-[4-(3,4-dichlorophenyl)piperazin-1-yl]
ethyl}piperidin-1-yl)propan-2-one
1-(4-{2-[4-(4-fluorophenyl)piperazin-1-yl]ethyl}piperidin-
1-yl)propan-2-one
4,5-dihydrofuran-3-carboxylic acid (4-{2-[4-(2-fluoro-3-tri-
fluoromethylphenyl)piperazin-1-yl]ethyl}cyclohexyl)
amide
N-(4-{2-[4-(4-chlorophenyl)-3,6-dihydro-2H-pyridin-1-yl]
ethyl}cyclohexyl)-2-ethoxyacetamide
N-(4-{2-[4-(4-chlorophenyl)-3,6-dihydro-2H-pyridin-1-yl]
ethyl}cyclohexyl)-4-cyanobutanamide
4-cyano-N-(4-{2-[4-(4-fluorophenyl)-3,6-dihydro-2H-pyri-
din-1-yl]ethyl}cyclohexyl)butanamide
pyrrolidine-2-carboxylic acid (4-{2-[4-(2-fluoro-3-trifluo-
romethylphenyl)piperazin-1-yl]ethyl}cyclohexyl)amide
N-(4-{2-[4-(3,4-dichlorophenyl)piperazin-1-yl]
ethyl}cyclohexyl)-4-methoxybutanamide
N-(4-{2-[4-(2,4-difluorophenyl)piperazin-1-yl]
ethyl}cyclohexyl)-2-ethoxyacetamide
N-(4-{2-[4-(2,4-difluorophenyl)piperazin-1-yl]
ethyl}cyclohexyl)-4-methoxybutanamide
4-cyano-N-(4-{2-[4-(3,4-dimethylphenyl)piperazin-1-yl]
ethyl}cyclohexyl)butanamide
N-(4-{2-[4-(3,4-dimethylphenyl)piperazin-1-yl]
ethyl}cyclohexyl)-4-methoxybutanamide
cyclopent-1-enecarboxylic acid (4-{2-[4-(3,4-dimethylphe-
nyl)piperazin-1-yl]ethyl}cyclohexyl)amide
N-(4-{2-[4-(3,4-dimethylphenyl)piperazin-1-yl]
ethyl}cyclohexyl)-2-ethoxyacetamide
N-(4-{2-[4-(3,4-dimethylphenyl)piperazin-1-yl]
ethyl}cyclohexyl)-3,3,3-trifluoropropanamide
4-cyano-N-(4-{2-[4-(5,6,7,8-tetrahydronaphthalen-2-yl)
piperazin-1-yl]ethyl}cyclohexyl)butanamide
N-(4-{2-[4-(3-cyanophenyl)piperazin-1-yl]
ethyl}cyclohexyl)-3,3,3-trifluoropropanamide
cyclopent-1-enecarboxylic acid (4-{2-[4-(3-cyanophenyl)
piperazin-1-yl]ethyl}cyclohexyl)amide
N-(4-{2-[4-(3-cyanophenyl)piperazin-1-yl]
ethyl}cyclohexyl)-4-methoxybutanamide
2-ethoxy-N-(4-{2-[4-(2-fluoro-5-trifluoromethylphenyl)
piperazin-1-yl]ethyl}cyclohexyl)acetamide
N-(4-{2-[4-(4-chloro-phenyl)piperazin-1-yl]ethyl}-cyclo-
hexyl)-2-ethoxyacetamide
N-(4-{2-[4-(2-fluoro-3-trifluoromethylphenyl)piperazin-1-
yl]ethyl}cyclohexyl)-2-propoxyacetamide
cyclopent-1-enecarboxylic acid (4-{2-[4-(4-chloro-2-fluo-
rophenyl)piperazin-1-yl]ethyl}cyclohexyl)amide
cyclopent-1-enecarboxylic acid (4-{2-[4-(2-fluoro-4-meth-
ylphenyl)piperazin-1-yl]ethyl}cyclohexyl)amide
2-cyano-N-(4-{2-[4-(3,4-dichloro-2-fluorophenyl)piper-
azin-1-yl]ethyl}cyclohexyl)acetamide
4-cyano-N-(4-{2-[4-(3,4-dichloro-2-fluorophenyl)piper-
azin-1-yl]ethyl}cyclohexyl)butanamide
N-(4-{2-[4-(2,5-dichlorophenyl)piperazin-1-yl]
ethyl}cyclohexyl)-2-ethoxyacetamide
4-cyano-N-(4-{2-[4-(2-cyano-3-fluorophenyl)piperazin-1-
yl]ethyl}cyclohexyl)butanamide
cyclopent-1-enecarboxylic acid (4-{2-[4-(2,4,5-trifluo-
rophenyl)piperazin-1-yl]ethyl}cyclohexyl)amide
4,5-dihydrofuran-3-carboxylic acid (4-{2-[4-(3-cyanophe-
nyl)piperazin-1-yl]ethyl}cyclohexyl)amide
cyclopent-1-enecarboxylic acid (4-{2-[4-(5-chloro-2-fluo-
rophenyl)piperazin-1-yl]ethyl}cyclohexyl)amide
4-cyano-N-(4-{2-[4-(3-oxazol-2-ylphenyl)piperazin-1-yl]
ethyl}cyclohexyl)butanamide
4,5-dihydrofuran-3-carboxylic acid (4-{2-[4-(2,4-difluo-
rophenyl)piperazin-1-yl]ethyl}cyclohexyl)amide
N-(4-{2-[4-(3-chloro-5-trifluoromethylphenyl)piperazin-1-
yl]ethyl}cyclohexyl)-2-cyanoacetamide
N-(4-{2-[4-(3-chloro-5-trifluoromethylphenyl)piperazin-1-
yl]ethyl}cyclohexyl)-4-cyanobutanamide
2-cyano-N-(4-{2-[4-(3-oxazol-2-ylphenyl)piperazin-1-yl]
ethyl}cyclohexyl)acetamide
2-ethoxy-N-(4-{2-[4-(4-fluorophenyl)-3,6-dihydro-2H-py-
ridin-1-yl]ethyl}cyclohexyl)acetamide
4,5-dihydrofuran-3-carboxylic acid(4-{2-[4-(3-oxazol-2-
ylphenyl)piperazin-1-yl]ethyl}cyclohexyl)amide
(4-{2-[4-(2,3-dimethylphenyl)piperazin-1-yl]
ethyl}piperidin-1-yl)acetic acid ethyl ester
cyclopent-1-enecarboxylic acid (4-{2-[4-(2-fluoro-5-meth-
ylphenyl)piperazin-1-yl]ethyl}cyclohexyl)amide
4-cyano-N-(4-{2-[4-(3-ethoxyphenyl)piperazin-1-yl]
ethyl}cyclohexyl)butanamide
cyclopent-1-enecarboxylic acid {4-[2-(4-phenyl-3,6-dihy-
dro-2H-pyridin-1-yl)ethyl]cyclohexyl}amide
cyclopent-1-enecarboxylic acid (4-{2-[4-(3-fluoro-4-meth-
ylphenyl)piperazin-1-yl]ethyl}cyclohexyl)amide 4-cyano-N-(4-{2-[4-(3-fluoro-4-methylphenyl)piperazin-1-yl]ethyl}cyclohexyl)butanamide
2-ethoxy-N-(4-{2-[4-(3-fluoro-4-methylphenyl)piperazin-1-yl]ethyl}cyclohexyl)acetamide
4-cyano-N-[4-(2-{4-[3-(1-hydroxypropyl)phenyl]piperazin-1-yl}ethyl)cyclohexyl]butanamide
pyrrolidine-2-carboxylic acid (4-{2-[4-(3-cyanophenyl)piperazin-1-yl]ethyl}cyclohexyl)amide, dihydrochloride
2-methoxy-N-(4-{2-[4-(3,4,5-trifluorophenyl)piperazin-1-yl]ethyl}cyclohexyl)acetamide
cyclopent-1-enecarboxylic acid (4-{2-[4-(2,3,4-trifluorophenylpiperazin-1-yl]ethyl}cyclohexyl)amide
4-cyano-N-(4-{2-[4-(4-trifluoromethylphenyl)piperazin-1-yl]ethyl}cyclohexyl)butanamide
N-(4-{2-[4-(2,5-dichlorophenyl)piperazin-1-yl]ethyl}cyclohexyl)-2-ethoxyacetamide
pyrrolidine-2-carboxylic acid (4-{2-[4-(2-fluoro-5-trifluoromethylphenyl)piperazin-1-yl]ethyl}cyclohexyl)amide
N-(4-{2-[4-(3-chloro-2-methylphenyl)piperazin-1-yl]ethyl}cyclohexyl)-4-methoxybutanamide
1-(4-{2-[4-(3,4-dimethylphenyl)piperazin-1-yl]ethyl}piperidin-1-yl)propan-2-one
1-(4-{2-[4-(3,4-dichloro-2-fluorophenyl)piperazin-1-yl]ethyl}piperidin-1-yl)propan-2-one
pyrrolidine-2-carboxylic acid (4-{2-[4-(2,4-difluorophenyl)piperazin-1-yl]ethyl}cyclohexyl)amide, dihydrochloride
N-(4-{2-[4-(3-chloro-2,4-difluorophenyl)piperazin-1-yl]ethyl}cyclohexyl)-2-cyanoacetamide
N-(4-{2-[4-(3-chloro-2,4-difluorophenyl)piperazin-1-yl]ethyl}cyclohexyl)-4-cyanobutanamide
1-(4-{2-[4-(2-fluoro-5-trifluoromethylphenyl)piperazin-1-yl]ethyl}piperidin-1-yl)propan-2-one, dihydrochloride
1-(4-{2-[4-(3-chloro-2-methoxyphenyl)piperazin-1-yl]ethyl}piperidin-1-yl)propan-2-one, dihydrochloride
2-cyano-N-(4-{2-[4-(4-trifluoromethylphenyl)-3,6-dihydro-2H-pyridin-1-yl]ethyl}cyclohexyl)acetamide
cyclopent-1-enecarboxylic acid {4-[2-(4-o-tolylpiperazin-1-yl)ethyl]cyclohexyl}amide
2-ethoxy-N-{4-[2-(4-o-tolylpiperazin-1-ylethyl]cyclohexyl}acetamide
4-cyano-N-{4-[2-(6-cyano-3,4-dihydro-1H-isoquinolin-2-yl)ethyl]cyclohexyl}butanamide
2-cyano-N-{4-[2-(6-cyano-3,4-dihydro-1H-isoquinolin-2-yl)ethyl]cyclohexyl}acetamide
N-(4-{2-[4-(3-ethylphenyl)piperazin-1-yl]ethyl}cyclohexyl)-4-methoxybutanamide
5,6-dihydro-4H-pyran-2-carboxylic acid (4-{2-[4-(3-ethylphenyl)piperazin-1-yl]ethyl}cyclohexyl)amide
5,6-dihydro-4H-pyran-2-carboxylic acid (4-{2-[4-(3-trifluoromethylphenyl)piperazin-1-yl]ethyl}cyclohexyl)amide
2-ethoxy-N-(4-{2-[4-(3-ethylphenyl)piperazin-1-yl]ethyl}cyclohexyl)acetamide
4,5-dihydrofuran-3-carboxylic acid (4-{2-[4-(3-trifluoromethylphenyl)piperazin-1-yl]ethyl}cyclohexyl)amide
5,6-dihydro-4H-pyran-2-carboxylic acid (4-{2-[4-(2,4-difluorophenyl)piperazin-1-yl]ethyl}cyclohexyl)amide
2-cyano-N-[4-(2-{4-[3-(1-hydroxypropyl)phenyl]piperazin-1-yl}ethyl)cyclohexyl]acetamide
cyclopent-1-enecarboxylic acid (4-{2-[4-(2,4-difluorophenyl)-3,6-dihydro-2H-pyridin-1-yl]ethyl}cyclohexyl)amide
4-methoxy-N-(4-{2-[4-(3,4,5-trifluorophenyl)piperazin-1-yl]ethyl}cyclohexyl)butanamide
1-{4-[2-(4-indan-5-ylpiperazin-1-yl)ethyl]piperidin-1-yl}propan-2-one, dihydrochloride
4-cyano-N-(4-{2-[4-(4-trifluoromethylphenyl)-3,6-dihydro-2H-pyridin-1-yl]ethyl}cyclohexyl)butanamide
cyclopent-1-enecarboxylic acid (4-{2-[4-(4-methoxyphenyl)piperazin-1-yl]ethyl}cyclohexyl)amide
2-ethoxy-N-(4-{2-[4-(4-methoxyphenyl)piperazin-1-yl]ethyl}cyclohexyl)acetamide
2-cyano-N-(4-{2-[4-(4-methoxyphenyl)piperazin-1-yl]ethyl}cyclohexyl)acetamide
2-cyano-N-(4-{2-[4-(3,5-difluoro-4-trifluoromethylphenyl)piperazin-1-yl]ethyl}cyclohexyl)acetamide
2-cyano-N-[4-(2-{4-[3-(1-hydroxy-2-methylpropyl)phenyl]piperazin-1-yl}ethyl)cyclohexyl]acetamide
1-(4-{2-[4-(5,6,7,8-tetrahydro-naphthalen-2-yl)piperazin-1-yl]ethyl}piperidin-1-yl)propan-2-one
N-(4-{2-[4-(3-chloro-5-methylphenyl)piperazin-1-yl]ethyl}cyclohexyl)-2-ethoxyacetamide
N-(4-{2-[4-(3-chloro-5-methylphenyl)piperazin-1-yl]ethyl}cyclohexyl)-4-methoxybutanamide
N-(4-{2-[4-(2-chloro-4-fluoro-5-methylphenyl)piperazin-1-yl]ethyl}cyclohexyl)-2-ethoxyacetamide
N-(4-{2-[4-(2-chloro-4-fluoro-5-methylphenyl)piperazin-1-yl]ethyl}cyclohexyl)-4-methoxybutanamide
1-(4-{2-[4-(3-chloro-5-fluorophenyl)piperazin-1-yl]ethyl}piperidin-1-yl)propan-2-one
4-cyano-N-(4-{2-[4-(4-methoxyphenyl)piperazin-1-yl]ethyl}cyclohexyl)butanamide
1-(4-{2-[4-(3,4-dihydro-2H-benzo[b][1,4]dioxepin-6-yl)piperazin-1-yl]ethyl}piperidin-1-yl)propan-2-one, dihydrochloride
1-{4-[2-(4-benzo[1,3]dioxol-5-ylpiperazin-1-yl)ethyl]piperidin-1-yl}propan-2-one
cyclopent-1-enecarboxylic acid (4-{2-[4-(2-fluorophenyl)-3,6-dihydro-2H-pyridin-1-yl]ethyl}cyclohexyl)amide
2-cyano-N-(4-{2-[4-(2-fluoro-5-trifluoromethylphenyl)piperazin-1-yl]ethyl}cyclohexyl)acetamide
1-(4-{2-[4-(4-trifluoromethylphenyl)piperazin-1-yl]ethyl}piperidin-1-yl)propan-2-one
1-(4-{2-[4-(3-trifluoromethylsulfanylphenyl)piperazin-1-yl]ethyl}piperidin-1-yl)propan-2-one
1-[4-(2-{4-[3-(1,1-difluoroethyl)phenyl]piperazin-1-yl}ethyl)piperidin-1-yl]propan-2-one, dihydrochloride
1-(4-{2-[4-(3-difluoromethylphenyl)piperazin-1-yl]ethyl}piperidin-1-yl)propan-2-one, dihydrochloride
1-{4-[2-(4-benzo[1,3]dioxol-4-ylpiperazin-1-yl)ethyl]piperidin-1-yl}propan-2-one, dihydrochloride
1-(4-{2-[4-(3-chloro-4-fluorophenyl)piperazin-1-yl]ethyl}piperidin-1-yl)propan-2-one
4-cyano-N-(4-{2-[4-(3-trifluoromethylphenyl)-3,6-dihydro-2H-pyridin-1-yl]ethyl}cyclohexyl)butanamide
N-(4-{2-[4-(3-chloro-4-fluorophenyl)piperazin-1-yl]ethyl}cyclohexyl)-2-cyanoacetamide
1-(4-{2-[4-(4-chlorophenyl)-3,6-dihydro-2H-pyridin-1-yl]ethyl}piperidin-1-yl)propan-2-one
4-(4-{2-[1-(2-oxopropyl)piperidin-4-yl]ethyl}piperazin-1-yl)-benzonitrile, dihydrochloride
1-(4-{2-[4-(2-fluoro-5-methylphenyl)piperazin-1-yl]ethyl}piperidin-1-yl)propan-2-one, dihydrochloride
N-(4-{2-[4-(3-chloro-4-fluorophenyl)piperazin-1-yl]ethyl}cyclohexyl)-4-cyanobutanamide
N-(4-{2-[4-(2-chloro-5-cyanophenyl)piperazin-1-yl]ethyl}cyclohexyl)-2-cyanoacetamide
1-(4-{2-[4-(2,6-di-tert-butylpyrimidin-4-yl)piperazin-1-yl]ethyl}piperidin-1-yl)propan-2-one, dihydrochloride
N-(4-{2-[4-(2-chloro-5-cyanophenyl)piperazin-1-yl]ethyl}cyclohexyl)-4-cyanobutanamide
N-(4-{2-[4-(3-chloro-2,4-difluorophenyl)piperazin-1-yl]ethyl}cyclohexyl)succinamide
1-(4-{2-[4-(3-acetylphenyl)piperazin-1-yl]ethyl}piperidin-1-yl)propan-2-one 1-[3-(4-{2-[1-(2-oxopropyl)piperidin-4-yl]ethyl}piperazin-1-yl)phenyl]propan-1-one
2-methyl-1-[3-(4-{2-[1-(2-oxopropyl)piperidin-4-yl]ethyl}piperazin-1-yl)phenyl]propan-1-one, dihydrochloride
1-[4-(2-{4-[3-(1-Hydroxyethyl)phenyl]piperazin-1-yl}ethyl)piperidin-1-yl]propan-2-one
1-[4-(2-{4-[3-(1-Hydroxypropyl)phenyl]piperazin-1-yl}ethyl)piperidin-1-yl]propan-2-one
1-[4-(2-{4-[3-(1-Hydroxy-2-methylpropyl)phenyl]piperazin-1-yl}ethyl)piperidin-1-yl]propan-2-one
3-{4-[2-(4-indan-4-ylpiperazin-1-yl)ethyl]piperidin-1-yl}-3-oxopropanenitrile, hydrochloride
1-{4-[2-(4-indan-4-ylpiperazin-1-yl)ethyl]piperidin-1-yl}propane-1,2-dione, hydrochloride
1-(4-{2-[4-(2,3-dichlorophenyl)piperazin-1-yl]ethyl}piperidin-1-yl)propane-1,2-dione, hydrochloride
3-(4-{2-[4-(2,3-dichlorophenyl)piperazin-1-yl]ethyl}piperidin-1-yl)-3-oxopropanenitrile, hydrochloride
2-cyano-N-(4-{2-[4-(4-trifluoromethylphenyl)piperazin-1-yl]ethyl}cyclohexyl)acetamide
1-(4-{2-[4-(2-ethoxyphenyl)piperazin-1-yl]ethyl}piperidin-1-yl)propan-2-one, dihydrochloride
1-(4-{2-[4-(4-fluorophenyl)-3,6-dihydro-2H-pyridin-1-yl]ethyl}piperidin-1-yl)propan-2-one
N-(4-{2-[4-(2-fluoro-5-trifluoromethylphenyl)piperazin-1-yl]ethyl}cyclohexyl)-4-methoxybutanamide
1-(4-{2-[4-(2,5-dichlorophenyl)piperazin-1-yl]ethyl}piperidin-1-yl)propan-2-one, dihydrochloride
1-(4-{2-[4-(3-chloro-4-methylphenyl)piperazin-1-yl]ethyl}piperidin-1-yl)propan-2-one
1-{4-[2-(4-indan-4-yl-3,6-dihydro-2H-pyridin-1-yl)ethyl]piperidin-1-yl}propan-2-one, dihydrochloride
4-{4-[2-(4-indan-4-ylpiperazin-1-yl)ethyl]piperidin-1-yl}-4-oxobutanamide
1-{4-[2-(4-indan-4-ylpiperazin-1-yl)ethyl]piperidin-1-ylbutane-1,2-dione, hydrochloride
1-(4-{2-[4-(3-methanesulfonylphenyl)piperazin-1-yl]ethyl}piperidin-1-yl)propan-2-one, dihydrochloride
1-(4-{2-[4-(3-chloro-2,4-difluorophenyl)piperazin-1-yl]ethyl}piperidin-1-yl)propan-2-one
1-{4-[2-(4-phenyl-3,6-dihydro-2H-pyridin-1-yl)ethyl]piperidin-1-yl}propan-2-one
2-cyano-N-(4-{2-[4-(3,5-dimethylphenyl)-3,6-dihydro-2H-pyridin-1-yl]ethyl}cyclohexyl)acetamide, hydrochloride
1-(4-{2-[4-(3-fluoro-4-methylphenyl)piperazin-1-yl]ethyl}piperidin-1-yl)propan-2-one, dihydrochloride
2-{2-[1-(2-oxopropyl)piperidin-4-yl]ethyl}-1,2,3,4-tetrahydroisoquinoline-6-carbonitrile, dihydrochloride
1-(4-{2-[4-(4-chloro-3-trifluoromethylphenyl)piperazin-1-yl]ethyl}piperidin-1-yl)propan-2-one, dihydrochloride
1-{4-[2-(4-biphenyl-3-ylpiperazin-1-yl)ethyl]piperidin-1-yl}propan-2-one, dihydrochloride
1-(4-{2-[4-(4-fluoro-2-methylphenyl)piperazin-1-yl]ethyl}piperidin-1-yl)propan-2-one, dihydrochloride
N-(4-{2-[4-(2-fluoro-5-trifluoromethylphenyl)piperazin-1-yl]ethyl}cyclohexyl)succinamide
1-(4-{2-[4-(2,5-dimethoxyphenyl)piperazin-1-yl]ethyl}piperidin-1-yl)propan-2-one, dihydrochloride
1-{4-[2-(4-indan-4-ylpiperidin-1-yl)ethyl]piperidin-1-yl}propan-2-one, dihydrochloride
1-(4-{2-[4-(4-fluorophenyl)piperidin-1-yl]ethyl}piperidin-1-yl)propan-2-one, dihydrochloride
1-(4-{2-[4-(2-methoxy-5-trifluoromethylphenyl)piperazin-1-yl]ethyl}piperidin-1-yl)propan-2-one, dihydrochloride
1-{4-[2-(4-indan-4-ylpiperazin-1-yl)ethyl]piperidin-1-yl}pentan-2-one, dihydrochloride
1-(4-{2-[4-(4-fluoro-3-trifluoromethylphenyl)piperazin-1-yl]ethyl}piperidin-1-yl)propan-2-one, dihydrochloride
1-(4-{2-[4-(2,6-dimethylphenyl)piperazin-1-yl]ethyl}piperidin-1-yl)propan-2-one, dihydrochloride
1-(4-{2-[4-(2-chloro-5-methoxyphenylpiperazin-1-yl]ethyl}piperidin-1-yl)propan-2-one, dihydrochloride
1-(4-{2-[4-(3-Hydroxymethylphenyl)piperazin-1-yl]ethyl}piperidin-1-yl)propan-2-one
1-(4-{2-[4-(6,7,8,9-tetrahydro-5H-benzocyclohepten-1-yl)piperazin-1-yl]ethyl}piperidin-1-yl)propan-2-one, dihydrochloride
1-(4-{2-[4-(6,7,8,9-tetrahydro-5H-benzocyclohepten-2-yl)piperazin-1-yl]ethyl}piperidin-1-yl)propan-2-one
3-cyano-N-(4-{2-[4-(4-trifluoromethylphenyl)piperazin-1-yl]ethyl}cyclohexyl)propanamide
3-cyano-N-(4-{2-[4-(3-cyanophenyl)piperazin-1-yl]ethyl}cyclohexyl)propanamide
2-cyano-N-(4-{2-[4-(2-fluoro-4-trifluoromethylphenyl)piperazin-1-yl]ethyl}cyclohexyl)acetamide
4-cyano-N-(4-{2-[4-(2-fluoro-4-trifluoromethylphenyl)piperazin-1-yl]ethyl}cyclohexyl)-butanamide
1-(4-{2-[4-(2-methoxy-5-methylphenyl)piperazin-1-yl]ethyl}piperidin-1-yl)propan-2-one, dihyrochloride
1-(4-{2-[4-(3-chloro-5-trifluoromethylphenyl)piperazin-1-yl]ethyl}piperidin-1-yl)propan-2-one, dihyrochloride
4-{4-[2-(4-indan-4-ylpiperazin-1-yl)ethyl]piperidin-1-yl}-4-oxo-butanonitrile
1-(4-{2-[4-(3-fluoro-5-trifluoromethylphenyl)piperazin-1-yl]ethyl}piperidin-1-yl)propan-2-one
1-(4-{2-[4-(2-fluoro-5-trifluoromethylphenyl)-3,6-dihydro-2H-pyridin-1-yl]ethyl}piperidin-1-yl)propan-2-one, dihyrochloride
4-methoxy-N-(4-{2-[4-(2,3,4-trifluorophenyl)piperazin-1-yl]ethyl}cyclohexyl)butanamide
N-(4-{2-[4-(3-cyanophenyl)piperazin-1-yl]ethyl}cyclohexyl)-4,4,4-trifluorobutanamide
N-(4-{2-[4-(3-cyanophenyl)piperazin-1-yl]ethyl}cyclohexyl)-3-methoxypropanamide
2-cyano-N-(4-{2-[4-(2-fluoro-5-trifluoromethylphenyl)-3,6-dihydro-2H-pyridin-1-yl]ethyl}cyclohexyl)acetamide
1-(4-{2-[4-(2,3,4-trifluorophenyl)piperazin-1-yl]ethyl}piperidin-1-yl)propan-2-one
1-(4-{2-[4-(3-phenoxyphenyl)piperazin-1-yl]ethyl}piperidin-1-yl)propan-2-one, dihyrochloride
1-(4-{2-[4-(3-isopropoxyphenyl)piperazin-1-yl]ethyl}piperidin-1-yl)propan-2-one, dihyrochloride
2-fluoro-5-(4-{2-[1-(2-oxopropyl)piperidin-4-yl]ethyl}piperazin-1-yl)benzonitrile
2-cyano-N-(4-{2-[4-(3-cyano-4-fluorophenyl)piperazin-1-yl]ethyl}cyclohexyl)acetamide
N-(4-{2-[4-(3-cyano-4-fluorophenyl)piperazin-1-yl]ethyl}cyclohexyl)-4-methoxybutanamide
4-cyano-N-(4-{2-[4-(3-cyano-4-fluorophenyl)piperazin-1-yl]ethyl}cyclohexyl)butanamide
1-(4-{2-[4-(2,5-difluorophenyl)piperazin-1-yl]ethyl}piperidin-1-yl)propan-2-one
2-cyano-N-(4-{2-[4-(3-fluoro-5-trifluoromethylphenyl)piperazin-1-yl]ethyl}cyclohexyl)acetamide
4-cyano-N-(4-{2-[4-(3-fluoro-5-trifluoromethylphenyl)piperazin-1-yl]ethyl}cyclohexyl)butanamide
1-(4-{2-[4-(3-tert-butylphenyl)piperazin-1-yl]ethyl}piperidin-1-yl)propan-2-one, dihydrochloride
1-(4-{2-[4-(2-trifluoromethylphenyl)piperazin-1-yl]ethyl}piperidin-1-yl)propan-2-one, dihydrochloride
3-cyano-N-(4-{2-[4-(2-fluoro-5-trifluoromethylphenyl)piperazin-1-yl]ethyl}cyclohexyl)propanamide N-(4-{2-[4-(2-fluoro-5-trifluoromethylphenyl)piperazin-1-yl]ethyl}cyclohexyl)-2-propoxyacetamide, hydrochloride
3,3,3-trifluoro-N-(4-{2-[4-(2-fluoro-5-trifluoromethylphenyl)piperazin-1-yl]ethyl}cyclohexyl)propanamide
N-(4-{2-[4-(2-fluoro-5-trifluoromethylphenyl)piperazin-1-yl]ethyl}cyclohexyl)malonamide
1-(4-{2-[4-(3-benzylphenyl)piperazin-1-yl]ethyl}piperidin-1-yl)propan-2-one, dihydrochloride
2-cyano-N-(4-{2-[4-(5-ethyl-2-fluorophenyl)piperazin-1-yl]ethyl}cyclohexyl)acetamide
4-cyano-N-(4-{2-[4-(5-ethyl-2-fluorophenyl)piperazin-1-yl]ethyl}cyclohexyl)butanamide
4-methoxy-N-{4-[2-(4-m-tolylpiperazin-1-yl)ethyl]cyclohexyl}butanamide
1-(4-{2-[4-(3,4-difluorophenyl)piperazin-1-yl]ethyl}piperidin-1-yl)propan-2-one, dihydrochloride
1-(4-{2-[4-(4-chlorophenyl)piperazin-1-yl]ethyl}piperidin-1-yl)propan-2-one, dihydrochloride
1-(4-{2-[4-(3-isopropylphenyl)piperazin-1-yl]ethyl}piperidin-1-yl)propan-2-one, dihydrochloride
5-{4-[2-(4-indan-4-ylpiperazin-1-yl)ethyl]piperidin-1-yl}-5-oxo-pentanenitrile, hydrochloride
2-ethoxy-1-{4-[2-(4-indan-4-ylpiperazin-1-yl)ethyl]piperidin-1-yl}ethanone, hydrochloride
3-(1-{2-[1-(2-oxopropyl)piperidin-4-yl]ethyl}-1,2,3,6-tetrahydropyridin-4-yl)benzonitrile
2-cyano-N-(4-{2-[4-(3-cyanophenyl)-3,6-dihydro-2H-pyridin-1-yl]ethyl}cyclohexyl)acetamide
N-(4-{2-[4-(3-cyanophenyl)-3,6-dihydro-2H-pyridin-1-yl]ethyl}cyclohexyl)-4-methoxybutanamide
N-(4-{2-[4-(3,4-dichloro-2-fluoro-phenyl)piperazin-1-yl]ethyl}cyclohexyl)-4-methoxybutanamide
1-(4-{2-[4-(5-chloro-2-fluorophenyl)piperazin-1-yl]ethyl}piperidin-1-yl)propan-2-one, dihydrochloride
1-(4-{2-[4-(3-methylsulfanylphenyl)piperazin-1-yl]ethyl}piperidin-1-yl)propan-2-one
2-cyano-N-(4-{2-[4-(3-cyano-2,4-difluorophenyl)piperazin-1-yl]ethyl}cyclohexyl)acetamide
4-cyano-N-(4-{2-[4-(3-cyano-2,4-difluorophenyl)piperazin-1-yl]ethyl}cyclohexyl)butanamide
N-(4-{2-[4-(3-fluoro-2-methylphenyl)piperazin-1-yl]ethyl}cyclohexyl)-4-methoxybutanamide
2,6-difluoro-3-(4-{2-[1-(2-oxo-propyl)piperidin-4-yl]ethyl}piperazin-1-yl)benzonitrile
N-(4-{2-[4-(3,5-dichlorophenyl)piperazin-1-yl]ethyl}cyclohexyl)-4-methoxybutanamide
N-(4-{2-[4-(3-cyano-2,4-difluorophenyl)piperazin-1-yl]ethyl}cyclohexyl)-4-methoxybutanamide
4-(4-{2-[4-(3-fluoro-5-trifluoromethylphenyl)piperazin-1-yl]ethyl}piperidin-1-yl)-4-oxobutanonitrile
1-(4-{2-[4-(3-methoxymethylphenyl)piperazin-1-yl]ethyl}piperidin-1-yl)propan-2-one, dihydrochloride
1-(4-{2-[4-(2,3,4,5-tetrafluorophenyl)piperazin-1-yl]ethyl}piperidin-1-yl)propan-2-one, dihydrochloride
1-(4-{2-[4-(2-chloro-5-trifluoromethylphenyl)piperazin-1-yl]ethyl}piperidin-1-yl)propan-2-one, dihydrochloride
1-(4-{2-[4-(3,4,5-trifluorophenyl)piperazin-1-yl]ethyl}piperidin-1-yl)propan-2-one
N-(4-{2-[4-(4-chlorophenyl)piperazin-1-yl]ethyl}cyclohexyl)-4-methoxybutanamide
1-(4-{2-[4-(2-tert-butyl-6-trifluoromethylpyrimidin-4-yl)piperazin-1-yl]ethyl}piperidin-1-yl)propan-2-one, trihydrochloride
N-(4-{2-[4-(2-fluoro-5-trifluoromethylphenyl)piperazin-1-yl]ethyl}cyclohexyl)-2-methoxyacetamide
1-(4-{2-[4-(2,4-dichlorophenyl)piperazin-1-yl]ethyl}piperidin-1-yl)propan-2-one, dihydrochloride
1-(4-{2-[4-(2,4,5-trichlorophenyl)piperazin-1-yl]ethyl}piperidin-1-yl)propan-2-one, dihydrochloride
4-(4-{2-[4-(3-chloro-5-trifluoromethylphenyl)piperazin-1-yl]ethyl}piperidin-1-yl)-4-oxobutanonitrile, hydrochloride
cyclopent-1-enecarboxylic acid (4-{2-[4-(2-fluoro-5-trifluoromethylphenylpiperazin-1-yl]ethyl}cyclohexyl)amide
N-(4-{2-[4-(2-fluoro-5-trifluoromethylphenyl)piperazin-1-yl]ethyl}cyclohexyl)-2-methanesulfonylacetamide
N-(4-{2-[4-(2-fluoro-4-methylphenyl)piperazin-1-yl]ethyl}cyclohexyl)-4-methoxybutanamide
2-cyano-N-(4-{2-[4-(2,3,4,5-tetrafluorophenyl)piperazin-1-yl]ethyl}cyclohexyl)acetamide
2-cyano-N-(4-{2-[4-(2,4-dichlorophenyl)piperazin-1-yl]ethyl}cyclohexyl)acetamide
1-(4-{2-[4-(5-chloro-2-methylphenyl)piperazin-1-yl]ethyl}piperidin-1-yl)propan-2-one, dihydrochloride
1-(4-{2-[4-(2,3-dihydrobenzo[1,4]dioxin-6-yl)piperazin-1-yl]ethyl}piperidin-1-yl)propan-2-one
4-cyano-N-(4-{2-[4-(2-fluoro-5-trifluoromethylphenyl)-3,6-dihydro-2H-pyridin-1-yl]ethyl}cyclohexyl)butanamide
N-(4-{2-[4-(2-fluoro-5-trifluoromethylphenyl)-3,6-dihydro-2H-pyridin-1-yl]ethyl}cyclohexyl)-4-methoxybutanamide
1-(4-{2-[4-(2,5-dimethylphenyl)piperazin-1-yl]ethyl}piperidin-1-yl)propan-2-one, dihydrochloride
N-(4-{2-[4-(3,5-dimethylphenyl)piperazin-1-yl]ethyl}cyclohexyl)-4-methoxybutanamide
3-cyano-N-(4-{2-[4-(3,5-dimethylphenyl)piperazin-1-yl]ethyl}cyclohexyl)propanamide
2-cyano-N-(4-{2-[4-(2,4,5-trichlorophenyl)piperazin-1-yl]ethyl}cyclohexyl)acetamide
1-(4-{2-[4-(3-fluoro-5-methylphenyl)piperazin-1-yl]ethyl}piperidin-1-yl)propan-2-one, dihydrochloride
N-(4-{2-[4-(3,4-dichloro-2-fluorophenyl)piperazin-1-yl]ethyl}cyclohexyl)-2-methoxyacetamide
3-cyano-N-(4-{2-[4-(3,4-dichloro-2-fluorophenyl)piperazin-1-yl]ethyl}cyclohexyl)propanamide
1-(4-{2-[4-(3-fluoro-5-trifluoromethylphenyl)-3,6-dihydro-2H-pyridin-1-yl]ethyl}piperidin-1-yl)propan-2-one, dihydrochloride
4-(4-{2-[4-(3-fluoro-5-trifluoromethylphenyl)-3,6-dihydro-2H-pyridin-1-yl]ethyl}piperidin-1-yl)-4-oxobutanonitrile, hydrochloride
2-cyano-N-(4-{2-[4-(3-fluoro-5-trifluoromethylphenyl)-3,6-dihydro-2H-pyridin-1-yl]ethyl}cyclohexyl)acetamide
4-cyano-N-(4-{2-[4-(3-fluoro-5-trifluoromethylphenyl)-3,6-dihydro-2H-pyridin-1-yl]ethyl}cyclohexyl)butanamide
2-cyano-N-(4-{2-[4-(3-fluoro-5-methylphenyl)piperazin-1-yl]ethyl}cyclohexyl)acetamide
4-cyano-N-(4-{2-[4-(3-fluoro-5-methylphenyl)piperazin-1-yl]ethyl}cyclohexyl)butanamide
1-(4-{2-[4-(2,3,4-trichlorophenyl)piperazin-1-yl]ethyl}piperidin-1-yl)propan-2-one, dihydrochloride
1-(4-{2-[4-(4-fluoro-3-methylphenyl)piperazin-1-yl]ethyl}piperidin-1-yl)propan-2-one, dihydrochloride
2-cyano-N-(4-{2-[4-(2,3,4-trichlorophenyl)piperazin-1-yl]ethyl}cyclohexyl)acetamide
1-{4-[2-(4-pentafluorophenylpiperazin-1-yl)ethyl]piperidin-1-yl}propan-2-one, dihydrochloride
5-cyano-pentanoic acid (4-{2-[4-(2-fluoro-5-trifluoromethylphenyl)piperazin-1-ylethyl}cyclohexyl)amide
N-(4-{2-[4-(3-chloro-2,4-difluorophenyl)piperazin-1-yl]ethyl}cyclohexyl)-3-cyanopropanamide
4-(4-{2-[4-(2,3-dichlorophenyl)piperazin-1-yl]ethyl}piperidin-1-yl)-4-oxobutanonitrile 2-methoxy-N-(4-{2-[4-(2-methyl-3-trifluoromethylphenyl)piperazin-1-yl]ethyl}cyclohexyl)acetamide
4-methoxy-N-(4-{2-[4-(2-methyl-3-trifluoromethylphenyl)piperazin-1-yl]ethyl}cyclohexyl)butanamide
4,4,4-trifluoro-N-(4-{2-[4-(2-fluoro-5-trifluoromethylphenyl)piperazin-1-yl]ethyl}cyclohexyl)butanamide
1-(4-{2-[4-(2,3-dichlorophenyl)piperazin-1-yl]ethyl}piperidin-1-yl)propan-2-one, dihydrochloride
N-(4-{2-[4-(3,5-bistrifluoromethylphenyl)piperazin-1-yl]ethyl}cyclohexyl)malonamide
1-(4-{2-[4-(2-ethylphenyl)-3,6-dihydro-2H-pyridin-1-yl]ethyl}piperidin-1-yl)propan-2-one, dihydrochloride
N-(4-{2-[4-(3-chloro-5-fluorophenyl)piperazin-1-yl]ethyl}cyclohexyl)-4-methoxybutanamide
N-(4-{2-[4-(3,5-bistrifluoromethylphenyl)piperazin-1-yl]ethyl}cyclohexyl)-4-methoxybutanamide
N-(4-{2-[4-(3-chloro-5-fluorophenyl)piperazin-1-yl]ethyl}cyclohexyl)-2-methoxyacetamide
N-(4-{2-[4-(3-chloro-5-fluorophenyl)piperazin-1-yl]ethyl}cyclohexyl)-3-cyanopropanamide
1-(4-{2-[4-(2,4,5-trifluorophenyl)piperazin-1-yl]ethyl}piperidin-1-yl)propan-2-one
5-cyano-pentanoic acid (4-{2-[4-(3-trifluoromethylphenyl)piperazin-1-yl]ethyl}cyclohexyl)amide
4,4,4-trifluoro-1-{4-[2-(4-indan-4-ylpiperazin-1-yl)ethyl]piperidin-1-yl}butan-1-one, hydrochloride
3,3,3-trifluoro-1-{4-[2-(4-indan-4-ylpiperazin-1-yl)ethyl]piperidin-1-yl}propan-1-one, hydrochloride
2-cyano-N-(4-{2-[4-(2-ethylphenyl)-3,6-dihydro-2H-pyridin-1-yl]ethyl}cyclohexyl)acetamide
4-cyano-N-(4-{2-[4-(2-ethylphenyl)-3,6-dihydro-2H-pyridin-1-yl]ethyl}cyclohexyl)butanamide
2-cyano-N-{4-[2-(4-o-tolyl-3,6-dihydro-2H-pyridin-1-yl)ethyl]cyclohexyl}acetamide
4-cyano-N-{4-[2-(4-o-tolyl-3,6-dihydro-2H-pyridin-1-yl)ethyl]cyclohexyl}butanamide
1-{4-[2-(4-o-tolyl-3,6-dihydro-2H-pyridin-1-yl)ethyl]piperidin-1-yl}propan-2-one, dihydrochloride
2-cyano-N-{4-[2-(4-pentafluorophenylpiperazin-1-yl)ethyl]cyclohexyl}acetamide
N-(4-{2-[4-(4-fluoro-3-trifluoromethylphenyl)piperazin-1-yl]ethyl}cyclohexyl)-4-methoxybutanamide
N-(4-{2-[4-(4-chloro-3-trifluoromethylphenyl)piperazin-1-yl]ethyl}cyclohexyl)-4-methoxybutanamide
N-(4-{2-[4-(4-chloro-3-trifluoromethylphenyl)piperazin-1-yl]ethyl}cyclohexyl)-4-cyanobutanamide
N-(4-{2-[4-(3-fluoro-5-trifluoromethylphenyl)piperazin-1-yl]ethyl}cyclohexyl)-4-methoxybutanamide
1-(4-{2-[4-(2-isobutylphenyl)piperazin-1-yl]ethyl}piperidin-1-yl)propan-2-one, dihydrochloride
1-(4-{2-[4-(3-isobutylphenyl)piperazin-1-yl]ethyl}piperidin-1-yl)propan-2-one, dihydrochloride
N-(4-{2-[4-(4-fluoro-3-trifluoromethylphenyl)piperazin-1-yl]ethyl}cyclohexyl)-2-methoxyacetamide
N-(4-{2-[4-(2,4-dichlorophenyl)piperazin-1-yl]ethyl}cyclohexyl)-4-methoxybutanamide
4-cyano-N-(4-{2-[4-(2,4-dichlorophenyl)piperazin-1-yl]ethyl}cyclohexyl)butanamide
2-cyano-cyclopropanecarboxylic acid (4-{2-[4-(2-fluoro-5-trifluoromethylphenyl)piperazin-1-yl]ethyl}cyclohexyl)amide
4-cyano-N-(4-{2-[4-(2,4,5-trichlorophenyl)piperazin-1-yl]ethyl}cyclohexyl)butanamide
4-cyano-N-(4-{2-[4-(2,3,4-trichlorophenyl)piperazin-1-yl]ethyl}cyclohexyl)butanamide
N-(4-{2-[4-(4-fluorophenyl)-3,6-dihydro-2H-pyridin-1-yl]ethyl}cyclohexyl)-4-methoxybutanamide
1-(4-{2-[4-(2-methylsulfanylphenyl)piperazin-1-yl]ethyl}piperidin-1-yl)propan-2-one, dihydrochloride
N-(4-{2-[4-(3-cyanophenyl)-3,6-dihydro-2H-pyridin-1-yl]ethyl}cyclohexyl)-2-methoxyacetamide
N-(4-{2-[4-(3-cyanophenyl)-3,6-dihydro-2H-pyridin-1-yl]ethyl}cyclohexyl)-4,4,4-trifluorobutanamide
2-chloro-6-(4-{2-[1-(2-oxopropyl)piperidin-4-yl]ethyl}piperazin-1-yl)benzonitrile, dihydrochloride
1-(4-{2-[4-(2,3-dichlorophenyl)piperazin-1-yl]ethylpiperidin-1-yl)butan-2-one
2-(4-{2-[4-(2,3-dimethylphenyl)piperazin-1-yl]ethyl}piperidin-1-yl)-N-methoxy-N-methylacetamide
1-(4-{2-[4-(2,3-dimethylphenyl)piperazin-1-yl]ethyl}piperidin-1-yl)-3-methylbutan-2-one, hydrochloride
1-(4-{2-[4-(2,3-dimethylphenyl)piperazin-1-yl]ethyl}piperidin-1-yl)butan-2-one, dihydrochloride
1-(4-{2-[4-(2,3-dimethylphenyl)piperazin-1-yl]ethyl}piperidin-1-yl)pentan-2-one
3-(4-{2-[4-(4-methoxybutanoylamino)cyclohexyl]ethyl}piperazin-1-yl)benzamide
[3-(4-{2-[1-(2-oxopropyl)piperidin-4-yl]ethyl}piperazin-1-yl)phenyl]carbamic acid ethyl ester
3-oxo-4-{2[4-(3-trifluoromethylphenyl)piperazin-1-yl]ethyl}piperidin-1-yl)butanenitrile, dihydrochloride
N-(4-{2-[4-(3-acetylphenyl)piperazin-1-yl]ethyl}cyclohexyl)-3,3,3-trifluoropropanamide
2-cyano-N-(4-{2-[4-(3-propanoylphenyl)piperazin-1-yl]ethyl}cyclohexyl)acetamide
4-cyano-N-(4-{2-[4-(3-propanoylphenyl)piperazin-1-yl]ethyl}cyclohexyl)butanamide
2-cyano-N-(4-{2-[4-(3-isobutanylphenyl)piperazin-1-yl]ethyl}cyclohexyl)acetamide, dihydrochloride
1-(4-{2-[4-(2-Isopropylphenyl)piperazin-1-yl]ethyl}piperidin-1-yl)propan-2-one
4-Methoxy-N-(4-{2-[4-(2,3,4,5-tetrafluorophenyl)piperazin-1-yl]ethyl}cyclohexyl)butyramide
4-Cyano-N-(4-{2-[4-(2,3,4,5-tetrafluorophenyl)piperazin-1-yl]ethyl}cyclohexyl)butyramide
2-Chloro-6-fluoro-3-(4-{2-[1-(2-oxopropyl)piperidin-4-yl]ethyl}piperazin-1-yl)benzonitrile
1-(4-{2-[4-(5-Chloro-2-methoxyphenyl)piperazin-1-yl]ethyl}piperidin-1-yl)propan-2-one
1-(4-{2-[4-(5-Methoxy-2-methylphenyl)piperazin-1-yl]ethyl}piperidin-1-yl)propan-2-one
2-Cyano-N-(4-{2-[4-(2-methyl-5-trifluoromethylphenyl)piperazin-1-yl]ethyl}cyclohexyl)acetamide
4-Cyano-N-(4-{2-[4-(2-methyl-5-trifluoromethylphenyl)piperazin-1-yl]ethyl}cyclohexyl)butyramide
1-(4-{2-[4-(3,5-Di-tert-butylphenyl)piperazin-1-yl]ethyl}piperidin-1-yl)propan-2-one
2-Cyano-N-(4-{2-[4-(4-fluorophenyl)-3,6-dihydro-2H-pyridin-1-yl]ethyl}cyclohexyl)acetamide
1-(4-{2-[4-(4-Methyl-3-trifluoromethylphenyl)piperazin-1-yl]ethyl}piperidin-1-yl)propan-2-one
2-Methyl-5-(4-{2-[1-(2-oxopropyl)piperidin-4-yl]ethyl}piperazin-1-yl)benzonitrile
1-(4-{2-[4-(3-Methoxy-5-trifluoromethylphenyl)piperazin-1-yl]ethyl}piperidin-1-yl)propan-2-one
1-(4-{2-[4-(2-Fluoro-4-trifluoromethylphenyl)piperazin-1-yl]ethyl}piperidin-1-yl)propan-2-one
1-(4-{2-[4-(3,5-Difluoro-4-trifluoromethylphenyl)piperazin-1-yl]ethyl}piperidin-1-yl)propan-2-one
1-(4-{2-[4-(2,3-Dichlorophenyl)-3,6-dihydro-2H-pyridin-1-yl]ethyl}piperidin-1-yl)propan-2-one
1-(4-{2-[4-(2,3-Dimethylphenyl)-3,6-dihydro-2H-pyridin-1-yl]ethyl}piperidin-1-yl)propan-2-one 1-{4-[2-(4-Benzothiazol-5-ylpiperazin-1-yl)ethyl]piperidin-1-yl}propan-2-one
1-(4-{2-[4-(4,5-Dichloro-2-fluorophenyl)piperazin-1-yl]ethyl}piperidin-1-yl)propan-2-one
1-(4-{2-[4-(3-Chloro-2-methylphenyl)piperazin-1-yl]ethyl}piperidin-1-yl)propan-2-one,
or their pharmaceutically acceptable salts, hydrates, or hydrated salts, or the polymorphic, cristalline structures of these compounds or their optical isomers, racemates, diastereomers or enantiomers.

More particularly:
1-(4-{2-[4-(3-Chloro-2-methylphenyl)piperazin-1-yl]ethyl}piperidin-1-yl)propan-2-one, dihydrochloride
1-(4-{2-[4-(2,3-Dichlorophenyl)piperazin-1-yl]ethyl}piperidin-1-yl)propan-2-one
4-Methoxy-N-(4-{2-[4-(3-trifluoromethylphenyl)piperazin-1-yl]ethyl}cyclohexyl)butanamide
N-(4-{2-[4-(3-Cyanophenyl)piperazin-1-yl]ethyl}cyclohexyl)-2-ethoxyacetamide
N-(4-{2-[4-(3-Cyanophenyl)piperazin-1-yl]ethyl}cyclohexyl)-2-methoxyacetamide
N-(4-{2-[4-(3,5-Bistrifluoromethylphenyl)piperazin-1-yl]ethyl}cyclohexyl)-2-cyanoacetamide
N-(4-{2-[4-(3-Cyano-5-trifluoromethylphenyl)piperazin-1-yl]ethyl}cyclohexyl)-2-methoxyacetamide
N-(4-{2-[4-(3-Cyano-5-trifluoromethylphenyl)piperazin-1-yl]ethyl}cyclohexyl)-2-ethoxyacetamide
2-Cyano-N-(4-{2-[4-(3,5-dimethylphenyl)piperazin-1-yl]ethyl}cyclohexyl)acetamide
2-Cyano-N-(4-{2-[4-(3-ethylphenyl)piperazin-1-yl]ethyl}cyclohexyl)acetamide
4-Cyano-N-(4-{2-[4-(3-trifluoromethylphenyl)piperazin-1-yl]ethyl}cyclohexyl)butanamide
2-Cyano-N-(4-{2-[4-(2-fluoro-5-trifluoromethylphenyl)piperazin-1-yl]ethyl}cyclohexyl)acetamide
5-N-(4-{2-[4-(3-Chloro-5-fluorophenyl)piperazin-1-yl]ethyl}cyclohexyl)-2-cyanoacetamide
4-Cyano-N-(4-{2-[4-(2-fluoro-5-trifluoromethylphenyl)piperazin-1-yl]ethyl}cyclohexyl)butanamide
N-(4-{2-[4-(5-Chloro-2-methylphenyl)piperazin-1-yl]ethyl}cyclohexyl)-3-cyanopropanamide
2-Cyano-N-(4-{2-[4-(4-trifluoromethylphenyl)piperazin-1-yl]ethyl}cyclohexyl)acetamide
2-Cyano-N-(4-{2-[4-(4-fluoro-3-trifluoromethylphenyl)piperazin-1-yl]ethyl}cyclohexyl)acetamide
4-Cyano-N-[4-(2-{4-[3-(1,1-difluoroethyl)phenyl]piperazin-1-yl}ethyl)cyclohexyl]butanamide
1-(4-{2-[4-(3-Propylphenyl)piperazin-1-yl]ethyl}piperidin-1-yl)propan-2-one, dihydrochloride
2-Cyano-N-(4-{2-[4-(3-methanesulfonylphenyl)piperazin-1-yl]ethyl}cyclohexyl)acetamide
1-{4-[2-(4-Indan-4-ylpiperazin-1-yl)ethyl]piperidin-1-yl}propan-2-one, dihydrochloride
2-Cyano-N-(4-{2-[4-(3-difluoromethylphenyl)piperazin-1-yl]ethyl}cyclohexyl)acetamide
2-Cyano-N-(4-{2-[4-(4-fluorophenyl)-3,6-dihydro-2H-pyridin-1-yl]ethyl}cyclohexyl)acetamide
N-(4-{2-[4-(3-Acetylphenyl)piperazin-1-yl]ethyl}cyclohexyl)-4-cyanobutanamide
Cyclopent-1-enecarboxylic acid (4-{2-[4-(2,4-difluorophenyl)piperazin-1-yl]ethyl}cyclohexyl)amide
4-Cyano-N-(4-{2-[4-(3,5-dimethoxyphenyl)piperazin-1-yl]ethyl}cyclohexyl)butanamide
2-Cyano-N-(4-{2-[4-(3,5-dimethylphenyl)-3,6-dihydro-2H-pyridin-1-yl]ethyl}cyclohexyl)acetamide
3,3,3-Trifluoro-N-(4-{2-[4-(3-methanesulfonylphenyl)piperazin-1-yl]ethyl}cyclohexyl)propanamide
N-(4-{2-[4-(3-Cyanophenyl)piperazin-1-yl]ethyl}cyclohexyl)-4-methoxybutanamide
4-Cyano-N-[4-(2-{4-[3-(1-hydroxypropyl)phenyl]piperazin-1-yl}ethyl)cyclohexyl]butanamide
N-(4-{2-[4-(3-Chloro-2,4-difluorophenyl)piperazin-1-yl]ethyl}cyclohexyl)-4-cyanobutanamide
2-Cyano-N-[4-(2-{4-[3-(1-hydroxypropyl)phenyl]piperazin-1-yl}ethyl)cyclohexyl]acetamide
N-(4-{2-[4-(3-Chloro-2,4-difluorophenyl)piperazin-1-yl]ethyl}cyclohexyl)succinamide
N-(4-{2-[4-(2-Fluoro-5-trifluoromethylphenyl)piperazin-1-yl]ethyl}cyclohexyl)-4-methoxybutanamide
1-{4-[2-(4-Indan-4-yl-3,6-dihydro-2H-pyridin-1-yl)ethyl]piperidin-1-yl}propan-2-one, dihydrochloride
1-(4-{2-[4-(2-Fluoro-5-trifluoromethylphenyl)-3,6-dihydro-2H-pyridin-1-yl]ethyl}piperidin-1-yl)propan-2-one, dihyrochloride
N-(4-{2-[4-(3-Cyanophenyl)piperazin-1-yl]ethyl}cyclohexyl)-4,4,4-trifluorobutanamide
N-(4-{2-[4-(3-Cyanophenyl)piperazin-1-yl]ethyl}cyclohexyl)-3-methoxypropanamide
1-(4-{2-[4-(2,3-Dichlorophenyl)piperazin-1-yl]ethyl}piperidin-1-yl)propan-2-one, dihydrochloride
or their pharmaceutically acceptable salts, free forms, hydrates, or hydrated salts, or the polymorphic, cristalline structures of these compounds or their optical isomers, racemates, diastereomers or enantiomers.

Still more preferably:
1-(4-{2-[4-(3-Chloro-2-methylphenyl)piperazin-1-yl]ethyl}piperidin-1-yl)propan-2-one, dihydrochloride
1-(4-{2-[4-(2,3-Dichlorophenyl)piperazin-1-yl]ethyl}piperidin-1-yl)propan-2-one
N-(4-{2-[4-(3-Cyanophenyl)piperazin-1-yl]ethyl}cyclohexyl)-2-methoxyacetamide
N-(4-{2-[4-(3,5-Bistrifluoromethylphenyl)piperazin-1-yl]ethyl}cyclohexyl)-2-cyanoacetamide
2-Cyano-N-(4-{2-[4-(3-methanesulfonylphenyl)piperazin-1-yl]ethyl}cyclohexyl)acetamide
2-Cyano-N-(4-{2-[4-(4-fluorophenyl)-3,6-dihydro-2H-pyridin-1-yl]ethyl}cyclohexyl)acetamide
2-Cyano-N-[4-(2-{4-[3-(1-hydroxypropyl)phenyl]piperazin-1-yl}ethyl)cyclohexyl]acetamide
N-(4-{2-[4-(3-Cyanophenyl)piperazin-1-yl]ethyl}cyclohexyl)-4,4,4-trifluorobutanamide
N-(4-{2-[4-(3-Cyanophenyl)piperazin-1-yl]ethyl}cyclohexyl)-3-methoxypropanamide
1-(4-{2-[4-(2,3-Dichlorophenyl)piperazin-1-yl]ethyl}piperidin-1-yl)propan-2-one, dihydrochloride
or their pharmaceutically acceptable salts, free forms, hydrates, or hydrated salts, or the polymorphic, cristalline structures of these compounds or their optical isomers, racemates, diastereomers or enantiomers.

As used hereabove or hereafter:

"Acyl" means an H—CO— or alkyl-CO— group wherein the alkyl group is as herein described. Preferred acyls contain a lower alkyl. Exemplary acyl groups include formyl, acetyl, propanoyl, 2-methylpropanoyl, butanoyl and palmitoyl.

"Acylamino" is an acyl-NH— group wherein acyl is as defined herein.

"Acylaminoalkyl" means an acyl-NH-alkyl wherein acyl and alkyl are as defined herein.

"Alcanediyl" means a —$(CH_2)_q$— wherein q is an integer from 3 to 6, preferably from 3 to 5.

"Alkenyl" means an aliphatic hydrocarbon group containing a carbon-carbon double bond and which may be straight or branched having 2 to 15 carbon atoms in the chain. Preferred alkenyl groups have 2 to 12 carbon atoms in the chain;

and more preferably about 2 to 4 carbon atoms in the chain. Exemplary alkenyl groups include ethenyl, propenyl, n-butenyl, i-butenyl, 3-methylbut-2-enyl, n-pentenyl, heptenyl, octenyl, nonenyl, decenyl.

"Alkoxy" means an alkyl-O— group wherein the alkyl group is as herein described. Exemplary alkoxy groups include methoxy, ethoxy, n-propoxy, i-propoxy, n-butoxy and heptoxy.

"Alkoxyalkyl" means an alkyl-O-alkyl- group wherein the alkyl groups are independent as herein described. Exemplary alkoxy groups include methoxyethyl, ethoxymethyl, n-butoxymethyl and cyclopentylmethyloxyethyl.

"Alkoxyalkoxyalkyl" means an alkyl-O-alkyl-O-alkyl- group wherein the alkyl groups independently are as defined above.

"Alkoxyalkylamino" means an alkyl-O-alkyl-NH— wherein alkyl is as defined herein.

"Alkoxy(alkyl)amino" means an alkyl-O—N(alkyl)- wherein alkyl is as defined herein.

"Alkoxycarbonylamino" means an alkyl-O—CO—NH— wherein alkyl is as defined herein.

"Alkyl" means an aliphatic hydrocarbon group which may be straight or branched having 1 to 20 carbon atoms in the chain. Preferred alkyl groups have 1 to 12 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, 3-pentyl, octyl, nonyl, decyl.

Alkyl groups may be substituted with a cyano group ("Cyanoalkyl"), a hydroxyl group ("Hydroxyalkyl"), a halogeno group ("Monohalogenoalkyl") or more ("Polyhalogenoalkyl").

"Alkylamino" means an alkyl-NH— group wherein the alkyl group is as herein described.

"Alkylcarbonylalkyl" means an alkyl-CO-alkyl- wherein alkyl are independently as defined herein.

"Alkylsulfanyl" means an alkyl-S— group wherein the alkyl group is as herein described.

"Alkylsulfanylalkyl" means an alkyl-S-alkyl- group wherein the alkyl groups are independently as herein described.

"Alkylsulfinyl" means an alkyl-SO— group wherein the alkyl group is as defined herein. Preferred groups are those wherein the alkyl group is lower alkyl.

"Alkylsulfinylalkyl" means an alkyl-SO-alkyl- group wherein the alkyl groups are independently as defined above. Preferred groups are those wherein the alkyl group is lower alkyl.

"Alkylsulfonyl" means an alkyl-SO$_2$— group wherein the alkyl group is as defined herein. Preferred groups are those wherein the alkyl group is lower alkyl.

"Alkylsulfonylalkyl" means an alkyl-SO$_2$-alkyl- group wherein the alkyl groups are independently as defined herein. Preferred groups are those wherein the alkyl group is lower alkyl.

"Alkylsulfonylamino" means an alkyl-SO$_2$—NH— wherein alkyl is as defined herein.

"Alkynyl" means an aliphatic hydrocarbon group containing a carbon-carbon triple bond and which may be straight or branched having 2 to 15 carbon atoms in the chain. Preferred alkynyl groups have 2 to 12 carbon atoms in the chain; and more preferably 2 to 4 carbon atoms in the chain. Exemplary alkynyl groups include ethynyl, propynyl, n-butynyl, 2-butynyl, 3-methylbutynyl, n-pentynyl, heptynyl, octynyl and decynyl.

"Aminocarbonylalkyl" means an NH$_2$—CO-alkyl- wherein alkyl is as defined herein.

"Aralkyl" means an aryl-alkyl- group wherein the aryl and alkyl are as herein described. Preferred aralkyls contain a lower alkyl moiety. Exemplary aralkyl groups include benzyl, 2-phenethyl and naphthylmethyl.

"Aryl" means an aromatic monocyclic or multicyclic hydrocarbon ring system of 6 to 14 carbon atoms, preferably of 6 to 10 carbon atoms. Exemplary aryl groups include phenyl or naphthyl.

"Arylaminoalkyl" means an aryl-NH-alkyl- wherein aryl and alkyl are as defined herein.

"Arylalkoxy" means an aryl-alkyl-O— group wherein the aryl or alkyl groups are as herein described.

"Aryloxy" means an aryl-O— group wherein the aryl group is as defined herein. Exemplary groups include phenoxy and 2-naphthyloxy.

"Aryloxyalkyl" means an aryl-O-alkyl- group wherein the aryl or alkyl groups are as herein described. An exemplary aryloxyalkyl groups is phenoxypropyl.

"Cycloalkenyl" means a non-aromatic mono- or multicyclic ring system of about 3 to about 10 carbon atoms, preferably of about 5 to about 10 carbon atoms, and which contains at least one carbon-carbon double bond. Preferred ring sizes of rings of the ring system include about 5 to about 6 ring atoms. Exemplary monocyclic cycloalkenyl include cyclopentenyl, cyclohexenyl, cycloheptenyl. An exemplary multicyclic cycloalkenyl is norbornenyl.

"Cycloalkyl" means a non-aromatic mono- or multicyclic hydrocarbon ring system of 3 to 10 carbon atoms, preferably of 5 to 10 carbon atoms. Preferred ring sizes of rings of the ring system include 5 to 6 ring atoms. Exemplary monocyclic cycloalkyl include cyclopentyl, cyclohexyl, cycloheptyl, and the like. Exemplary multicyclic cycloalkyl include 1-decalin, norbornyl, adamant-(1- or 2-)yl.

"Dialkylamino" means an (alkyl)$_2$N— group wherein the alkyl groups are independently as herein described.

"Dialkylaminoalkyl" means an (alkyl)$_2$N-alkyl- group wherein the alkyl groups are independently as herein described.

"Halogeno" refers to fluorine, chlorine, bromine or iodine atom; preferably fluorine and chlorine atom.

As used herein, the term "Heteroaryl" or aromatic heterocycles refers to a 5 to 14, preferably 5 to 10 membered aromatic hetero, mono-, bi- or multicyclic ring. Examples include pyrrolyl, pyridyl, pyrazolyl, thienyl, pyrimidinyl, pyrazinyl, tetrazolyl, indolyl, quinolinyl, purinyl, imidazolyl, thiazolyl, benzothiazolyl, furanyl, benzofuranyl, 1,2,4-thiadiazolyl, isothiazolyl, triazoyl, isoquinolyl, benzothienyl, isobenzofuryl, carbazolyl, benzimidazolyl, isoxazolyl, pyridyl-N-oxide, as well as the fused systems resulting from the condensation with a phenyl group.

As used herein, the terms "Heterocycle" or "Heterocyclic" refer to a saturated, partially unsaturated or unsaturated, non aromatic stable 3 to 14, preferably 5 to 10 membered mono, bi or multicyclic rings wherein at least one member of the ring is a hetero atom. Typically, heteroatoms include, but are not limited to, oxygen, nitrogen, sulfur, selenium, and phosphorus atoms. Preferable heteroatoms are oxygen, nitrogen and sulfur.

Suitable heterocycles are also disclosed in *The Handbook of Chemistry and Physics,* 76$^{th}$ Edition, CRC Press, Inc., 1995-1996, pages 2-25 to 2-26, the disclosure of which is hereby incorporated by reference.

Preferred non aromatic heterocyclic include, but are not limited to pyrrolidinyl, pyrazolidinyl, imidazolidinyl, oxiranyl, tetrahydrofuranyl, dioxolanyl, dioxanyl, piperidyl, piperazinyl, morpholinyl, pyranyl, imidazolinyl, pyrrolinyl, pyrazolinyl, thiazolidinyl, tetrahydrothiopyranyl, dithianyl, thiomorpholinyl, dihydropyranyl, tetrahydropyranyl, dihydropyranyl, tetrahydro-pyridyl, dihydropyridyl, tetrahydropyrimidinyl, dihydrothiopyranyl, azepanyl, as well as the fused systems resulting from the condensation with a phenyl group.

"Oxoalkyl" means an alkyl where a $CH_2$ is replaced by a CO wherein alkyl is as defined herein.

"Polymethylenedioxy" means a $—O—(CH_2)_p—O—$ wherein p is an intenger from 1 to 4.

"Fused arylheterocyclyl" means a fused aryl and heterocyclyl as defined herein. Preferred fused arylheterocyclyls are those wherein the aryl thereof is phenyl and the heterocyclyl consists of about 5 to about 6 ring atoms. A fused arylheterocyclyl as a variable may be bonded through any atom of the ring system thereof capable of such. The designation of the aza, oxa or thia as a prefix before heterocyclyl portion of the fused arylheterocyclyl define that at least a nitrogen, oxygen or sulphur atom is present respectively as a ring atom. The nitrogen atom of a fused arylheterocyclyl may be a basic nitrogen atom. The nitrogen or sulphur atom of the heterocyclyl portion of the fused arylheterocyclyl may also be optionally oxidized to the corresponding N-oxide, S-oxide or S,S-dioxide. Exemplary preferred fused arylheterocyclyl ring systems include indolinyl, 1,2,3,4-tetrahydroisoquinoline, 1,2,3,4-tetrahydroquinoline, 1H-2,3-dihydroisoindol-2-yl, 2,3-dihydrobenz[f]isoindol-2-yl, 1,2,3,4-tetrahydrobenz[g]isoquinolin-2-yl.

"Fused arylcycloalkyl" means a fused aryl and cycloalkyl as defined herein. Preferred fused arylcycloalkyls are those wherein the aryl thereof is phenyl and the cycloalkyl consists of about 5 to about 6 ring atoms. A fused arylcycloalkyl as a variable may be bonded through any atom of the ring system thereof capable of such. Exemplary fused arylcycloalkyl includes 1,2,3,4-tetrahydronaphthyl.

As used herein, "pharmaceutically acceptable salts" refer to derivatives of the disclosed compounds wherein the parent compound is modified by making acid or base salts thereof. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propanoic, succinic, tartaric, citric, methanesulfonic, benzenesulfonic, glucuronic, glutamic, benzoic, salicylic, toluenesulfonic, oxalic, fumaric, maleic, and the like. Further addition salts include ammonium salts such as tromethamine, meglumine, epolamine, etc., metal salts such as sodium, potassium, calcium, zinc or magnesium. Hydrochloride and oxalate salts are preferred.

The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two. Generally, non-aqueous media like ether, ethyl acetate, ethanol, isopropanol, or acetonitrile are preferred. Lists of suitable salts are found in *Remington's Pharmaceutical Sciences*, 17$^{th}$ ed., Mack Publishing Company, Easton, Pa., 1985, p. 1418, the disclosure of which is hereby incorporated by reference.

The compounds of the general formula (I) having geometrical and stereomers are also a part of the invention.

According to a further object, the present invention is also concerned with the process of preparation of the compounds of formula (I).

The compounds and process of the present invention may be prepared in a number of ways well known to those skilled in the art. The compounds can be synthesized, for example, by application or adaptation of the methods described below, or variations thereon as appreciated by the skilled artisan. The appropriate modifications and substitutions will be readily apparent and well known or readily obtainable from the scientific literature to those skilled in the art.

In particular, such methods can be found in R. C. Larock, *Comprehensive Organic Transformations*, VCH publishers, 1989.

It will be appreciated that the compounds of the present invention may contain one or more asymmetrically substituted carbon atoms, and may be isolated in optically active or racemic forms. Thus, all chiral, diastereomeric, racemic forms and all geometric isomeric forms of a structure are intended, unless the specific stereochemistry or isomeric form is specifically indicated. It is well known in the art how to prepare and isolate such optically active forms. For example, mixtures of stereomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

Compounds of the present invention may be prepared by a variety of synthetic routes. The reagents and starting materials are commercially available, or readily synthesized by well-known techniques by one of ordinary skill in the arts. All substituents, unless otherwise indicated, are as previously defined.

In the reactions described hereinafter, it may be necessary to protect reactive functional groups, for example hydroxy, amino, imino, thio or carboxy groups, where these are desired in the final product, to avoid their unwanted participation in the reactions. Conventional protecting groups may be used in accordance with standard practice, for examples see T. W. Greene and P. G. M. Wuts in Protective Groups in Organic Chemistry, John Wiley and Sons, 1991; J. F. W. McOmie in Protective Groups in Organic Chemistry, Plenum Press, 1973.

Some reactions may be carried out in the presence of a base. There is no particular restriction on the nature of the base to be used in this reaction, and any base conventionally used in reactions of this type may equally be used here, provided that it has no adverse effect on other parts of the molecule. Examples of suitable bases include: sodium hydroxide, potassium carbonate, triethylamine, alkali metal hydrides, such as sodium hydride and potassium hydride; alkyllithium compounds, such as methyllithium and butyllithium; and alkali metal alkoxides, such as sodium methoxide and sodium ethoxide.

Usually, reactions are carried out in a suitable solvent. A variety of solvents may be used, provided that it has no adverse effect on the reaction or on the reagents involved. Examples of suitable solvents include: hydrocarbons, which may be aromatic, aliphatic or cycloaliphatic hydrocarbons, such as hexane, cyclohexane, methylcyclohexane, toluene and xylene; amides, such as N,N-dimethylformamide; alcohols such as ethanol and methanol and ethers, such as diethyl ether, methyl tert-butyl ether, methyl cyclopentyl ether and tetrahydrofuran.

The reactions can take place over a wide range of temperatures. In general, we find it convenient to carry out the reaction at a temperature of from 0° C. to 150° C. (more preferably from about room temperature to 100° C.). The time required for the reaction may also vary widely, depending on many factors, notably the reaction temperature and the nature of the reagents. However, provided that the reaction is effected under the preferred conditions outlined above, a period of from 3 hours to 20 hours will usually suffice.

The compound thus prepared may be recovered from the reaction mixture by conventional means. For example, the compounds may be recovered by distilling off the solvent from the reaction mixture or, if necessary, after distilling off the solvent from the reaction mixture, pouring the residue into water followed by extraction with a waterimmiscible organic solvent and distilling off the solvent from the extract. Additionally, the product can, if desired, be further purified by various well-known techniques, such as recrystallization, reprecipitation or the various chromatography techniques, notably column chromatography or preparative thin layer chromatography.

The process of preparation of a compound of formula (I) of the invention is another object of the present invention.

According to a first aspect, compounds of the invention of the formula (I) can be obtained from corresponding compounds of formula (II)

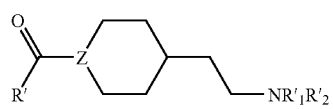

(II)

wherein R', R'$_1$ and R'$_2$ represent respectively R, R$_1$ and R$_2$ or a precursor group of respectively R, R$_1$ and R$_2$.

More precisely, compounds of formula (I) can be obtained by a method comprising the steps of:

a) converting the compound of formula (II) into a compound of formula (I); and optionally b) isolating the obtained compound of formula (I).

According to the present invention, "precursor group" of a functional group refers to any group which can, by one or more reactions, lead to the desired function, by means of one or more suitable reagents. Those reactions include the deprotections of functional groups, as well as usual addition, substitution, reduction, oxidation or functionalization reaction.

Preferably, a compound of formula (I) in which Ar in NR$_1$R$_2$ is substituted with an acyl group can be prepared from a corresponding compound of formula (II) in which Ar in NR$_1$R$_2$ is substituted with an hydroxylated chain. This reaction can be performed by Swern or Swern Moffatt oxidation as well as action of metallic oxide such as chromium or manganese oxides.

Preferably, a compound of formula (I) in which Z is e) can be prepared from a corresponding compound of formula (II) in which Z is f by reduction. This reaction can be performed with hydrogen and a transition metal catalyst such as palladium or nickel.

Preferably, a compound of formula (I) in which R is alkyl can be prepared from a corresponding compound of formula in which R is alkoxy by hydrolyzing this ester into the corresponding acid (R=OH), converting the acid into Weinreb's amide (R=N(Me)OMe) and finally reacting with a grignard's reagent.

Preferably, a compound of formula (I) in which Z is e) or f and R is an amine can be prepared from the corresponding acid (R=OH) by a peptidic coupling reaction. This reaction is performed using reagents such as a carbodiimide, carbonyldiimidazole or a chloroformate in the presence of catalysts such as DMAP, HOBt in an inert solvent such as dichloromethane, N,N-dimethylformamide, tetrahydrofuran or ethyl acetate at a temperature comprised between 0° C. and 40° C.

Compounds of the invention of the formula (II) in which Z is

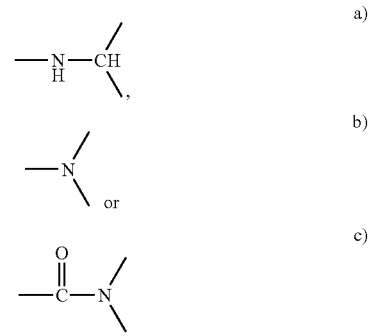

can be prepared by coupling compounds of formula (III) with acid or acid derivatives R'COX or R'COCOX

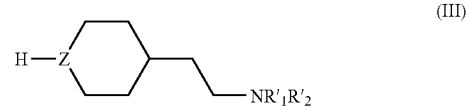

(III)

in which R' and NR'$_1$R'$_2$ are as defined in general formula (II) and Z is chosen from the group selected within:

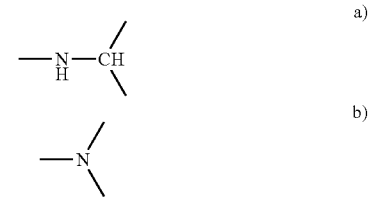

More precisely, when the reaction can be a peptidic coupling with R'COOH or R'COCOOH and is performed using reagents such as a carbodiimide, carbonyldiimidazole or a chloroformate in the presence of catalysts such as DMAP, HOBt in an inert solvent such as dichloromethane, N,N-dimethylformamide, tetrahydrofuran or ethyl acetate at a temperature comprised between 0° C. and 40° C.

Compound R'COX or R'COCOX can also be an activated form of a carboxylate such as an acid chloride (X=Cl), an imidazolide (X=imidazol-1-yl), an hydroxysuccinimidoyl (X=OSu), a paranitrophenyl ester (X=4-nitrophenoxy), a mixed anhydride or a symmetric anhydride. The reaction is performed in an inert solvent such as dichloromethane, N,N-dimethylformamide, tetrahydrofuran or ethyl acetate at a temperature comprised between 0° C. and 40° C., optionally in the presence of a catalyst such as DMAP or HOBt and a base such as triethylamine or a carbonate.

Compounds of formula (III) can be obtained by deprotection of compounds of formula (IV)

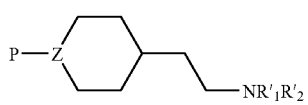
(IV)

where P represent a nitrogen protecting group such as benzyloxycarbonyl or tertbutoxycarbonyl.

When P is benzyloxycarbonyl, deprotection can be performed using dihydrogen, cyclohexene or a formate in the presence of a catalyst such as palladium on charcoal in an alcohol such as methanol or ethanol at a temperature comprised between room temperature and 80° C., or with aluminum trichloride in the presence of anisole.

When P is tert-butoxycarbonyl, deprotection can be performed using trimethylsilyliodide, or a Brönsted acid such as trifluoroacetic acid or hydrochloric acid, or a Lewis acid such as tin tetrachloride in a suitable solvent at a temperature comprised between 0 and 40° C.

Compounds of formula (IV) can be prepared by nucleophilic substitution of compounds of formula (V)

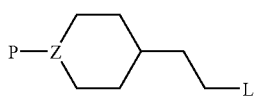
(V)

where L represents a leaving group such as an halogen or a sulfonate (mesylate or arylsulfonate).

This substitution can be performed by mixing compound (V) and the amine $HNR'_1R'_2$ in a suitable solvent such as acetonitrile, acetone, N,N-dimethylformamide, dichloromethane or an alcohol, in the presence of a base such as a carbonate, a bicarbonate or a tertiary amine, at a temperature comprised between room temperature and the refluxing temperature.

Compounds of formula (V) can be prepared from the corresponding alcohol of formula (VI)

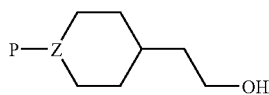
(VI)

This reaction can be performed using thionyl chloride with or without imidazole, or a phosphine and tetrahalomethane or hexahaloethane, or a sulfonyl chloride or anhydride in a suitable solvent at a temperature comprised between 0° and 40° C.

Alternatively, compounds of formula (II) in which Z represents

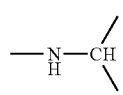
a)

can be prepared from compounds of formula (VII) by reductive amination

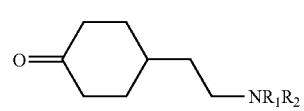
(VII)

This reaction can be performed with an ammonium such as ammonium acetate or chloride in the presence of a reducing agent such as sodium triacetoxyborohydride, sodium borohydride or sodium cyanoborohydride in an alcohol such as methanol or ethanol and optionally water at a temperature comprised between −20° C. and reflux.

Compounds of formula (VII) can be prepared by deprotecting spiroketal of formula (VII)

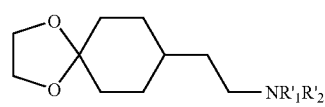
(VIII)

This deprotection can be performed with an acid such as hydrochloric acid, sulfuric acid or a sulfonic acid in an alcohol such as methanol or ethanol and water at a temperature comprised between room temperature and reflux.

Compounds of formula (VIII) can be prepared from the corresponding mesylate

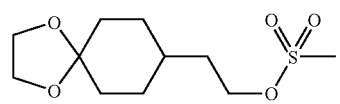 [SMILES: CS(=O)(=O)OCCC1CCC2(CC1)OCCO2]

This substitution can be performed by mixing the mesylate and the amine $HNR'_1R'_2$ in a suitable solvent such as acetonitrile, acetone, N,N-dimethylformamide, dichloromethane or an alcohol, in the presence of a base such as a carbonate, a bicarbonate or a tertiary amine, at a temperature comprised between room temperature and the refluxing temperature.

Compounds of formula (VIII) can also be prepared by reduction of amides of formula (IX)

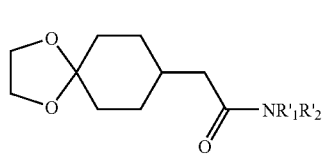
(IX)

This reduction can be performed with lithium aluminum hydride in an ether such as diethyl ether, methyl tert-butyl ether, methyl cyclopentyl ether or tetrahydrofuran at a temperature comprised between 0° C. and reflux.

Compounds of formula (VIII) can also be prepared from the corresponding further mesylate of formula:

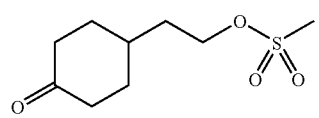

This substitution can be performed by mixing the mesylate and the amine HNR'$_1$R'$_2$ in a suitable solvent such as acetonitrile, acetone, N,N-dimethylformamide, dichloromethane or an alcohol, in the presence of a base such as a carbonate, a bicarbonate or a tertiary amine, at a temperature comprised between room temperature and the refluxing temperature.

This further mesylate can be prepared from the corresponding 4-(2-hydroxyethyl)cyclohexanone

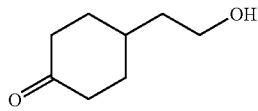

This reaction can be performed by reacting 4-(2-hydroxyethyl)cyclohexanone with methanesulfonyl chloride, methanesulfonyl fluoride or methanesulfonic anhydride in the presence of an organic or inorganic base such as pyridine, triethylamine, 1,4-diazabicyclo[2,2,2]octane, 1,5-diazabicyclo[4,3,0]non-5-ene, 1,8-diazabicyclo[5,4,0]undec-7-ene, a carbonate or a bicarbonate in an inert solvent such as dichloromethane, dichloroethane, an aromatic solvent, an ether or a mixture thereof, at a temperature comprised between −20° C. and the refluxing temperature.

4-(2-hydroxyethyl)cyclohexanone is a known intermediate in various industrial fields such as pharmaceutical synthesis and liquid crystals elaboration, it can be prepared from 4-(2-hydroxyethyl)cyclohexanol by selective oxydation

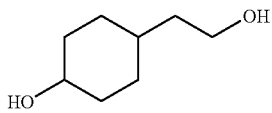

This oxydation can be performed with an oxydant able to convert a secondary alcohol into a ketone in the presence of a primary alcohol. Such oxydant can be a hypochlorite salt such as sodium or calcium hypochlorite in a suitable solvent such as a carboxylic acid, water, or a mixture thereof.

Alternatively, non selective oxydant can be used with prior protection of the primary alcohol before the oxydation step.

4-(2-hydroxyethyl)cyclohexanol is a known intermediate in various industrial fields such as pharmaceutical synthesis and liquid crystals elaboration, it can be prepared by reduction of 4-(2-hydroxyethyl)phenol

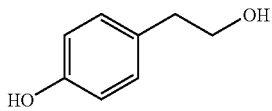

This reduction can be performed with hydrogen or a hydrogen donor (such as cyclohexene, formic acid, formic acid triethylamine eutectic mixture) in the presence of a metal catalyst (such as palladium, platinum, nickel or ruthenium supported on charcoal, silica or alumina) eventually in the presence of an additive (such as borax, sodium acetate, potassium acetate, lithium acetate, sodium hydroxyde, lithium hydroxyde, potassium carbonate, sodium carbonate, potassium hydrogenocarbonate or sodium hydrogenocarbonate in a suitable solvent such as an alcohol (methanol, ethanol, isopropanol), water, a carboxylic acid (acetic acid, propanoic acid), an ether (diethyl ether, methyl tert-butyl ether, tetrahydrofurane, dioxane, cyclopentyl methyl ether), an aromatic solvent (toluene, xylene) or a mixture thereof Amides of formula (IX) can be prepared by condensing amine HNR'$_1$R'$_2$ with (1,4-dioxaspiro[4.5]dec-8-yl)acetic acid.

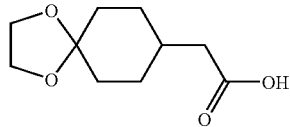

This reaction can be performed using reagents such as a carbodiimide, carbonyldiimidazole or a chloroformate in the presence of catalysts such as DMAP, HOBt in an inert solvent such as dichloromethane, N,N-dimethylformamide, tetrahydrofuran or ethyl acetate at a temperature comprised between 0° C. and 40° C.

According to a third aspect, compounds of the invention of the formula (II) in which Z is

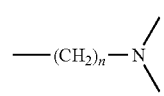

c)

can be prepared by alkylating compounds of formula (III) with haloketones R'CO(CH$_2$)$_n$Br or R'CO(CH$_2$)$_n$Cl

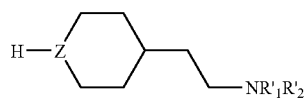

(III)

in which NR'$_1$R'$_2$ is as defined in formula (II) and Z is

b)

This alkylation can be performed by reacting the amine of formula (III) and the haloketone R'CO(CH$_2$)$_n$Br or R'CO(CH$_2$)$_n$Cl in the presence of base such as a carbonate or a bicarbonate in an inert solvent such as acetonitrile or a ketone (acetone, methylisobutylketone, methylethylketone) or an alcohol (methanol, ethanol or isopropanol) at a temperature comprised between room temperature and reflux.

According to a fourth aspect, compounds of the invention of the formula (II) in which Z is

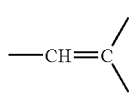

f)

can be prepared by condensing a compound of formula (VII) with a (triphenyl-λ$^5$-phosphanylidene)acetic acid ester by refluxing in an inert solvent like toluene or a (diethoxyphosphoryl)acetic acid ester in the presence of a base such as sodium hydroxyde or sodium hydride at a temperature comprised between 0° C. and 40° C. in a solvent such as an ether (tetrahydrofuran, methyl-tert-butyl ether, methyl cyclopentyl ether).

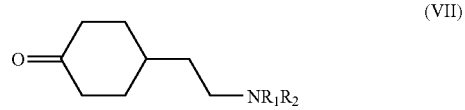

(VII)

These general methods can be summarised in the following scheme:

preparation of pharmaceutical compositions intended to prevent and/or treat a neuropsychiatric illness or any illness involving the dopamine $D_3$ receptor. Said neuropsychiatric illnesses are preferably selected from Parkinson's disease, schizophrenia, dementia, psychosis or psychotic states, depression, mania, anxiety, dyskinesias, equilibration disorders, Gilles de la Tourette's disease.

According to the invention, said prevention and/or treatment of Parkinson's disease is preferably an adjunct therapy for Parkinson's disease.

Other illnesses include substance dependency, sexual disorders, motor disorders, cardiovascular disorders, hormonal disorders, renal insufficiency or diabetes.

According to the invention, substance dependency is taken to mean any state associated withdrawal, abstinence and/or

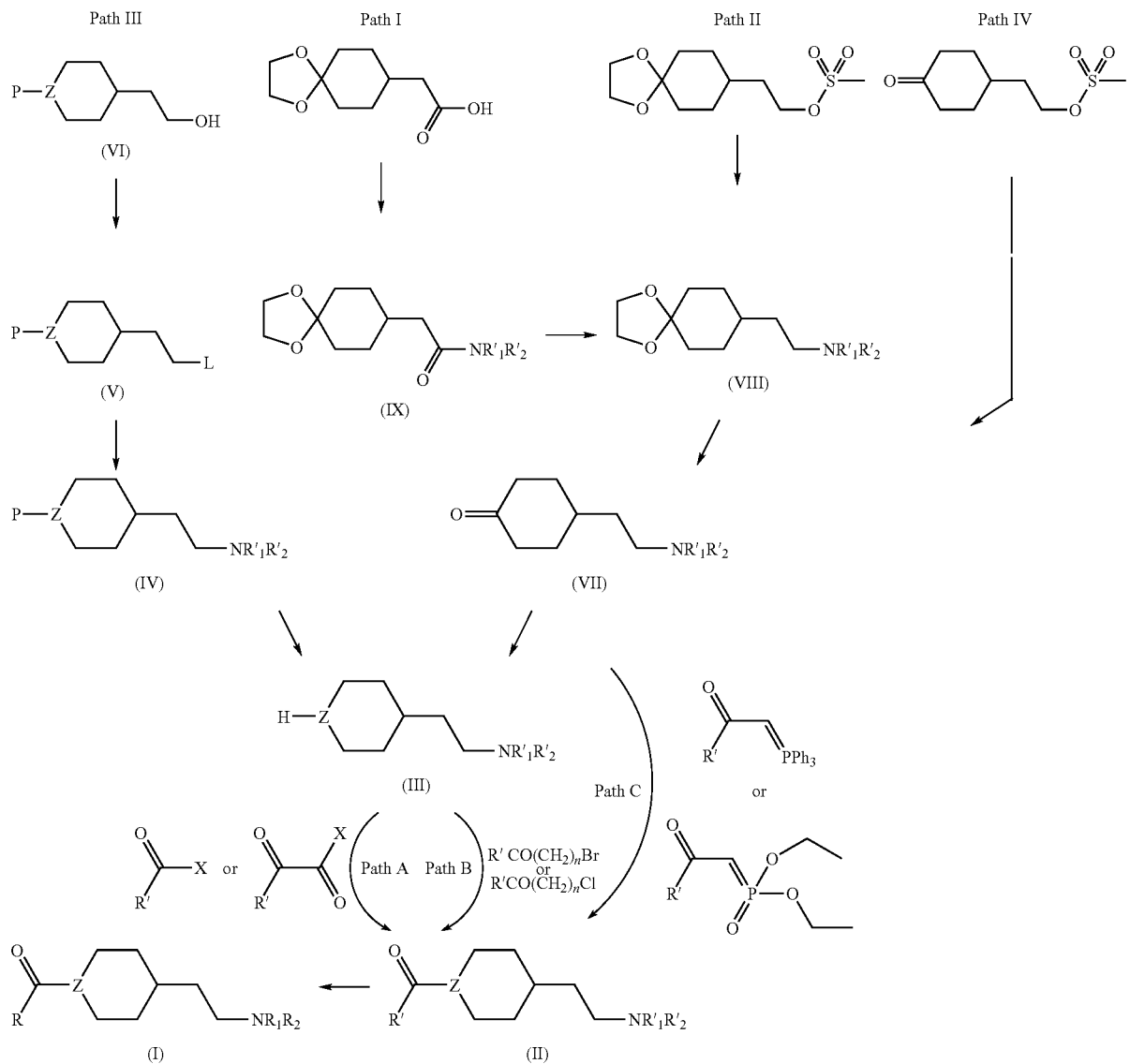

According to a further object, the present invention is also concerned with pharmaceutical compositions comprising a compound of formula (I) together with a pharmaceutically acceptable excipient or carrier.

According to another object, the present invention also relates to the use of compounds of general formula (I) for the detoxification of an individual dependent on any agent, in particular therapeutically active agents, such as opioids, and/or drugs such as cocaine, heroin, or alternatively alcohol and/or nicotine.

According to the invention, sexual disorders are in particular taken to mean impotence, in particular male impotence.

According to the invention, motor disorders are in particular taken to mean essential or iatrogenic dyskinesia, and/or essential or iatrogenic tremor.

According to the invention, cardiovascular disorders comprise hypertension, cardiac failure.

According to the invention, hormonal disorders comprise menopausal disorders or growth disorders.

According to another object, the present invention also relates to the above-mentioned therapeutic treatment methods comprising the administration of a compound according to the invention together with a pharmaceutically acceptable carrier or excipient to a patient in the need thereof.

According to a further object, the present invention also relates to combinations comprising a compound of the invention and one or more further active ingredient(s).

In particular, for treating neuropsychiatric disorders, compounds of the invention may be advantageously administered with one or more other neuropsychiatric agent(s) such as anxyolytic, antipsychotic, antidepressant, precognitive or antidementia agents.

Also, for treating cardiovascular or metabolic disorders, compounds of the invention may be advantageously administered with one or more antihypertensive, cardiotonic or antidiabetic agent(s).

The identification of those subjects who are in need of treatment of herein-described diseases and conditions is well within the ability and knowledge of one skilled in the art. A clinician skilled in the art can readily identify, by the use of clinical tests, physical examination, genetic tests and medical/family history, those subjects who are in need of such treatment.

A therapeutically effective amount can be readily determined by the attending diagnostician, as one skilled in the art, by the use of conventional techniques and by observing results obtained under analogous circumstances. In determining the therapeutically effective amount, a number of factors are considered by the attending diagnostician, including, but not limited to: the species of subject; its size, age, and general health; the specific disease involved; the degree of involvement or the severity of the disease; the response of the individual subject; the particular compound administered; the mode of administration; the bioavailability characteristic of the preparation administered; the dose regimen selected; the use of concomitant medication; and other relevant circumstances.

The amount of a compound of formula (I), which is required to achieve the desired biological effect, will vary depending upon a number of factors, including the dosage of the drug to be administered, the chemical characteristics (e.g. hydrophobicity) of the compounds employed, the potency of the compounds, the type of disease, the diseased state of the patient and the route of administration.

"Pharmaceutically" or "pharmaceutically acceptable" refer to molecular entities and compositions that do not produce an adverse, allergic or other untoward reaction when administered to an animal, or a human, as appropriate.

As used herein, "pharmaceutically acceptable carrier" includes any diluents, adjuvants, excipients, or vehicles, such as preserving agents, fillers, disintegrating agents, wetting agents, emulsifying agents, suspending agents, solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

In the context of the invention, the term "treating" or "treatment", as used herein, means reversing, alleviating, inhibiting the progress of, or preventing the disorder or condition to which such term applies, or one or more symptoms of such disorder or condition.

"Therapeutically effective amount" means an amount of a compound/medicament according to the present invention effective in producing the desired therapeutic effect.

According to the invention, the term "patient", or "patient in need thereof", is intended for a human or non-human mammal affected or likely to be affected with a neuropsychological disorder. Preferably, the patient is a human.

In general terms, the compounds of this invention may be provided in an aqueous physiological buffer solution containing 0.1 to 10% w/v compound for parenteral administration. Typical dose ranges are from 1 µg/kg to 0.1 g/kg of body weight per day; a preferred dose range is from 0.01 mg/kg to 10 mg/kg of body weight per day. A preferred daily dose for adult humans includes 5, 50, 100 and 200 mg, and an equivalent dose in a human child. The preferred dosage of drug to be administered is likely to depend on such variables as the type and extent of progression of the disease or disorder, the overall health status of the particular patient, the relative biological efficacy of the compound selected, and formulation of the compound excipient, and its route of administration.

The compounds of the present invention are capable of being administered in unit dose forms, wherein the term "unit dose" means a single dose which is capable of being administered to a patient, and which can be readily handled and packaged, remaining as a physically and chemically stable unit dose comprising either the active compound itself, or as a pharmaceutically acceptable composition, as described hereinafter. As such, typical daily dose ranges are from 0.01 to 10 mg/kg of body weight. By way of general guidance, unit doses for humans range from 0.1 mg to 1000 mg per day. Preferably the unit dose range is from 1 to 500 mg administered one to four times a day, and even more preferably from 10 mg to 300 mg, two times a day. Compounds provided herein can be formulated into pharmaceutical compositions by admixture with one or more pharmaceutically acceptable excipients. Such compositions may be prepared for use in oral administration, particularly in the form of tablets or capsules; or parenteral administration, particularly in the form of liquid solutions, suspensions or emulsions; or intranasally, particularly in the form of powders, nasal drops, or aerosols; or dermally, for example, topically or via trans-dermal patches.

The compositions may conveniently be administered in unit dosage form and may be prepared by any of the methods well known in the pharmaceutical art, for example, as described in *Remington: The Science and Practice of Pharmacy,* 20$^{th}$ ed.; Gennaro, A. R., Ed.; Lippincoft Williams & Wilkins: Philadelphia, Pa., 2000. Pharmaceutically compatible binding agents and/or adjuvant materials can be included as part of the composition. Oral compositions will generally include an inert diluent carrier or an edible carrier.

The tablets, pills, powders, capsules, troches and the like can contain one or more of any of the following ingredients, or compounds of a similar nature: a binder such as microcrystalline cellulose, or gum tragacanth; a diluent such as starch or lactose; a disintegrant such as starch and cellulose derivatives; a lubricant such as magnesium stearate; a glidant such as colloidal silicon dioxide; a sweetening agent such as sucrose or saccharin; or a flavoring agent such as peppermint, or methyl salicylate. Capsules can be in the form of a hard capsule or soft capsule, which are generally made from gelatin blends optionally blended with plasticizers, as well as a starch capsule. In addition, dosage unit forms can contain various other materials that modify the physical form of the dosage unit, for example, coatings of sugar, shellac, or enteric agents. Other oral dosage forms syrup or elixir may contain sweetening agents, preservatives, dyes, colorings, and flavorings. In addition, the active compounds may be incorporated into fast dissolve, modified-release or sustained-release preparations and formulations, and wherein such sustained-release formulations are preferably bi-modal.

Preferred formulations include pharmaceutical compositions in which a compound of the present invention is formulated for oral or parenteral administration, or more preferably those in which a compound of the present invention is formulated as a tablet. Preferred tablets contain lactose, cornstarch, magnesium silicate, croscarmellose sodium, povidone, magnesium stearate, or talc in any combination. It is also an aspect of the present disclosure that a compound of the present invention may be incorporated into a food product or a liquid.

Liquid preparations for administration include sterile aqueous or non-aqueous solutions, suspensions, and emulsions. The liquid compositions may also include binders, buffers, preservatives, chelating agents, sweetening, flavoring and coloring agents, and the like. Non-aqueous solvents include alcohols, propylene glycol, polyethylene glycol, vegetable oils such as olive oil, and organic esters such as ethyl oleate. Aqueous carriers include mixtures of alcohols and water, buffered media, and saline. In particular, biocompatible, biodegradable lactide polymer, lactide/glycolide copolymer, or polyoxyethylene-polyoxypropylene copolymers may be useful excipients to control the release of the active compounds. Intravenous vehicles can include fluid and nutrient replenishers, electrolyte replenishers, such as those based on Ringer's dextrose, and the like. Other potentially useful parenteral delivery systems for these active compounds include ethylene-vinyl acetate copolymer particles, osmotic pumps, implantable infusion systems, and liposomes.

Alternative modes of administration include formulations for inhalation, which include such means as dry powder, aerosol, or drops. They may be aqueous solutions containing, for example, polyoxyethylene-9-lauryl ether, glycocholate and deoxycholate, or oily solutions for administration in the form of nasal drops, or as a gel to be applied intranasally. Formulations for buccal administration include, for example, lozenges or pastilles and may also include a flavored base, such as sucrose or acacia, and other excipients such as glycocholate. Formulations suitable for rectal administration are preferably presented as unit-dose suppositories, with a solid based carrier, such as cocoa buffer, and may include a salicylate. Formulations for topical application to the skin preferably take the form of an ointment, cream, lotion, paste, gel, spray, aerosol, or oil. Carriers which can be used include petroleum jelly, lanolin, polyethylene glycols, alcohols, or their combinations. Formulations suitable for transdermal administration can be presented as discrete patches and can be lipophilic emulsions or buffered, aqueous solutions, dissolved and/or dispersed in a polymer or an adhesive.

The following examples illustrate the invention, but do not limit it. The starting products used are products which are known or prepared using known methods.

Unless otherwise stated, percentages are weight percentages.

EXAMPLES

Melting points are determined on Buchi capillary melting point apparatus.

Proton NMR spectra are recorded on a Bruker 250 MHz NMR instrument. Deuterochloroform is used as solvent unless otherwise stated. The chemicals shifts δ are expressed in ppm. The following abbreviations are used to denote signal patterns: s=singlet, d=doublet, t=triplet, q=quadruplet, m=multiplet, ms=massif. The coupling contents are expressed in Hz. The spectra recorded are consistent with the proposed structures.

TLC are performed on 0.25 mm silica gel F254 plates.

Arylpiperazines are commercially available or can be prepared according to methods described in French patent applications FR 04 11303 and FR 04 12763. The 2,4-di-tert-butyl-6-piperazin-1-ylpyrimidine and 2-tert-butyl-6-trifluoromethyl-4-piperazin-1-ylpyrimidine can be prepared according to US 2004/0259882 A1, 1-(6-trifluoromethyl-benzo[b]thiophene-3yl)piperazine (WO 02/066469); N-(3-piperazin-1-ylphenyl)methanesulfonamide (*Pharmazie*, 57, (8), 515-518, (2002)).

The 4-aryl-3,6-dihydro-2H-pyridine and 4-arylpiperidine are commercially available or can be prepared according to methods described in French application FR 04 12763.

The 1,2,3,4-tetrahydroisoquinoline-7-carbonitrile can be prepared according to *Synth. Commun.*, 25, (20), 3255-3261, (2001).

3-Oxazol-2-ylaniline can be prepared according to *J. Org. Chem.* 42, (19), 3208-3209, (1977).

The carboxylic acid derivatives are commercially available or prepared. The 3-cyanopropanoic acid can be prepared from β-propanolactone according to *J. Am. Chem. Soc.*, 74, 1323, (1952); 4-cyanobutanoic acid (*J. Org. Chem.*, 61, (19), 6486-6487, (1996); 2-methoxy-2-methylpropanoic (*Tetrahedron*, 53, (42), 14286, (1997)); 2-isopropoxyacetic acid (*Tetrahedron*, 59, 7915-7920, (2003); 2-tert-butoxyacetic acid (*Bioorg. Med. Chem.* 11, 4287-4293, (2003); cyanodimethylacetic acid (*J. Org. Chem.*, 46, (24), 4907-4911, (1981); methanesulfonylacetic acid, (*Arch. Pharm. Med. Chem.* 333, 293-298, (2000)); 5,6-dihydro-4H-pyran-3-carboxylic acid and 4,5-dihydrofuran-3-carboxylic acid (*Synthesis*, 12, 1016-1017, (1986)); 5-cyanopentanoic acid, (*Tetrahedron*, 48, 43, 9531-9536, (1992)); (2-cyanoethoxy)acetic acid, U.S. Pat. No. 4,105,687.

Some acids have been prepared by usual saponification of the corresponding ethyl ester with aqueous sodium hydroxide solution: trans-2-cyanocyclopropanecarboxylic acid from trans-2-cyanocyclopropanecarboxylic acid ethyl ester (*Synthesis*, 301-303, (1982)); 5-cyano-2,2-difluoropentanoic acid from 5-cyano-2,2-difluoro-pentanoic acid ethyl ester (*J. Fluorine Chem.* 121, 105-107, (2003)).

Preparation A: 1-[2-(1,4-dioxaspiro[4.5]dec-8-yl)ethyl]-4-(3-hydroxymethylphenyl)piperazine

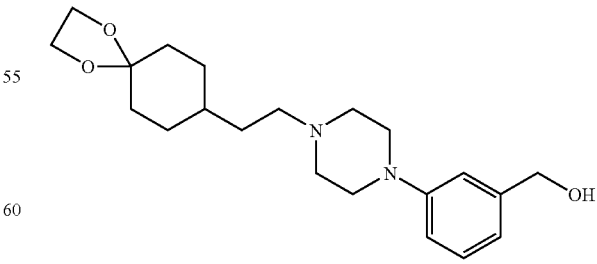

To a cooled solution of 2.5 g (6.25 mmol) of 1-[2-(1,4-dioxaspiro[4.5]dec-8-yl)ethyl]-4-(3-ethoxycarbonylphenyl)piperazine (prepared by path II), is added, under argon, 0.36 g (9.36 mmol) of lithium aluminum hydride. The suspension is stirred overnight at room temperature. Hydrolysis is performed at 0° C. by slow addition of 0.35 mL of water, 0.35 mL of 15% aqueous sodium hydroxide solution and 1.0 mL of water. The slurry is stirred for 15 minutes at room temperature then magnesium sulfate is added. The mixture is filtered and the salts are washed with ethyl acetate. The filtrate is concentrated under reduced pressure to give 2.0 g (89%) of 1-[2-(1,4-dioxaspiro[4.5]dec-8-yl)ethyl]-4-(3-hydroxymethylphenyl)piperazine as a solid.

¹H NMR: 7.25 (t, 1H, J=7.5); 6.95 (s, 1H); 6.9 to 6.8 (ms, 2H); 4.65 (s, 2H); 3.95 (s, 4H); 3.2 (m, 4H); 2.6 (m, 4H); 2.4 (m, 2H); 2.0 (broad s, 1H); 1.85 to 1.65 (ms, 4H); 1.65 to 1.4 (ms, 3H); 1.4 to 1.2 (ms, 4H)

Preparation B: 1-[2-(1,4-dioxaspiro[4.5]dec-8-yl)ethyl]-4-(3-methoxymethylphenyl)piperazine

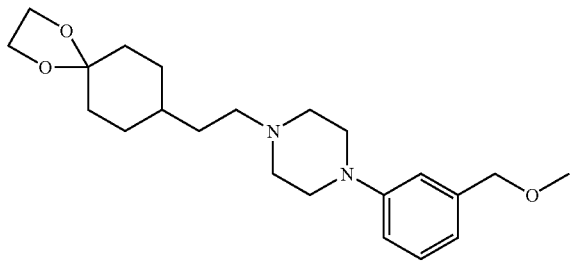 [SMILES: COCc1cccc(N2CCN(CCC3CCC4(CC3)OCCO4)CC2)c1]

To a solution of 1.2 g (3.42 mmol) of 1-[2-(1,4-dioxaspiro[4.5]dec-8-yl)ethyl]-4-(3-hydroxymethylphenyl)piperazine (preparation A) in 15 mL of dimethyl sulfoxide are added, at room temperature, 1.0 g (17.2 mmol) of potassium fluoride, 0.52 g (3.66 mmol) of iodomethane and 0.68 g (10.3 mmol) of potassium hydroxide. The mixture is stirred overnight at room temperature, partitioned between with ethyl acetate and water. The aqueous phase is separated and the organic phase is washed with water, dried over magnesium sulfate, filtered and concentrated. The oily residue is purified by chromatography over silica gel (eluant hetane/ethyl acetate 1/1) to give 0.3 g of 1-[2-(1,4-dioxaspiro[4.5]dec-8-yl)ethyl]-4-(3-methoxymethylphenyl)piperazine as an oil.

¹H NMR: 7.25 (t, 1H, J=7.5); 6.9 (s, 1H); 6.9 to 6.75 (ms, 2H); 4.4 (s, 2H); 3.95 (s, 4H); 3.35 (s, 3H); 3.2 (m, 4H); 2.6 (m, 4H); 2.45 (m, 2H); 1.85 to 1.65 (ms, 4H); 1.65 to 1.4 (ms, 3H); 1.4 to 1.2 (ms, 4H)

Preparation C: 1-[2-(1,4-dioxaspiro[4.5]dec-8-yl)ethyl]-4-(3-(1-hydroxyethyl)phenyl)piperazine

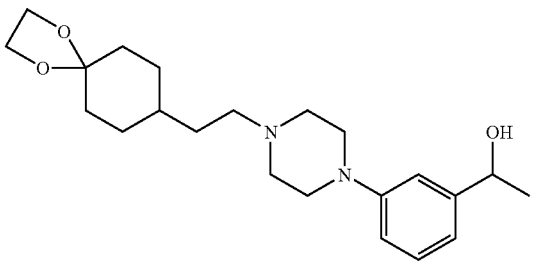 [SMILES: CC(O)c1cccc(N2CCN(CCC3CCC4(CC3)OCCO4)CC2)c1]

To a cooled solution of 1.6 g (4.3 mmol) of 1-[2-(1,4-dioxaspiro[4.5]dec-8-yl)ethyl]-4-(3-acetylphenyl)piperazine (prepared by path II) in 15 mL of methanol is added, by portion, 0.18 g (4.7 mmol) of sodium borohydride. The mixture is stirred for 3 hours at room temperature. Methanol is evaporated under reduced pressure and the residue is taken off with water and extracted twice with ethyl acetate. The organic phases are combined, washed with water, then brine, dried over magnesium sulfate, filtered and concentrated to give 1.61 g (100%) of 1-[2-(1,4-dioxaspiro[4.5]dec-8-yl)ethyl]-4-(3-(1-hydroxyethyl)phenyl)piperazine as an oil.

¹H NMR: 7.25 (t, 1H, J=7.5); 7.0 (s, 1H); 6.9 to 6.75 (ms, 2H); 4.85 (q, 1H, J=7.5); 3.95 (s, 4H); 3.2 (m, 4H); 2.6 (m, 4H); 2.4 (m, 2H); 2.0 (broad s, 1H); 1.8 to 1.65 (ms, 4H); 1.6 to 1.4 (ms, 7H); 1.4 to 1.2 (ms, 3H)

Preparation D:
1-[3-(1,1-difluoroethyl)phenyl]piperazine, hydrochloride

Step 1: 1-(1,1-difluoroethyl)-3-nitrobenzene

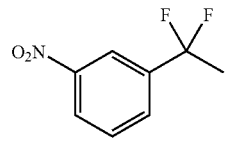

A mixture of 2.0 g (12 mmol) of 1-(3-nitrophenyl)ethanone and 7.4 g (16.7 mmol) of 50% bis(2-methoxyethyl)aminosulfurtrifluoride solution in toluene is warmed to 80° C. overnight. The mixture is slowly poured into cooled water and extracted twice with ethyl acetate. The organic phases are combined, washed with an aqueous saturated sodium hydrogen carbonate solution, then with brine, dried over magnesium sulfate, filtered and concentrated under reduced pressure. The residue (2.5 g) is purified over 160 g of silica gel (eluant heptane/ethyl acetate 85/15) to give 1.6 g (71%) of 1-(1,1-difluoroethyl)-3-nitrobenzene as an oil.

¹H NMR: 8.4 (s, 1H); 8.3 (d, 1H, J=7.5); 7.9 (d, 1H, J=7.5); 7.65 (t, 1H, J=7.5); 2.0 (t, 3H, J=17.5)

Step 2: 3-(1,1-difluoroethyl)aniline

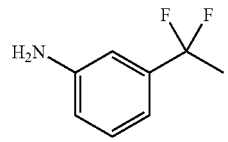

A mixture of 3.0 g (16 mmol) of 1-(1,1-difluoroethyl)-3-nitrobenzene, 18.0 g (80 mmol) of tin chloride dihydrate and 50 mL of ethanol is refluxed for one hour. The mixture is slowly poured on cooled water. The pH is adjusted to 7 by addition of an aqueous 10N solution of sodium hydroxide, then adjusted to 9 by addition of an aqueous saturated solution of sodium hydrogen carbonate. The product is extracted 4 times with ethyl acetate. The organic phases are combined, dried over magnesium sulfate, filtered and concentrated under reduced pressure. The oily residue (2.2 g) is purified over 100 g of silica gel (eluant heptane/ethyl acetate 2/1) to give 1.7 g (68%) of 3-(1,1-difluoroethyl)aniline as an oil.

$^1$H NMR: 7.2 (t, 1H, J=7.5); 6.9 (d, 1H, J=7.5); 6.8 (s, 1H); 6.9 (d, 1H, J=7.5); 3.8 (broad s, 2H); 1.9 (t, 3H, J=17.5)

Step 3: 1-[3-(1,1-difluoroethyl)phenyl]piperazine, hydrochloride

A mixture of 2.5 g (15.9 mmol) of 3-(1,1-difluoroethyl) aniline and 2.8 g (15.9 mmol) of bis(2-chloroethyl)amine in 20 mL of chlorobenzene is refluxed overnight. After cooling to room temperature, diethyl ether is added and precipitation occurs. The solid is filtered, washed with diethyl ether and dried under reduced pressure to give 3.8 g (90%) of 1-[3-(1,1-difluoro-ethyl)phenyl]piperazine, hydrochloride as a white solid.

$^1$H NMR (DMSO D$_6$): 9.2 (broad s, 2H); 7.3 (t, 1H, J=7.5); 7.15 to 6.95 (ms, 2H); 7.0 (d, 1H, J=7.5); 3.4 (m, 4H); 3.2 (m, 4H); 1.9 (t, 3H, J=14.5)

Preparation E:
1-(3-difluoromethylphenyl)piperazine, hydrochloride

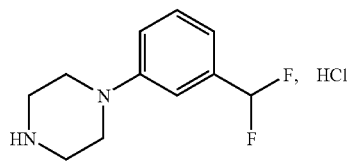

Step 1: 1-difluoromethyl-3-nitrobenzene

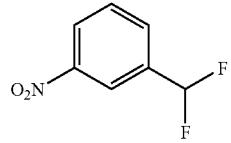 [SMILES: O=[N+]([O-])c1cccc(C(F)F)c1]

To a solution of 2.6 g (17 mmol) of 3-nitrobenzaldehyde in 5 mL of dichloromethane is added 11.4 mL of 50% bis(2-methoxyethyl)aminosulfurtrifluoride solution in toluene. The mixture is stirred overnight at room temperature, washed twice with a saturated aqueous sodium hydrogen carbonate solution then with brine, dried over magnesium sulfate, filtered and concentrated under reduced pressure. The residue is purified over 150 g of silica gel (eluant heptane/ethyl acetate 85/15) to give 2.3 g (78%) of 1-difluoromethyl-3-nitrobenzene as an oil.

$^1$H NMR: 8.4 (s, 1H); 8.35 (d, 1H, J=7.5); 7.9 (d, 1H, J=7.5); 7.7 (t, 1H, J=7.5); 7.0 (t, 1H, J=55)

Step 2: 1-(3-difluoromethylphenyl)piperazine, hydrochloride

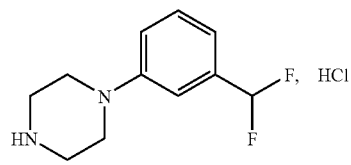

The 1-(3-difluoromethylphenyl)piperazine, hydrochloride is obtained from 1-difluoromethyl-3-nitrobenzene using the procedure described in preparation D, steps 2 and 3.

$^1$H NMR (DMSO D$_6$): 9.25 (broad s, 2H); 7.35 (m, 1H); 7.2 (m, 2H); 7.0 (d, 1H, J=7.5); 6.9 (t, 1H, J=55); 3.4 (m, 4H); 3.2 (m, 4H)

Preparation F: 1-(3-{4-[2-(1,4-dioxaspiro[4.5]dec-8-yl)ethyl]piperazin-1-yl}phenyl)propan-1-ol

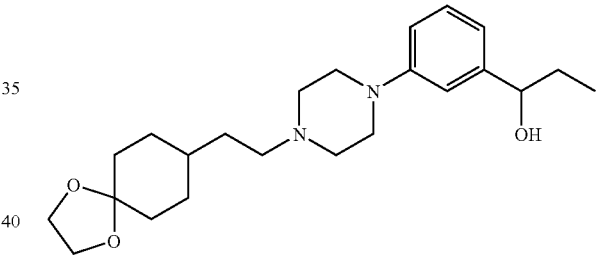

Step 1: 3-{4-[2-(1,4-dioxaspiro[4.5]dec-8-yl)ethyl] piperazin-1-yl}benzoic acid

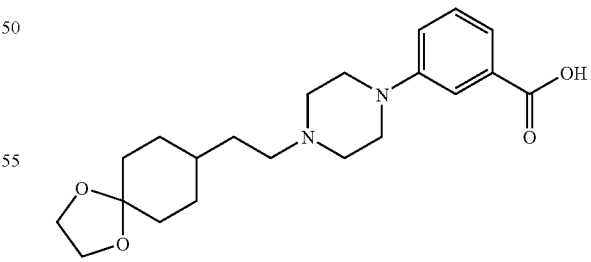

To a solution of 3.75 g (9.3 mmol) of 3-{4-[2-(1,4-dioxaspiro[4.5]dec-8-yl)ethyl]piperazin-1-yl}benzoic acid ethyl ester in 20 mL of ethanol are added 10.2 mL of an aqueous 1N sodium hydroxide solution. Stirring is maintained overnight. The mixture is cooled and 2.55 mL (10.2 mmol) of 4N hydrochloric acid solution are added. After evaporation under reduced pressure, the solid is taken off with ethyl acetate, filtered and dried at 50° C. under vacuum to give 3.7 g of crude 3-{4-[2-(1,4-dioxaspiro[4.5]dec-8-yl)ethyl]piperazin-1-yl}benzoic acid.

Step 2: 3-{4-[2-(1,4-dioxaspiro[4.5]dec-8-yl)ethyl]piperazin-1-yl}-N-methoxy-N-methylbenzamide

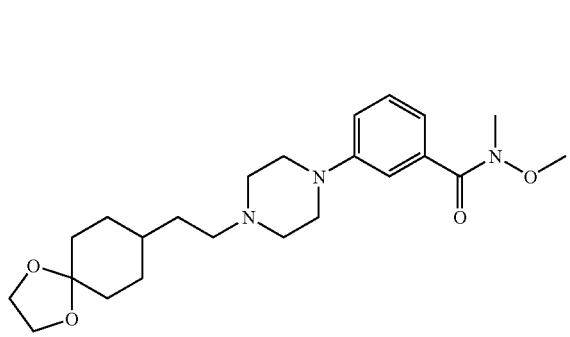 [SMILES: CON(C)C(=O)c1cccc(N2CCN(CCC3CCC4(CC3)OCCO4)CC2)c1]

The 3-{4-[2-(1,4-dioxaspiro[4.5]dec-8-yl)ethyl]piperazin-1-yl}-N-methoxy-N-methylbenzamide is obtained from 3-{4-[2-(1,4-dioxa-spiro[4.5]dec-8-yl)ethyl]piperazin-1-yl}benzoic acid using the procedure described in example 4, step c giving the title compound in 85% yield.

¹H NMR: 7.25 (m, 1H); 7.2 (m, 1H); 7.15 (m, 1H); 7.0 (m, 1H); 3.95 (s, 4H); 3.6 (s, 3H); 3.35 (s, 3H); 3.3 (m, 4H); 2.65 (m, 4H); 2.45 (m, 2H); 1.75 (m, 4H); 1.65 to 1.4 (ms, 4H); 1.4 to 1.2 (ms, 3H)

Step 3: 1-(3-{4-[2-(1,4-dioxaspiro[4.5]dec-8-yl)ethyl]piperazin-1-yl}phenyl)propan-1-one

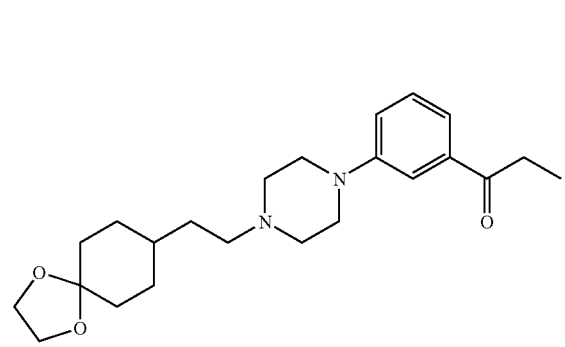 [SMILES: CCC(=O)c1cccc(N2CCN(CCC3CCC4(CC3)OCCO4)CC2)c1]

To a solution of 1.6 g (3.8 mmol) of 3-{4-[2-(1,4-dioxaspiro[4.5]dec-8-yl)ethyl]piperazin-1-yl}-N-methoxy-N-methylbenzamide in 25 mL of dry tetrahydrofuran cooled to 0° C. are added 8 mL of 1M ethylmagnesium bromide solution in tetrahydrofuran. The mixture is stirred for 90 minutes then poured in 100 mL of an aqueous saturated sodium hydrogen carbonate solution. The product is extracted twice with ethyl acetate. The organic phases are combined, dried over magnesium sulfate, filtered and concentrated under reduced pressure. The residue (1.4 g) is purified over 50 g of silica gel (eluant heptane/ethyl acetate 1/1) to give 1.06 g (72%) of 1-(3-{4-[2-(1,4-dioxaspiro[4.5]dec-8-yl)ethyl]piperazin-1-yl}phenyl)propan-1-one as an oil.

¹H NMR: 7.55 (s, 1H); 7.45 (m, 1H); 7.35 (t, 1H, J=7.5); 7.15 (m, 1H); 3.95 (s, 4H); 3.3 (m, 4H); 3.0 (q, 2H, J=7.5); 2.65 (m, 4H); 2.5 (m, 2H); 1.8 (m, 4H); 1.7 to 1.35 (ms, 4H); 1.35 to 1.25 (ms, 3H); 1.2 (t, 3H, J=7.5)

Step 4: 1-(3-{4-[2-(1,4-dioxaspiro[4.5]dec-8-yl)ethyl]piperazin-1-yl}phenyl)propan-1-ol

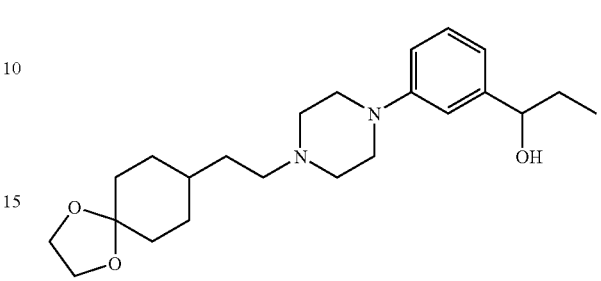

The 1-(3-{4-[2-(1,4-dioxaspiro[4.5]dec-8-yl)ethyl]piperazin-1-yl}phenyl)propan-1-ol is prepared from 1-(3-{4-[2-(1,4-dioxaspiro[4.5]dec-8-yl)ethyl]piperazin-1-yl}phenyl)propan-1-one using the procedure described in preparation C.

¹H NMR: 7.25 (t, 1H, J=7.5); 6.95 (s, 1H); 6.9 to 6.75 (ms, 2H); 4.55 (m, 1H); 3.95 (s, 4H); 3.25 (m, 4H); 2.65 (m, 4H); 2.5 (m, 2H); 2.0 (m, 1H); 1.9 to 1.75 (ms, 6H); 1.65 to 1.4 (ms, 5H); 1.4 to 1.2 (ms, 5H)

Preparation G: 1-(3-{4-[2-(1,4-dioxaspiro[4.5]dec-8-yl)ethyl]piperazin-1-yl}phenyl)-2-methylpropan-1-ol

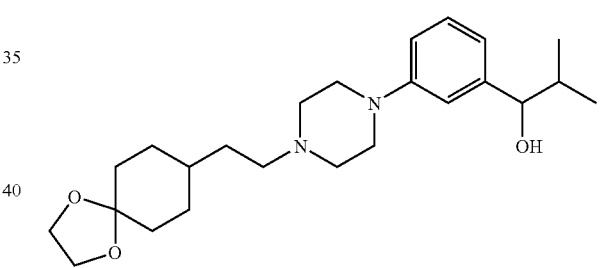

Step 1: 1-(3-{4-[2-(1,4-dioxaspiro[4.5]dec-8-yl)ethyl]piperazin-1-yl}phenyl)-2-methylpropan-1-one

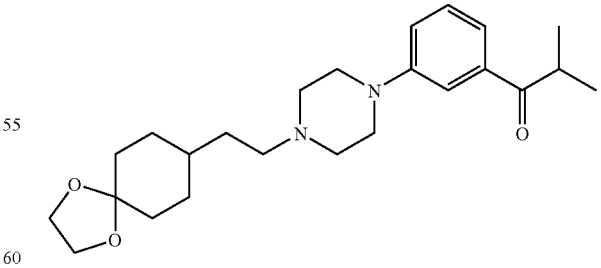

The 1-(3-{4-[2-(1,4-dioxaspiro[4.5]dec-8-yl)ethyl]piperazin-1-yl}phenyl)-2-methylpropan-1-one is prepared by addition of isopropylmagnesium bromide onto 3-{4-[2-(1,4-dioxaspiro[4.5]dec-8-yl)ethyl]piperazin-1-yl}-N-methoxy-N-methylbenzamide using the procedure described in preparation F, step 3, to give the title compound in 27% yield.

¹H NMR: 7.5 (s, 1H); 7.4 to 7.25 (ms, 2H); 7.1 (d, 1H, J=7.5); 3.95 (s, 4H); 3.55 (m, 1H); 3.35 (m, 4H); 2.7 (m, 4H); 2.55 (m, 2H); 1.75 (m, 4H); 1.65 to 1.45 (ms, 5H); 1.45 to 1.2 (ms, 8H)

Step 2: 1-(3-{4-[2-(1,4-dioxaspiro[4.5]dec-8-yl) ethyl]piperazin-1-yl}phenyl)-2-methylpropan-1-ol

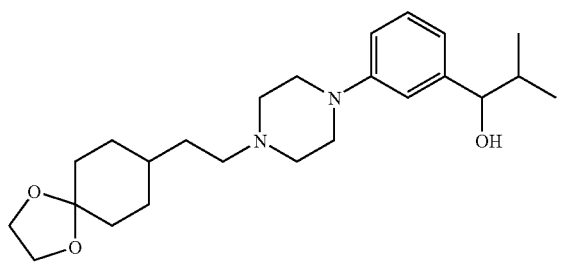 [SMILES: CC(C)C(O)c1cccc(N2CCN(CCC3CCC4(CC3)OCCO4)CC2)c1]

The 1-(3-{4-[2-(1,4-dioxaspiro[4.5]dec-8-yl)ethyl]piperazin-1-yl}phenyl)-2-methylpropan-1-ol is prepared from 1-(3-{4-[2-(1,4-dioxaspiro[4.5]dec-8-yl)ethyl]piperazin-1-yl}phenyl)-2-methylpropan-1-one using the procedure described in preparation C.

¹H NMR: 7.25 (t, 1H, J=7.5); 6.9 (s, H); 6.9 to 6.75 (m, 2H); 4.3 (m, 1H); 3.95 (s, 4H); 3.35 (m, 4H); 2.8 (m, 4H); 2.65 (m, 2H); 1.95 (m, 1H); 1.85 (m, 1H); 1.8 to 1.2 (ms, 11H); 1.0 (d, 3H, J=7.5); 0.8 (d, 3H, J=7.5)

Preparation H: 4-(2-{4-[3-(methoxymethylcarbamoyl)phenyl]piperazin-1-yl}ethyl)piperidine-1-carboxylic acid tert-butyl ester

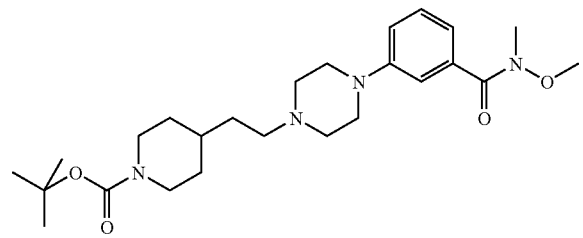 [SMILES: CON(C)C(=O)c1cccc(N2CCN(CCC3CCN(C(=O)OC(C)(C)C)CC3)CC2)c1]

Step 1: 4-{2-[4-(3-carboxyphenyl)piperazin-1-yl]ethyl}piperidine-1-carboxylic acid tert-butyl ester

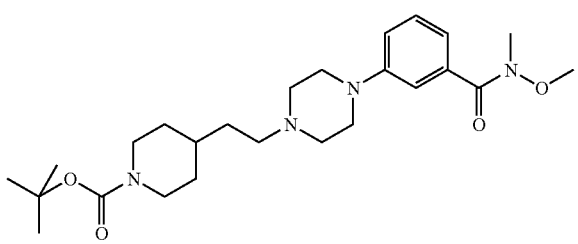 [SMILES: CON(C)C(=O)c1cccc(N2CCN(CCC3CCN(C(=O)OC(C)(C)C)CC3)CC2)c1]

To a solution of 2.8 g (12.8 mmol) of 4-{2-[4-(3-ethoxycarbonylphenyl)piperazin-1-yl]ethyl}piperidine-1-carboxylic acid tert-butyl ester are added 12.8 mL of 1N aqueous sodium hydroxide solution. The mixture is stirred overnight at room temperature then concentrated under reduced pressure. The residue is acidified with 12.8 mL of 1N aqueous hydrochloric acid solution. The product is extracted with ethyl acetate, washed with water, dried over magnesium sulfate, filtered and concentrated under reduced pressure to give 2.5 g (47%) of 4-{2-[4-(3-carboxyphenyl)piperazin-1-yl]ethyl}piperidine-1-carboxylic acid tert-butyl ester.

¹H NMR: 8.5 (broad s, 1H); 7.7 to 7.5 (ms, 2H); 7.3 (t, 1H, J=7.5); 7.1 (d, 1H, J=7.5); 4.1 (m, 2H); 3.45 (m, 4H); 3.1 (m, 4H); 2.85 (m, 2H); 2.7 (m, 2H); 1.7 (m, 2H); 1.65 to 1.35 (ms, 12H); 1.3 to 1.0 (ms, 2H)

Step 2: 4-[2-(4-{3-[methoxy(methyl)carbamoyl]phenyl}piperazin-1-yl)ethyl]piperidine-1-carboxylic acid tert-butyl ester

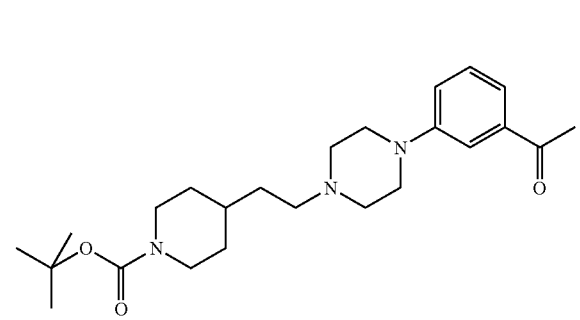 [SMILES: CC(=O)c1cccc(N2CCN(CCC3CCN(C(=O)OC(C)(C)C)CC3)CC2)c1]

The 4-[2-(4-{3-[methoxy(methyl)carbamoyl]phenyl} piperazin-1-yl)ethyl]piperidine-1-carboxylic acid tert-butyl ester is prepared from 4-{2-[4-(3-carboxyphenyl)piperazin-1-yl]ethyl}piperidine-1-carboxylic acid tert-butyl ester using the procedure described in preparation F, step 2.

¹H NMR: 7.25 (t, 1H, J=7.5); 7.2 (s, 1H); 7.1 (d, 1H, J=7.5), 7.0 (d, 1H, J=7.5); 4.1 (m, 2H); 3.6 (s, 3H); 3.3 (s, 3H); 3.2 (m, 4H); 2.8 to 2.5 (m, 6H); 2.4 (m, 2H); 1.7 (m, 2H); 1.65 to 1.2 (ms, 12H); 1.3 to 1.0 (ms, 2H)

Preparations I, J and K:

Starting from 4-[2-(4-{3-[methoxy(methyl)carbamoyl]phenyl}piperazin-1-yl)ethyl]-piperidine-1-carboxylic acid tert-butyl ester and using the procedure described in preparation F, step 3, the following compounds are obtained:

Preparation I: 4-{2-[4-(3-acetylphenyl)piperazin-1-yl]ethyl}piperidine-1-carboxylic acid tert-butyl ester

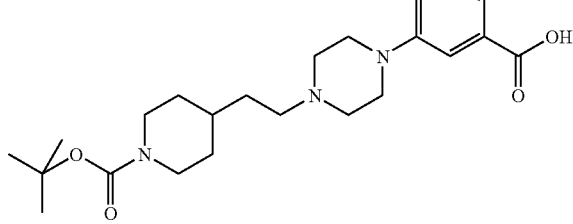

A solution of methylmagnesium chloride is used.

Yield: 88%

¹H NMR: 7.5 (s, 1H); 7.4 (d, 1H, J=7.5); 7.35 (t, 1H, J=7.5); 7.15 (d, 1H, J=7.5); 4.1 (m, 2H); 3.3 (m, 4H); 1.7 (m,

2H); 1.65 to 1.55 (ms, 7H); 2.45 (m, 2H); 1.7 (m, 2H); 1.6 to 1.35 (ms, 12H); 1.25 to 1.0 (ms, 2H)

Preparation J: 4-{2-[4-(3-propanoylphenyl)piperazin-1-yl]ethyl}piperidine-1-carboxylic acid tert-butyl ester

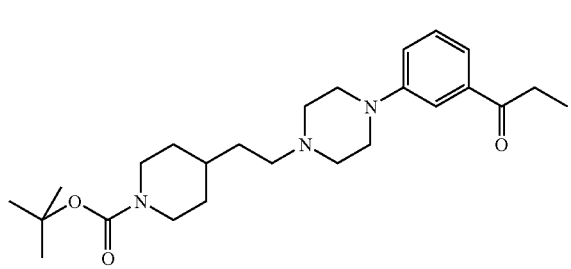 [SMILES: CCC(=O)c1cccc(N2CCN(CCC3CCN(C(=O)OC(C)(C)C)CC3)CC2)c1]

A solution of ethylmagnesium bromide is used.

Yield: 80%

$^1$H NMR: 7.55 (s, 1H); 7.4 (d, 1H, J=7.5); 7.3 (t, 1H, J=7.5); 7.1 (d, 1H, J=7.5); 4.1 (m, 2H); 3.3 (m, 4H); 3.0 (q, 2H, J=7.5); 3.7 (m, 2H); 2.6 (m, 4H); 2.45 (m, 2H); 1.65 (m, 2H); 1.6 to 1.35 (ms, 12H); 1.3 to 1.0 (ms, 5H)

Preparation K: 4-{2-[4-(3-isobutanylphenyl)piperazin-1-yl]ethyl}piperidine-1-carboxylic acid tert-butyl ester

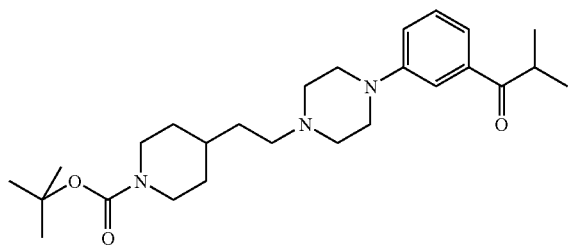 [SMILES: CC(C)C(=O)c1cccc(N2CCN(CCC3CCN(C(=O)OC(C)(C)C)CC3)CC2)c1]

A solution of isopropylmagnesium bromide is used.

Yield: 60%

$^1$H NMR: 7.5 (s, 1H); 7.5 to 7.25 (ms, 2H); 7.1 (d, 1H, J=7.5); 4.1 (m, 2H); 3.55 (m, 1H); 3.3 (m, 4H); 2.7 (m, 2H); 2.6 (m, 4H); 2.45 (m, 2H); 1.7 (m, 2H); 1.6 to 1.35 (ms, 12H); 1.3 to 1.0 (ms, 8H)

Preparations L, M and N:

Starting from preparations I, J and K and using the reduction procedure described in preparation C, the following compounds are obtained:

Preparation L: 4-(2-{4-[3-(1-hydroxyethyl)phenyl]piperazin-1-yl}ethyl)piperidine-1-carboxylic acid tert-butyl ester

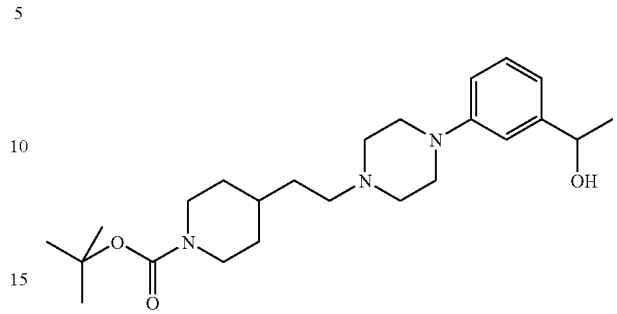

Yield: quantitative $^1$H NMR: 7.3 (t, 1H, J=7.5); 6.95 (s, 1H); 6.9 to 6.8 (ms, 2H); 4.85 (q, 1H, J=6.5); 4.1 (m, 2H); 3.25 (m, 4H); 2.7 (m, 2H); 2.6 (m, 4H); 2.55 (m, 2H); 1.85 (broad s, 1H); 1.7 (m, 2H); 1.55 to 1.4 (ms, 15H); 1.25 to 1.0 (ms, 2H)

Preparation M: 4-(2-{4-[3-(1-hydroxypropyl)phenyl]piperazin-1-yl}ethyl)piperidine-1-carboxylic acid tert-butyl ester

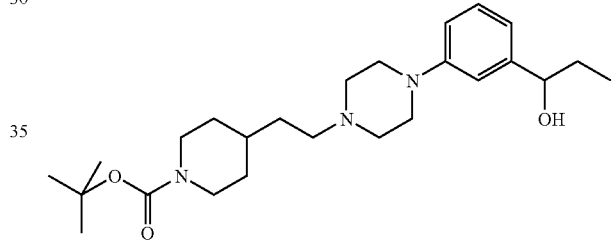

Yield: quantitative $^1$H NMR: 7.25 (t, 1H, J=7.5); 6.9 (s, 1H); 6.9 to 6.75 (ms, 2H); 4.55 (t, 1H, J=7.5); 4.1 (m, 2H); 3.2 (m, 4H); 1.7 (m, 2H); 2.6 (m, 2H); 2.45 (m, 4H); 1.95 to 1.6 (ms, 5H); 1.6 to 1.4 (ms, 12H); 1.3 to 1.05 (ms, 2H); 0.9 (t, 3H, J=7.5)

Preparation N: 4-(2-{4-[3-(1-hydroxy-2-methylpropyl)phenyl]piperazin-1-yl}ethyl)piperidine-1-carboxylic acid tert-butyl ester

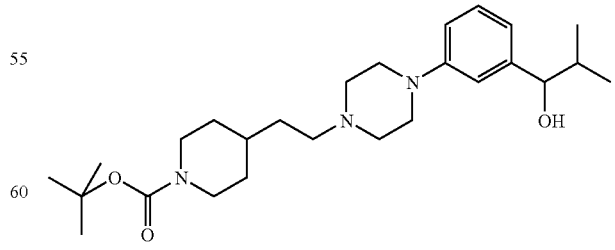

Yield: 78%

$^1$H NMR: 7.25 (t, 1H, J=7.5); 6.9 (s, 1H); 6.85 (d, 1H, J=7.5); 6.8 (d, 1H, J=7.5); 4.3 (d, 1H); 4.2 (m, 2H); 3.25 (m, 4H); 1.7 (m, 2H); 2.6 (m, 4H); 2.45 (m, 2H); 1.95 (m, 1H);

1.85 (broad s, 1H); 1.7 (m, 2H); 1.65 to 1.35 (ms, 12H); 1.3 to 1.05 (ms, 2H); 1.0 (d, 3H, J=7.5); 0.8 (d, 3H, J=7.5)

Preparation O: 4-{2-[4-(3-hydroxymethylphenyl)piperazin-1-yl]ethyl}piperidine-1-carboxylic acid tert-butyl ester

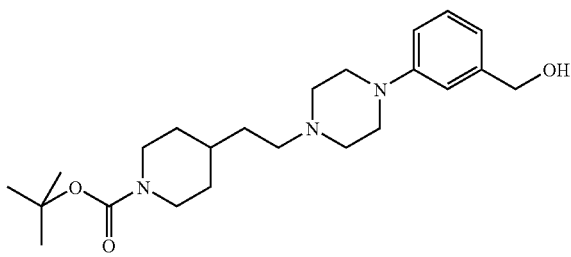 [SMILES: CC(C)(C)OC(=O)N1CCC(CCN2CCN(c3cccc(CO)c3)CC2)CC1]

A solution of 1.5 g (3.59 mmol) of 4-{2-[4-(3-carboxyphenyl)piperazin-1-yl]ethyl}piperidine-1-carboxylic acid tert-butyl ester in 20 mL of dry tetrahydrofuran is cooled to −10° C. under argon. An addition of 11 mL of a 1M solution of boranetetrahydrofuran complex in tetrahydrofuran is performed at −10° C. Stirring is maintained overnight at room temperature. The mixture is cooled to 0° C. and 12 mL of 1N aqueous sodium hydroxide solution are added. The product is extracted with ethyl acetate, washed with water, dried over magnesium sulfate, filtered and concentrated under reduced pressure. The residue is stirred with diisopropyl ether, filtered and dried under reduced pressure to give 1.0 g (69%) of 4-{2-[4-(3-hydroxymethylphenyl)piperazin-1-yl]ethyl}piperidine-1-carboxylic acid tert-butyl ester.

1H NMR: 7.25 (m, 1H); 6.95 (s, 1H); 6.9 to 6.75 (ms, 2H); 4.7 (s, 2H); 4.1 (m, 2H); 3.6 (m, 2H); 3.4 to 3.1 (ms, 4H); 3.0 to 2.8 (ms, 4H); 2.7 (m, 2H); 1.85 (m, 2H); 1.75 to 1.55 (ms, 3H); 1.55 to 1.3 (ms, 10H); 1.2 (m, 2H)

Preparation P: 4-{2-[4-(3-methoxymethylphenyl)piperazin-1-yl]ethyl}piperidine-1-carboxylic acid tert-butyl ester

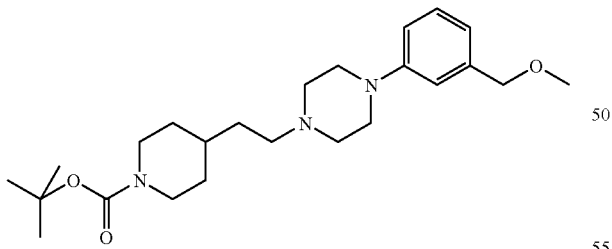

A solution of 0.4 g (1 mmol) of 4-{2-[4-(3-hydroxymethylphenyl)piperazin-1-yl]ethyl}piperidine-1-carboxylic acid tert-butyl ester in 10 mL of dry dimethyl sulfoxyde is cooled at a temperature close to 5° C. and 40 mg (1 mmol) of sodium hydride (60% suspension) is added. The mixture is stirred for 30 minutes at room temperature then 140 mg (1 mmol) of iodomethane are added and stirring is maintained overnight at room temperature. The mixture is concentrated under reduced pressure. The residue is dissolved in ethyl acetate, washed with water, dried over magnesium sulfate, filtered and concentrated under reduced pressure to give 0.3 g (73%) of crude 4-{2-[4-(3-methoxymethylphenyl)piperazin-1-yl]ethyl}piperidine-1-carboxylic acid tert-butyl ester which is used without purification in the next step.

TLC (eluant dichloromethane/methanol/ammonia solution 90/10/1): Rf: 0.6

Preparation Q: 2-isobutylaniline

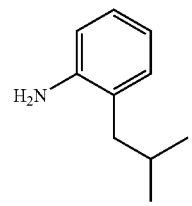

Step 1: 2-methyl-1-(2-nitrophenyl)propan-1-one and 2-methyl-1-(3-nitrophenyl)propan-1-one

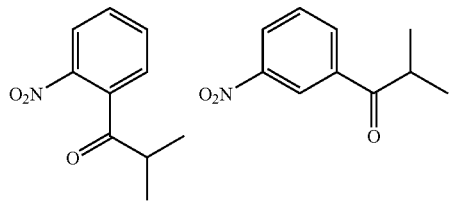

To a cooled solution of 14.8 g (100 mmol) of 2-methyl-1-phenylpropan-1-one in 2 mL of glacial acetic acid are added over a period of one hour, 90 g of fuming nitric acid. The mixture is stirred at 5° C. for 90 minutes then poured on crushed ice. The product is extracted 3 times with diethyl ether. The organic phases are combined, washed with an aqueous saturated sodium hydrogen carbonate solution, dried over magnesium sulfate, filtered and concentrated under reduced pressure. The oily residue (20 g) is purified over 350 g of silica gel (eluant heptane/ethyl acetate 4/1) to give a first crop of 7.1 g containing manly 2-methyl-1-(2-nitrophenyl)propan-1-one and a second crop of 10.2 g containing mainly 2-methyl-1-(3-nitrophenyl)propan-1-one. These two fractions were used without further purification in the next step.

Step 2: 2-isobutylaniline

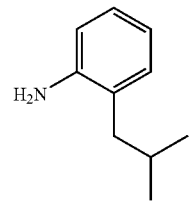

To a cooled solution of 5.7 g (29.5 mmol) of 2-methyl-1-(2-nitrophenyl)propan-1-one in 35 mL of ethanol and 7 mL of concentrated hydrochloric acid is added under inert atmosphere, 0.7 g of 10% palladium on activated carbon. The mixture is hydrogenated at 50° C. under 4 bar for 2 hours. The suspension is filtered over celite and the filtrate is concentrated under reduced pressure. The residue is dissolved in water, alcalinized to pH 9 with a concentrated solution of sodium hydroxide and extracted 3 times with ethyl acetate. The organic phases are combined, washed with water then with brine, dried over magnesium sulfate, filtered and concentrated under reduced pressure. The oily yellow residue (5 g) is purified over 150 g of silica gel (eluant heptane/ethyl acetate 2/1) to give 1.2 g (27%) of 2-isobutylaniline as an oil.

¹H NMR: 7.1 to 6.95 (ms, 2H); 6.8 to 6.65 (ms, 2H); 3.6 (broad s, 2H); 2.4 (d, 2H, J=7.5); 1.95 (m, 1H, J=7.5); 1.0 (d, 6H, J=7.5)

Preparation R: 3-isobutylaniline

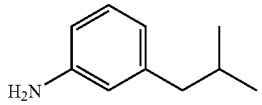

The 3-isobutylaniline is prepared by catalytic hydrogenation of 2-methyl-1-(3-nitrophenyl)propan-1-one using the procedure described for preparation O to give the title compound in 46% yield.

¹H NMR: 7.05 (t, 1H, J=7.5); 6.65 to 6.55 (m, 2H); 6.5 (s, 1H); 3.6 (broad s, 2H); 2.4 (d, 2H, J=7.5); 1.85 (m, 1H, J=7.5); 0.9 (d, 6H, J=7.5)

Preparation S: (3-{4-[2-(1,4-dioxaspiro[4.5]dec-8-yl)ethyl]piperazin-1-yl}phenyl)carbamic acid ethyl ester

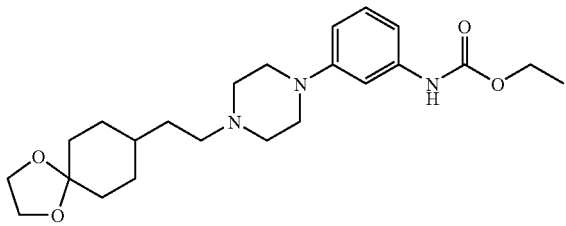 [SMILES: CCOC(=O)Nc1cccc(N2CCN(CCC3CCC4(CC3)OCCO4)CC2)c1]

Step 1: 3-{4-[2-(1,4-dioxaspiro[4.5]dec-8-yl)ethyl]piperazin-1-yl}aniline

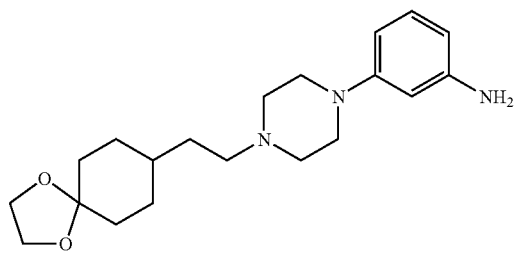 [SMILES: Nc1cccc(N2CCN(CCC3CCC4(CC3)OCCO4)CC2)c1]

To a cooled solution of 2.6 g (7.1 mmol) of 1-[2-(1,4-dioxaspiro[4.5]dec-8-yl)ethyl]-4-(3-nitrophenyl)piperazine in 50 mL of methanol are added under inert atmosphere, 0.5 g of 10% palladium on activated carbon. The mixture is hydrogenated at 40° C. under 4 bar for 17 hours. The suspension is filtered over celite and the filtrate is concentrated under reduced pressure to give 2.3 g (97%) of 3-{4-[2-(1,4-dioxaspiro[4.5]dec-8-yl)ethyl]piperazin-1-yl}aniline.

¹H NMR: 7.1 (t, 1H, J=7.5); 6.35 (d, 1H, J=7.5=; 6.3 (s, 1H); 6.2 (d, 1H, J=7.5); 3.95 (s, 4H); 3.2 (m, 4H); 3.6 (broad s, 2H); 2.6 (m, 4H); 2.4 (m, 2H); 1.75 (m, 2H); 1.65 to 1.4 (ms, 4H); 1.4 to 1.2 (ms, 3H)

Step 2: (3-{4-[2-(1,4-dioxaspiro[4.5]dec-8-yl)ethyl]piperazin-1-yl}phenyl)carbamic acid ethyl ester

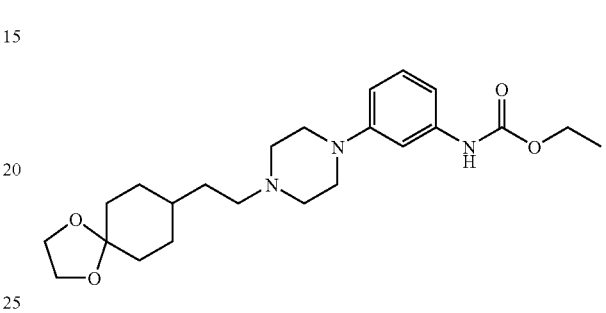

To a cooled solution of 1 g (3 mmol) of 3-{4-[2-(1,4-dioxaspiro[4.5]dec-8-yl)ethyl]piperazin-1-yl}aniline in 30 mL of dichloromethane and 0.3 g (3 mmol) of triethylamine, is slowly added 0.32 g (3 mmol) of ethyl chloroformate. The mixture is stirred overnight at room temperature then concentrated under reduced pressure. The product is dissolved in ethyl acetate, washed twice with water, dried over magnesium sulfate, filtered and concentrated under reduced pressure. The oily residue is purified over 10 g of silica gel (eluant dichloromethane/methanol 95/5) to give 0.35 g (29%) of (3-{4-[2-(1,4-dioxaspiro[4.5]dec-8-yl)ethyl]piperazin-1-yl}phenyl) carbamic acid ethyl ester.

¹H NMR: 7.25 to 7.1 (ms, 2H); 6.7 (d, 1H, J=7.5); 6.6 (d, 1H, J=7.5); 6.5 (s, 1H); 4.2 (q, 2H, J=7.5); 3.95 (s, 4H); 3.2 (m, 4H); 2.6 (m, 4H); 2.45 (m, 2H); 1.85 to 1.4 (ms, 8H); 1.4 to 1.15 (ms, 6H)

Preparation T: N-(3-{4-[2-(1,4-dioxaspiro[4.5]dec-8-yl)ethyl]piperazin-1-yl}phenyl)methanesulfonamide

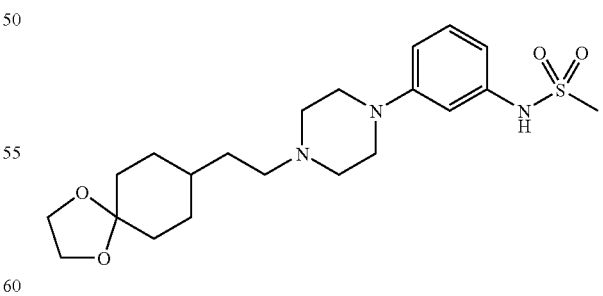

The N-(3-{4-[2-(1,4-dioxaspiro[4.5]dec-8-yl)ethyl]piperazin-1-yl}phenyl)methanesulfonamide, is prepared from 3-{4-[2-(1,4-dioxaspiro[4.5]dec-8-yl)ethyl]piperazin-1-yl}aniline and methanesulfonyl chloride using the procedure described for preparation S, step 2 giving the title compound in 89% yield.

$^1$H NMR: 7.2 (t, 1H, J=7.5); 8.3 (broad s, 1H); 7.05 (s, 1H); 6.95 (d, 1H, J=7.5); 6.65 (d, 1H, J=7.5); 3.95 (s, 4H); 3.6 (m, 4H); 3.15 (m, 4H); 3.0 (s, 3H); 1.9 to 1.65 (ms, 6H); 1.6 to 1.2 (ms, 7H)

Preparation U: 4-(2-hydroxyethyl)cyclohexanone

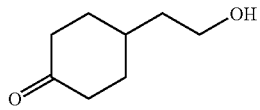

Step 1: 4-(2-hydroxyethyl)cyclohexanol

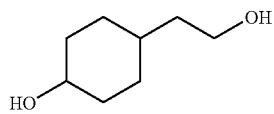

In a 1 L reactor are successively introduced: 50 g (362 mmol) of 4-(2-hydroxyethyl)phenol, 5 g (13.6 mmol) of sodium tetraborate decahydrate, 500 mL of isopropanol, 5 g of palladium (10% on charcoal washed with isopropanol). The vessel is closed, purged three times with nitrogen and three times with hydrogen. The mixture is stirred for 22 hours under 10 bar pressure of hydrogen at 80° C., cooled back to room temperature, filtered over a celite pad and rinsed with isopropanol. Filtrate is concentrated under reduced pressure, toluene (100 mL) is added and evaporated under reduced pressure. This last procedure being repetited to remove trace amount of isopropanol and gives 52 g (99% yield) of 4-(2-hydroxyethyl)cyclohexanol as a clear viscous oil.

TLC (ethyl acetate/heptane 75/25): Rf=0.2

Step 2: 4-(2-hydroxyethyl)cyclohexanone

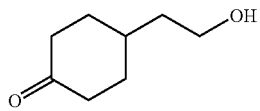

To a solution of 10 g (69 mmol) of 4-(2-hydroxyethyl)cyclohexanol in 50 mL of acetic acid maintained at a temperature between 18 and 21° C. are added over 35 min 35.9 mL (79 mmol) of an aqueous sodium hypochlorite solution. The mixture is further stirred for 45 min, TLC analysis indicating disappearance of starting material. Isopropanol (0.8 mL) is added, followed 10 min later by water (75 mL) and dichloromethane (100 mL). The two phases are separated by decantation and the aqueous phase is extracted with dichloromethane (50 mL). Combined organic phases are washed with an aqueous 3N sodium hydroxide solution (70 mL). This alcaline aqueous phase is extraced back with dichloromethane (30 mL). Combined organic phases are dried over magnesium sulfate and concentrated under reduced pressure to give 9.42 g (95%) of the title compound.

TLC (ethyl acetate/heptane 75/25): Rf=0.29

Preparation V: 4-(2-fluoro-5-trifluoromethylphenyl)-1-[2-(4-oxocyclohexyl)ethyl]-piperazine

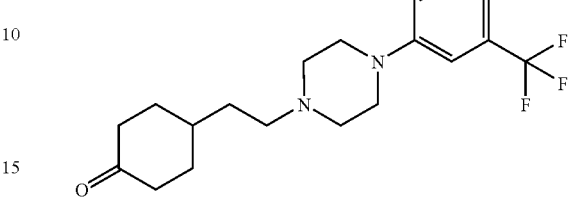

Step 1: 4-(2-hydroxyethyl)cyclohexanone mesylate

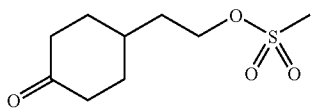

To a solution of 15.25 g (107.24 mmol) 4-(2-hydroxyethyl)cyclohexanone in 115 mL of dichloromethane cooled at a temperature close to 0° C., is added 18 mL (129.5 mmol) of triethylamine, then 9.25 mL (119.50 mmol) of mesyl chloride. The mixture is stirred for two hours at room temperature. Water (120 mL) is added. The organic phase is separated by decantation, washed with a saturated aqueous solution of sodium hydrogenocarbonate (100 mL), dried over magnesium sulfate and concentrated under reduced pressure to give 28 g of 4-(2-hydroxyethyl)cyclohexanone mesylate used without further purification in the next step.

$^1$H NMR: 4.30 (t, 2H, J=7.5); 3.05 (s, 3H); 2.40 (m, 4H); 2.20 to 2.05 (m, 2H); 2.00 (m, 1H); 1.8 (q, 2H, J=6.5); 1.60 to 1.85 (m, 2H)

Step 2: 4-(2-fluoro-5-trifluoromethylphenyl)-1-[2-(4-oxocyclohexyl)ethyl]piperazine

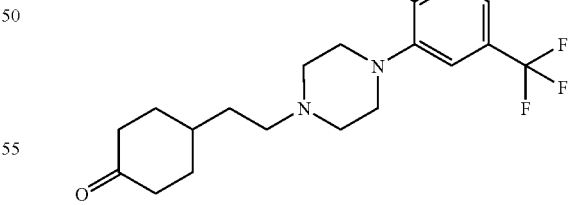

Path IV

A mixture of 11.6 g (52.66 mmol) of 4-(2-hydroxyethyl)cyclohexanone mesylate, of 13.72 g (55.27 mmol) of 1-(2-fluoro-5-trifluoromethylphenyl)piperazine and 8.37 g (60.65 mmol) of potassium carbonate in 220 mL of acetonitrile is refluxed overnight, then cooled back to room temperature. Water (80 mL) is added. Organics are extracted with ethyl acetate (100 mL). The organic phase is washed with water (20 mL), dried over magnesium sulfate and concentrated under reduced pressure to give a crude product. Purification by column chromatography over 320 g of silica gel (eluant dichloromethane/methanol 98/2 to 96/4) yields 15.86 g of 4-(2-fluoro-5-trifluoromethylphenyl)-1-[2-(4-oxocyclohexyl)ethyl]piperazine melting at 75-76° C.

$^1$H NMR: 7.30 to 7.00 (m, 3H); 3.20 (m, 4H); 2.65 (m, 4H); 2.50 (t, 2H, J=7.5); 2.40 (m, 4H); 2.10 (m, 2H); 1.80 (m, 1H); 1.70 to 1.35 (m, 4H)

Example 1

2-cyano-N-(4-{2-[4-(3-trifluoromethylphenyl)piperazin-1-yl]ethyl}cyclohexyl)acetamide (trans isomer)

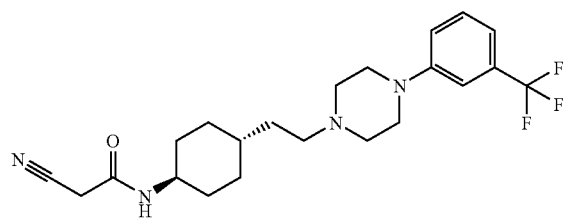 [SMILES: N#CCC(=O)N[C@H]1CC[C@H](CCN2CCN(c3cccc(C(F)(F)F)c3)CC2)CC1]

Path I

Step a: (1,4-dioxaspiro[4.5]dec-8-yl)acetic acid

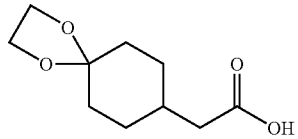 [SMILES: O=C(O)CC1CCC2(CC1)OCCO2]

To a solution of 4 g (17.5 mmol of (1,4-dioxaspiro[4.5]dec-8-yl)acetic acid ethyl ester (*Tetrahedron*, 51, 37, 10259-10280, (1995)) in 35 mL of ethanol are added 22 mL (22 mmol) of an aqueous N sodium hydroxide solution. The mixture is stirred overnight at room temperature.

After concentration, the residue is taken off in cooled water, neutralized with 22 mL of an aqueous N hydrochloric acid solution and extracted 4 times with diethyl ether. The organic phases are combined, dried over magnesium sulfate, filtered and concentrated under reduced pressure to give 3.0 g (85%) of (1,4-dioxaspiro[4.5]dec-8-yl)acetic acid as an oil that crystallizes upon standing.

$^1$H NMR: 3.95 (s, 4H); 2.3 (d, 2H, J=7.5); 2.0 to 1.7 (ms, 5H); 1.6 (m, 2H); 1.5 to 1.2 (ms, 2H)

Step b: 2-(1,4-dioxaspiro[4.5]dec-8-yl)-1-[4-(3-trifluoromethylphenyl)-piperazin-1yl]ethanone

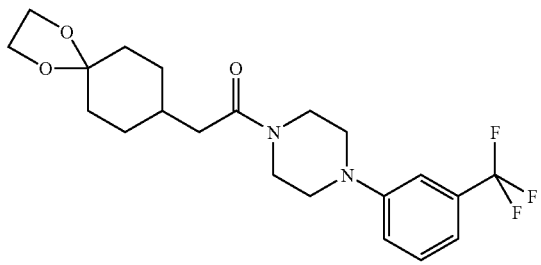 [SMILES: O=C(CC1CCC2(CC1)OCCO2)N1CCN(c2cccc(C(F)(F)F)c2)CC1]

To a solution of 1.5 g (7.5 mmol) of (1,4-dioxaspiro[4.5]dec-8-yl)acetic acid in 50 mL of dichloromethane stabilized on amylene are successively added at room temperature, 1.0 g (7.5 mmol) of 1-hydroxybenzotriazole and 1.43 g (7.5 mmol) of 3-ethyl-1-(3-dimethylaminopropyl)carbodiimide hydrochloride. The mixture is stirred for 10 minutes then 2.0 g (7.5 mmol) of 1-(3-trifluoromethylphenyl)piperazine hydrochloride and 2.3 mL (16.5 mmol) of triethylamine are added. The mixture is stirred overnight at room temperature.

After concentration under reduced pressure, the residue is dissolved in ethyl acetate and washed with water. The organic phase is dried over magnesium sulfate, filtered and concentrated under reduced pressure. The solid (3.6 g) is purified by chromatography over 150 g of silica gel (eluant dichloromethane/methanol 97.5/2.5) to give 2.5 g (81%) of 2-(1,4-dioxaspiro[4.5]dec-8-yl)-1-[4-(3-trifluoromethylphenyl)piperazin-1yl]ethanone as an oil.

$^1$H NMR: 7.4 (t, 1H, J=7.5); 7.2 to 7.0 (ms, 3H); 3.95 (s, 4H); 3.8 (m, 2H); 2.7 (m, 2H); 3.2 (m, 4H); 2.4 (d, 2H, J=7.5); 1.95 (m, 1H); 1.9 to 1.7 (ms, 4H); 1.7 to 1.5 (ms, 2H); 1.45 to 1.2 (ms, 2H)

Step c: 1-[2-(1,4-dioxaspiro[4.5]dec-8-yl)ethyl]-4-(3-trifluoromethylphenyl)piperazine

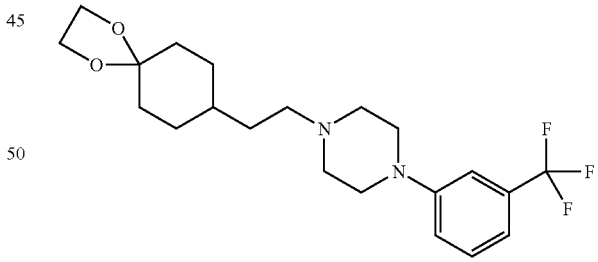

In a three necked round bottom flask, 30 mL of diethyl ether are cooled to −10° C. The system is purged with argon and 0.48 g (12.75 mmol) of lithium aluminum hydride is added. The suspension is stirred and a solution of 3.5 g (8.5 mmol) of 2-(1,4-dioxaspiro[4.5]dec-8-yl)-1-[4-(3-trifluoromethylphenyl)-piperazin-1-yl]ethanone in 20 mL of diethyl ether is added so that the internal temperature does not exceed 10° C. The mixture is refluxed for 4 hours then stirred overnight at room temperature.

Hydrolysis is performed at 0° C. by slow addition of 0.5 mL of water, 0.5 mL of 15% aqueous sodium hydroxide solution and 1.5 mL of water. The slurry is stirred for 15 minutes at room temperature then magnesium sulfate is added. The mixture is filtered and the salts are washed with a large amount of diethyl ether. The filtrate is concentrated under reduced pressure to give 2.5 g (74%) of 1-[2-(1,4-dioxaspiro[4.5]dec-8-yl)ethyl]-4-(3-trifluoromethylphenyl) piperazine as an oil.

$^1$H NMR: 7.35 (t, 1H, J=7.5); 7.15 (ms, 3H); 3.95 (s, 4H); 3.25 (m, 4H); 2.6 (m, 4H); 2.45 (m, 2H); 1.85 to 1.65 (ms, 4H); 1.65 to 1.45 (ms, 4H); 1.45 to 1.2 (ms, 3H)

Path II

Step a: 1-[2-(1,4-dioxaspiro[4.5]dec-8-yl)ethyl]-4-(3-trifluoromethylphenyl)piperazine

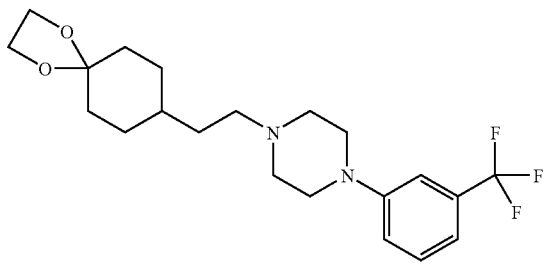 [SMILES: FC(F)(F)c1cccc(N2CCN(CCC3CCC4(CC3)OCCO4)CC2)c1]

A mixture of 10 g (37.8 mmol) of 2-(1,4-dioxaspiro[4.5]dec-8-yl)ethylmethanesulfonate (*Tetrahedron*, 51, 37, 10259-10280, (1995)), 10.05 g (37.8 mmol) of 1-(3-trifluoromethylphenyl)piperazine hydrochloride, 10.97 g (79.38 mmol) of potassium carbonate and 100 mL of acetonitrile is refluxed overnight.

After concentration of the solvent, the residue is taken off with 100 mL of ethyl acetate and washed with water (twice 50 mL). Organic phase is dried over magnesium sulfate, filtered and concentrated under reduced pressure. The oil thus obtained is purified by chromatography over 250 g of silica gel (eluant heptane/ethyl acetate 50/50) to give 14.4 g (95%) of 1-[2-(1,4-dioxaspiro[4.5]dec-8-yl)ethyl]-4-(3-trifluoromethylphenyl)piperazine as a colorless oil.

$^1$H NMR: 7.35 (t, 1H, J=7.5); 7.15 (ms, 3H); 3.95 (s, 4H); 3.25 (m, 4H); 2.6 (m, 4H); 2.45 (m, 2H); 1.85 to 1.65 (ms, 4H); 1.65 to 1.45 (ms, 4H); 1.45 to 1.2 (ms, 3H)

Step b: 4-{2-[4-(3-trifluoromethylphenyl)piperazin-1-yl]ethyl}cyclohexanone

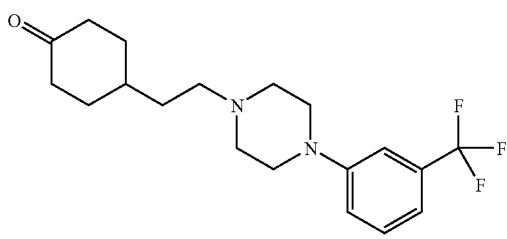 [SMILES: O=C1CCC(CCN2CCN(c3cccc(C(F)(F)F)c3)CC2)CC1]

A solution of 14.4 g (36.1 mmol) of 1-[2-(1,4-dioxaspiro[4.5]dec-8-yl)ethyl]-4-(3-trifluoromethylphenyl)piperazine, 70 mL of methanol, 59 mL of water and 11 mL of a 2N aqueous hydrochloric acid solution is stirred overnight at room temperature.

An aqueous saturated solution of sodium hydrogen carbonate is added until pH 10. Ethanol is evaporated under reduced pressure and the oily residue is dissolved in 100 mL of ethyl acetate. The organic phase is washed with water (4 times 30 mL), dried over magnesium sulfate, filtered and concentrated to give 11.62 g (91%) of 4-{2-[4-(3-trifluoromethylphenyl)piperazin-1-yl]ethyl}cyclo-hexanone as a colorless oil.

$^1$H NMR: 7.35 (t, 1H, J=7.5); 7.2 to 7.0 (ms, 3H); 3.3 (m, 4H); 2.6 (m, 4H); 2.5 (t, 2H, J=7.5); 2.4 (m, 4H); 2.1 (m, 2H); 1.8 (m, 1H); 1.7 to 1.35 (ms, 4H)

Step c: 4-{2-[4-(3-trifluoromethylphenyl)piperazin-1-yl]ethyl}cyclo-hexylamine, dihydrochloride

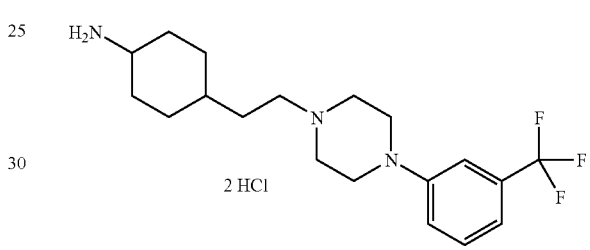

A mixture of 5.75 g (16.2 mmol) of 4-{2-[4-(3-trifluoromethylphenyl)piperazin-1-yl]ethyl}cyclohexanone, 12.51 g (162.3 mmol) of ammonium acetate, 200 mL of methanol and 4.07 g (64.8 mmol) sodium cyanoborohydride is refluxed for 3 hours.

Methanol is concentrated under reduced pressure and the residue is taken off in 20 mL of water. A concentrated aqueous hydrochloric solution is added under cooling until the end of gaseous evolution. The mixture is basified with 35% sodium hydroxide and extracted with dichloromethane (3 times 50 mL). The organic phases are combined, dried over magnesium sulfate, filtered and concentrated under reduced pressure to give an oil that consists in about a 65%/35% mixture ($^1$H NMR determination) of trans and cis 4-{2-[4-(3-trifluoromethylphenyl)piperazin-1-yl]ethyl}cyclohexylamine.

The isomers are partially separated by dissolution in a hydrochloric acid ethyl acetate solution. After evaporation of the solvent, the solid is mixed with 10 mL of acetonitrile and warmed to 50° C. The suspension is filtered, the solid is washed with acetonitrile (5 mL) and with diethyl ether (15 mL). The hygroscopic solid is dried at 50° C. under reduced pressure to give 4.3 g (62%) of about 80%/20% ($^1$H NMR determination) of trans and cis 4-{2-[4-(3-trifluoromethylphenyl)piperazin-1-yl]ethyl}cyclohexylamine, dihydrochloride as a white solid.

Melting point 300-305° C. (decomposition)

The $^1$H NMR spectra is performed on the free base.

$^1$H NMR: 7.35 (t, 1H, J=7); 7.15 to 7.0 (ms, 3H); 3.25 (m, 4H); 3.0 (m, 0.2H equatorial); 2.7 to 2.35 (ms, 4.8H); 2.0 to 1.35 (ms, 11H); 1.35 to 0.9 (ms, 4H)

Path A 2-cyano-N-(4-{2-[4-(3-trifluoromethylphenyl)piperazin-1-yl]ethyl}cyclohexyl)acetamide

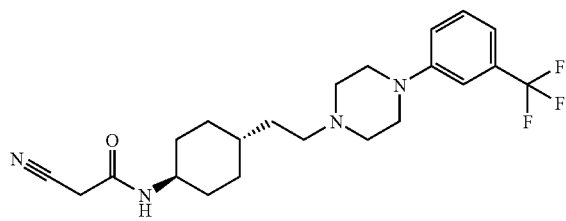 [SMILES: N#CCC(=O)N[C@H]1CC[C@H](CCN2CCN(c3cccc(C(F)(F)F)c3)CC2)CC1]

To a solution of 43 mg (0.5 mmol) of cyanoacetic acid in 5 mL of dichloromethane stabilized on amylene are successively added 68 mg (0.5 mmol) of 1-hydroxybenzotriazole, 96 mg (0.5 mmol) of 3-ethyl-1-(3-dimethylaminopropyl)-carbodiimide hydrochloride and 0.21 mL (1.5 mmol) of triethylamine. The mixture is stirred for 15 minutes then 214 mg (0.5 mmol) of the 80%/20% trans/cis 4-{2-[4-(3-trifluoromethylphenyl)piperazin-1-yl]ethyl}cyclohexylamine dihydrochloride is added. The mixture is stirred overnight at room temperature.

Volatiles are evaporated under reduced pressure, residue is dissolved in ethyl acetate and washed with an aqueous saturated sodium hydrogen carbonate solution, then with water. The organic phase is dried over magnesium sulfate, filtered and concentrated under reduced pressure. The residual solid is recristallized in a mixture of diisopropyl ether/ethanol 9/1. After filtration, the solid is washed with diisopropyl ether and dried under reduced pressure to give 62 mg (29%) of trans 2-cyano-N-(4-{2-[4-(3-trifluoro-methylphenyl)piperazin-1-yl]ethyl}cyclohexyl)acetamide as a cream colored solid.

Melting point: 185° C.

$^1$H NMR: 7.35 (t, 1H, J=7.5); 7.15 to 7.0 (ms, 3H); 5.85 (d, 1H, J=7.5); 3.75 (m, 1H); 3.35 (s, 2H); 3.25 (m, 4H); 2.6 (m, 4H); 2.45 (m, 2H); 2.05 (m, 2H); 1.85 (m, 2H); 1.45 (m, 2H); 1.4 to 1.0 (ms, 5H)

Example 2

1-(4-{2-[4-(3-trifluoromethylphenyl)piperazin-1-yl]ethyl}-piperidin-1-yl)propane-1,2-dione, hydrochloride

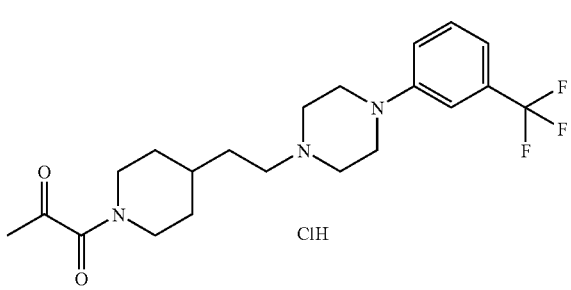 [SMILES: CC(=O)C(=O)N1CCC(CCN2CCN(c3cccc(C(F)(F)F)c3)CC2)CC1 ; Cl]

Path III

Step a: 4-(2-methanesulfonyloxyethyl)piperidine-1-carboxylic acid tert-butyl ester

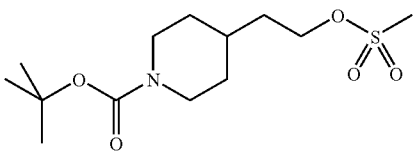 [SMILES: CC(C)(C)OC(=O)N1CCC(CCOS(C)(=O)=O)CC1]

To a cooled solution of 3 g (13 mmol) of 4-(2-hydroxyethyl)piperidine-1-carboxylic acid tert-butyl ester (commercially available) in 20 mL of dichloromethane and 1.45 g (14.5 mmol) of triethylamine is added a solution of 1.5 g (13 mmol) of methanesulfonyl chloride in 4 mL of dichloromethane. The mixture is stirred for 2 hours at room temperature.

After washing with water, the organic phase is dried over magnesium sulfate, filtered and concentrated to give 4 g (100%) of 4-(2-methanesulfonyloxyethyl)piperidine-1-carboxylic acid tert-butyl ester as a white solid.

TLC: 0.53 (heptane/ethyl acetate 1/1)

$^1$H NMR: 4.3 (t, 2H, J=7.5); 4.1 (m, 2H); 3.0 (s, 3H); 2.7 (m, 2H); 1.8 to 1.6 (ms, 5H); 1.45 (s, 9H); 1.25 to 1.0 (ms, 2H)

Step b: 4-{2[4-(3-trifluoromethylphenyl)piperazin-1-yl]-ethyl}piperidine-1-carboxylic acid tert-butyl ester, hydrochloride

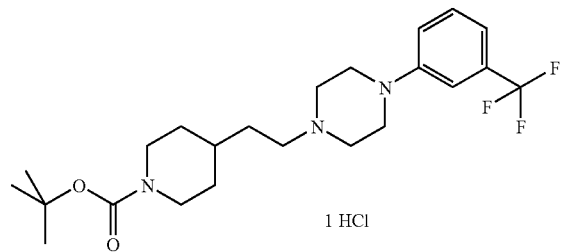 [SMILES: CC(C)(C)OC(=O)N1CCC(CCN2CCN(c3cccc(C(F)(F)F)c3)CC2)CC1 ; "1 HCl"]

A mixture of 1 g (3.25 mmol) of 4-(2-methanesulfonyloxyethyl)-piperidine-1-carboxylic acid tert-butyl ester, 0.87 g (3.25 mmol) of 1-(3-trifluoromethylphenyl)piperazine hydrochloride, 0.95 g (6.9 mmol) of potassium carbonate and 20 mL of acetonitrile is refluxed overnight.

After concentration of solvent, the residue is taken off with ethyl acetate and water. Organic phase is separated, washed with a 0.5N aqueous solution of hydrochloric acid, dried over magnesium sulfate, filtered and partially concentrated. The solid is filtered, washed with diethyl ether and dried under reduced pressure to give 1.1 g (71%) of 4-{2[4-(3-trifluoromethyl-phenyl)piperazin-1-yl]-ethyl}piperidine-1-carboxylic acid tert-butyl ester, hydrochloride as a white solid.

Melting point 188° C.

$^1$H NMR: 13.1 (broad s, 1H); 7.4 (t, 1H, J=7.5); 7.25 (d, 1H, J=7.5); 7.2 to 7.0 (ms, 2H); 4.1 (m, 2H); 3.9 to 3.5 (ms, 6H); 3.15 to 2.8 (ms, 4H); 2.7 (m, 2H); 1.95 (m, 2H); 1.8 to 1.5 (ms, 3H); 1.45 (s, 9H); 1.3 (m, 2H)

Step c: 1-(2-piperidin-4-ylethyl)-4-(3-trifluoromethylphenyl)piperazine, dihydrochloride

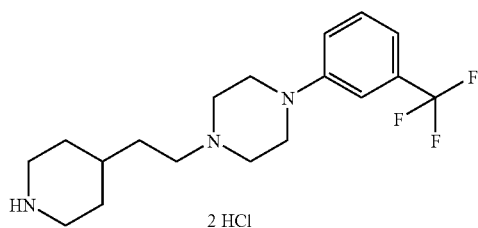 [SMILES: FC(F)(F)c1cccc(N2CCN(CCC3CCNCC3)CC2)c1 ; "2 HCl"]

To a solution of 0.5 g (1.0 mmol) of 4-{2[4-(3-trifluoromethylphenyl)piperazin-1-yl]ethyl}piperidine-1-carboxylic acid tert-butyl ester, hydrochloride in 5 mL of ethyl acetate and 2.5 mL of methanol are added 2.5 mL of a saturated hydrogen chloride solution in diethyl ether. The mixture is stirred for 2 hours at room temperature (precipitation occurs rapidly).

The solid is filtered, washed with diethyl ether and dried under reduced pressure to give 0.41 g (100%) of 1-(2-piperidin-4-ylethyl)-4-(3-trifluoro-methylphenyl)piperazine, dihydrochloride as a white solid.

Melting point: 260° C.

$^1$H NMR (DMSO D$_6$): 11.2 (broad s, 1H); 8.95 (broad s, 1H); 8.8 (broad s, 1H); 7.45 (t, 1H, J=7.5); 7.35 (d, 1H, J=7.5); 7.3 (s, 1H); 7.1 (d, 1H, J=7.5); 3.95 (m, 2H); 3.6 (m, 2H); 3.4 to 2.95 (ms, 8H); 2.8 (m, 2H); 1.9 to 1.5 (ms, 5H); 1.5 to 1.2 (ms, 2H)

Path A

1-(4-{2-[4-(3-trifluoromethylphenyl)piperazin-1-yl]ethyl}piperidin-1-yl)propane-1,2-dione, hydrochloride

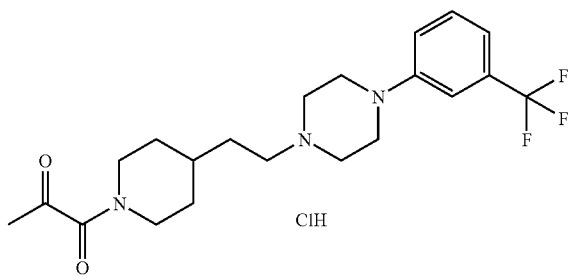 [SMILES: CC(=O)C(=O)N1CCC(CCN2CCN(c3cccc(C(F)(F)F)c3)CC2)CC1 ; Cl]

1-(2-Piperidin-4-ylethyl)-4-(3-trifluoromethylphenyl)piperazine, dihydrochloride 150 mg (0.36 mmol) and 38 mg (0.43 mmol) of pyruvic acid are coupled according the process described in example 1, path A.

After work-up, the residue is purified over 5 g of silica gel (eluant dichloromethane/methanol 99/1). The oily product is dissolved in 1 mL of ethyl acetate and acidified by a saturated hydrogen chloride solution in diethyl ether. The solid is filtered, washed with diethyl ether and dried under reduced pressure to give 55 mg (35%) of 1-(4-{2-[4-(3-trifluoromethylphenyl)piperazin-1-yl]ethyl}piperidin-1-yl)propane-1,2-dione, hydrochloride as a white solid.

Melting point: 200° C.

$^1$H NMR (DMSO D$_6$): 10.8 (broad s, 1H); 7.45 (t, 1H, J=7.5); 7.3 (d, 1H, J=7.5); 7.25 (s, 1H); 7.15 (d, 1H, J=7.5); 4.2 (m, 1H); 3.95 (m, 2H); 3.55 (m, 2H); 3.3 to 2.95 (ms, 8H); 2.75 (m, 1H); 2.3 (s, 3H); 1.85 to 1.55 (ms, 5H); 1.25 to 0.95 (ms, 2H)

Example 3

1-(4-{2-[4-(3-trifluoromethylphenyl)piperazin-1-yl]ethyl}-piperidin-1-yl)propan-2-one

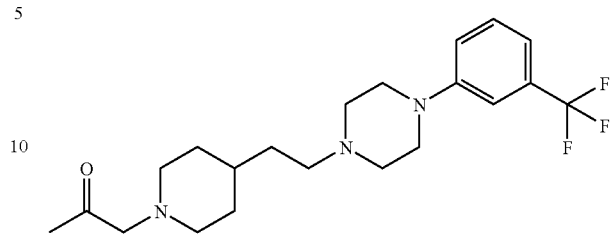

Path B

A mixture of 0.35 g (0.84 mmol) of 1-(2-piperidin-4-ylethyl)-4-(3-trifluoromethylphenyl)piperazine, dihydrochloride, 0.41 g (2.97 mmol) of potassium carbonate, 10 mL of acetonitrile and 0.1 g (1.08 mmol) of chloroacetone is stirred at room temperature overnight.

After concentration of solvent, the residue is partioned into ethyl acetate and water. Aqueous phase is separated. Organic phase is washed 3 times with water, dried over magnesium sulfate, filtered and concentrated under reduced pressure to give 0.24 g (72%) of 1-(4-{2-[4-(3-trifluoromethyl-phenyl)piperazin-1-yl]ethyl}piperidin-1-yl)propan-2-one as a white solid.

Melting point: 82° C.

$^1$H NMR: 7.35 (t, 1H, J=7.5); 7.2 to 7.0 (ms, 3H); 3.25 (m, 4H); 3.15 (s, 2H); 2.85 (m, 2H); 2.6 (m, 4H); 2.4 (t, 2H, J=7.5); 2.15 (s, 3H); 2.05 (m, 2H); 1.8 (m, 2H); 1.6 to 1.2 (ms, 5H)

Example 4

N-methoxy-N-methyl-2-(4-{2-[4-(3-trifluoromethylphenyl)-piperazin-1-yl]ethyl}cyclohexylidene)acetamide

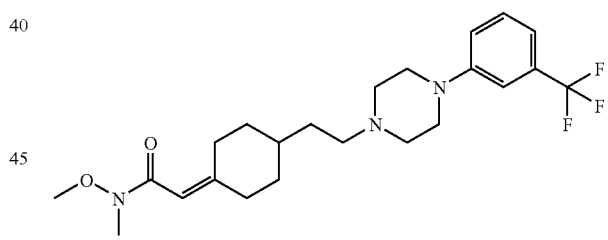

Path C

Step a: (4-{2-[4-(3-trifluoromethylphenyl)piperazin-1-yl]ethyl}cyclohexylidene)acetic acid ethyl ester

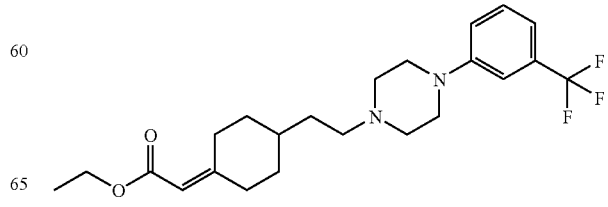

A mixture of 2.77 g (7.8 mmol) of 4-{2-[4-(3-trifluoromethyl-phenyl)piperazin-1-yl]ethyl}cyclohexanone (example 1, path 11, step b) and 3.13 g (9.0 mmol) of (triphenyl-$\lambda^5$-phosphanylidene)acetic acid ethyl ester in 40 mL of toluene is refluxed overnight. After concentration of toluene, the residue is taken off in diethyl ether and the solid is filtered. The filtrate is concentrated and purified over 150 g of silica gel (eluant dichloromethane/heptane 98/2) to give 1.48 g (45%) of (4-{2-[4-(3-trifluoromethylphenyl)piperazin-1-yl]ethyl}cyclohexylidene)acetic acid ethyl ester as an oil.

$^1$H NMR: 7.35 (t, 1H); 7.2 to 7.0 (m, 3H); 5.6 (s, 1H); 4.15 (q, 2H, J=7.5); 3.75 (m, 1H); 3.25 (m, 4H); 2.6 (m, 4H); 2.45 (t, 2H, J=7.5); 2.4 to 1.85 (ms, 5H); 1.85 to 1.4 (ms, 4H); 1.3 (t, 3H, J=7.5); 1.25 to 1.05 (m, 2H)

Step b: (4-{2-[4-(3-trifluoromethylphenyl)piperazin-1-yl]ethyl}cyclo-hexylidene)acetic acid, hydrochloride

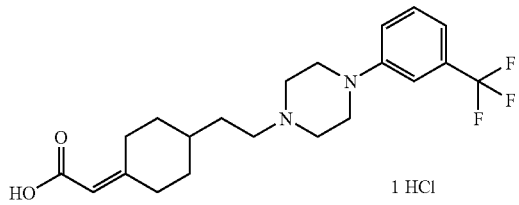 [SMILES: O=C(O)C=C1CCC(CCN2CCN(c3cccc(C(F)(F)F)c3)CC2)CC1 ; "1 HCl"]

1 HCl

To a solution of 0.88 g (2.1 mmol) of (4-{2-[4-(3-trifluoromethylphenyl)piperazin-1-yl]ethyl}cyclohexylidene)acetic acid ethyl ester in 8 mL of methanol are added 2.2 mL of an aqueous N sodium hydroxide solution. Stirring is maintained overnight at room temperature. Methanol is evaporated under reduced pressure and the residue is diluted in 20 mL of water and washed with diethyl ether. The aqueous phase is cooled, acidified to pH 1 with an aqueous 1N solution of hydrochloric acid. The solid is filtrated, washed with water and dried under reduced pressure to give 0.36 g (44%) of (4-{2-[4-(3-trifluoromethylphenyl)piperazin-1-yl]ethyl}cyclohexylidene)acetic acid, hydro-chloride as a white solid.

$^1$H NMR (DMSO D$_6$): 11.95 (broad s, 1H); 10.7 (broad s, 1H); 7.45 (t, 1H, J=7.5); 7.3 (d, 1H, J=7.5); 7.25 (s, 1H); 7.15 (d, 1H, J=7.5); 5.5 (s, 1H); 3.9 (m, 2H); 3.7 to 3.4 (ms, 3H); 3.3 to 2.9 (ms, 7H); 2.45 to 1.45 (ms, 7H); 1.05 (m, 2H)

Step c: N-methoxy-N-methyl-2-(4-{2-[4-(3-trifluoromethylphenyl)piperazin-1-yl]ethyl}cyclohexylidene)acetamide

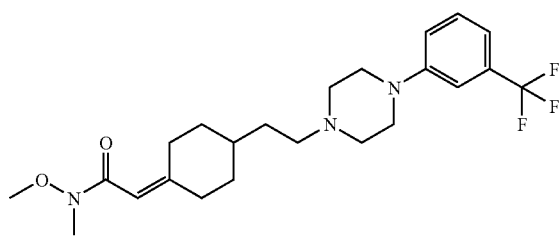 [SMILES: CON(C)C(=O)C=C1CCC(CCN2CCN(c3cccc(C(F)(F)F)c3)CC2)CC1]

To a solution of 200 mg (0.46 mmol) of (4-{2-[4-(3-trifluoromethylphenyl)piperazin-1-yl]ethyl}cyclohexylidene) acetic acid, hydrochloride in 5 mL of dichloromethane stabilized on amylene are successively added 63 mg (0.46 mmol) of 1-hydroxybenzotriazole, 88 mg (0.46 mmol) of 3-ethyl-1-(3-dimethylaminopropyl)carbodiimide hydrochloride and 140 mg (1.4 mmol) of triethylamine. The mixture is stirred for 15 minutes then 45 mg (0.46 mmol) of N,O-dimethylhydroxylamine hydrochloride are added. The mixture is stirred overnight at room temperature, then evaporated under reduced pressure. The residue is dissolved in ethyl acetate and washed twice with water. The organic phase is dried over magnesium sulfate, filtered and concentrated under reduced pressure. The residue is purified over 10 g of silica gel (eluant dichloromethane/methanol 98/2) to give 143 mg (71%) of N-methoxy-N-methyl-2-(4-{2-[4-(3-trifluoromethylphenyl)piperazin-1-yl]ethyl}cyclohexylidene)acetamide as an oil.

$^1$H NMR: 7.35 (t, 1H, J=7.5); 7.15 to 7.0 (ms, 3H); 6.05 (s, 1H); 3.7 (s, 3H); 3.6 (m, 1H); 3.25 (m, 4H); 3.2 (s, 4H); 2.6 (m, 4H); 2.45 (t, 2H, J=7.5); 2.4 to 2.1 (ms, 2H); 2.1 to 1.85 (ms, 3H); 1.6 to 1.4 (m, 2H); 1.4 to 1.05 (ms, 2H)

Example 5

1-(4-{2-[4-(3-trifluoromethylphenyl)piperazin-1-yl]ethyl}-cyclohexylidene)propan-2-one

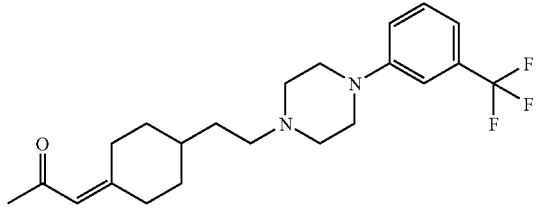 [SMILES: CC(=O)C=C1CCC(CCN2CCN(c3cccc(C(F)(F)F)c3)CC2)CC1]

To a solution of 114 mg (0.25 mmol) of N-methoxy-N-methyl-2-(4-{2-[4-(3-trifluoromethylphenyl)piperazin-1-yl]ethyl}-cyclohexylidene)acetamide in 5 mL of dry tetrahydrofuran cooled to 0° C. is added 0.2 mL (0.50 mmol) of a 22% methylmagnesium chloride solution in tetrahydrofuran. The mixture is warmed up to 5° C. and stirred for 90 minutes. Hydrolysis is performed by slow addition of 3 mL of water. The product is extracted 3 times with ethyl acetate. The organic phases are combined, dried over magnesium sulfate, filtered and concentrated under reduced pressure. The obtained residue is purified over 5 g of silica gel (eluant dichloromethane/methanol 95/5) to give 43 mg (44%) of 1-(4-{2-[4-(3-trifluoromethylphenyl)piperazin-1-yl]ethyl}cyclohexylidene)propan-2-one as an oil.

$^1$H NMR: 7.35 (t, 1H, J=7.5); 7.2 to 7.0 (ms, 3H); 6.0 (s, 1H); 3.7 (m, 1H); 3.25 (m, 4H); 2.6 (m, 4H); 2.45 (m, 4H); 2.25 (m, 2H); 2.2 (s, 3H); 1.95 (m, 3H); 1.7 to 1.4 (ms, 1H); 1.35 to 1.0 (ms, 2H)

Example 6

1-(4-{2-[4-(3-trifluoromethylphenyl)piperazin-1-yl]ethyl}cyclohexyl)propan-2-one, hydrochloride

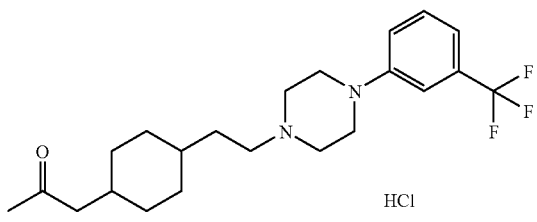 [SMILES: CC(=O)CC1CCC(CCN2CCN(c3cccc(C(F)(F)F)c3)CC2)CC1 ; Cl]

HCl

A solution of 33 mg (0.08 mmol) of 1-(4-{2-[4-(3-trifluoro-methylphenyl)piperazin-1-yl]ethyl}cyclohexylidene)propan-2-one is cooled and purged with argon. After addition of 5 mg of 10% palladium on activated carbon, the mixture is hydrogenated at room temperature and atmospheric pressure overnight. The suspension is filtrated over a bed of celite and the filtrate is concentrated under reduced pressure. The residue is dissolved in acetonitrile, acidified by a saturated hydrochloric acid ethyl acetate solution, filtered and dried under reduced pressure to give 29 mg (85%) of 1-(4-{2-[4-(3-trifluoromethylphenyl)piperazin-1-yl]ethyl}cyclohexyl)propan-2-one, hydrochloride as a white solid.

Melting point: 160° C.

$^1$H NMR: 7.35 (t, 1H, J=7.5); 7.2 to 7.0 (ms, 3H); 3.5 (broad s, 1H); 3.25 (m, 4H); 2.6 (m, 4H); 2.5 to 2.3 (ms, 4H); 2.2 (s, 3H); 1.9 to 1.65 (ms, 4H); 1.65 to 1.15 (ms, 6H); 1.0 (m, 2H)

Example 7

N-(4-{2-[4-(3-acetylphenyl)piperazin-1-yl]ethyl}cyclohexyl)-2-cyanoacetamide trans/cis 80/20

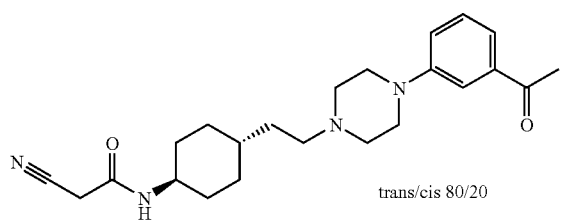 [SMILES: CC(=O)c1cccc(N2CCN(CC[C@H]3CC[C@H](NC(=O)CC#N)CC3)CC2)c1]

trans/cis 80/20

A solution of 44 mg (0.35 mmol) of oxalyl chloride in 1 mL of dichloromethane is purged with argon and cooled to a temperature close to −70° C. A solution of 66 mg (0.8 mmol) of dimethyl sulfoxide in 1 mL of dichloromethane is added. Stirring is maintained at a temperature close to −70° C. for 15 minutes and a solution of 120 mg (0.3 mmol) of 2-cyano-N-[4-(2-{4-[3-(1-hydroxyethyl)phenyl]piperazin-1-yl}ethyl)cyclohexyl]acetamide trans/cis 80/20 in 4 mL of dichloromethane is added. After an additional stirring for 15 minutes at a temperature close to −70° C., 110 mg (1.08 mmol) of triethylamine are added. The mixture is allowed to warm to room temperature then stirred overnight at room temperature. The mixture is poured into water and extracted twice with ethyl acetate. The organic phases are combined, washed with water, then brine, dried over magnesium sulfate, filtered and concentrated under reduced pressure. The oily residue is purified over 5 g silica gel (eluant dichloromethane/methanol 98/2 then 95/5). To give 25 mg (21%) of N-(4-{2-[4-(3-acetylphenyl)piperazin-1-yl]ethyl}cyclohexyl)-2-cyanoacetamide trans/cis 80/20 as a white solid.

Melting point 160° C.

$^1$H NMR: 7.5 (s, 1H); 7.45 (d, 1H, J=7.5); 7.35 (t, 1H, J=7.5); 7.1 (d, 1H J=7.5); 6.15 (broad d, 0.2H); 5.9 (broad d, 0.8H); 4.05 (m, 0.2H); 3.8 (m, 0.8H); 3.4 (s, 0.4H); 3.35 (s, 1.6H); 3.2 (m, 4H); 2.65 (m, 4H); 2.6 (s, 3H); 2.45 (m, 2H); 2.05 (m, 2H); 1.85 (m, 2H); 1.8 to 1.4 (ms, 4H); 1.4 to 1.0 (ms, 3H)

The following table summarises some further examples and the way they can be obtained.

| Ex | Structure | Name | M.P. (° C.) | Synthetic Path |
|----|-----------|------|-------------|----------------|
| 8 | 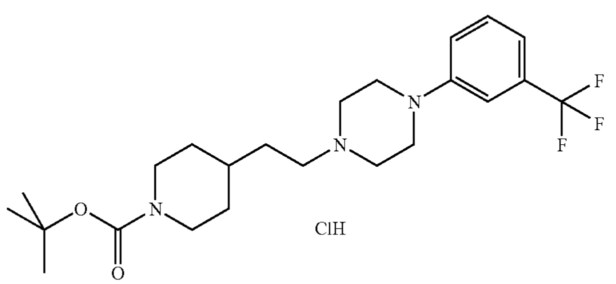 [SMILES: CC(C)(C)OC(=O)N1CCC(CCN2CCN(c3cccc(C(F)(F)F)c3)CC2)CC1 ; Cl] | 4-{2-[4-(3-Trifluoromethylphenyl)piperazin-1-yl]ethyl}piperidine-1-carboxylic acid tert-butyl ester, hydrochloride | 188 | IIIB |
| 9 | 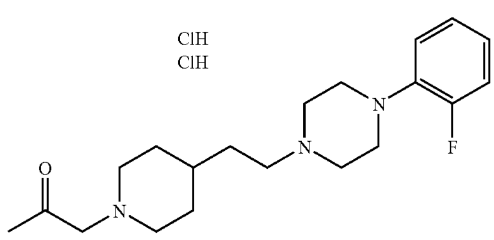 [SMILES: CC(=O)CN1CCC(CCN2CCN(c3ccccc3F)CC2)CC1 ; Cl ; Cl] | 1-(4-{2-[4-(2-Fluorophenyl)piperazin-1-yl]ethyl}piperidin-1-yl)propan-2-one, dihydrochloride | 250 | IIIB |

| Ex | Structure | Name | M.P. (° C.) | Synthetic Path |
|---|---|---|---|---|
| 10 | 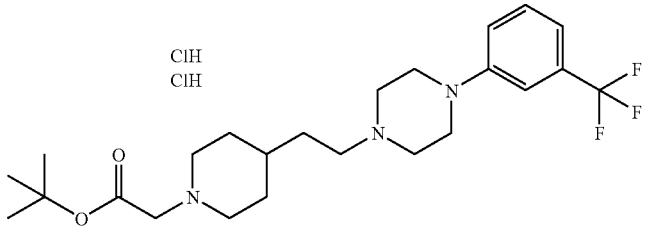 [SMILES: CC(C)(C)OC(=O)CN1CCC(CCN2CCN(c3cccc(C(F)(F)F)c3)CC2)CC1 ; Cl ; Cl] | (4-{2-[4-(3-Trifluoromethylphenyl)piperazin-1-yl]ethyl}piperidin-1-yl)acetic acid tert-butyl ester, dihydrochloride | 245 | IIIB |
| 11 | 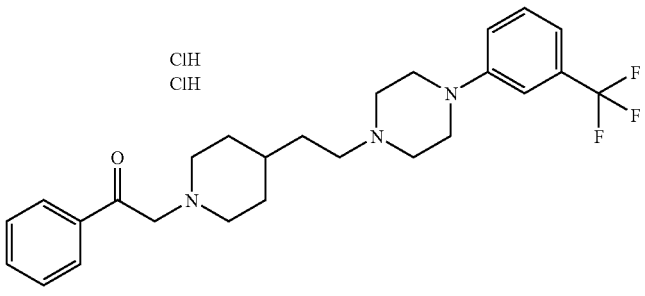 [SMILES: O=C(CN1CCC(CCN2CCN(c3cccc(C(F)(F)F)c3)CC2)CC1)c1ccccc1 ; Cl ; Cl] | 1-Phenyl-2-(4-{2-[4-(3-trifluoromethylphenyl)piperazin-1-yl]ethyl}piperidin-1-yl)ethanone, dihydrochloride | 260 | IIIB |
| 12 | 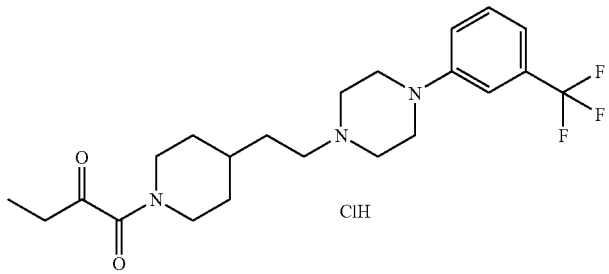 [SMILES: CCC(=O)C(=O)N1CCC(CCN2CCN(c3cccc(C(F)(F)F)c3)CC2)CC1 ; Cl] | 1-(4-{2-[4-(3-Trifluoromethylphenyl)piperazin-1-yl]ethyl}piperidin-1-yl)butane-1,2-dione, hydrochloride | 148 | IIIA |
| 13 | 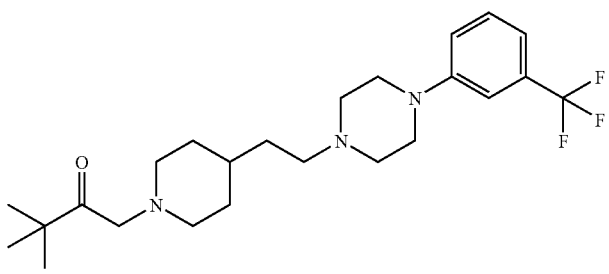 [SMILES: CC(C)(C)C(=O)CN1CCC(CCN2CCN(c3cccc(C(F)(F)F)c3)CC2)CC1] | 3,3-Dimethyl-1-(4-{2-[4-(3-trifluoromethylphenyl)piperazin-1-yl]ethyl}piperidin-1-yl)butan-2-one | | IIIB |
| 14 | 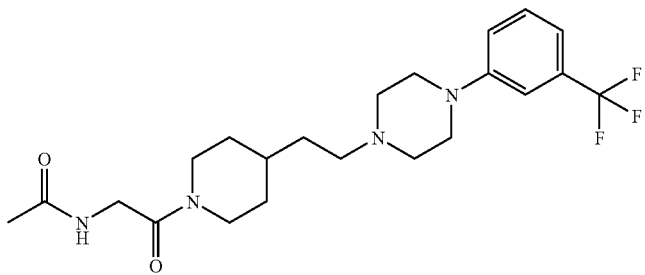 [SMILES: CC(=O)NCC(=O)N1CCC(CCN2CCN(c3cccc(C(F)(F)F)c3)CC2)CC1] | N-[2-Oxo-2-(4-{2-[4-(3-trifluoromethylphenyl)piperazin-1-yl]ethyl}piperidin-1-yl)ethyl]acetamide | 133 | IIIA |

-continued

| Ex | Structure | Name | M.P. (°C.) | Synthetic Path |
|---|---|---|---|---|
| 15 | 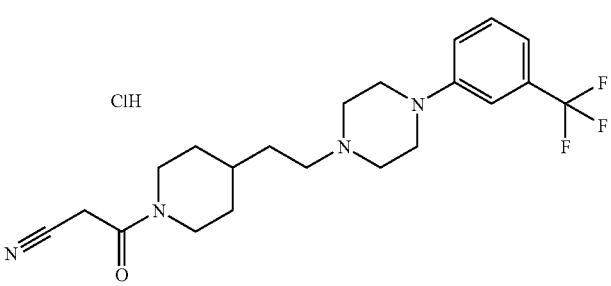 [SMILES: N#CCC(=O)N1CCC(CCN2CCN(c3cccc(C(F)(F)F)c3)CC2)CC1 ; Cl] | 3-Oxo-3-(4-{2-[4-(3-trifluoromethylphenyl)piperazin-1-yl]ethyl}piperidin-1-yl)propanenitrile, hydrochloride | 184 | IIIA |
| 16 | 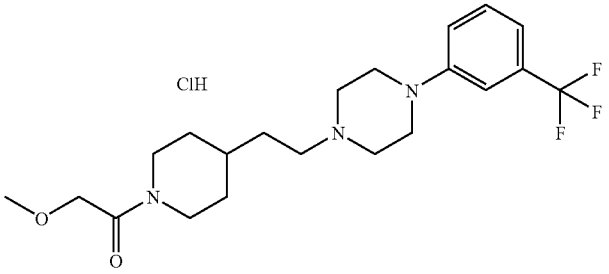 [SMILES: COCC(=O)N1CCC(CCN2CCN(c3cccc(C(F)(F)F)c3)CC2)CC1 ; Cl] | 2-Methoxy-1-(4-{2-[4-(3-trifluoromethylphenyl)piperazin-1-yl]ethyl}piperidin-1-yl)ethanone, hydrochloride | 150 | IIIA |
| 17 | 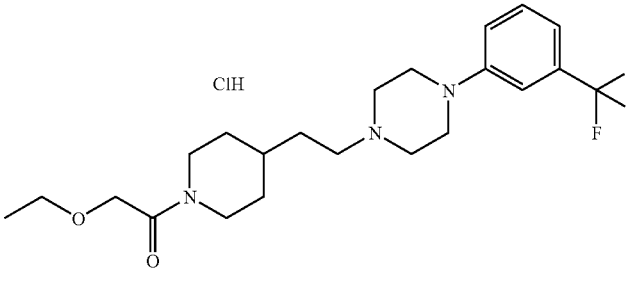 | 2-Ethoxy-1-(4-{2-[4-(3-trifluoromethylphenyl)piperazin-1-yl]ethyl}piperidin-1-yl)ethanone, hydrochloride | 145 | IIIA |
| 18 | 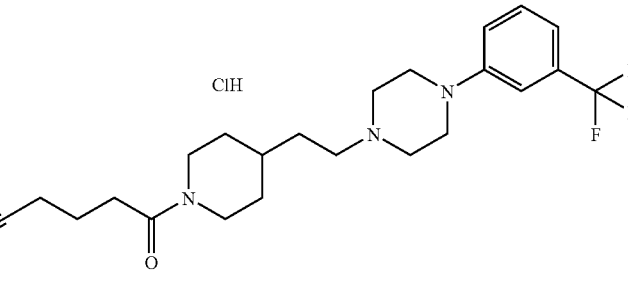 | 5-Oxo-5-(4-{2-[4-(3-trifluoromethylphenyl)piperazin-1-yl]ethyl}piperidin-1-yl)pentanenitrile, hydrochloride | 95 | IIIA |
| 19 | 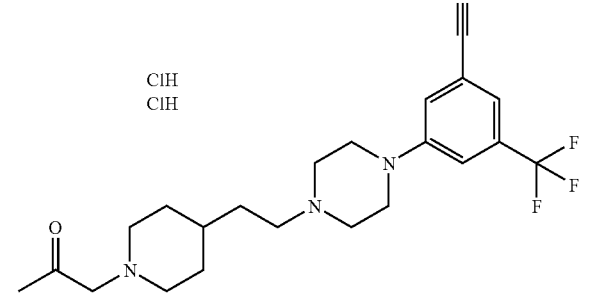 | 3-(4-{2-[1-(2-Oxopropyl)piperidin-4-yl]ethyl}piperazin-1-yl)-5-trifluoromethylbenzonitrile, dihydrochloride | 280 | IIIB |

-continued

| Ex | Structure | Name | M.P. (° C.) | Synthetic Path |
|---|---|---|---|---|
| 20 | 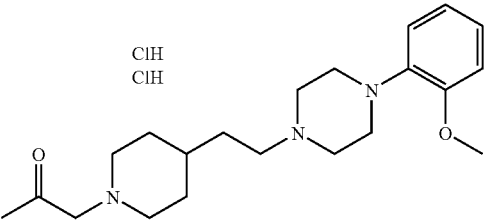 [SMILES: COc1ccccc1N1CCN(CCC2CCN(CC(C)=O)CC2)CC1 ; Cl ; Cl] | 1-(4-{2-[4-(2-Methoxy-phenyl)piperazin-1-yl]ethyl}piperidin-1-yl)propan-2-one, dihydrochloride | 260 | IIIB |
| 21 | 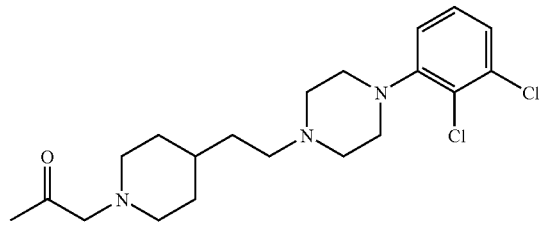 [SMILES: CC(=O)CN1CCC(CCN2CCN(c3cccc(Cl)c3Cl)CC2)CC1] | 1-(4-{2-[4-(2,3-Dichlorophenyl)piperazin-1-yl]ethyl}piperidin-1-yl)propan-2-one | 87 | IIIB |
| 22 | 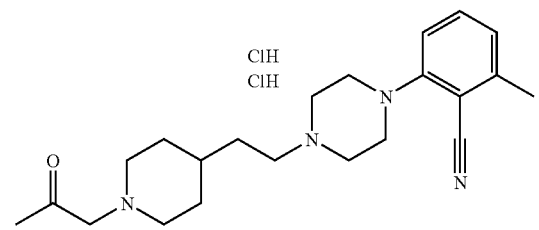 [SMILES: CC(=O)CN1CCC(CCN2CCN(c3cccc(C)c3C#N)CC2)CC1 ; Cl ; Cl] | 2-Methyl-6-(4-{2-[1-(2-oxopropyl)piperidin-4-yl]ethyl}piperazin-1-yl)benzonitrile, dihydrochloride | 215 | IIIB |
| 23 | 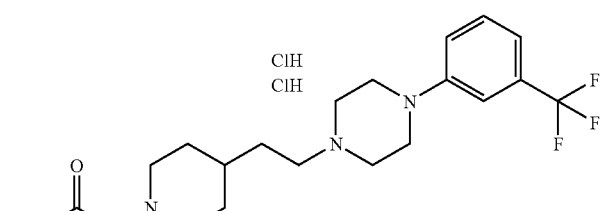 | 2-(4-{2-[4-(3-Trifluoromethylphenyl)piperazin-1-yl]ethyl}piperidin-1-yl)acetamide, dihydrochloride | 120 | IIIB |
| 24 | 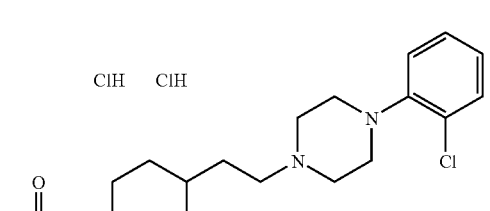 | 1-(4-{2-[4-(2-Chlorophenyl)-piperazin-1-yl]ethyl}piperidin-1-yl)propan-2-one, dihydrochloride | 265 | IIIB |
| 25 | 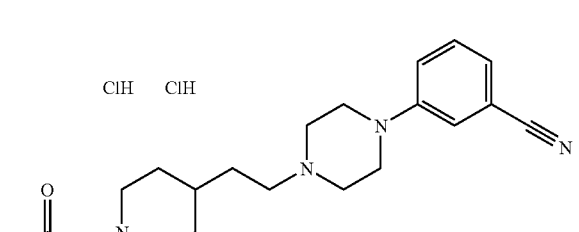 | 3-(4-{2-[1-(2-Oxopropyl)piperidin-4-yl]ethyl}piperazin-1-yl)benzonitrile, dihydrochloride | 250 | IIIB |

-continued

| Ex | Structure | Name | M.P. (° C.) | Synthetic Path |
|---|---|---|---|---|
| 26 | 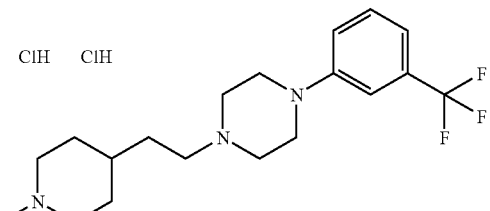 | (4-{2-[4-(3-Trifluoromethyl-phenyl)piperazin-1-yl]ethyl}piperidin-1-yl)acetic acid ethyl ester, dihydrochloride | 240 | IIIB |
| 27 | 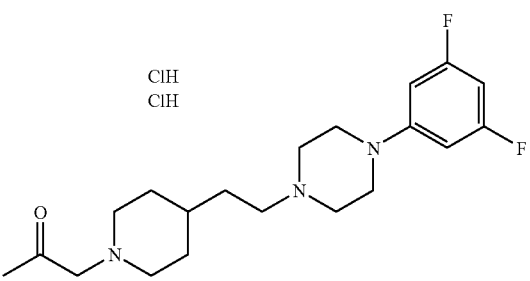 [SMILES: CC(=O)CN1CCC(CCN2CCN(c3cc(F)cc(F)c3)CC2)CC1 ; Cl ; Cl] | 1-(4-{2-[4-(3,5-Difluorophenyl)-piperazin-1-yl]ethyl}piperidin-1-yl)propan-2-one, dihydrochloride | 260 | IIIB |
| 28 | 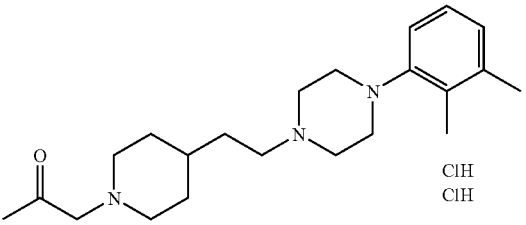 [SMILES: CC(=O)CN1CCC(CCN2CCN(c3cccc(C)c3C)CC2)CC1 ; Cl ; Cl] | 1-(4-{2-[4-(2,3-Dimethylphenyl)-piperazin-1-yl]ethyl}piperidin-1-yl)propan-2-one, dihydrochloride | 290 | IIIB |
| 29 | 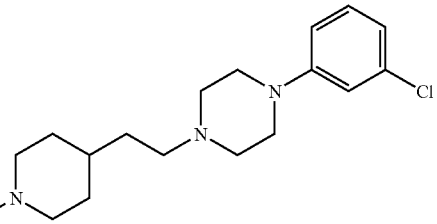 | 1-(4-{2-[4-(3-Chlorophenyl)-piperazin-1-yl]ethyl}piperidin-1-yl)propan-2-one | 114 | IIIB |
| 30 | 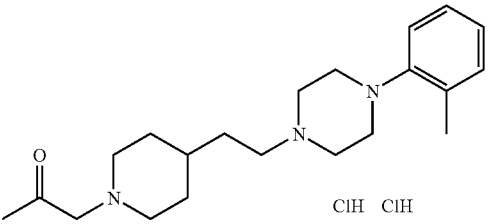 [SMILES: CC(=O)CN1CCC(CCN2CCN(c3ccccc3C)CC2)CC1 ; Cl ; Cl] | 1-{4-[2-(4-o-Tolylpiperazin-1-yl)-ethyl]piperidin-1-yl}propan-2-one, dihydrochloride | 289 | IIIB |
| 31 | 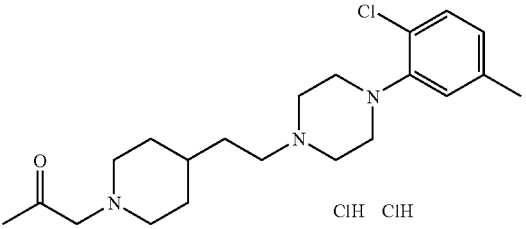 [SMILES: CC(=O)CN1CCC(CCN2CCN(c3cc(C)ccc3Cl)CC2)CC1 ; Cl ; Cl] | 1-(4-{2-[4-(2-Chloro-5-methylphenyl)piperazin-1-yl]ethyl}piperidin-1-yl)propan-2-one, dihydrochloride | 283 | IIIB |

-continued

| Ex | Structure | Name | M.P. (° C.) | Synthetic Path |
|---|---|---|---|---|
| 32 | 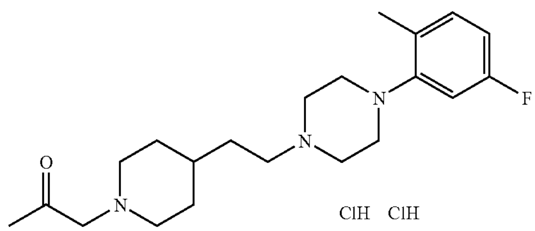 [SMILES: CC(=O)CN1CCC(CCN2CCN(c3cc(F)ccc3C)CC2)CC1 ; Cl ; Cl] | 1-(4-{2-[4-(5-Fluoro-2-methylphenyl)piperazin-1-yl]ethyl}piperidin-1-yl)propan-2-one, dihydrochloride | 281 | IIIB |
| 33 | 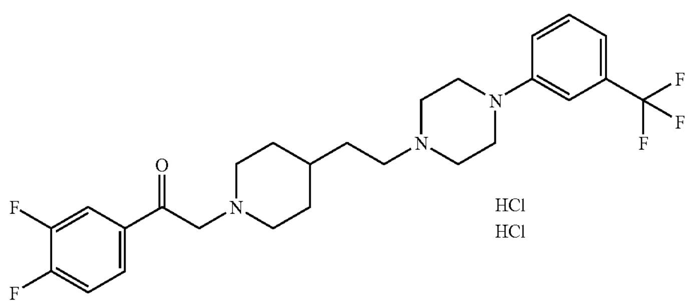 [SMILES: O=C(CN1CCC(CCN2CCN(c3cccc(C(F)(F)F)c3)CC2)CC1)c1ccc(F)c(F)c1 ; Cl ; Cl] | 1-(3,4-Difluorophenyl)-2-(4-{2-[4-(3-trifluoromethylphenyl)-piperazin-1-yl]ethyl}piperidin-1-yl)ethanone | 220 | IIIB |
| 34 | 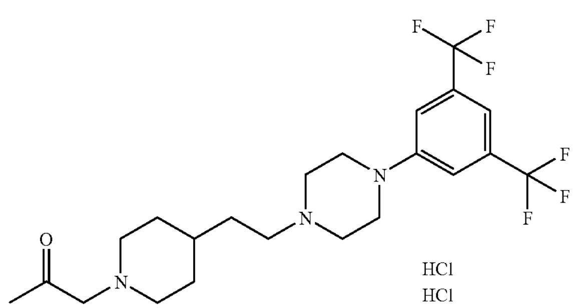 [SMILES: CC(=O)CN1CCC(CCN2CCN(c3cc(C(F)(F)F)cc(C(F)(F)F)c3)CC2)CC1 ; Cl ; Cl] | 1-(4-{2-[4-(3,5-Bistrifluoromethyl-phenyl)piperazin-1-yl]ethyl}-piperidin-1-yl)propan-2-one | 260 | IIIB |
| 35 | 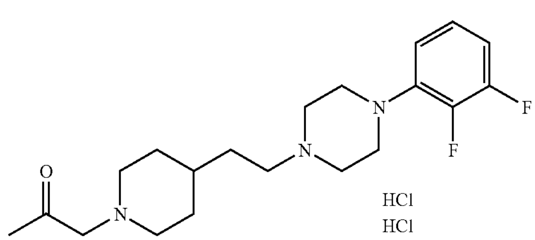 [SMILES: CC(=O)CN1CCC(CCN2CCN(c3cccc(F)c3F)CC2)CC1 ; Cl ; Cl] | 1-(4-{2-[4-(2,3-Difluorophenyl)-piperazin-1-yl]ethyl}piperidin-1-yl)propan-2-one | 270 | IIIB |
| 36 | 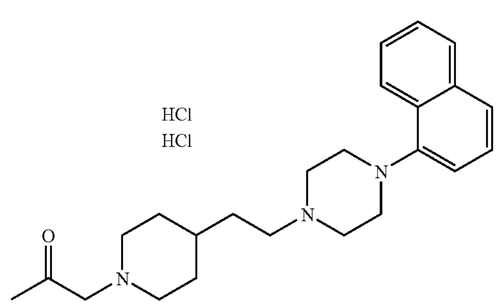 [SMILES: CC(=O)CN1CCC(CCN2CCN(c3cccc4ccccc34)CC2)CC1 ; Cl ; Cl] | 1-{4-[2-(4-Naphthalen-1-ylpiperazin-1-yl)ethyl]piperidin-1-yl}propan-2-one | 338 | IIIB |

-continued

| Ex | Structure | Name | M.P. (° C.) | Synthetic Path |
|---|---|---|---|---|
| 37 | 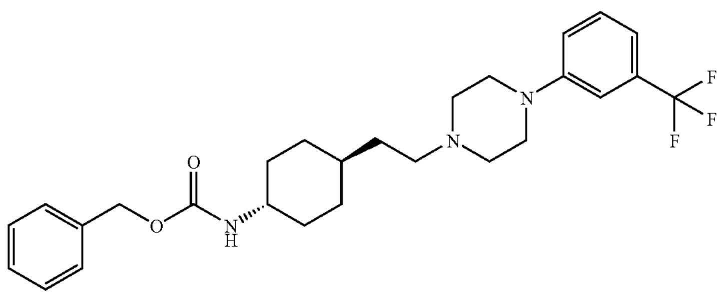 [SMILES: O=C(N[C@H]1CC[C@H](CCN2CCN(c3cccc(C(F)(F)F)c3)CC2)CC1)OCc1ccccc1] | (4-{2-[4-(3-Trifluoromethyl-phenyl)piperazin-1-yl]ethyl}cyclohexyl)carbamic acid benzyl ester | | IIA |
| 38 | 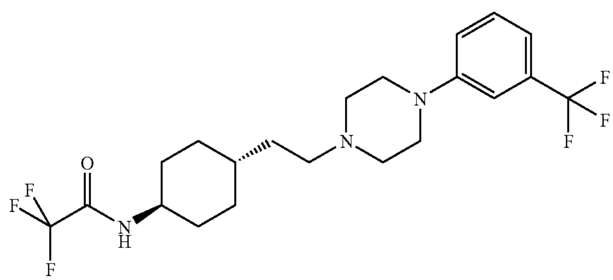 [SMILES: O=C(N[C@H]1CC[C@H](CCN2CCN(c3cccc(C(F)(F)F)c3)CC2)CC1)C(F)(F)F] | 2,2,2-Trifluoro-N-(4-{2-[4-(3-trifluoromethylphenyl)piperazin-1-yl]ethyl}cyclohexyl)acetamide | 134 | IIA |
| 39 | 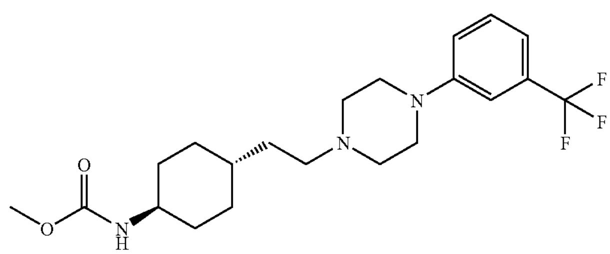 [SMILES: COC(=O)N[C@H]1CC[C@H](CCN2CCN(c3cccc(C(F)(F)F)c3)CC2)CC1] | (4-{2-[4-(3-Trifluoromethyl-phenyl)piperazin-1-yl]ethyl}cyclo-hexyl)carbamic acid methyl ester | 135 | IIA |
| 40 | 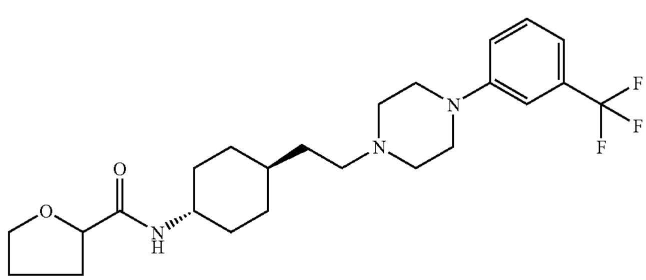 [SMILES: O=C(N[C@H]1CC[C@H](CCN2CCN(c3cccc(C(F)(F)F)c3)CC2)CC1)C1CCCO1] | Tetrahydrofuran-2-carboxylic acid (4-{2-[4-(3-trifluoromethylphenyl)piperazin-1-yl]ethyl}cyclohexyl)amide | 135 | IIA |
| 41 | 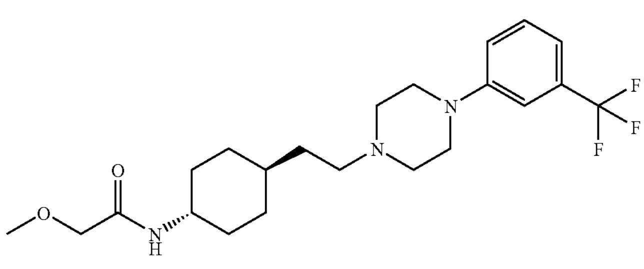 [SMILES: COCC(=O)N[C@H]1CC[C@H](CCN2CCN(c3cccc(C(F)(F)F)c3)CC2)CC1] | 2-Methoxy-N-(4-{2-[4-(3-trifluoromethylphenyl)piperazin-1-yl]ethyl}cyclohexyl)acetamide | 123 | IIA |

-continued

| Ex | Structure | Name | M.P. (° C.) | Synthetic Path |
|---|---|---|---|---|
| 42 | 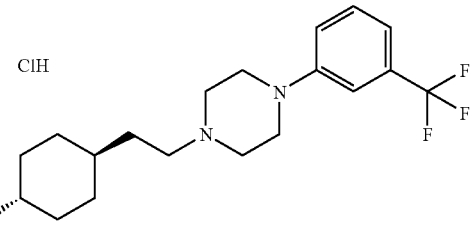 | 2-Methoxy-N-(4-{2-[4-(3-trifluoromethylphenyl)piperazin-1-yl]ethyl}cyclohexyl)acetamide, hydrochloride | 217 | IIA |
| 43 | 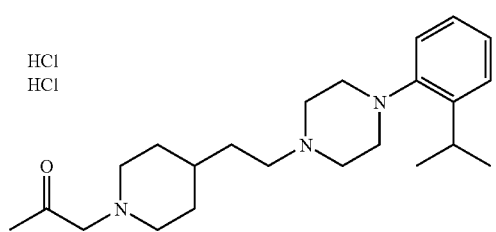 [SMILES: CC(=O)CN1CCC(CCN2CCN(c3ccccc3C(C)C)CC2)CC1 ; Cl ; Cl] | 1-(4-{2-[4-(2-Isopropylphenyl)-piperazin-1-yl]ethyl}piperidin-1-yl)propan-2-one | 260 | IIIB |
| 44 | 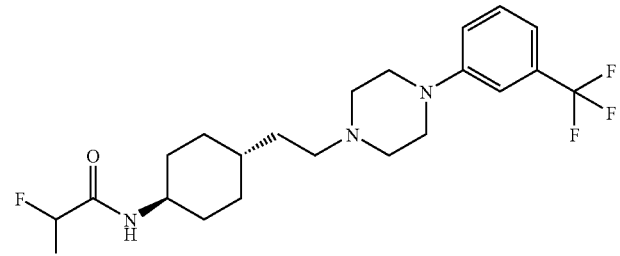 | 2,2-Difluoro-N-(4-{2-[4-(3-trifluoromethylphenyl)piperazin-1-yl]ethyl}cyclohexyl)acetamide | 128 | IIA |
| 45 | 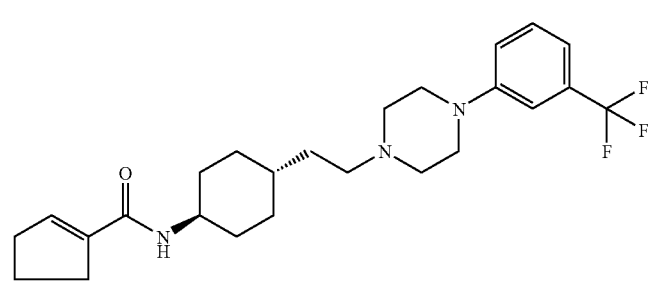 [SMILES: O=C(N[C@H]1CC[C@H](CCN2CCN(c3cccc(C(F)(F)F)c3)CC2)CC1)C1=CCCC1] | Cyclopent-1-enecarboxylic acid (4-{2-[4-(3-trifluoromethyl-phenyl)piperazin-1-yl]ethyl}cyclohexyl)amide | 175 | IIA |
| 46 | 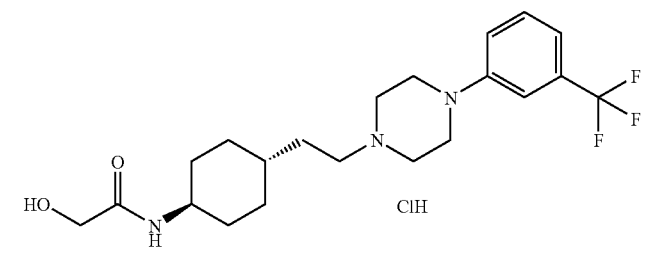 [SMILES: O=C(CO)N[C@H]1CC[C@H](CCN2CCN(c3cccc(C(F)(F)F)c3)CC2)CC1 ; Cl] | 2-Hydroxy-N-(4-{2-[4-(3-trifluoromethylphenyl)piperazin-1-yl]ethyl}cyclohexyl)acetamide, hydrochloride | | IIA |
| 47 | 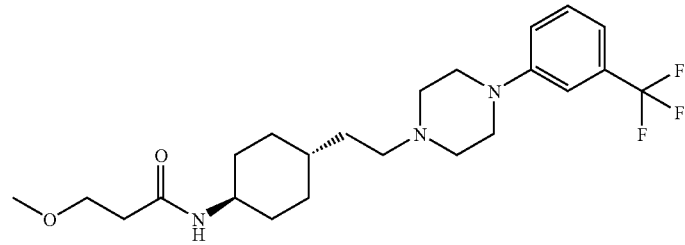 [SMILES: COCCC(=O)N[C@H]1CC[C@H](CCN2CCN(c3cccc(C(F)(F)F)c3)CC2)CC1] | 3-Methoxy-N-(4-{2-[4-(3-trifluoromethylphenyl)piperazin-1-yl]ethyl}cyclohexyl)propanamide | 125 | IIA |

-continued

| Ex | Structure | Name | M.P. (° C.) | Synthetic Path |
|---|---|---|---|---|
| 48 | 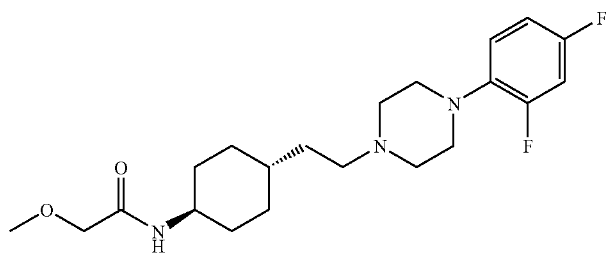 [SMILES: COCC(=O)N[C@H]1CC[C@H](CCN2CCN(c3ccc(F)cc3F)CC2)CC1] | N-(4-{2-[4-(2,4-Difluorophenyl)-piperazin-1-yl]ethyl}cyclohexyl)-2-methoxyacetamide | 154 | IIA |
| 49 | 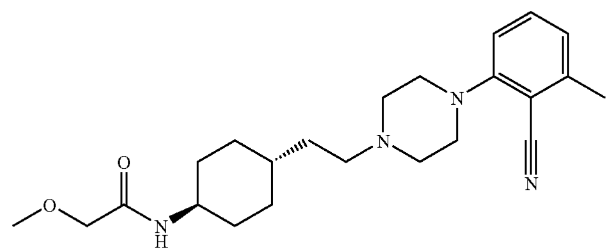 | N-(4-{2-[4-(2-Cyano-3-methylphenyl)piperazin-1-yl]ethyl}cyclohexyl)-2-methoxyacetamide | 136 | IIA |
| 50 | 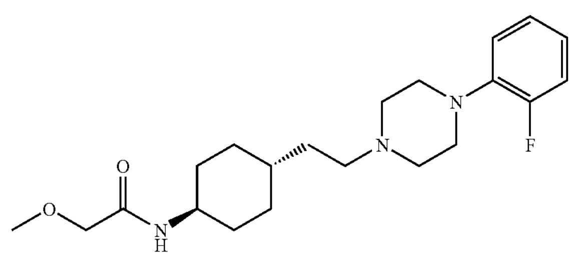 [SMILES: COCC(=O)N[C@H]1CC[C@H](CCN2CCN(c3ccccc3F)CC2)CC1] | N-(4-{2-[4-(2-Fluorophenyl)-piperazin-1-yl]ethyl}cyclohexyl)-2-methoxyacetamide | 143-144 | IIA |
| 51 | 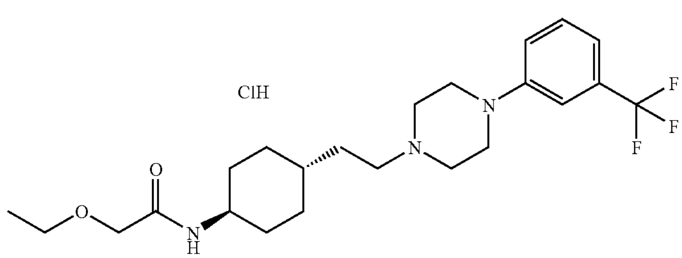 [SMILES: CCOCC(=O)N[C@H]1CC[C@H](CCN2CCN(c3cccc(C(F)(F)F)c3)CC2)CC1 ; Cl] | 2-Ethoxy-N-(4-{2-[4-(3-trifluoromethylphenyl)piperazin-1-yl]ethyl}cyclohexyl)acetamide, hydrochloride | 184 | IIA |
| 52 | 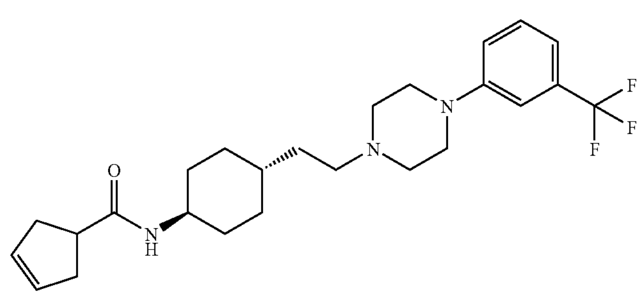 [SMILES: O=C(N[C@H]1CC[C@H](CCN2CCN(c3cccc(C(F)(F)F)c3)CC2)CC1)C1CC=CC1] | Cyclopent-3-enecarboxylic acid (4-{2-[4-(3-trifluoromethylphenyl)-piperazin-1-yl]ethyl}cyclohexyl)-amide | 183 | IIA |

-continued

| Ex | Structure | Name | M.P. (° C.) | Synthetic Path |
|---|---|---|---|---|
| 53 | 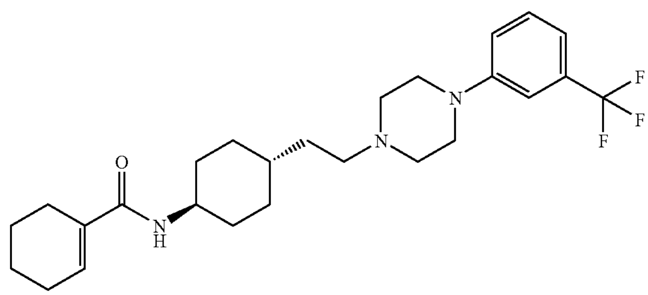 [SMILES: O=C(N[C@H]1CC[C@H](CCN2CCN(c3cccc(C(F)(F)F)c3)CC2)CC1)C1=CCCCC1] | Cyclohex-1-enecarboxylic acid (4-{2-[4-(3-trifluoromethylphenyl)-piperazin-1-yl]ethyl}cyclohexyl)-amide | 175 | IIA |
| 54 | 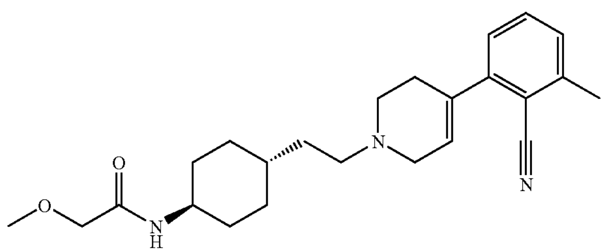 | N-(4-{2-[4-(2-Cyano-3-methylphenyl)-3,6-dihydro-2H-pyridin-1-yl]ethyl}cyclohexyl)-2-methoxyacetamide | 158 | IIA |
| 55 | 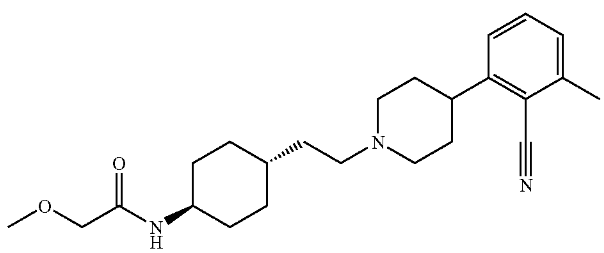 | N-(4-{2-[4-(2-Cyano-3-methylphenyl)piperidin-1-yl]ethyl}cyclohexyl)-2-methoxyacetamide | 141 | IIA |
| 56 | 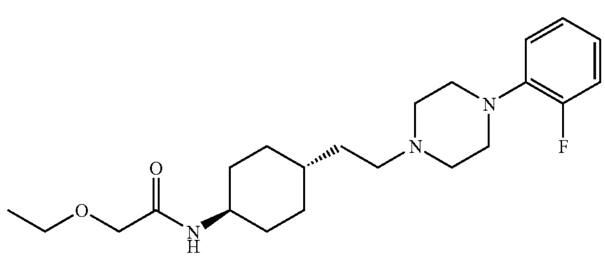 [SMILES: CCOCC(=O)N[C@H]1CC[C@H](CCN2CCN(c3ccccc3F)CC2)CC1] | 2-Ethoxy-N-(4-{2-[4-(2-fluorophenyl)piperazin-1-yl]ethyl}cyclohexyl)acetamide | 117-118 | IIA |
| 57 | 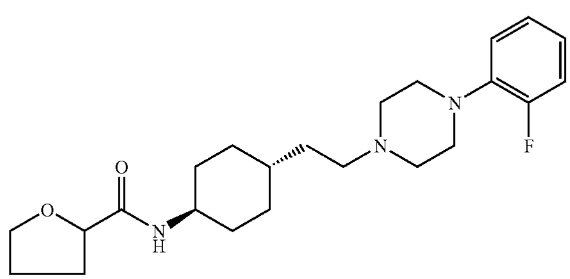 [SMILES: O=C(N[C@H]1CC[C@H](CCN2CCN(c3ccccc3F)CC2)CC1)C1CCCO1] | Tetrahydrofuran-2-carboxylic acid (4-{2-[4-(2-fluorophenyl)piperazin-1-yl]ethyl}cyclohexyl)amide | 119-120 | IIA |

| Ex | Structure | Name | M.P. (° C.) | Synthetic Path |
|---|---|---|---|---|
| 58 | 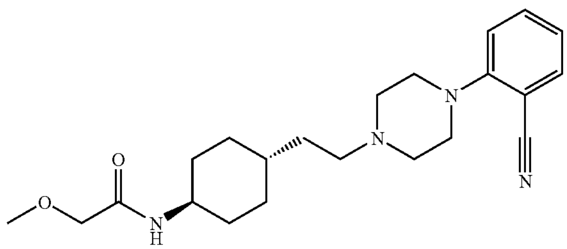 [SMILES: COCC(=O)N[C@H]1CC[C@H](CCN2CCN(c3ccccc3C#N)CC2)CC1] | N-(4-{2-[4-(2-Cyanophenyl)-piperazin-1-yl]ethyl}cyclohexyl)-2-methoxyacetamide | 113 | IIA |
| 59 | 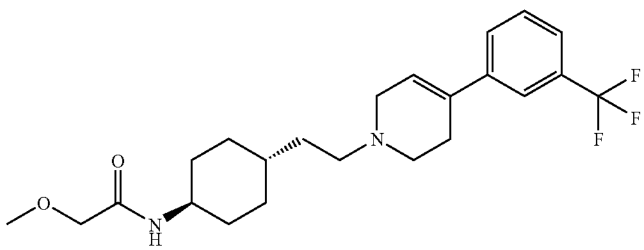 [SMILES: COCC(=O)N[C@H]1CC[C@H](CCN2CC=C(c3cccc(C(F)(F)F)c3)CC2)CC1] | 2-Methoxy-N-(4-{2-[4-(3-trifluoromethylphenyl)-3,6-dihydro-2H-pyridin-1-yl]ethyl}cyclohexyl)acetamide trans/cis 95/5 | | IIA |
| 60 | 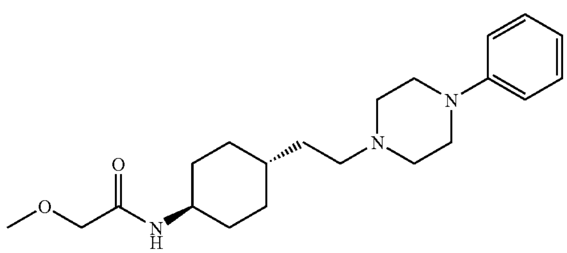 [SMILES: COCC(=O)N[C@H]1CC[C@H](CCN2CCN(c3ccccc3)CC2)CC1] | 2-Methoxy-N-{4-[2-(4-phenylpiperazin-1-yl)ethyl]-cyclohexyl}acetamide | 136 | IIA |
| 61 | 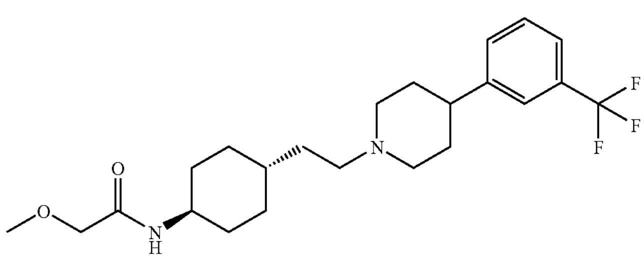 [SMILES: COCC(=O)N[C@H]1CC[C@H](CCN2CCC(c3cccc(C(F)(F)F)c3)CC2)CC1] | 2-Methoxy-N-(4-{2-[4-(3-trifluoromethylphenyl)piperidin-1-yl]ethyl}cyclohexyl)acetamide trans/cis 95/5 | 82 | IIA |
| 62 | 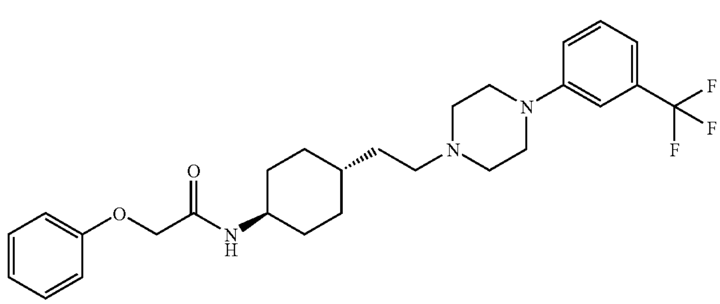 [SMILES: O=C(COc1ccccc1)N[C@H]1CC[C@H](CCN2CCN(c3cccc(C(F)(F)F)c3)CC2)CC1] | 2-Phenoxy-N-(4-{2-[4-(3-trifluoromethylphenyl)piperazin-1-yl]ethyl}cyclohexyl)acetamide | | IIA |

-continued

| Ex | Structure | Name | M.P. (° C.) | Synthetic Path |
|---|---|---|---|---|
| 63 | 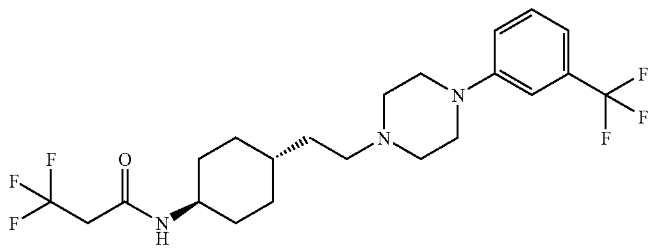 [SMILES: O=C(CC(F)(F)F)N[C@H]1CC[C@H](CCN2CCN(c3cccc(C(F)(F)F)c3)CC2)CC1] | 3,3,3-Trifluoro-N-(4-{2-[4-(3-trifluoromethylphenyl)piperazin-1-yl]ethyl}cyclohexyl)propanamide | 156 | IIA |
| 64 | 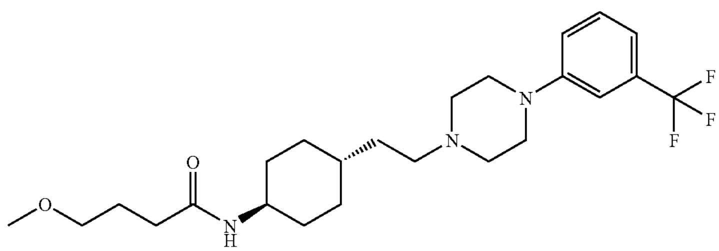 | 4-Methoxy-N-(4-{2-[4-(3-trifluoromethylphenyl)piperazin-1-yl]ethyl}cyclohexyl)butanamide | 149 | IIA |
| 65 | 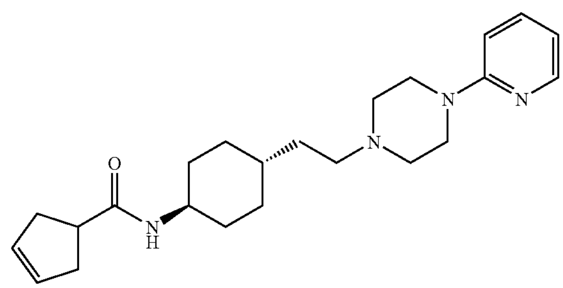 [SMILES: O=C(N[C@H]1CC[C@H](CCN2CCN(c3ccccn3)CC2)CC1)C1CC=CC1] | Cyclopent-3-enecarboxylic acid {4-[2-(4-pyridin-2-ylpiperazin-1-yl)ethyl]cyclohexyl}amide | 208 | IIA |
| 66 | 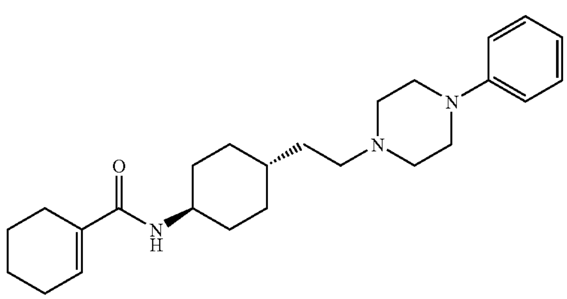 [SMILES: O=C(N[C@H]1CC[C@H](CCN2CCN(c3ccccc3)CC2)CC1)C1=CCCCC1] | Cyclohex-1-enecarboxylic acid {4-[2-(4-phenylpiperazin-1-yl)ethyl]cyclohexyl}amide trans/cis 90/10 | 193 | IIA |
| 67 | 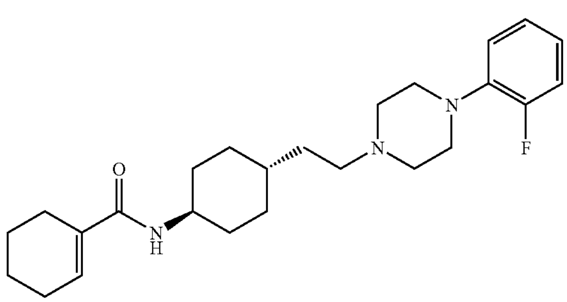 [SMILES: O=C(N[C@H]1CC[C@H](CCN2CCN(c3ccccc3F)CC2)CC1)C1=CCCCC1] | Cyclohex-1-enecarboxylic acid (4-{2-[4-(2-fluorophenyl)-piperazin-1-yl]ethyl}cyclohexyl)-amide | 209 | IIA |

-continued

| Ex | Structure | Name | M.P. (°C.) | Synthetic Path |
|---|---|---|---|---|
| 68 | 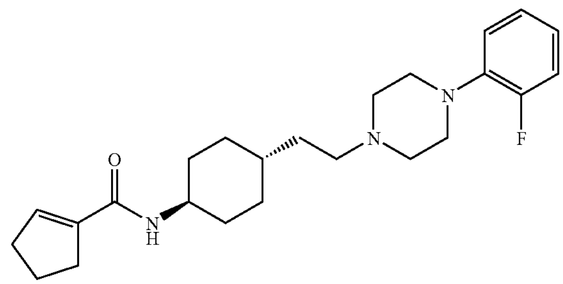 [SMILES: O=C(N[C@H]1CC[C@H](CCN2CCN(c3ccccc3F)CC2)CC1)C1=CCCC1] | Cyclopent-1-enecarboxylic acid (4-{2-[4-(2-fluorophenyl)-piperazin-1-yl]ethyl}-cyclohexyl)amide | 210-211 | IIA |
| 69 | 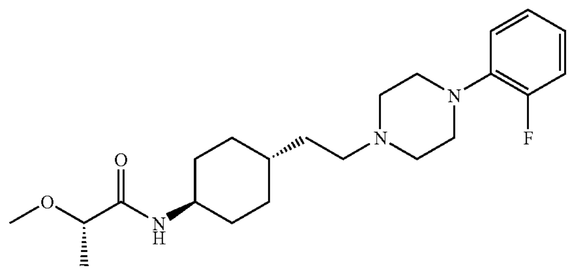 [SMILES: CO[C@@H](C)C(=O)N[C@H]1CC[C@H](CCN2CCN(c3ccccc3F)CC2)CC1] | N-(2-{2-[4-(2-Fluorophenyl)-piperazin-1-yl]ethyl}cyclohexyl)-2-methoxypropanamide | 159 | IIA |
| 70 | 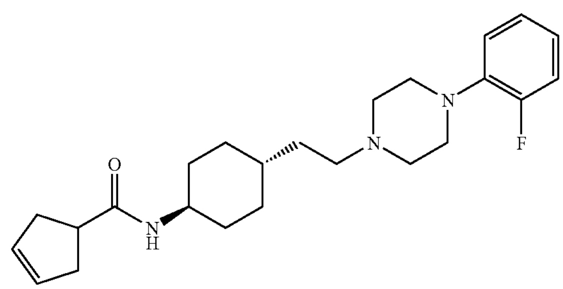 [SMILES: O=C(N[C@H]1CC[C@H](CCN2CCN(c3ccccc3F)CC2)CC1)C1CC=CC1] | Cyclopent-3-enecarboxylic acid (4-{2-[4-(2-fluorophenyl)-piperazin-1-yl]ethyl}-cyclohexyl)amide trans/cis 95/5 | 204 | IIA |
| 71 | 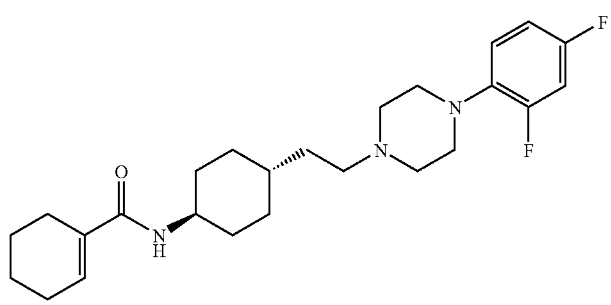 [SMILES: O=C(N[C@H]1CC[C@H](CCN2CCN(c3ccc(F)cc3F)CC2)CC1)C1=CCCCC1] | Cyclohex-1-enecarboxylic acid (4-{2-[4-(2,4-difluorophenyl)-piperazin-1-yl]ethyl}-cyclohexyl)amide | 203 | IIA |
| 72 | 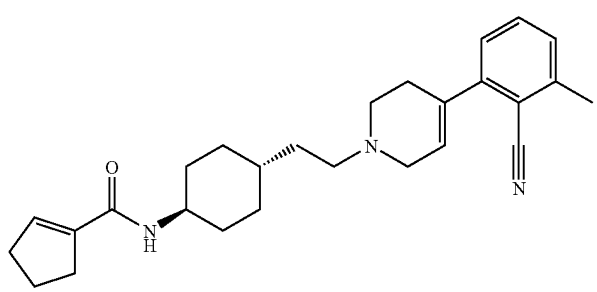 [SMILES: Cc1cccc(C2=CCN(CC[C@H]3CC[C@H](NC(=O)C4=CCCC4)CC3)CC2)c1C#N] | Cyclopent-1-enecarboxylic acid (4-{2-[4-(2-cyano-3-methylphenyl)-3,6-dihydro-2H-pyridin-1-yl]ethyl}cyclohexyl)-amide | 183 | IIA |

| Ex | Structure | Name | M.P. (° C.) | Synthetic Path |
|---|---|---|---|---|
| 73 | 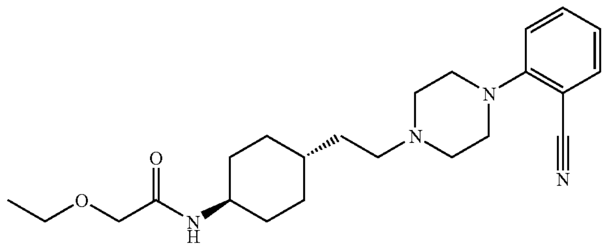 [SMILES: CCOCC(=O)N[C@H]1CC[C@H](CCN2CCN(c3ccccc3C#N)CC2)CC1] | N-(4-{2-[4-(2-Cyanophenyl)-piperazin-1-yl]ethyl}cyclohexyl)-2-ethoxyacetamide | 96 | IIA |
| 74 | 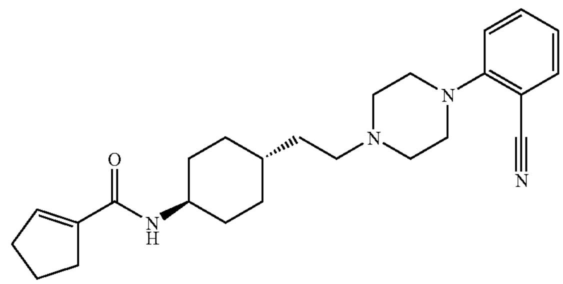 [SMILES: N#Cc1ccccc1N1CCN(CC[C@H]2CC[C@H](NC(=O)C3=CCCC3)CC2)CC1] | Cyclopent-1-enecarboxylic acid (4-{2-[4-(2-cyanophenyl)-piperazin-1-yl]ethyl}cyclohexyl)-amide | 167 | IIA |
| 75 | 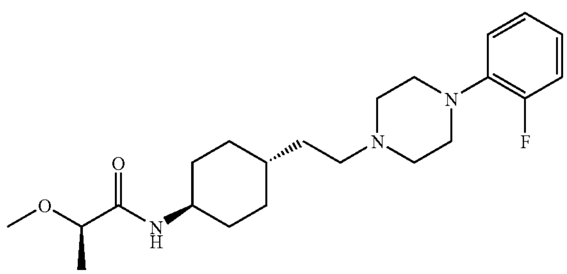 [SMILES: CO[C@H](C)C(=O)N[C@H]1CC[C@H](CCN2CCN(c3ccccc3F)CC2)CC1] | N-(4-{2-[4-(2-Fluorophenyl)-piperazin-1-yl]ethyl}cyclohexyl)-2-methoxypropanamide | 162 | IIA |
| 76 | 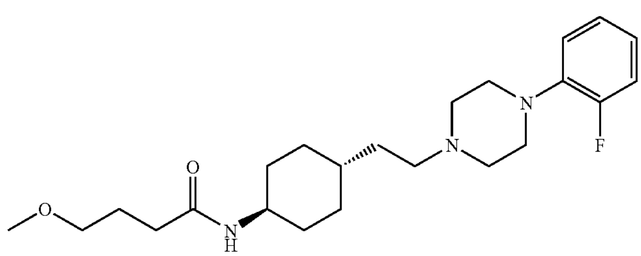 [SMILES: COCCCC(=O)N[C@H]1CC[C@H](CCN2CCN(c3ccccc3F)CC2)CC1] | N-(4-{2-[4-(2-Fluorophenyl)-piperazin-1-yl]ethyl}cyclohexyl)-4-methoxybutanamide | 175 | IIA |
| 77 | 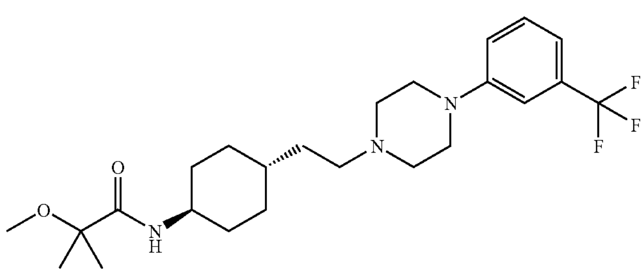 [SMILES: COC(C)(C)C(=O)N[C@H]1CC[C@H](CCN2CCN(c3cccc(C(F)(F)F)c3)CC2)CC1] | 2-Methoxy-2-methyl-N-(4-{2-[4-(3-trifluoromethylphenyl)-piperazin-1-yl]ethyl}cyclohexyl)-propanamide | 105 | IIA |

-continued

| Ex | Structure | Name | M.P. (° C.) | Synthetic Path |
|---|---|---|---|---|
| 78 | 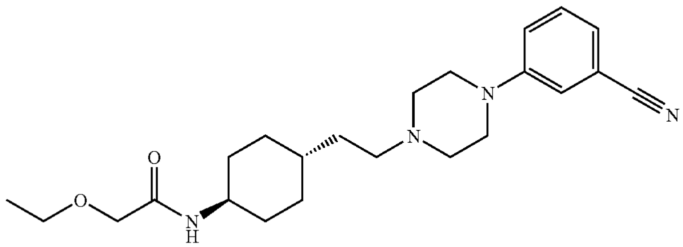 [SMILES: CCOCC(=O)N[C@H]1CC[C@H](CCN2CCN(c3cccc(C#N)c3)CC2)CC1] | N-(4-{2-[4-(3-Cyanophenyl)-piperazin-1-yl]ethyl}cyclohexyl)-2-ethoxyacetamide trans/cis 75/25 | 90 | IIA |
| 79 | 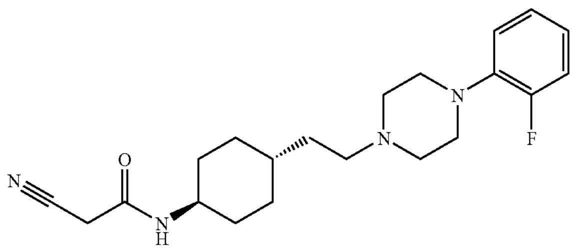 [SMILES: N#CCC(=O)N[C@H]1CC[C@H](CCN2CCN(c3ccccc3F)CC2)CC1] | 2-Cyano-N-(4-{2-[4-(2-fluorophenyl)piperazin-1-yl]ethyl}cyclohexyl)acetamide | 179-180 | IIA |
| 80 | 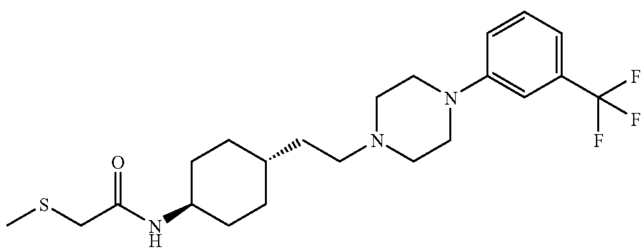 [SMILES: CSCC(=O)N[C@H]1CC[C@H](CCN2CCN(c3cccc(C(F)(F)F)c3)CC2)CC1] | 2-Methylsulfanyl-N-(4-{2-[4-(3-trifluoromethylphenyl)piperazin-1-yl]ethyl}cyclohexyl)acetamide | 128 | IIA |
| 81 | 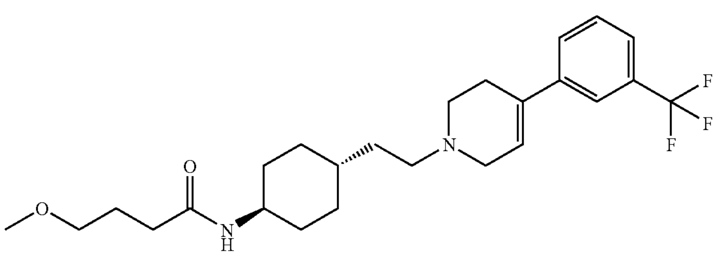 [SMILES: COCCCC(=O)N[C@H]1CC[C@H](CCN2CC=C(c3cccc(C(F)(F)F)c3)CC2)CC1] | 4-Methoxy-N-(4-{2-[4-(3-trifluoromethylphenyl)-3,6-dihydro-2H-pyridin-1-yl]ethyl}cyclohexyl)butanamide | 145 | IIA |
| 82 | 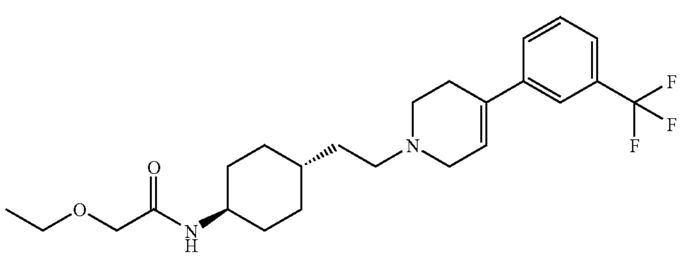 [SMILES: CCOCC(=O)N[C@H]1CC[C@H](CCN2CC=C(c3cccc(C(F)(F)F)c3)CC2)CC1] | 2-Ethoxy-N-(4-{2-[4-(3-trifluoromethylphenyl)-3,6-dihydro-2H-pyridin-1-yl]ethyl}cyclohexyl)acetamide trans/cis 95/5 | 75 | IIA |
| 83 | 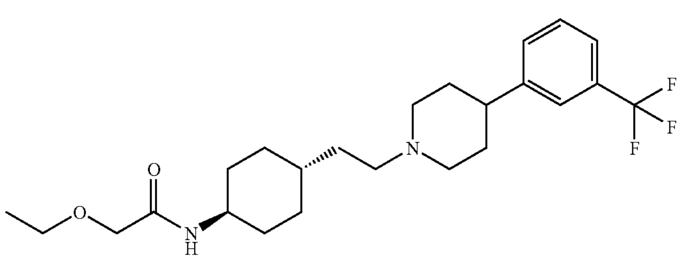 [SMILES: CCOCC(=O)N[C@H]1CC[C@H](CCN2CCC(c3cccc(C(F)(F)F)c3)CC2)CC1] | 2-Ethoxy-N-(4-{2-[4-(3-trifluoromethylphenyl)piperidin-1-yl]ethyl}cyclohexyl)acetamide | 84 | IIA |

-continued

| Ex | Structure | Name | M.P. (° C.) | Synthetic Path |
|---|---|---|---|---|
| 84 | 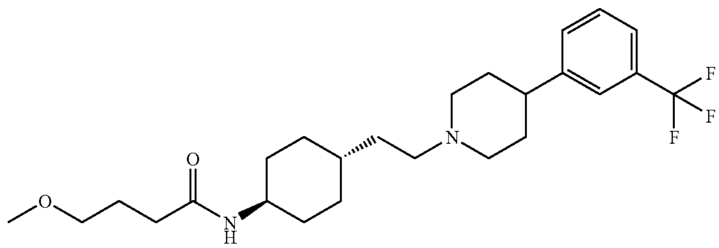 [SMILES: COCCCC(=O)N[C@H]1CC[C@H](CCN2CCC(c3cccc(C(F)(F)F)c3)CC2)CC1] | 4-Methoxy-N-(4-{2-[4-(3-trifluoromethylphenyl)piperidin-1-yl]ethyl}cyclohexyl)butanamide | 134 | IIA |
| 85 | ClH | 2-(2-Methoxyethoxy)-N-(4-{2-[4-(3-trifluoromethylphenyl)-piperazin-1-yl]ethyl}cyclohexyl)-acetamide, hydrochloride trans/cis 75/25 | | IIA |
| 86 | 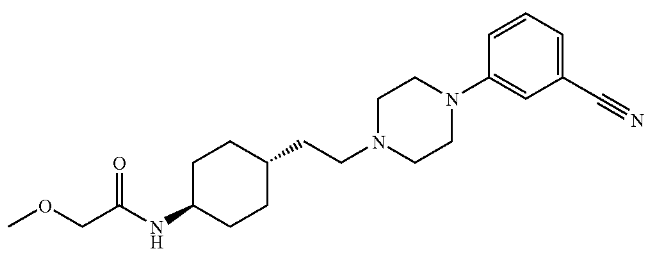 [SMILES: COCC(=O)N[C@H]1CC[C@H](CCN2CCN(c3cccc(C#N)c3)CC2)CC1] | N-(4-{2-[4-(3-Cyanophenyl)piperazin-1-yl]ethyl}cyclohexyl)-2-methoxyacetamide | 138 | IIA |
| 87 | 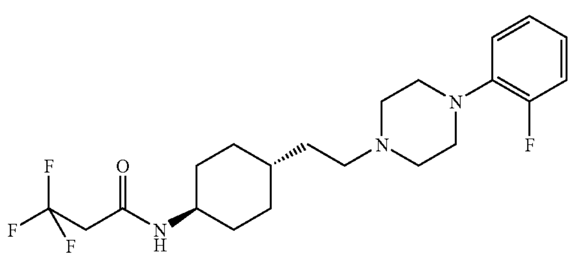 [SMILES: O=C(CC(F)(F)F)N[C@H]1CC[C@H](CCN2CCN(c3ccccc3F)CC2)CC1] | 3,3,3-Trifluoro-N-(4-{2-[4-(2-fluorophenyl)piperazin-1-yl]ethyl}cyclohexyl)propanamide | 207 | IIA |
| 88 | 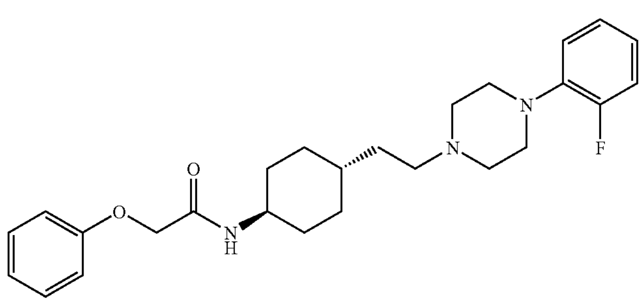 [SMILES: O=C(COc1ccccc1)N[C@H]1CC[C@H](CCN2CCN(c3ccccc3F)CC2)CC1] | N-(4-{2-[4-(2-Fluorophenyl)-piperazin-1-yl]ethyl}cyclohexyl)-2-phenoxyacetamide | 172 | IIA |

-continued

| Ex | Structure | Name | M.P. (° C.) | Synthetic Path |
|---|---|---|---|---|
| 89 | 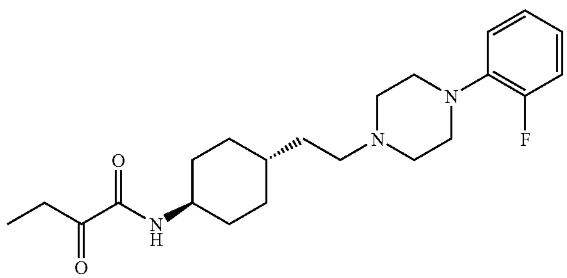 [SMILES: CCC(=O)C(=O)N[C@H]1CC[C@H](CCN2CCN(c3ccccc3F)CC2)CC1] | N-(4-{2-[4-(2-Fluorophenyl)-piperazin-1-yl]ethyl}cyclohexyl)-2-oxobutanamide | 156 | IIA |
| 90 | 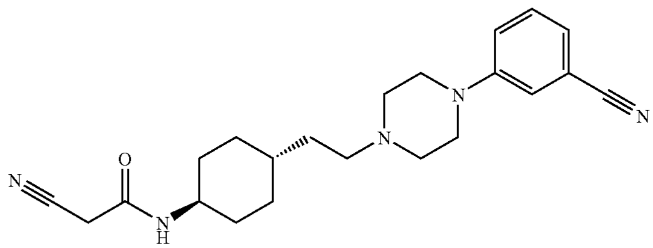 [SMILES: N#CCC(=O)N[C@H]1CC[C@H](CCN2CCN(c3cccc(C#N)c3)CC2)CC1] | 2-Cyano-N-(4-{2-[4-(3-cyanophenyl)piperazin-1-yl]ethyl}cyclohexyl)acetamide trans/cis 75/25 | 188 | IIA |
| 91 | 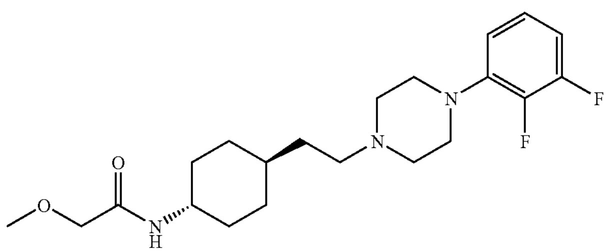 [SMILES: COCC(=O)N[C@H]1CC[C@H](CCN2CCN(c3cccc(F)c3F)CC2)CC1] | N-(4-{2-[4-(2,3-Difluorophenyl)-piperazin-1-yl]ethyl}cyclohexyl)-2-methoxyacetamide | 155 | IIA |
| 92 | 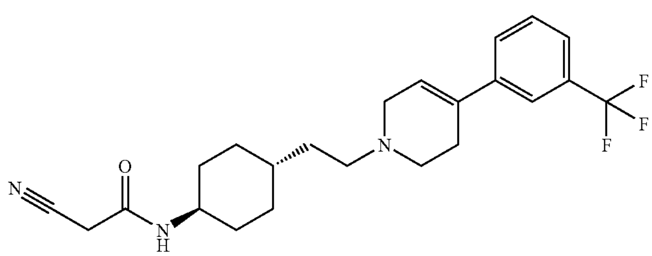 [SMILES: N#CCC(=O)N[C@H]1CC[C@H](CCN2CC=C(c3cccc(C(F)(F)F)c3)CC2)CC1] | 2-Cyano-N-(4-{2-[4-(3-trifluoromethylphenyl)-3,6-dihydro-2H-pyridin-1-yl]ethyl}cyclohexyl)acetamide | 149 | IIA |
| 93 | 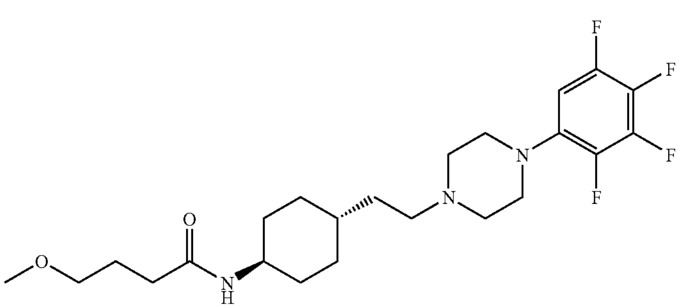 [SMILES: COCCCC(=O)N[C@H]1CC[C@H](CCN2CCN(c3cc(F)c(F)c(F)c3F)CC2)CC1] | 4-Methoxy-N-(4-{2-[4-(2,3,4,5-tetrafluorophenyl)piperazin-1-yl]ethyl}cyclohexyl)butyramide | 201 | IIA |

-continued

| Ex | Structure | Name | M.P. (° C.) | Synthetic Path |
|---|---|---|---|---|
| 94 | 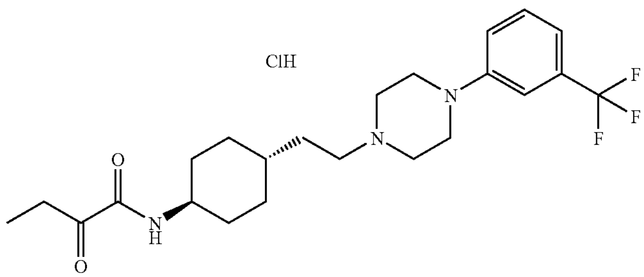 [SMILES: CCC(=O)C(=O)N[C@H]1CC[C@H](CCN2CCN(c3cccc(C(F)(F)F)c3)CC2)CC1 ; Cl] | 2-Oxo-N-(4-{2-[4-(3-trifluoromethylphenyl)piperazin-1-yl]ethyl}cyclohexyl)butanamide, hydrochloride trans/cis 70/30 | | IIA |
| 95 | 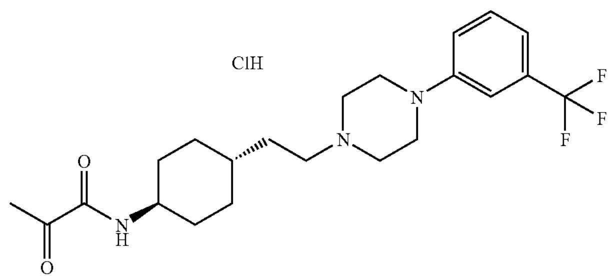 [SMILES: CC(=O)C(=O)N[C@H]1CC[C@H](CCN2CCN(c3cccc(C(F)(F)F)c3)CC2)CC1 ; Cl] | 2-Oxo-N-(4-{2-[4-(3-trifluoromethylphenyl)piperazin-1-yl]ethyl}cyclohexyl)propanamide, hydrochloride trans/cis 70/30 | | IIA |
| 96 | 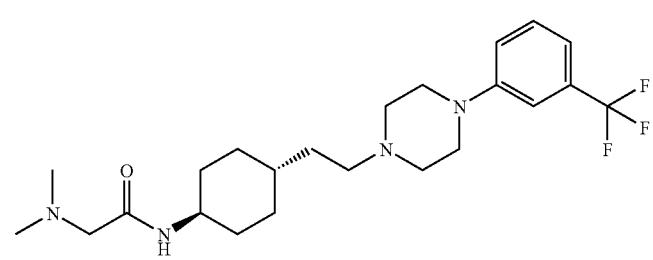 | 2-Dimethylamino-N-(4-{2-[4-(3-trifluoromethylphenyl)piperazin-1-yl]ethyl}cyclohexyl)acetamide | | IIA |
| 97 | 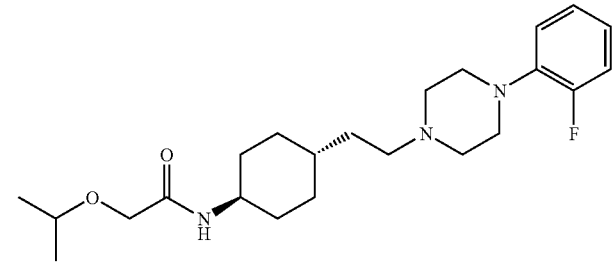 [SMILES: CC(C)OCC(=O)N[C@H]1CC[C@H](CCN2CCN(c3ccccc3F)CC2)CC1] | N-(4-{2-[4-(2-Fluorophenyl)-piperazin-1-yl]ethyl}cyclohexyl)-2-isopropoxyacetamide | 96 | IIA |
| 98 | 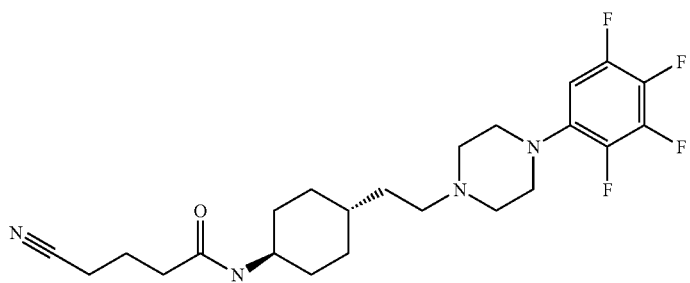 | 4-Cyano-N-(4-{2-[4-(2,3,4,5-tetrafluorophenyl)piperazin-1-yl]ethyl}cyclohexyl)butyramide | 180 | IIA |

-continued

| Ex | Structure | Name | M.P. (° C.) | Synthetic Path |
|---|---|---|---|---|
| 99 | 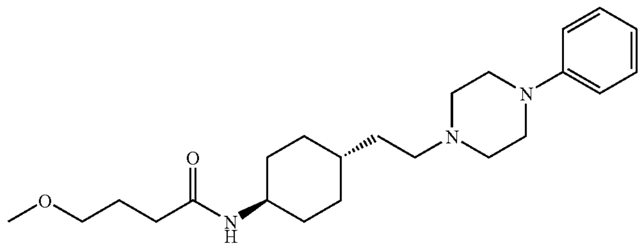 [SMILES: COCCCC(=O)N[C@H]1CC[C@H](CCN2CCN(c3ccccc3)CC2)CC1] | 4-Methoxy-N-{4-[2-(4-phenylpiperazin-1-yl)ethyl]cyclohexyl}butanamide | 172 | IIA |
| 100 | 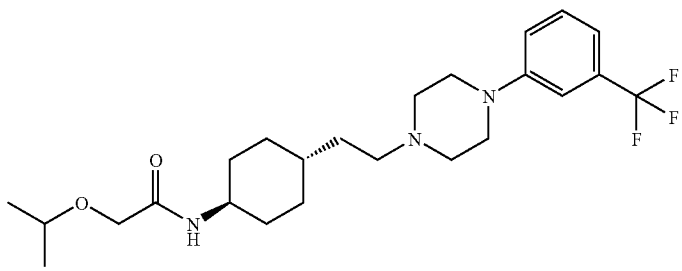 [SMILES: CC(C)OCC(=O)N[C@H]1CC[C@H](CCN2CCN(c3cccc(C(F)(F)F)c3)CC2)CC1] | 2-Isopropoxy-N-(4-{2-[4-(3-trifluoromethylphenyl)piperazin-1-yl]ethyl}cyclohexyl)acetamide trans/cis 80/20 | | IIA |
| 101 | 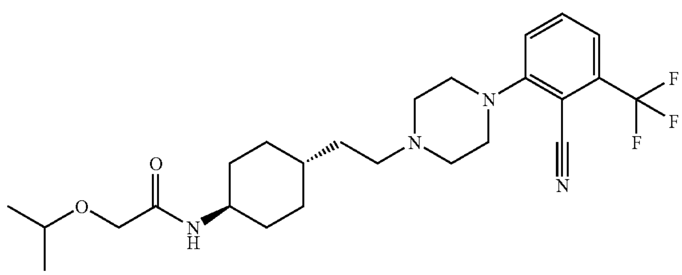 [SMILES: CC(C)OCC(=O)N[C@H]1CC[C@H](CCN2CCN(c3cccc(C(F)(F)F)c3C#N)CC2)CC1] | N-(4-{2-[4-(2-Cyano-3-trifluoromethylphenyl)piperazin-1-yl]ethyl}cyclohexyl)-2-isopropoxyacetamide | 144 | IIA |
| 102 | 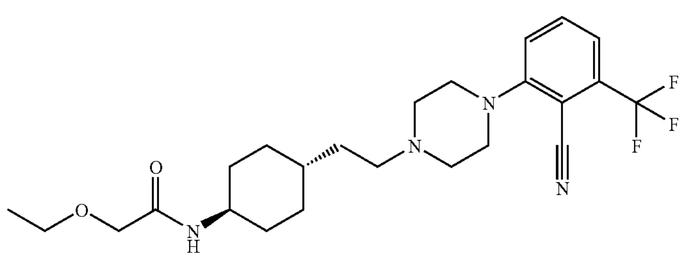 [SMILES: CCOCC(=O)N[C@H]1CC[C@H](CCN2CCN(c3cccc(C(F)(F)F)c3C#N)CC2)CC1] | N-(4-{2-[4-(2-Cyano-3-trifluoromethylphenyl)piperazin-1-yl]ethyl}cyclohexyl)-2-ethoxyacetamide | 173 | IIA |
| 103 | 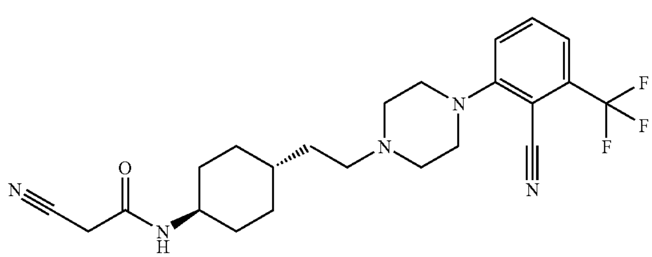 [SMILES: N#CCC(=O)N[C@H]1CC[C@H](CCN2CCN(c3cccc(C(F)(F)F)c3C#N)CC2)CC1] | 2-Cyano-N-(4-{2-[4-(2-cyano-3-trifluoromethylphenyl)piperazin-1-yl]ethyl}cyclohexyl)acetamide | 222 | IIA |

-continued

| Ex | Structure | Name | M.P. (° C.) | Synthetic Path |
|---|---|---|---|---|
| 104 | 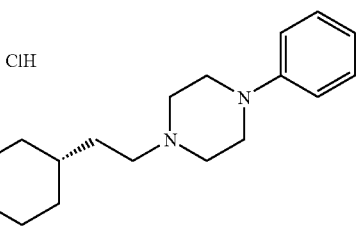 ClH | 2-Cyano-N-{4-[2-(4-phenyl-piperazin-1-yl)ethyl]cyclohexyl}-acetamide, hydrochloride | 243 | IIA |
| 105 | 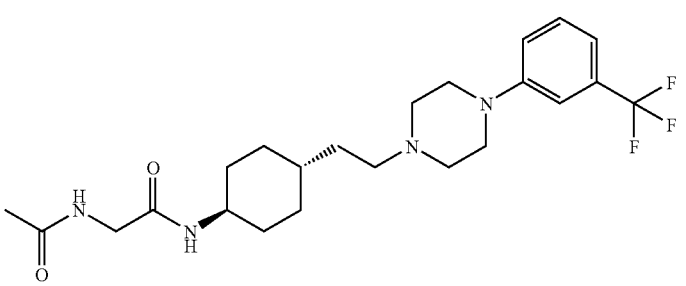 [SMILES: CC(=O)NCC(=O)N[C@H]1CC[C@H](CCN2CCN(c3cccc(C(F)(F)F)c3)CC2)CC1] | 2-Acetylamino-N-(4-{2-[4-(3-trifluoromethylphenyl)piperazin-1-yl]ethyl}cyclohexyl)acetamide | 187 | IIA |
| 106 | 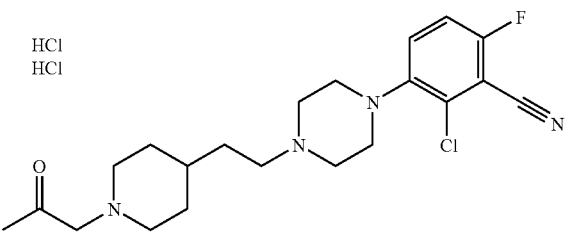 [SMILES: CC(=O)CN1CCC(CCN2CCN(c3ccc(F)c(C#N)c3Cl)CC2)CC1 ; Cl ; Cl] HCl HCl | 2-Chloro-6-fluoro-3-(4-{2-[1-(2-oxopropyl)piperidin-4-yl]ethyl}piperazin-1-yl)benzonitrile | 291 | IIIB |
| 107 | 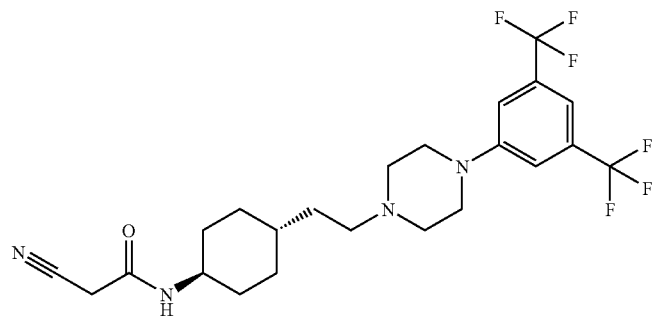 [SMILES: N#CCC(=O)N[C@H]1CC[C@H](CCN2CCN(c3cc(C(F)(F)F)cc(C(F)(F)F)c3)CC2)CC1] | N-(4-{2-[4-(3,5-Bistrifluoro-methylphenyl)piperazin-1-yl]ethyl}cyclohexyl)-2-cyanoacetamide | 196 | IIA |
| 108 | 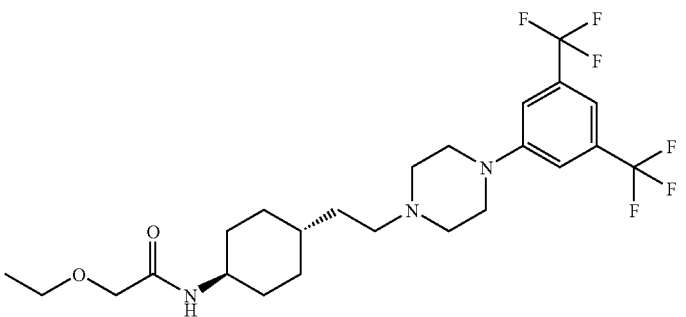 [SMILES: CCOCC(=O)N[C@H]1CC[C@H](CCN2CCN(c3cc(C(F)(F)F)cc(C(F)(F)F)c3)CC2)CC1] | N-(4-{2-[4-(3,5-Bistrifluoro-methylphenyl)piperazin-1-yl]ethyl}cyclohexyl)-2-ethoxyacetamide | 135 | IIA |

| Ex | Structure | Name | M.P. (° C.) | Synthetic Path |
|---|---|---|---|---|
| 109 | 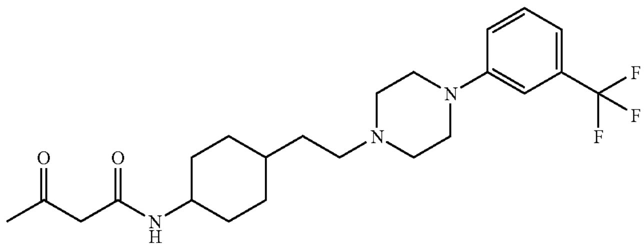 [SMILES: CC(=O)CC(=O)NC1CCC(CCN2CCN(c3cccc(C(F)(F)F)c3)CC2)CC1] | 3-Oxo-N-(4-{2-[4-(3-trifluoromethylphenyl)piperazin-1-yl]ethyl}cyclohexyl)butanamide trans/cis 70/30 | | IIA |
| 110 | 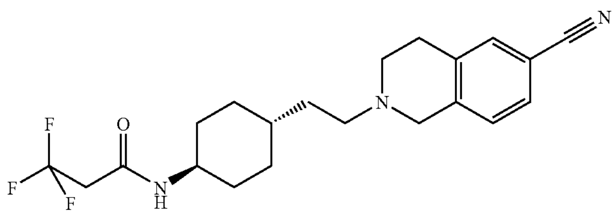 [SMILES: N#Cc1ccc2c(c1)CCN(CC[C@H]1CC[C@H](NC(=O)CC(F)(F)F)CC1)C2] | N-{4-[2-(6-Cyano-3,4-dihydro-1H-isoquinolin-2-yl)ethyl]cyclohexyl}-3,3,3-trifluoropropanamide | 215 | IIA |
| 111 | 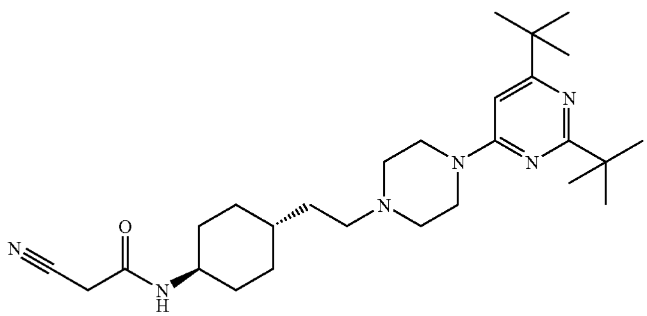 [SMILES: CC(C)(C)c1cc(N2CCN(CC[C@H]3CC[C@H](NC(=O)CC#N)CC3)CC2)nc(C(C)(C)C)n1] | 2-Cyano-N-(4-{2-[4-(2,6-di-tert-butylpyrimidin-4-yl)piperazin-1-yl]ethyl}cyclohexyl)acetamide trans/cis 65/35 | 145 | IIA |
| 112 | 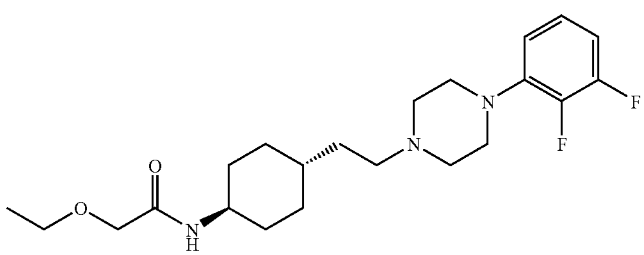 [SMILES: CCOCC(=O)N[C@H]1CC[C@H](CCN2CCN(c3cccc(F)c3F)CC2)CC1] | N-(4-{2-[4-(2,3-Difluorophenyl)-piperazin-1-yl]ethyl}cyclohexyl)-2-ethoxyacetamide | 140 | IIA |
| 113 | 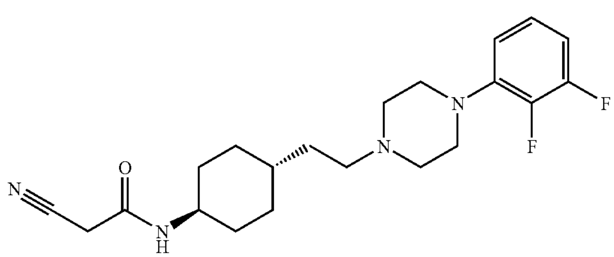 [SMILES: N#CCC(=O)N[C@H]1CC[C@H](CCN2CCN(c3cccc(F)c3F)CC2)CC1] | 2-Cyano-N-(4-{2-[4-(2,3-difluorophenyl)piperazin-1-yl]ethyl}cyclohexyl)acetamide | 190 | IIA |
| 114 | 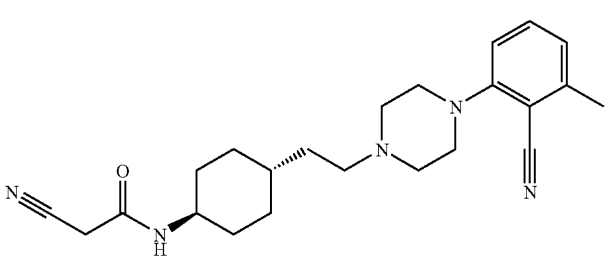 [SMILES: Cc1cccc(N2CCN(CC[C@H]3CC[C@H](NC(=O)CC#N)CC3)CC2)c1C#N] | 2-Cyano-N-(4-{2-[4-(2-cyano-3-methylphenyl)piperazin-1-yl]ethyl}cyclohexyl)acetamide | 221 | IIA |

-continued

| Ex | Structure | Name | M.P. (° C.) | Synthetic Path |
|---|---|---|---|---|
| 115 | 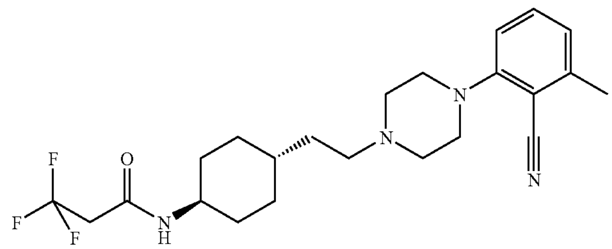 [SMILES: Cc1cccc(N2CCN(CC[C@H]3CC[C@H](NC(=O)CC(F)(F)F)CC3)CC2)c1C#N] | N-(4-{2-[4-(2-Cyano-3-methylphenyl)piperazin-1-yl]ethyl}cyclohexyl)-3,3,3-trifluoropropanamide | 207 | IIA |
| 116 | 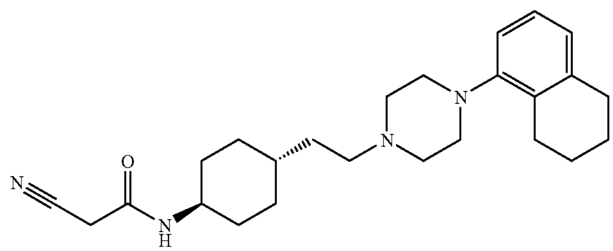 [SMILES: N#CCC(=O)N[C@H]1CC[C@H](CCN2CCN(c3cccc4c3CCCC4)CC2)CC1] | 2-Cyano-N-(4-{2-[4-(5,6,7,8-tetrahydronaphthalen-1-yl)piperazin-1-yl]ethyl}cyclohexyl)acetamide | 175 | IIA |
| 117 | 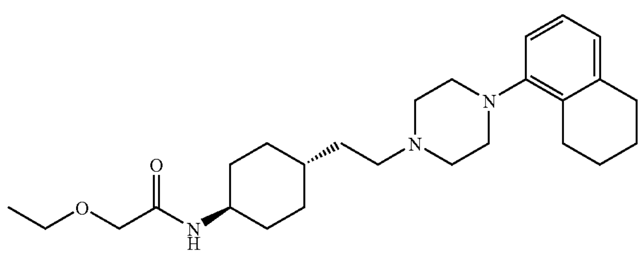 [SMILES: CCOCC(=O)N[C@H]1CC[C@H](CCN2CCN(c3cccc4c3CCCC4)CC2)CC1] | 2-Ethoxy-N-(4-{2-[4-(5,6,7,8-tetrahydronaphthalen-1-yl)piperazin-1-yl]ethyl}-cyclohexyl)acetamide | 91 | IIA |
| 118 | 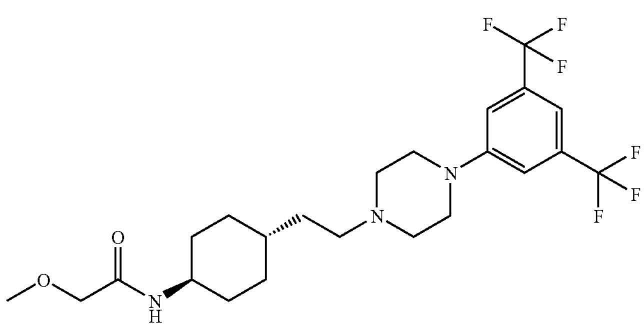 [SMILES: COCC(=O)N[C@H]1CC[C@H](CCN2CCN(c3cc(C(F)(F)F)cc(C(F)(F)F)c3)CC2)CC1] | N-(4-{2-[4-(3,5-Bistrifluoromethylphenyl)piperazin-1-yl]ethyl}cyclohexyl)-2-methoxyacetamide | 164 | IIA |
| 119 | 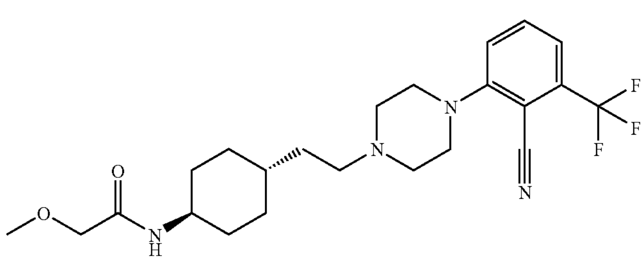 [SMILES: COCC(=O)N[C@H]1CC[C@H](CCN2CCN(c3cccc(C(F)(F)F)c3C#N)CC2)CC1] | N-(4-{2-[4-(2-Cyano-3-trifluoromethylphenyl)piperazin-1-yl]ethyl}cyclohexyl)-2-methoxyacetamide | 172 | IIA |

-continued

| Ex | Structure | Name | M.P. (° C.) | Synthetic Path |
|---|---|---|---|---|
| 120 | 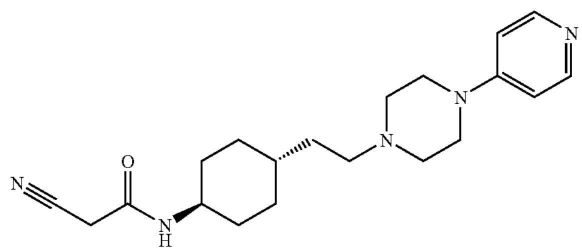 [SMILES: N#CCC(=O)N[C@H]1CC[C@H](CCN2CCN(c3ccncc3)CC2)CC1] | 2-Cyano-N-{4-[2-(4-pyridin-4-ylpiperazin-1-yl)ethyl]cyclohexyl}acetamide trans/cis 65/35 | | IIA |
| 121 | 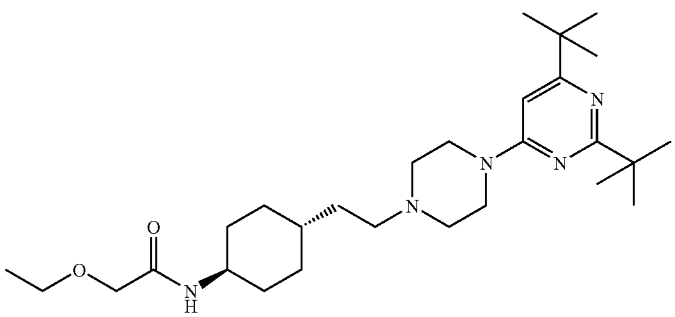 [SMILES: CCOCC(=O)N[C@H]1CC[C@H](CCN2CCN(c3cc(C(C)(C)C)nc(C(C)(C)C)n3)CC2)CC1] | N-(4-{2-[4-(2,6-Di-tert-butylpyrimidin-4-yl)piperazin-1-yl]ethyl}cyclohexyl)-2-ethoxyacetamide | 104 | IIA |
| 122 | 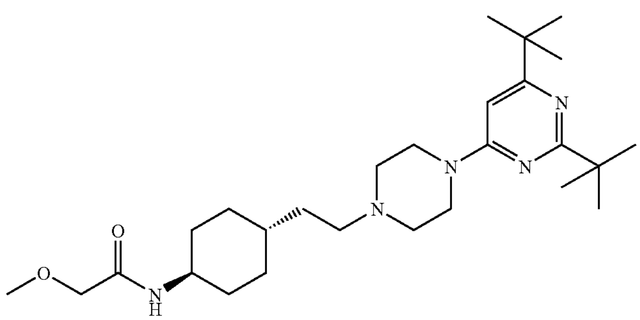 [SMILES: COCC(=O)N[C@H]1CC[C@H](CCN2CCN(c3cc(C(C)(C)C)nc(C(C)(C)C)n3)CC2)CC1] | N-(4-{2-[4-(2,6-Di-tert-butylpyrimidin-4-yl)piperazin-1-yl]ethyl}cyclohexyl)-2-methoxyacetamide | 130 | IIA |
| 123 | 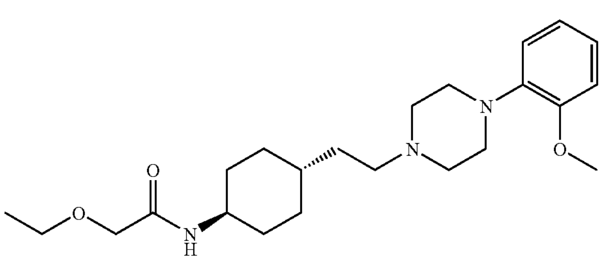 [SMILES: CCOCC(=O)N[C@H]1CC[C@H](CCN2CCN(c3ccccc3OC)CC2)CC1] | 2-Ethoxy-N-(4-{2-[4-(2-methoxyphenyl)piperazin-1-yl]ethyl}cyclohexyl)acetamide | 210-214 | IIA |
| 124 | 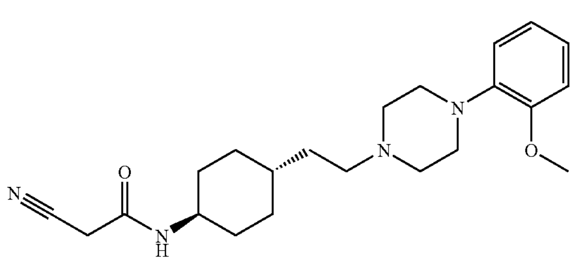 [SMILES: COc1ccccc1N1CCN(CC[C@H]2CC[C@H](NC(=O)CC#N)CC2)CC1] | 2-Cyano-N-(4-{2-[4-(2-methoxyphenyl)piperazin-1-yl]ethyl}cyclohexyl)acetamide | 187 | IIA |

| Ex | Structure | Name | M.P. (° C.) | Synthetic Path |
|---|---|---|---|---|
| 125 | 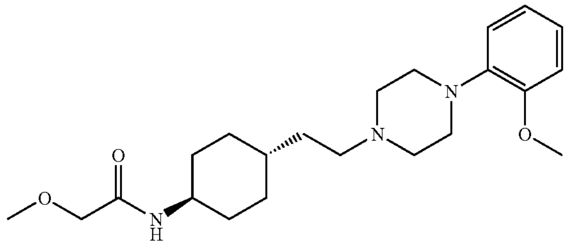 | 2-Methoxy-N-(4-{2-[4-(2-methoxyphenyl)piperazin-1-yl]ethyl}cyclohexyl)acetamide | 125-126 | IIA |
| 126 | 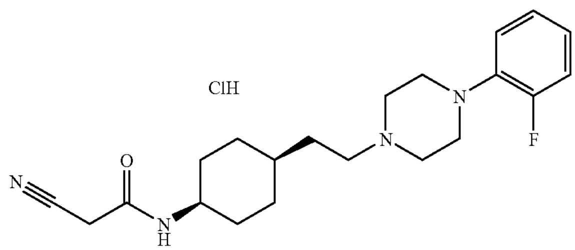 [SMILES: N#CCC(=O)N[C@H]1CC[C@@H](CCN2CCN(c3ccccc3F)CC2)CC1 ; Cl] | 2-Cyano-N-(4-{2-[4-(2-fluorophenyl)piperazin-1-yl]ethyl}cyclohexyl)acetamide, hydrochloride | 153 | IIA |
| 127 | 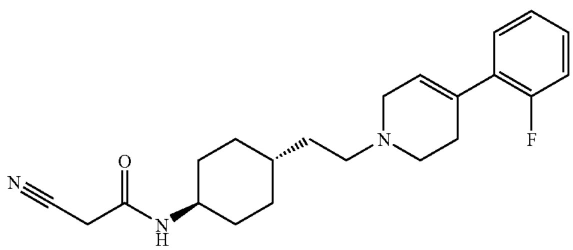 [SMILES: N#CCC(=O)N[C@H]1CC[C@H](CCN2CC=C(c3ccccc3F)CC2)CC1] | 2-Cyano-N-(4-{2-[4-(2-fluorophenyl)-3,6-dihydro-2H-pyridin-1-yl]ethyl}cyclohexyl)-acetamide trans/cis 90/10 | 156 | IIA |
| 128 | 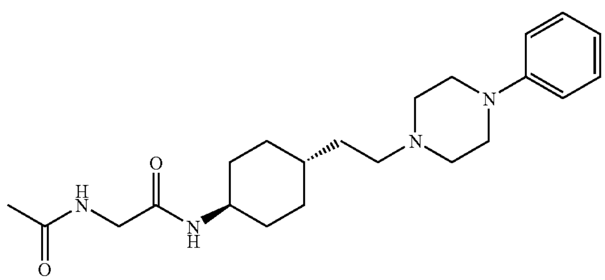 [SMILES: CC(=O)NCC(=O)N[C@H]1CC[C@H](CCN2CCN(c3ccccc3)CC2)CC1] | 2-Acetylamino-N-{4-[2-(4-phenylpiperazin-1-yl)ethyl]cyclohexyl}acetamide | 227 | IIA |
| 129 | 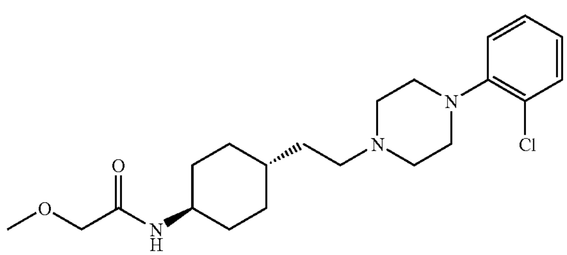 | N-(4-{2-[4-(2-Chlorophenyl)-piperazin-1-yl]ethyl}cyclohexyl)-2-methoxyacetamide | 100 | IIA |
| 130 | 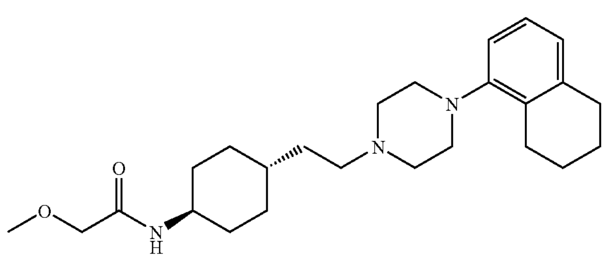 [SMILES: COCC(=O)N[C@H]1CC[C@H](CCN2CCN(c3cccc4c3CCCC4)CC2)CC1] | 2-Methoxy-N-(4-{2-[4-(5,6,7,8-tetrahydronaphthalen-1-yl)piperazin-1-yl]ethyl}cyclohexyl)acetamide | 120 | IIA |

| Ex | Structure | Name | M.P. (° C.) | Synthetic Path |
|---|---|---|---|---|
| 131 | 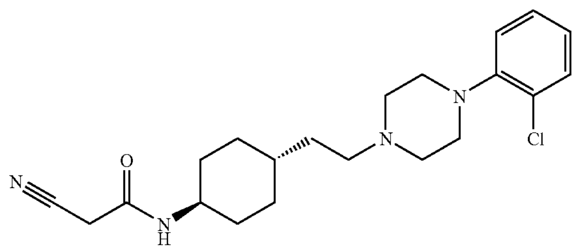 [SMILES: N#CCC(=O)N[C@H]1CC[C@H](CCN2CCN(c3ccccc3Cl)CC2)CC1] | N-(4-{2-[4-(2-Chlorophenyl)-piperazin-1-yl]ethyl}cyclohexyl)-2-cyanoacetamide | 194 | IIA |
| 132 | 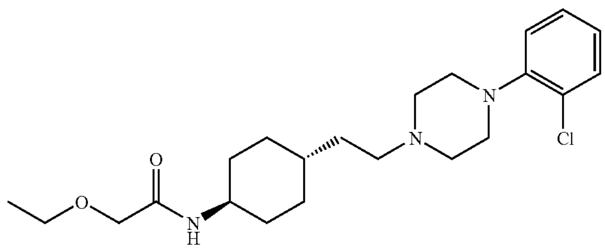 | N-(4-{2-[4-(2-Chlorophenyl)-piperazin-1-yl]ethyl}cyclohexyl)-2-ethoxyacetamide | 108 | IIA |
| 133 | 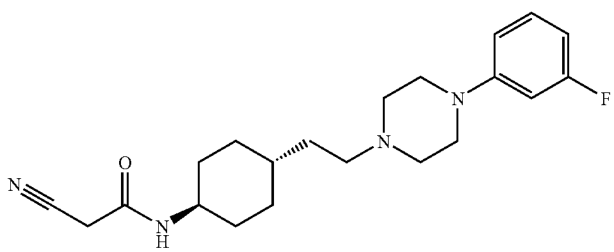 [SMILES: N#CCC(=O)N[C@H]1CC[C@H](CCN2CCN(c3cccc(F)c3)CC2)CC1] | 2-Cyano-N-(4-{2-[4-(3-fluorophenyl-piperazin-1-yl]ethyl}cyclohexyl)acetamide | 202 | IIA |
| 134 | 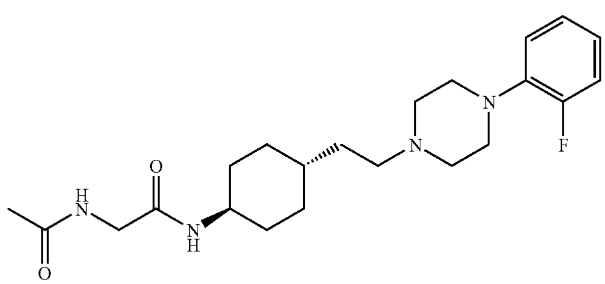 [SMILES: CC(=O)NCC(=O)N[C@H]1CC[C@H](CCN2CCN(c3ccccc3F)CC2)CC1] | 2-Acetylamino-N-(4-{2-[4-(2-fluorophenyl)piperazin-1-yl]ethyl}cyclohexyl)acetamide | 217 | IIA |
| 135 | 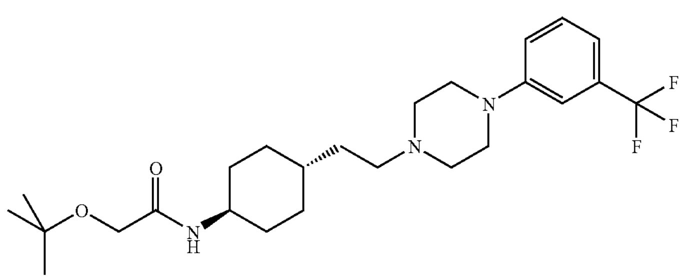 [SMILES: CC(C)(C)OCC(=O)N[C@H]1CC[C@H](CCN2CCN(c3cccc(C(F)(F)F)c3)CC2)CC1] | 2-tert-Butoxy-N-(4-{2-[4-(3-trifluoromethylphenyl)piperazin-1-yl]ethyl}cyclohexyl)acetamide trans/cis 95/5 | 81 | IIA |

-continued

| Ex | Structure | Name | M.P. (° C.) | Synthetic Path |
|---|---|---|---|---|
| 136 | 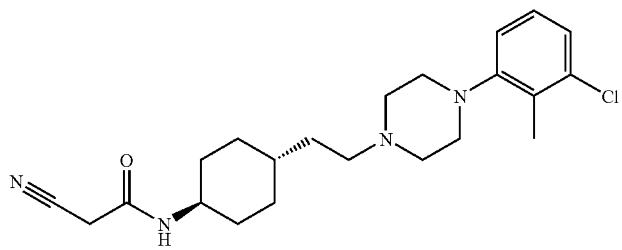 | N-(4-{2-[4-(3-Chloro-2-methylphenyl)piperazin-1-yl]ethyl}cyclohexyl)-2-cyanoacetamide | 179-182 | IIA |
| 137 | 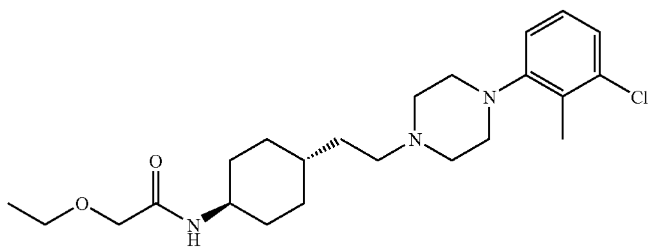 [SMILES: CCOCC(=O)N[C@H]1CC[C@H](CCN2CCN(c3cccc(Cl)c3C)CC2)CC1] | N-(4-{2-[4-(3-Chloro-2-methylphenyl)piperazin-1-yl]ethyl}cyclohexyl)-2-ethoxyacetamide | 143 | IIA |
| 138 | 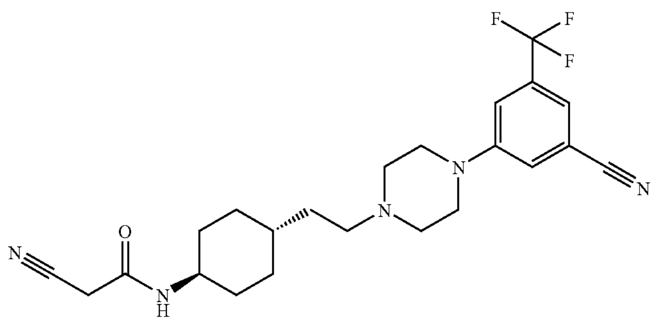 [SMILES: N#CCC(=O)N[C@H]1CC[C@H](CCN2CCN(c3cc(C#N)cc(C(F)(F)F)c3)CC2)CC1] | 2-Cyano-N-(4-{2-[4-(3-cyano-5-trifluoromethylphenyl)piperazin-1-yl]ethyl}cyclohexyl)acetamide | 186 | IIA |
| 139 | 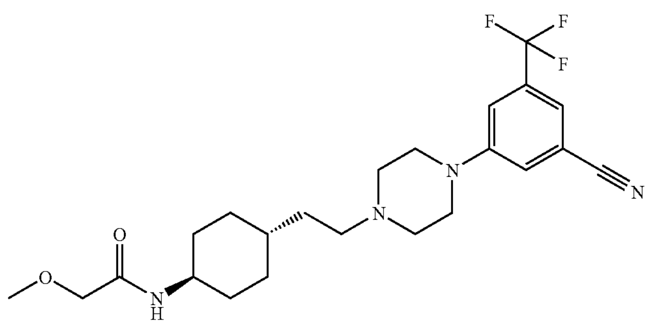 [SMILES: COCC(=O)N[C@H]1CC[C@H](CCN2CCN(c3cc(C#N)cc(C(F)(F)F)c3)CC2)CC1] | N-(4-{2-[4-(3-Cyano-5-trifluoromethylphenyl)piperazin-1-yl]ethyl}cyclohexyl)-2-methoxyacetamide | 140 | IIA |
| 140 | 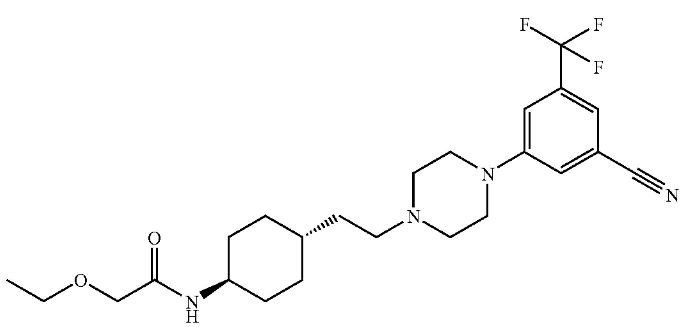 [SMILES: CCOCC(=O)N[C@H]1CC[C@H](CCN2CCN(c3cc(C#N)cc(C(F)(F)F)c3)CC2)CC1] | N-(4-{2-[4-(3-Cyano-5-trifluoromethylphenyl)piperazin-1-yl]ethyl}cyclohexyl)-2-ethoxyacetamide | 133 | IIA |

-continued

| Ex | Structure | Name | M.P. (° C.) | Synthetic Path |
|---|---|---|---|---|
| 141 | 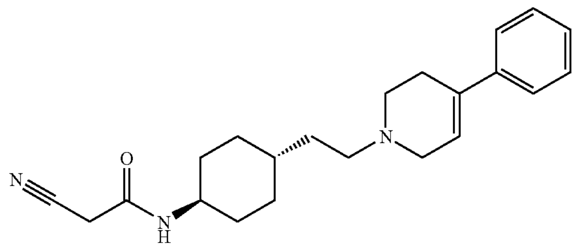 [SMILES: N#CCC(=O)N[C@H]1CC[C@H](CCN2CC=C(c3ccccc3)CC2)CC1] | 2-Cyano-N-{4-[2-(4-phenyl-3,6-dihydro-2H-pyridin-1-yl)ethyl]cyclohexyl}acetamide | 203 | IIA |
| 142 | 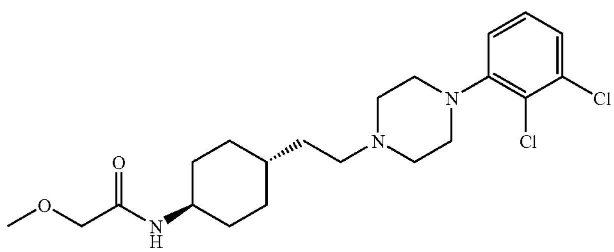 [SMILES: COCC(=O)N[C@H]1CC[C@H](CCN2CCN(c3cccc(Cl)c3Cl)CC2)CC1] | N-(4-{2-[4-(2,3-Dichlorophenyl)-piperazin-1-yl]ethyl}cyclohexyl)-2-methoxyacetamide | 148 | IIA |
| 143 | 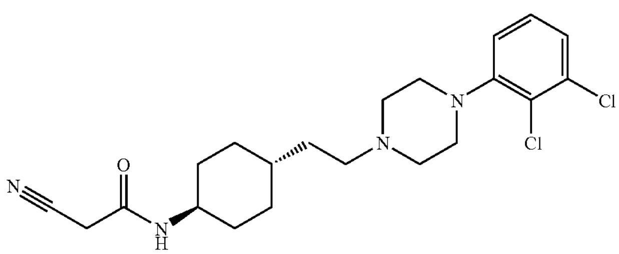 | 2-Cyano-N-(4-{2-[4-(2,3-dichlorophenyl)piperazin-1-yl]ethyl}cyclohexyl)acetamide | 188 | IIA |
| 144 | 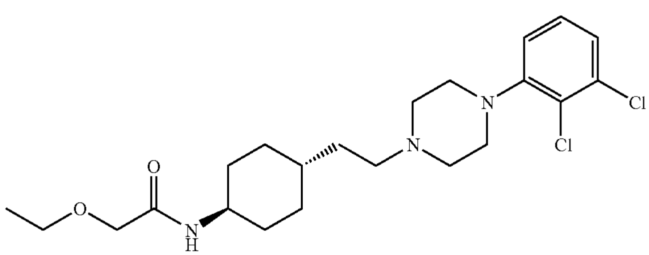 [SMILES: CCOCC(=O)N[C@H]1CC[C@H](CCN2CCN(c3cccc(Cl)c3Cl)CC2)CC1] | N-(4-{2-[4-(2,3-Dichlorophenyl)-piperazin-1-yl]ethyl}cyclohexyl)-2-ethoxyacetamide | 143 | IIA |
| 145 | 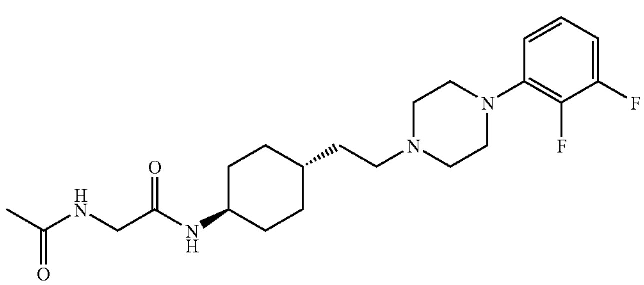 [SMILES: CC(=O)NCC(=O)N[C@H]1CC[C@H](CCN2CCN(c3cccc(F)c3F)CC2)CC1] | 2-Acetylamino-N-(4-{2-[4-(2,3-difluorophenyl)piperazin-1-yl]ethyl}cyclohexyl)acetamide | 218 | IIA |

-continued

| Ex | Structure | Name | M.P. (° C.) | Synthetic Path |
|---|---|---|---|---|
| 146 | 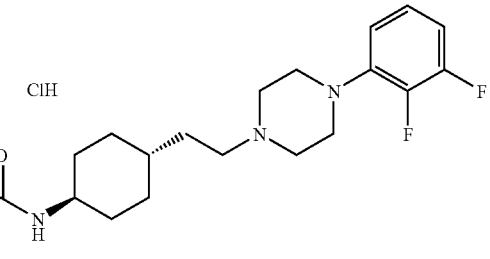 | N-(4-{2-[4-(2,3-Difluorophenyl)-piperazin-1-yl]ethyl}cyclohexyl)2-isopropoxyacetamide, hydrochloride | 215 | IIA |
| 147 | 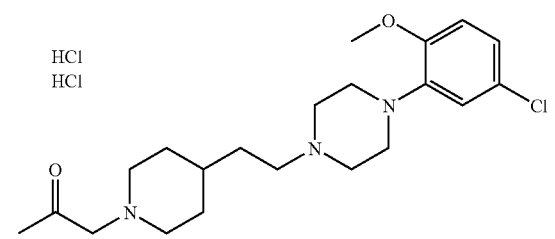 [SMILES: COc1ccc(Cl)cc1N1CCN(CCC2CCN(CC(C)=O)CC2)CC1 ; Cl ; Cl] | 1-(4-{2-[4-(5-Chloro-2-methoxyphenyl)piperazin-1-yl]ethyl}piperidin-1-yl)propan-2-one | 275 | IIIB |
| 148 | 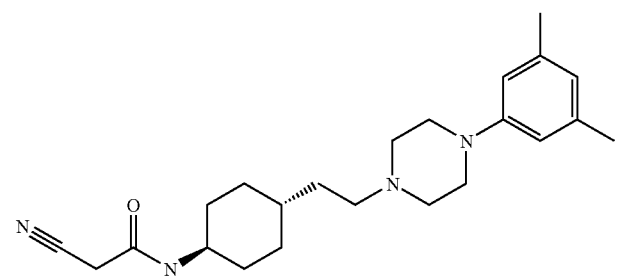 | 2-Cyano-N-(4-{2-[4-(3,5-dimethylphenyl)piperazin-1-yl]ethyl}cyclohexyl)acetamide | 192 | IIA |
| 149 | 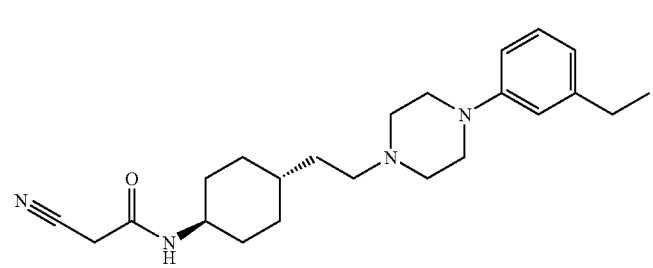 [SMILES: CCc1cccc(N2CCN(CC[C@H]3CC[C@H](NC(=O)CC#N)CC3)CC2)c1] | 2-Cyano-N-(4-{2-[4-(3-ethylphenyl)piperazin-1-yl]ethyl}cyclohexyl)acetamide | 142 | IIA |
| 150 | 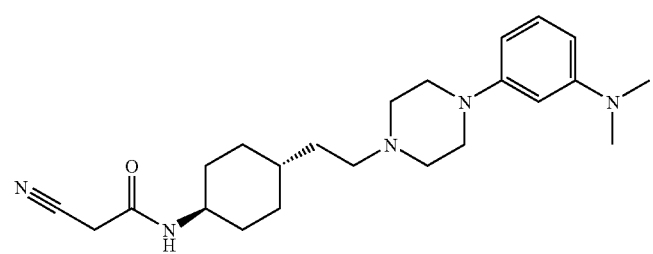 [SMILES: CN(C)c1cccc(N2CCN(CC[C@H]3CC[C@H](NC(=O)CC#N)CC3)CC2)c1] | 2-Cyano-N-(4-{2-[4-(3-dimethylaminophenyl)piperazin-1-yl]ethyl}cyclohexyl)acetamide | 177 | IIA |

| Ex | Structure | Name | M.P. (°C.) | Synthetic Path |
|---|---|---|---|---|
| 151 | 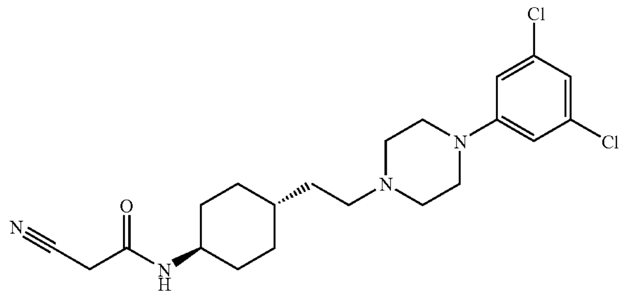 [SMILES: N#CCC(=O)N[C@H]1CC[C@H](CCN2CCN(c3cc(Cl)cc(Cl)c3)CC2)CC1] | 2-Cyano-N-(4-{2-[4-(3,5-dichlorophenyl)piperazin-1-yl]ethyl}cyclohexyl)acetamide | 200 | IIA |
| 152 | 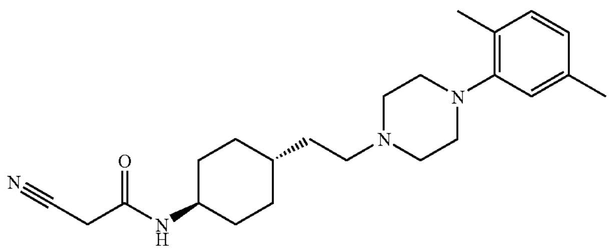 [SMILES: Cc1ccc(C)c(N2CCN(CC[C@H]3CC[C@H](NC(=O)CC#N)CC3)CC2)c1] | 2-Cyano-N-(4-{2-[4-(2,5-dimethylphenyl)piperazin-1-yl]ethyl}cyclohexyl)acetamide | 184 | IIA |
| 153 | 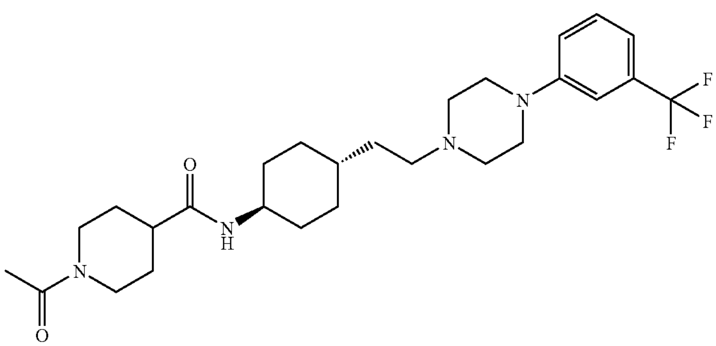 [SMILES: CC(=O)N1CCC(C(=O)N[C@H]2CC[C@H](CCN3CCN(c4cccc(C(F)(F)F)c4)CC3)CC2)CC1] | 1-Acetylpiperidine-4-carboxylic acid (4-{2-[4-(3-trifluoromethylphenyl)piperazin-1-yl]ethyl}cyclohexyl)amide | 173 | IIA |
| 154 | 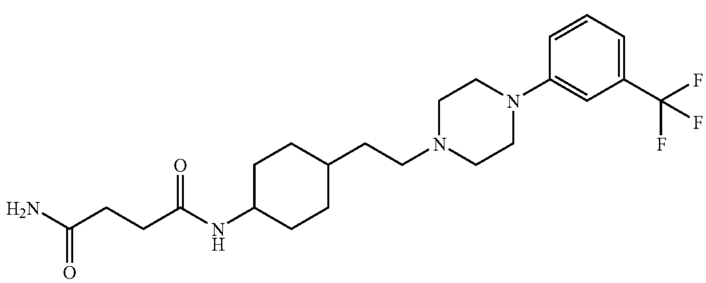 [SMILES: NC(=O)CCC(=O)NC1CCC(CCN2CCN(c3cccc(C(F)(F)F)c3)CC2)CC1] | N-(4-{2-[4-(3-Trifluoromethylphenyl)piperazin-1-yl]ethyl}cyclohexyl)succinamide trans/cis 65/35 | | IIA |
| 155 | 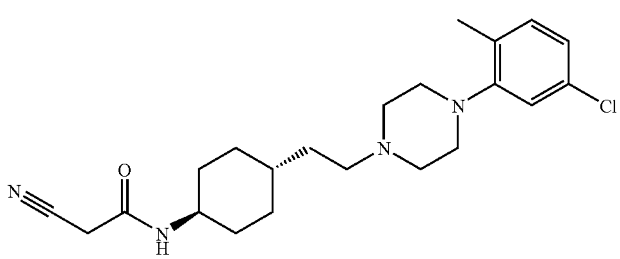 [SMILES: Cc1ccc(Cl)cc1N1CCN(CC[C@H]2CC[C@H](NC(=O)CC#N)CC2)CC1] | N-(4-{2-[4-(5-Chloro-2-methylphenyl)piperazin-1-yl]ethyl}cyclohexyl)-2-cyanoacetamide | 171-172 | IIA |

| Ex | Structure | Name | M.P. (° C.) | Synthetic Path |
|---|---|---|---|---|
| 156 | 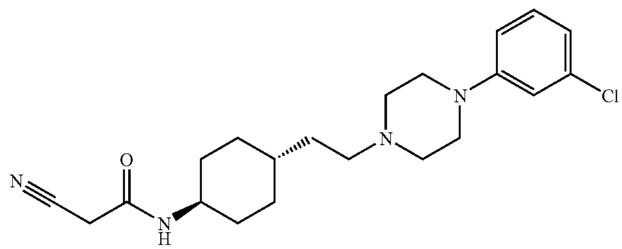 [SMILES: N#CCC(=O)N[C@H]1CC[C@H](CCN2CCN(c3cccc(Cl)c3)CC2)CC1] | N-(4-{2-[4-(3-Chlorophenyl)-piperazin-1-yl]ethyl}cyclohexyl)-2-cyanoacetamide | 186-187 | IIA |
| 157 | 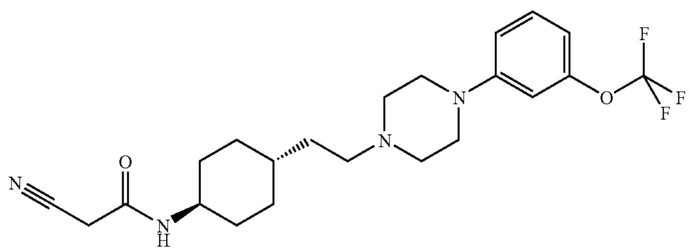 [SMILES: N#CCC(=O)N[C@H]1CC[C@H](CCN2CCN(c3cccc(OC(F)(F)F)c3)CC2)CC1] | 2-Cyano-N-(4-{2-[4-(3-trifluoromethoxyphenyl)piperazin-1-yl]ethyl}cyclohexyl)acetamide | 173-174 | IIA |
| 158 | 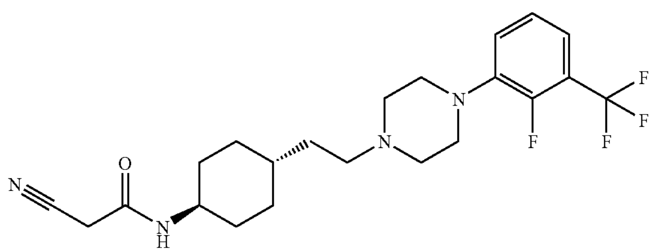 | 2-Cyano-N-(4-{2-[4-(2-fluoro-3-trifluoromethylphenyl)piperazin-1-yl]ethyl}cyclohexyl)acetamide | 194 | IIA |
| 159 | 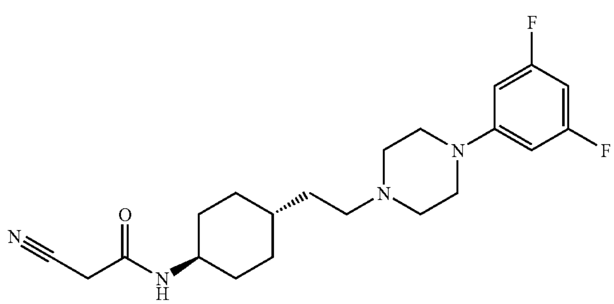 [SMILES: N#CCC(=O)N[C@H]1CC[C@H](CCN2CCN(c3cc(F)cc(F)c3)CC2)CC1] | 2-Cyano-N-(4-{2-[4-(3,5-difluorophenyl)piperazin-1-yl]ethyl}cyclohexyl)acetamide trans/cis 95/5 | 196 | IIA |
| 160 | 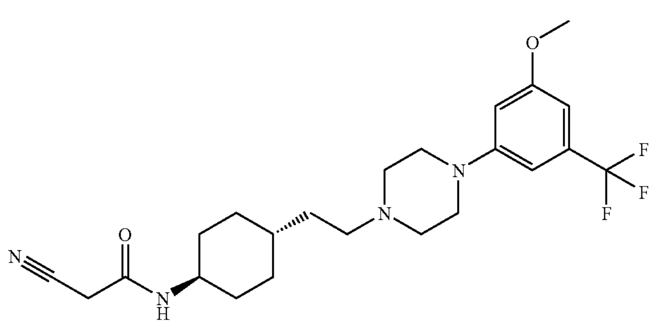 [SMILES: COc1cc(N2CCN(CC[C@H]3CC[C@H](NC(=O)CC#N)CC3)CC2)cc(C(F)(F)F)c1] | 2-Cyano-N-(4-{2-[4-(3-methoxy-5-trifluoromethylphenyl)piperazin-1-yl]ethyl}cyclohexyl)acetamide | 183-184 | IIA |

-continued

| Ex | Structure | Name | M.P. (° C.) | Synthetic Path |
|---|---|---|---|---|
| 161 | 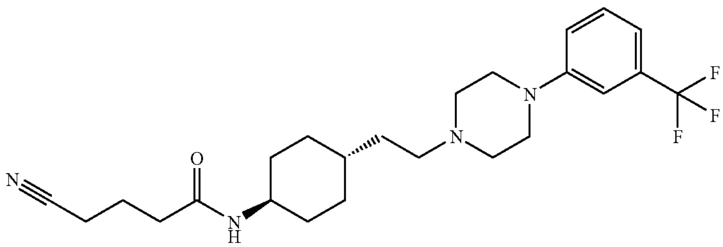 [SMILES: N#CCCCC(=O)N[C@H]1CC[C@H](CCN2CCN(c3cccc(C(F)(F)F)c3)CC2)CC1] | 4-Cyano-N-(4-{2-[4-(3-trifluoromethylphenyl)piperazin-1-yl]ethyl}cyclohexyl)butanamide | 149 | IIA |
| 162 | 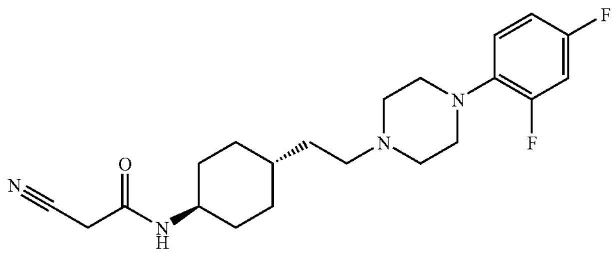 [SMILES: N#CCC(=O)N[C@H]1CC[C@H](CCN2CCN(c3ccc(F)cc3F)CC2)CC1] | 2-Cyano-N-(4-{2-[4-(2,4-difluorophenyl)piperazin-1-yl]ethyl}cyclohexyl)acetamide | 188 | IIA |
| 163 | ClH | 2-Cyano-N-(4-{2-[4-(3-isopropoxyphenyl)piperazin-1-yl]ethyl}cyclohexyl)acetamide, hydrochloride | 191 | IIA |
| 164 | ClH | 2-Cyano-N-(4-{2-[4-(3-methoxyphenyl)piperazin-1-yl]ethyl}cyclohexyl)acetamide, hydrochloride | 219 | IIA |
| 165 | 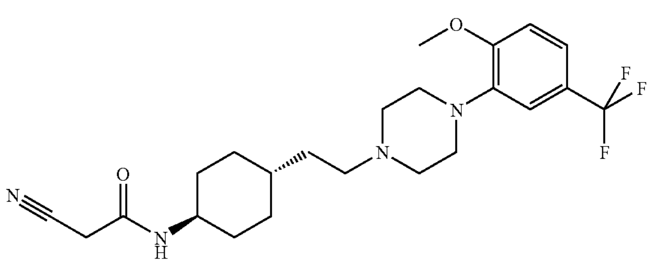 [SMILES: COc1ccc(C(F)(F)F)cc1N1CCN(CC[C@H]2CC[C@H](NC(=O)CC#N)CC2)CC1] | 2-Cyano-N-(4-{2-[4-(2-methoxy-5-trifluoromethylphenyl)piperazin-1-yl]ethyl}cyclohexyl)acetamide | 183 | IIA |
| 166 | 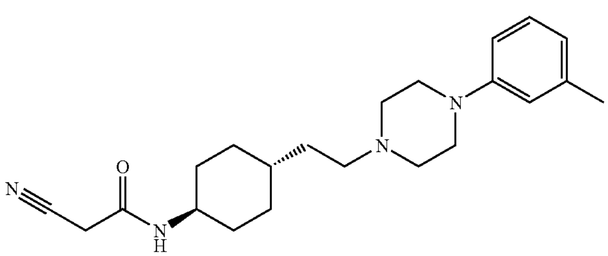 [SMILES: Cc1cccc(N2CCN(CC[C@H]3CC[C@H](NC(=O)CC#N)CC3)CC2)c1] | 2-Cyano-N-{4-[2-(4-m-tolylpiperazin-1-yl)ethyl]cyclohexyl}acetamide | 175 | IIA |

| Ex | Structure | Name | M.P. (° C.) | Synthetic Path |
|---|---|---|---|---|
| 167 | 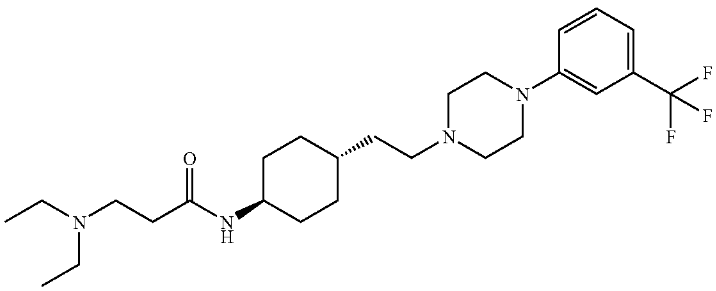 [SMILES: CCN(CC)CCC(=O)N[C@H]1CC[C@H](CCN2CCN(c3cccc(C(F)(F)F)c3)CC2)CC1] | 3-Diethylamino-N-(4-{2-[4-(3-trifluoromethylphenyl)piperazin-1-yl]ethyl}cyclohexyl)propanamide trans/cis 85/15 | 77 | IIA |
| 168 | 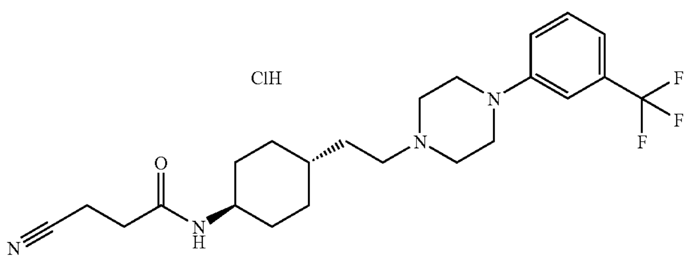 [SMILES: N#CCCC(=O)N[C@H]1CC[C@H](CCN2CCN(c3cccc(C(F)(F)F)c3)CC2)CC1 ; Cl] | 3-Cyano-N-(4-{2-[4-(3-trifluoromethylphenyl)propanamide, hydrochloride | 230 | IIA |
| 169 | 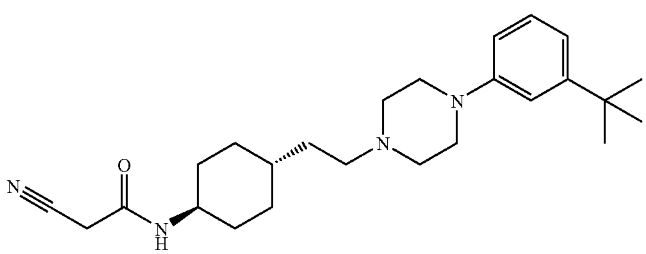 [SMILES: CC(C)(C)c1cccc(N2CCN(CC[C@H]3CC[C@H](NC(=O)CC#N)CC3)CC2)c1] | N-(4-{2-[4-(3-tert-Butylphenyl)piperazin-1-yl]ethyl}cyclohexyl)-2-cyanoacetamide | 150 | IIA |
| 170 | 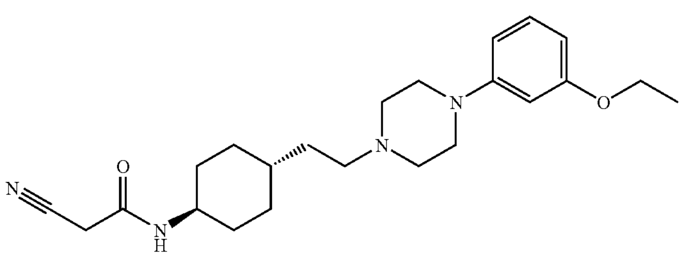 [SMILES: CCOc1cccc(N2CCN(CC[C@H]3CC[C@H](NC(=O)CC#N)CC3)CC2)c1] | 2-Cyano-N-(4-{2-[4-(3-ethoxyphenyl)piperazin-1-yl]ethyl}cyclohexyl)acetamide | 157-159 | IIA |
| 171 | 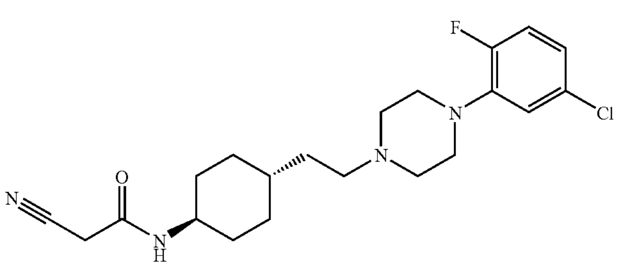 [SMILES: N#CCC(=O)N[C@H]1CC[C@H](CCN2CCN(c3cc(Cl)ccc3F)CC2)CC1] | N-(4-{2-[4-(5-Chloro-2-fluorophenyl)piperazin-1-yl]ethyl}cyclohexyl)-2-cyanoacetamide | 200 | IIA |

-continued

| Ex | Structure | Name | M.P. (° C.) | Synthetic Path |
|---|---|---|---|---|
| 172 | 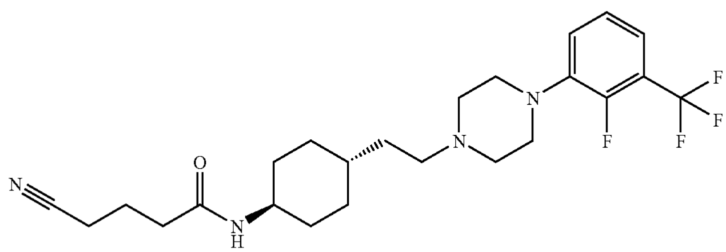 [SMILES: N#CCCCC(=O)N[C@H]1CC[C@H](CCN2CCN(c3cccc(C(F)(F)F)c3F)CC2)CC1] | 4-Cyano-N-(4-{2-[4-(2-fluoro-3-trifluoromethylphenyl)piperazin-1-yl]ethyl}cyclohexyl)butanamide | 158-162 | IIA |
| 173 | 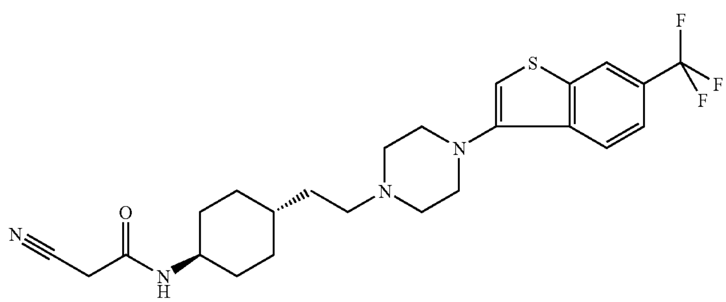 [SMILES: N#CCC(=O)N[C@H]1CC[C@H](CCN2CCN(c3csc4cc(C(F)(F)F)ccc34)CC2)CC1] | 2-Cyano-N-(4-{2-[4-(6-trifluoromethylbenzo[b]thiophen-3-yl)piperazin-1-yl]ethyl}cyclohexyl)acetamide | 216 | IA |
| 174 | 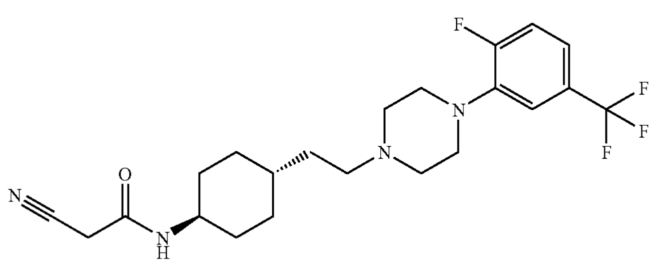 [SMILES: N#CCC(=O)N[C@H]1CC[C@H](CCN2CCN(c3cc(C(F)(F)F)ccc3F)CC2)CC1] | 2-Cyano-N-(4-{2-[4-(2-fluoro-5-trifluoromethylphenyl)piperazin-1-yl]ethyl}cyclohexyl)acetamide | 197 | IIA |
| 175 | 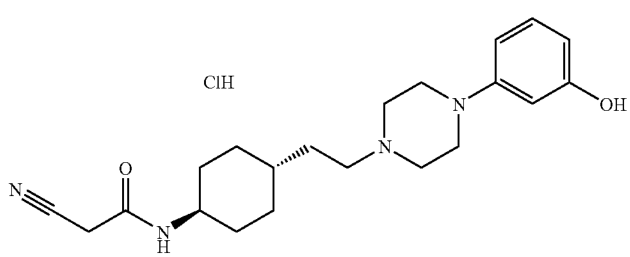 [SMILES: N#CCC(=O)N[C@H]1CC[C@H](CCN2CCN(c3cccc(O)c3)CC2)CC1 ; Cl] | 2-Cyano-N-(4-{2-[4-(3-hydroxyphenyl)piperazin-1-yl]ethyl}cyclohexyl)acetamide, hydrochloride | | IIA |
| 176 | 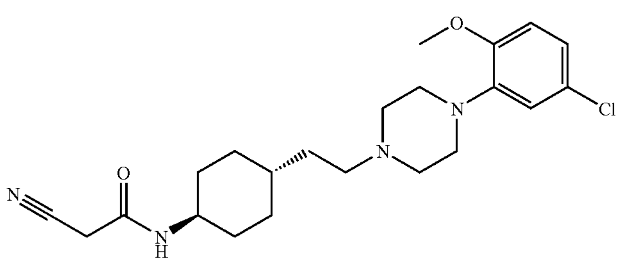 [SMILES: COc1ccc(Cl)cc1N1CCN(CC[C@H]2CC[C@H](NC(=O)CC#N)CC2)CC1] | N-(4-{2-[4-(5-Chloro-2-methoxyphenyl)piperazin-1-yl]ethyl}cyclohexyl)-2-cyanoacetamide | 180 | IIA |

| Ex | Structure | Name | M.P. (° C.) | Synthetic Path |
|---|---|---|---|---|
| 177 | 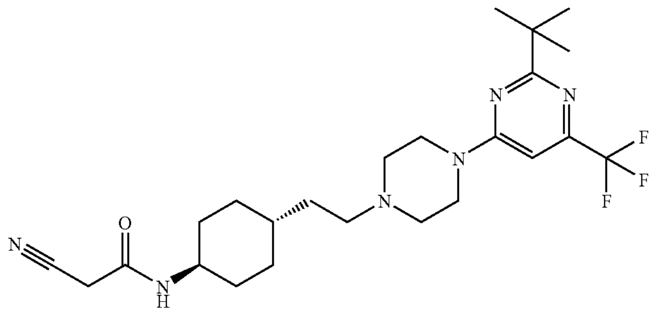 [SMILES: CC(C)(C)c1nc(N2CCN(CC[C@H]3CC[C@H](NC(=O)CC#N)CC3)CC2)cc(C(F)(F)F)n1] | N-(4-{2-[4-(2-tert-Butyl-6-trifluoromethylpyrimidin-4-yl)piperazin-1-yl]ethyl}cyclohexyl)-2-cyanoacetamide trans/cis 85/15 | 188 | IIA |
| 178 | 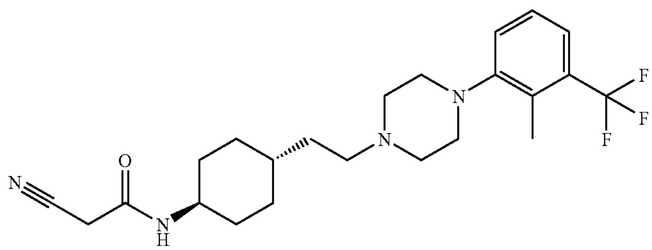 [SMILES: Cc1c(N2CCN(CC[C@H]3CC[C@H](NC(=O)CC#N)CC3)CC2)cccc1C(F)(F)F] | 2-Cyano-N-(4-{2-[4-(2-methyl-3-trifluoromethylphenyl)piperazin-1-yl]ethyl}cyclohexyl)acetamide | 181 | IIA |
| 179 | 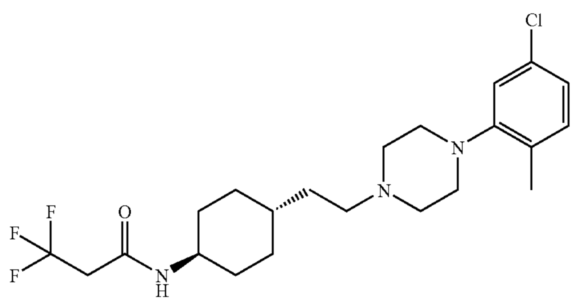 [SMILES: Cc1ccc(Cl)cc1N1CCN(CC[C@H]2CC[C@H](NC(=O)CC(F)(F)F)CC2)CC1] | N-(4-{2-[4-(5-Chloro-2-methylphenyl)piperazin-1-yl]ethyl}cyclohexyl)-3,3,3-trifluoropropanamide | 177-178 | IIA |
| 180 | 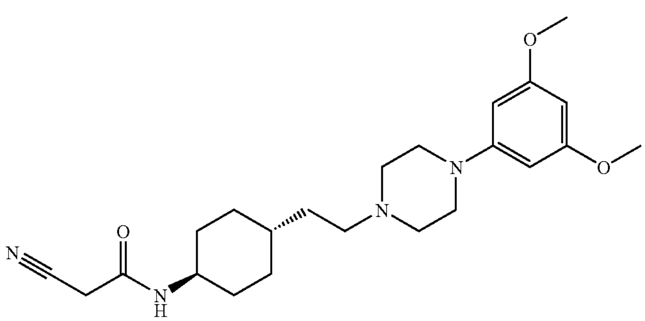 [SMILES: COc1cc(OC)cc(N2CCN(CC[C@H]3CC[C@H](NC(=O)CC#N)CC3)CC2)c1] | 2-Cyano-N-(4-{2-[4-(3,5-dimethoxyphenyl)piperazin-1-yl]ethyl}cyclohexyl)acetamide | 181-183 | IIA |
| 181 | 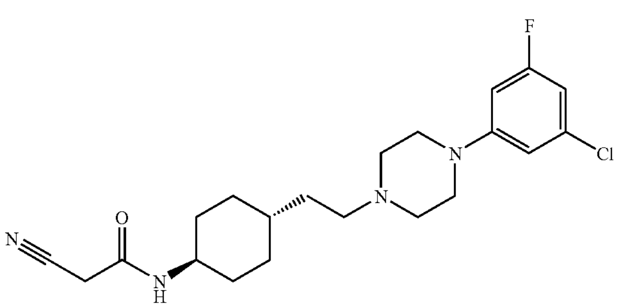 | N-(4-{2-[4-(3-Chloro-5-fluorophenyl)piperazin-1-yl]ethyl}cyclohexyl)-2-cyanoacetamide | 181-183 | IIA |

-continued

| Ex | Structure | Name | M.P. (° C.) | Synthetic Path |
|---|---|---|---|---|
| 182 | 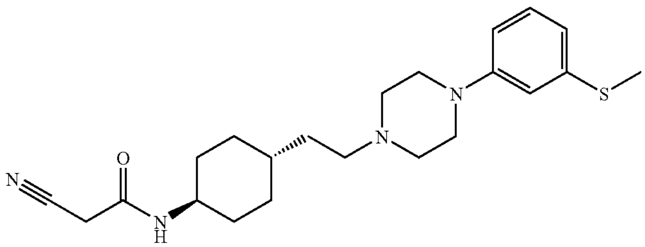 [SMILES: CSc1cccc(N2CCN(CC[C@H]3CC[C@H](NC(=O)CC#N)CC3)CC2)c1] | 2-Cyano-N-(4-{2-[4-(3-methylsulfanylphenyl)piperazin-1-yl]ethyl}cyclohexyl)acetamide | 132 | IIA |
| 183 | 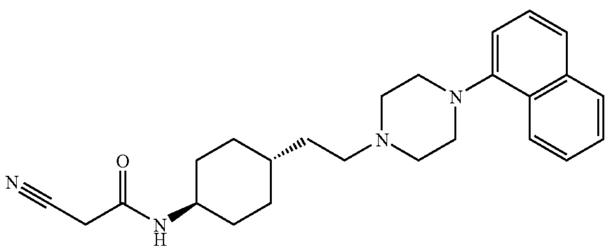 [SMILES: N#CCC(=O)N[C@H]1CC[C@H](CCN2CCN(c3cccc4ccccc34)CC2)CC1] | 2-Cyano-N-{4-[2-(4-naphthalen-1-ylpiperazin-1-yl)ethyl]cyclohexyl}acetamide | 174 | IIA |
| 184 | 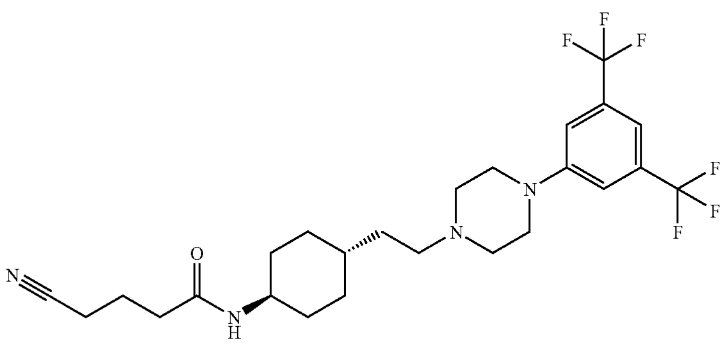 [SMILES: N#CCCCC(=O)N[C@H]1CC[C@H](CCN2CCN(c3cc(C(F)(F)F)cc(C(F)(F)F)c3)CC2)CC1] | N-(4-{2-[4-(3,5-Bistrifluoromethylphenyl)piperazin-1-yl]ethyl}cyclohexyl)-4-cyanobutanamide | 166 | IIA |
| 185 | 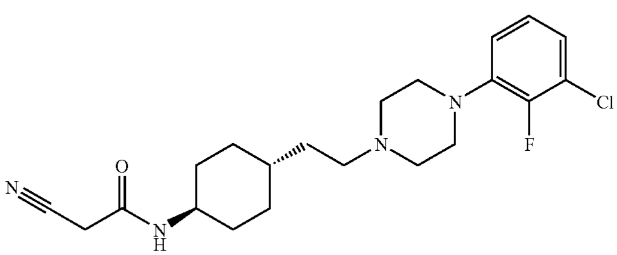 [SMILES: N#CCC(=O)N[C@H]1CC[C@H](CCN2CCN(c3cccc(Cl)c3F)CC2)CC1] | N-(4-{2-[4-(3-Chloro-2-fluorophenyl)piperazin-1-yl]ethyl}cyclohexyl)-2-cyanoacetamide | 183 | IIA |
| 186 | 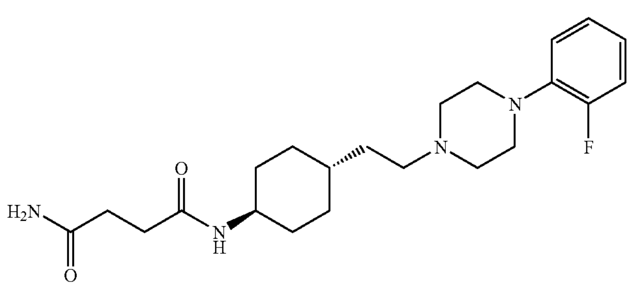 [SMILES: NC(=O)CCC(=O)N[C@H]1CC[C@H](CCN2CCN(c3ccccc3F)CC2)CC1] | N-(4-{2-[4-(2-Fluorophenyl)piperazin-1-yl]ethyl}cyclohexyl)succinamide | 255 | IIA |

-continued

| Ex | Structure | Name | M.P. (° C.) | Synthetic Path |
|---|---|---|---|---|
| 187 | 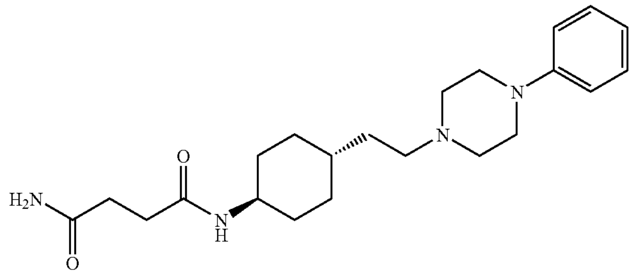 [SMILES: NC(=O)CCC(=O)N[C@H]1CC[C@H](CCN2CCN(c3ccccc3)CC2)CC1] | N-{4-[2-(4-Phenylpiperazin-1-yl)ethyl]cyclohexyl}succinamide | 252 | IIA |
| 188 | 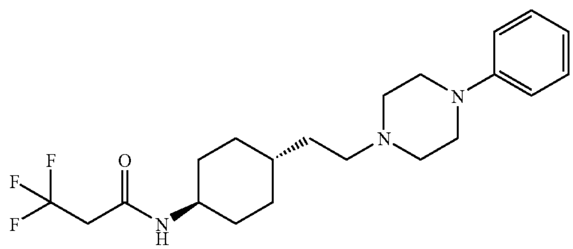 [SMILES: O=C(CC(F)(F)F)N[C@H]1CC[C@H](CCN2CCN(c3ccccc3)CC2)CC1] | 3,3,3-Trifluoro-N-{4-[2-(4-phenylpiperazin-1-yl)ethyl]cyclohexyl}propanamide | 185 | IIA |
| 189 | 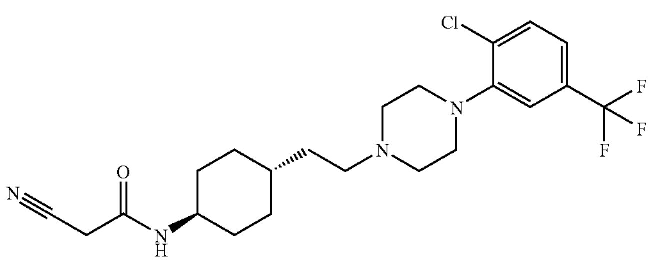 [SMILES: N#CCC(=O)N[C@H]1CC[C@H](CCN2CCN(c3cc(C(F)(F)F)ccc3Cl)CC2)CC1] | N-(4-{2-[4-(2-Chloro-5-trifluoromethylphenyl)piperazin-1-yl]ethyl}cyclohexyl)-2-cyanoacetamide | 203-204 | IIA |
| 190 | 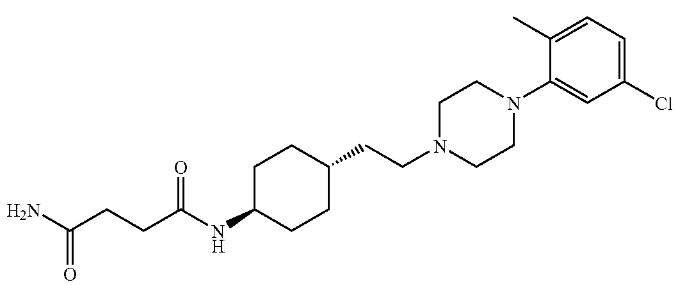 [SMILES: Cc1ccc(Cl)cc1N1CCN(CC[C@H]2CC[C@H](NC(=O)CCC(N)=O)CC2)CC1] | N-(4-{2-[4-(5-Chloro-2-methylphenyl)piperazin-1-yl]ethyl}cyclohexyl)succinamide | 237-240 | IIA |
| 191 | 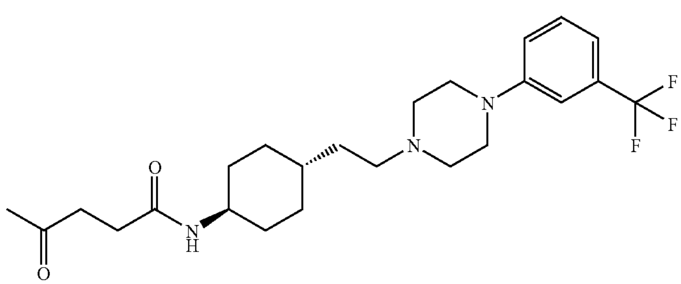 [SMILES: CC(=O)CCC(=O)N[C@H]1CC[C@H](CCN2CCN(c3cccc(C(F)(F)F)c3)CC2)CC1] | 4-Oxo-pentanoic acid (4-{2-[4-(3-trifluoromethylphenyl)piperazin-1-yl]ethyl}cyclohexyl)amide | 159 | IIA |

-continued

| Ex | Structure | Name | M.P. (° C.) | Synthetic Path |
|---|---|---|---|---|
| 192 | 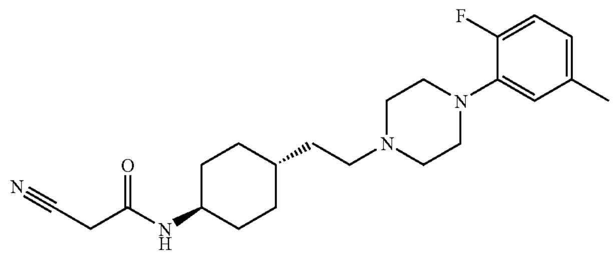 [SMILES: Cc1ccc(F)c(N2CCN(CC[C@H]3CC[C@H](NC(=O)CC#N)CC3)CC2)c1] | 2-Cyano-N-(4-{2-[4-(2-fluoro-5-methylphenyl)piperazin-1-yl]ethyl}cyclohexyl)acetamide | 178 | IIA |
| 193 | 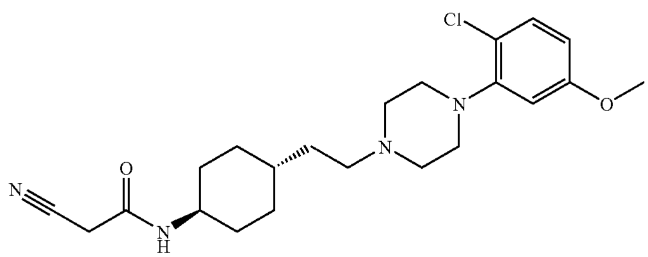 [SMILES: COc1ccc(Cl)c(N2CCN(CC[C@H]3CC[C@H](NC(=O)CC#N)CC3)CC2)c1] | N-(4-{2-[4-(2-Chloro-5-methoxyphenyl)piperazin-1-yl]ethyl}cyclohexyl)-2-cyanoacetamide | 165 | IIA |
| 194 | 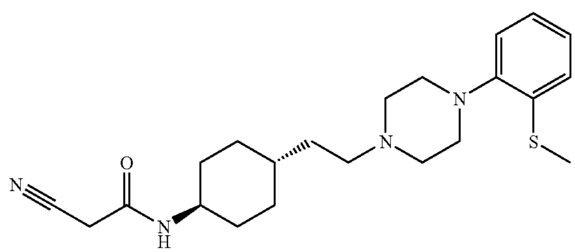 [SMILES: CSc1ccccc1N1CCN(CC[C@H]2CC[C@H](NC(=O)CC#N)CC2)CC1] | 2-Cyano-N-(4-{2-[4-(2-methylsulfanylphenyl)piperazin-1-yl]ethyl}cyclohexyl)acetamide | 146 | IIA |
| 195 | 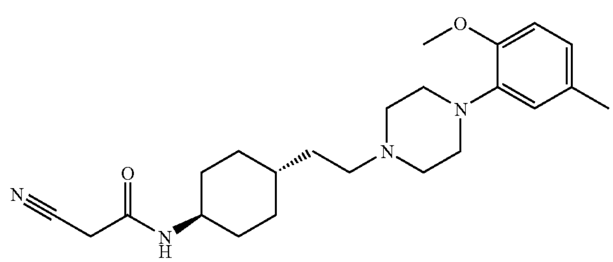 [SMILES: COc1ccc(C)cc1N1CCN(CC[C@H]2CC[C@H](NC(=O)CC#N)CC2)CC1] | 2-Cyano-N-(4-{2-[4-(2-methoxy-5-methylphenyl)piperazin-1-yl]ethyl}cyclohexyl)acetamide | 178 | IIA |
| 196 | 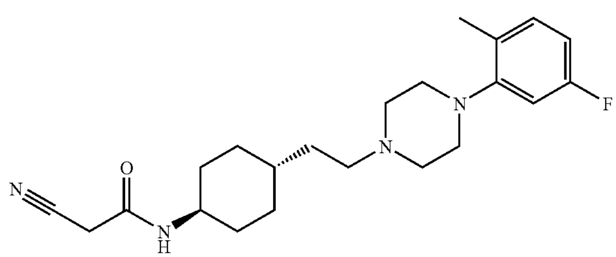 [SMILES: Cc1ccc(F)cc1N1CCN(CC[C@H]2CC[C@H](NC(=O)CC#N)CC2)CC1] | 2-Cyano-N-(4-{2-[4-(5-fluoro-2-methylphenyl)piperazin-1-yl]ethyl}cyclohexyl)acetamide | 159 | IIA |
| 197 | 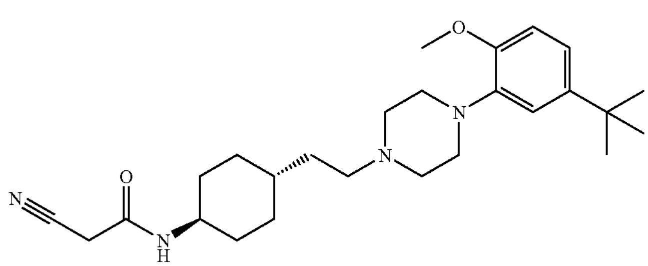 [SMILES: COc1ccc(C(C)(C)C)cc1N1CCN(CC[C@H]2CC[C@H](NC(=O)CC#N)CC2)CC1] | N-(4-{2-[4-(5-tert-Butyl-2-methoxyphenyl)piperazin-1-yl]ethyl}cyclohexyl)-2-cyanoacetamide | 163 | IIA |

-continued

| Ex | Structure | Name | M.P. (° C.) | Synthetic Path |
|---|---|---|---|---|
| 198 | 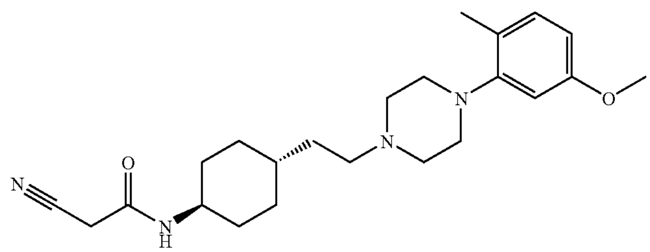 [SMILES: COc1ccc(C)c(N2CCN(CC[C@H]3CC[C@H](NC(=O)CC#N)CC3)CC2)c1] | 2-Cyano-N-(4-{2-[4-(5-methoxy-2-methylphenyl)piperazin-1-yl]ethyl}cyclohexyl)acetamide | 178-180 | IIA |
| 199 | 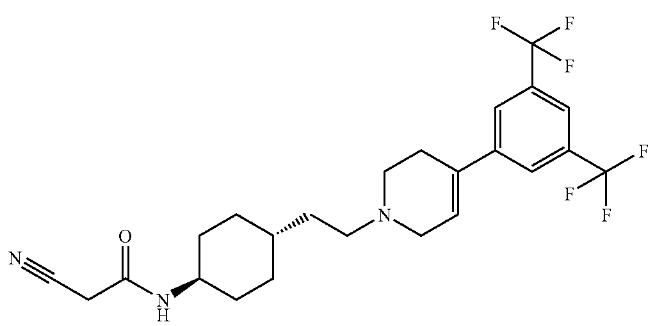 [SMILES: N#CCC(=O)N[C@H]1CC[C@H](CCN2CC=C(c3cc(C(F)(F)F)cc(C(F)(F)F)c3)CC2)CC1] | N-(4-{2-[4-(3,5-Bistrifluoromethylphenyl)-3,6-dihydro-2H-pyridin-1-yl]ethyl}cyclohexyl)-2-cyanoacetamide | 174 | IIA |
| 200 | 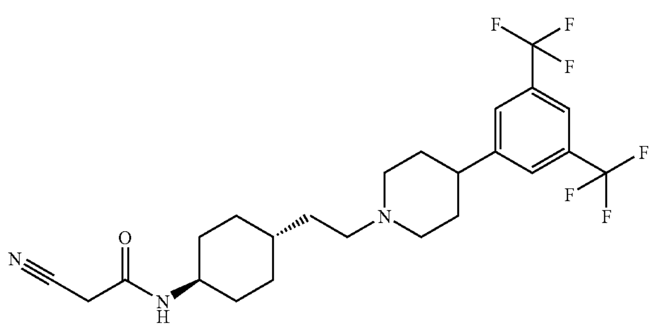 [SMILES: N#CCC(=O)N[C@H]1CC[C@H](CCN2CCC(c3cc(C(F)(F)F)cc(C(F)(F)F)c3)CC2)CC1] | N-(4-{2-[4-(3,5-Bis-trifluoromethylphenyl)piperidin-1-yl]ethyl}cyclohexyl)-2-cyanoacetamide | 164 | IIA |
| 201 | HCl HCl | 1-(4-{2-[4-(2,3-Dichlorophenyl)-3,6-dihydro-2H-pyridin-1-yl]ethyl}piperidin-1-yl)propan-2-one | 296-297 | IIIB |
| 202 | 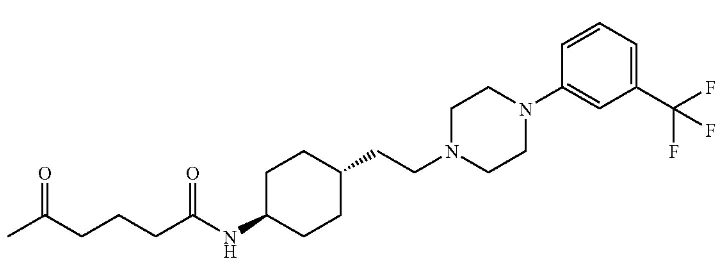 [SMILES: CC(=O)CCCC(=O)N[C@H]1CC[C@H](CCN2CCN(c3cccc(C(F)(F)F)c3)CC2)CC1] | 5-Oxo-hexanoic acid (4-{2-[4-(3-trifluoromethylphenyl)piperazin-1-yl]ethyl}cyclohexyl)amide | 158 | IIA |

-continued

| Ex | Structure | Name | M.P. (° C.) | Synthetic Path |
|---|---|---|---|---|
| 203 | 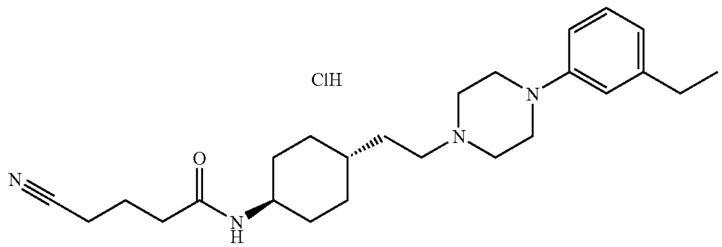 [SMILES: CCc1cccc(N2CCN(CC[C@H]3CC[C@H](NC(=O)CCCC#N)CC3)CC2)c1 ; Cl] | 4-Cyano-N-(4-{2-[4-(3-ethylphenyl)piperazin-1-yl]ethyl}cyclohexyl)butanamide, hydrochloride trans/cis 85/15 | 205 | IIA |
| 204 | 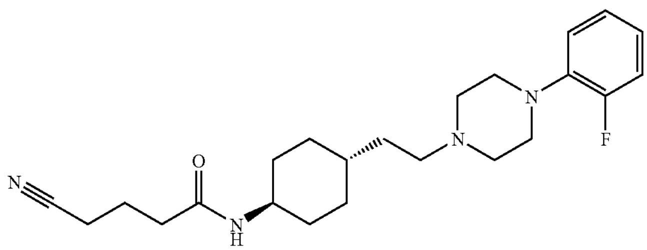 | 4-Cyano-N-(4-{2-[4-(2-fluorophenyl)piperazin-1-yl]ethyl}cyclohexyl)butanamide | 170 | IIA |
| 205 | 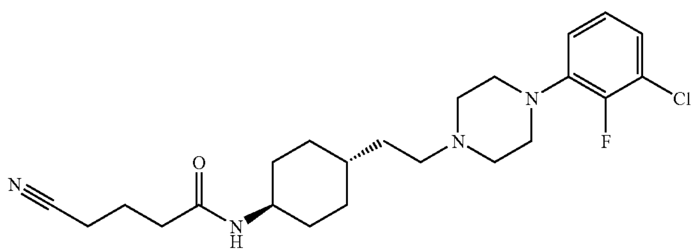 [SMILES: N#CCCCC(=O)N[C@H]1CC[C@H](CCN2CCN(c3cccc(Cl)c3F)CC2)CC1] | N-(4-{2-[4-(3-Chloro-2-fluorophenyl)piperazin-1-yl]ethyl}cyclohexyl)-4-cyanobutanamide | 186 | IIA |
| 206 | 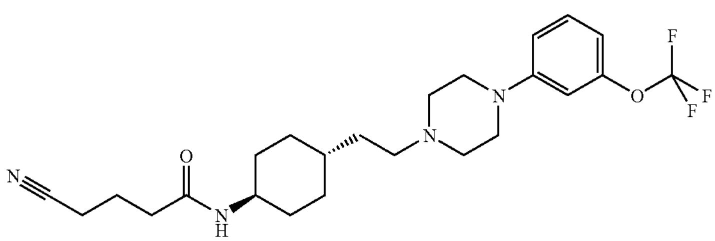 | 4-Cyano-N-(4-{2-[4-(3-trifluoromethoxyphenyl)piperazin-1-yl]ethyl}cyclohexyl)butanamide | 133-134 | IIA |
| 207 | 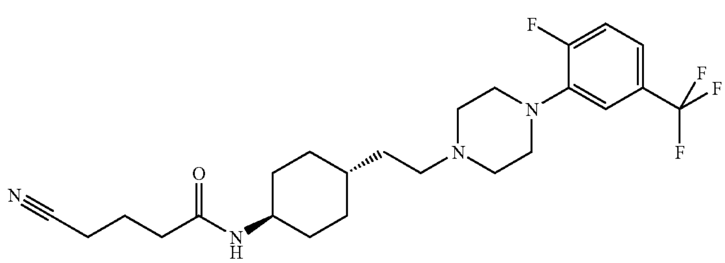 [SMILES: N#CCCCC(=O)N[C@H]1CC[C@H](CCN2CCN(c3cc(C(F)(F)F)ccc3F)CC2)CC1] | 4-Cyano-N-(4-{2-[4-(2-fluoro-5-trifluoromethylphenyl)piperazin-1-yl]ethyl}cyclohexyl)butanamide | 138-139 | IIA |
| 208 | 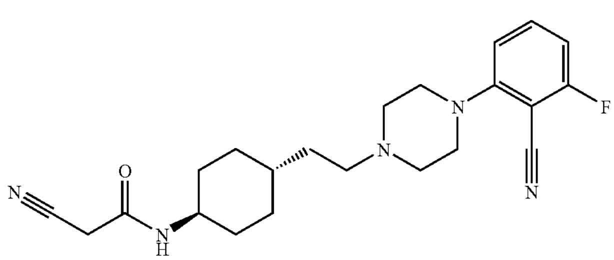 [SMILES: N#CCC(=O)N[C@H]1CC[C@H](CCN2CCN(c3cccc(F)c3C#N)CC2)CC1] | 2-Cyano-N-(4-{2-[4-(2-cyano-3-fluorophenyl-piperazin-1-yl]ethyl}cyclohexyl)acetamide | 187-189 | IIA |

-continued

| Ex | Structure | Name | M.P. (° C.) | Synthetic Path |
|---|---|---|---|---|
| 209 | 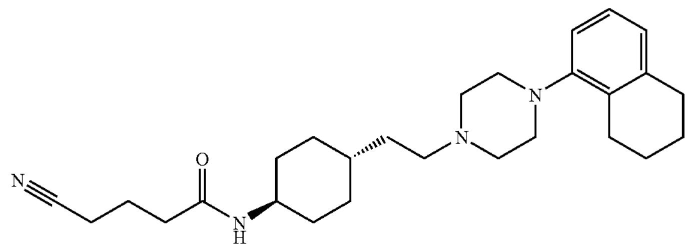 [SMILES: N#CCCCC(=O)N[C@H]1CC[C@H](CCN2CCN(c3cccc4c3CCCC4)CC2)CC1] | 4-Cyano-N-(4-{2-[4-(5,6,7,8-tetrahydronaphthalen-1-yl)piperazin-1-yl]ethyl}cyclohexyl)butanamide | 148 | IIA |
| 210 | 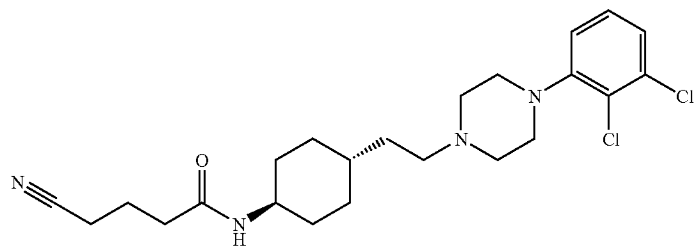 [SMILES: N#CCCCC(=O)N[C@H]1CC[C@H](CCN2CCN(c3cccc(Cl)c3Cl)CC2)CC1] | 4-Cyano-N-(4-{2-[4-(2,3-dichlorophenyl)piperazin-1-yl]ethyl}cyclohexyl)butanamide | 192 | IIA |
| 211 | 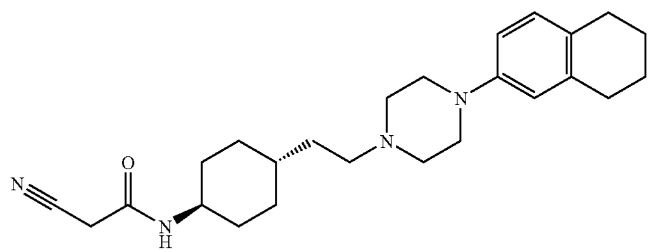 [SMILES: N#CCC(=O)N[C@H]1CC[C@H](CCN2CCN(c3ccc4c(c3)CCCC4)CC2)CC1] | 2-Cyano-N-(4-{2-[4-(5,6,7,8-tetrahydronaphthalen-2-yl)piperazin-1-yl]ethyl}cyclohexyl)acetamide | 200 | IIA |
| 212 | 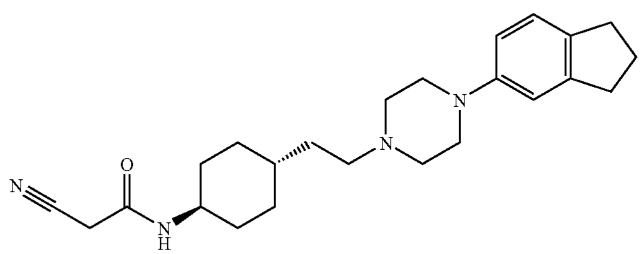 [SMILES: N#CCC(=O)N[C@H]1CC[C@H](CCN2CCN(c3ccc4c(c3)CCC4)CC2)CC1] | 2-Cyano-N-{4-[2-(4-indan-5-ylpiperazin-1-yl)ethyl]cyclohexyl}acetamide | 210 | IIA |
| 213 | 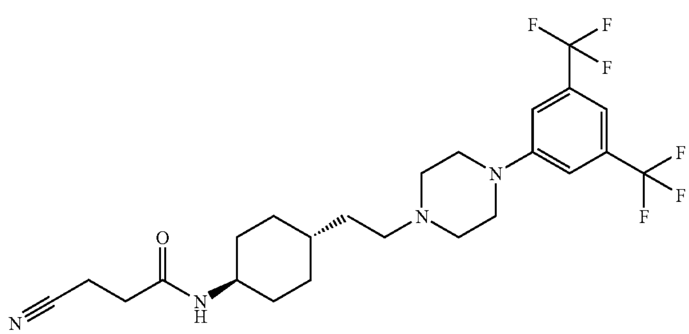 [SMILES: N#CCCC(=O)N[C@H]1CC[C@H](CCN2CCN(c3cc(C(F)(F)F)cc(C(F)(F)F)c3)CC2)CC1] | N-(4-{2-[4-(3,5-Bistrifluoromethylphenyl)piperazin-1-yl]ethyl}cyclohexyl)-3-cyanopropanamide | 158-159 | IIA |

-continued

| Ex | Structure | Name | M.P. (° C.) | Synthetic Path |
|---|---|---|---|---|
| 214 | 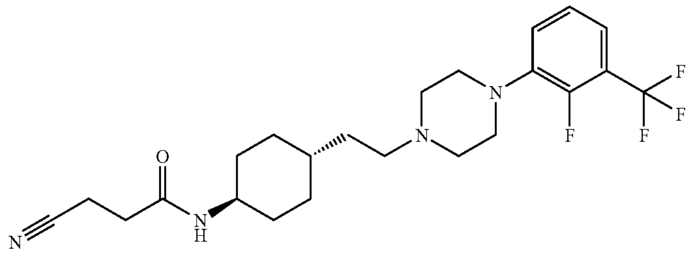 [SMILES: N#CCCC(=O)N[C@H]1CC[C@H](CCN2CCN(c3cccc(C(F)(F)F)c3F)CC2)CC1] | 3-Cyano-N-(4-{2-[4-(2-fluoro-3-trifluoromethylphenyl)piperazin-1-yl]ethyl}cyclohexyl)propanamide trans/cis 95/5 | 153 | IIA |
| 215 | 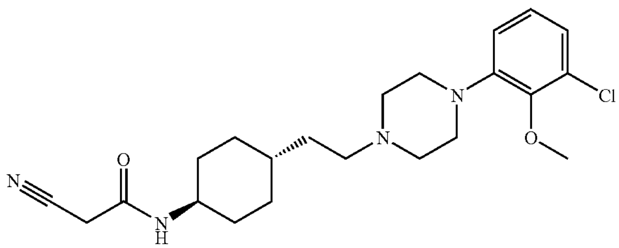 [SMILES: COc1c(Cl)cccc1N1CCN(CC[C@H]2CC[C@H](NC(=O)CC#N)CC2)CC1] | N-(4-{2-[4-(3-Chloro-2-methoxyphenyl)piperazin-1-yl]ethyl}cyclohexyl)-2-cyanoacetamide | 122 | IIA |
| 216 | 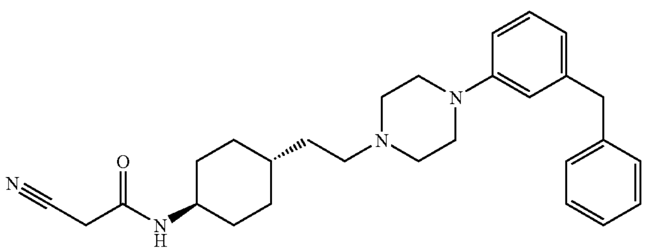 [SMILES: N#CCC(=O)N[C@H]1CC[C@H](CCN2CCN(c3cccc(Cc4ccccc4)c3)CC2)CC1] | N-(4-{2-[4-(3-Benzylphenyl)-piperazin-1-yl]ethyl}cyclohexyl)-2-cyanoacetamide | 168 | IIA |
| 217 | 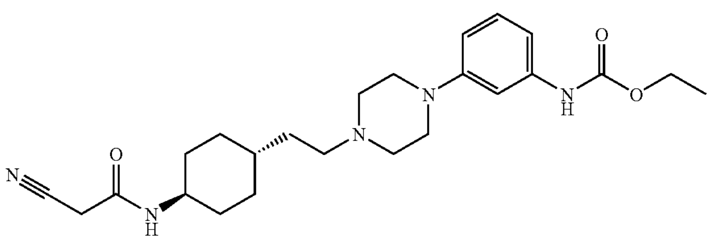 [SMILES: CCOC(=O)Nc1cccc(N2CCN(CC[C@H]3CC[C@H](NC(=O)CC#N)CC3)CC2)c1] | [3-(4-{2-[4-(2-Cyanoacetylamino)cyclohexyl]ethyl}piperazin-1-yl)phenyl]carbamic acid ethyl ester | 170 | IIA |
| 218 | 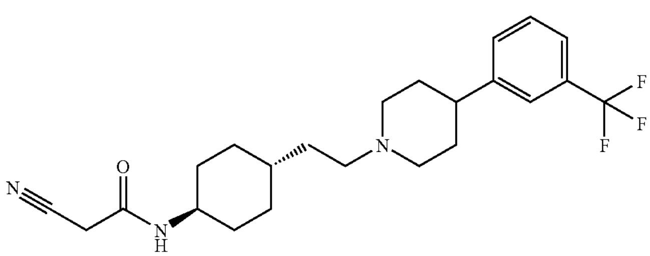 [SMILES: N#CCC(=O)N[C@H]1CC[C@H](CCN2CCC(c3cccc(C(F)(F)F)c3)CC2)CC1] | 2-Cyano-N-(4-{2-[4-(3-trifluoromethylphenyl)piperidin-1-yl]ethyl}cyclohexyl)acetamide | 129 | IIA |
| 219 | 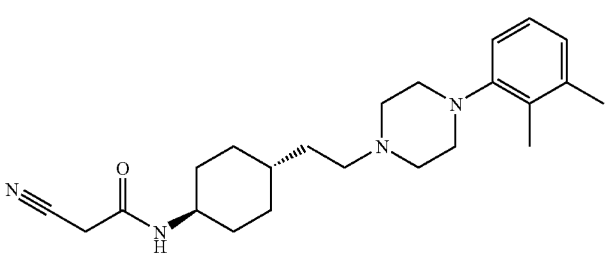 [SMILES: Cc1cccc(N2CCN(CC[C@H]3CC[C@H](NC(=O)CC#N)CC3)CC2)c1C] | 2-Cyano-N-(4-{2-[4-(2,3-dimethylphenyl)piperazin-1-yl]ethyl}cyclohexyl)acetamide | 166 | IIA |

-continued

| Ex | Structure | Name | M.P. (° C.) | Synthetic Path |
|---|---|---|---|---|
| 220 | 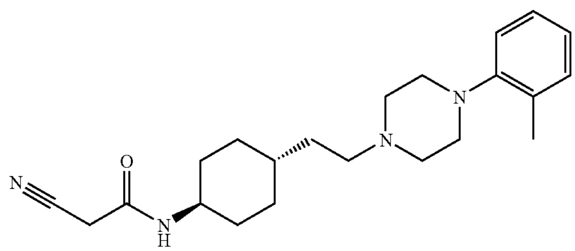 [SMILES: Cc1ccccc1N1CCN(CC[C@H]2CC[C@H](NC(=O)CC#N)CC2)CC1] | 2-Cyano-N-{4-[2-(4-o-tolylpiperazin-1-yl)ethyl]cyclohexyl}acetamide | 150 | IIA |
| 221 | 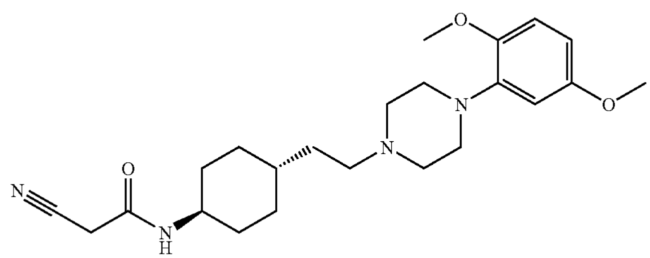 [SMILES: COc1ccc(OC)c(N2CCN(CC[C@H]3CC[C@H](NC(=O)CC#N)CC3)CC2)c1] | 2-Cyano-N-(4-{2-[4-(2,5-dimethoxyphenyl)piperazin-1-yl]ethyl}cyclohexyl)acetamide | 171-173 | IIA |
| 222 | 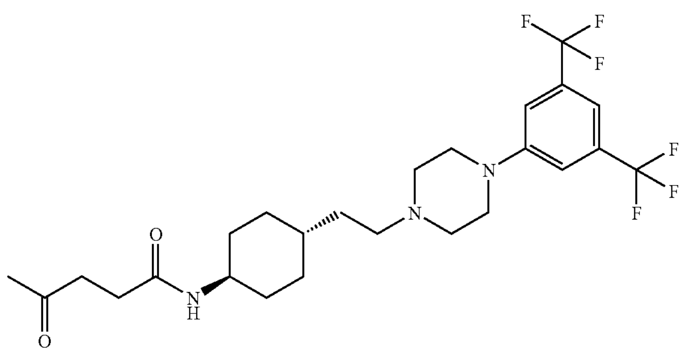 [SMILES: CC(=O)CCC(=O)N[C@H]1CC[C@H](CCN2CCN(c3cc(C(F)(F)F)cc(C(F)(F)F)c3)CC2)CC1] | 4-Oxopentanoic acid (4-{2-[4-(3,5-bis-trifluoromethylphenyl)piperazin-1-yl]ethyl}cyclohexyl)amide | 172-174 | IIA |
| 223 | 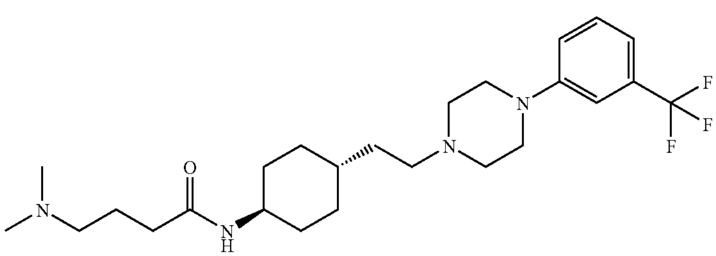 [SMILES: CN(C)CCCC(=O)N[C@H]1CC[C@H](CCN2CCN(c3cccc(C(F)(F)F)c3)CC2)CC1] | 4-Dimethylamino-N-(4-{2-[4-(3-trifluoromethylphenyl)piperazin-1-yl]ethyl}cyclohexyl)butanamide | 128 | IIA |
| 224 | 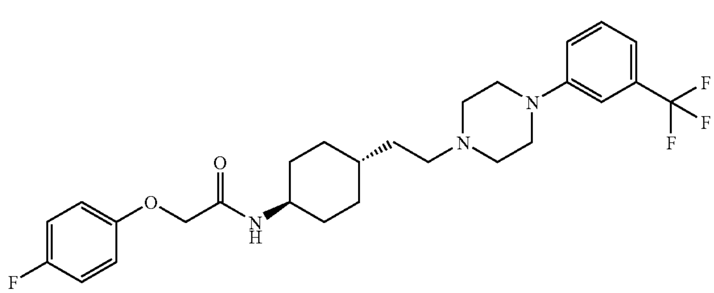 [SMILES: O=C(COc1ccc(F)cc1)N[C@H]1CC[C@H](CCN2CCN(c3cccc(C(F)(F)F)c3)CC2)CC1] | 2-(4-Fluorophenoxy)-N-(4-{2-[4-(3-trifluoromethylphenyl)-piperazin-1-yl]ethyl}cyclohexyl)-acetamide | 119 | IIA |

-continued

| Ex | Structure | Name | M.P. (° C.) | Synthetic Path |
|---|---|---|---|---|
| 225 | 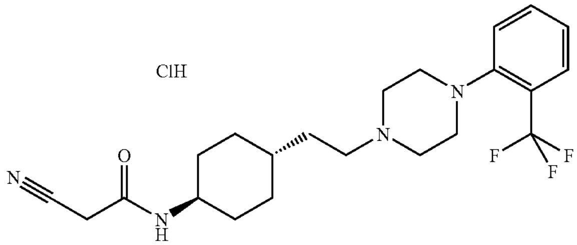 [SMILES: N#CCC(=O)N[C@H]1CC[C@H](CCN2CCN(c3ccccc3C(F)(F)F)CC2)CC1 ; Cl] | 2-Cyano-N-(4-{2-[4-(2-trifluoromethylphenyl)piperazin-1-yl]ethyl}cyclohexyl)acetamide, hydrochloride | 278 | IIA |
| 226 | 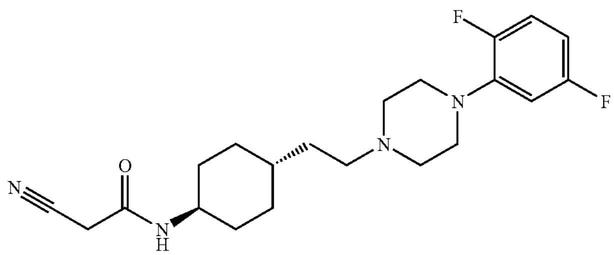 [SMILES: N#CCC(=O)N[C@H]1CC[C@H](CCN2CCN(c3cc(F)ccc3F)CC2)CC1] | 2-Cyano-N-(4-{2-[4-(2,5-difluorophenyl)piperazin-1-yl]ethyl}cyclohexyl)acetamide | 198 | IIA |
| 227 | 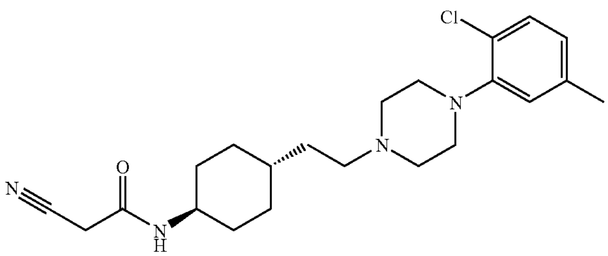 | N-(4-{2-[4-(2-Chloro-5-methylphenyl)piperazin-1-yl]ethyl}cyclohexyl)-2-cyanoacetamide | 174 | IIA |
| 228 | 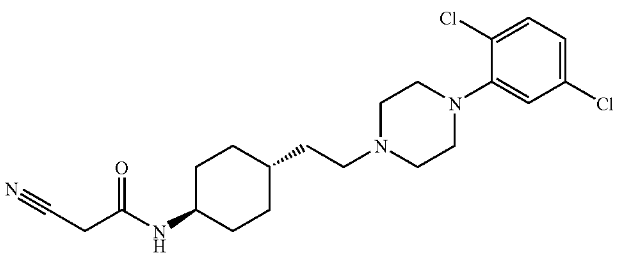 [SMILES: N#CCC(=O)N[C@H]1CC[C@H](CCN2CCN(c3cc(Cl)ccc3Cl)CC2)CC1] | 2-Cyano-N-(4-{2-[4-(2,5-dichlorophenyl)piperazin-1-yl]ethyl}cyclohexyl)acetamide | 182-184 | IIA |
| 229 | 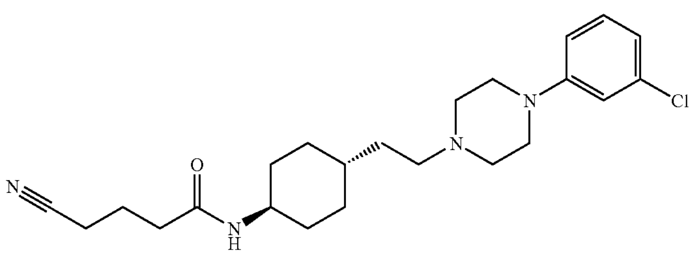 [SMILES: N#CCCCC(=O)N[C@H]1CC[C@H](CCN2CCN(c3cccc(Cl)c3)CC2)CC1] | N-(4-{2-[4-(3-Chlorophenyl)piperazin-1-yl]ethyl}cyclohexyl)-4-cyanobutanamide | 171-173 | IIA |
| 230 | 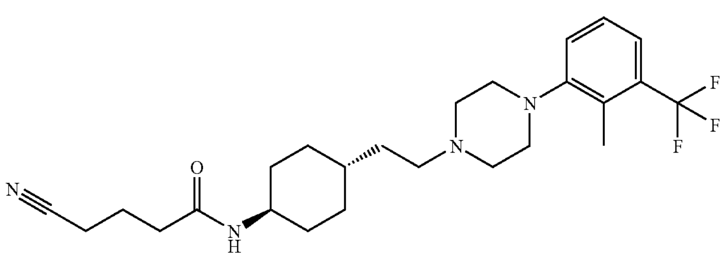 [SMILES: Cc1c(N2CCN(CC[C@H]3CC[C@H](NC(=O)CCCC#N)CC3)CC2)cccc1C(F)(F)F] | 4-Cyano-N-(4-{2-[4-(2-methyl-3-trifluoromethylphenyl)piperazin-1-yl]ethyl}cyclohexyl)butanamide | 162 | IIA |

-continued

| Ex | Structure | Name | M.P. (° C.) | Synthetic Path |
|---|---|---|---|---|
| 231 | 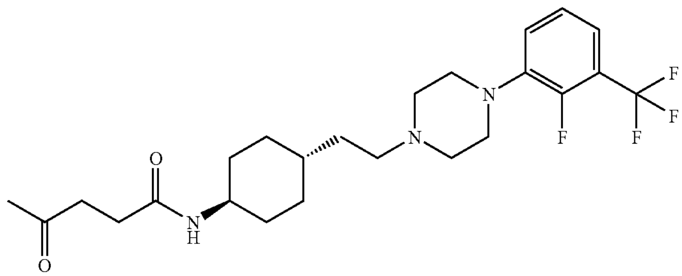 [SMILES: CC(=O)CCC(=O)N[C@H]1CC[C@H](CCN2CCN(c3cccc(C(F)(F)F)c3F)CC2)CC1] | 4-Oxopentanoic acid (4-{2-[4-(2-fluoro-3-trifluoromethyl-phenyl)piperazin-1-yl]ethyl}cyclohexyl)amide | 178 | IIA |
| 232 | 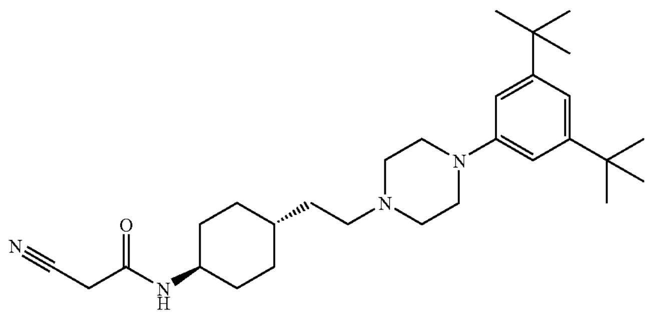 [SMILES: CC(C)(C)c1cc(N2CCN(CC[C@H]3CC[C@H](NC(=O)CC#N)CC3)CC2)cc(C(C)(C)C)c1] | 2-Cyano-N-(4-{2-[4-(3,5-di-tert-butylphenyl)piperazin-1-yl]ethyl}cyclohexyl)acetamide | 168 | IIA |
| 233 | 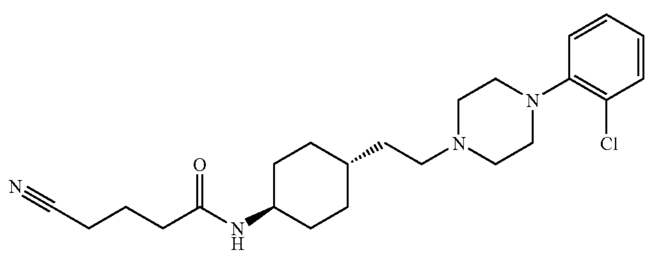 | N-(4-{2-[4-(2-Chlorophenyl)piperazin-1-yl]ethyl}cyclohexyl)-4-cyanobutanamide | 142 | IIA |
| 234 | 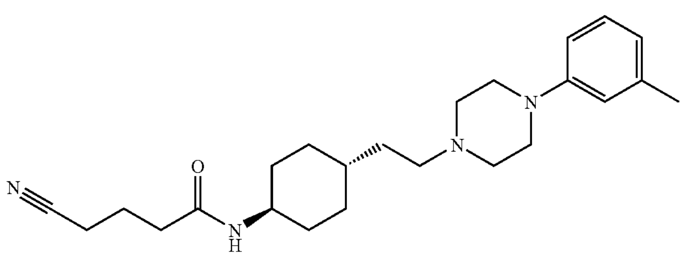 [SMILES: Cc1cccc(N2CCN(CC[C@H]3CC[C@H](NC(=O)CCCC#N)CC3)CC2)c1] | 4-Cyano-N-{4-[2-(4-m-tolylpiperazin-1-yl)ethyl]cyclohexyl}butanamide | 150 | IIA |
| 235 | 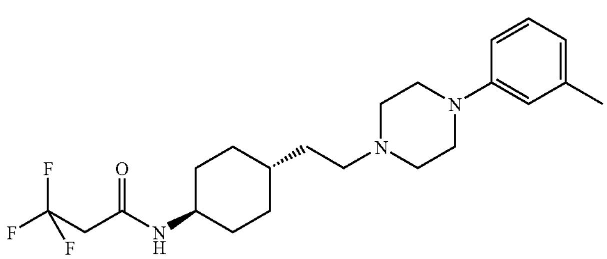 [SMILES: Cc1cccc(N2CCN(CC[C@H]3CC[C@H](NC(=O)CC(F)(F)F)CC3)CC2)c1] | 3,3,3-Trifluoro-N-{4-[2-(4-m-tolylpiperazin-1-yl)ethyl]cyclohexyl}propanamide | 170 | IIA |

-continued

| Ex | Structure | Name | M.P. (° C.) | Synthetic Path |
|---|---|---|---|---|
| 236 | 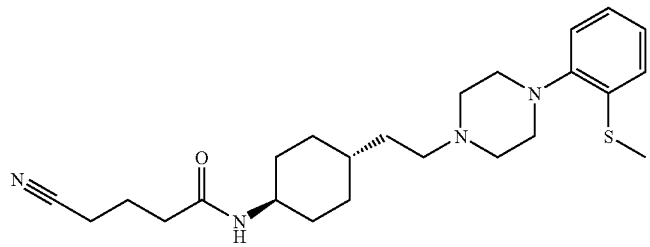 [SMILES: CSc1ccccc1N1CCN(CC[C@H]2CC[C@H](NC(=O)CCCC#N)CC2)CC1] | 4-Cyano-N-(4-{2-[4-(2-methylsulfanylphenyl)piperazin-1-yl]ethyl}cyclohexyl)butanamide | 130 | IIA |
| 237 | 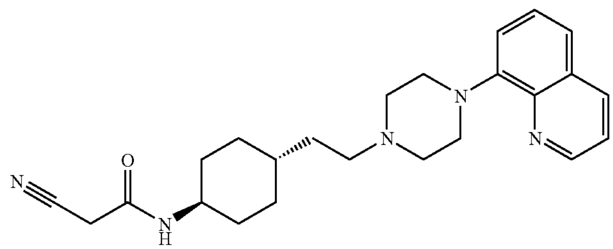 [SMILES: N#CCC(=O)N[C@H]1CC[C@H](CCN2CCN(c3cccc4cccnc34)CC2)CC1] | 2-Cyano-N-{4-[2-(4-quinolin-8-ylpiperazin-1-yl)ethyl]-cyclohexyl}acetamide | 225 | IIA |
| 238 | 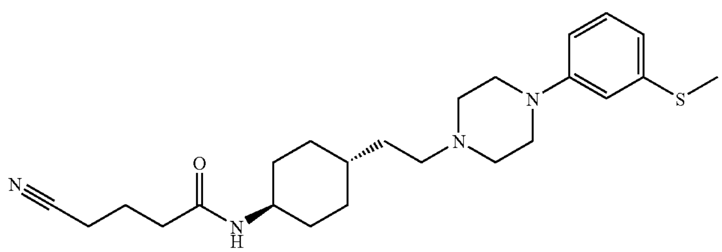 [SMILES: CSc1cccc(N2CCN(CC[C@H]3CC[C@H](NC(=O)CCCC#N)CC3)CC2)c1] | 4-Cyano-N-(4-{2-[4-(3-methylsulfanylphenyl)piperazin-1-yl]ethyl}cyclohexyl)butanamide | 127 | IIA |
| 239 | 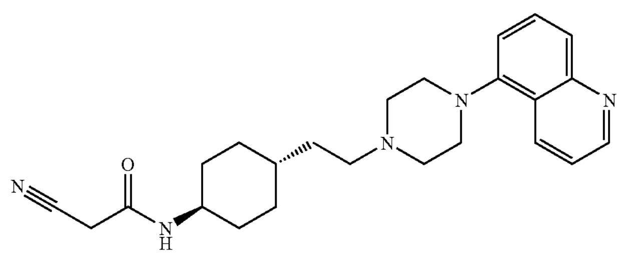 [SMILES: N#CCC(=O)N[C@H]1CC[C@H](CCN2CCN(c3cccc4ncccc34)CC2)CC1] | 2-Cyano-N-{4-[2-(4-quinolin-5-ylpiperazin-1-yl)ethyl]cyclohexyl}acetamide | 220 | IIA |
| 240 | 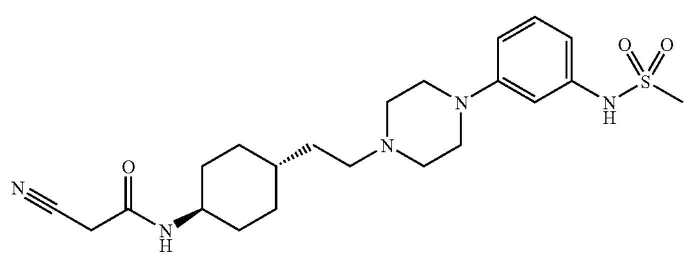 [SMILES: CS(=O)(=O)Nc1cccc(N2CCN(CC[C@H]3CC[C@H](NC(=O)CC#N)CC3)CC2)c1] | 2-Cyano-N-(4-{2-[4-(3-methanesulfonylaminophenyl)piperazin-1-yl]ethyl}cyclohexyl)-acetamide | 194 | IIA |
| 241 | 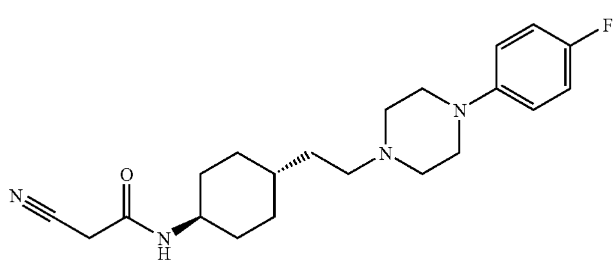 [SMILES: N#CCC(=O)N[C@H]1CC[C@H](CCN2CCN(c3ccc(F)cc3)CC2)CC1] | 2-Cyano-N-(4-{2-[4-(4-fluorophenyl)piperazin-1-yl]ethyl}cyclohexyl)acetamide | 209 | IIA |

-continued

| Ex | Structure | Name | M.P. (° C.) | Synthetic Path |
|---|---|---|---|---|
| 242 | 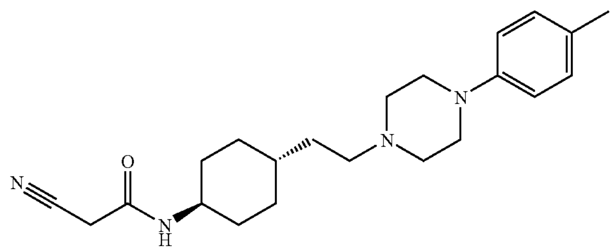 [SMILES: Cc1ccc(N2CCN(CC[C@H]3CC[C@H](NC(=O)CC#N)CC3)CC2)cc1] | 2-Cyano-N-{4-[2-(4-p-tolylpiperazin-1-yl)ethyl]cyclohexyl}acetamide | 237 | IIA |
| 243 | 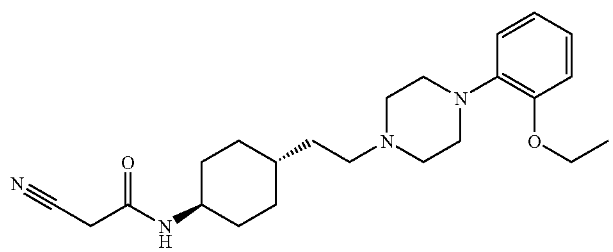 [SMILES: CCOc1ccccc1N1CCN(CC[C@H]2CC[C@H](NC(=O)CC#N)CC2)CC1] | 2-Cyano-N-(4-{2-[4-(2-ethoxyphenyl)piperazin-1-yl]ethyl}cyclohexyl)acetamide | 138 | IIA |
| 244 | 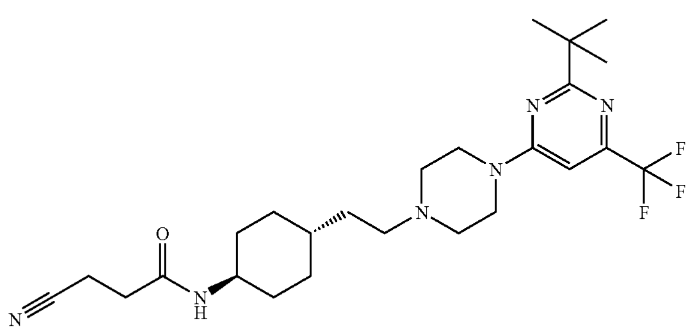 [SMILES: CC(C)(C)c1nc(N2CCN(CC[C@H]3CC[C@H](NC(=O)CCC#N)CC3)CC2)cc(C(F)(F)F)n1] | N-(4-{2-[4-(2-tert-Butyl-6-trifluoromethylpyrimidin-4-yl)piperazin-1-yl]ethyl}cyclohexyl-1-cyano-propanamide trans/cis 80/20 | 151 | IIA |
| 245 | 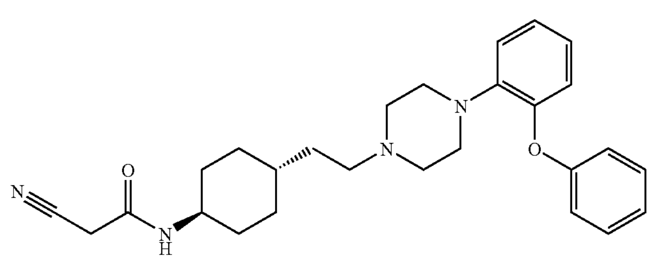 [SMILES: N#CCC(=O)N[C@H]1CC[C@H](CCN2CCN(c3ccccc3Oc3ccccc3)CC2)CC1] | 2-Cyano-N-(4-{2-[4-(2-phenoxyphenyl)piperazin-1-yl]ethyl}cyclohexyl)acetamide | 169 | IIA |
| 246 | 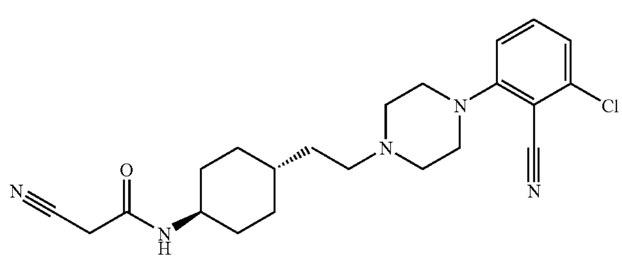 [SMILES: N#CCC(=O)N[C@H]1CC[C@H](CCN2CCN(c3cccc(Cl)c3C#N)CC2)CC1] | N-(4-{2-[4-(3-Chloro-2-cyanophenyl)piperazin-1-yl]ethyl}cyclohexyl)-2-cyanoacetamide | 232-233 | IIA |

-continued

| Ex | Structure | Name | M.P. (° C.) | Synthetic Path |
|---|---|---|---|---|
| 247 | 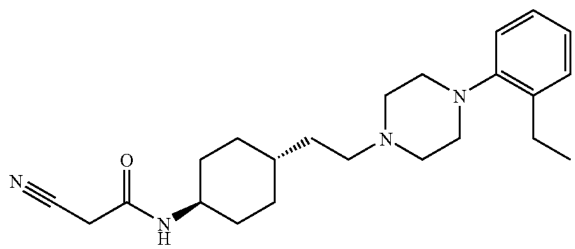 | 2-Cyano-N-(4-{2-[4-(2-ethylphenyl)piperazin-1-yl]ethyl}cyclohexyl)acetamide | 142-143 | IIA |
| 248 | 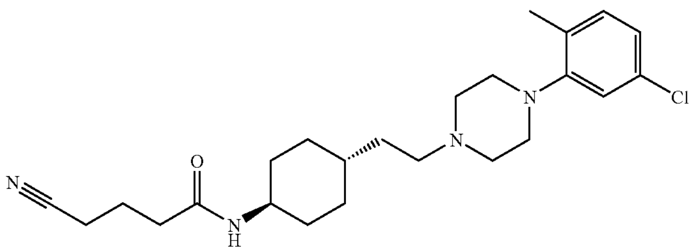 [SMILES: Cc1ccc(Cl)cc1N1CCN(CC[C@H]2CC[C@H](NC(=O)CCCC#N)CC2)CC1] | N-(4-{2-[4-(5-Chloro-2-methylphenyl)piperazin-1-yl]ethyl}cyclohexyl)-4-cyanobutanamide | 152-153 | IIA |
| 249 | 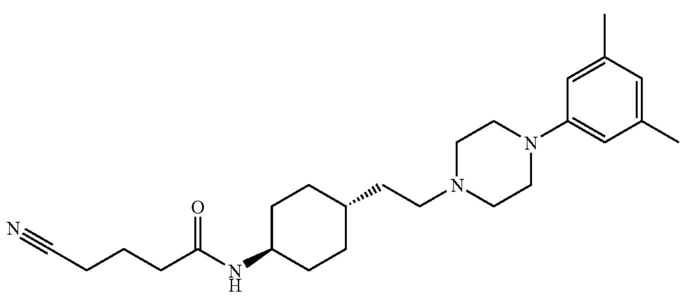 [SMILES: Cc1cc(C)cc(N2CCN(CC[C@H]3CC[C@H](NC(=O)CCCC#N)CC3)CC2)c1] | 4-Cyano-N-(4-{2-[4-(3,5-dimethylphenyl)piperazin-1-yl]ethyl}cyclohexyl)butanamide | 169 | IIA |
| 250 | 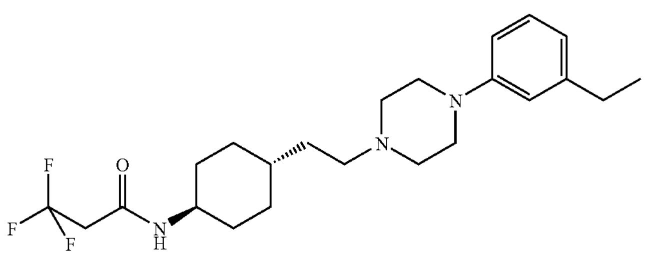 [SMILES: CCc1cccc(N2CCN(CC[C@H]3CC[C@H](NC(=O)CC(F)(F)F)CC3)CC2)c1] | N-(4-{2-[4-(3-Ethylphenyl)piperazin-1-yl]ethyl}cyclohexyl)-3,3,3-trifluoropropanamide | 154 | IIA |
| 251 | 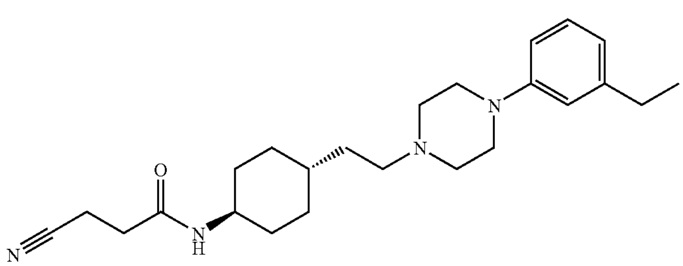 [SMILES: CCc1cccc(N2CCN(CC[C@H]3CC[C@H](NC(=O)CCC#N)CC3)CC2)c1] | 3-Cyano-N-(4-{2-[4-(3-ethylphenyl)piperazin-1-yl]ethyl}cyclohexyl)propanamide | 143 | IIA |

-continued

| Ex | Structure | Name | M.P. (° C.) | Synthetic Path |
|---|---|---|---|---|
| 252 | HCl HCl | 1-(4-{2-[4-(5-Methoxy-2-methylphenyl)piperazin-1-yl]ethyl}piperidin-1-yl)propan-2-one | 283 | IIIB |
| 253 | 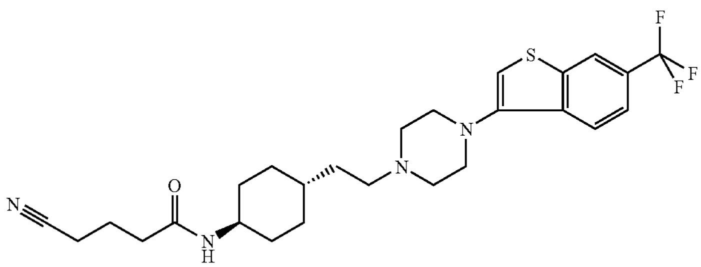 [SMILES: N#CCCCC(=O)N[C@H]1CC[C@H](CCN2CCN(c3csc4cc(C(F)(F)F)ccc34)CC2)CC1] | 4-Cyano-N-(4-{2-[4-(6-trifluoromethylbenzo[b]thiophen-3-yl)piperazin-1-yl]ethyl}cyclohexyl)butanamide | 169 | IA |
| 254 | 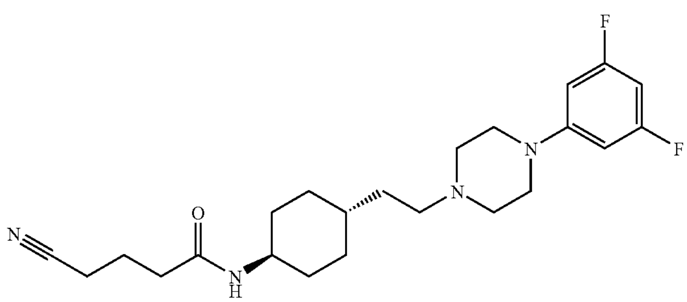 [SMILES: N#CCCCC(=O)N[C@H]1CC[C@H](CCN2CCN(c3cc(F)cc(F)c3)CC2)CC1] | 4-Cyano-N-(4-{2-[4-(3,5-difluorophenyl)piperazin-1-yl]ethyl}cyclohexyl)butanamide | 165 | IIA |
| 255 | 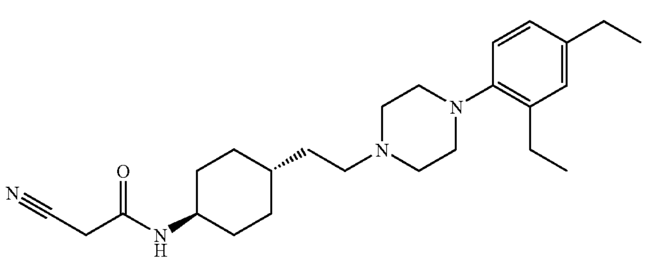 [SMILES: CCc1ccc(N2CCN(CC[C@H]3CC[C@H](NC(=O)CC#N)CC3)CC2)c(CC)c1] | 2-Cyano-N-(4-{2-[4-(2,4-diethylphenyl)piperazin-1-yl]ethyl}cyclohexyl)acetamide | 183 | IIA |
| 256 | 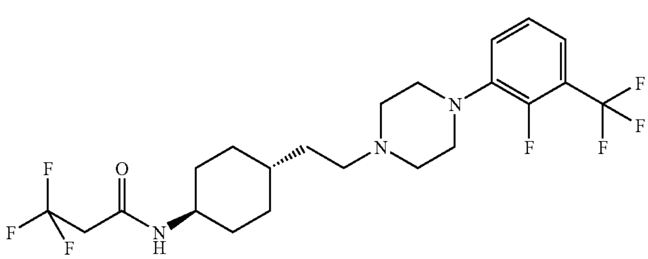 [SMILES: O=C(CC(F)(F)F)N[C@H]1CC[C@H](CCN2CCN(c3cccc(C(F)(F)F)c3F)CC2)CC1] | 3,3,3-Trifluoro-N-(4-{2-[4-(2-fluoro-3-trifluoromethylphenyl)piperazin-1-yl]ethyl}cyclohexyl)-propanamide | 198 | IIA |

-continued

| Ex | Structure | Name | M.P. (° C.) | Synthetic Path |
|---|---|---|---|---|
| 257 | 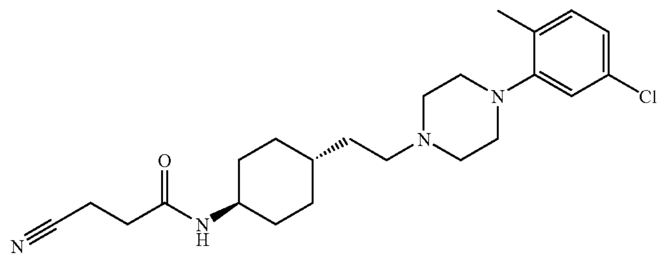 [SMILES: Cc1ccc(Cl)cc1N1CCN(CC[C@H]2CC[C@H](NC(=O)CCC#N)CC2)CC1] | N-(4-{2-[4-(5-Chloro-2-methylphenyl)piperazin-1-yl]ethyl}cyclohexyl)-3-cyanopropanamide | 133-134 | IIA |
| 258 | 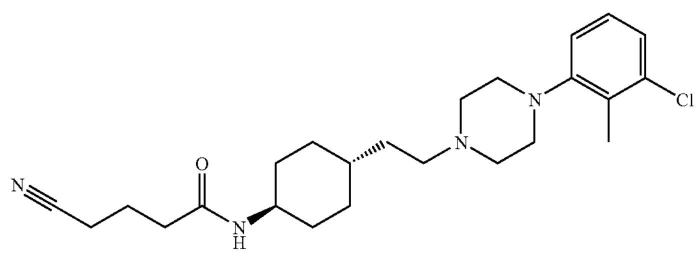 | N-(4-{2-[4-(3-Chloro-2-methylphenyl)piperazin-1-yl]ethyl}cyclohexyl)-4-cyanobutanamide | 180-183 | IIA |
| 259 | 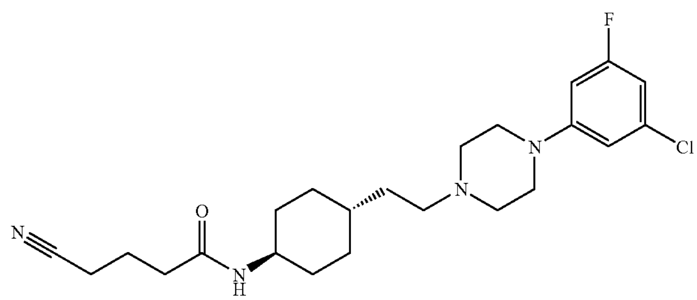 [SMILES: N#CCCCC(=O)N[C@H]1CC[C@H](CCN2CCN(c3cc(F)cc(Cl)c3)CC2)CC1] | N-(4-{2-[4-(3-Chloro-5-fluorophenyl)piperazin-1-yl]ethyl}cyclohexyl)-4-cyanobutanamide | 158-159 | IIA |
| 260 | 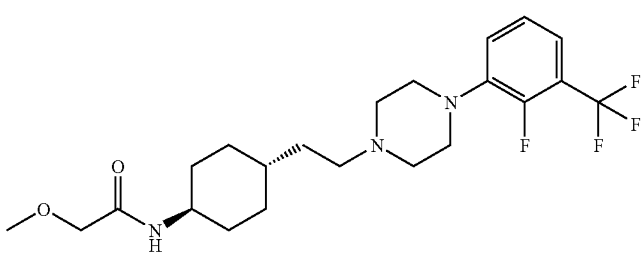 [SMILES: COCC(=O)N[C@H]1CC[C@H](CCN2CCN(c3cccc(C(F)(F)F)c3F)CC2)CC1] | N-(4-{2-[4-(2-Fluoro-3-trifluoromethylphenyl)piperazin-1-yl]ethyl}cyclohexyl)-2-methoxyacetamide | 142 | IIA |
| 261 | trans/cis 98/2 | 4-Cyano-N-(4-{2-[4-(3,5-dichlorophenyl)piperazin-1-yl]ethyl}cyclohexyl)butanamide trans/cis 98/2 | 179 | IIA |

-continued

| Ex | Structure | Name | M.P. (° C.) | Synthetic Path |
|---|---|---|---|---|
| 262 | 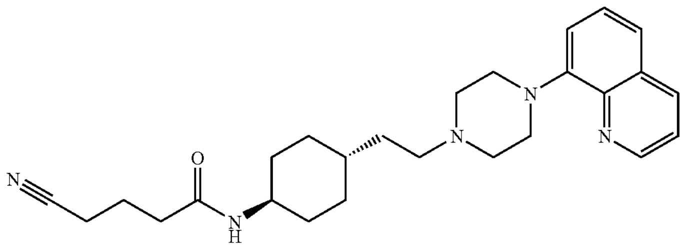 [SMILES: N#CCCCC(=O)N[C@H]1CC[C@H](CCN2CCN(c3cccc4cccnc34)CC2)CC1] | 4-Cyano-N-{4-[2-(4-quinolin-8-ylpiperazin-1-yl)ethyl]cyclohexyl}butanamide | 180 | IIA |
| 263 | HCl HCl | 1-(4-{2-[4-(2,3-Dimethylphenyl)-3,6-dihydro-2H-pyridin-1-yl]ethyl}piperidin-1-yl)propan-2-one | 310 | IIIB |
| 264 | 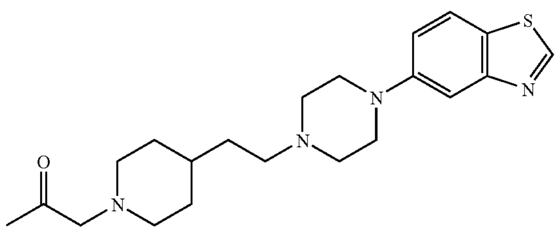 [SMILES: CC(=O)CN1CCC(CCN2CCN(c3ccc4scnc4c3)CC2)CC1] | 1-{4-[2-(4-Benzothiazol-5-ylpiperazin-1-yl)ethyl]piperidin-1-yl}propan-2-one | 110 | IIIB |
| 265 | 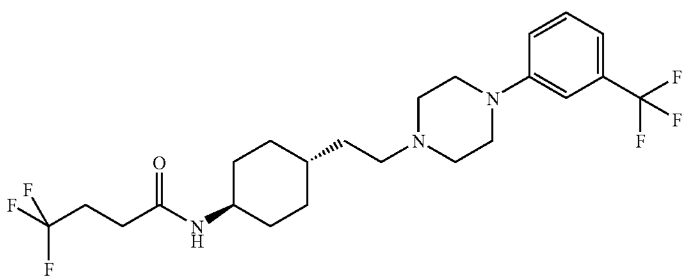 [SMILES: O=C(CCC(F)(F)F)N[C@H]1CC[C@H](CCN2CCN(c3cccc(C(F)(F)F)c3)CC2)CC1] | 4,4,4-Trifluoro-N-(4-{2-[4-(3-trifluoromethylphenyl)piperazin-1-yl]ethyl}cyclohexyl)butanamide | 152 | IIA |
| 266 | 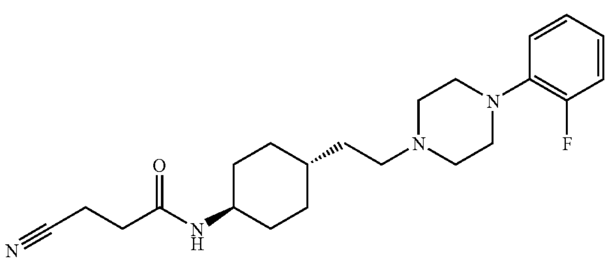 [SMILES: N#CCCC(=O)N[C@H]1CC[C@H](CCN2CCN(c3ccccc3F)CC2)CC1] | 3-Cyano-N-(4-{2-[4-(2-fluorophenyl)piperazin-1-yl]ethyl}cyclohexyl)propanamide | 164 | IIA |
| 267 | 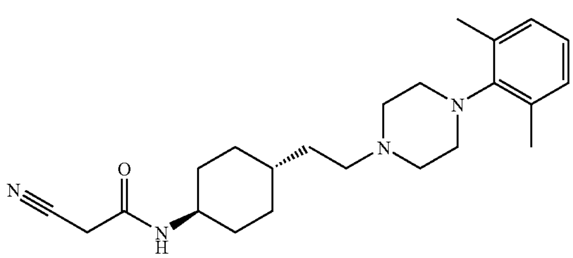 [SMILES: Cc1cccc(C)c1N1CCN(CC[C@H]2CC[C@H](NC(=O)CC#N)CC2)CC1] | 2-Cyano-N-(4-{2-[4-(2,6-dimethylphenyl)piperazin-1-yl]ethyl}cyclohexyl)acetamide | 143 | IIA |

-continued

| Ex | Structure | Name | M.P. (° C.) | Synthetic Path |
|---|---|---|---|---|
| 268 | 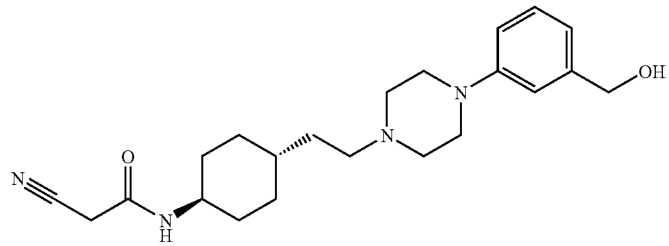 [SMILES: N#CCC(=O)N[C@H]1CC[C@H](CCN2CCN(c3cccc(CO)c3)CC2)CC1] | 2-Cyano-N-(4-{2-[4-(3-hydroxymethylphenyl)piperazin-1-yl]ethyl}cyclohexyl)acetamide | 180 | IIA |
| 269 | 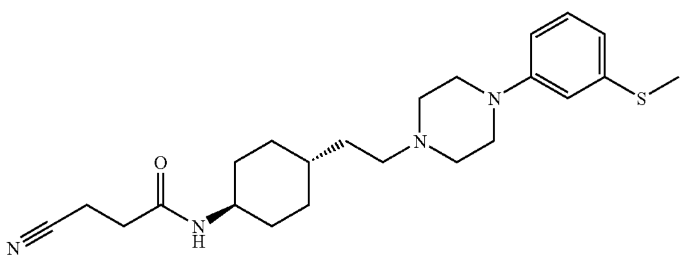 [SMILES: CSc1cccc(N2CCN(CC[C@H]3CC[C@H](NC(=O)CCC#N)CC3)CC2)c1] | 3-Cyano-N-(4-{2-[4-(3-methylsulfanylphenyl)piperazin-1-yl]ethyl}cyclohexyl)-propanamide | 98 | IIA |
| 270 | 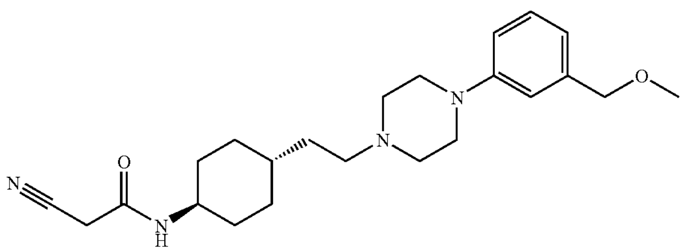 [SMILES: COCc1cccc(N2CCN(CC[C@H]3CC[C@H](NC(=O)CC#N)CC3)CC2)c1] | 2-Cyano-N-(4-{2-[4-(3-methoxymethylphenyl)piperazin-1-yl]ethyl}cyclohexyl)acetamide | 117 | IIA |
| 271 | 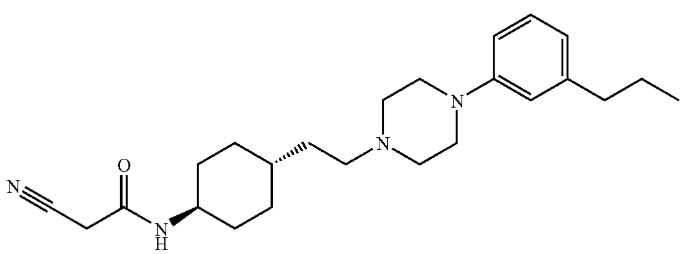 [SMILES: CCCc1cccc(N2CCN(CC[C@H]3CC[C@H](NC(=O)CC#N)CC3)CC2)c1] | 2-Cyano-N-(4-{2-[4-(3-propylphenyl)piperazin-1-yl]ethyl}cyclohexyl)acetamide | 132 | IIA |
| 272 | 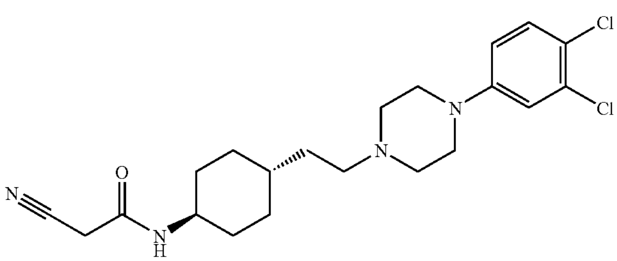 [SMILES: N#CCC(=O)N[C@H]1CC[C@H](CCN2CCN(c3ccc(Cl)c(Cl)c3)CC2)CC1] | 2-Cyano-N-(4-{2-[4-(3,4-dichlorophenyl)piperazin-1-yl]ethyl}cyclohexyl)acetamide | 216 | IIA |
| 273 | trans/cis 80/20 | 2-Cyano-N-[4-(2-{4-[3-(2-hydroxyethyl)phenyl]piperazin-1-yl}ethyl)cyclohexyl]acetamide trans/cis 80/20 | 160 | IIA |

-continued

| Ex | Structure | Name | M.P. (° C.) | Synthetic Path |
|---|---|---|---|---|
| 274 | 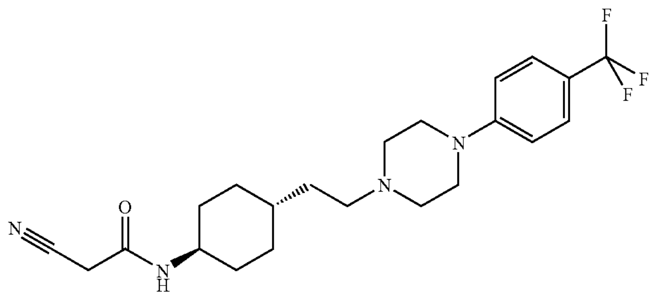 [SMILES: N#CCC(=O)N[C@H]1CC[C@H](CCN2CCN(c3ccc(C(F)(F)F)cc3)CC2)CC1] | 2-Cyano-N-(4-{2-[4-(4-trifluoromethylphenyl)piperazin-1-yl]ethyl}cyclohexyl)acetamide | 240 | IIA |
| 275 | 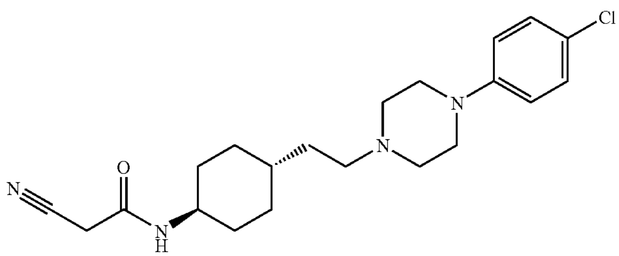 [SMILES: N#CCC(=O)N[C@H]1CC[C@H](CCN2CCN(c3ccc(Cl)cc3)CC2)CC1] | N-(4-{2-[4-(4-Chlorophenyl)piperazin-1-yl]ethyl}cyclohexyl)-2-cyanoacetamide | 247 | IIA |
| 276 | 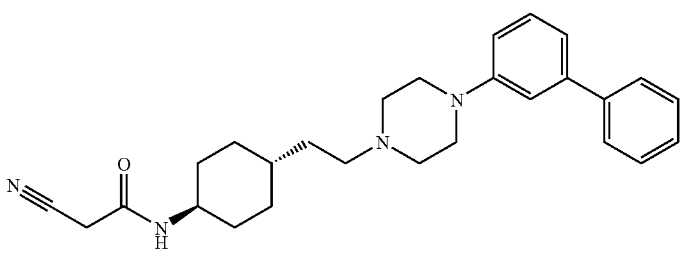 [SMILES: N#CCC(=O)N[C@H]1CC[C@H](CCN2CCN(c3cccc(-c4ccccc4)c3)CC2)CC1] | N-{4-[2-(4-Biphenyl-3-yl-piperazin-1-yl)ethyl]cyclohexyl}-2-cyanoacetamide | 157 | IIA |
| 277 | 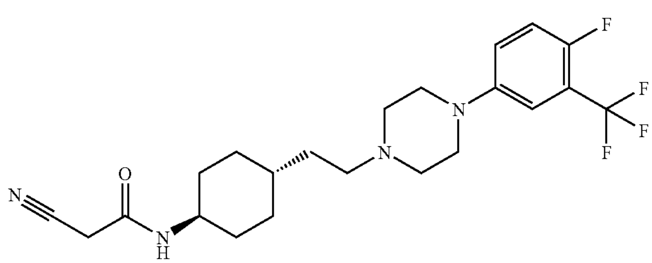 [SMILES: N#CCC(=O)N[C@H]1CC[C@H](CCN2CCN(c3ccc(F)c(C(F)(F)F)c3)CC2)CC1] | 2-Cyano-N-(4-{2-[4-(4-fluoro-3-trifluoromethylphenyl)piperazin-1-yl]ethyl}cyclohexyl)acetamide | 181 | IIA |
| 278 | 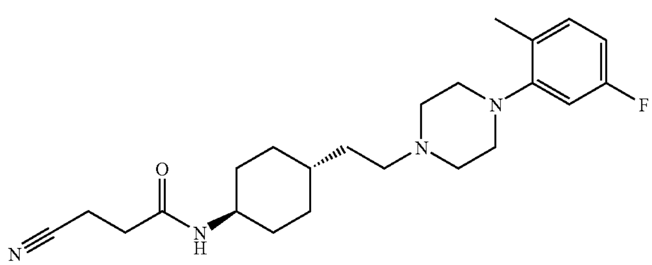 [SMILES: Cc1ccc(F)cc1N1CCN(CC[C@H]2CC[C@H](NC(=O)CCC#N)CC2)CC1] | 3-Cyano-N-(4-{2-[4-(5-fluoro-2-methylphenyl)piperazin-1-yl]ethyl}cyclohexyl)propanamide | 146 | IIA |

-continued

| Ex | Structure | Name | M.P. (° C.) | Synthetic Path |
|---|---|---|---|---|
| 279 | 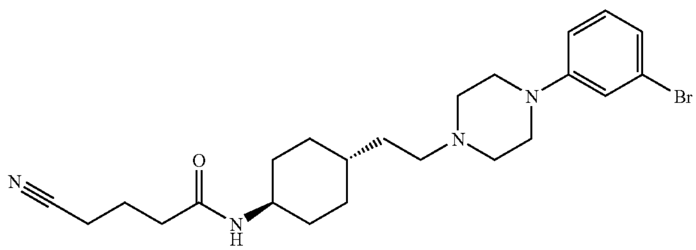 [SMILES: N#CCCCC(=O)N[C@H]1CC[C@H](CCN2CCN(c3cccc(Br)c3)CC2)CC1] | 4-Cyano-N-(4-{2-[4-(5-fluoro-2-methylphenyl)piperazin-1-yl]ethyl}cyclohexyl)butanamide | 155 | IIA |
| 280 | 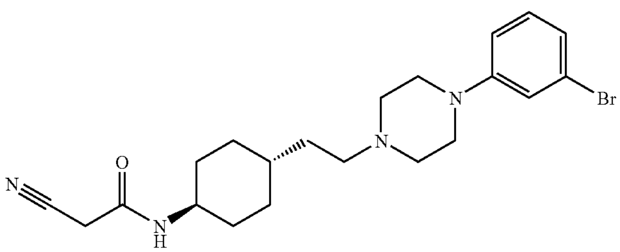 [SMILES: N#CCC(=O)N[C@H]1CC[C@H](CCN2CCN(c3cccc(Br)c3)CC2)CC1] | N-(4-{2-[4-(3-Bromophenyl)piperazin-1-yl]ethyl}cyclohexyl)-2-cyanoacetamide | 168 | IIA |
| 281 | trans/cis 90/10 | 2-Cyano-N-[4-(2-{4-[3-(1,1-difluoroethyl)phenyl]piperazin-1-yl}ethyl)cyclohexyl]acetamide trans/cis 90/10 | 150 | IIA |
| 282 | 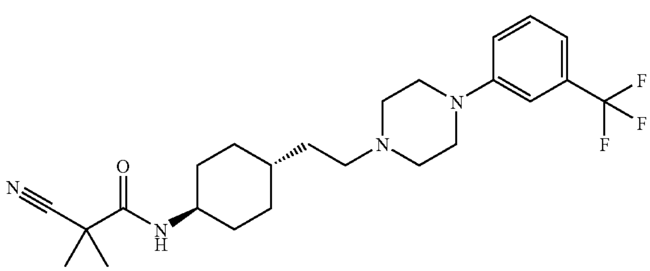 [SMILES: CC(C)(C#N)C(=O)N[C@H]1CC[C@H](CCN2CCN(c3cccc(C(F)(F)F)c3)CC2)CC1] | 2-Cyano-2,2-dimethyl-N-(4-{2-[4-(3-trifluoromethylphenyl)-piperazin-1-yl]ethyl}cyclohexyl)-acetamide | 150 | IIA |
| 283 | 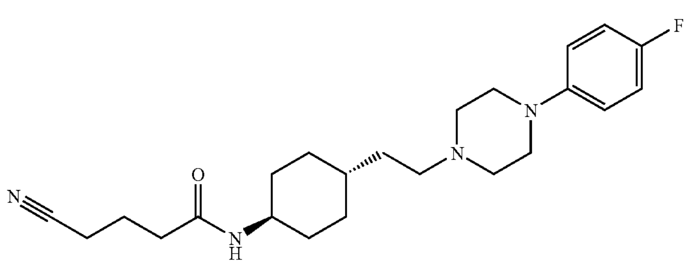 [SMILES: N#CCCCC(=O)N[C@H]1CC[C@H](CCN2CCN(c3ccc(F)cc3)CC2)CC1] | 4-Cyano-N-(4-{2-[4-(4-fluorophenyl)piperazin-1-yl]ethyl}cyclohexyl)butanamide | 154 | IIA |

| Ex | Structure | Name | M.P. (° C.) | Synthetic Path |
|---|---|---|---|---|
| 284 | 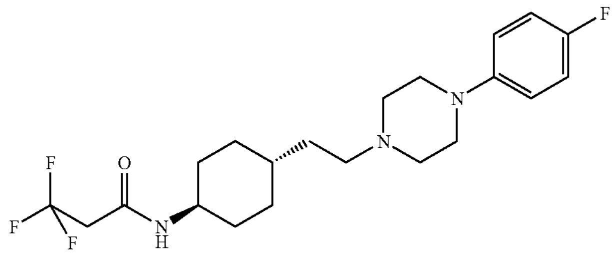 [SMILES: O=C(CC(F)(F)F)N[C@H]1CC[C@H](CCN2CCN(c3ccc(F)cc3)CC2)CC1] | 3,3,3-Trifluoro-N-(4-{2-[4-(4-fluorophenyl)piperazin-1-yl]ethyl}cyclohexyl)propanamide | 200 | IIA |
| 285 | 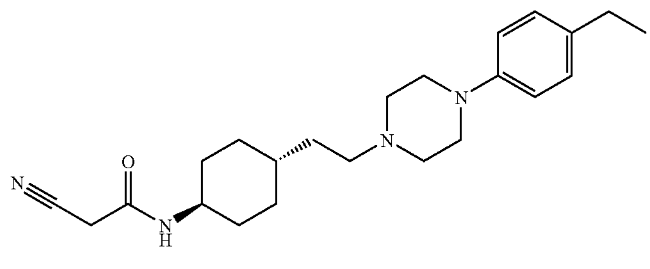 [SMILES: CCc1ccc(N2CCN(CC[C@H]3CC[C@H](NC(=O)CC#N)CC3)CC2)cc1] | 2-Cyano-N-(4-{2-[4-(4-ethylphenyl)piperazin-1-yl]ethyl}cyclohexyl)acetamide | 210 | IIA |
| 286 | 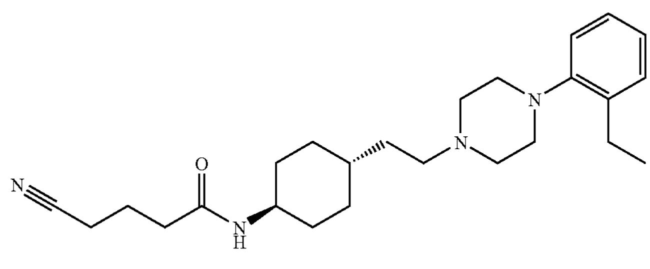 [SMILES: CCc1ccccc1N1CCN(CC[C@H]2CC[C@H](NC(=O)CCCC#N)CC2)CC1] | 4-Cyano-N-(4-{2-[4-(2-ethylphenyl)piperazin-1-yl]ethyl}cyclohexyl)butanamide | 124 | IIA |
| 287 | 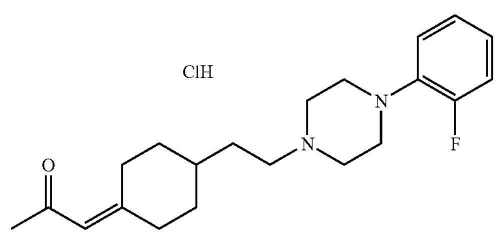 [SMILES: CC(=O)C=C1CCC(CCN2CCN(c3ccccc3F)CC2)CC1 ; Cl] | 1-(4-{2-[4-(2-Fluorophenyl)-piperazin-1-yl]ethyl}cyclohexylidene)propan-2-one, hydrochloride | 226-8 | IIC |
| 288 | 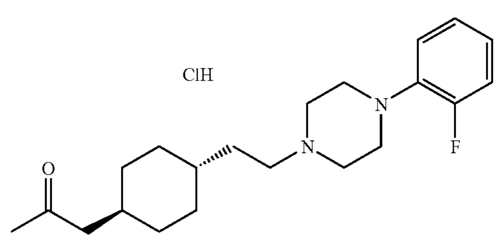 [SMILES: CC(=O)C[C@H]1CC[C@H](CCN2CCN(c3ccccc3F)CC2)CC1 ; Cl] | 1-(4-{2-[4-(2-Fluorophenyl)-piperazin-1-yl]ethyl}cyclohexyl)-propan-2-one, hydrochloride trans/cis 80/20 | 233-236 | IIC |

-continued

| Ex | Structure | Name | M.P. (° C.) | Synthetic Path |
|---|---|---|---|---|
| 289 | 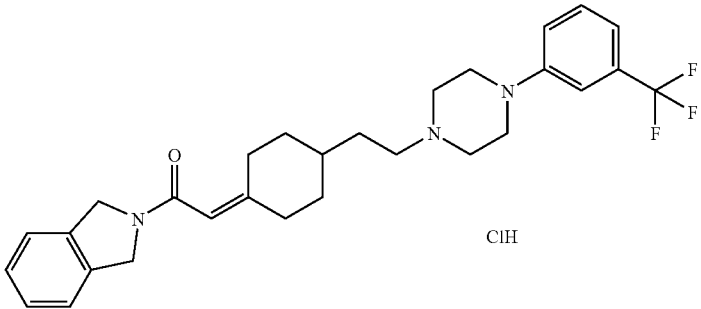 [SMILES: O=C(C=C1CCC(CCN2CCN(c3cccc(C(F)(F)F)c3)CC2)CC1)N1Cc2ccccc2C1 ; Cl] | 1-(1,3-Dihydroisoindol-2-yl)-2-(4-{2-[4-(3-trifluoromethylphenyl)-piperazin-1-yl]ethyl}cyclo-hexylidene)ethanone, hydrochloride | 260 | IIC |
| 290 | 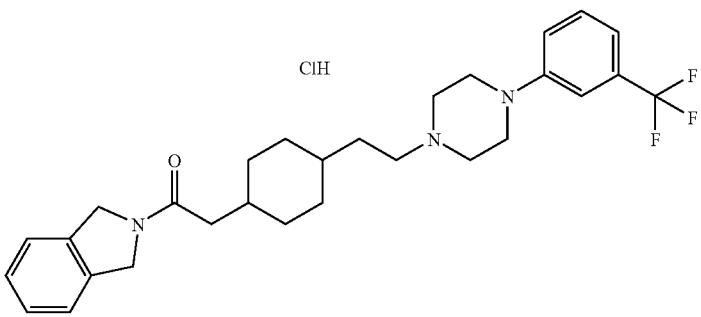 [SMILES: O=C(CC1CCC(CCN2CCN(c3cccc(C(F)(F)F)c3)CC2)CC1)N1Cc2ccccc2C1 ; Cl] | 1-(1,3-Dihydroisoindol-2-yl)-2-(4-{2-[4-(3-trifluoromethylphenyl)piperazin-1-yl]ethyl}cyclohexyl)ethanone, hydrochloride 60/40 mixture of isomers | | IIC |
| 291 | 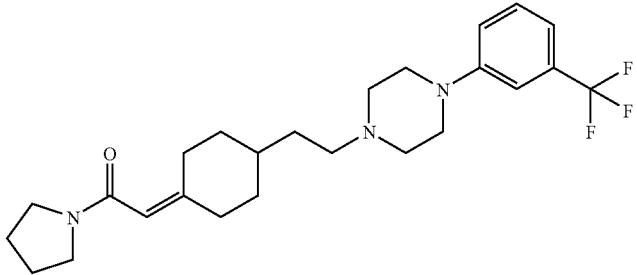 [SMILES: O=C(C=C1CCC(CCN2CCN(c3cccc(C(F)(F)F)c3)CC2)CC1)N1CCCC1] | 1-Pyrrolidin-1-yl-2-(4-{2-[4-(3-trifluoromethylphenyl)piperazin-1-yl]ethyl}cyclohexylidene)ethanone | 87 | IIC |
| 292 | 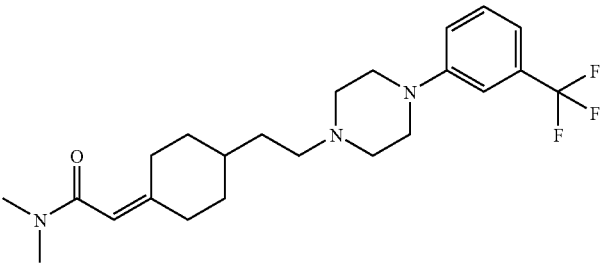 [SMILES: CN(C)C(=O)C=C1CCC(CCN2CCN(c3cccc(C(F)(F)F)c3)CC2)CC1] | N,N-Dimethyl-2-(4-{2-[4-(3-trifluoromethylphenyl)piperazin-1-yl]ethyl}cyclohexylidene)acetamide | 66 | IIC |
| 293 | 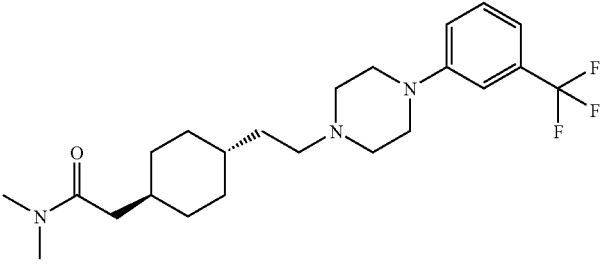 [SMILES: CN(C)C(=O)C[C@H]1CC[C@H](CCN2CCN(c3cccc(C(F)(F)F)c3)CC2)CC1] | N,N-Dimethyl-2-(4-{2-[4-(3-trifluoromethylphenyl)piperazin-1-yl]ethyl}cyclohexyl)acetamide trans/cis 80/20 | | IIC |

-continued

| Ex | Structure | Name | M.P. (° C.) | Synthetic Path |
|---|---|---|---|---|
| 294 | 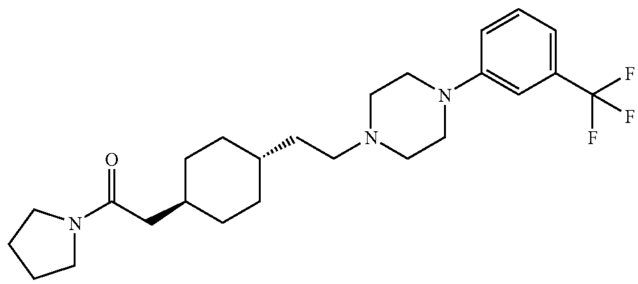 [SMILES: O=C(C[C@H]1CC[C@H](CCN2CCN(c3cccc(C(F)(F)F)c3)CC2)CC1)N1CCCC1] | 1-Pyrrolidin-1-yl-2-(4-{2-[4-(3-trifluoromethylphenyl)piperazin-10yl]ethyl}cyclohexyl)ethanone | 131 | IIC |
| 295 | 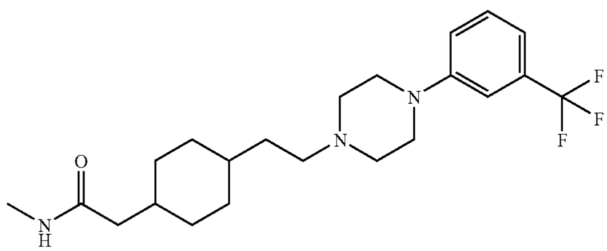 [SMILES: CNC(=O)CC1CCC(CCN2CCN(c3cccc(C(F)(F)F)c3)CC2)CC1] | N-Methyl-2-(4-{2-[4-(3-trifluoromethylphenyl)piperazin-1-yl]ethyl}cyclohexyl)acetamide cis/trans 50/50 | 196 | IIC |
| 296 | 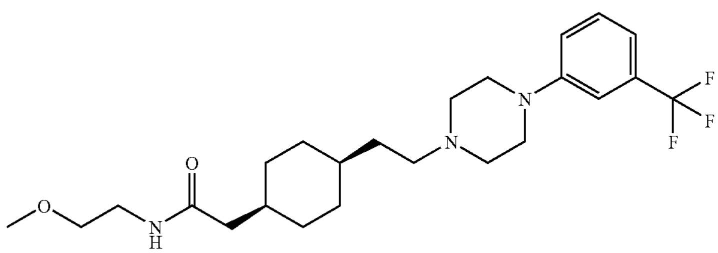 [SMILES: COCCNC(=O)C[C@H]1CC[C@@H](CCN2CCN(c3cccc(C(F)(F)F)c3)CC2)CC1] | N-(2-Methoxyethyl)-2-(4-{2-[4-(3-trifluoromethylphenyl)piperazin-1-yl]ethyl}cyclohexyl)acetamide | | IIC |
| 297 | 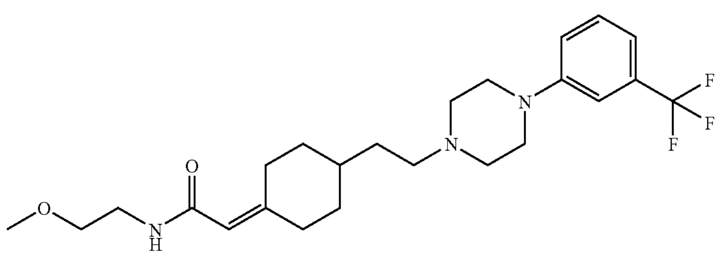 [SMILES: COCCNC(=O)C=C1CCC(CCN2CCN(c3cccc(C(F)(F)F)c3)CC2)CC1] | N-(2-Methoxyethyl)-2-(4-{2-[4-(3-trifluoromethylphenyl)piperazin-1-yl]ethyl}cyclohexylidene)acetamide | | IIC |
| 298 | 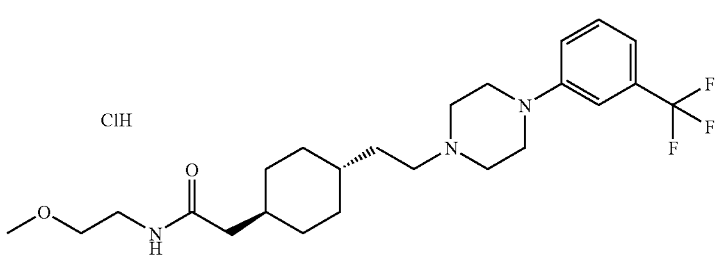 [SMILES: COCCNC(=O)C[C@H]1CC[C@H](CCN2CCN(c3cccc(C(F)(F)F)c3)CC2)CC1 ; Cl] | N-(2-Methoxyethyl)-2-(4-{2-[4-(3-trifluoromethylphenyl)piperazin-1-yl]ethyl}cyclohexyl)acetamide, hydrochloride | 143 | IIC |

-continued

| Ex | Structure | Name | M.P. (° C.) | Synthetic Path |
|---|---|---|---|---|
| 299 | 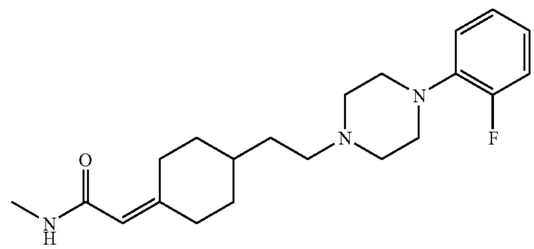 [SMILES: CNC(=O)C=C1CCC(CCN2CCN(c3ccccc3F)CC2)CC1] | 2-(4-{2-[4-(2-Fluorophenyl)piperazin-1-yl]ethyl}cyclohexylidene)-N-methylacetamide | 135 | IIC |
| 300 | 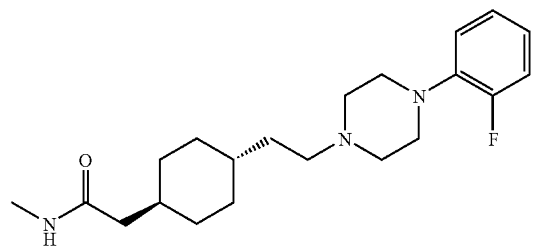 [SMILES: CNC(=O)C[C@H]1CC[C@H](CCN2CCN(c3ccccc3F)CC2)CC1] | 2-(4-{2-[4-(2-Fluorophenyl)-piperazin-1-yl]ethyl}cyclohexyl)-N-methylacetamide | 165-166 | IIC |
| 301 | 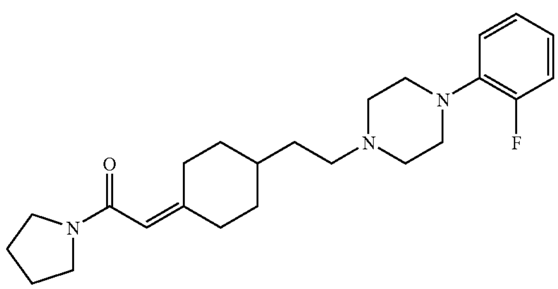 [SMILES: O=C(C=C1CCC(CCN2CCN(c3ccccc3F)CC2)CC1)N1CCCC1] | 2-(4-{2-[4-(2-Fluorophenyl)-piperazin-1-yl]ethyl}cyclohexylidene)-1-pyrrolidin-1-ylethanone | 109-110 | IIC |
| 302 | 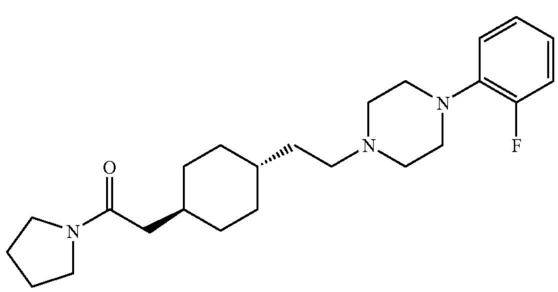 [SMILES: O=C(C[C@H]1CC[C@H](CCN2CCN(c3ccccc3F)CC2)CC1)N1CCCC1] | 2-(4-{2-[4-(2-Fluorophenyl)-piperazin-1-yl]ethyl}cyclohexyl)-1-pyrrolidin-1-ylethanone | 92-93 | IIC |
| 303 | 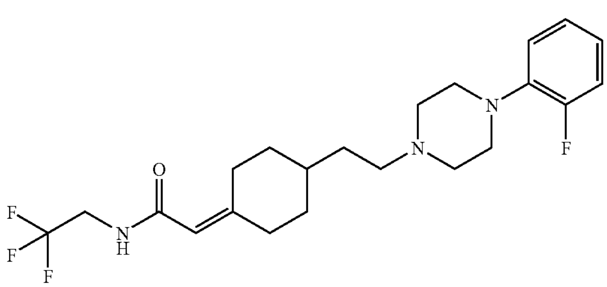 [SMILES: O=C(C=C1CCC(CCN2CCN(c3ccccc3F)CC2)CC1)NCC(F)(F)F] | 2-(4-{2-[4-(2-Fluorophenyl)-piperazin-1-yl]ethyl}cyclo-hexylidene)-N-(2,2,2-trifluoroethyl)acetamide | 125 | IIC |

-continued

| Ex | Structure | Name | M.P. (° C.) | Synthetic Path |
|---|---|---|---|---|
| 304 | 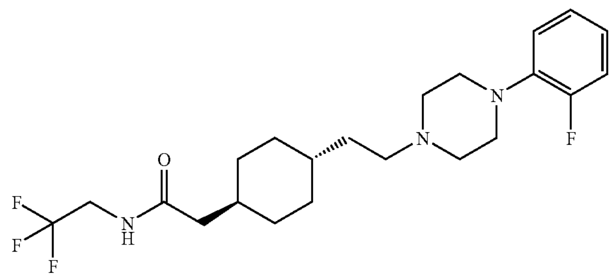 [SMILES: O=C(C[C@H]1CC[C@H](CCN2CCN(c3ccccc3F)CC2)CC1)NCC(F)(F)F] | 2-(4-{2-[4-(2-Fluorophenyl)piperazin-1-yl]ethyl}cyclohexyl)-N-(2,2,2-trifluoroethyl)acetamide | 158-9 | IIC |
| 305 | 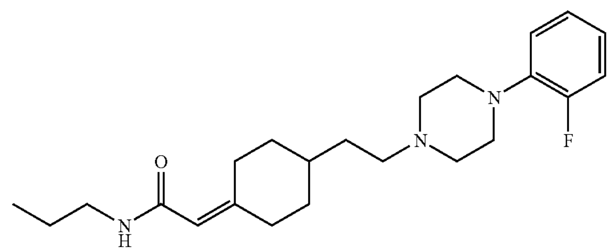 [SMILES: CCCNC(=O)C=C1CCC(CCN2CCN(c3ccccc3F)CC2)CC1] | 2-(4-{2-[4-(2-Fluorophenyl)piperazin-1-yl]ethyl}cyclohexylidene-N-propylacetamide | 120-121 | IIC |
| 306 | 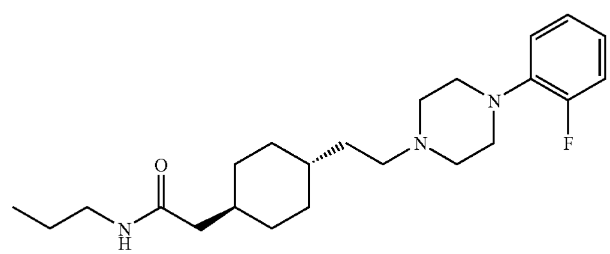 [SMILES: CCCNC(=O)C[C@H]1CC[C@H](CCN2CCN(c3ccccc3F)CC2)CC1] | 2-(4-{2-[4-(2-Fluorophenyl)-piperazin-1-yl]ethyl}cyclohexyl)-N-propylacetamide | 150 | IIC |
| 307 | 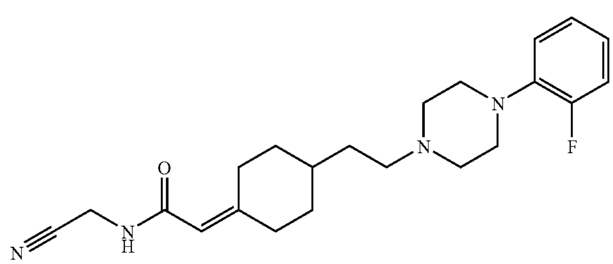 [SMILES: N#CCNC(=O)C=C1CCC(CCN2CCN(c3ccccc3F)CC2)CC1] | N-Cyanomethyl-2-(4-{2-[4-(2-fluorophenyl)piperazin-1-yl]ethyl}cyclohexylidene)acetamide | 140-142 | IIC |
| 308 | 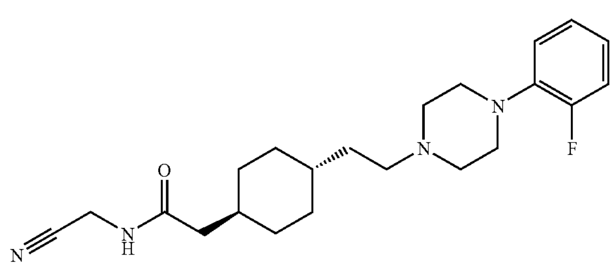 [SMILES: N#CCNC(=O)C[C@H]1CC[C@H](CCN2CCN(c3ccccc3F)CC2)CC1] | N-Cyanomethyl-2-(4-{2-[4-(2-fluorophenyl)piperazin-1-yl]ethyl}cyclohexyl)acetamide trans/cis 90/10 | 164-167 | IIC |

-continued

| Ex | Structure | Name | M.P. (° C.) | Synthetic Path |
|---|---|---|---|---|
| 309 | ClH ClH | 1-(4-Fluorophenyl)-2-(4-{2-[4-(3-trifluoromethylphenyl)piperazin-1-yl]ethyl}piperidin-1-yl)ethanone, dihydrochloride | 265 | IIIB |
| 310 | 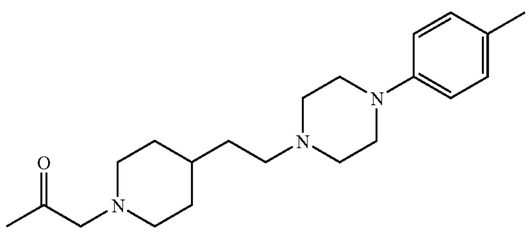 [SMILES: CC(=O)CN1CCC(CCN2CCN(c3ccc(C)cc3)CC2)CC1] | 1-{4-[2-(4-p-Tolylpiperazin-1-yl)ethyl]piperidin-1-yl}propan-2-one | 92 | IIIB |
| 311 | 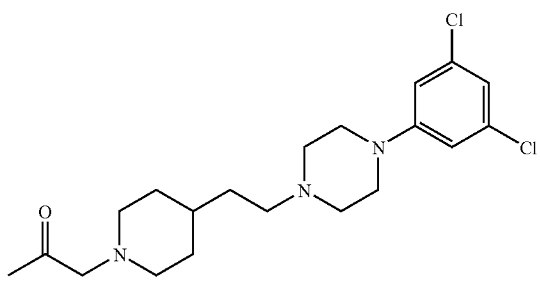 [SMILES: CC(=O)CN1CCC(CCN2CCN(c3cc(Cl)cc(Cl)c3)CC2)CC1] | 1-(4-{2-[4-(3,5-Dichlorophenyl)-piperazin-1-yl]ethyl}piperidin-1-yl)propan-2-one | 126 | IIIB |
| 312 | 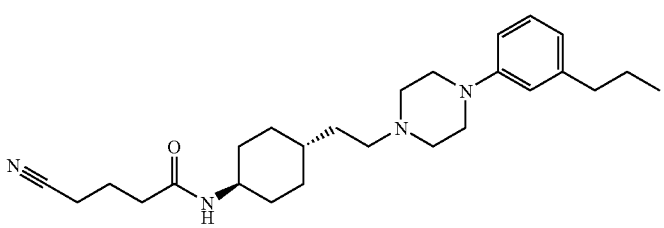 [SMILES: CCCc1cccc(N2CCN(CC[C@H]3CC[C@H](NC(=O)CCCC#N)CC3)CC2)c1] | 4-Cyano-N-(4-{2-[4-(3-propylphenyl)piperazin-1-yl]ethyl}cyclohexyl)butanamide | 142 | IIA |
| 313 | 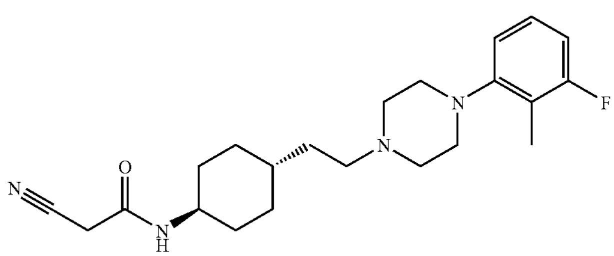 [SMILES: Cc1c(F)cccc1N1CCN(CC[C@H]2CC[C@H](NC(=O)CC#N)CC2)CC1] | 2-Cyano-N-(4-{2-[4-(3-fluoro-2-methylphenyl)piperazin-1-yl]ethyl}cyclohexyl)acetamide | 174 | IIA |
| 314 | 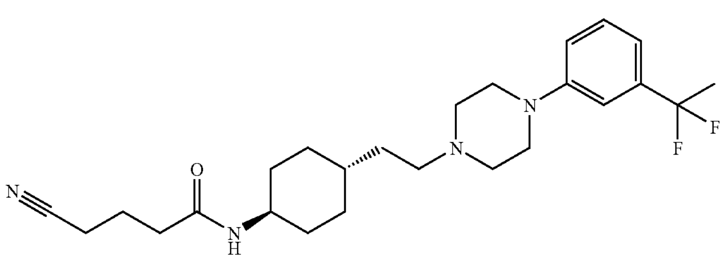 [SMILES: CC(F)(F)c1cccc(N2CCN(CC[C@H]3CC[C@H](NC(=O)CCCC#N)CC3)CC2)c1] | 4-Cyano-N-[4-(2-{4-[3-(1,1-difluoroethyl)phenyl]piperazin-1-yl}ethyl)cyclohexyl]butanamide | 179 | IIA |

-continued

| Ex | Structure | Name | M.P. (°C.) | Synthetic Path |
|---|---|---|---|---|
| 315 | 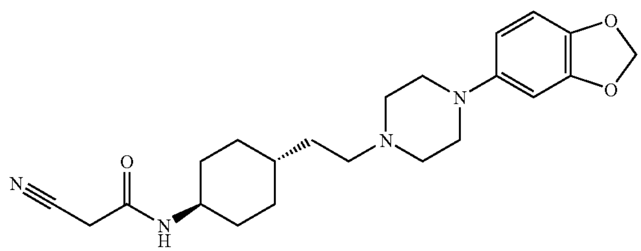 [SMILES: N#CCC(=O)N[C@H]1CC[C@H](CCN2CCN(c3ccc4c(c3)OCO4)CC2)CC1] | N-{4-[2-(4-Benzo[1,3]dioxol-5-ylpiperazin-1-yl)ethyl]cyclohexyl}-2-cyanoacetamide | 226 | IIA |
| 316 | 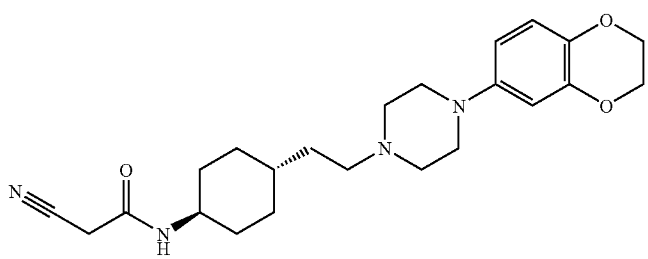 [SMILES: N#CCC(=O)N[C@H]1CC[C@H](CCN2CCN(c3ccc4c(c3)OCCO4)CC2)CC1] | 2-Cyano-N-(4-{2-[4-(2,3-dihydrobenzo[1,4]dioxin-6-yl)piperazin-1-yl]ethyl}cyclohexyl)acetamide | 208 | IIA |
| 317 | 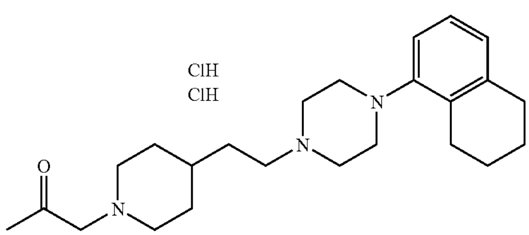 [SMILES: CC(=O)CN1CCC(CCN2CCN(c3cccc4c3CCCC4)CC2)CC1 ; Cl ; Cl] | 1-(4-{2-[4-(5,6,7,8-Tetrahydronaphthalen-1-yl)piperazin-1-yl]piperidin-1-yl)propan-2-one | 320 | IIIB |
| 318 | 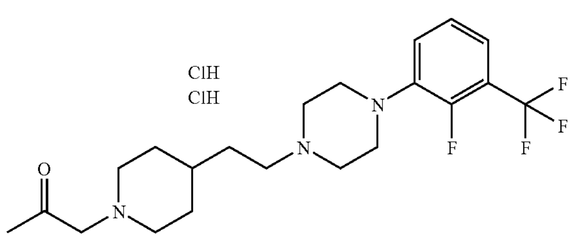 [SMILES: CC(=O)CN1CCC(CCN2CCN(c3cccc(C(F)(F)F)c3F)CC2)CC1 ; Cl ; Cl] | 1-(4-{2-[4-(2-Fluoro-3-trifluoromethylphenyl)piperazin-1-yl]ethyl}piperidin-1-yl)propan-2-one, dihydrochloride | 270 | IIIB |
| 319 | 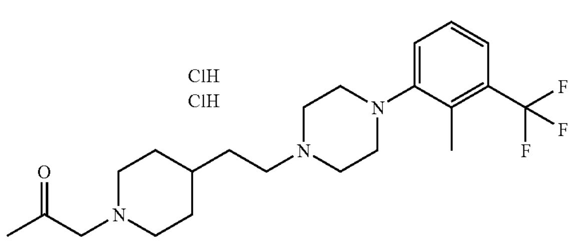 [SMILES: CC(=O)CN1CCC(CCN2CCN(c3cccc(C(F)(F)F)c3C)CC2)CC1 ; Cl ; Cl] | 1-(4-{2-[4-(2-Methyl-3-trifluoromethylphenyl)piperazin-1-yl]ethyl}piperidin-1-yl)propan-2-one, dihydrochloride | 300 | IIIB |
| 320 | 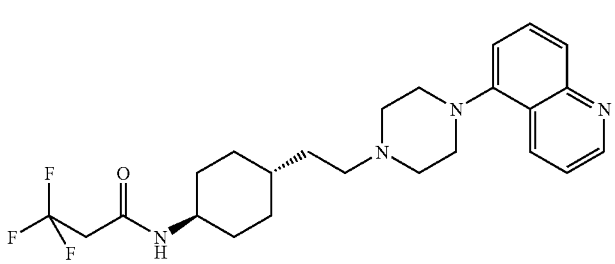 [SMILES: O=C(CC(F)(F)F)N[C@H]1CC[C@H](CCN2CCN(c3cccc4ncccc34)CC2)CC1] | 3,3,3-Trifluoro-N-{4-[2-(4-quinolin-5-ylpiperazin-1-yl)ethyl]cyclohexyl}propanami-de | 207 | IIA |

| Ex | Structure | Name | M.P. (° C.) | Synthetic Path |
|---|---|---|---|---|
| 321 | 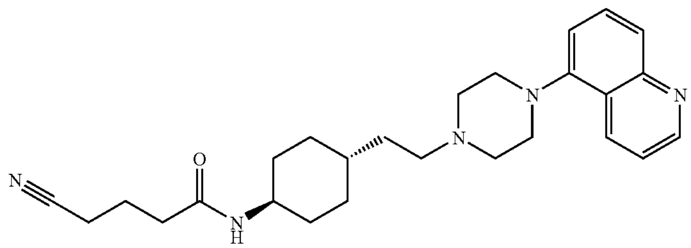 [SMILES: N#CCCCC(=O)N[C@H]1CC[C@H](CCN2CCN(c3cccc4ncccc34)CC2)CC1] | 4-Cyano-N-{4-[2-(4-quinolin-5-ylpiperazin-1-yl)ethyl]cyclohexyl}butanamide | 155 | IIA |
| 322 | 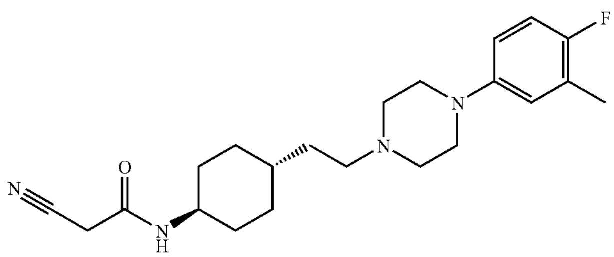 | 2-Cyano-N-(4-{2-[4-(4-fluoro-3-methylphenyl)piperazin-1-yl]ethyl}cyclohexyl)acetamide | 192 | IIA |
| 323 | 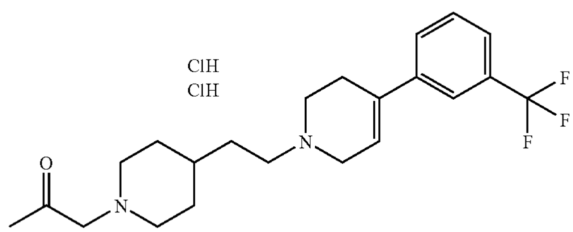 [SMILES: CC(=O)CN1CCC(CCN2CC=C(c3cccc(C(F)(F)F)c3)CC2)CC1 ; Cl ; Cl] | 1-(4-{2-[4-(3-Trifluoromethylphenyl)-3,6-dihydro-2H-pyridin-1-yl]ethyl}piperidin-1-yl)propan-2-one, dihydrochloride | 268 | IIIB |
| 324 | 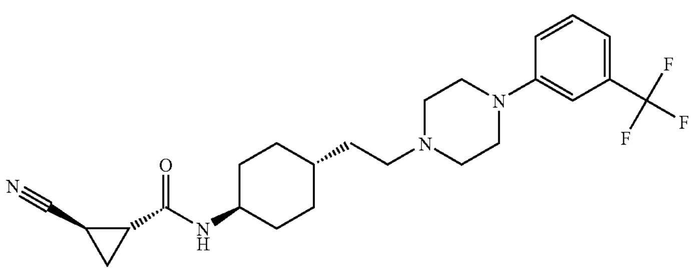 | 2-Cyano-cyclopropanecarboxylic acid (4-{2-[4-(3-trifluoromethylphenyl)piperazin-1-yl]ethyl}cyclohexyl) amide | 159 | IIA |
| 325 | 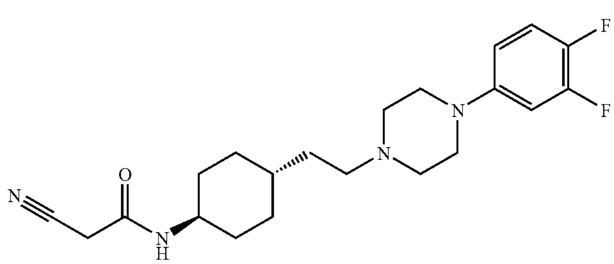 [SMILES: N#CCC(=O)N[C@H]1CC[C@H](CCN2CCN(c3ccc(F)c(F)c3)CC2)CC1] | 2-Cyano-N-(4-{2-[4-(3,4-difluorophenyl)piperazin-1-yl]ethyl}cyclohexyl)acetamide | 197 | IIA |
| 326 | 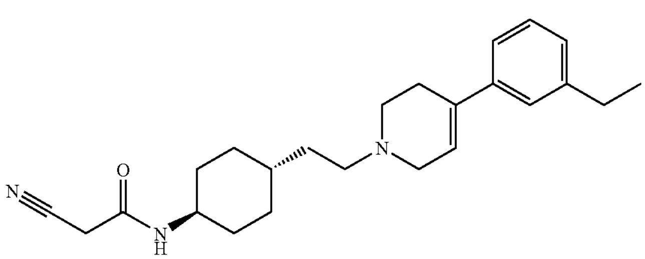 [SMILES: CCc1cccc(C2=CCN(CC[C@H]3CC[C@H](NC(=O)CC#N)CC3)CC2)c1] | 2-Cyano-N-(4-{2-[4-(3-ethylphenyl)-3,6-dihydro-2H-pyridin-1-yl]ethyl}cyclohexyl)-acetamide | 158 | IIA |

-continued

| Ex | Structure | Name | M.P. (° C.) | Synthetic Path |
|---|---|---|---|---|
| 327 | 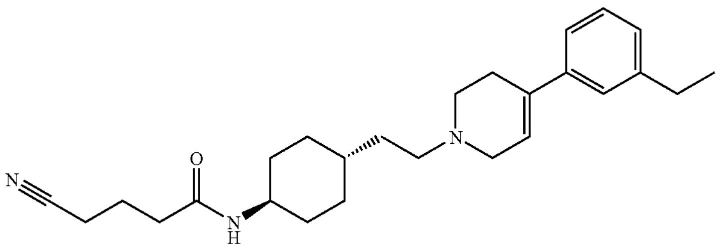 [SMILES: CCc1cccc(C2=CCN(CC[C@H]3CC[C@H](NC(=O)CCCC#N)CC3)CC2)c1] | 4-Cyano-N-(4-{2-[4-(3-ethylphenyl)-3,6-dihydro-2H-pyridin-1-yl]ethyl}cyclohexyl)butanamide | 147 | IIA |
| 328 | 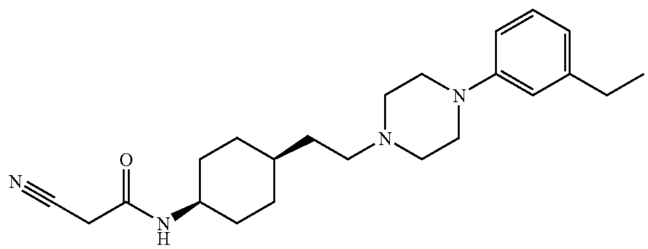 [SMILES: CCc1cccc(N2CCN(CC[C@H]3CC[C@@H](NC(=O)CC#N)CC3)CC2)c1] | 2-Cyano-N-(4-{2-[4-(3-ethylphenyl)piperazin-1-yl]ethyl}cyclohexyl)acetamide | 101 | IIA |
| 329 | 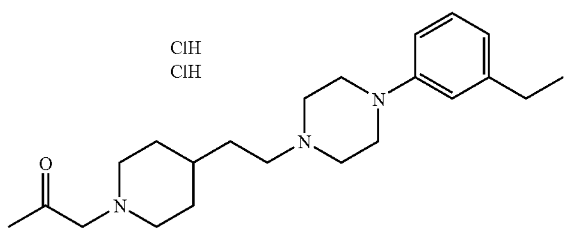 [SMILES: CCc1cccc(N2CCN(CCC3CCN(CC(C)=O)CC3)CC2)c1 ; Cl ; Cl] | 1-(4-{2-[4-(3-Ethylphenyl)-piperazin-1-yl]ethyl}piperidin-1-yl)propan-2-one, dihydrochloride | 266 | IIIB |
| 330 | 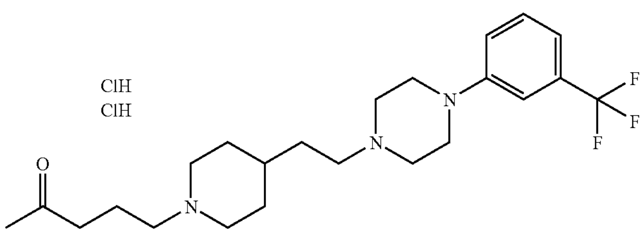 [SMILES: CC(=O)CCCN1CCC(CCN2CCN(c3cccc(C(F)(F)F)c3)CC2)CC1 ; Cl ; Cl] | 5-(4-{2-[4-(3-Trifluoromethyl-phenyl)piperazin-1-yl]ethyl}piperidin-1-yl)pentan-2-one, dihydrochloride | 315 | IIIB |
| 331 | 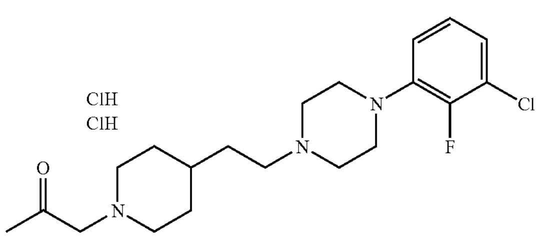 [SMILES: CC(=O)CN1CCC(CCN2CCN(c3cccc(Cl)c3F)CC2)CC1 ; Cl ; Cl] | 1-(4-{2-[4-(3-Chloro-2-fluorophenyl)piperazin-1-yl]ethyl}piperidin-1-yl)propan-2-one, dihydrochloride | 270 | IIIB |
| 332 | 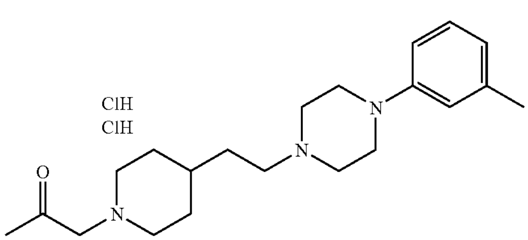 [SMILES: CC(=O)CN1CCC(CCN2CCN(c3cccc(C)c3)CC2)CC1 ; Cl ; Cl] | 1-{4-[2-(4-m-Tolylpiperazin-1-yl)ethyl]piperidin-1-yl}propan-2-one, dihydrochloride | 260 | IIIB |

-continued

| Ex | Structure | Name | M.P. (° C.) | Synthetic Path |
|---|---|---|---|---|
| 333 | ClH ClH | 1-(4-{2-[4-(3-Fluoro-2-methylphenyl)piperazin-1-yl]ethyl}piperidin-1-yl)propan-2-one, dihydrochloride | 317 | IIIB |
| 334 | 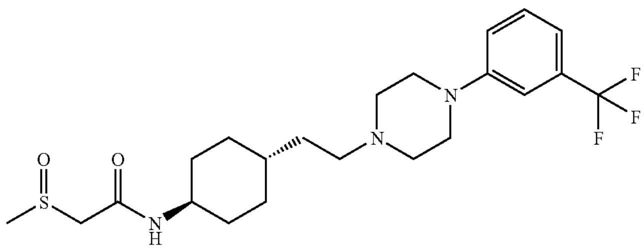 [SMILES: CS(=O)CC(=O)N[C@H]1CC[C@H](CCN2CCN(c3cccc(C(F)(F)F)c3)CC2)CC1] | 2-Methanesulfinyl-N-(4-{2-[4-(3-trifluoromethylphenyl)piperazin-1-yl]ethyl}cyclohexyl)acetamide | 153 | IIA |
| 335 | 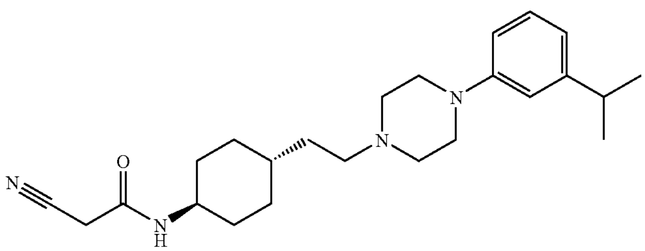 [SMILES: CC(C)c1cccc(N2CCN(CC[C@H]3CC[C@H](NC(=O)CC#N)CC3)CC2)c1] | 2-Cyano-N-(4-{2-[4-(3-isopropylphenyl)piperazin-1-yl]ethyl}cyclohexyl)acetamide | 153 | IIA |
| 336 | 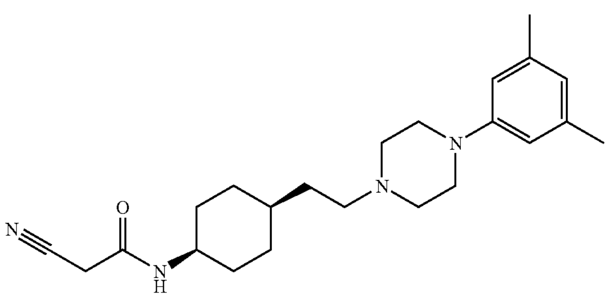 [SMILES: Cc1cc(C)cc(N2CCN(CC[C@H]3CC[C@@H](NC(=O)CC#N)CC3)CC2)c1] | 2-Cyano-N-(4-{2-[4-(3,5-dimethylphenyl)piperazin-1-yl]ethyl}cyclohexyl)acetamide | 119 | IIA |
| 337 | 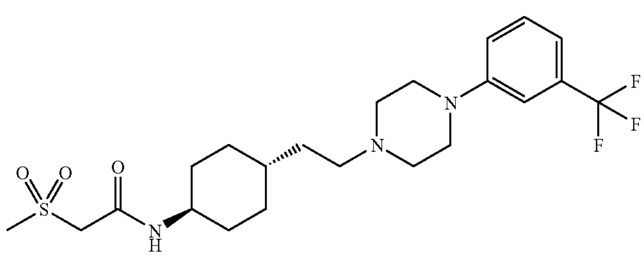 [SMILES: CS(=O)(=O)CC(=O)N[C@H]1CC[C@H](CCN2CCN(c3cccc(C(F)(F)F)c3)CC2)CC1] | 2-Methanesulfonyl-N-(4-{2-[4-(3-trifluoromethylphenyl)piperazin-1-yl]ethyl}cyclohexyl)acetamide | 158 | IIA |
| 338 | ClH ClH | 1-{4-[2-(4-Quinolin-8-ylpiperazin-1-yl)ethyl[piperidin-1-yl}propan-2-one, dihydrochloride | 270 | IIIB |

-continued

| Ex | Structure | Name | M.P. (° C.) | Synthetic Path |
|---|---|---|---|---|
| 339 | 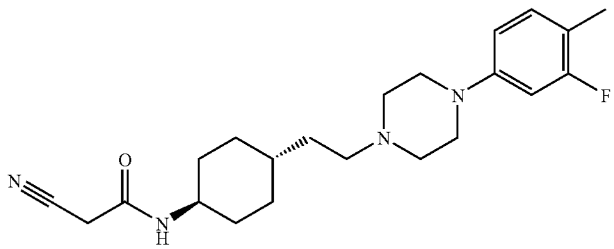 [SMILES: Cc1ccc(N2CCN(CC[C@H]3CC[C@H](NC(=O)CC#N)CC3)CC2)cc1F] | 2-Cyano-N-(4-{2-[4-(3-fluoro-4-methylphenyl)piperazin-1-yl]ethyl}cyclohexyl)acetamide | 208 | IIA |
| 340 | 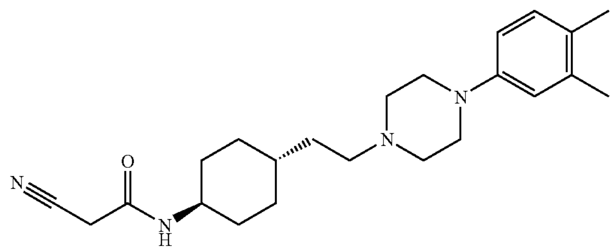 [SMILES: Cc1ccc(N2CCN(CC[C@H]3CC[C@H](NC(=O)CC#N)CC3)CC2)cc1C] | 2-Cyano-N-(4-{2-[4-(3,4-dimethylphenyl)piperazin-1-yl]ethyl}cyclohexyl)acetamide | 210 | IIA |
| 341 | 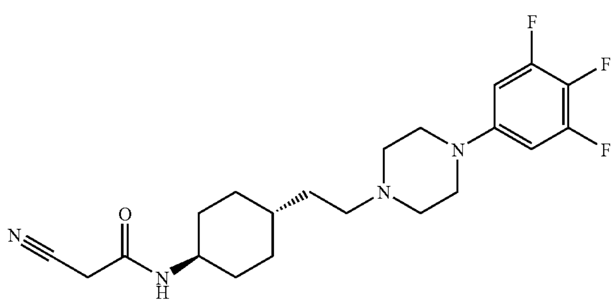 [SMILES: N#CCC(=O)N[C@H]1CC[C@H](CCN2CCN(c3cc(F)c(F)c(F)c3)CC2)CC1] | 2-Cyano-N-(4-{2-[4-(3,4,5-trifluorophenyl)piperazin-1-yl]ethyl}cyclohexyl)acetamide | 209 | IIA |
| 342 | 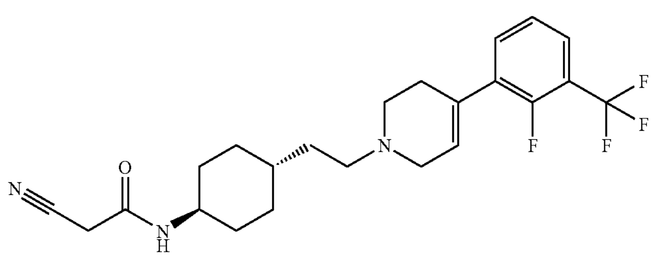 [SMILES: N#CCC(=O)N[C@H]1CC[C@H](CCN2CC=C(c3cccc(C(F)(F)F)c3F)CC2)CC1] | 2-Cyano-N-(4-{2-[4-(2-fluoro-3-trifluoromethylphenyl)-3,6-dihydro-2H-pyridin-1-yl]ethyl}cyclohexyl)acetamide | 171 | IIA |
| 343 | 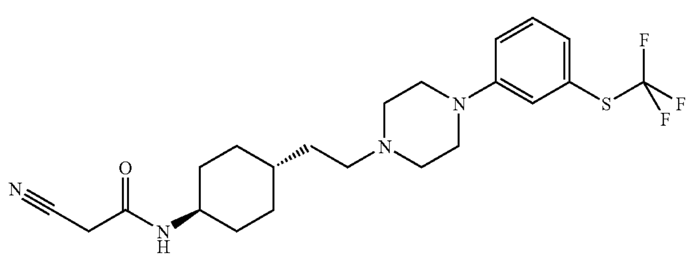 [SMILES: N#CCC(=O)N[C@H]1CC[C@H](CCN2CCN(c3cccc(SC(F)(F)F)c3)CC2)CC1] | 2-Cyano-N-(4-{2-[4-(3-trifluoromethylsulfanylphenyl)piperazin-1-yl]ethyl}cyclohexyl)-acetamide | 165 | IIA |

| Ex | Structure | Name | M.P. (° C.) | Synthetic Path |
|---|---|---|---|---|
| 344 | 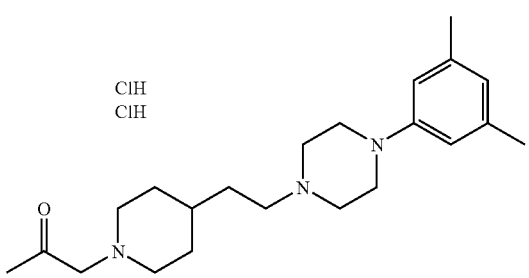 [SMILES: CC(=O)CN1CCC(CCN2CCN(c3cc(C)cc(C)c3)CC2)CC1 ; Cl ; Cl] | 1-(4-{2-[4-(3,5-Dimethylphenyl)piperazin-1-yl]ethyl}piperidin-1-yl)propan-2-one, dihydrochloride | 275 | IIIB |
| 345 | 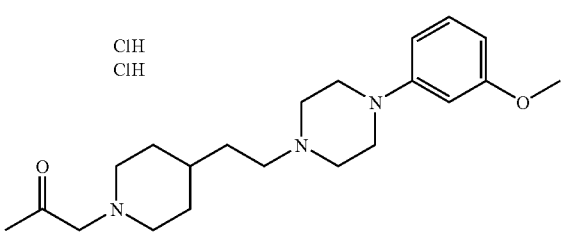 [SMILES: COc1cccc(N2CCN(CCC3CCN(CC(C)=O)CC3)CC2)c1 ; Cl ; Cl] | 1-(4-{2-[4-(3-Methoxyphenyl)piperazin-1-yl]ethyl}piperidin-1-yl)propan-2-one, dihydrochloride | 265 | IIIB |
| 346 | 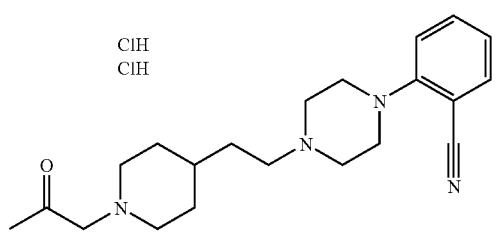 [SMILES: CC(=O)CN1CCC(CCN2CCN(c3ccccc3C#N)CC2)CC1 ; Cl ; Cl] | 2-(4-{2-[1-(2-Oxopropyl)piperidin-4-yl]ethyl}piperazin-1-yl)benzonitrile, dihydrochloride | 290 | IIIB |
| 347 | 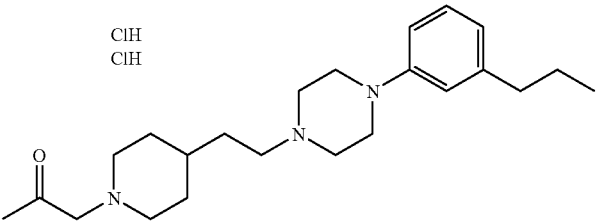 [SMILES: CCCc1cccc(N2CCN(CCC3CCN(CC(C)=O)CC3)CC2)c1 ; Cl ; Cl] | 1-(4-{2-[4-(3-Propylphenyl)-piperazin-1-yl]ethyl}piperidin-1-yl)propan-2-one, dihydrochloride | 256 | IIIB |
| 348 | 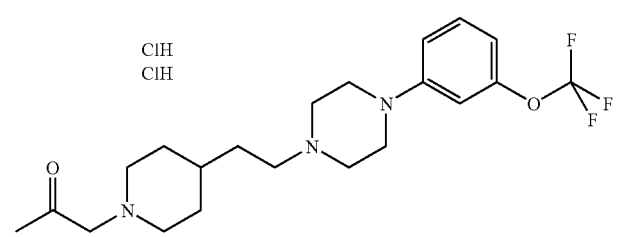 [SMILES: CC(=O)CN1CCC(CCN2CCN(c3cccc(OC(F)(F)F)c3)CC2)CC1 ; Cl ; Cl] | 1-(4-{2-[4-(3-Trifluoromethoxy-phenyl)piperazin-1-yl]ethyl}piperidin-1-yl)propan-2-one, dihydrochloride | 275 | IIIB |
| 349 | 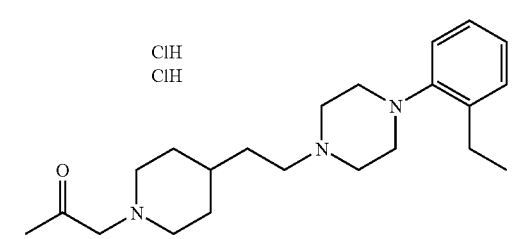 [SMILES: CCc1ccccc1N1CCN(CCC2CCN(CC(C)=O)CC2)CC1 ; Cl ; Cl] | 1-(4-{2-[4-(2-Ethylphenyl)-piperazin-1-yl]ethyl}piperidin-1-yl)propan-2-one, dihydrochloride | 291 | IIIB |

-continued

| Ex | Structure | Name | M.P. (° C.) | Synthetic Path |
|---|---|---|---|---|
| 350 | 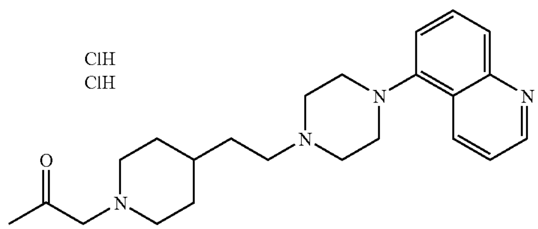 [SMILES: CC(=O)CN1CCC(CCN2CCN(c3cccc4ncccc34)CC2)CC1 ; Cl ; Cl] | 1-{4-[2-(4-Quinolin-5-ylpiperazin-1-yl)ethyl]piperidin-1-yl}propan-2-one, dihydrochloride | 295 | IIIB |
| 351 | 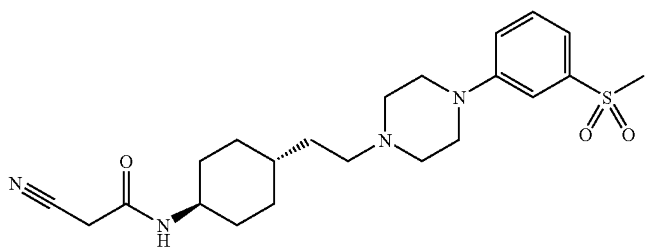 [SMILES: CS(=O)(=O)c1cccc(N2CCN(CC[C@H]3CC[C@H](NC(=O)CC#N)CC3)CC2)c1] | 2-Cyano-N-(4-{2-[4-(3-methanesulfonylphenyl)piperazin-1-yl]ethyl}cyclohexyl)acetamide | 195 | IIA |
| 352 | 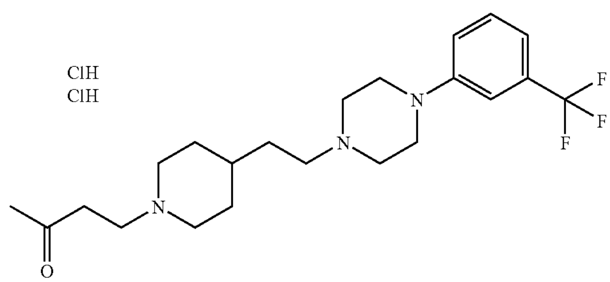 [SMILES: CC(=O)CCN1CCC(CCN2CCN(c3cccc(C(F)(F)F)c3)CC2)CC1 ; Cl ; Cl] | 4-(4-{2-[4-(3-Trifluoromethyl-phenyl)piperazin-1-yl]ethyl}piperidin-1-yl)butan-2-one, dihydrochloride | | IIIB |
| 353 | 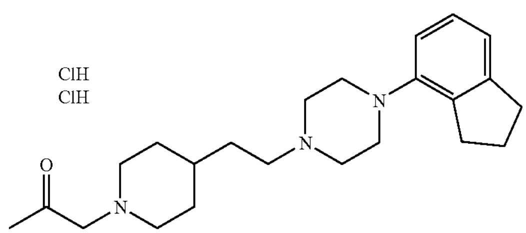 [SMILES: CC(=O)CN1CCC(CCN2CCN(c3cccc4c3CCC4)CC2)CC1 ; Cl ; Cl] | 1-{4-[2-(4-Indan-4-ylpiperazin-1-yl)ethyl]piperidin-1-yl}propan-2-one, dihydrochloride | 295 | IIIB |
| 354 | 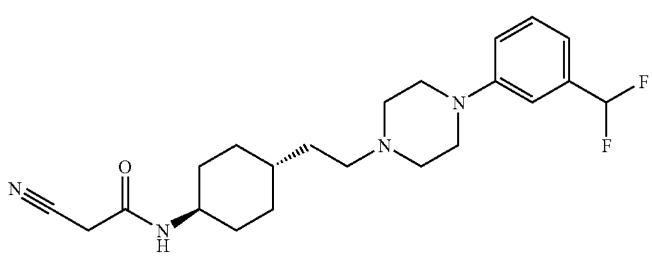 [SMILES: N#CCC(=O)N[C@H]1CC[C@H](CCN2CCN(c3cccc(C(F)F)c3)CC2)CC1] | 2-Cyano-N-(4-{2-[4-(3-difluoromethylphenyl)piperazin-1-yl]ethyl}cyclohexyl)acetamide | 185 | IIA |
| 355 | 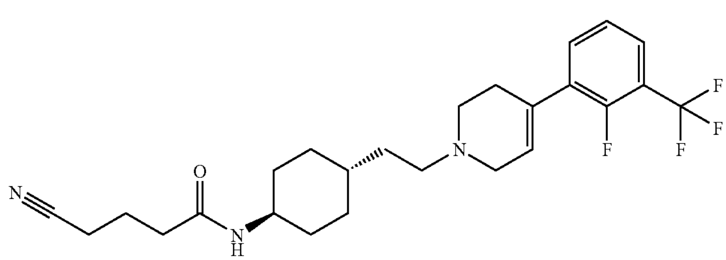 [SMILES: N#CCCCC(=O)N[C@H]1CC[C@H](CCN2CC=C(c3cccc(C(F)(F)F)c3F)CC2)CC1] | 4-Cyano-N-(4-{2-[4-(2-Fluoro-3-trifluoromethylphenyl)-3,6-dihydro-2H-pyridin-1-yl]ethyl}cyclohexyl)butanamide | 130 | IIA |

| Ex | Structure | Name | M.P. (° C.) | Synthetic Path |
|---|---|---|---|---|
| 356 | 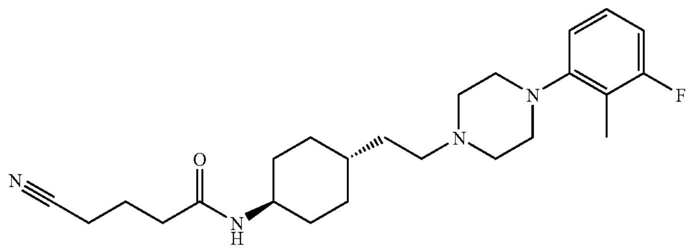 [SMILES: Cc1c(F)cccc1N1CCN(CC[C@H]2CC[C@H](NC(=O)CCCC#N)CC2)CC1] | 4-Cyano-N-(4-{2-[4-(3-fluoro-2-methylphenyl)piperazin-1-yl]ethyl}cyclohexyl)butanamide | 159 | IIA |
| 357 | 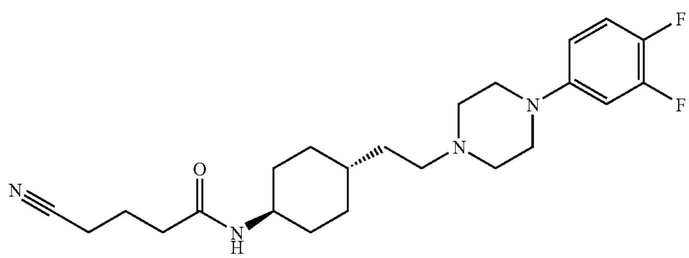 [SMILES: N#CCCCC(=O)N[C@H]1CC[C@H](CCN2CCN(c3ccc(F)c(F)c3)CC2)CC1] | 4-Cyano-N-(4-{2-[4-(3,4-difluorophenyl)piperazin-1-yl]ethyl}cyclohexyl)butanamide | 141 | IIA |
| 358 | 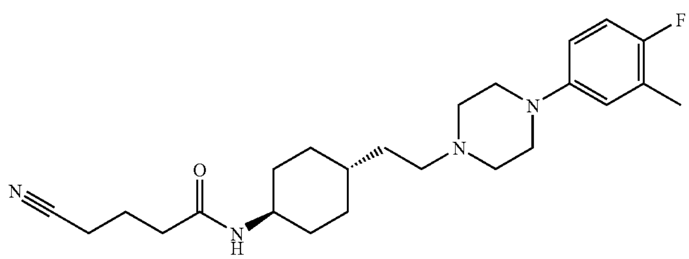 [SMILES: Cc1cc(N2CCN(CC[C@H]3CC[C@H](NC(=O)CCCC#N)CC3)CC2)ccc1F] | 4-Cyano-N-(4-{2-[4-(4-fluoro-3-methylphenyl)piperazin-1-yl]ethyl}cyclohexylbutanamide | 160 | IIA |
| 359 | 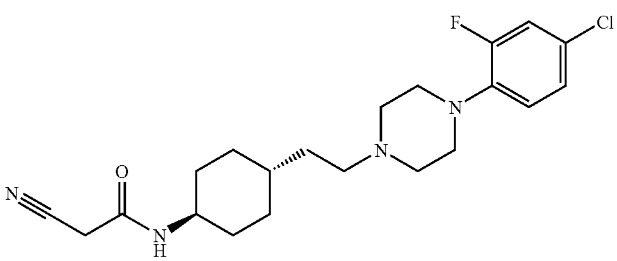 [SMILES: N#CCC(=O)N[C@H]1CC[C@H](CCN2CCN(c3ccc(Cl)cc3F)CC2)CC1] | N-(4-{2-[4-(4-Chloro-2-fluorophenyl)piperazin-1-yl]ethyl}cyclohexyl)-2-cyanoacetamide | 218 | IIA |
| 360 | 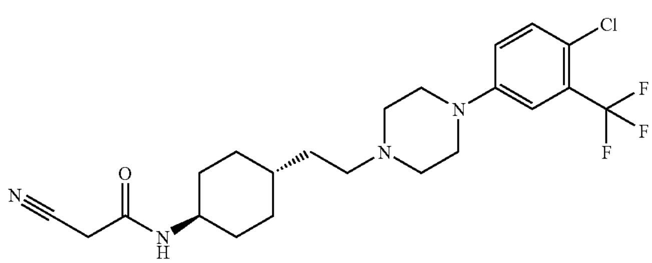 [SMILES: N#CCC(=O)N[C@H]1CC[C@H](CCN2CCN(c3ccc(Cl)c(C(F)(F)F)c3)CC2)CC1] | N-(4-{2-[4-(4-Chloro-3-trifluoromethylphenyl)piperazin-1-yl]ethyl}cyclohexyl)-2-cyanoacetamide | 187 | IIA |

-continued

| Ex | Structure | Name | M.P. (° C.) | Synthetic Path |
|---|---|---|---|---|
| 361 | 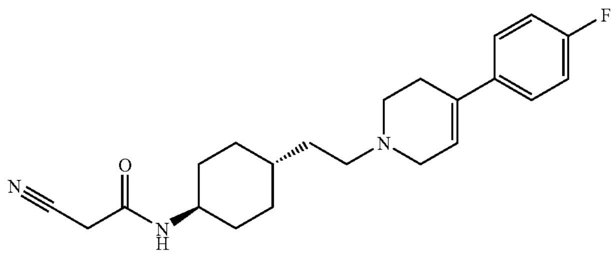 [SMILES: N#CCC(=O)N[C@H]1CC[C@H](CCN2CC=C(c3ccc(F)cc3)CC2)CC1] | 2-Cyano-N-(4-{2-[4-(4-fluorophenyl)-3,6-dihydro-2H-pyridin-1-yl]ethyl}cyclohexyl)-acetamide | 202 | IIA |
| 362 | 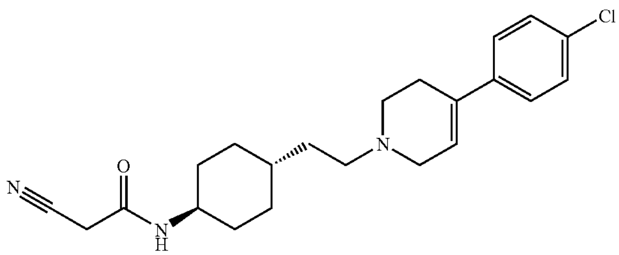 [SMILES: N#CCC(=O)N[C@H]1CC[C@H](CCN2CC=C(c3ccc(Cl)cc3)CC2)CC1] | N-(4-{2-[4-(4-Chlorophenyl)-3,6-dihydro-2H-pyridin-1-yl]ethyl}cyclohexyl)-2-cyanoacetamide | 220 | IIA |
| 363 | 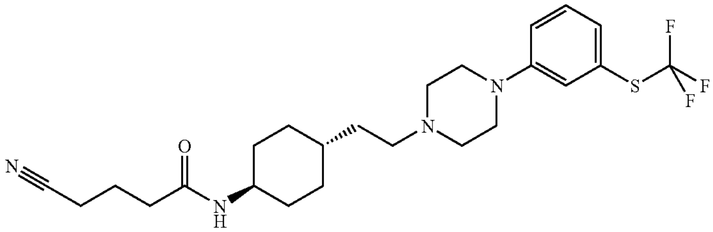 [SMILES: N#CCCCC(=O)N[C@H]1CC[C@H](CCN2CCN(c3cccc(SC(F)(F)F)c3)CC2)CC1] | 4-Cyano-N-(4-{2-[4-(3-trifluoromethylsulfanylphenyl)piperazin-1-yl]ethyl}cyclohexyl)butanamide | 150 | IIA |
| 364 | 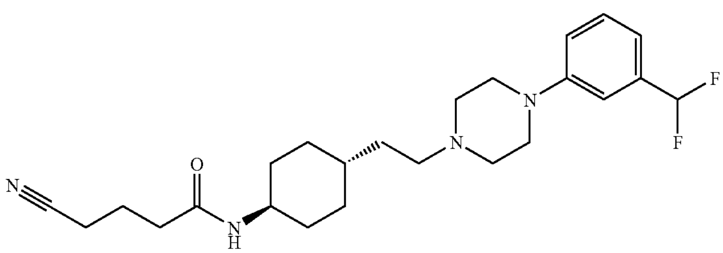 [SMILES: N#CCCCC(=O)N[C@H]1CC[C@H](CCN2CCN(c3cccc(C(F)F)c3)CC2)CC1] | 4-Cyano-N-(4-{2-[4-(3-difluoromethylphenyl)piperazin-1-yl]ethyl}cyclohexyl)butanamide | 155 | IIA |
| 365 | 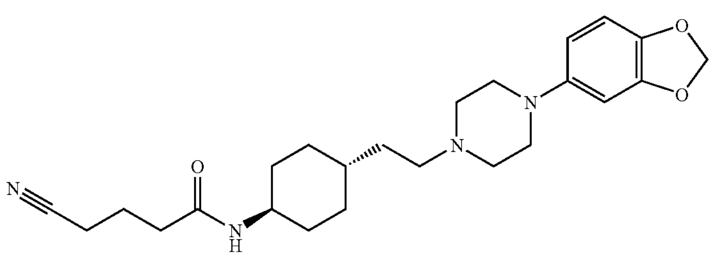 [SMILES: N#CCCCC(=O)N[C@H]1CC[C@H](CCN2CCN(c3ccc4c(c3)OCO4)CC2)CC1] | N-{4-[2-(4-Benzo[1,3]dioxol-5-ylpiperazin-1-yl)ethyl]cyclohexyl}-4-cyanobutanamide | 189 | IIA |
| 366 | 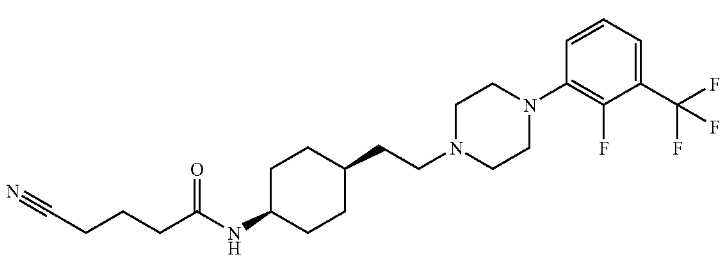 [SMILES: N#CCCCC(=O)N[C@H]1CC[C@@H](CCN2CCN(c3cccc(C(F)(F)F)c3F)CC2)CC1] | 4-Cyano-N-(4-{2-[4-(2-fluoro-3-trifluoromethylphenyl)piperazin-1-yl]ethyl}cyclohexyl)butanamide | 95 | IIA |

-continued

| Ex | Structure | Name | M.P. (° C.) | Synthetic Path |
|---|---|---|---|---|
| 367 | 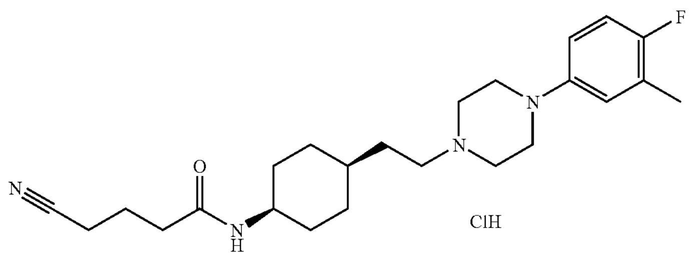 [SMILES: Cc1cc(N2CCN(CC[C@H]3CC[C@@H](NC(=O)CCCC#N)CC3)CC2)ccc1F ; Cl] | 4-Cyano-N-(4-{2-[4-(4-fluoro-3-methylphenyl)piperazin-1-yl]ethyl}cyclohexyl)butanamide, hydrochloride | | IIIB |
| 368 | 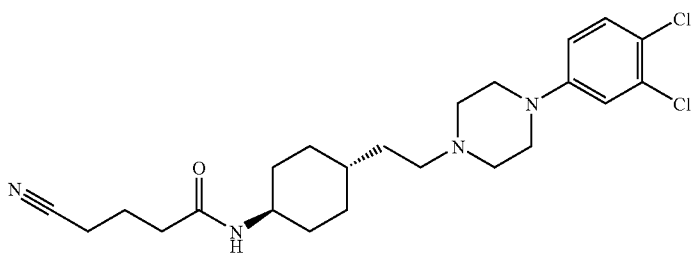 [SMILES: N#CCCCC(=O)N[C@H]1CC[C@H](CCN2CCN(c3ccc(Cl)c(Cl)c3)CC2)CC1] | 4-Cyano-N-(4-{2-[4-(3,4-dichlorophenyl)piperazin-1-yl]ethyl}cyclohexyl)butanamide | 151 | IIA |
| 369 | 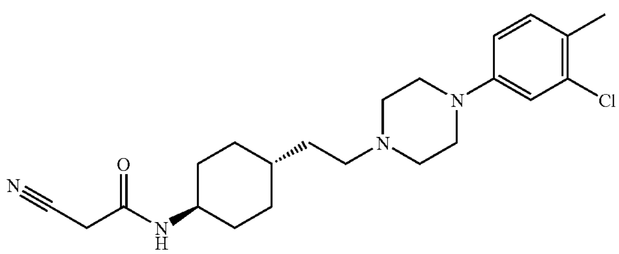 [SMILES: Cc1ccc(N2CCN(CC[C@H]3CC[C@H](NC(=O)CC#N)CC3)CC2)cc1Cl] | N-(4-{2-[4-(3-Chloro-4-methylphenyl)piperazin-1-yl]ethyl}cyclohexyl)-2-cyanoacetamide | 220 | IIA |
| 370 | 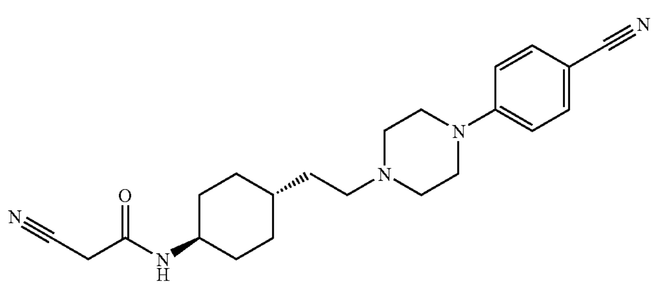 [SMILES: N#CCC(=O)N[C@H]1CC[C@H](CCN2CCN(c3ccc(C#N)cc3)CC2)CC1] | 2-Cyano-N-(4-{2-[4-(4-cyanophenyl)piperazin-1-yl]ethyl}cyclohexyl)acetamide | 228 | IIA |
| 371 | 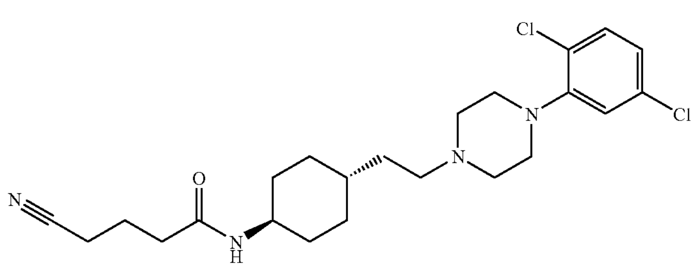 | 4-Cyano-N-(4-{2-[4-(2,5-dichlorophenyl)piperazin-1-yl]ethyl}cyclohexyl)butanamide | 179 | IIA |

-continued

| Ex | Structure | Name | M.P. (° C.) | Synthetic Path |
|---|---|---|---|---|
| 372 | 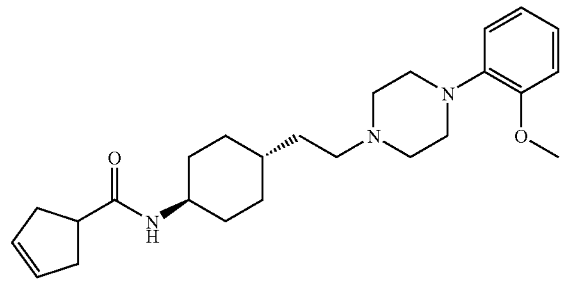 [SMILES: COc1ccccc1N1CCN(CC[C@H]2CC[C@H](NC(=O)C3CC=CC3)CC2)CC1] | Cyclopent-3-enecarboxylic acid (4-{2-[4-(2-methoxyphenyl)piperazin-1-yl]ethyl}cyclohexyl) amide | 202 | IIA |
| 373 | 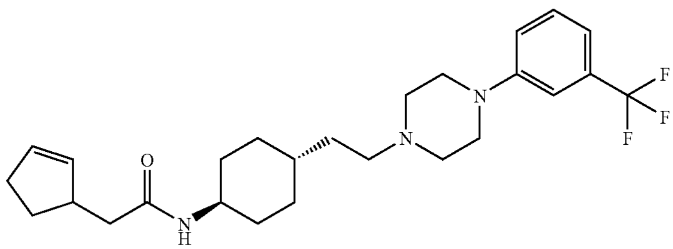 [SMILES: O=C(CC1C=CCC1)N[C@H]1CC[C@H](CCN2CCN(c3cccc(C(F)(F)F)c3)CC2)CC1] | 2-Cyclopent-2-enyl-N-(4-{2-[4-(3-trifluoromethylphenyl)piperazin-1-yl]ethyl}cyclohexyl)acetamide | 154 | IIA |
| 374 | 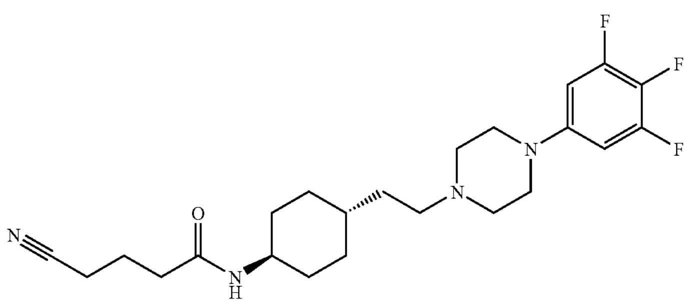 [SMILES: N#CCCCC(=O)N[C@H]1CC[C@H](CCN2CCN(c3cc(F)c(F)c(F)c3)CC2)CC1] | 4-Cyano-N-(4-{2-[4-(3,4,5-trifluorophenyl)piperazin-1-yl]ethyl}cyclohexyl)butanamide | 156 | IIA |
| 375 | 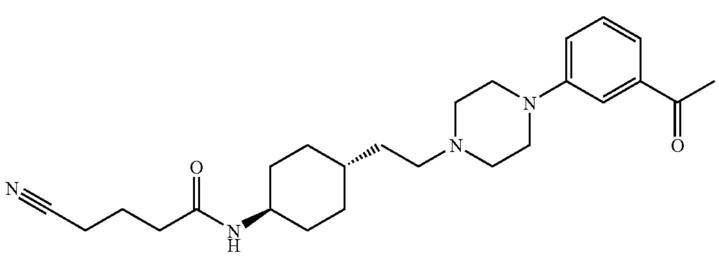 [SMILES: CC(=O)c1cccc(N2CCN(CC[C@H]3CC[C@H](NC(=O)CCCC#N)CC3)CC2)c1] | N-(4-{2-[4-(3-Acetylphenyl)-piperazin-1-yl]ethylcyclohexyl)-4-cyanobutanamide | 181 | IIA |
| 376 | 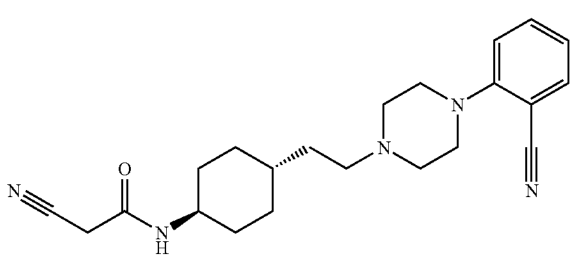 [SMILES: N#CCC(=O)N[C@H]1CC[C@H](CCN2CCN(c3ccccc3C#N)CC2)CC1] | 2-Cyano-N-(4-{2-[4-(2-cyanophenyl)piperazin-1-yl]ethyl}cyclohexyl)acetamide | 190 | IIA |

-continued

| Ex | Structure | Name | M.P. (° C.) | Synthetic Path |
|---|---|---|---|---|
| 377 | 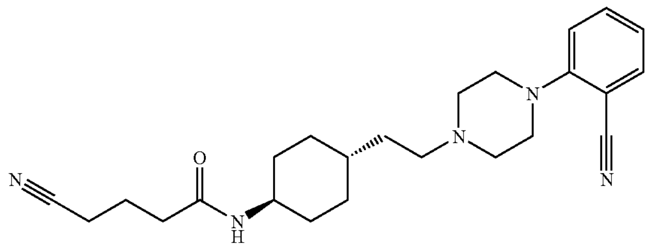 [SMILES: N#CCCCC(=O)N[C@H]1CC[C@H](CCN2CCN(c3ccccc3C#N)CC2)CC1] | 4-Cyano-N-(4-{2-[4-(2-cyanophenyl)piperazin-1-yl]ethyl}cyclohexyl)butanamide | 160 | IIA |
| 378 | 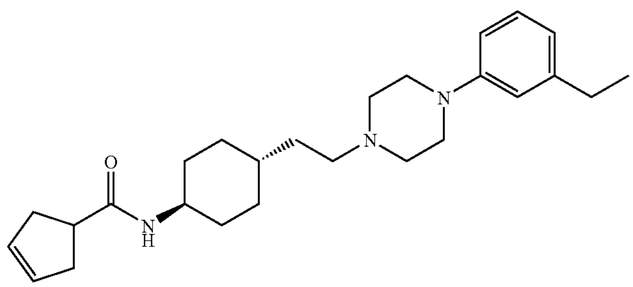 [SMILES: CCc1cccc(N2CCN(CC[C@H]3CC[C@H](NC(=O)C4CC=CC4)CC3)CC2)c1] | Cyclopent-3-enecarboxylic acid (4-{2-[4-(3-ethylphenyl)piperazin-1-yl]ethyl}cyclohexyl) amide | 185 | IIA |
| 379 | 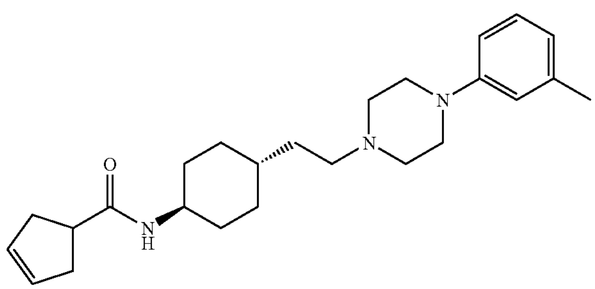 [SMILES: Cc1cccc(N2CCN(CC[C@H]3CC[C@H](NC(=O)C4CC=CC4)CC3)CC2)c1] | Cyclopent-3-enecarboxylic acid {4-[2-(4-m-tolylpiperazin-1-yl)ethyl]cyclohexyl} | 200 | IIA |
| 380 | 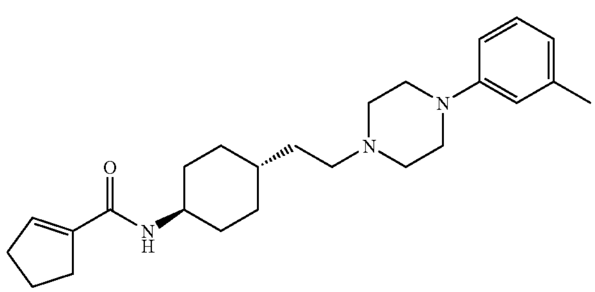 [SMILES: Cc1cccc(N2CCN(CC[C@H]3CC[C@H](NC(=O)C4=CCCC4)CC3)CC2)c1] | Cyclopent-1-enecarboxylic acid {4-[2-(4-m-tolylpiperazin-1-yl)ethyl]cyclohexyl} amide | 188 | IIA |
| 381 | 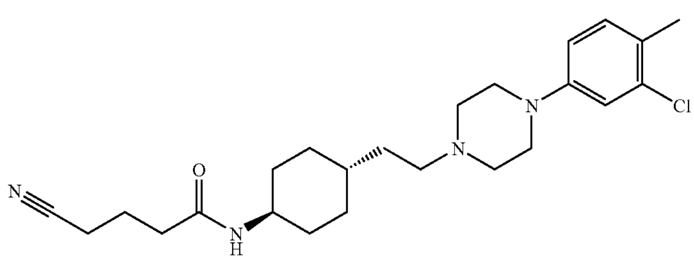 [SMILES: Cc1ccc(N2CCN(CC[C@H]3CC[C@H](NC(=O)CCCC#N)CC3)CC2)cc1Cl] | N-(4-{2-[4-(3-Chloro-4-methylphenyl)piperazin-1-yl]ethyl}cyclohexyl)-4-cyanobutanamide | 168 | IIA |

| Ex | Structure | Name | M.P. (° C.) | Synthetic Path |
|---|---|---|---|---|
| 382 | 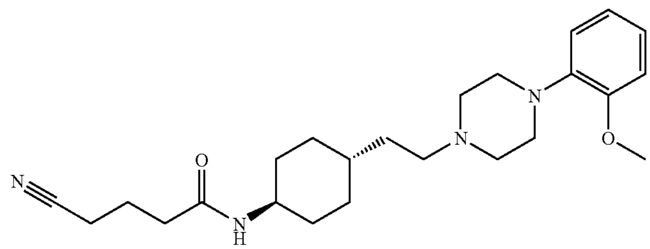 | 4-Cyano-N-(4-{2-[4-(2-methoxyphenyl)piperazin-1-yl]ethyl}cyclohexyl)butanamide | 147 | IIA |
| 383 | 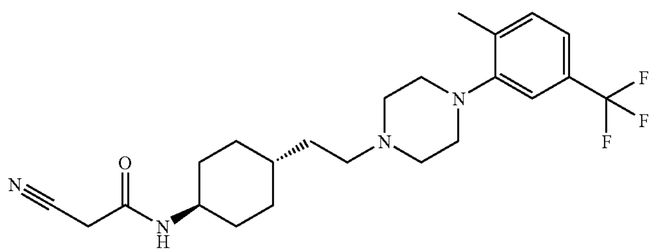 [SMILES: Cc1ccc(C(F)(F)F)cc1N1CCN(CC[C@H]2CC[C@H](NC(=O)CC#N)CC2)CC1] | 2-Cyano-N-(4-{2-[4-(2-methyl-5-trifluoromethylphenyl)piperazin-1-yl]ethyl}cyclohexyl)acetamide | 192 | IIA |
| 384 | 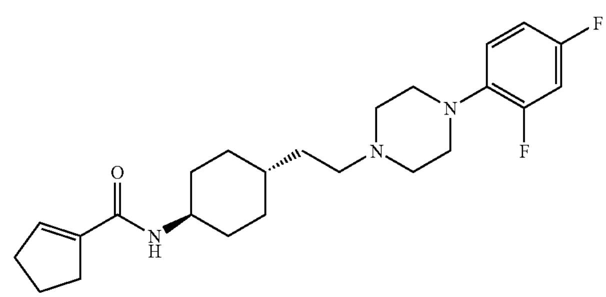 [SMILES: O=C(N[C@H]1CC[C@H](CCN2CCN(c3ccc(F)cc3F)CC2)CC1)C1=CCCC1] | Cyclopent-1-enecarboxylic acid (4-{2-[4-(2,4-difluorphenyl)-piperazin-1-yl]ethyl}cyclohexyl)amide | 205 | IIA |
| 385 | 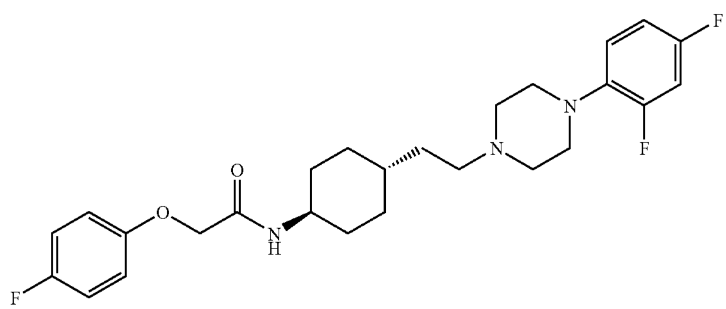 [SMILES: O=C(COc1ccc(F)cc1)N[C@H]1CC[C@H](CCN2CCN(c3ccc(F)cc3F)CC2)CC1] | N-(4-{2-[4-(2,4-Difluorophenyl)piperazin-1-yl]ethyl}cyclohexyl)-2-(4-fluorophenoxy)acetamide | 162 | IIA |
| 386 | 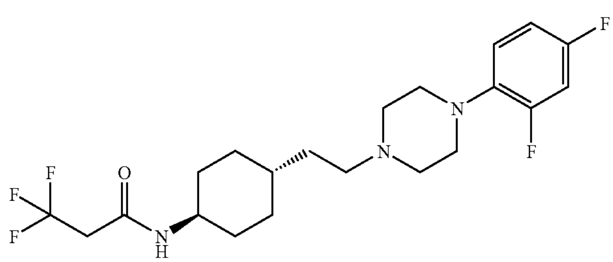 [SMILES: O=C(CC(F)(F)F)N[C@H]1CC[C@H](CCN2CCN(c3ccc(F)cc3F)CC2)CC1] | N-(4-{2-[4-(2,4-Difluorophenyl)piperazin-1-yl]ethyl}cyclohexyl)-3,3,3-trifluoropropanamide | 184 | IIA |

| Ex | Structure | Name | M.P. (° C.) | Synthetic Path |
|---|---|---|---|---|
| 387 | 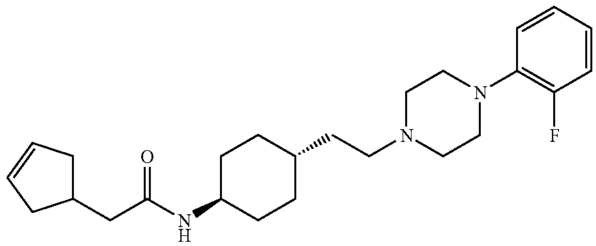 [SMILES: O=C(CC1CC=CC1)N[C@H]1CC[C@H](CCN2CCN(c3ccccc3F)CC2)CC1] | 2-Cyclopent-3-enyl-N-(4-{2-[4-(2-fluorophenyl)piperazin-1-yl]ethyl}cyclohexyl)acetamide | 188 | IIA |
| 388 | 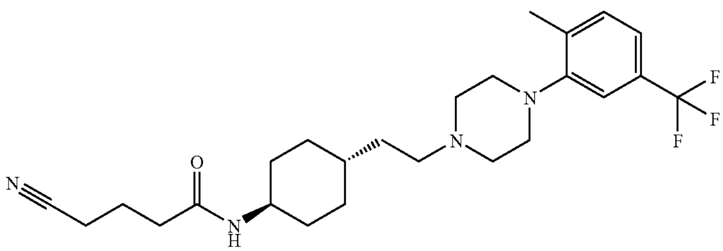 [SMILES: Cc1ccc(C(F)(F)F)cc1N1CCN(CC[C@H]2CC[C@H](NC(=O)CCCC#N)CC2)CC1] | 4-Cyano-N-(4-{2-[4-(2-methyl-5-trifluoromethylphenyl)piperazin-1-yl]ethyl}cyclohexyl)butyramide | 153 | IIA |
| 389 | 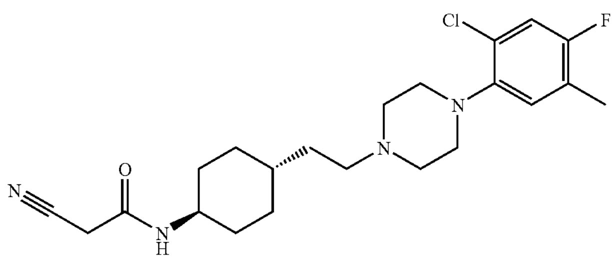 | N-(4-{2-[4-(2-Chloro-4-fluoro-5-methylphenyl)piperazin-1-yl]ethyl}cyclohexyl)-2-cyanoacetamide | 177 | IIA |
| 390 | 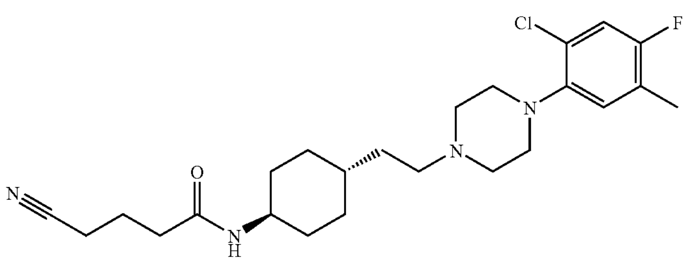 | N-(4-{2-[4-(2-Chloro-4-fluoro-5-methylphenyl)piperazin-1-yl]ethyl}cyclohexyl)-4-cyanobutanamide | 158 | IIA |
| 391 | 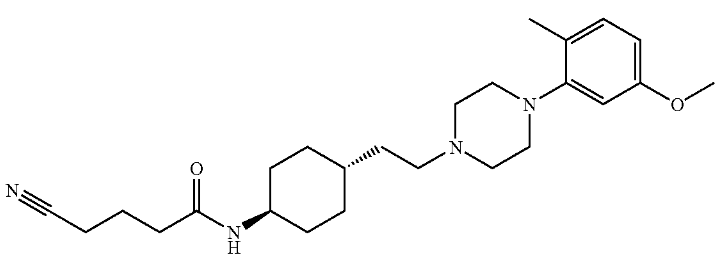 [SMILES: COc1ccc(C)c(N2CCN(CC[C@H]3CC[C@H](NC(=O)CCCC#N)CC3)CC2)c1] | 4-Cyano-N-(4-{2-[4-(5-methoxy-2-methylphenyl)piperazin-1-yl]ethyl}cyclohexyl)butanamide | 170 | IIA |

| Ex | Structure | Name | M.P. (° C.) | Synthetic Path |
|---|---|---|---|---|
| 392 | 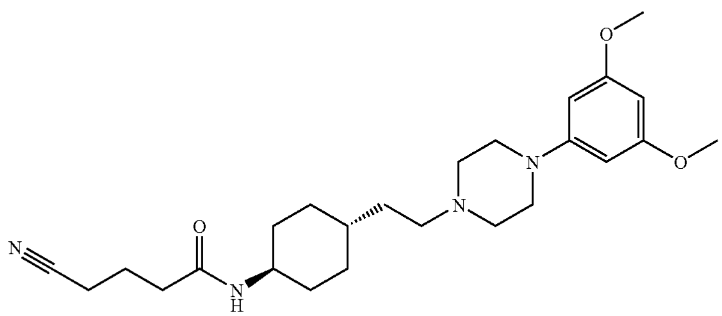 [SMILES: COc1cc(OC)cc(N2CCN(CC[C@H]3CC[C@H](NC(=O)CCCC#N)CC3)CC2)c1] | 4-Cyano-N-(4-{2-[4-(3,5-dimethoxyphenyl)piperazin-1-yl]ethyl}cyclohexyl)butanamide | 147 | IIA |
| 393 | 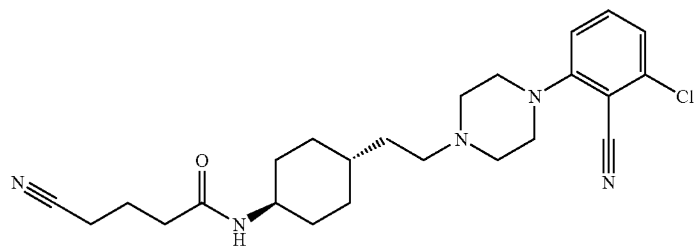 [SMILES: N#CCCCC(=O)N[C@H]1CC[C@H](CCN2CCN(c3cccc(Cl)c3C#N)CC2)CC1] | N-(4-{2-[4-(3-Chloro-2-cyanophenyl)piperazin-1-yl]ethyl}cyclohexyl)-4-cyanobutanamide | 189 | IIA |
| 394 | 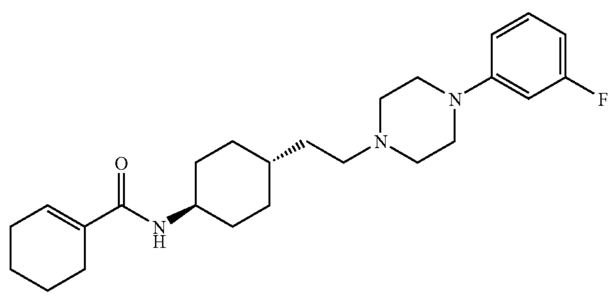 [SMILES: O=C(N[C@H]1CC[C@H](CCN2CCN(c3cccc(F)c3)CC2)CC1)C1=CCCCC1] | Cyclohex-1-enecarboxylic acid (4-{2-[4-(3-fluorophenyl)-piperazin-1-yl]ethyl}cyclohexylamide | 195 | IIA |
| 395 | 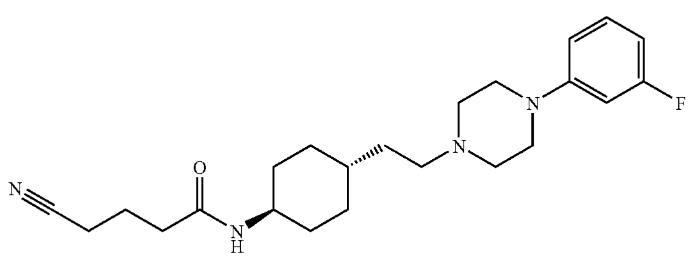 [SMILES: N#CCCCC(=O)N[C@H]1CC[C@H](CCN2CCN(c3cccc(F)c3)CC2)CC1] | 4-Cyano-N-(4-{2-[4-(3-fluorophenyl)piperazin-1-yl]ethyl}cyclohexyl)butanamide | 170 | IIA |
| 396 | 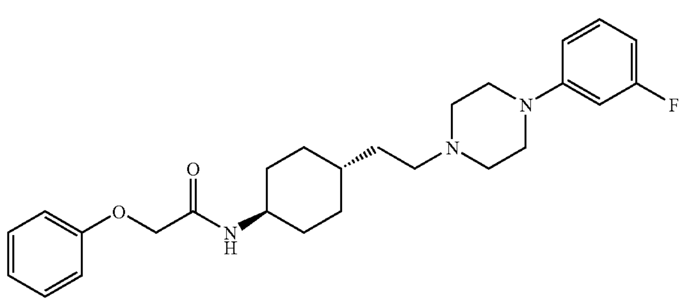 [SMILES: O=C(COc1ccccc1)N[C@H]1CC[C@H](CCN2CCN(c3cccc(F)c3)CC2)CC1] | N-(4-{2-[4-(3-Fluorophenyl)piperazin-1-yl]ethyl}cyclohexyl)-2-phenoxyacetamide | 150 | IIA |

-continued

| Ex | Structure | Name | M.P. (° C.) | Synthetic Path |
|---|---|---|---|---|
| 397 | 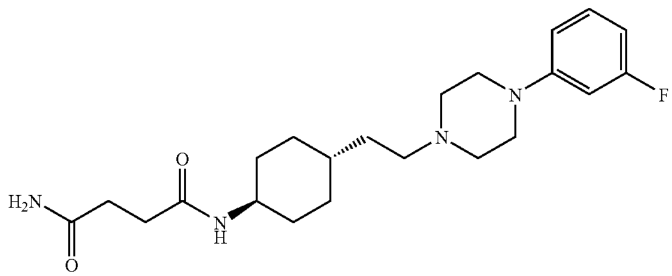 [SMILES: NC(=O)CCC(=O)N[C@H]1CC[C@H](CCN2CCN(c3cccc(F)c3)CC2)CC1] | N-(4-{2-[4-(3-Fluorophenyl)-piperazin-1-yl]ethyl}cyclohexyl)-succinamide | 255 | IIA |
| 398 | 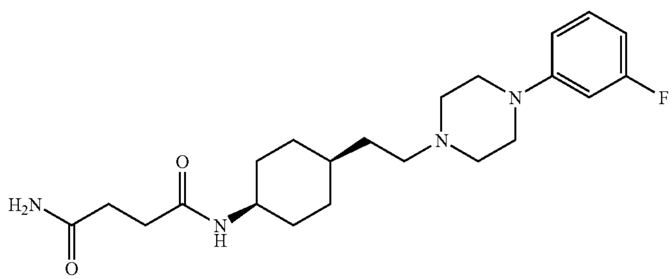 [SMILES: NC(=O)CCC(=O)N[C@H]1CC[C@@H](CCN2CCN(c3cccc(F)c3)CC2)CC1] | N-(4-{2-[4-(3-Fluorophenyl)-piperazin-1-yl]ethyl}cyclohexyl)-succinamide | 169 | IIA |
| 399 | 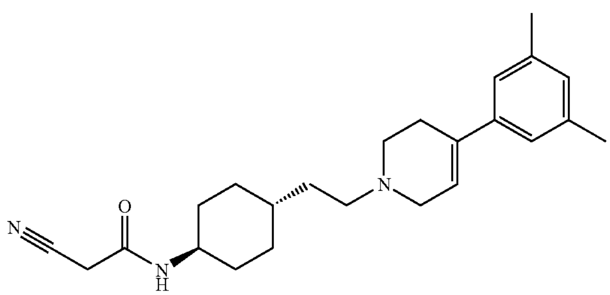 [SMILES: Cc1cc(C)cc(C2=CCN(CC[C@H]3CC[C@H](NC(=O)CC#N)CC3)CC2)c1] | 2-Cyano-N-(4-{2-[4-(3,5-dimethylphenyl)-3,6-dihydro-2H-pyridin-1-yl]ethyl}cyclohexyl)-acetamide | 182 | IIA |
| 400 | 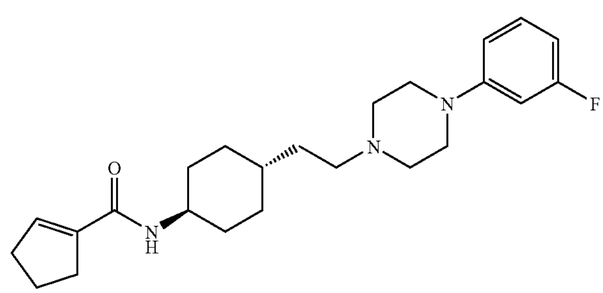 [SMILES: O=C(N[C@H]1CC[C@H](CCN2CCN(c3cccc(F)c3)CC2)CC1)C1=CCCC1] | Cyclopent-1-enecarboxylic acid (4-{2-[4-(3-fluorophenyl)-piperazin-1-yl]ethyl}cyclohexyl) amide | 202 | IIA |
| 401 | 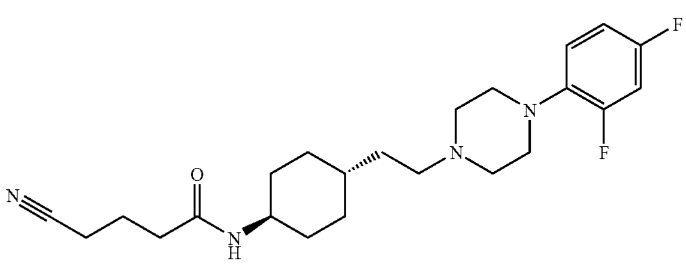 | 4-Cyano-N-(4-{2-[4-(2,4-difluorophenyl)piperazin-1-yl]ethyl}cyclohexyl)butanamide | 167 | IIA |

-continued

| Ex | Structure | Name | M.P. (° C.) | Synthetic Path |
|---|---|---|---|---|
| 402 | 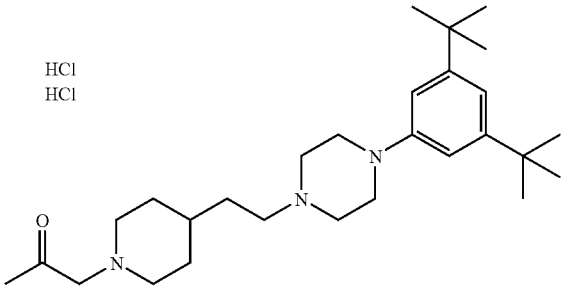 [SMILES: CC(=O)CN1CCC(CCN2CCN(c3cc(C(C)(C)C)cc(C(C)(C)C)c3)CC2)CC1 ; Cl ; Cl] | 1-(4-{2-[4-(3,5-Di-tert-butylphenyl)piperazin-1-yl]ethyl}piperidin-1-yl)propan-2-one | 308 | IIIB |
| 403 | 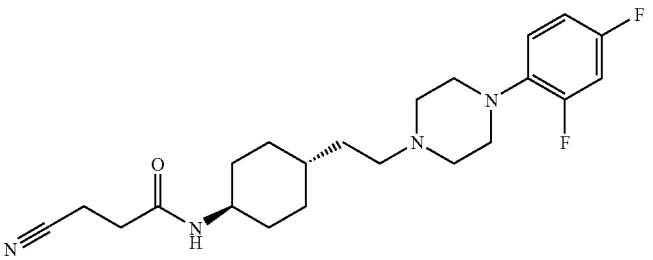 [SMILES: N#CCCC(=O)N[C@H]1CC[C@H](CCN2CCN(c3ccc(F)cc3F)CC2)CC1] | 3-Cyano-N-(4-{2-[4-(2,4-difluorophenyl)piperazin-1-yl]ethyl}cyclohexyl)propanamide | 165 | IIA |
| 404 | 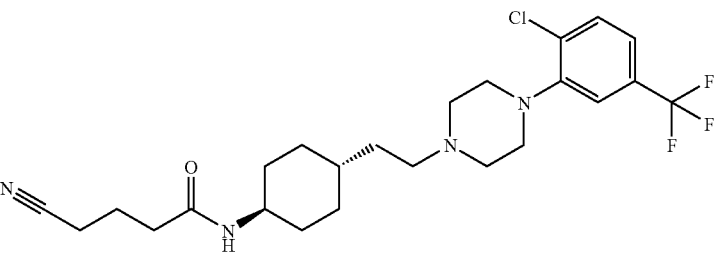 | N-(4-{2-[4-(2-Chloro-5-trifluoromethylphenyl)piperazin-1-yl]ethyl}cyclohexyl)-4-cyanobutanamide | 168 | IIA |
| 405 | 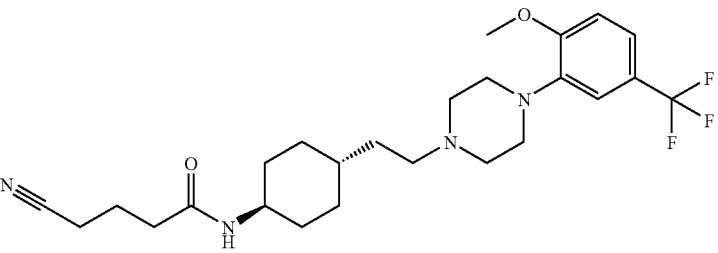 [SMILES: COc1ccc(C(F)(F)F)cc1N1CCN(CC[C@H]2CC[C@H](NC(=O)CCCC#N)CC2)CC1] | 4-Cyano-N-(4-{2-[4-(2-methoxy-5-trifluoromethylphenyl)piperazin-1-yl]ethyl}cyclohexyl)butanamide | 136 | IIA |
| 406 | 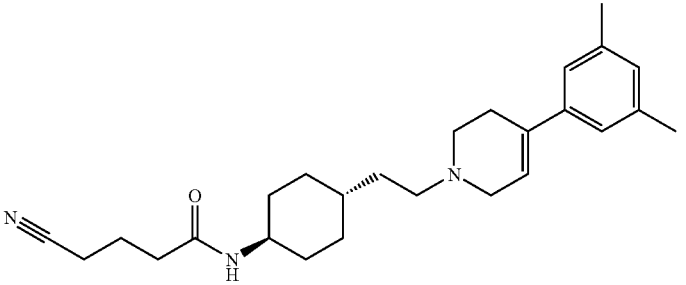 [SMILES: Cc1cc(C)cc(C2=CCN(CC[C@H]3CC[C@H](NC(=O)CCCC#N)CC3)CC2)c1] | 4-Cyano-N-(4-{2-[4-(3,5-dimethylphenyl)-3,6-dihydro-2H-pyridin-1-yl]ethyl}cyclohexyl)-butanamide | 166 | IIA |

-continued

| Ex | Structure | Name | M.P. (° C.) | Synthetic Path |
|---|---|---|---|---|
| 407 | 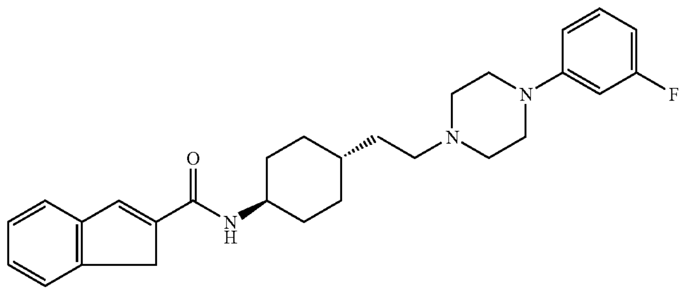 [SMILES: O=C(N[C@H]1CC[C@H](CCN2CCN(c3cccc(F)c3)CC2)CC1)C1=Cc2ccccc2C1] | 1H-Indene-2-carboxylic acid (4-{2-[4-(3-fluorophenyl)piperazin-1-yl]ethyl}cyclohexyl) amide | 242 | IIA |
| 408 | 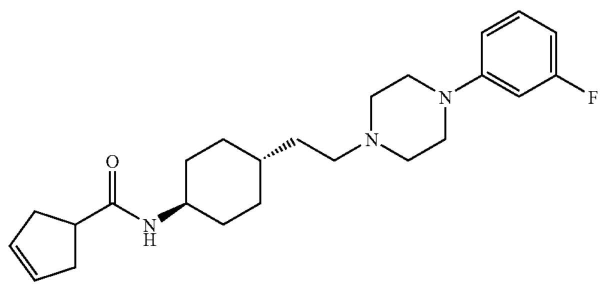 [SMILES: O=C(N[C@H]1CC[C@H](CCN2CCN(c3cccc(F)c3)CC2)CC1)C1CC=CC1] | Cyclopent-3-enecarboxylic acid (4-{2-[4-(3-fluorophenyl)-piperazin-1-yl]ethyl}cyclohexyl) amide | 215 | IIA |
| 409 | 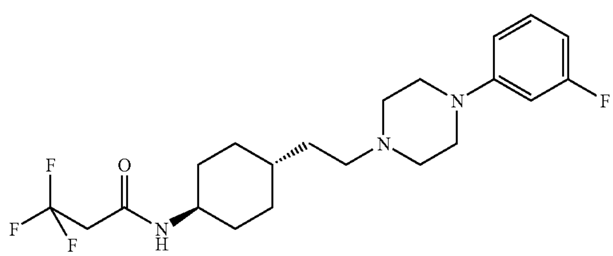 [SMILES: O=C(CC(F)(F)F)N[C@H]1CC[C@H](CCN2CCN(c3cccc(F)c3)CC2)CC1] | 3,3,3-Trifluoro-N-(4-{2-[4-(3-fluorophenyl)piperazin-1-yl]ethyl}cyclohexyl)propanamide | 195 | IIA |
| 410 | 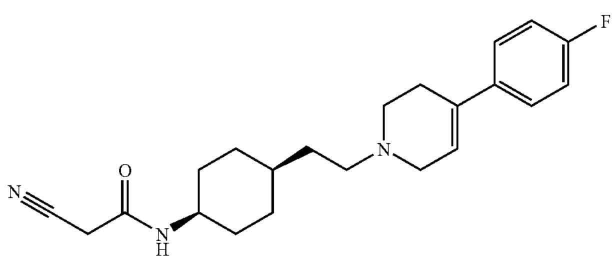 [SMILES: N#CCC(=O)N[C@H]1CC[C@@H](CCN2CC=C(c3ccc(F)cc3)CC2)CC1] | 2-Cyano-N-(4-{2-[4-(4-fluorophenyl)-3,6-dihydro-2H-pyridin-1-yl]ethyl}cyclohexyl)-acetamide | 147 | IIA |
| 411 | 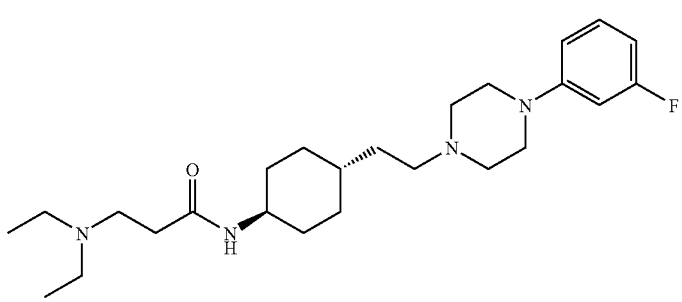 [SMILES: CCN(CC)CCC(=O)N[C@H]1CC[C@H](CCN2CCN(c3cccc(F)c3)CC2)CC1] | 3-Diethylamino-N-(4-{2-[4-(3-fluorophenyl)piperazin-1-yl]ethyl}cyclohexyl)propanamide | 118 | IIA |

-continued

| Ex | Structure | Name | M.P. (° C.) | Synthetic Path |
|---|---|---|---|---|
| 412 | 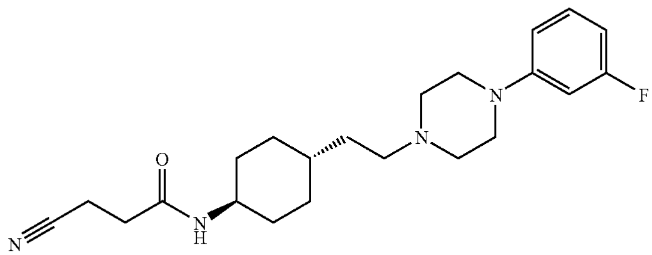 | 3-Cyano-N-(4-{2-[4-(3-fluorophenyl)piperazin-1-yl]ethyl}cyclohexyl)propanamide | 186 | IIA |
| 413 | 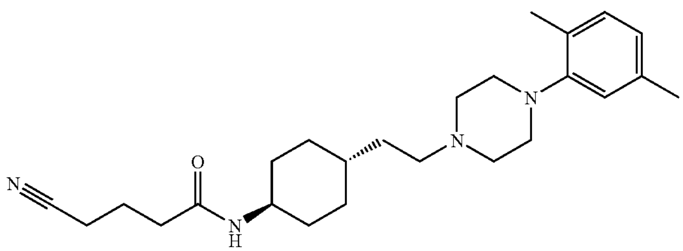 [SMILES: Cc1ccc(C)c(N2CCN(CC[C@H]3CC[C@H](NC(=O)CCCC#N)CC3)CC2)c1] | 4-Cyano-N-(4-{2-[4-(2,5-dimethylphenyl)piperazin-1-yl]ethyl}cyclohexyl)butanamide | 158 | IIA |
| 414 | 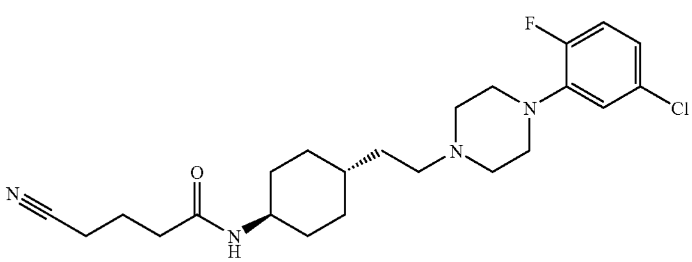 [SMILES: N#CCCCC(=O)N[C@H]1CC[C@H](CCN2CCN(c3cc(Cl)ccc3F)CC2)CC1] | N-(4-{2-[4-(5-Chloro-2-fluorophenyl)piperazin-1-yl]ethyl}cyclohexyl)-4-cyanobutanamide | 165 | IIA |
| 415 | 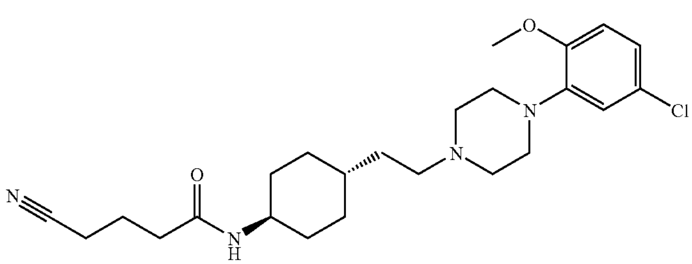 [SMILES: COc1ccc(Cl)cc1N1CCN(CC[C@H]2CC[C@H](NC(=O)CCCC#N)CC2)CC1] | N-(4-{2-[4-(5-Chloro-2-methoxyphenyl)piperazin-1-yl]ethyl}cyclohexyl)-4-cyanobutanamide | 152 | IIA |
| 416 | 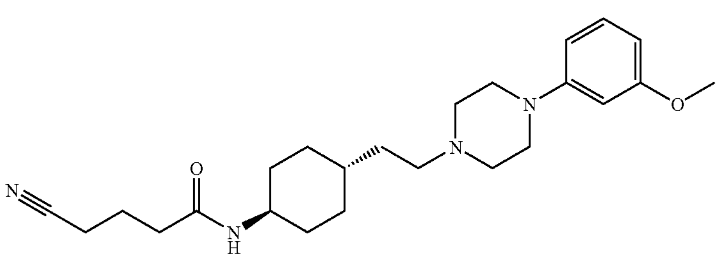 | 4-Cyano-N-(4-{2-[4-(3-methoxyphenyl)piperazin-1-yl]ethyl}cyclohexyl)butanamide | 145 | IIA |

-continued

| Ex | Structure | Name | M.P. (° C.) | Synthetic Path |
|---|---|---|---|---|
| 417 | 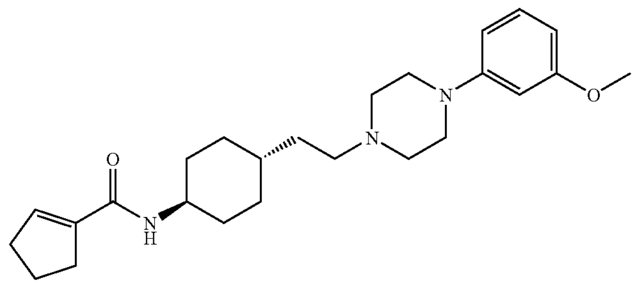 [SMILES: COc1cccc(N2CCN(CC[C@H]3CC[C@H](NC(=O)C4=CCCC4)CC3)CC2)c1] | Cyclopent-1-enecarboxylic acid (4-{2-[4-(3-methoxyphenyl)-piperazin-1-yl]ethyl}cyclohexyl)amide | 160 | IIA |
| 418 | 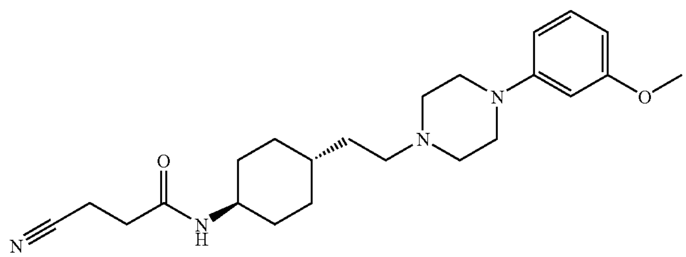 | 3-Cyano-N-(4-{2-[4-(3-methoxyphenyl)piperazin-1-yl]ethyl}cyclohexyl)propanamide | 140 | IIA |
| 419 | 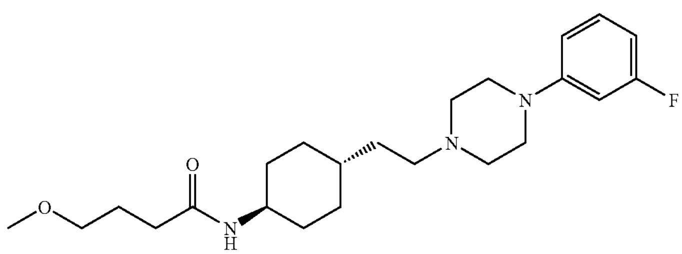 [SMILES: COCCCC(=O)N[C@H]1CC[C@H](CCN2CCN(c3cccc(F)c3)CC2)CC1] | N-(4-{2-[4-(3-Fluorophenyl)piperazin-1-yl]ethyl}cyclohexyl)-4-methoxybutanamide | 165 | IIA |
| 420 | 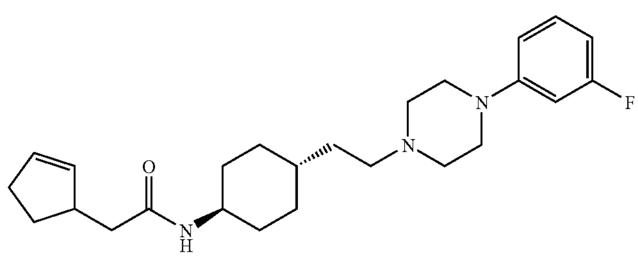 [SMILES: O=C(CC1C=CCC1)N[C@H]1CC[C@H](CCN2CCN(c3cccc(F)c3)CC2)CC1] | 2-Cyclopent-2-enyl-N-(4-{2-[4-(3-fluorophenyl)piperazin-1-yl]ethyl}cyclohexyl)acetamide | 188 | IIA |
| 421 | 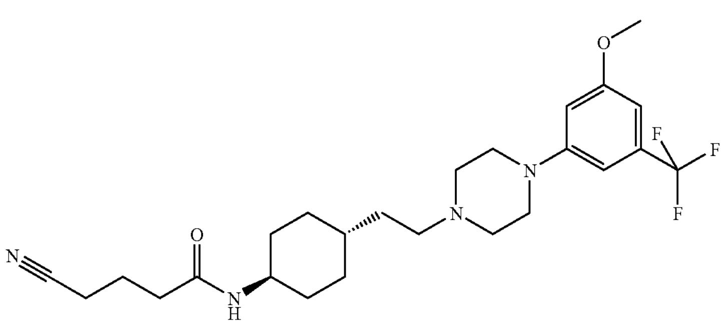 [SMILES: COc1cc(N2CCN(CC[C@H]3CC[C@H](NC(=O)CCCC#N)CC3)CC2)cc(C(F)(F)F)c1] | 4-Cyano-N-(4-{2-[4-(3-methoxy-5-trifluoromethylphenyl)piperazin-1-yl]ethyl}cyclohexyl)butanamide | 147 | IIA |

-continued

| Ex | Structure | Name | M.P. (° C.) | Synthetic Path |
|---|---|---|---|---|
| 422 | 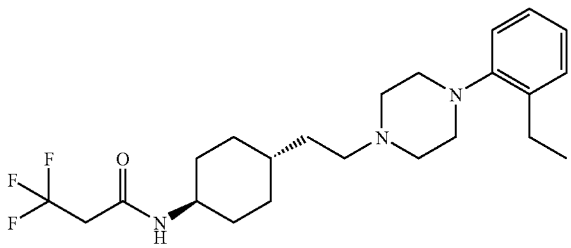 [SMILES: CCc1ccccc1N1CCN(CC[C@H]2CC[C@H](NC(=O)CC(F)(F)F)CC2)CC1] | N-(4-{2-[4-(2-Ethylphenyl)piperazin-1-yl]ethyl}cyclohexyl)-3,3,3-trifluoropropanamide | 135 | IIA |
| 423 | 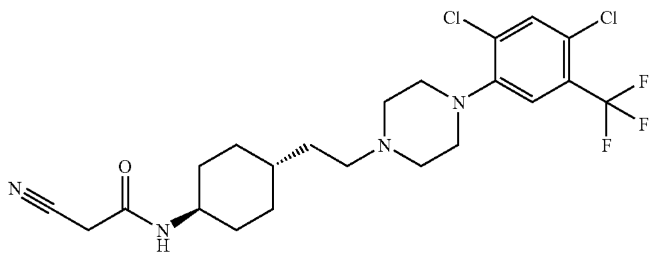 [SMILES: N#CCC(=O)N[C@H]1CC[C@H](CCN2CCN(c3cc(C(F)(F)F)c(Cl)cc3Cl)CC2)CC1] | 2-Cyano-N-(4-{2-[4-(2,4-dichloro-5-trifluoromethylphenyl)piperazin-1-yl]ethyl}cyclohexyl)acetamide | 193 | IIA |
| 424 | 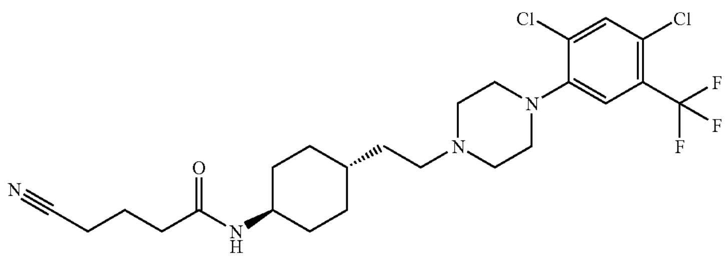 [SMILES: N#CCCCC(=O)N[C@H]1CC[C@H](CCN2CCN(c3cc(C(F)(F)F)c(Cl)cc3Cl)CC2)CC1] | 4-Cyano-N-(4-{2-[4-(2,4-dichloro-5-trifluoromethylphenyl)piperazin-1-yl]ethyl}cyclohexyl)butanamide | 188 | IIA |
| 425 | 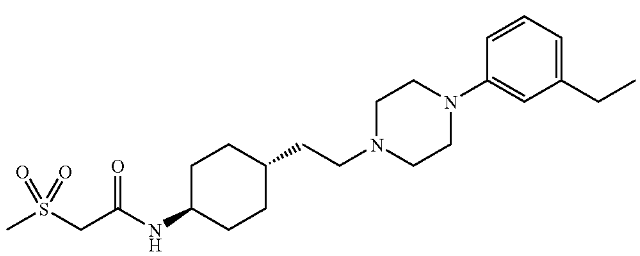 [SMILES: CCc1cccc(N2CCN(CC[C@H]3CC[C@H](NC(=O)CS(C)(=O)=O)CC3)CC2)c1] | N-(4-{2-[4-(3-Ethylphenyl)-piperazin-1-yl]ethyl}cyclohexyl)-2-methanesulfonylacetamide | 185 | IIA |
| 426 | 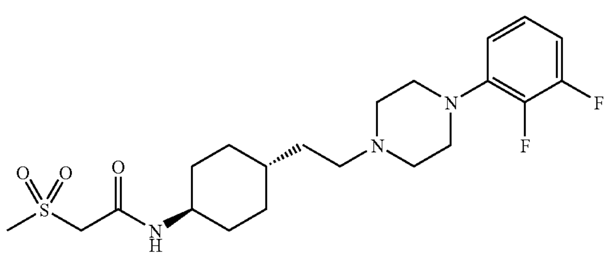 [SMILES: CS(=O)(=O)CC(=O)N[C@H]1CC[C@H](CCN2CCN(c3cccc(F)c3F)CC2)CC1] | N-(4-{2-[4-(2,3-Difluorophenyl)-piperazin-1-yl]ethyl}cyclohexyl)-2-methanesulfonylacetamide | 214 | IIA |
| 427 | 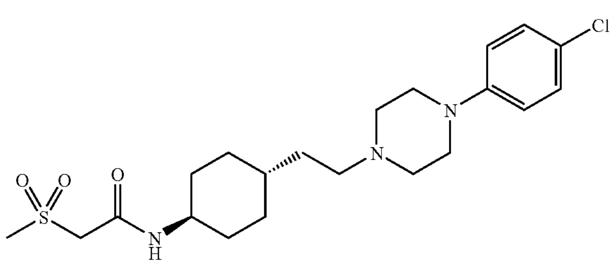 [SMILES: CS(=O)(=O)CC(=O)N[C@H]1CC[C@H](CCN2CCN(c3ccc(Cl)cc3)CC2)CC1] | N-(4-{2-[4-(4-Chlorophenyl)-piperazin-1-yl]ethyl}cyclohexyl)-2-methanesulfonylacetamide | 214 | IIA |

-continued

| Ex | Structure | Name | M.P. (° C.) | Synthetic Path |
|---|---|---|---|---|
| 428 | 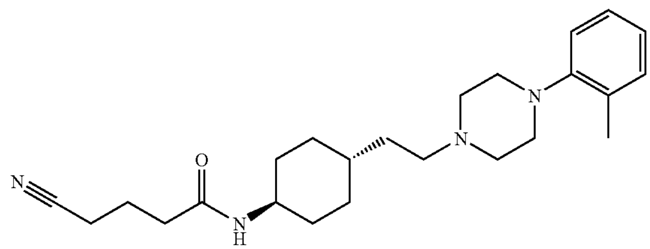 [SMILES: Cc1ccccc1N1CCN(CC[C@H]2CC[C@H](NC(=O)CCCC#N)CC2)CC1] | 4-Cyano-N-{4-[2-(4-o-tolylpiperazin-1-yl)ethyl]cyclohexyl}butanamide | 160 | IIA |
| 429 | 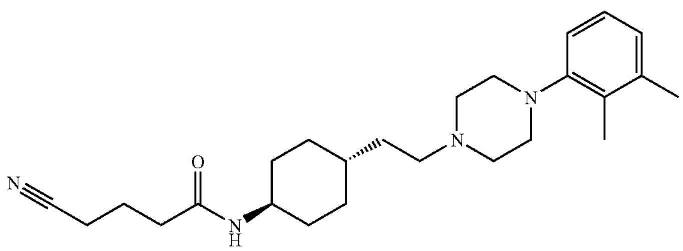 [SMILES: Cc1cccc(N2CCN(CC[C@H]3CC[C@H](NC(=O)CCCC#N)CC3)CC2)c1C] | 4-Cyano-N-(4-{2-[4-(2,3-dimethylphenyl)piperazin-1-yl]ethyl}cyclohexyl)butanamide | 162 | IIA |
| 430 | 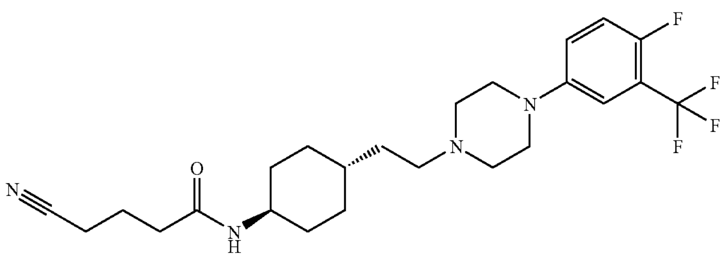 | 4-Cyano-N-(4-{2-[4-(4-fluoro-3-trifluoromethylphenyl)piperazin-1-yl]ethyl}cyclohexyl)butanamide | 149 | IIA |
| 431 | 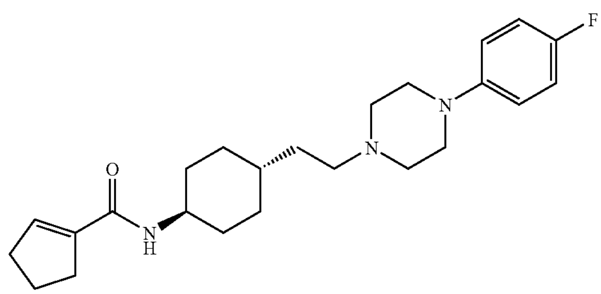 [SMILES: O=C(N[C@H]1CC[C@H](CCN2CCN(c3ccc(F)cc3)CC2)CC1)C1=CCCC1] | Cyclopent-1-enecarboxylic acid (4-{2-[4-(4-fluorophenyl)-piperazin-1-yl]ethyl}cyclohexyl)amide | 227 | IIA |
| 432 | 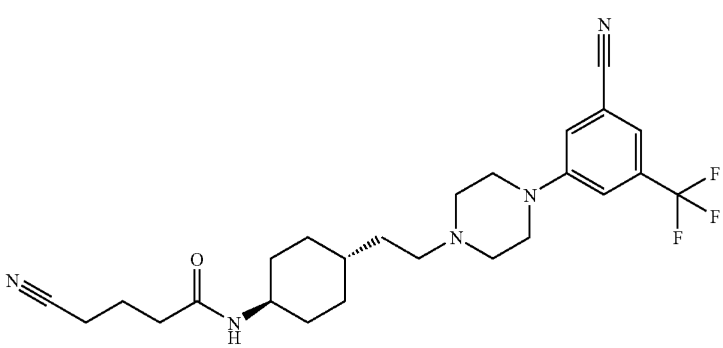 [SMILES: N#CCCCC(=O)N[C@H]1CC[C@H](CCN2CCN(c3cc(C#N)cc(C(F)(F)F)c3)CC2)CC1] | 4-Cyano-N-(4-{2-[4-(3-cyano-5-trifluoromethylphenyl)piperazin-1-yl]ethyl}cyclohexyl)butanamide | 174 | IIA |

-continued

| Ex | Structure | Name | M.P. (° C.) | Synthetic Path |
|---|---|---|---|---|
| 433 | 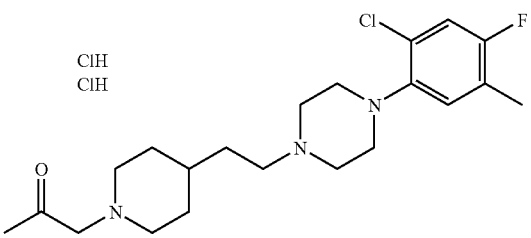 [SMILES: CC(=O)CN1CCC(CCN2CCN(c3cc(C)c(F)cc3Cl)CC2)CC1 ; Cl ; Cl] | 1-(4-{2-[4-(2-Chloro-4-fluoro-5-methylphenyl)piperazin-1-yl]ethyl}piperidin-1-yl)propan-2-one, dihydrochloride | 344 | IIIB |
| 434 | 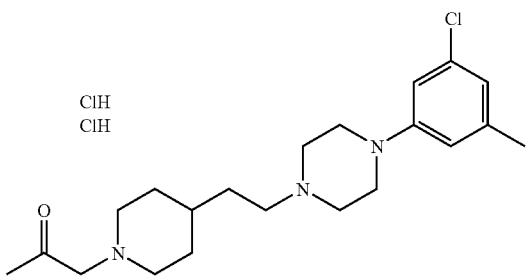 [SMILES: CC(=O)CN1CCC(CCN2CCN(c3cc(C)cc(Cl)c3)CC2)CC1 ; Cl ; Cl] | 1-(4-{2-[4-(3-Chloro-5-methylphenyl)piperazin-1-yl]ethyl}piperidin-1-yl)propan-2-one, dihydrochloride | 300 | IIIB |
| 435 | 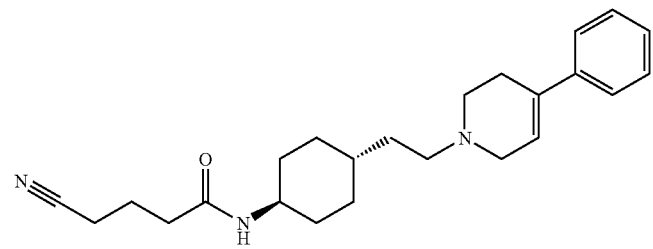 [SMILES: N#CCCCC(=O)N[C@H]1CC[C@H](CCN2CC=C(c3ccccc3)CC2)CC1] | 4-Cyano-N-{4-[2-(4-phenyl-3,6-dihydro-2H-pyridin-1-yl)ethyl]cyclohexyl}butanamide | 171 | IIA |
| 436 | 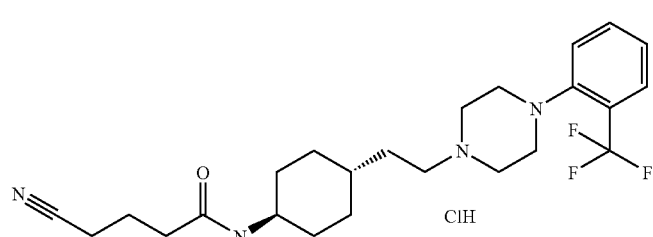 | 4-Cyano-N-(4-{2-[4-(2-trifluoromethylphenyl)piperazin-1-yl]ethylcyclohexyl)butanamide, hydrochloride | 248 | IIA |
| 437 | 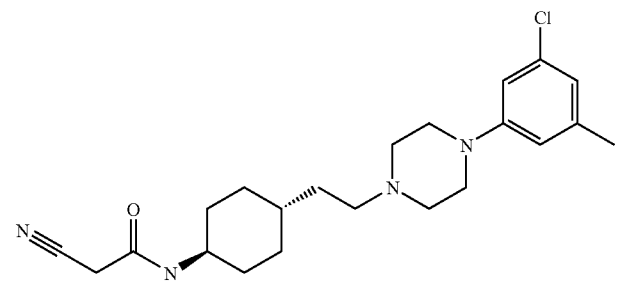 | N-(4-{2-[4-(3-Chloro-5-methylphenyl)piperazin-1-yl]ethyl}cyclohexyl)-2-cyanoacetamide | 185 | IIA |

-continued

| Ex | Structure | Name | M.P. (°C.) | Synthetic Path |
|---|---|---|---|---|
| 438 | 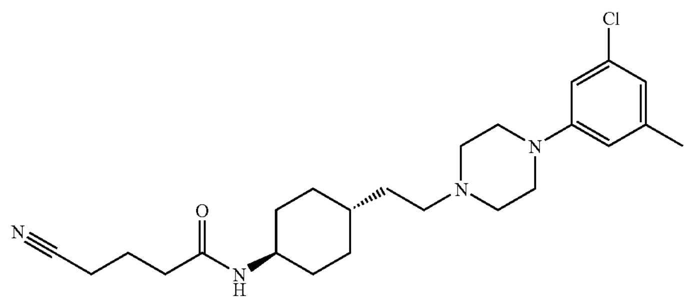 [SMILES: Cc1cc(Cl)cc(N2CCN(CC[C@H]3CC[C@H](NC(=O)CCCC#N)CC3)CC2)c1] | N-(4-{2-[4-(3-Chloro-5-methylphenyl)piperazin-1-yl]ethyl}cyclohexyl)-4-cyanobutanamide | 165 | IIA |
| 439 | 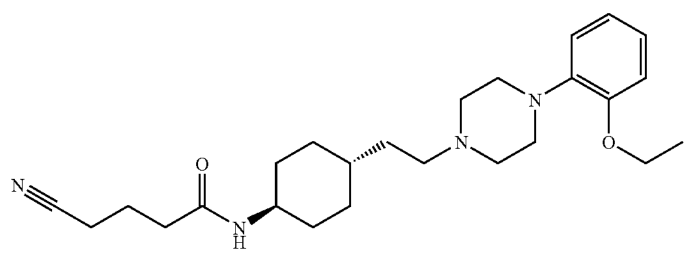 [SMILES: CCOc1ccccc1N1CCN(CC[C@H]2CC[C@H](NC(=O)CCCC#N)CC2)CC1] | 4-Cyano-N-(4-{2-[4-(2-ethoxyphenyl)piperazin-1-yl]ethyl}cyclohexyl)butanamide | 137 | IIA |
| 440 | 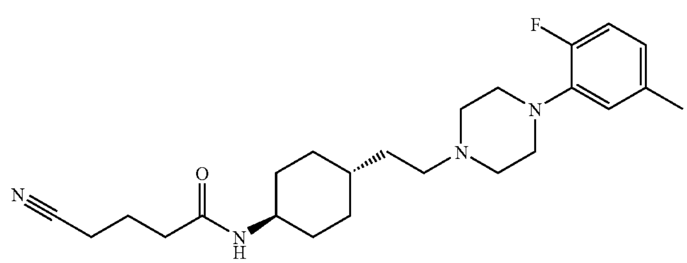 [SMILES: Cc1ccc(F)c(N2CCN(CC[C@H]3CC[C@H](NC(=O)CCCC#N)CC3)CC2)c1] | 4-Cyano-N-(4-{2-[4-(2-fluoro-5-methylphenyl)piperazin-1-yl]ethyl}cyclohexyl)butanamide | 156 | IIA |
| 441 | 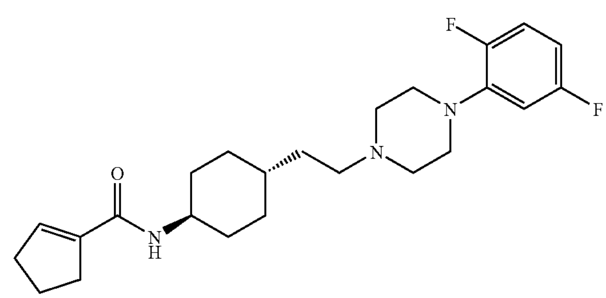 [SMILES: O=C(N[C@H]1CC[C@H](CCN2CCN(c3cc(F)ccc3F)CC2)CC1)C1=CCCC1] | Cyclopent-1-enecarboxylic acid (4-{2-[4-(2,5-difluorophenyl)-piperazin-1-yl]ethyl}cyclohexyl)amide | 209 | IIA |
| 442 | 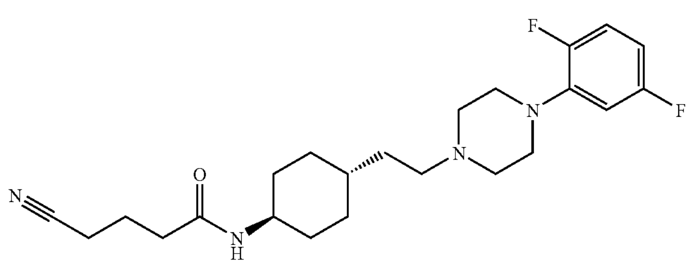 [SMILES: N#CCCCC(=O)N[C@H]1CC[C@H](CCN2CCN(c3cc(F)ccc3F)CC2)CC1] | 4-Cyano-N-(4-{2-[4-(2,5-difluorophenyl)piperazin-1-yl]ethyl}cyclohexyl)butanamide | 159 | IIA |

| Ex | Structure | Name | M.P. (° C.) | Synthetic Path |
|---|---|---|---|---|
| 443 | 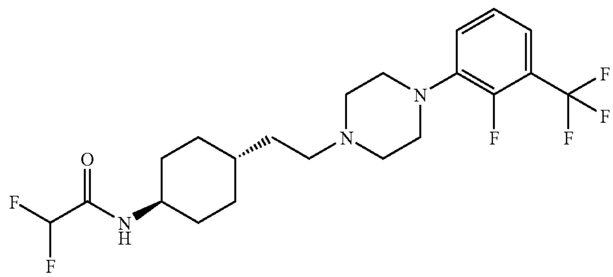 [SMILES: O=C(N[C@H]1CC[C@H](CCN2CCN(c3cccc(C(F)(F)F)c3F)CC2)CC1)C(F)F] | 2,2-Difluoro-N-(4-{2-[4-(2-fluoro-3-trifluoromethylphenyl)piperazin-1-yl]ethyl}cyclohexyl)acetamide | 156 | IIA |
| 444 | HCl HCl | 1-(4-{2-[4-(4-Methyl-3-trifluoromethylphenyl)piperazin-1-yl]ethyl}piperidin-1-yl)propan-2-one | 325 | IIIB |
| 445 | 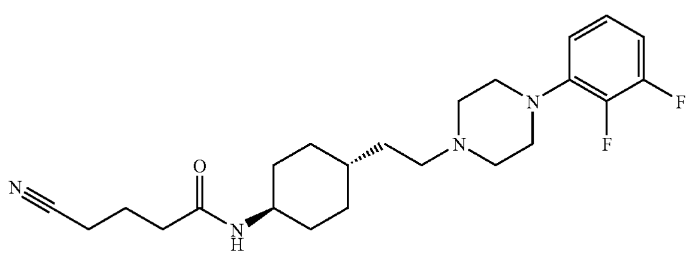 [SMILES: N#CCCCC(=O)N[C@H]1CC[C@H](CCN2CCN(c3cccc(F)c3F)CC2)CC1] | 4-Cyano-N-(4-{2-[4-(2,3-difluorophenyl)piperazin-1-yl]ethyl}cyclohexyl)butanamide | 197 | IIA |
| 446 | 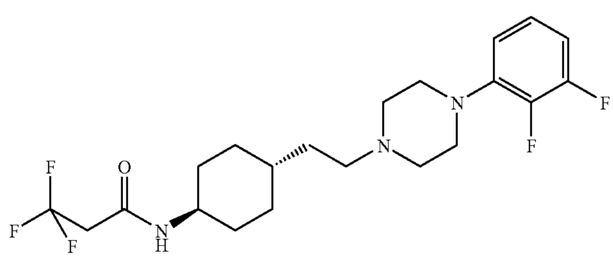 [SMILES: O=C(CC(F)(F)F)N[C@H]1CC[C@H](CCN2CCN(c3cccc(F)c3F)CC2)CC1] | N-(4-{2-[4-(2,3-Difluorophenyl)piperazin-1-yl]ethyl}cyclohexyl)-3,3,3-trifluoropropanamide | 220 | IIA |
| 447 | 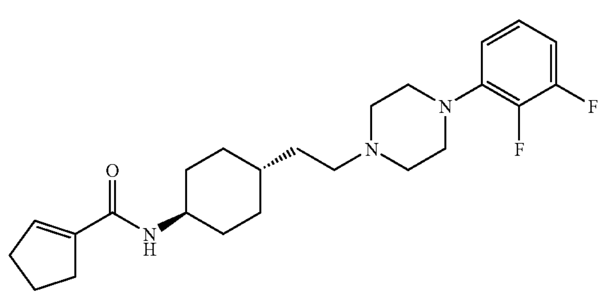 [SMILES: O=C(N[C@H]1CC[C@H](CCN2CCN(c3cccc(F)c3F)CC2)CC1)C1=CCCC1] | Cyclopent-1-enecarboxylic acid (4-{2-[4-(2,3-difluorophenyl)-piperazin-1-yl]ethyl}cyclohexyl)amide | 225 | IIA |

| Ex | Structure | Name | M.P. (° C.) | Synthetic Path |
|---|---|---|---|---|
| 448 | 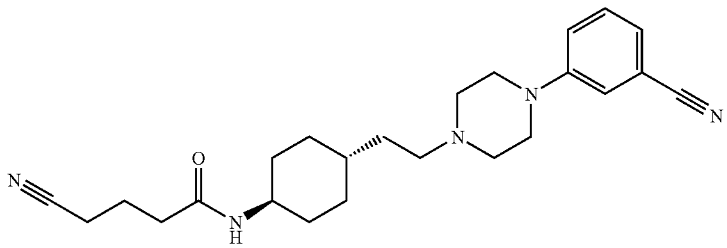 [SMILES: N#CCCCC(=O)N[C@H]1CC[C@H](CCN2CCN(c3cccc(C#N)c3)CC2)CC1] | 4-Cyano-N-(4-{2-[4-(3-cyanophenyl)piperazin-1-yl]ethyl}cyclohexyl)butanamide | 184 | IIA |
| 449 | 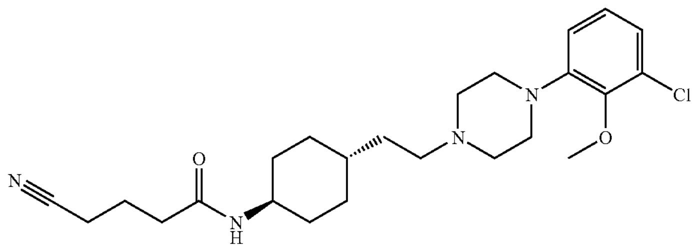 [SMILES: COc1c(Cl)cccc1N1CCN(CC[C@H]2CC[C@H](NC(=O)CCCC#N)CC2)CC1] | N-(4-{2-[4-(3-Chloro-2-methoxyphenyl)piperazin-1-yl]ethyl}cyclohexyl)-4-cyanobutanamide | 118 | IIA |
| 450 | 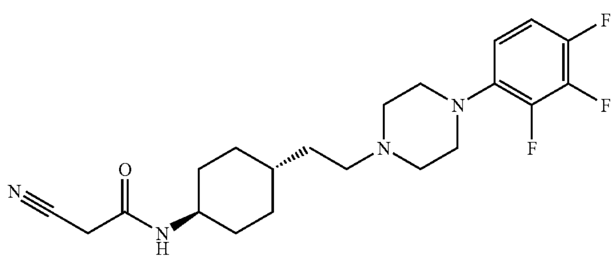 [SMILES: N#CCC(=O)N[C@H]1CC[C@H](CCN2CCN(c3ccc(F)c(F)c3F)CC2)CC1] | 2-Cyano-N-(4-{2-[4-(2,3,4-trifluorophenyl)piperazin-1-yl]ethyl}cyclohexyl)acetamide | 207 | IIA |
| 451 | 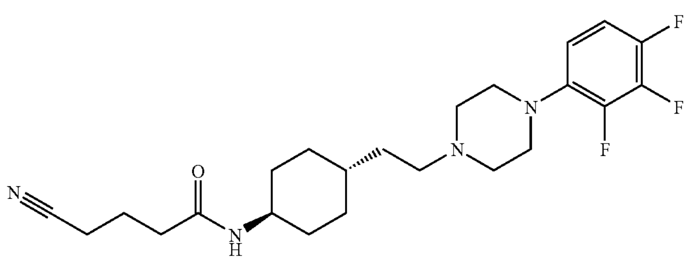 [SMILES: N#CCCCC(=O)N[C@H]1CC[C@H](CCN2CCN(c3ccc(F)c(F)c3F)CC2)CC1] | 4-Cyano-N-(4-{2-[4-(2,3,4-trifluorophenyl)piperazin-1-yl]ethyl}cyclohexyl)butanamide | 178 | IIA |
| 452 | 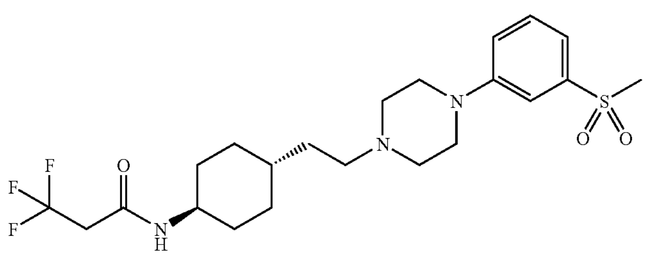 [SMILES: CS(=O)(=O)c1cccc(N2CCN(CC[C@H]3CC[C@H](NC(=O)CC(F)(F)F)CC3)CC2)c1] | 3,3,3-Trifluoro-N-(4-{2-[4-(3-methanesulfonylphenyl)piperazin-1-yl]ethyl}cyclohexyl)-propanamide | 173 | IIA |
| 453 | 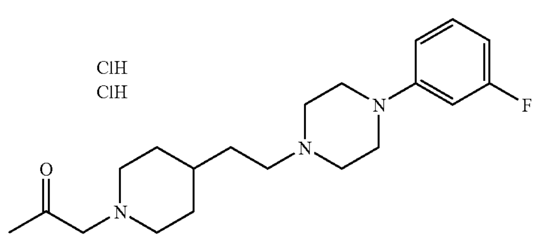 [SMILES: CC(=O)CN1CCC(CCN2CCN(c3cccc(F)c3)CC2)CC1 ; Cl ; Cl] | 1-(4-{2-[4-(3-Fluorophenyl)piperazin-1-yl]ethyl}piperidin-1-yl)propan-2-one, dihydrochloride | 268 | IIIB |

-continued

| Ex | Structure | Name | M.P. (° C.) | Synthetic Path |
|---|---|---|---|---|
| 454 | 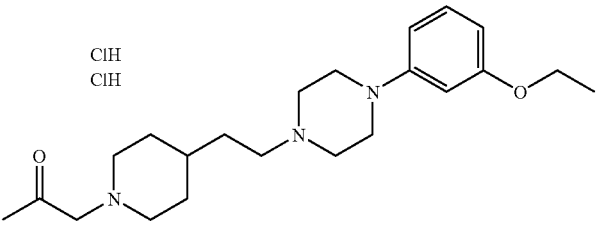 [SMILES: CCOc1cccc(N2CCN(CCC3CCN(CC(C)=O)CC3)CC2)c1 ; Cl ; Cl] | 1-(4-{2-[4-(3-Ethoxyphenyl)piperazin-1-yl]ethyl}piperidin-1-yl)propan-2-one, dihydrochloride | 246 | IIIB |
| 455 | 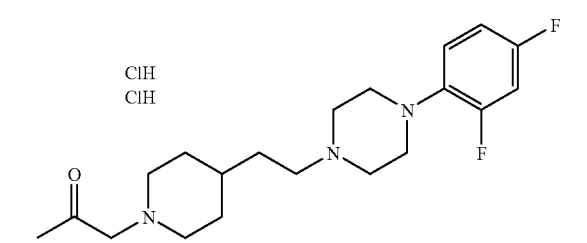 [SMILES: CC(=O)CN1CCC(CCN2CCN(c3ccc(F)cc3F)CC2)CC1 ; Cl ; Cl] | 1-(4-{2-[4-(2,4-Difluorophenyl)piperazin-1-yl]ethyl}piperidin-1-yl)propan-2-one, dihydrochloride | 260 | IIIB |
| 456 | 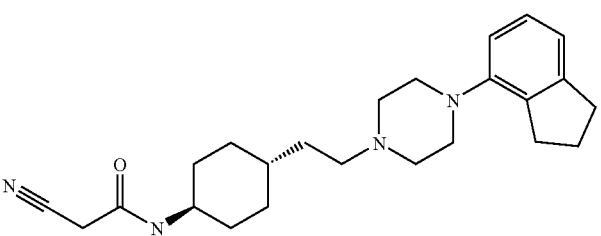 | 2-Cyano-N-{4-[2-(4-indan-4-ylpiperazin-1-yl)ethyl]cyclohexyl}acetamide | 175 | IIIB |
| 457 | 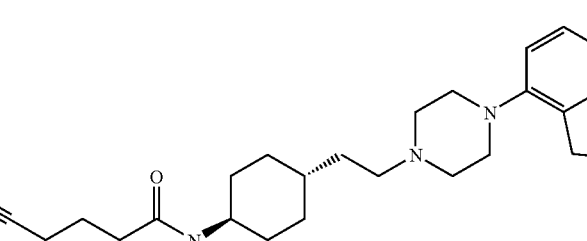 | 4-Cyano-N-{4-[2-(4-indan-4-ylpiperazin-1-yl)ethyl]cyclohexyl}butanamide | 157 | IIA |
| 458 | 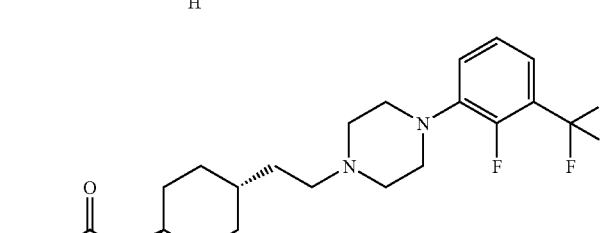 | Cyclopent-1-enecarboxylic acid (4-{2-[4-(2-fluoro-3-trifluoromethylphenyl)piperazin-1-yl]ethyl}cyclohexyl) amide | 190 | IIA |
| 459 | 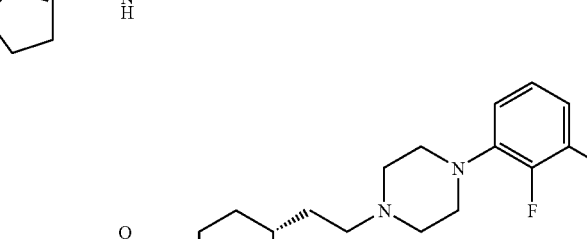 | N-(4-{2-[4-(2-Fluoro-3-trifluoromethylphenyl)piperazin-1-yl]ethyl}cyclohexyl)succinamide | 244 | IIA |

| Ex | Structure | Name | M.P. (°C.) | Synthetic Path |
|---|---|---|---|---|
| 460 | 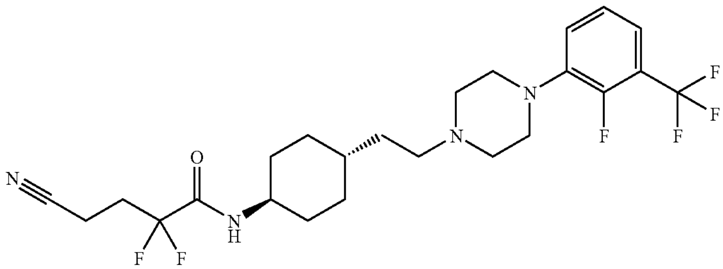 [SMILES: N#CCCC(F)(F)C(=O)N[C@H]1CC[C@H](CCN2CCN(c3cccc(C(F)(F)F)c3F)CC2)CC1] | 4-Cyano-2,2-difluoro-N-(4-{2-[4-(2-fluoro-3-trifluoromethyl-phenyl)piperazin-1-yl]ethyl}cyclohexyl)butanamide | 151 | IIA |
| 461 | 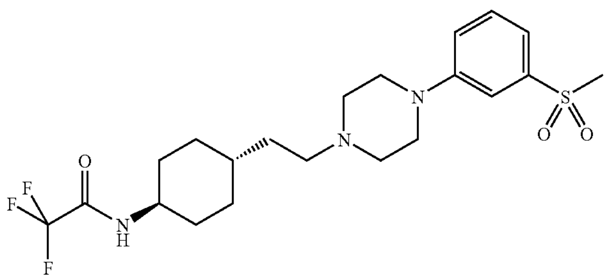 [SMILES: CS(=O)(=O)c1cccc(N2CCN(CC[C@H]3CC[C@H](NC(=O)C(F)(F)F)CC3)CC2)c1] | 2,2,2-Trifluoro-N-(4-{2-[4-(3-methanesulfonylphenyl)piperazin-1-yl]ethyl}cyclohexyl)acetamide | 132 | IIA |
| 462 | 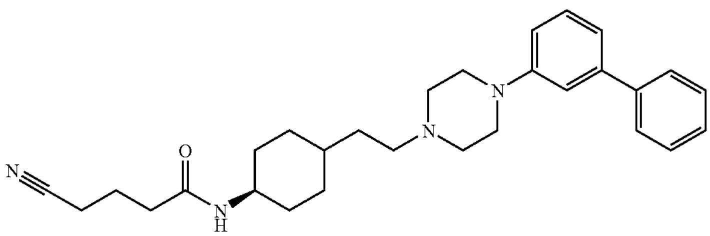 | N-{4-[2-(4-Biphenyl-3-ylpiperazin-1-yl)ethyl]cyclohexyl}-4-cyanobutanamide | 119 | IIA |
| 463 | 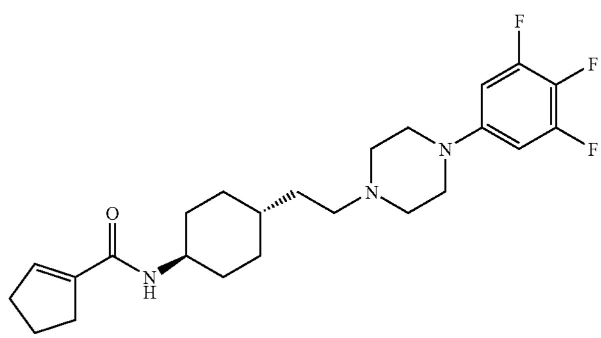 [SMILES: O=C(N[C@H]1CC[C@H](CCN2CCN(c3cc(F)c(F)c(F)c3)CC2)CC1)C1=CCCC1] | Cyclopent-1-enecarboxylic acid (4-{2-[4-(3,4,5-trifluorophenyl)piperazin-1-yl]ethyl}cyclohexyl) amide | 208 | IIA |
| 464 | 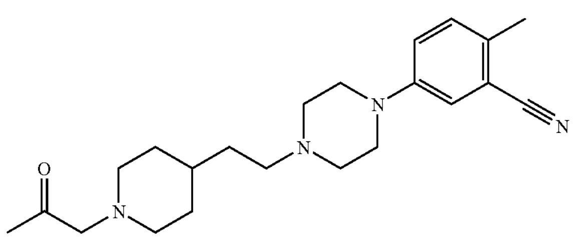 [SMILES: CC(=O)CN1CCC(CCN2CCN(c3ccc(C)c(C#N)c3)CC2)CC1] | 2-Methyl-5-(4-{2-[1-(2-oxopropyl)piperidin-4-yl]ethyl}piperazin-1-yl)benzonitrile | 107 | IIIB |

-continued

| Ex | Structure | Name | M.P. (° C.) | Synthetic Path |
|---|---|---|---|---|
| 465 | 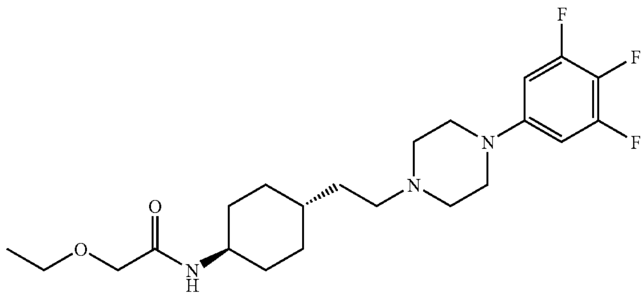 [SMILES: CCOCC(=O)N[C@H]1CC[C@H](CCN2CCN(c3cc(F)c(F)c(F)c3)CC2)CC1] | 2-Ethoxy-N-(4-{2-[4-(3,4,5-trifluorophenyl)piperazin-1-yl]ethyl}cyclohexyl)acetamide | 133 | IIA |
| 466 | 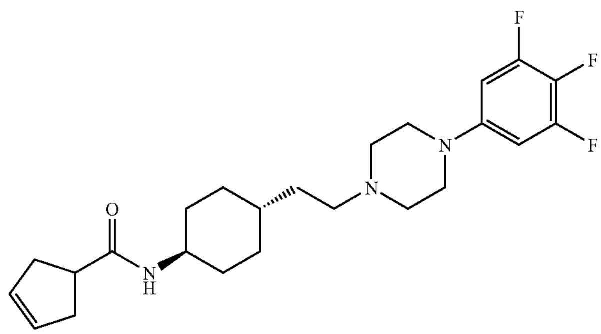 [SMILES: O=C(N[C@H]1CC[C@H](CCN2CCN(c3cc(F)c(F)c(F)c3)CC2)CC1)C1CC=CC1] | Cyclopent-3-enecarboxylic acid (4-{2-[4-(3,4,5-trifluorophenyl)piperazin-1-yl]ethyl}cyclohexyl) amide | 224 | IIA |
| 467 | 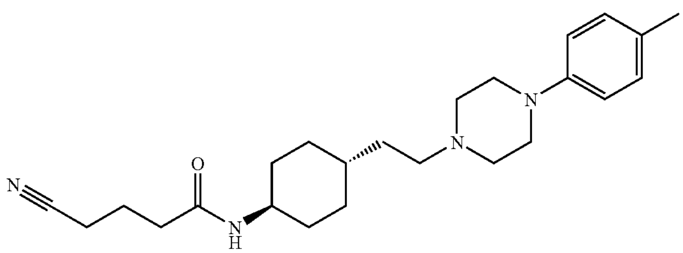 [SMILES: Cc1ccc(N2CCN(CC[C@H]3CC[C@H](NC(=O)CCCC#N)CC3)CC2)cc1] | 4-Cyano-N-{4-[2-(4-p-tolylpiperazin-1-yl)ethyl]cyclohexyl}butanamide | 189 | IIA |
| 468 | HCl HCl | 1-(4-{2-[4-(3-Methoxy-5-trifluoromethylphenyl)piperazin-1-yl]ethyl}piperidin-1-yl)propan-2-one | 277-278 | IIIB |
| 469 | 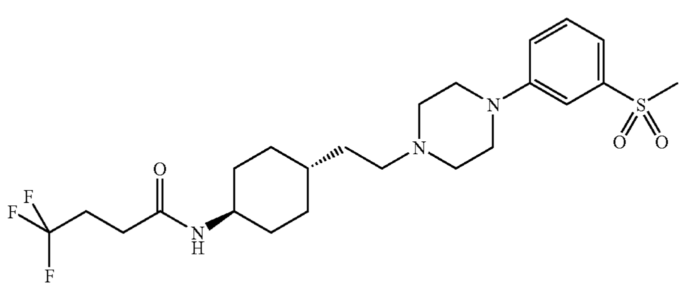 [SMILES: CS(=O)(=O)c1cccc(N2CCN(CC[C@H]3CC[C@H](NC(=O)CCC(F)(F)F)CC3)CC2)c1] | 4,4,4-Trifluoro-N-(4-{2-[4-(3-methanesulfonylphenyl)piperazin-1-yl]ethyl}cyclohexyl)butanamide | 205 | IIA |

| Ex | Structure | Name | M.P. (°C.) | Synthetic Path |
|---|---|---|---|---|
| 470 | 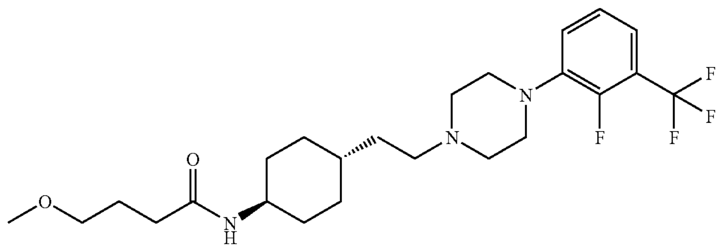 | N-(4-{2-[4-(2-Fluoro-3-trifluoromethylphenyl)piperazin-1-yl]ethyl}cyclohexyl)-4-methoxybutanamide | 175 | IIA |
| 471 | 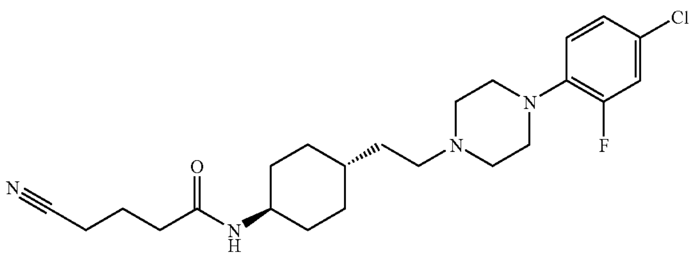 | N-(4-{2-[4-(4-Chloro-2-fluorophenyl)piperazin-1-yl]ethyl}cyclohexyl)-4-cyanobutanamide | 171 | IIA |
| 472 | 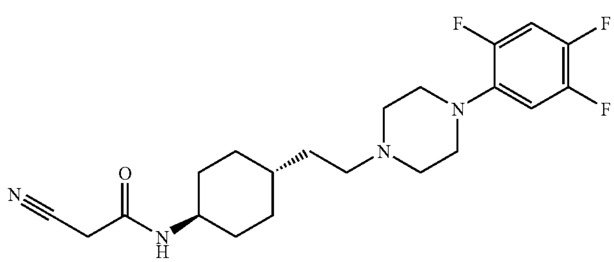 [SMILES: N#CCC(=O)N[C@H]1CC[C@H](CCN2CCN(c3cc(F)c(F)cc3F)CC2)CC1] | 2-Cyano-N-(4-{2-[4-(2,4,5-trifluorophenyl)piperazin-1-yl]ethyl}cyclohexyl)acetamide | 188 | IIA |
| 473 | 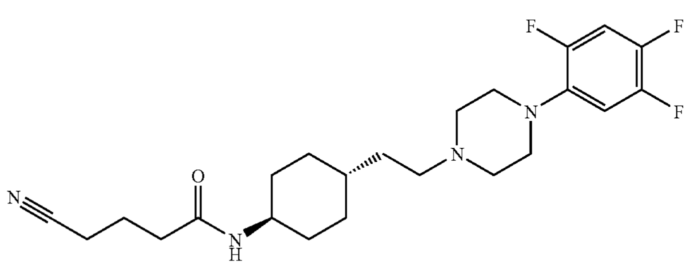 [SMILES: N#CCCCC(=O)N[C@H]1CC[C@H](CCN2CCN(c3cc(F)c(F)cc3F)CC2)CC1] | 4-Cyano-N-(4-{2-[4-(2,4,5-trifluorophenyl)piperazin-1-yl]ethyl}cyclohexyl)butanamide | 153 | IIA |
| 474 | 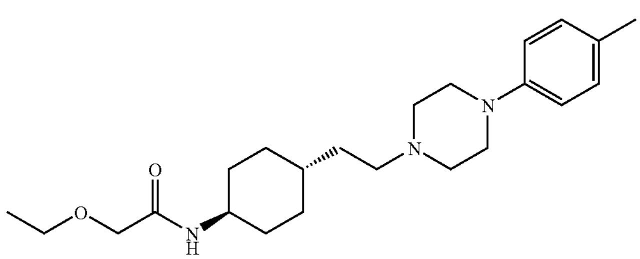 [SMILES: CCOCC(=O)N[C@H]1CC[C@H](CCN2CCN(c3ccc(C)cc3)CC2)CC1] | 2-Ethoxy-N-{4-[2-(4-p-tolylpiperazin-1-yl)ethyl]cyclohexyl}acetamide | 130 | IIA |

| Ex | Structure | Name | M.P. (°C.) | Synthetic Path |
|---|---|---|---|---|
| 475 | 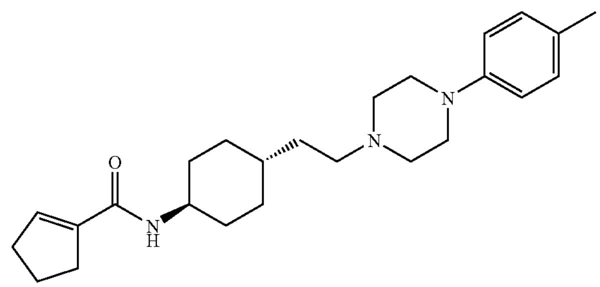 [SMILES: Cc1ccc(N2CCN(CC[C@H]3CC[C@H](NC(=O)C4=CCCC4)CC3)CC2)cc1] | Cyclopent-1-enecarboxylic acid {4-[2-(4-p-tolylpiperazin-1-yl)ethyl]cyclohexyl} amide | 227 | IIA |
| 476 | 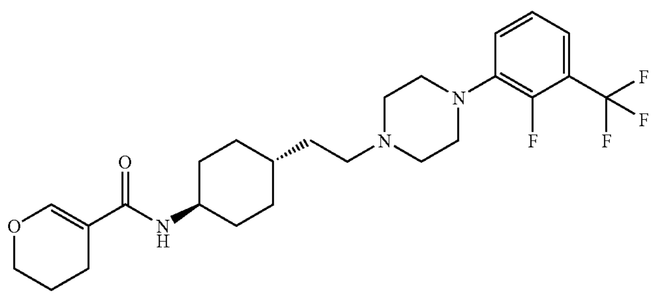 [SMILES: O=C(N[C@H]1CC[C@H](CCN2CCN(c3cccc(C(F)(F)F)c3F)CC2)CC1)C1=COCCC1] | 5,6-Dihydro-4H-pyran-3-carboxylic acid (4-{2-[4-(2-fluoro-3-trifluoromethylphenyl)piperazin-1-yl]ethyl}cyclohexyl amide | 207 | IIA |
| 477 | 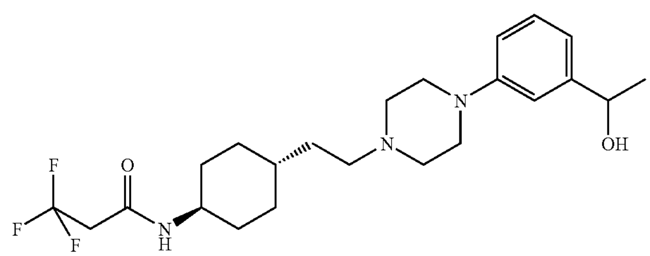 [SMILES: CC(O)c1cccc(N2CCN(CC[C@H]3CC[C@H](NC(=O)CC(F)(F)F)CC3)CC2)c1] | 3,3,3-Trifluoro-N-[4-(2-{4-[3-(1-hydroxyethyl)phenyl]piperazin-1-yl}ethyl)cyclohexyl]propanamide | 190 | IIA |
| 478 | 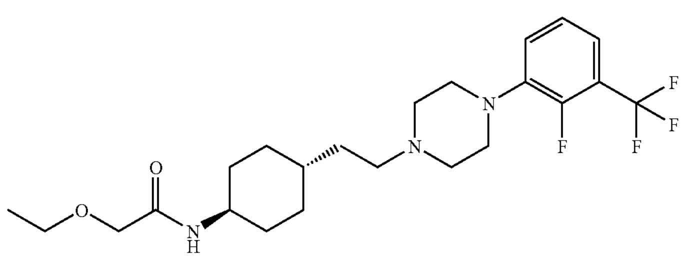 [SMILES: CCOCC(=O)N[C@H]1CC[C@H](CCN2CCN(c3cccc(C(F)(F)F)c3F)CC2)CC1] | 2-Ethoxy-N-(4-{2-[4-(2-fluoro-3-trifluoromethylphenyl)piperazin-1-yl]ethyl}cyclohexyl)acetamide | 125 | IIA |
| 479 | 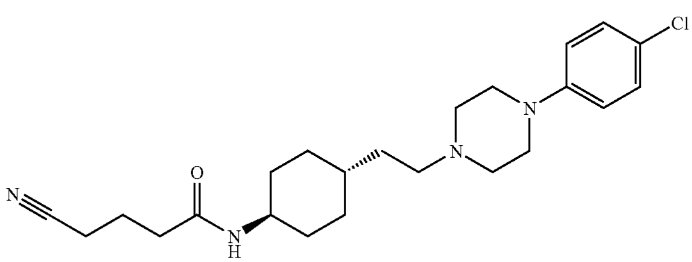 | N-(4-{2-[4-(4-Chlorophenyl)piperazin-1-yl]ethyl}cyclohexyl)-4-cyanobutanamide | 190 | IIA |

-continued

| Ex | Structure | Name | M.P. (° C.) | Synthetic Path |
|---|---|---|---|---|
| 480 | 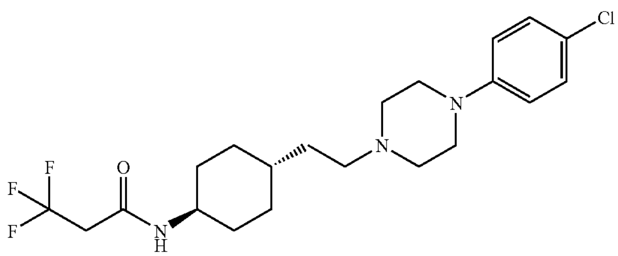 [SMILES: O=C(CC(F)(F)F)N[C@H]1CC[C@H](CCN2CCN(c3ccc(Cl)cc3)CC2)CC1] | N-(4-{2-[4-(4-Chlorophenyl)-piperazin-1-yl]ethyl}cyclohexyl)-3,3,3-trifluoropropanamide | 234 | IIA |
| 481 | ClH ClH | 1-(4-{2-[4-(4-Chloro-2-fluorophenyl)piperazin-1-yl]ethyl}piperidin-1-yl)propan-2-one | 206 | IIIB |
| 482 | 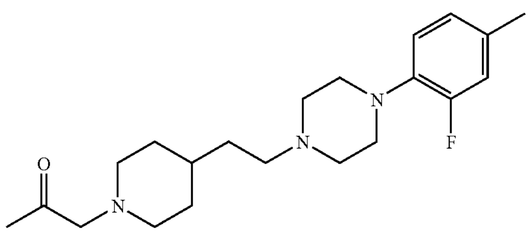 [SMILES: CC(=O)CN1CCC(CCN2CCN(c3ccc(C)cc3F)CC2)CC1] | 1-(4-{2-[4-(2-Fluoro-4-methylphenyl)piperazin-1-yl]ethyl}piperidin-1-yl)propan-2-one | 65 | IIIB |
| 483 | 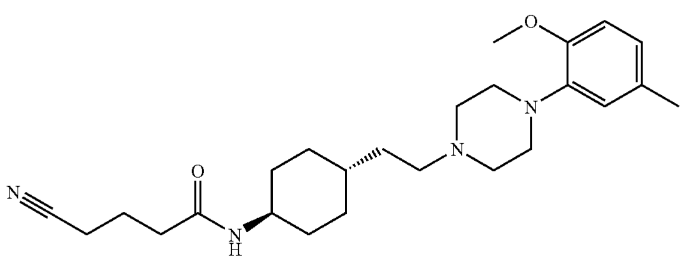 [SMILES: COc1ccc(C)cc1N1CCN(CC[C@H]2CC[C@H](NC(=O)CCCC#N)CC2)CC1] | 4-Cyano-N-(4-{2-[4-(2-methoxy-5-methylphenyl)piperazin-1-yl]ethyl}cyclohexyl)butanamide | 164 | IIA |
| 484 | 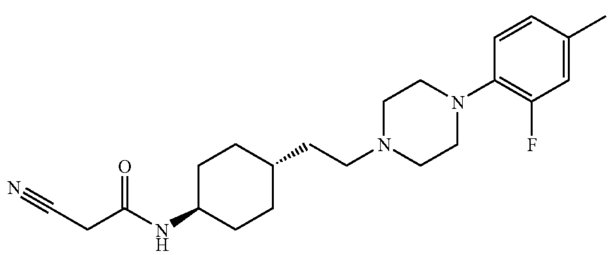 [SMILES: Cc1ccc(N2CCN(CC[C@H]3CC[C@H](NC(=O)CC#N)CC3)CC2)c(F)c1] | 2-Cyano-N-(4-{2-[4-(2-fluoro-4-methylphenyl)piperazin-1-yl]ethyl}cyclohexyl)acetamide | 197 | IIA |
| 485 | 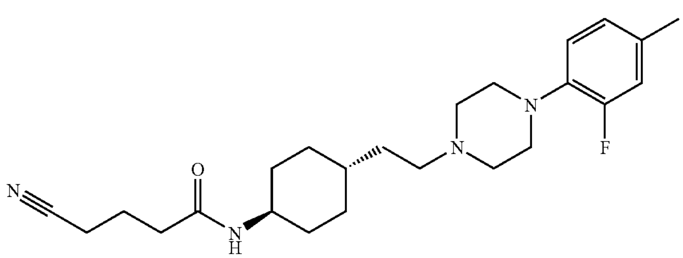 [SMILES: Cc1ccc(N2CCN(CC[C@H]3CC[C@H](NC(=O)CCCC#N)CC3)CC2)c(F)c1] | 4-Cyano-N-(4-{2-[4-(2-fluoro-4-methylphenyl)piperazin-1-yl]ethyl}cyclohexyl)butanamide | 173 | IIA |

-continued

| Ex | Structure | Name | M.P. (° C.) | Synthetic Path |
|---|---|---|---|---|
| 486 | 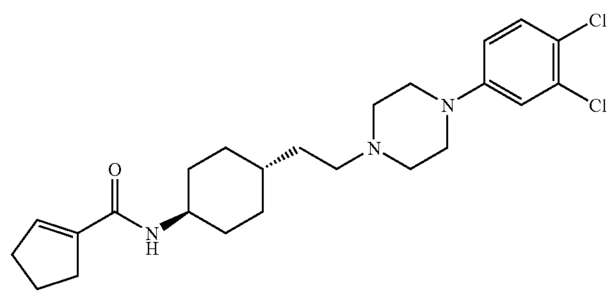 [SMILES: O=C(N[C@H]1CC[C@H](CCN2CCN(c3ccc(Cl)c(Cl)c3)CC2)CC1)C1=CCCC1] | Cyclopent-1-enecarboxylic acid (4-{2-[4-(3,4-dichlorophenyl)piperazin-1-yl]ethyl}cyclohexyl) amide | 202 | IIA |
| 487 | 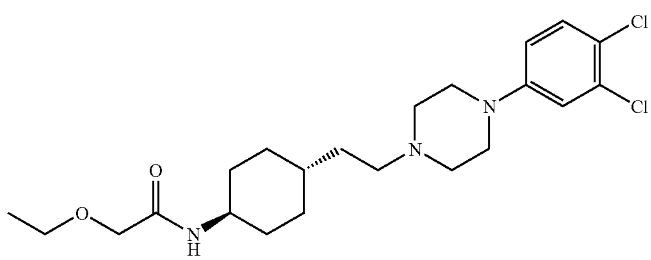 [SMILES: CCOCC(=O)N[C@H]1CC[C@H](CCN2CCN(c3ccc(Cl)c(Cl)c3)CC2)CC1] | N-(4-{2-[4-(3,4-Dichlorophenyl)piperazin-1-yl]ethyl}cyclohexyl)-2-ethoxyacetamide | 112 | IIA |
| 488 | 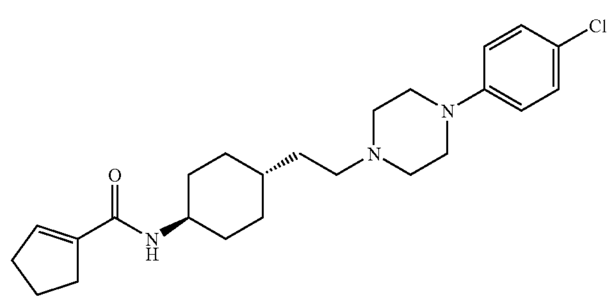 [SMILES: O=C(N[C@H]1CC[C@H](CCN2CCN(c3ccc(Cl)cc3)CC2)CC1)C1=CCCC1] | Cyclopent-1-enecarboxylic acid (4-{2-[4-(4-chlorophenyl)-piperazin-1-yl]ethyl}cyclohexyl) amide | 237 | IIA |
| 489 | 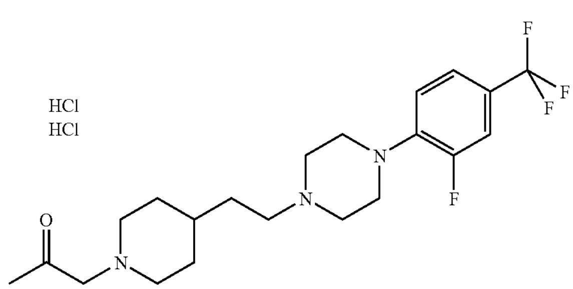 [SMILES: CC(=O)CN1CCC(CCN2CCN(c3ccc(C(F)(F)F)cc3F)CC2)CC1 ; Cl ; Cl] | 1-(4-{2-[4-(2-Fluoro-4-trifluoromethylphenyl)piperazin-1-yl]ethyl}piperidin-1-yl)propan-2-one | 278-279 | IIIB |
| 490 | 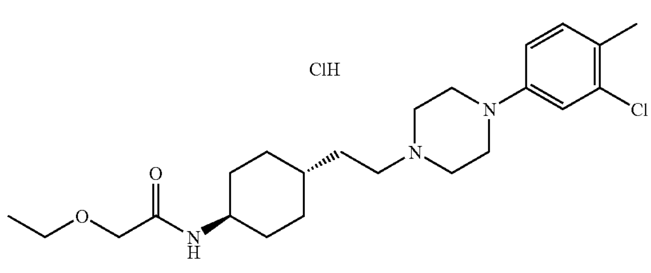 [SMILES: CCOCC(=O)N[C@H]1CC[C@H](CCN2CCN(c3ccc(C)c(Cl)c3)CC2)CC1 ; Cl] | N-(4-{2-[4-(3-Chloro-4-methylphenyl)piperazin-1-yl]ethyl}cyclohexyl)-2-ethoxyacetamide | 162 | IIA |

-continued

| Ex | Structure | Name | M.P. (° C.) | Synthetic Path |
|---|---|---|---|---|
| 491 | 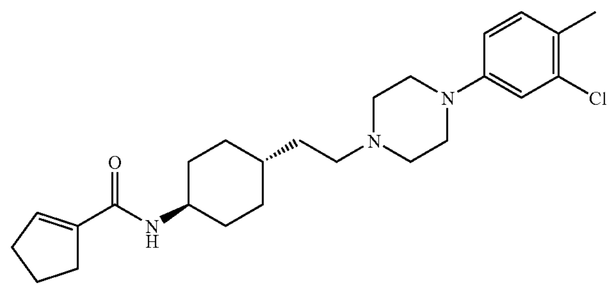 [SMILES: Cc1ccc(N2CCN(CC[C@H]3CC[C@H](NC(=O)C4=CCCC4)CC3)CC2)cc1Cl] | Cyclopent-1-enecarboxylic acid (4-{2-[4-(3-chloro-4-methylphenyl)piperazin-1-yl]ethyl}cyclohexyl) amide | 197 | IIA |
| 492 | 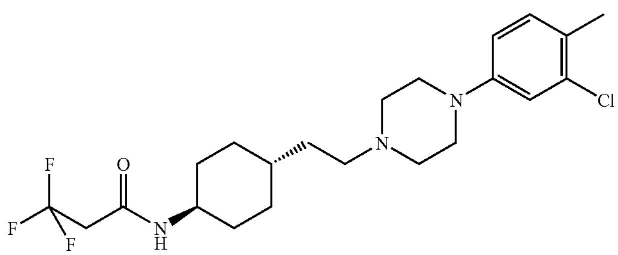 [SMILES: Cc1ccc(N2CCN(CC[C@H]3CC[C@H](NC(=O)CC(F)(F)F)CC3)CC2)cc1Cl] | N-(4-{2-[4-(3-Chloro-4-methylphenyl)piperazin-1-yl]ethyl}cyclohexyl)-3,3,3-trifluoropropanamide | 192 | IIA |
| 493 | 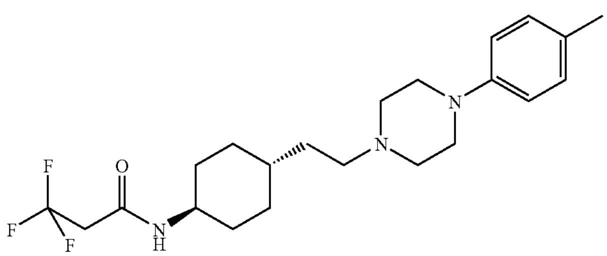 [SMILES: Cc1ccc(N2CCN(CC[C@H]3CC[C@H](NC(=O)CC(F)(F)F)CC3)CC2)cc1] | 3,3,3-Trifluoro-N-{4-[2-(4-p-tolylpiperazin-1-yl)ethyl]cyclohexyl}propanamide | 217 | IIA |
| 494 | 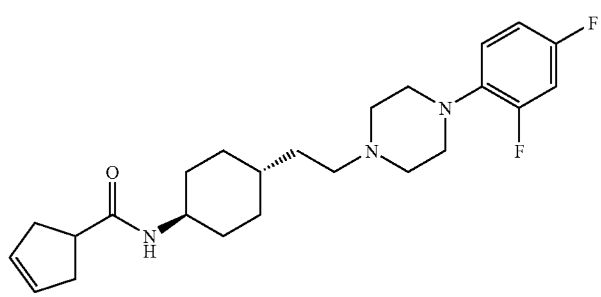 [SMILES: O=C(N[C@H]1CC[C@H](CCN2CCN(c3ccc(F)cc3F)CC2)CC1)C1CC=CC1] | Cyclopent-3-enecarboxylic acid (4-{2-[4-(2,4-difluorophenyl)-piperazin-1-yl]ethyl}cyclohexyl) amide | 199 | IIA |
| 495 | 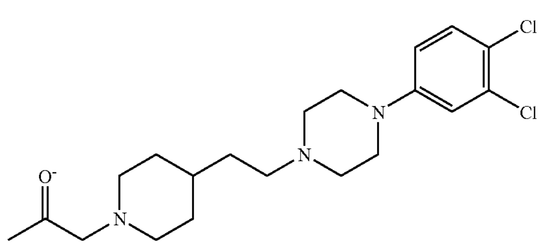 | 1-(4-{2-[4-(3,4-Dichlorophenyl)-piperazin-1-yl]ethyl}piperidin-1-yl)propan-2-one | 114 | IIIB |

-continued

| Ex | Structure | Name | M.P. (° C.) | Synthetic Path |
|---|---|---|---|---|
| 496 | 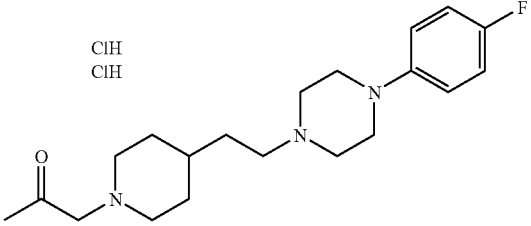 [SMILES: CC(=O)CN1CCC(CCN2CCN(c3ccc(F)cc3)CC2)CC1 ; Cl ; Cl] | 1-(4-{2-[4-(4-Fluorophenyl)-piperazin-1-yl]ethyl}piperidin-1-yl)propan-2-one | 270 | IIIB |
| 497 | 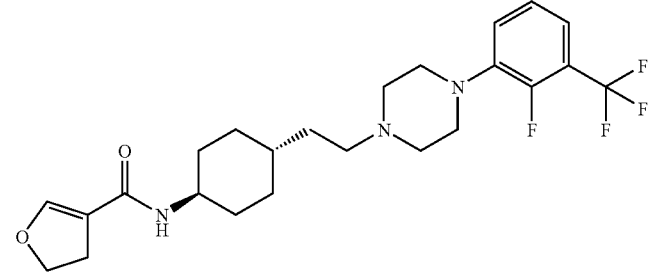 [SMILES: O=C(N[C@H]1CC[C@H](CCN2CCN(c3cccc(C(F)(F)F)c3F)CC2)CC1)C1=COCC1] | 4,5-Dihydrofuran-3-carboxylic acid (4-{2-[4-(2-fluoro-3-trifluoromethylphenyl)piperazin-1-yl]ethyl}cyclohexyl) amide | 192 | IIA |
| 498 | 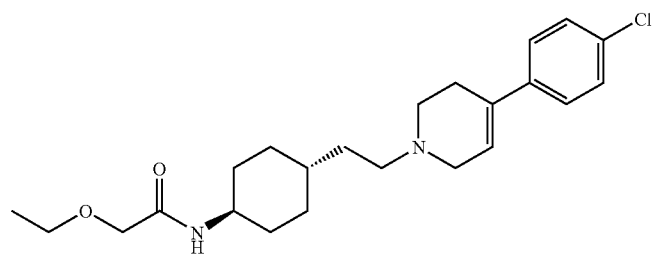 [SMILES: CCOCC(=O)N[C@H]1CC[C@H](CCN2CC=C(c3ccc(Cl)cc3)CC2)CC1] | N-(4-{2-[4-(4-Chlorophenyl)-3,6-dihydro-2H-pyridin-1-yl]ethyl}cyclohexyl)-2-ethoxyacetamide | 149 | IIA |
| 499 | 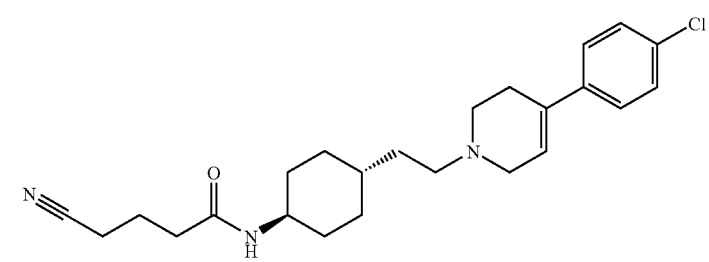 [SMILES: N#CCCCC(=O)N[C@H]1CC[C@H](CCN2CC=C(c3ccc(Cl)cc3)CC2)CC1] | N-(4-{2-[4-(4-Chlorophenyl)-3,6-dihydro-2H-pyridin-1-yl]ethyl}cyclohexyl)-4-cyanobutanamide | 198 | IIA |
| 500 | 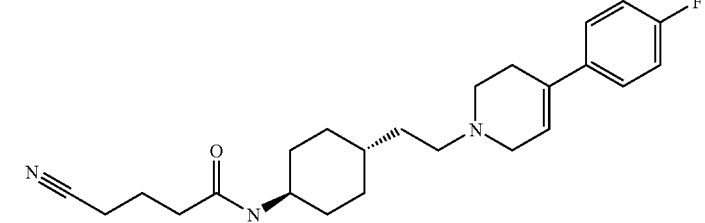 | 4-Cyano-N-(4-{2-[4-(4-fluorophenyl)-3,6-dihydro-2H-pyridin-1-yl]ethyl}cyclohexyl)-butanamide | 180 | IIA |

-continued

| Ex | Structure | Name | M.P. (° C.) | Synthetic Path |
|---|---|---|---|---|
| 501 | 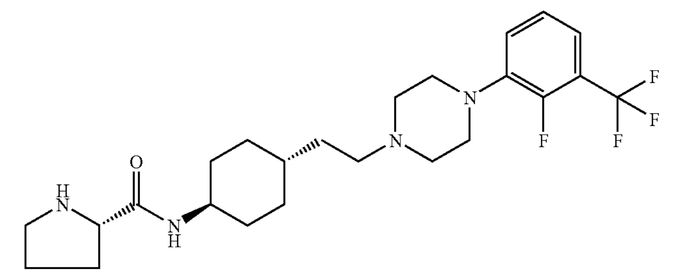 [SMILES: O=C(N[C@H]1CC[C@H](CCN2CCN(c3cccc(C(F)(F)F)c3F)CC2)CC1)[C@@H]1CCCN1] | Pyrrolidine-2-carboxylic acid (4-{2-[4-(2-fluoro-3-trifluoromethylphenyl)piperazin-1-yl]ethyl}cyclohexyl) amide | 140 | IIA |
| 502 | 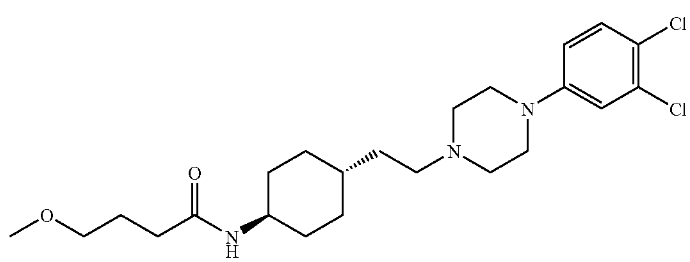 [SMILES: COCCCC(=O)N[C@H]1CC[C@H](CCN2CCN(c3ccc(Cl)c(Cl)c3)CC2)CC1] | N-(4-{2-[4-(3,4-Dichlorophenyl)piperazin-1-yl]ethyl}cyclohexyl)-4-methoxybutanamide | 175 | IIA |
| 503 | 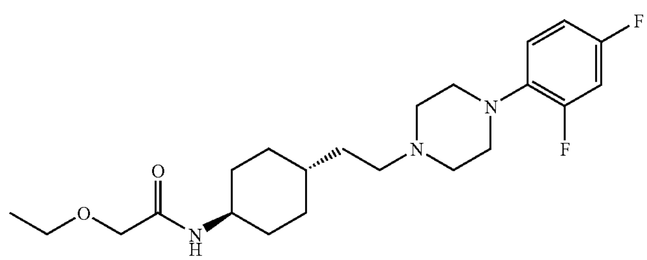 [SMILES: CCOCC(=O)N[C@H]1CC[C@H](CCN2CCN(c3ccc(F)cc3F)CC2)CC1] | N-(4-{2-[4-(2,4-Difluorophenyl)piperazin-1-yl]ethyl}cyclohexyl)-2-ethoxyacetamide | 130 | IIA |
| 504 | 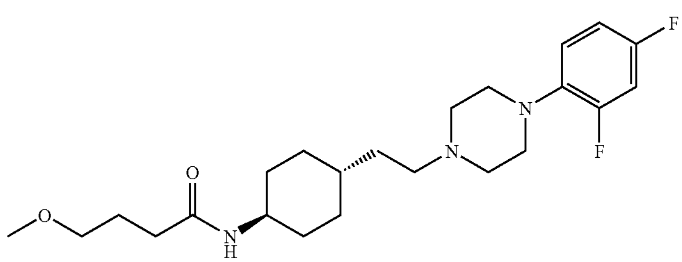 [SMILES: COCCCC(=O)N[C@H]1CC[C@H](CCN2CCN(c3ccc(F)cc3F)CC2)CC1] | N-(4-{2-[4-(2,4-Difluorophenyl)piperazin-1-yl]ethyl}cyclohexyl)-4-methoxybutanamide | 185 | IIA |
| 505 | 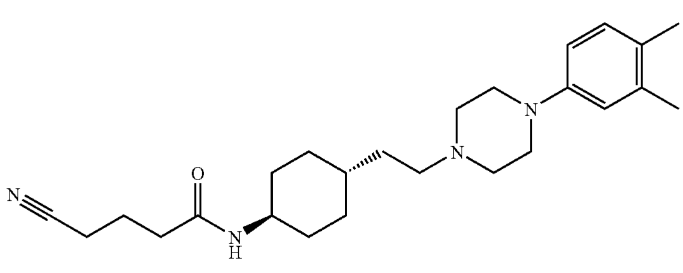 [SMILES: Cc1ccc(N2CCN(CC[C@H]3CC[C@H](NC(=O)CCCC#N)CC3)CC2)cc1C] | 4-Cyano-N-(4-{2-[4-(3,4-dimethylphenyl)piperazin-1-yl]ethyl}cyclohexyl)butanamide | 172 | IIA |

-continued

| Ex | Structure | Name | M.P. (° C.) | Synthetic Path |
|---|---|---|---|---|
| 506 | 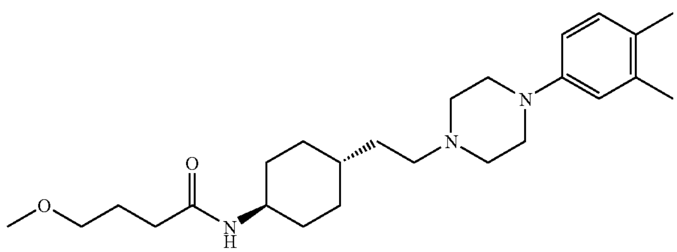 | N-(4-{2-[4-(3,4-Dimethylphenyl)piperazin-1-yl]ethyl}cyclohexyl)-4-methoxybutanamide | 161 | IIA |
| 507 | 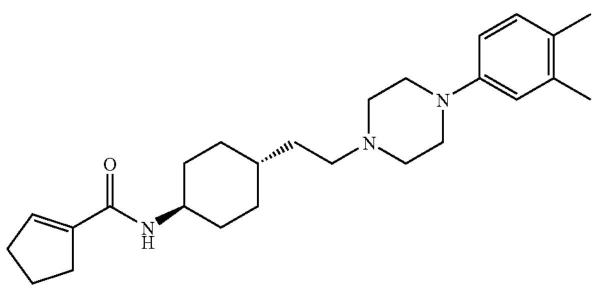 [SMILES: Cc1ccc(N2CCN(CC[C@H]3CC[C@H](NC(=O)C4=CCCC4)CC3)CC2)cc1C] | Cyclopent-1-enecarboxylic acid (4-{2-[4-(3,4-dimethylphenyl)-piperazin-1-yl]ethyl}cyclohexyl) amide | 201 | IIA |
| 508 | 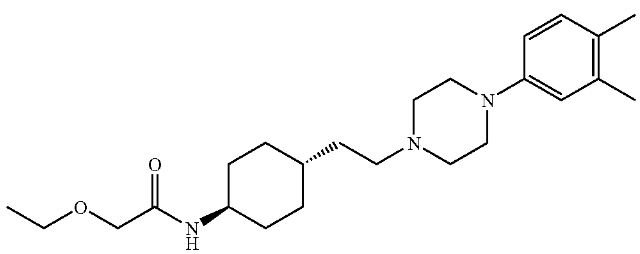 [SMILES: CCOCC(=O)N[C@H]1CC[C@H](CCN2CCN(c3ccc(C)c(C)c3)CC2)CC1] | N-(4-{2-[4-(3,4-Dimethylphenyl)piperazin-1-yl]ethyl}cyclohexyl)-2-ethoxyacetamide | 122 | IIA |
| 509 | 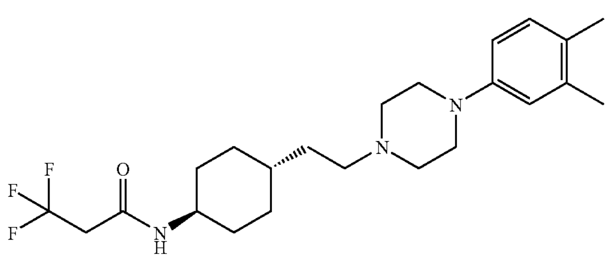 [SMILES: Cc1ccc(N2CCN(CC[C@H]3CC[C@H](NC(=O)CC(F)(F)F)CC3)CC2)cc1C] | N-(4-{2-[4-(3,4-Dimethylphenyl)piperazin-1-yl]ethyl}cyclohexyl)-3,3,3-trifluoropropanamide | 199 | IIA |
| 510 | 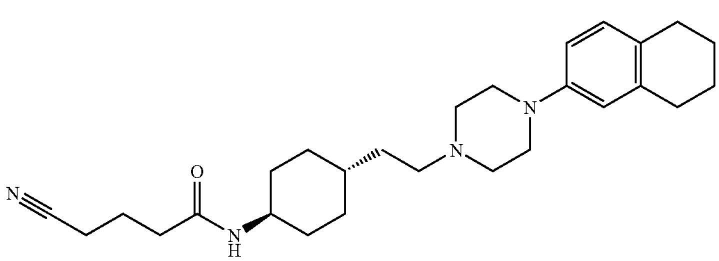 [SMILES: N#CCCCC(=O)N[C@H]1CC[C@H](CCN2CCN(c3ccc4c(c3)CCCC4)CC2)CC1] | 4-Cyano-N-(4-{2-[4-(5,6,7,8-tetrahydronaphthalen-2-yl)piperazin-1-yl]ethyl}cyclohexyl)butanamide | 170 | IIA |

| Ex | Structure | Name | M.P. (° C.) | Synthetic Path |
|---|---|---|---|---|
| 511 | 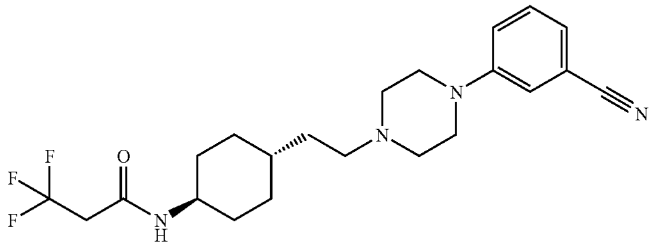 [SMILES: N#Cc1cccc(N2CCN(CC[C@H]3CC[C@H](NC(=O)CC(F)(F)F)CC3)CC2)c1] | N-(4-{2-[4-(3-Cyanophenyl)piperazin-1-yl]ethyl}cyclohexyl)-3,3,3-trifluoropropanamide | 180 | IIA |
| 512 | 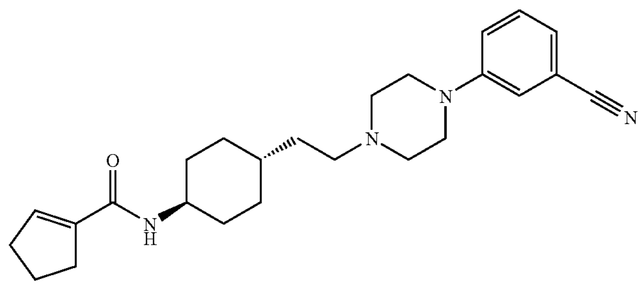 [SMILES: N#Cc1cccc(N2CCN(CC[C@H]3CC[C@H](NC(=O)C4=CCCC4)CC3)CC2)c1] | Cyclopent-1-enecarboxylic acid (4-{2-[4-(3-cyanophenyl)-piperazin-1-yl]ethyl}cyclohexyl)amide | 191 | IIA |
| 513 | 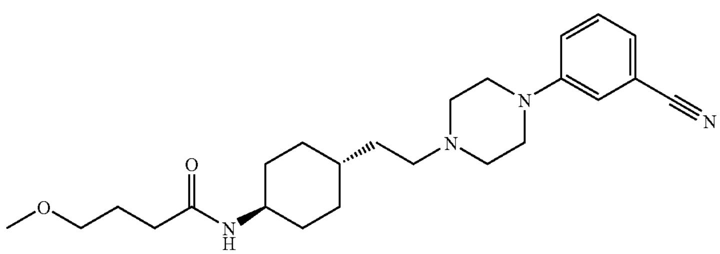 [SMILES: COCCCC(=O)N[C@H]1CC[C@H](CCN2CCN(c3cccc(C#N)c3)CC2)CC1] | N-(4-{2-[4-(3-Cyanophenyl)-piperazin-1-yl]ethyl}cyclohexyl)-4-methoxybutanamide | 168 | IIA |
| 514 | 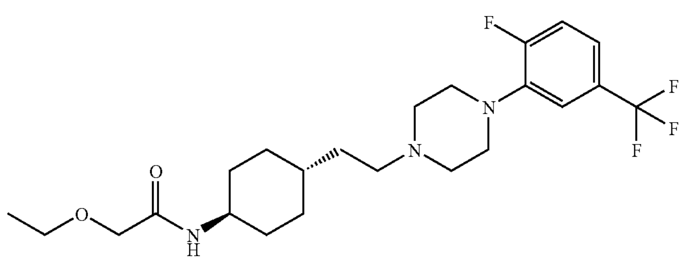 [SMILES: CCOCC(=O)N[C@H]1CC[C@H](CCN2CCN(c3cc(C(F)(F)F)ccc3F)CC2)CC1] | 2-Ethoxy-N-(4-{2-[4-(2-fluoro-5-trifluoromethylphenyl)piperazin-1-yl]ethyl}cyclohexyl)acetamide | 128 | IIA |
| 515 | 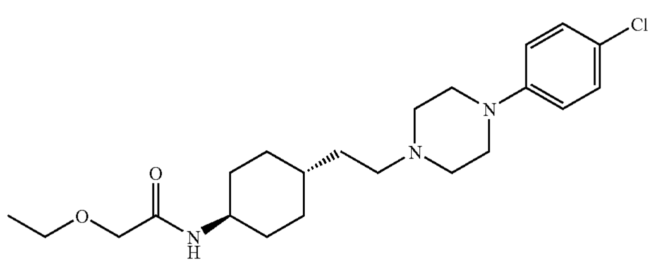 [SMILES: CCOCC(=O)N[C@H]1CC[C@H](CCN2CCN(c3ccc(Cl)cc3)CC2)CC1] | N-(4-{2-[4-(4-Chloro-phenyl)piperazin-1-yl]ethyl}-cyclohexyl)-2-ethoxyacetamide | 154 | IIA |

-continued

| Ex | Structure | Name | M.P. (° C.) | Synthetic Path |
|---|---|---|---|---|
| 516 | 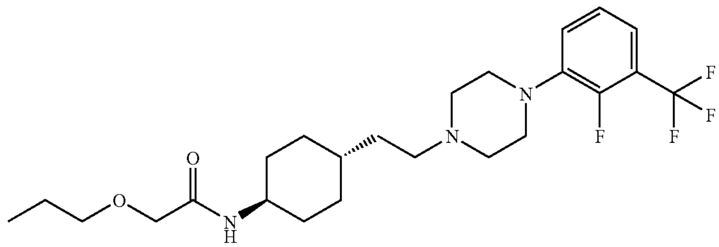 | N-(4-{2-[4-(2-Fluoro-3-trifluoromethylphenyl)piperazin-1-yl]ethyl}cyclohexyl)-2-propoxyacetamide | 102 | IIA |
| 517 | 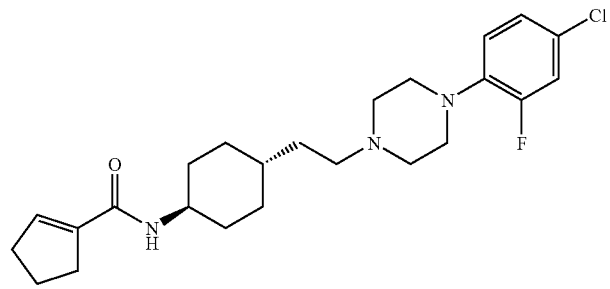 [SMILES: O=C(N[C@H]1CC[C@H](CCN2CCN(c3ccc(Cl)cc3F)CC2)CC1)C1=CCCC1] | Cyclopent-1-enecarboxylic acid (4-{2-[4-(4-chloro-2-fluorophenyl)piperazin-1-yl]ethyl}cyclohexyl) amide | 216 | IIA |
| 518 | 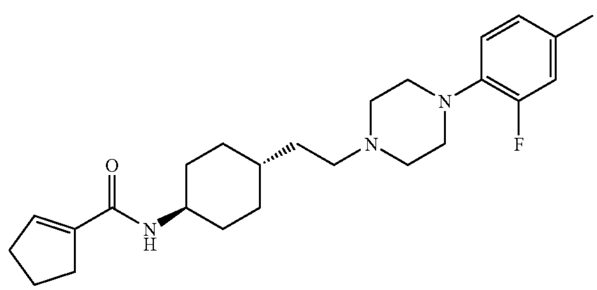 [SMILES: Cc1ccc(N2CCN(CC[C@H]3CC[C@H](NC(=O)C4=CCCC4)CC3)CC2)c(F)c1] | Cyclopent-1-enecarboxylic acid (4-{2-[4-(2-fluoro-4-methylphenyl)piperazin-1-yl]ethyl}cyclohexyl) amide | 202 | IIA |
| 519 | 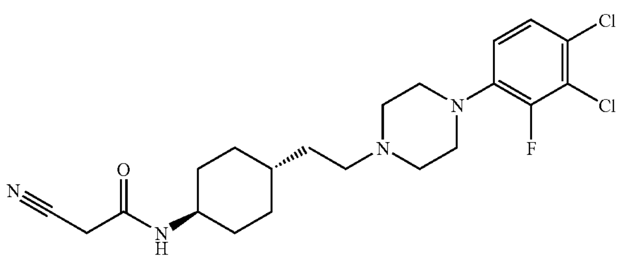 [SMILES: N#CCC(=O)N[C@H]1CC[C@H](CCN2CCN(c3ccc(Cl)c(Cl)c3F)CC2)CC1] | 2-Cyano-N-(4-{2-[4-(3,4-dichloro-2-fluorophenyl)piperazin-1-yl]ethyl}cyclohexyl)acetamide | 237 | IIA |
| 520 | 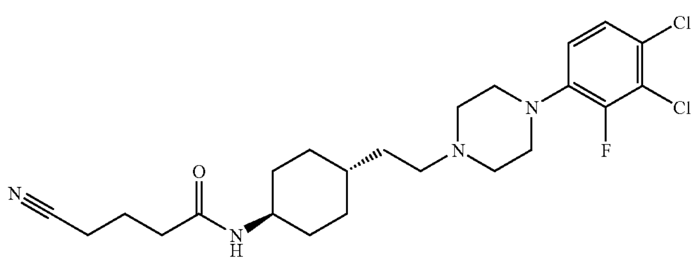 | 4-Cyano-N-(4-{2-[4-(3,4-dichloro-2-fluorophenyl)piperazin-1-yl]ethyl}cyclohexyl)butanamide | 199 | IIA |

| Ex | Structure | Name | M.P. (° C.) | Synthetic Path |
|---|---|---|---|---|
| 521 | 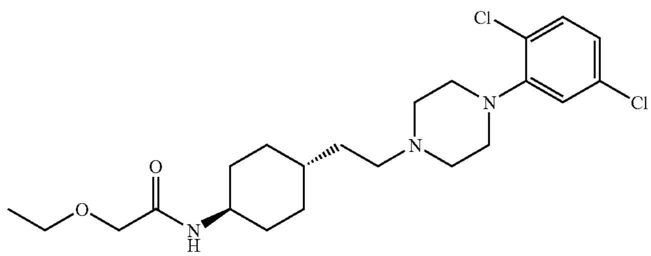 [SMILES: CCOCC(=O)N[C@H]1CC[C@H](CCN2CCN(c3cc(Cl)ccc3Cl)CC2)CC1] | N-(4-{2-[4-(2,5-Dichlorophenyl)-piperazin-1-yl]ethyl}cyclohexyl)-2-ethoxyacetamide | 128 | IIA |
| 522 | 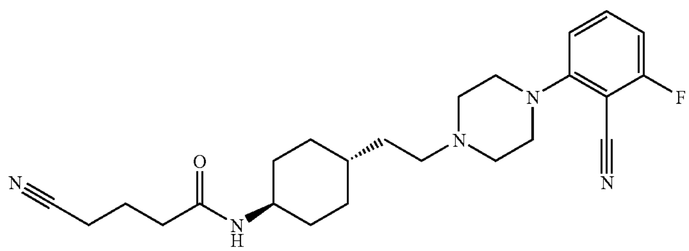 [SMILES: N#CCCCC(=O)N[C@H]1CC[C@H](CCN2CCN(c3cccc(F)c3C#N)CC2)CC1] | 4-Cyano-N-(4-{2-[4-(2-cyano-3-fluorophenyl)piperazin-1-yl]ethyl}cyclohexyl)butanamide | 175 | IIA |
| 523 | 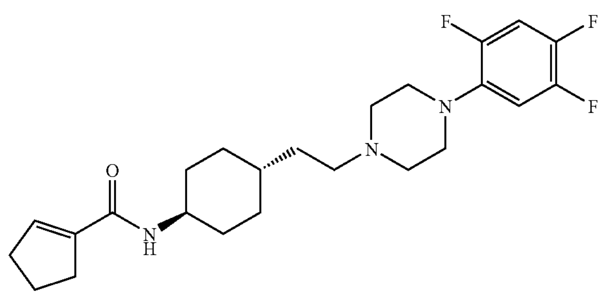 [SMILES: O=C(N[C@H]1CC[C@H](CCN2CCN(c3cc(F)c(F)cc3F)CC2)CC1)C1=CCCC1] | Cyclopent-1-enecarboxylic acid (4-{2-[4-(2,4,5-trifluorophenyl)piperazin-1-yl]ethyl}cyclohexyl) amide | 199 | IIA |
| 524 | 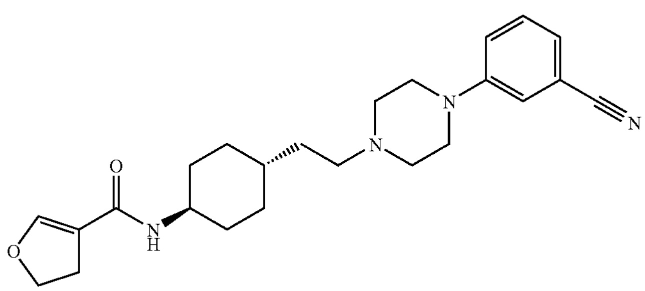 [SMILES: N#Cc1cccc(N2CCN(CC[C@H]3CC[C@H](NC(=O)C4=COCC4)CC3)CC2)c1] | 4,5-Dihydrofuran-3-carboxylic acid (4-{2-[4-(3-cyanophenyl)piperazin-1-yl]ethyl}cyclohexyl) amide | 165 | IIA |
| 525 | 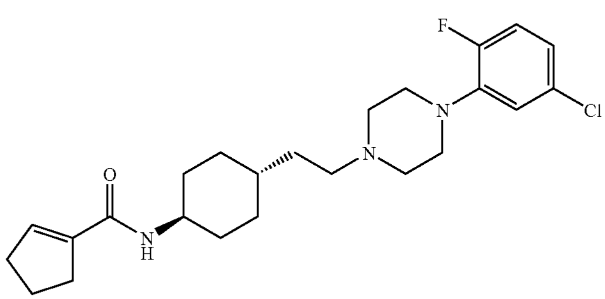 [SMILES: O=C(N[C@H]1CC[C@H](CCN2CCN(c3cc(Cl)ccc3F)CC2)CC1)C1=CCCC1] | Cyclopent-1-enecarboxylic acid (4-{2-[4-(5-chloro-2-fluorophenyl)piperazin-1-yl]ethyl}cyclohexyl) amide | 198 | IIA |

-continued

| Ex | Structure | Name | M.P. (° C.) | Synthetic Path |
|---|---|---|---|---|
| 526 | 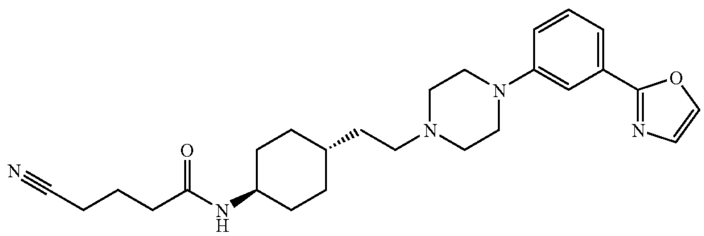 [SMILES: N#CCCCC(=O)N[C@H]1CC[C@H](CCN2CCN(c3cccc(-c4ncco4)c3)CC2)CC1] | 4-Cyano-N-(4-{2-[4-(3-oxazol-2-ylphenyl)piperazin-1-yl]ethyl}cyclohexyl)butanamide | 192 | IIA |
| 527 | 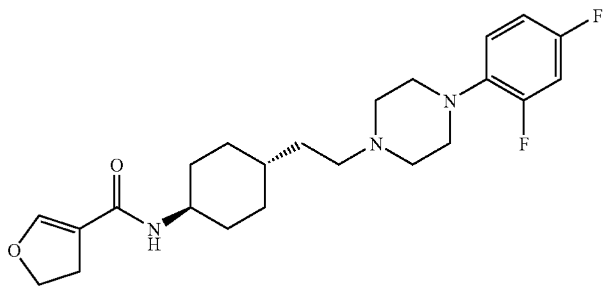 [SMILES: O=C(N[C@H]1CC[C@H](CCN2CCN(c3ccc(F)cc3F)CC2)CC1)C1=COCC1] | 4,5-Dihydrofuran-3-carboxylic acid (4-{2-[4-(2,4-difluorophenyl)piperazin-1-yl]ethyl}cyclohexyl) amide | 192 | IIA |
| 528 | 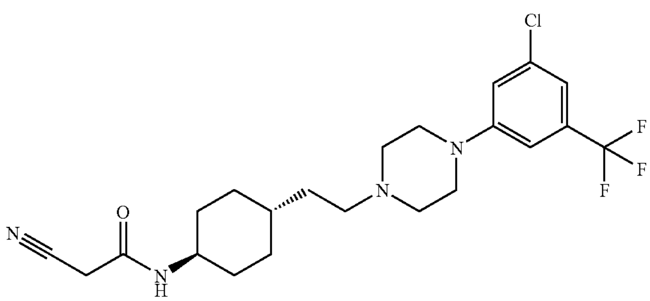 [SMILES: N#CCC(=O)N[C@H]1CC[C@H](CCN2CCN(c3cc(Cl)cc(C(F)(F)F)c3)CC2)CC1] | N-(4-{2-[4-(3-Chloro-5-trifluoromethylphenyl)piperazin-1-yl]ethyl}cyclohexyl)-2-cyanoacetamide | 172 | IIA |
| 529 | 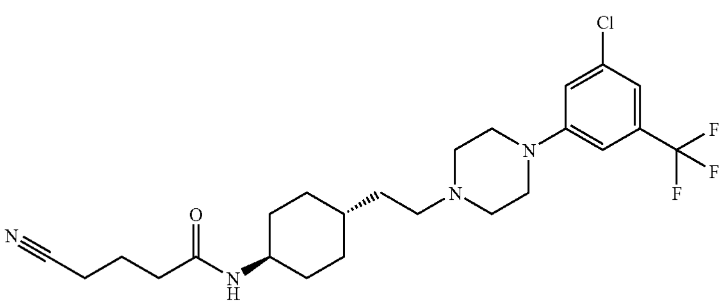 | N-(4-{2-[4-(3-Chloro-5-trifluoromethylphenyl)piperazin-1-yl]ethyl}cyclohexyl)-4-cyanobutanamide | 152 | IIA |
| 530 | 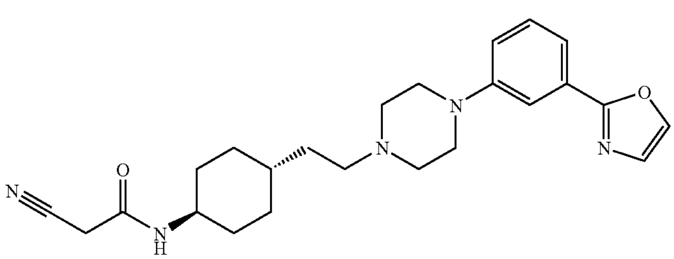 [SMILES: N#CCC(=O)N[C@H]1CC[C@H](CCN2CCN(c3cccc(-c4ncco4)c3)CC2)CC1] | 2-Cyano-N-(4-{2-[4-(3-oxazol-2-ylphenyl)piperazin-1-yl]ethyl}cyclohexyl)acetamide | 185 | IIA |

-continued

| Ex | Structure | Name | M.P. (° C.) | Synthetic Path |
|---|---|---|---|---|
| 531 | 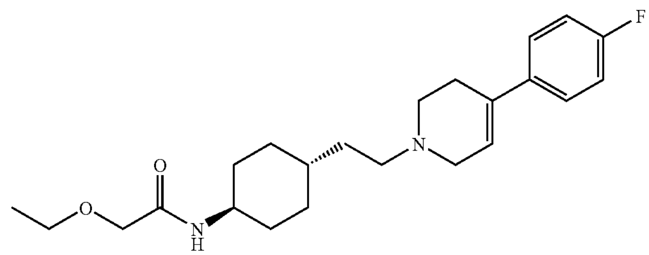 [SMILES: CCOCC(=O)N[C@H]1CC[C@H](CCN2CC=C(c3ccc(F)cc3)CC2)CC1] | 2-Ethoxy-N-(4-{2-[4-(4-fluorophenyl)-3,6-dihydro-2H-pyridin-1-yl]ethyl}cyclohexyl)-acetamide | 122 | IIA |
| 532 | 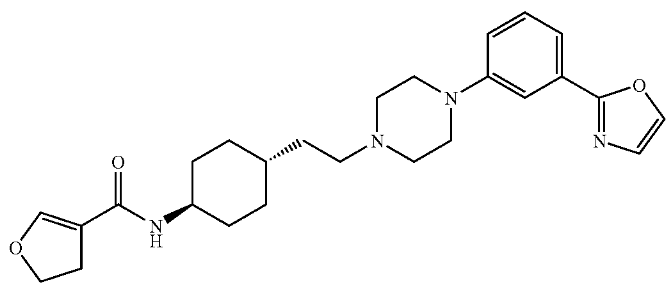 [SMILES: O=C(N[C@H]1CC[C@H](CCN2CCN(c3cccc(-c4ncco4)c3)CC2)CC1)C1=COCC1] | 4,5-Dihydrofuran-3-carboxylic acid(4-{2-[4-(3-oxazol-2-ylphenyl)piperazin-1-yl]ethyl}cyclohexyl) amide | 202 | IIA |
| 533 | 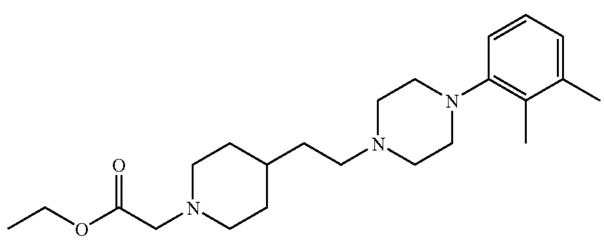 [SMILES: CCOC(=O)CN1CCC(CCN2CCN(c3cccc(C)c3C)CC2)CC1] | (4-{2-[4-(2,3-Dimethylphenyl)piperazin-1-yl]ethyl}piperidin-1-yl)acetic acid ethyl ester | 82 | IIIB |
| 534 | 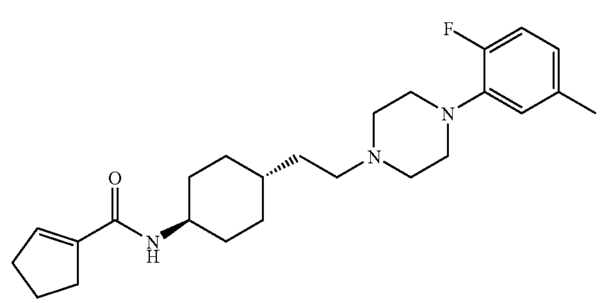 [SMILES: Cc1ccc(F)c(N2CCN(CC[C@H]3CC[C@H](NC(=O)C4=CCCC4)CC3)CC2)c1] | Cyclopent-1-enecarboxylic acid (4-{2-[4-(2-fluoro-5-methylphenyl)piperazin-1-yl]ethyl}cyclohexyl) amide | 174 | IIA |
| 535 | 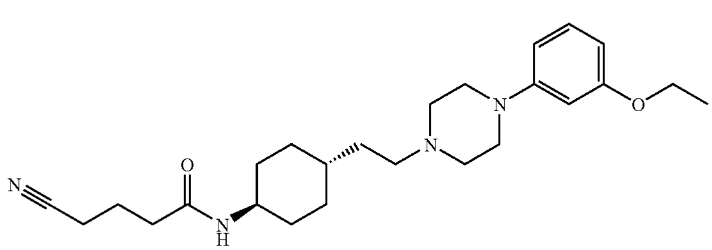 [SMILES: CCOc1cccc(N2CCN(CC[C@H]3CC[C@H](NC(=O)CCCC#N)CC3)CC2)c1] | 4-Cyano-N-(4-{2-[4-(3-ethoxyphenyl)piperazin-1-yl]ethyl}cyclohexyl)butanamide | 121 | IIA |

| Ex | Structure | Name | M.P. (° C.) | Synthetic Path |
|---|---|---|---|---|
| 536 | 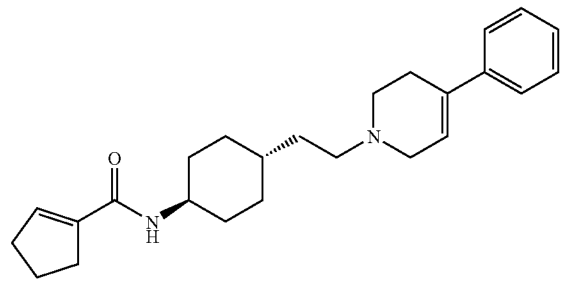 | Cyclopent-1-enecarboxylic acid {4-[2-(4-phenyl-3,6-dihydro-2H-pyridin-1-yl)ethyl]cyclohexyl} amide | 202 | IIA |
| 537 | 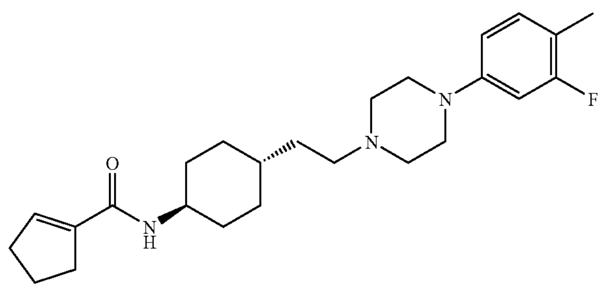 [SMILES: Cc1ccc(N2CCN(CC[C@H]3CC[C@H](NC(=O)C4=CCCC4)CC3)CC2)cc1F] | Cyclopent-1-enecarboxylic acid (4-{2-[4-(3-fluoro-4-methylphenyl)piperazin-1-yl]ethyl}cyclohexyl) amide | 220 | IIA |
| 538 | 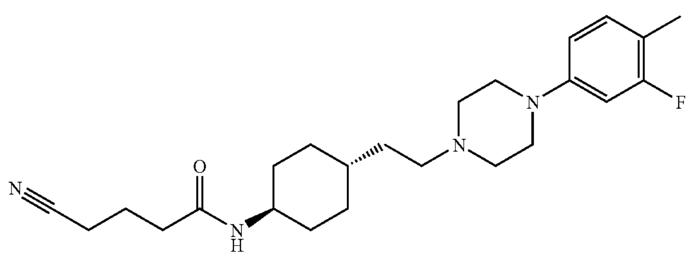 [SMILES: Cc1ccc(N2CCN(CC[C@H]3CC[C@H](NC(=O)CCCC#N)CC3)CC2)cc1F] | 4-Cyano-N-(4-{2-[4-(3-fluoro-4-methylphenyl)piperazin-1-yl]ethyl}cyclohexyl)butanamide | 180 | IIA |
| 539 | 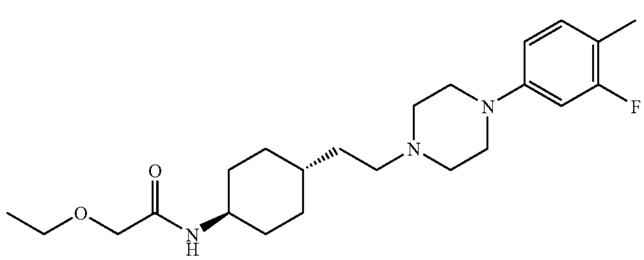 [SMILES: CCOCC(=O)N[C@H]1CC[C@H](CCN2CCN(c3ccc(C)c(F)c3)CC2)CC1] | 2-Ethoxy-N-(4-{2-[4-(3-fluoro-4-methylphenyl)piperazin-1-yl]ethyl}cyclohexyl)acetamide | 124 | IIA |
| 540 | 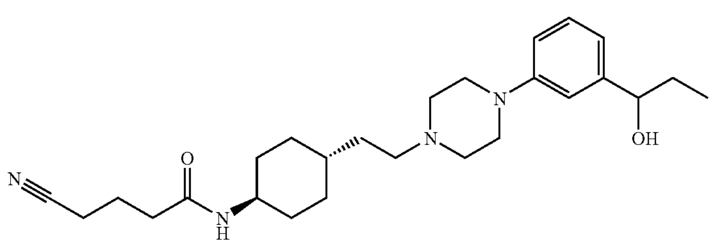 [SMILES: CCC(O)c1cccc(N2CCN(CC[C@H]3CC[C@H](NC(=O)CCCC#N)CC3)CC2)c1] | 4-Cyano-N-[4-(2-{4-[3-(1-hydroxypropyl)phenyl]piperazin-1-yl}ethyl)cyclohexyl]butanamide | 151 | IIA |

| Ex | Structure | Name | M.P. (° C.) | Synthetic Path |
|---|---|---|---|---|
| 541 | 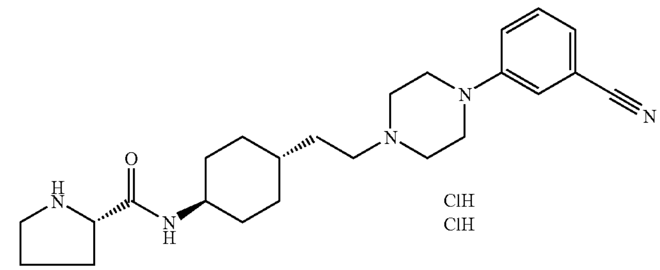 [SMILES: N#Cc1cccc(N2CCN(CC[C@H]3CC[C@H](NC(=O)[C@@H]4CCCN4)CC3)CC2)c1 ; Cl ; Cl] | Pyrrolidine-2-carboxylic acid (4-{2-[4-(3-cyanophenyl)piperazin-1-yl]ethyl}cyclohexyl) amide, dihydrochloride | 314 | IIA |
| 542 | 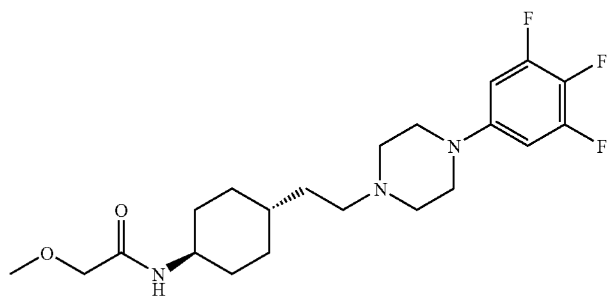 [SMILES: COCC(=O)N[C@H]1CC[C@H](CCN2CCN(c3cc(F)c(F)c(F)c3)CC2)CC1] | 2-Methoxy-N-(4-{2-[4-(3,4,5-trifluorophenyl)piperazin-1-yl]ethyl}cyclohexyl)acetamide | 153 | IIA |
| 543 | 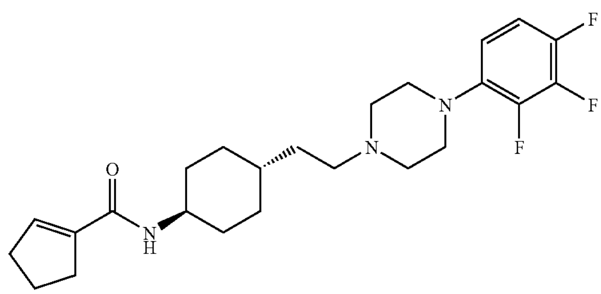 [SMILES: O=C(N[C@H]1CC[C@H](CCN2CCN(c3ccc(F)c(F)c3F)CC2)CC1)C1=CCCC1] | Cyclopent-1-enecarboxylic acid (4-{2-[4-(2,3,4-trifluorophenyl)piperazin-1-yl]ethyl}cyclohexyl) amide | 213 | IIA |
| 544 | 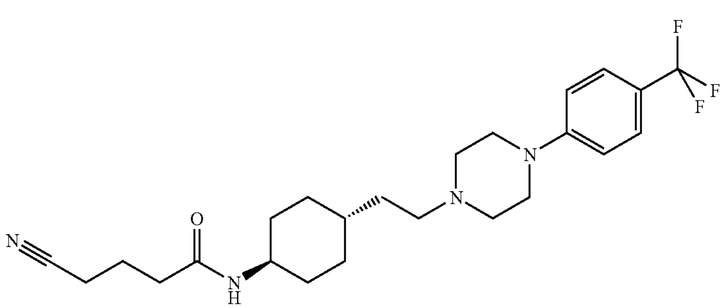 [SMILES: N#CCCCC(=O)N[C@H]1CC[C@H](CCN2CCN(c3ccc(C(F)(F)F)cc3)CC2)CC1] | 4-Cyano-N-(4-{2-[4-(4-trifluoromethylphenyl)piperazin-1-yl]ethyl}cyclohexyl)butanamide | 207 | IIA |
| 545 | 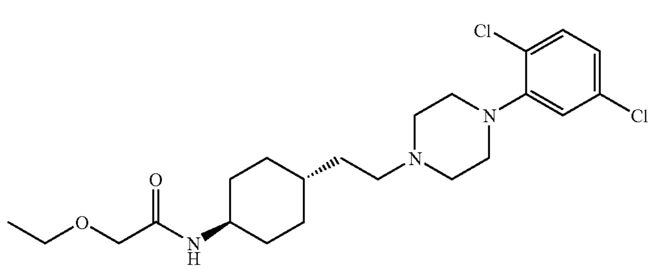 [SMILES: CCOCC(=O)N[C@H]1CC[C@H](CCN2CCN(c3cc(Cl)ccc3Cl)CC2)CC1] | N-(4-{2-[4-(2,5-Dichlorophenyl)piperazin-1-yl]ethyl}cyclohexyl)-2-ethoxyacetamide | 128 | IIA |

-continued

| Ex | Structure | Name | M.P. (°C.) | Synthetic Path |
|---|---|---|---|---|
| 546 | 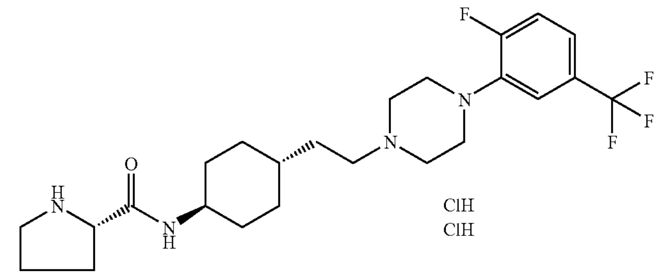 [SMILES: O=C(N[C@H]1CC[C@H](CCN2CCN(c3cc(C(F)(F)F)ccc3F)CC2)CC1)[C@@H]1CCCN1 ; Cl ; Cl] | Pyrrolidine-2-carboxylic acid (4-{2-[4-(2-fluoro-5-trifluoromethylphenyl)piperazin-1-yl]ethyl}cyclohexyl) amide | 274 | IIA |
| 547 | 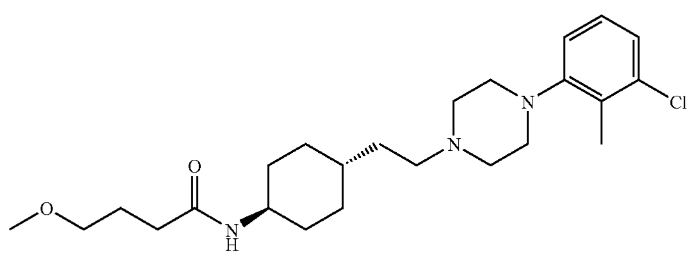 [SMILES: COCCCC(=O)N[C@H]1CC[C@H](CCN2CCN(c3cccc(Cl)c3C)CC2)CC1] | N-(4-{2-[4-(3-Chloro-2-methylphenyl)piperazin-1-yl]ethyl}cyclohexyl)-4-methoxybutanamide | 188 | IIA |
| 548 | 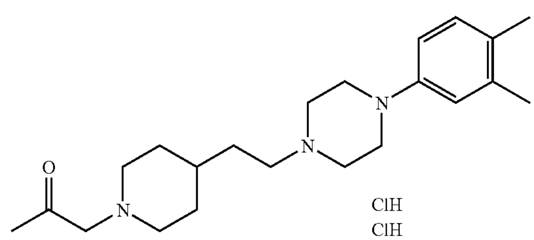 [SMILES: CC(=O)CN1CCC(CCN2CCN(c3ccc(C)c(C)c3)CC2)CC1 ; Cl ; Cl] | 1-(4-{2-[4-(3,4-Dimethylphenyl)-piperazin-1-yl]ethyl}piperidin-1-yl)propan-2-one | 275 | IIIB |
| 549 | 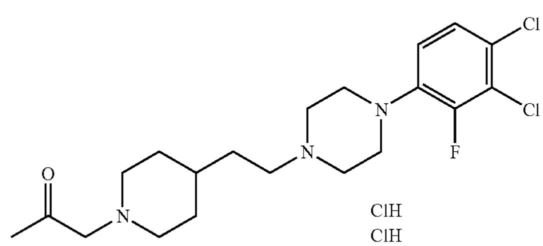 [SMILES: CC(=O)CN1CCC(CCN2CCN(c3ccc(Cl)c(Cl)c3F)CC2)CC1 ; Cl ; Cl] | 1-(4-{2-[4-(3,4-Dichloro-2-fluorophenyl)piperazin-1-yl]ethyl}piperidin-1-yl)propan-2-one | 230 | IIIB |
| 550 | 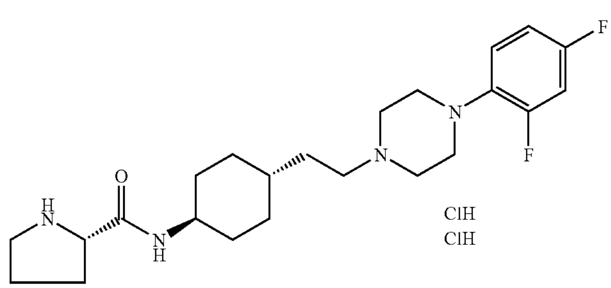 [SMILES: O=C(N[C@H]1CC[C@H](CCN2CCN(c3ccc(F)cc3F)CC2)CC1)[C@@H]1CCCN1 ; Cl ; Cl] | Pyrrolidine-2-carboxylic acid (4-{2-[4-(2,4-difluorophenyl)-piperazin-1-yl]ethyl}cyclohexyl) amide, dihydrochloride | 260 | IIA |

| Ex | Structure | Name | M.P. (°C.) | Synthetic Path |
|---|---|---|---|---|
| 551 | 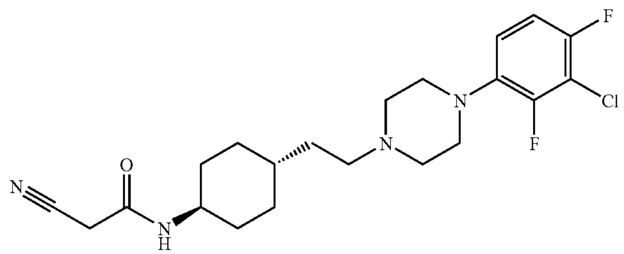 [SMILES: N#CCC(=O)N[C@H]1CC[C@H](CCN2CCN(c3ccc(F)c(Cl)c3F)CC2)CC1] | N-(4-{2-[4-(3-Chloro-2,4-difluorophenyl)piperazin-1-yl]ethyl}cyclohexyl)-2-cyanoacetamide | 198 | IIA |
| 552 | 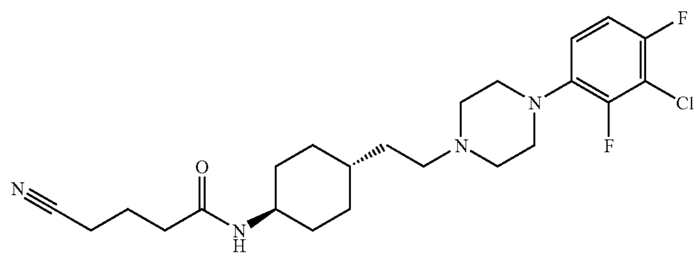 [SMILES: N#CCCCC(=O)N[C@H]1CC[C@H](CCN2CCN(c3ccc(F)c(Cl)c3F)CC2)CC1] | N-(4-{2-[4-(3-Chloro-2,4-difluorophenyl)piperazin-1-yl]ethyl}cyclohexyl)-4-cyanobutanamide | 192 | IIA |
| 553 | ClH ClH | 1-(4-{2-[4-(2-Fluoro-5-trifluoromethylphenyl)piperazin-1-yl]ethyl}piperidin-1-yl)propan-2-one, dihydrochloride | 230 | IIIB |
| 554 | ClH ClH | 1-(4-{2-[4-(3-Chloro-2-methoxyphenyl)piperazin-1-yl]ethyl}piperidin-1-yl)propan-2-one, dihydrochloride | 270 | IIIB |
| 555 | 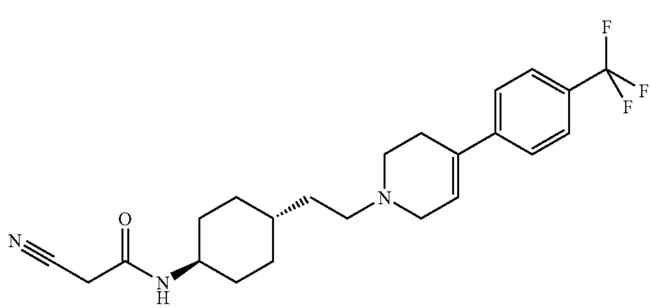 [SMILES: N#CCC(=O)N[C@H]1CC[C@H](CCN2CC=C(c3ccc(C(F)(F)F)cc3)CC2)CC1] | 2-Cyano-N-(4-{2-[4-(4-trifluoromethylphenyl)-3,6-dihydro-2H-pyridin-1-yl]ethyl}cyclohexyl)acetamide | 217 | IIA |

-continued

| Ex | Structure | Name | M.P. (° C.) | Synthetic Path |
|---|---|---|---|---|
| 556 | 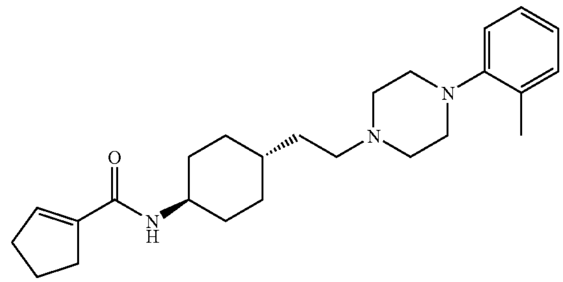 [SMILES: Cc1ccccc1N1CCN(CC[C@H]2CC[C@H](NC(=O)C3=CCCC3)CC2)CC1] | Cyclopent-1-enecarboxylic acid {4-[2-(4-o-tolylpiperazin-1-yl)ethyl]cyclohexyl} amide | 181 | IIA |
| 557 | 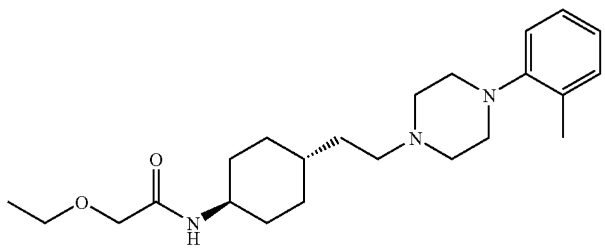 [SMILES: CCOCC(=O)N[C@H]1CC[C@H](CCN2CCN(c3ccccc3C)CC2)CC1] | 2-Ethoxy-N-{4-[2-(4-o-tolylpiperazin-1-ylethyl]cyclohexyl}acetamide | 101 | IIA |
| 558 | 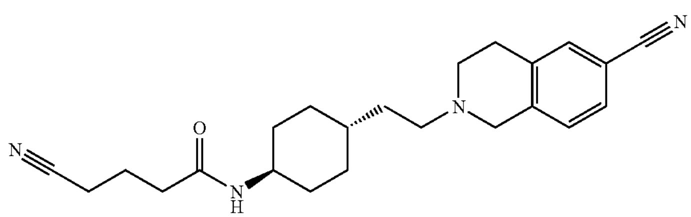 [SMILES: N#CCCCC(=O)N[C@H]1CC[C@H](CCN2CCc3cc(C#N)ccc3C2)CC1] | 4-Cyano-N-{4-[2-(6-cyano-3,4-dihydro-1H-isoquinolin-2-yl)ethyl]cyclohexyl}butanamide | 177 | IIA |
| 559 | 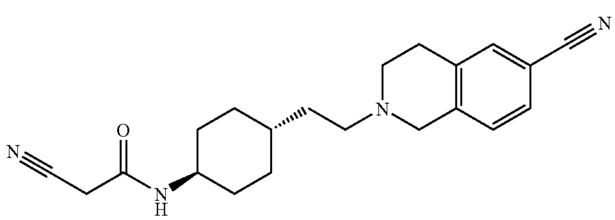 [SMILES: N#CCC(=O)N[C@H]1CC[C@H](CCN2CCc3cc(C#N)ccc3C2)CC1] | 2-Cyano-N-{4-[2-(6-cyano-3,4-dihydro-1H-isoquinolin-2-yl)ethyl]cyclohexyl}acetamide | 206 | IIA |
| 560 | 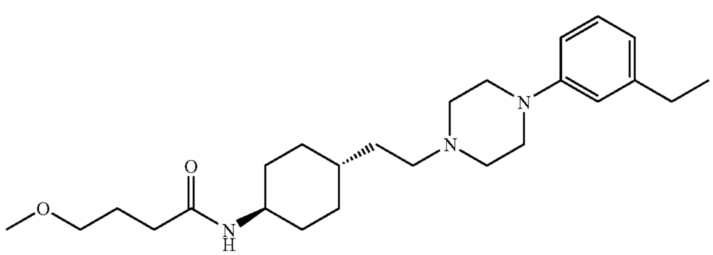 [SMILES: CCc1cccc(N2CCN(CC[C@H]3CC[C@H](NC(=O)CCCOC)CC3)CC2)c1] | N-(4-{2-[4-(3-Ethylphenyl)piperazin-1-yl]ethyl}cyclohexyl)-4-methoxybutanamide | 130 | IIA |
| 561 | 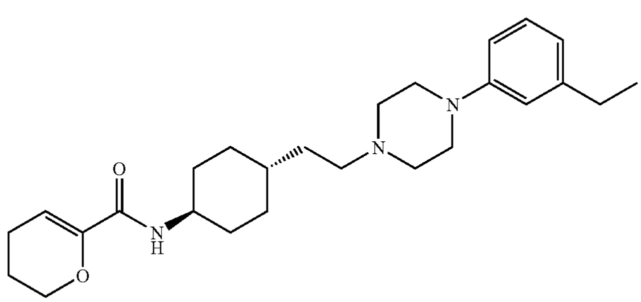 [SMILES: CCc1cccc(N2CCN(CC[C@H]3CC[C@H](NC(=O)C4=CCCCO4)CC3)CC2)c1] | 5,6-Dihydro-4H-pyran-2-carboxylic acid (4-{2-[4-(3-ethylphenyl)piperazin-1-yl]ethyl}cyclohexyl) amide | 135 | IIA |

-continued

| Ex | Structure | Name | M.P. (° C.) | Synthetic Path |
|---|---|---|---|---|
| 562 | 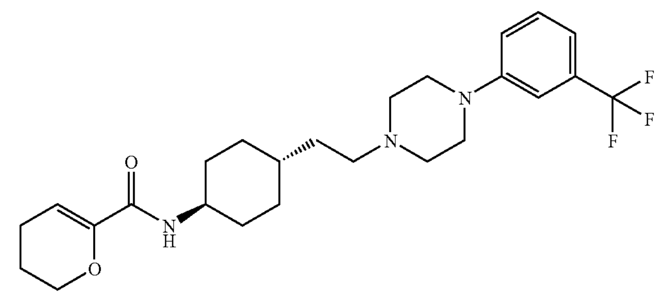 [SMILES: O=C(N[C@H]1CC[C@H](CCN2CCN(c3cccc(C(F)(F)F)c3)CC2)CC1)C1=CCCCO1] | 5,6-Dihydro-4H-pyran-2-carboxylic acid (4-{2-[4-(3-trifluoromethylphenyl)piperazin-1-yl]ethyl}cyclohexyl) amide | 142 | IIA |
| 563 | 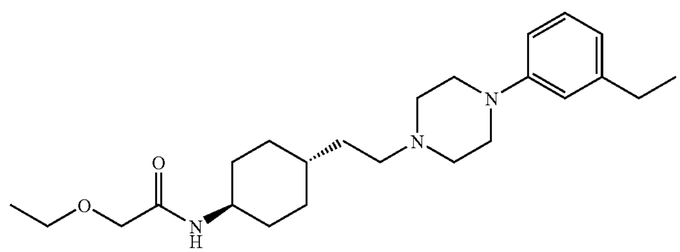 [SMILES: CCOCC(=O)N[C@H]1CC[C@H](CCN2CCN(c3cccc(CC)c3)CC2)CC1] | 2-Ethoxy-N-(4-{2-[4-(3-ethylphenyl)piperazin-1-yl]ethyl}cyclohexyl)acetamide | 100 | IIA |
| 564 | 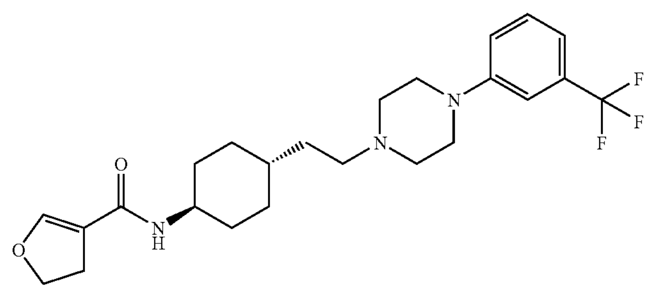 [SMILES: O=C(N[C@H]1CC[C@H](CCN2CCN(c3cccc(C(F)(F)F)c3)CC2)CC1)C1=COCC1] | 4,5-Dihydrofuran-3-carboxylic acid (4-{2-[4-(3-trifluoromethylphenyl)piperazin-1-yl]ethyl}cyclohexyl) amide | 175 | IIA |
| 565 | 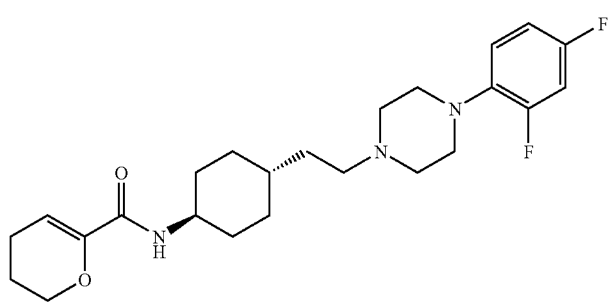 [SMILES: O=C(N[C@H]1CC[C@H](CCN2CCN(c3ccc(F)cc3F)CC2)CC1)C1=CCCCO1] | 5,6-Dihydro-4H-pyran-2-carboxylic acid (4-{2-[4-(2,4-difluorophenyl)piperazin-1-yl]ethyl}cyclohexyl) amide | 160 | IIA |
| 566 | 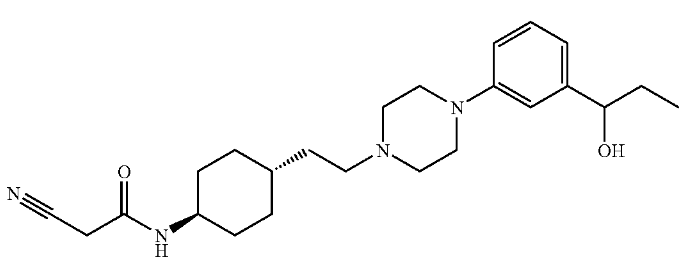 [SMILES: CCC(O)c1cccc(N2CCN(CC[C@H]3CC[C@H](NC(=O)CC#N)CC3)CC2)c1] | 2-Cyano-N-[4-(2-{4-[3-(1-hydroxypropyl)phenyl]piperazin-1-yl}ethyl)cyclohexyl]acetamide | 157 | IIA |

| Ex | Structure | Name | M.P. (° C.) | Synthetic Path |
|---|---|---|---|---|
| 567 | 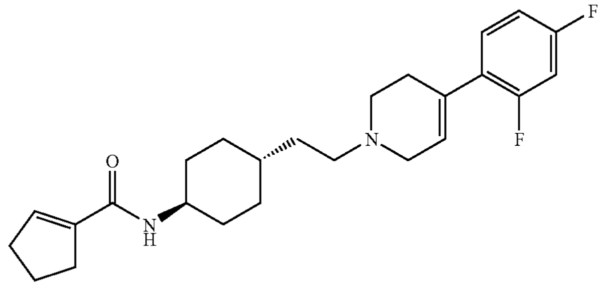 | Cyclopent-1-enecarboxylic acid (4-{2-[4-(2,4-difluorophenyl)-3,6-dihydro-2H-pyridin-1-yl]ethyl}cyclohexyl) amide | 166 | IIA |
| 568 | 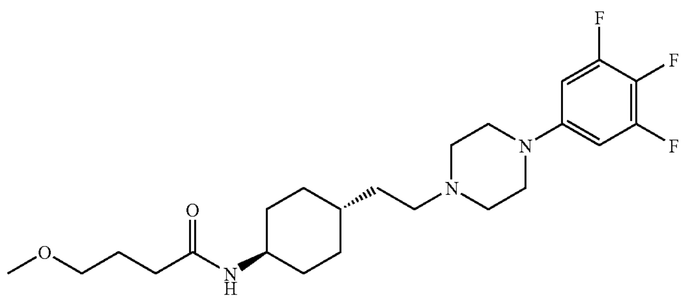 [SMILES: COCCCC(=O)N[C@H]1CC[C@H](CCN2CCN(c3cc(F)c(F)c(F)c3)CC2)CC1] | 4-Methoxy-N-(4-{2-[4-(3,4,5-trifluorophenyl)piperazin-1-yl]ethyl}cyclohexyl)butanamide | 194 | IIA |
| 569 | ClH ClH | 1-{4-[2-(4-Indan-5-ylpiperazin-1-yl)ethyl]piperidin-1-yl}propan-2-one, dihydrochloride | 291 | IIIB |
| 570 | 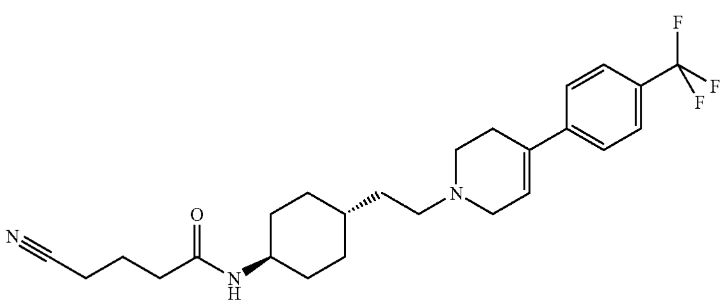 | 4-Cyano-N-(4-{2-[4-(4-trifluoromethylphenyl)-3,6-dihydro-2H-pyridin-1-yl]ethyl}cyclohexyl)butanamide | 185 | IIA |
| 571 | 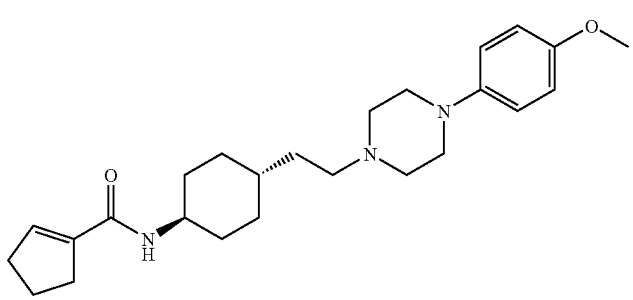 [SMILES: COc1ccc(N2CCN(CC[C@H]3CC[C@H](NC(=O)C4=CCCC4)CC3)CC2)cc1] | Cyclopent-1-enecarboxylic acid (4-{2-[4-(4-methoxyphenyl)-piperazin-1-yl]ethyl}cyclohexyl) amide | 205 | IIA |

-continued

| Ex | Structure | Name | M.P. (° C.) | Synthetic Path |
|---|---|---|---|---|
| 572 | 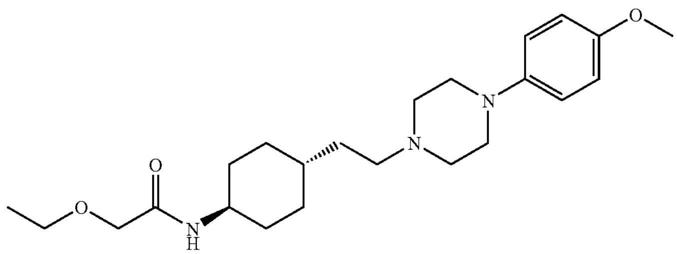 [SMILES: CCOCC(=O)N[C@H]1CC[C@H](CCN2CCN(c3ccc(OC)cc3)CC2)CC1] | 2-Ethoxy-N-(4-{2-[4-(4-methoxyphenyl)piperazin-1-yl]ethyl}cyclohexyl)acetamide | 132 | IIA |
| 573 | 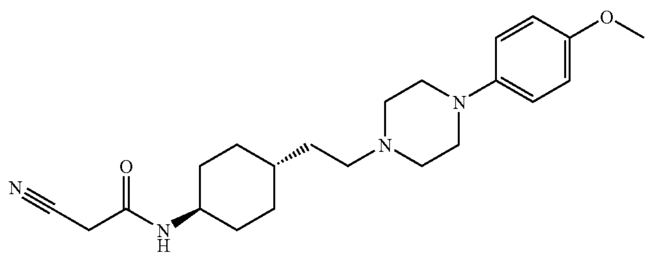 [SMILES: COc1ccc(N2CCN(CC[C@H]3CC[C@H](NC(=O)CC#N)CC3)CC2)cc1] | 2-Cyano-N-(4-{2-[4-(4-methoxyphenyl)piperazin-1-yl]ethyl}cyclohexyl)acetamide | 227 | IIA |
| 574 | 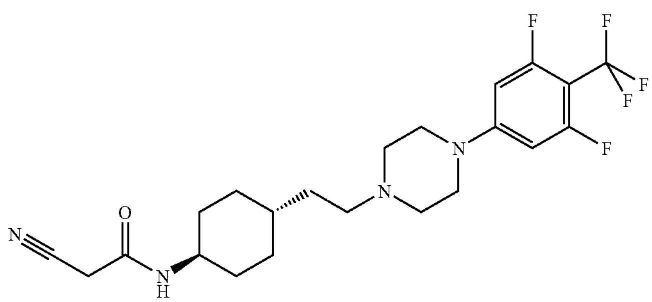 [SMILES: N#CCC(=O)N[C@H]1CC[C@H](CCN2CCN(c3cc(F)c(C(F)(F)F)c(F)c3)CC2)CC1] | 2-Cyano-N-(4-{2-[4-(3,5-difluoro-4-trifluoromethylphenyl)piperazin-1-yl]ethyl}cyclohexyl)acetamide | 231 | IIA |
| 575 | 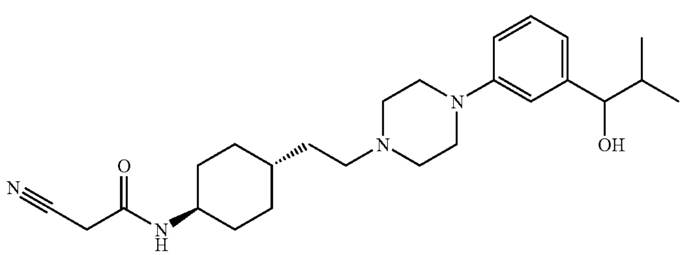 [SMILES: CC(C)C(O)c1cccc(N2CCN(CC[C@H]3CC[C@H](NC(=O)CC#N)CC3)CC2)c1] | 2-Cyano-N-[4-(2-{4-[3-(2-hydroxy-2-methylpropyl)phenyl]piperazin-1-yl}ethyl)cyclohexyl]acetamide | 119 | IIA |
| 576 | 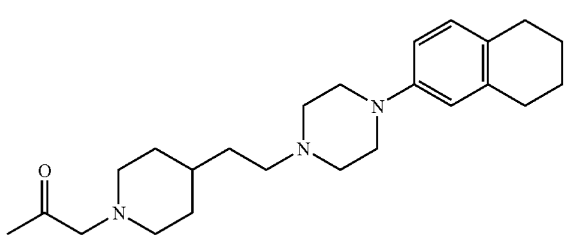 [SMILES: CC(=O)CN1CCC(CCN2CCN(c3ccc4c(c3)CCCC4)CC2)CC1] | 1-(4-{2-[4-(6,7,8,9-Tetrahydro-naphthalen-2-yl)piperazin-1-yl]piperidin-1-yl)propan-2-one | 75 | IIIB |

-continued

| Ex | Structure | Name | M.P. (° C.) | Synthetic Path |
|---|---|---|---|---|
| 577 | 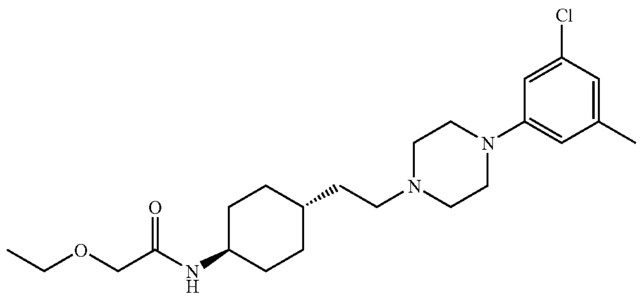 [SMILES: CCOCC(=O)N[C@H]1CC[C@H](CCN2CCN(c3cc(C)cc(Cl)c3)CC2)CC1] | N-(4-{2-[4-(3-Chloro-5-methylphenyl)piperazin-1-yl]ethyl}cyclohexyl)-2-ethoxyacetamide | 100 | IIA |
| 578 | 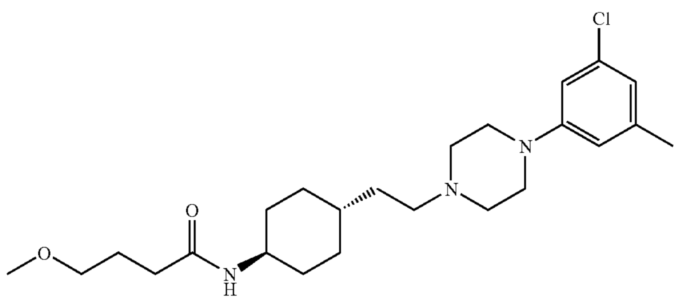 | N-(4-{2-[4-(3-Chloro-5-methylphenyl)piperazin-1-yl]ethyl}cyclohexyl)-4-methoxybutanamide | 167 | IIA |
| 579 | 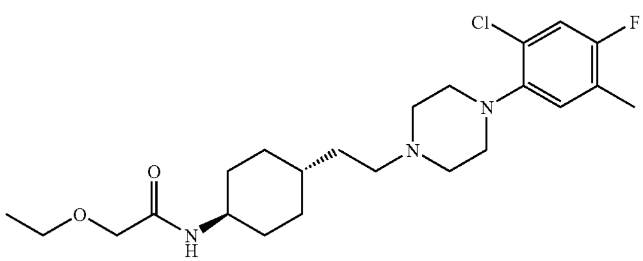 [SMILES: CCOCC(=O)N[C@H]1CC[C@H](CCN2CCN(c3cc(C)c(F)cc3Cl)CC2)CC1] | N-(4-{2-[4-(2-Chloro-4-fluoro-5-methylphenyl)piperazin-1-yl]ethyl}cyclohexyl)-2-ethoxyacetamide | 132 | IIA |
| 580 | 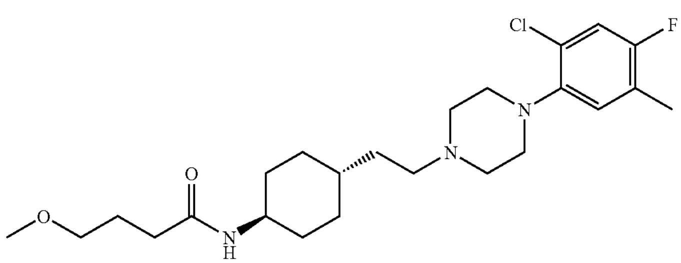 [SMILES: COCCCC(=O)N[C@H]1CC[C@H](CCN2CCN(c3cc(C)c(F)cc3Cl)CC2)CC1] | N-(4-{2-[4-(2-Chloro-4-fluoro-5-methylphenyl)piperazin-1-yl]ethyl}cyclohexyl)-4-methoxybutanamide | 171 | IIA |
| 581 | 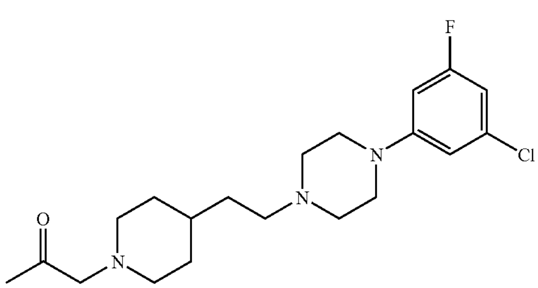 | 1-(4-{2-[4-(3-Chloro-5-fluorophenyl)piperazin-1-yl]ethyl}piperidin-1-yl)propan-2-one | 107 | IIIB |

| Ex | Structure | Name | M.P. (°C.) | Synthetic Path |
|---|---|---|---|---|
| 582 | 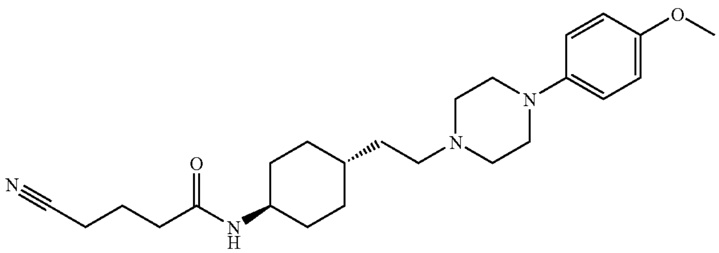 [SMILES: COc1ccc(N2CCN(CC[C@H]3CC[C@H](NC(=O)CCCC#N)CC3)CC2)cc1] | 4-Cyano-N-(4-{2-[4-(4-methoxyphenyl)piperazin-1-yl]ethyl}cyclohexyl)butanamide | 200 | IIA |
| 583 | ClH ClH | 1-(4-{2-[4-(3,4-Dihydro-2H-benzo[b][1,4]dioxepin-6-yl)piperazin-1-yl]ethyl}piperidin-1-yl)propan-2-one, dihydrochloride | 280 | IIIB |
| 584 | 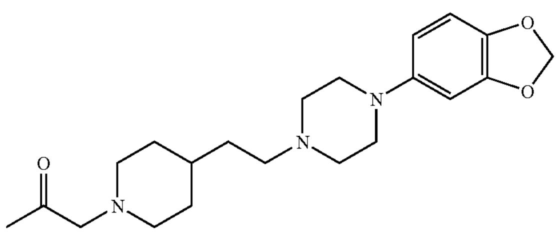 [SMILES: CC(=O)CN1CCC(CCN2CCN(c3ccc4c(c3)OCO4)CC2)CC1] | 1-{4-[2-(4-Benzo[1,3]dioxol-5-ylpiperazin-1-yl)ethyl]piperidin-1-yl}propan-2-one | 113 | IIIB |
| 585 | 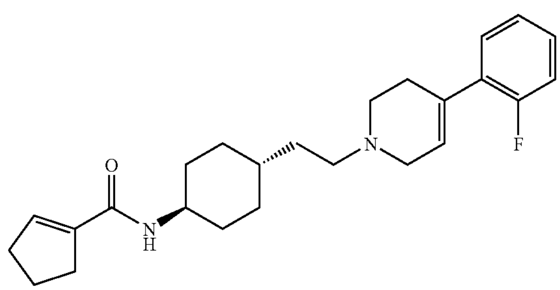 [SMILES: O=C(N[C@H]1CC[C@H](CCN2CC=C(c3ccccc3F)CC2)CC1)C1=CCCC1] | Cyclopent-1-enecarboxylic acid (4-{2-[4-(2-fluorophenyl)-3,6-dihydro-2H-pyridin-1-yl]ethyl}cyclohexyl) amide | 192 | IIA |
| 586 | 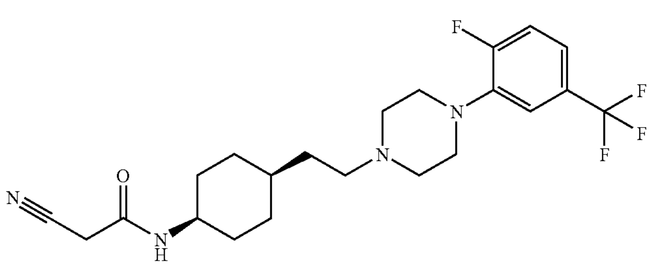 [SMILES: N#CCC(=O)N[C@H]1CC[C@@H](CCN2CCN(c3cc(C(F)(F)F)ccc3F)CC2)CC1] | 2-Cyano-N-(4-{2-[4-(2-fluoro-5-trifluoromethylphenyl)piperazin-1-yl]ethyl}cyclohexyl)acetamide | 152 | IIA |

-continued

| Ex | Structure | Name | M.P. (° C.) | Synthetic Path |
|---|---|---|---|---|
| 587 | 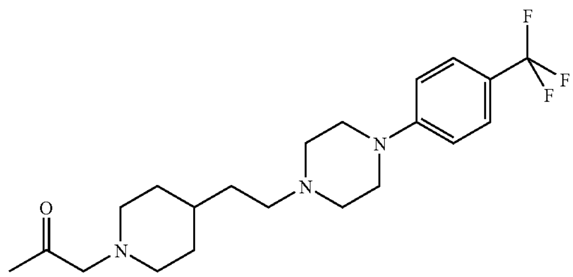 [SMILES: CC(=O)CN1CCC(CCN2CCN(c3ccc(C(F)(F)F)cc3)CC2)CC1] | 1-(4-{2-[4-(4-Trifluoromethylphenyl)piperazin-1-yl]ethyl}pipericin-1-yl)propan-2-one | 104 | IIIB |
| 588 | 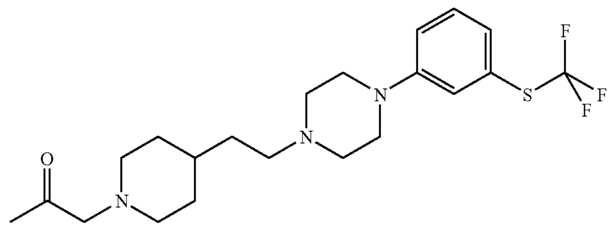 [SMILES: CC(=O)CN1CCC(CCN2CCN(c3cccc(SC(F)(F)F)c3)CC2)CC1] | 1-(4-{2-[4-(4-Trifluoromethylsulfanylphenyl)piperazin-1-yl]ethyl}piperidin-1-yl)propan-2-one | 67 | IIIB |
| 589 | HCl HCl | 1-[4-(2-{4-[3-(1,1-Difluoroethyl)phenyl]piperazin-1-yl}ethyl)piperidin-1-yl]propan-2-one, dihydrochloride | 256 | IIIB |
| 590 | HCl HCl | 1-(4-{2-[4-(3-Difluoromethyl-phenyl)piperazin-1-yl]ethyl}piperidin-1-yl)propan-2-one, dihydrochloride | 265 | IIIB |
| 591 | HCl HCl | 1-{4-[2-(4-Benzo[1,3]dioxol-4-ylpiperazin-1-yl)ethyl]piperidin-1-yl}propan-2-one, dihydrochloride | 264 | IIIB |
| 592 | 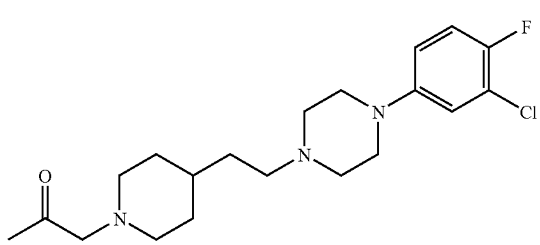 [SMILES: CC(=O)CN1CCC(CCN2CCN(c3ccc(F)c(Cl)c3)CC2)CC1] | 1-(4-{2-[4-(3-Chloro-4-fluorophenyl)piperazin-1-yl]ethyl}piperidin-1-yl)propan-2-one | 92 | IIIB |

-continued

| Ex | Structure | Name | M.P. (°C.) | Synthetic Path |
|---|---|---|---|---|
| 593 | 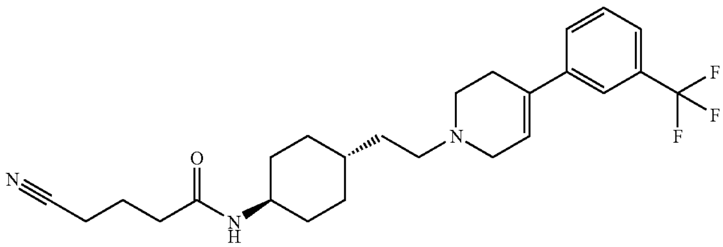 [SMILES: N#CCCCC(=O)N[C@H]1CC[C@H](CCN2CC=C(c3cccc(C(F)(F)F)c3)CC2)CC1] | 4-Cyano-N-(4-{2-[4-(3-trifluoromethylphenyl)-3,6-dihydro-2H-pyridin-1-yl]ethyl}cyclohexyl)butanamide | 102 | IIA |
| 594 | 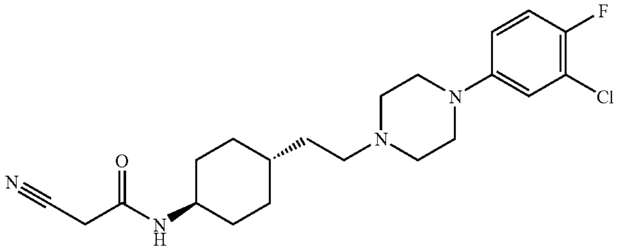 | N-(4-{2-[4-(3-Chloro-4-fluorophenyl)piperazin-1-yl]ethyl}cyclohexyl)-2-cyanoacetamide | 176 | IIA |
| 595 | 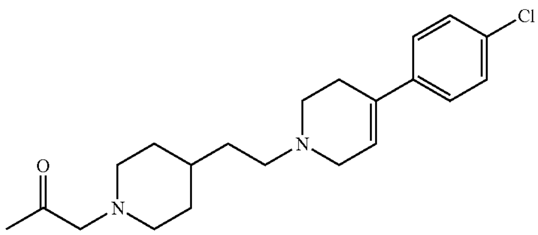 [SMILES: CC(=O)CN1CCC(CCN2CC=C(c3ccc(Cl)cc3)CC2)CC1] | 1-(4-{2-[4-(4-Chlorophenyl)-3,6-dihydro-2H-pyridin-1-yl]ethyl}piperidin-1-yl)propan-2-one | 101 | IIIB |
| 596 | HCl HCl | 4-(4-{2-[1-(2-Oxopropyl)piperidin-4-yl]ethyl}piperazin-1-yl)-benzonitrile, dihydrochloride | 295 | IIIB |
| 597 | HCl HCl | 1-(4-{2-[4-(2-Fluoro-5-methylphenyl)piperazin-1-yl]ethyl}piperidin-1-yl)propan-2-one, dihydrochloride | 275 | IIIB |
| 598 | 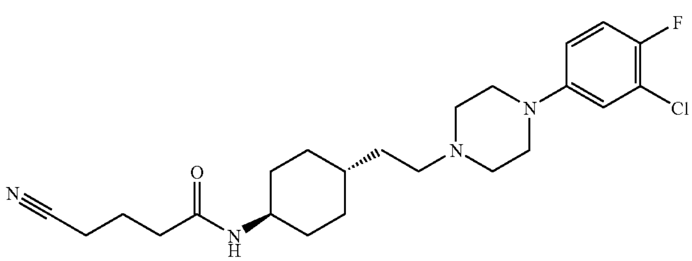 [SMILES: N#CCCCC(=O)N[C@H]1CC[C@H](CCN2CCN(c3ccc(F)c(Cl)c3)CC2)CC1] | N-(4-{2-[4-(3-Chloro-4-fluorophenyl)piperazin-1-yl]ethyl}cyclohexyl)-4-cyanobutanamide | 142 | IIA |

-continued

| Ex | Structure | Name | M.P. (° C.) | Synthetic Path |
|---|---|---|---|---|
| 599 | 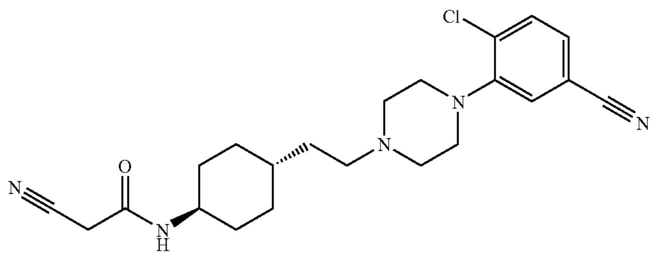 [SMILES: N#CCC(=O)N[C@H]1CC[C@H](CCN2CCN(c3cc(C#N)ccc3Cl)CC2)CC1] | N-(4-{2-[4-(2-Chloro-5-cyanophenyl)piperazin-1-yl]ethyl}cyclohexyl)-2-cyanoacetamide | 225 | IIA |
| 600 | HCl HCl | 1-(4-{2-[4-(2,6-Di-tert-butylpyrimidin-4-yl)piperazin-1-yl]ethyl}piperidin-1-yl)propan-2-one, dihydrochloride | 310 | IIIB |
| 601 | 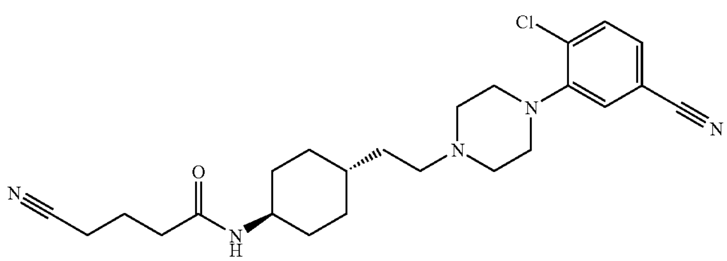 [SMILES: N#CCCCC(=O)N[C@H]1CC[C@H](CCN2CCN(c3cc(C#N)ccc3Cl)CC2)CC1] | N-(4-{2-[4-(2-Chloro-5-cyanophenyl)piperazin-1-yl]ethyl}cyclohexyl)-4-cyanobutanamide | 206 | IIA |
| 602 | 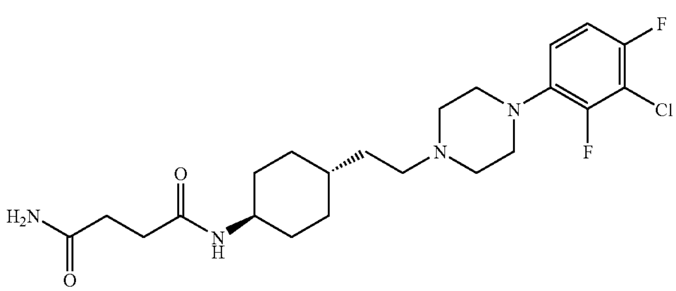 [SMILES: NC(=O)CCC(=O)N[C@H]1CC[C@H](CCN2CCN(c3ccc(F)c(Cl)c3F)CC2)CC1] | N-(4-{2-[4-(3-Chloro-2,4-difluorophenyl)piperazin-1-yl]ethyl}cyclohexyl)succinamide | 257 | IIA |
| 603 | 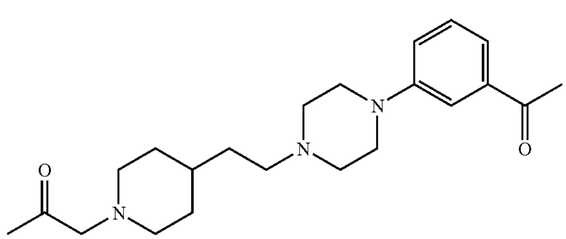 [SMILES: CC(=O)CN1CCC(CCN2CCN(c3cccc(C(C)=O)c3)CC2)CC1] | 1-(4-{2-[4-(3-Acetylphenyl)-piperazin-1-yl]ethyl}piperidin-1-yl)propan-2-one | 85 | IIIB |

-continued

| Ex | Structure | Name | M.P. (° C.) | Synthetic Path |
|---|---|---|---|---|
| 604 | 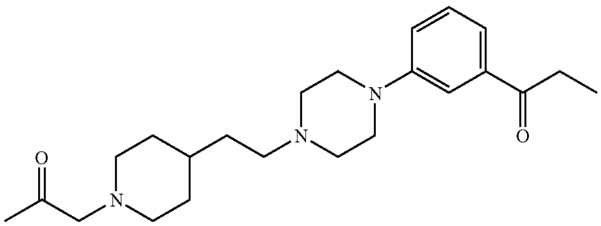 [SMILES: CCC(=O)c1cccc(N2CCN(CCC3CCN(CC(C)=O)CC3)CC2)c1] | 1-[3-(4-{2-[1-(2-Oxopropyl)piperidin-4-yl]ethyl}piperazin-1-yl)phenyl]propan-1-one | 68 | IIIB |
| 605 | HCl HCl | 2-Methyl-1-[3-(4-{2-[1-(2-oxopropyl)piperidin-4-yl]ethyl}-piperazin-1-yl)phenyl]propan-1-one, dihydrochloride | 250 | IIIB |
| 606 | 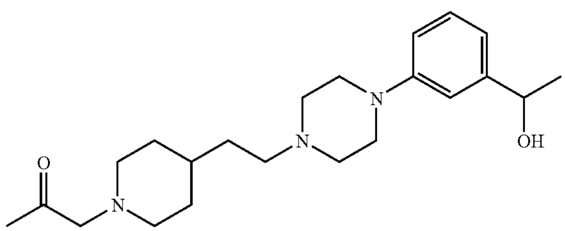 [SMILES: CC(=O)CN1CCC(CCN2CCN(c3cccc(C(C)O)c3)CC2)CC1] | 1-[4-(2-{4-[3-(1-Hydroxyethyl)phenyl]piperazin-1-yl}ethyl)piperidin-1-yl]propan-2-one | 97 | IIIB |
| 607 | 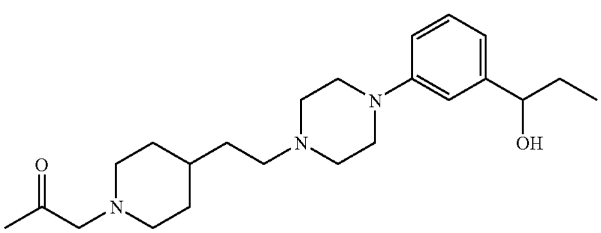 [SMILES: CCC(O)c1cccc(N2CCN(CCC3CCN(CC(C)=O)CC3)CC2)c1] | 1-[4-(2-{4-[3-(1-Hydroxypropyl)phenyl]piperazin-1-yl}ethyl)piperidin-1-yl]propan-2-one | 83 | IIIB |
| 608 | 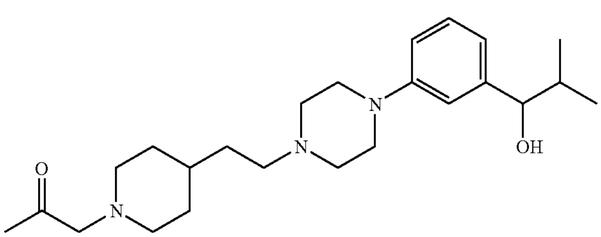 [SMILES: CC(=O)CN1CCC(CCN2CCN(c3cccc(C(O)C(C)C)c3)CC2)CC1] | 1-[4-(2-{4-[3-(1-Hydroxy-2-methylpropyl)phenyl]piperazin-1-yl}ethyl)piperidin-1-yl]propan-2-one | 78 | IIIB |
| 609 | HCl | 3-{4-[2-(4-[4-Indan-4-ylpiperazin1-yl)ethyl]piperidin-1-yl}-3-oxopropanenitrile, hydrochloride | 210 | IIIA |

-continued

| Ex | Structure | Name | M.P. (° C.) | Synthetic Path |
|---|---|---|---|---|
| 610 | 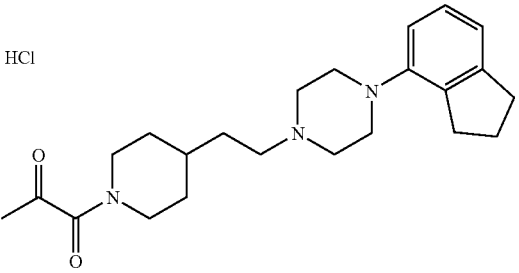 [SMILES: CC(=O)C(=O)N1CCC(CCN2CCN(c3cccc4c3CCC4)CC2)CC1 ; Cl] | 1-{4-[2-(4-Indan-4-ylpiperazin-1-yl)ethyl]piperidin-1-yl}propane-1,2-dione, hydrochloride | 225 | IIIA |
| 611 | 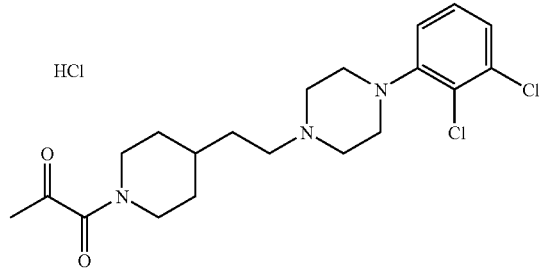 [SMILES: CC(=O)C(=O)N1CCC(CCN2CCN(c3cccc(Cl)c3Cl)CC2)CC1 ; Cl] | 1-(4-{2-[4-(2,3-Dichlorophenyl)piperazin-1-yl]ethyl}piperidin-1-yl)propane-1,2-dione, hydrochloride | 244 | IIIA |
| 612 | 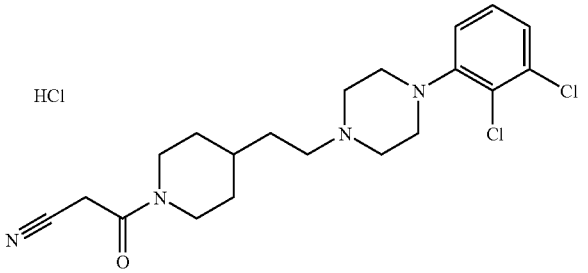 [SMILES: N#CCC(=O)N1CCC(CCN2CCN(c3cccc(Cl)c3Cl)CC2)CC1 ; Cl] | 3-(4-{2-[4-(2,3-Dichlorophenyl)piperazin-1-yl]ethyl}piperidin-1-yl)-3-oxopropanenitrile, hydrochloride | 228 | IIIA |
| 613 | 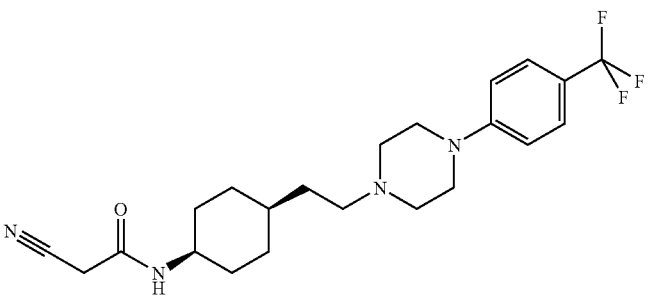 [SMILES: N#CCC(=O)N[C@H]1CC[C@@H](CCN2CCN(c3ccc(C(F)(F)F)cc3)CC2)CC1] | 2-Cyano-N-(4-{2-[4-(4-trifluoromethylphenyl)piperazin-1-yl]ethyl}cyclohexyl)acetamide | 156 | IIA |
| 614 | 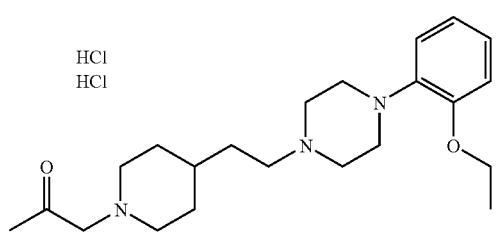 [SMILES: CCOc1ccccc1N1CCN(CCC2CCN(CC(C)=O)CC2)CC1 ; Cl ; Cl] | 1-(4-{2-[4-(2-Ethoxyphenyl)piperazin-1-yl]ethyl}piperidin-1-yl)propan-2-one, dihydrochloride | 271 | IIIB |

-continued

| Ex | Structure | Name | M.P. (° C.) | Synthetic Path |
|---|---|---|---|---|
| 615 | 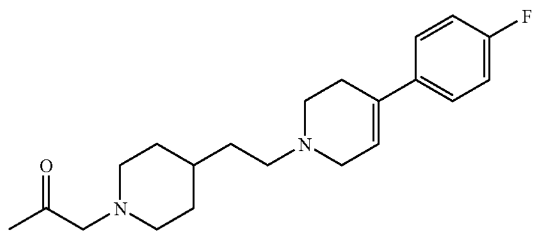 [SMILES: CC(=O)CN1CCC(CCN2CC=C(c3ccc(F)cc3)CC2)CC1] | 1-(4-{2-[4-(4-Fluorophenyl)-3,6-dihydro-2H-pyridin-1-yl]ethyl}piperidin-1-yl)propan-2-one | 72 | IIIB |
| 616 | 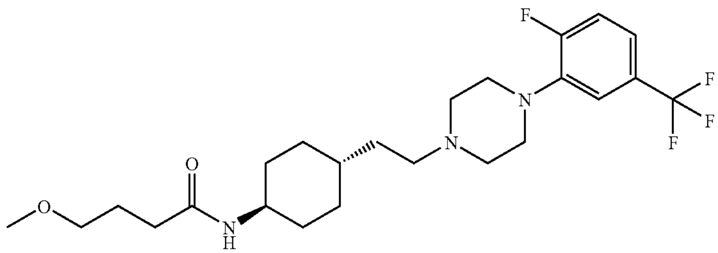 | N-(4-{2-[4-(2-Fluoro-5-trifluoromethylphenyl)piperazin-1-yl]ethyl}cyclohexyl)-4-methoxybutanamide | 177 | IIA |
| 617 | HCl HCl | 1-(4-{2-[4-(2,5-Dichlorophenyl)piperazin-1-yl]ethyl}piperidin-1-yl)propan-2-one, dihydrochloride | 172 | IIIB |
| 618 | 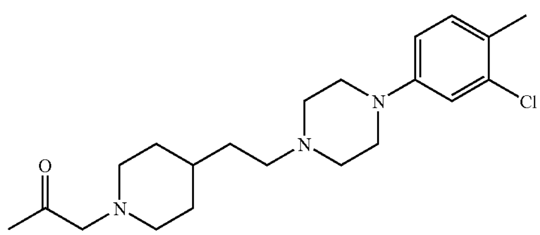 [SMILES: CC(=O)CN1CCC(CCN2CCN(c3ccc(C)c(Cl)c3)CC2)CC1] | 1-(4-{2-[4-(3-Chloro-4-methylphenyl)piperazin-1-yl]ethyl}piperidin-1-yl)propan-2-one | 103 | IIIB |
| 619 | HCl HCl | 1-{4-[2-(4-Indan-4-yl-3,6-dihydro-2H-pyridin-1-yl)ethyl]piperidin-1-yl}propan-2-one, dihydrochloride | 291 | IIIB |
| 620 | HCl | 4-{4-[2-(4-Indan-4-ylpiperazin-1-yl)ethyl]piperidin-1-yl}-4-oxobutanamide | 137 | IIIA |

| Ex | Structure | Name | M.P. (° C.) | Synthetic Path |
|---|---|---|---|---|
| 621 | 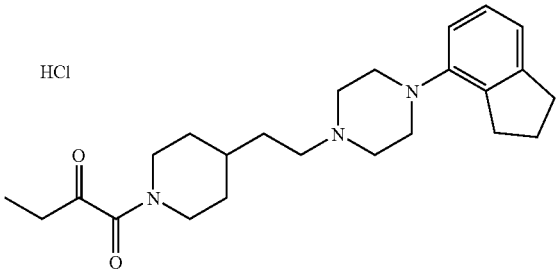 [SMILES: CCC(=O)C(=O)N1CCC(CCN2CCN(c3cccc4c3CCC4)CC2)CC1 ; Cl] | 1-{4-[2-(4-Indan-4-ylpiperazin-1-yl)ethyl]piperidin-1-yl}butane-1,2-dione, hydrochloride | 202 | IIIA |
| 622 | 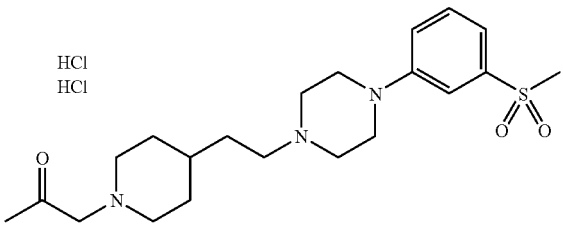 [SMILES: CC(=O)CN1CCC(CCN2CCN(c3cccc(S(C)(=O)=O)c3)CC2)CC1 ; Cl ; Cl] | 1-(4-{2-[4-(3-Methanesulfonylphenyl)piperazin-1-yl]ethyl}piperidin-1-yl)propan-2-one, dihydrochloride | 260 | IIIB |
| 623 | 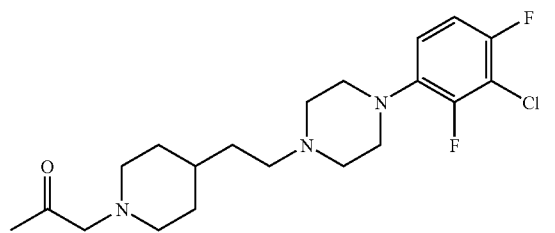 [SMILES: CC(=O)CN1CCC(CCN2CCN(c3ccc(F)c(Cl)c3F)CC2)CC1] | 1-(4-{2-[4-(3-Chloro-2,4-difluorophenyl)piperazin-1-yl]ethyl}piperidin-1-yl)propan-2-one | 82 | IIIB |
| 624 | 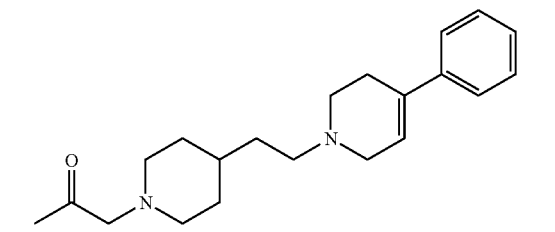 [SMILES: CC(=O)CN1CCC(CCN2CC=C(c3ccccc3)CC2)CC1] | 1-{4-[2-(4-Phenyl-3,6-dihydro-2H-pyridin-1-yl)ethyl]piperidin-1-yl}propan-2-one | 80 | IIIB |
| 625 | 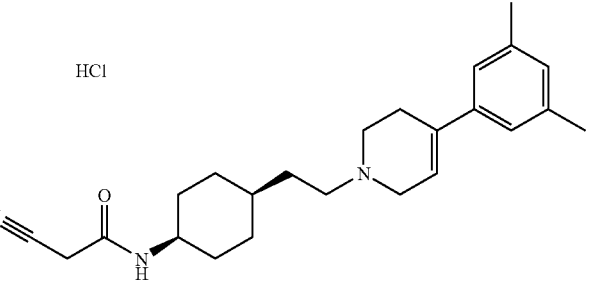 | 2-Cyano-N-(4-{2-[4-(3,5-dimethylphenyl)-3,6-dihydro-2H-pyridin-1-yl]ethyl}cyclohexyl)acetamide, hydrochloride | 220 | IIA |
| 626 | 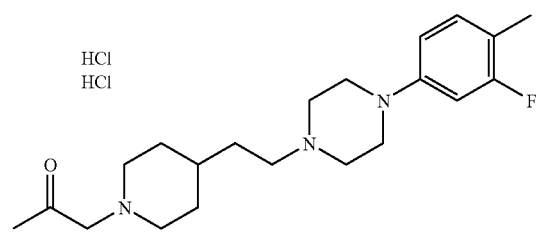 [SMILES: CC(=O)CN1CCC(CCN2CCN(c3ccc(C)c(F)c3)CC2)CC1 ; Cl ; Cl] | 1-(4-{2-[4-(3-Fluoro-4-methylphenyl)piperazin-1-yl]ethyl}piperidin-1-yl)propan-2-one, dihydrochloride | 276 | IIIB |

-continued

| Ex | Structure | Name | M.P. (° C.) | Synthetic Path |
|---|---|---|---|---|
| 627 | 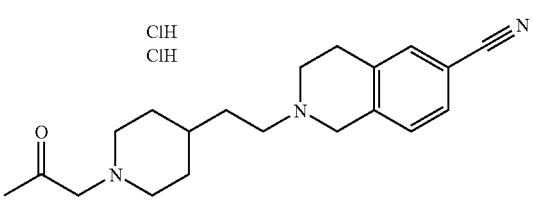 [SMILES: CC(=O)CN1CCC(CCN2CCc3cc(C#N)ccc3C2)CC1 ; Cl ; Cl] ClH ClH | 2-{2-[1-(2-Oxopropyl)piperidin-4-yl]ethyl}-1,2,3,4-tetrahydroisoquinoline-6-carbonitrile, dihydrochloride | 249 | IIIB |
| 628 | 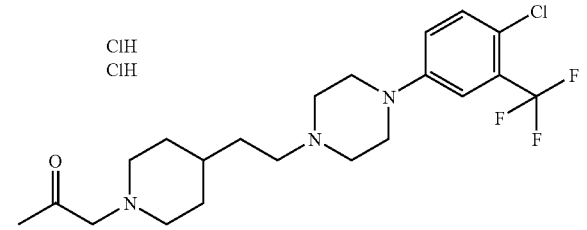 [SMILES: CC(=O)CN1CCC(CCN2CCN(c3ccc(Cl)c(C(F)(F)F)c3)CC2)CC1 ; Cl ; Cl] ClH ClH | 1-(4-{2-[4-(4-Chloro-3-trifluoromethylphenyl)piperazin-1-yl]ethyl}piperidin-1-yl)propan-2-one, dihydrochloride | 263 | IIIB |
| 629 | 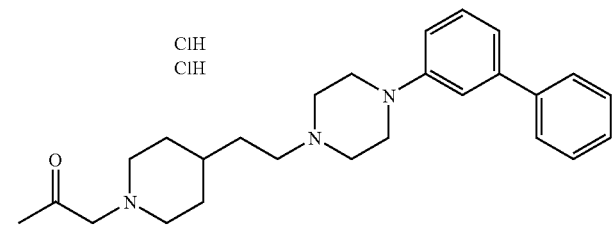 [SMILES: CC(=O)CN1CCC(CCN2CCN(c3cccc(-c4ccccc4)c3)CC2)CC1 ; Cl ; Cl] ClH ClH | 1-{4-[2-(4-Biphenyl-3-ylpiperazin-1-yl)ethyl]piperidin-1-yl}propan-2-one, dihydrochloride | 235 | IIIB |
| 630 | 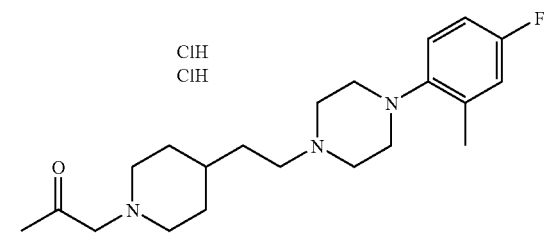 [SMILES: CC(=O)CN1CCC(CCN2CCN(c3ccc(F)cc3C)CC2)CC1 ; Cl ; Cl] ClH ClH | 1-(4-{2-[4-(4-Fluoro-2-methylphenyl)piperazin-1-yl]ethyl}piperidin-1-yl)propan-2-one, dihydrochloride | 283 | IIIB |
| 631 | 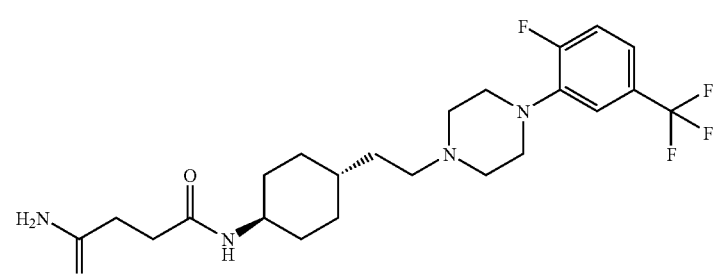 | N-(4-{2-[4-(2-Fluoro-5-trifluoromethylphenyl)piperazin-1-yl]ethyl}cyclohexyl)succinamide | 238 | IIA |
| 632 | 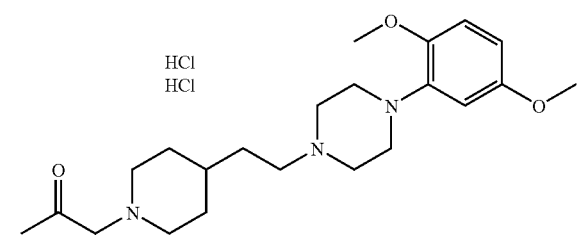 [SMILES: COc1ccc(OC)c(N2CCN(CCC3CCN(CC(C)=O)CC3)CC2)c1 ; Cl ; Cl] HCl HCl | 1-(4-{2-[4-(2,5-Dimethoxyphenyl)piperazin-1-yl]ethyl}piperidin-1-yl)propan-2-one, dihydrochloride | 268 | IIIB |

-continued

| Ex | Structure | Name | M.P. (° C.) | Synthetic Path |
|---|---|---|---|---|
| 633 | HCl HCl | 1-{4-[2-(4-Indan-4-ylpiperidin-1-yl)ethyl]piperidin-1-yl}propan-2-one, dihydrochloride | 339 | IIIB |
| 634 | HCl HCl | 1-(4-{2-[4-(4-Fluorophenyl)piperidin-1-yl]ethyl}piperidin-1-yl)propan-2-one, dihydrochloride | | IIIB |
| 635 | HCl HCl | 1-(4-{2-[4-(2-Methoxy-5-trifluoromethylphenyl)piperazin-1-yl]ethyl}piperidin-1-yl)propan-2-one, dihydrochloride | 260 | IIIB |
| 636 | HCl HCl | 1-{4-[2-(4-Indan-4-ylpiperazin-1-yl)ethyl]piperidin-1-yl}pentan-2-one, dihydrochloride | 270 | IIIB |
| 637 | HCl HCl | 1-(4-{2-[4-(4-Fluoro-3-trifluoromethylphenyl)piperazin-1-yl]ethyl}piperidin-1-yl)propan-2-one, dihydrochloride | 266 | IIIB |
| 638 | HCl HCl | 1-(4-{2-[4-(2,6-Dimethylphenyl)piperazin-1-yl]ethyl}piperidin-1-yl)propan-2-one, dihydrochloride | 249 | IIIB |

| Ex | Structure | Name | M.P. (° C.) | Synthetic Path |
|---|---|---|---|---|
| 639 | 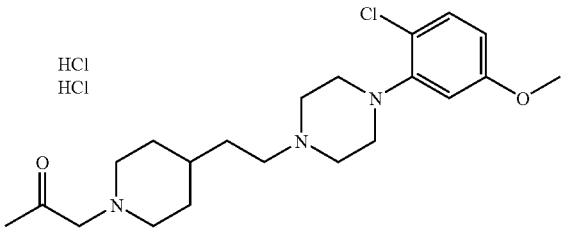 [SMILES: COc1ccc(Cl)c(N2CCN(CCC3CCN(CC(C)=O)CC3)CC2)c1 ; Cl ; Cl] | 1-(4-{2-[4-(2-Chloro-5-methoxyphenylpiperazin-1-yl]ethyl}piperidin-1-yl)propan-2-one, dihydrochloride | 263 | IIIB |
| 640 | 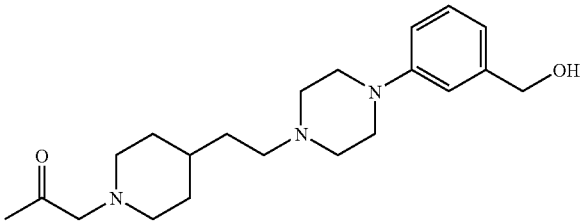 [SMILES: CC(=O)CN1CCC(CCN2CCN(c3cccc(CO)c3)CC2)CC1] | 1-(4-{2-[4-(3-Hydroxymethylphenyl)piperazin-1-yl]ethyl}piperidin-1-yl)propan-2-one | 84 | IIIB |
| 641 | 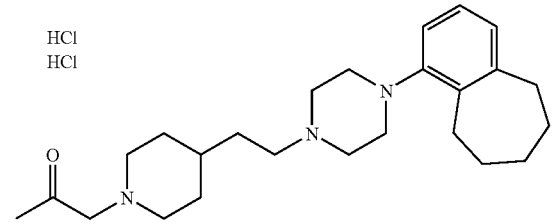 [SMILES: CC(=O)CN1CCC(CCN2CCN(c3cccc4c3CCCCC4)CC2)CC1 ; Cl ; Cl] | 1-(4-{2-[4-(6,7,8,9-Tetrahydro-5H-benzocyclohepten-1-yl)piperazin-1-yl]ethyl}piperidin-1-yl)propan-2-one, dihydrochloride | 300 | IIIB |
| 642 | 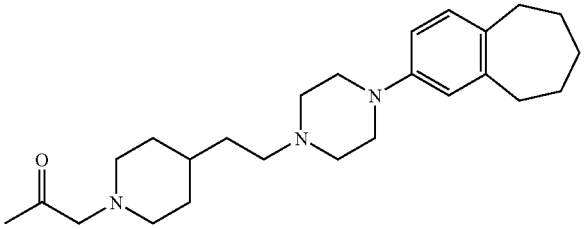 [SMILES: CC(=O)CN1CCC(CCN2CCN(c3ccc4c(c3)CCCCC4)CC2)CC1] | 1-(4-{2-[4-(6,7,8,9-Tetrahydro-5H-benzocyclohepten-2-yl)piperazin-1-yl]ethyl}piperidin-1-yl)propan-2-one | 98 | IIIB |
| 643 | 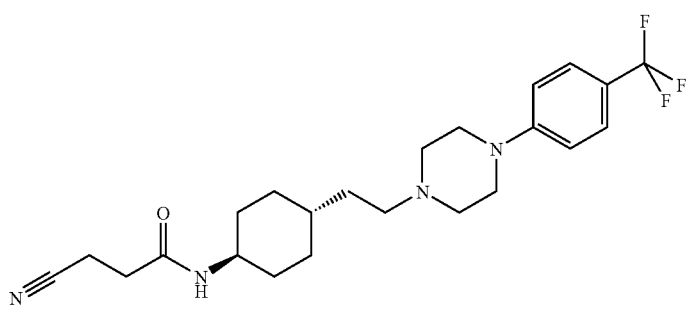 [SMILES: N#CCCC(=O)N[C@H]1CC[C@H](CCN2CCN(c3ccc(C(F)(F)F)cc3)CC2)CC1] | 3-Cyano-N-(4-{2-[4-(4-trifluoromethylphenyl)piperazin-1-yl]ethyl}cyclohexyl)propanamide | 207 | IIA |
| 644 | 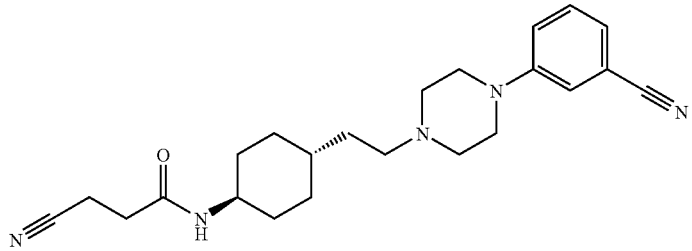 [SMILES: N#CCCC(=O)N[C@H]1CC[C@H](CCN2CCN(c3cccc(C#N)c3)CC2)CC1] | 3-Cyano-N-(4-{2-[4-(3-cyanophenyl)piperazin-1-yl]ethyl}cyclohexyl)propanamide | 160 | IIA |

-continued

| Ex | Structure | Name | M.P. (° C.) | Synthetic Path |
|---|---|---|---|---|
| 645 | 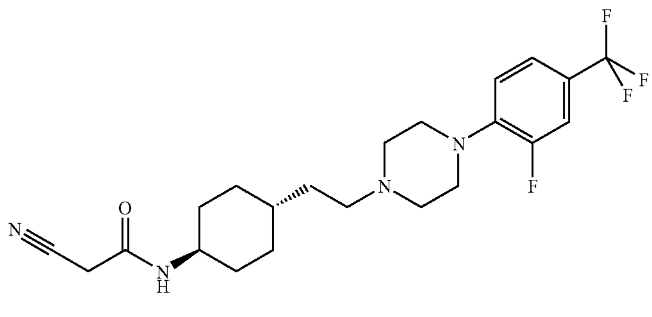 [SMILES: N#CCC(=O)N[C@H]1CC[C@H](CCN2CCN(c3ccc(C(F)(F)F)cc3F)CC2)CC1] | 2-Cyano-N-(4-{2-[4-(2-fluoro-4-trifluoromethylphenyl)piperazin-1-yl]ethyl}cyclohexyl)acetamide | 212 | IIA |
| 646 | 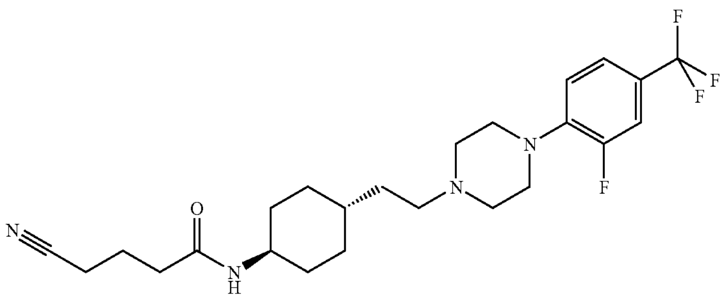 [SMILES: N#CCCCC(=O)N[C@H]1CC[C@H](CCN2CCN(c3ccc(C(F)(F)F)cc3F)CC2)CC1] | 4-Cyano-N-(4-{2-[4-(2-fluoro-4-trifluoromethylphenyl)piperazin-1-yl]ethyl}cyclohexyl)-butanamide | 165 | IIA |
| 647 | 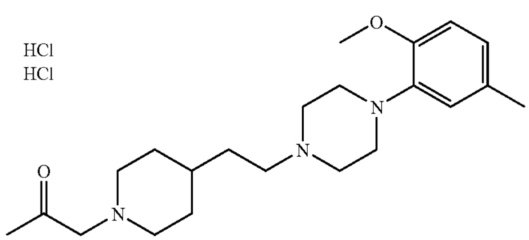 [SMILES: COc1ccc(C)cc1N1CCN(CCC2CCN(CC(C)=O)CC2)CC1 ; Cl ; Cl] | 1-(4-{2-[4-(2-Methoxy-5-methylphenyl)piperazin-1-yl]ethyl}piperidin-1-yl)propan-2-one, dihydrochloride | 260 | IIIB |
| 648 | 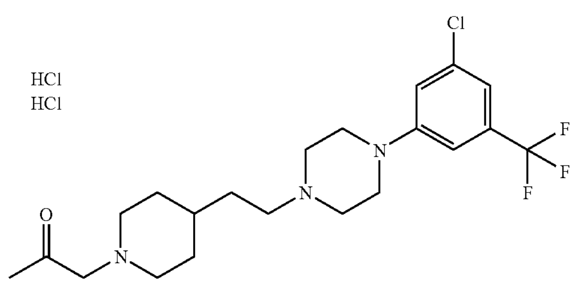 [SMILES: CC(=O)CN1CCC(CCN2CCN(c3cc(Cl)cc(C(F)(F)F)c3)CC2)CC1 ; Cl ; Cl] | 1-(4-{2-[4-(3-Chloro-5-trifluoromethylphenyl)piperazin-1-yl]ethyl}piperidin-1-yl)propan-2-one, dihydrochloride | 289 | IIIB |
| 649 | 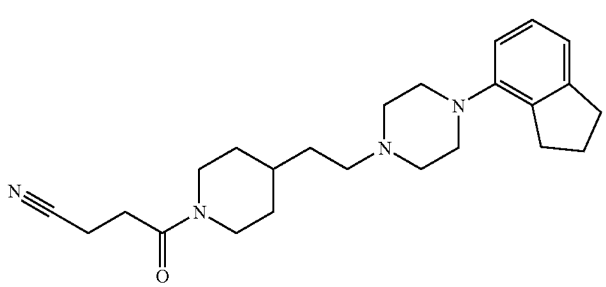 [SMILES: N#CCCC(=O)N1CCC(CCN2CCN(c3cccc4c3CCC4)CC2)CC1] | 4-{4-[2-(4-Indan-4-ylpiperazin-1-yl)ethyl]piperidin-1-yl}-4-oxo-butanonitrile | | IIIA |

| Ex | Structure | Name | M.P. (° C.) | Synthetic Path |
|---|---|---|---|---|
| 650 | 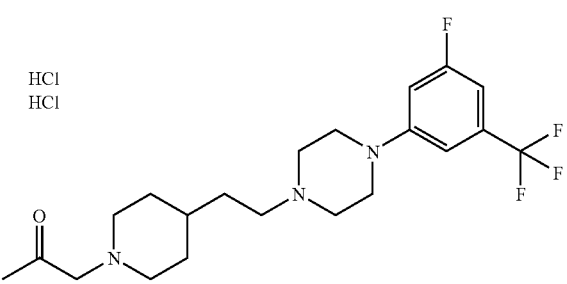 [SMILES: CC(=O)CN1CCC(CCN2CCN(c3cc(F)cc(C(F)(F)F)c3)CC2)CC1 ; Cl ; Cl] | 1-(4-{2-[4-(3-Fluoro-5-trifluoromethylphenyl)piperazin-1-yl]ethyl}piperidin-1-yl)propan-2-one | 295 | IIIB |
| 651 | 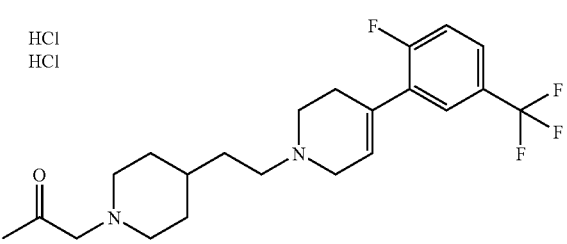 [SMILES: CC(=O)CN1CCC(CCN2CC=C(c3cc(C(F)(F)F)ccc3F)CC2)CC1 ; Cl ; Cl] | 1-(4-{2-[4-(2-Fluoro-5-trifluoromethylphenyl)-3,6-dihydro-2H-pyridin-1-yl]ethyl}piperidin-1-yl)propan-2-one, dihydrochloride | 282 | IIIB |
| 652 | 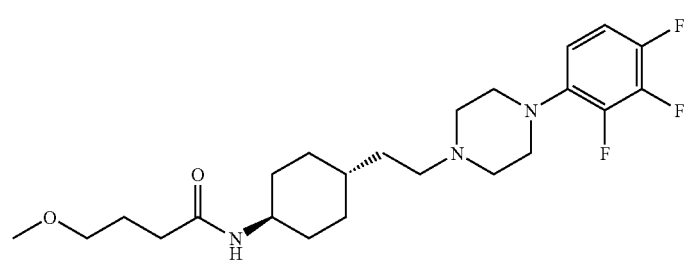 [SMILES: COCCCC(=O)N[C@H]1CC[C@H](CCN2CCN(c3ccc(F)c(F)c3F)CC2)CC1] | 4-Methoxy-N-(4-{2-[4-(2,3,4-trifluorophenyl)piperazin-1-yl]ethyl}cyclohexyl)butanamide | 203 | IIA |
| 653 | 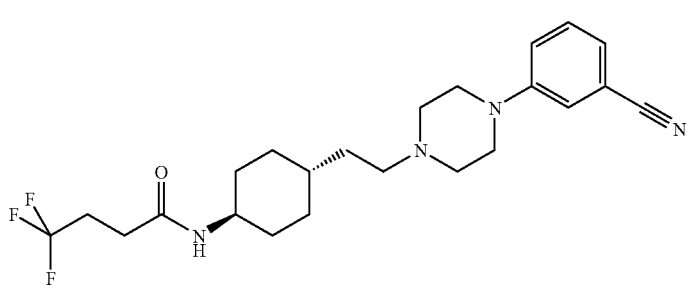 | N-(4-{2-[4-(3-Cyanophenyl)piperazin-1-yl]ethyl}cyclohexyl)-4,4,4-trifluorobutanamide | 176 | IIA |
| 654 | 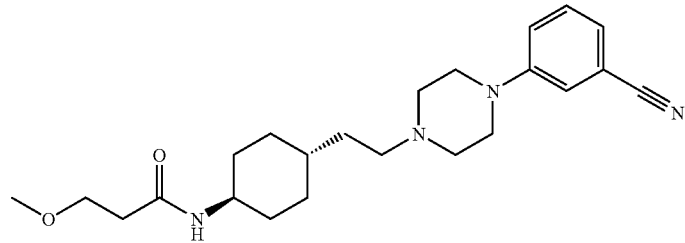 | N-(4-{2-[4-(3-Cyanophenyl)piperazin-1-yl]ethyl}cyclohexyl)-3-methoxypropanamide | 145 | IIA |

-continued

| Ex | Structure | Name | M.P. (° C.) | Synthetic Path |
|---|---|---|---|---|
| 655 | 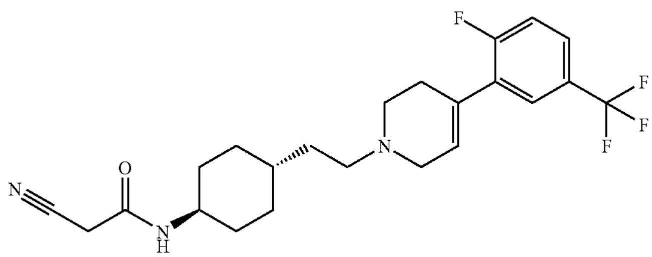 [SMILES: N#CCC(=O)N[C@H]1CC[C@H](CCN2CC=C(c3cc(C(F)(F)F)ccc3F)CC2)CC1] | 2-Cyano-N-(4-{2-[4-(2-fluoro-5-trifluoromethylphenyl)-3,6-dihydro-2H-pyridin-1-yl]ethyl}cyclohexyl)acetamide | 168 | IIA |
| 656 | 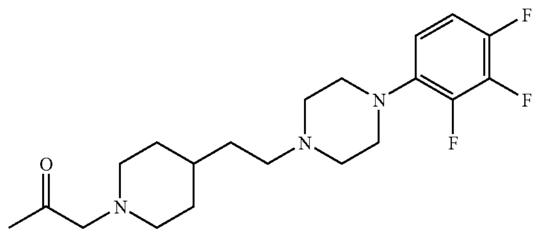 [SMILES: CC(=O)CN1CCC(CCN2CCN(c3ccc(F)c(F)c3F)CC2)CC1] | 1-(4-{2-[4-(2,3,4-Trifluorophenyl)piperazin-1-yl]piperidin-1-yl)propan-2-one | 88 | IIIB |
| 657 | HCl HCl | 1-(4-{2-[4-(3-Phenoxyphenyl)piperazin-1-yl]ethyl}piperidin-1-yl)propan-2-one, dihydrochloride | 241 | IIIB |
| 658 | HCl HCl | 1-(4-{2-[4-(3-Isopropoxyphenyl)piperazin-1-yl]ethyl}piperidin-1-yl)propan-2-one, dihydrochloride | 237 | IIIB |
| 659 | 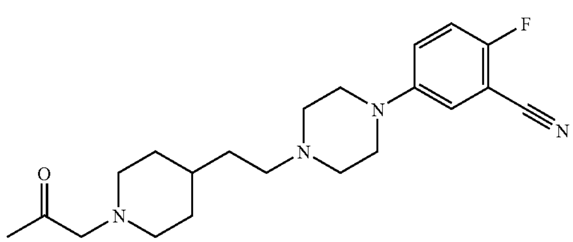 [SMILES: CC(=O)CN1CCC(CCN2CCN(c3ccc(F)c(C#N)c3)CC2)CC1] | 2-Fluoro-5-(4-{2-[1-(2-oxopropyl)piperidin-4-yl]ethyl}piperazin-1-yl)benzonitrile | 102 | IIIB |
| 660 | 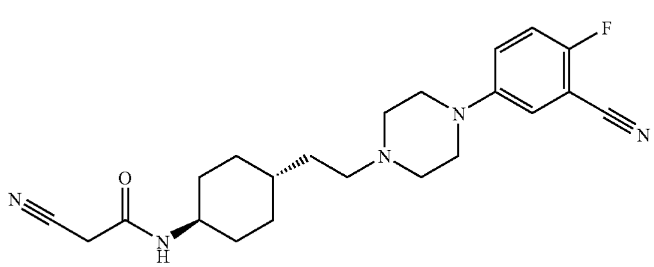 [SMILES: N#CCC(=O)N[C@H]1CC[C@H](CCN2CCN(c3ccc(F)c(C#N)c3)CC2)CC1] | 2-Cyano-N-(4-{2-[4-(3-cyano-4-fluorophenyl)piperazin-1-yl]ethyl}cyclohexyl)acetamide | 185 | IIA |

US 8,802,678 B2

-continued

| Ex | Structure | Name | M.P. (° C.) | Synthetic Path |
|---|---|---|---|---|
| 661 | 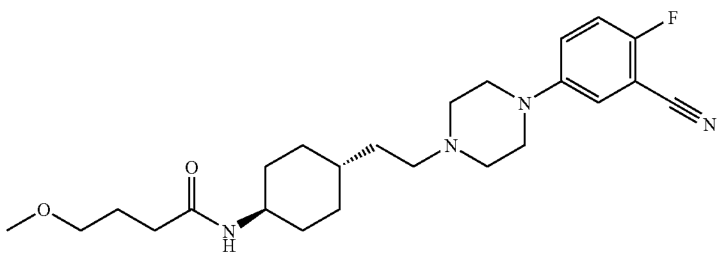 [SMILES: COCCCC(=O)N[C@H]1CC[C@H](CCN2CCN(c3ccc(F)c(C#N)c3)CC2)CC1] | N-(4-{2-[4-(3-Cyano-4-fluorophenyl)piperazin-1-yl]ethyl}cyclohexyl)-4-methoxybutanamide | 197 | IIA |
| 662 | 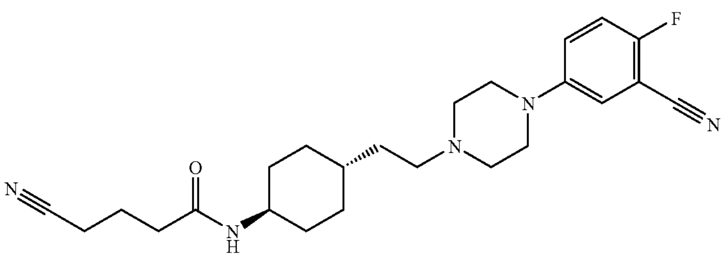 [SMILES: N#CCCCC(=O)N[C@H]1CC[C@H](CCN2CCN(c3ccc(F)c(C#N)c3)CC2)CC1] | 4-Cyano-N-(4-{2-[4-(3-cyano-4-fluorophenyl)piperazin-1-yl]ethyl}cyclohexyl)butanamide | 158 | IIA |
| 663 | 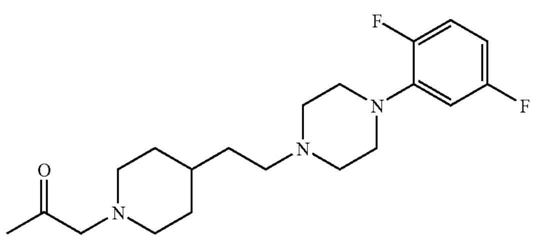 [SMILES: CC(=O)CN1CCC(CCN2CCN(c3cc(F)ccc3F)CC2)CC1] | 1-(4-{2-[4-(2,5-Difluorophenyl)piperazin-1-yl]ethyl}piperidin-1-yl)propan-2-one | 90 | IIIB |
| 664 | 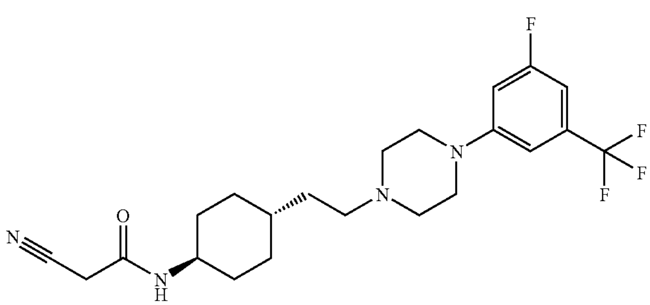 | 2-Cyano-N-(4-{2-[4-(3-fluoro-5-trifluoromethylphenyl)piperazin-1-yl]ethyl}cyclohexyl)acetamide | 178 | IIA |
| 665 | 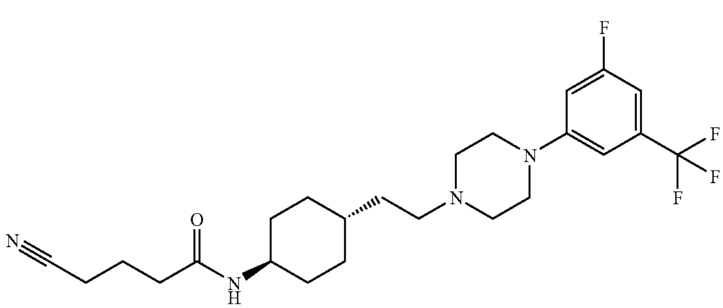 [SMILES: N#CCCCC(=O)N[C@H]1CC[C@H](CCN2CCN(c3cc(F)cc(C(F)(F)F)c3)CC2)CC1] | 4-Cyano-N-(4-{2-[4-(3-fluoro-5-trifluoromethylphenyl)piperazin-1-yl]ethyl}cyclohexyl)butanamide | 163 | IIA |

| Ex | Structure | Name | M.P. (° C.) | Synthetic Path |
|---|---|---|---|---|
| 666 | 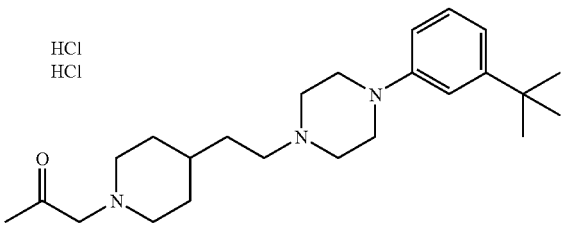 [SMILES: CC(=O)CN1CCC(CCN2CCN(c3cccc(C(C)(C)C)c3)CC2)CC1 ; Cl ; Cl] | 1-(4-{2-[4-(3-tert-Butylphenyl)piperazin-1-yl]ethyl}piperidin-1-yl)propan-2-one, dihydrochloride | 257 | IIIB |
| 667 | 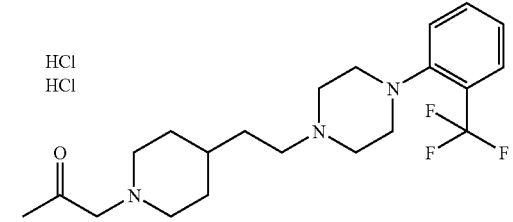 [SMILES: CC(=O)CN1CCC(CCN2CCN(c3ccccc3C(F)(F)F)CC2)CC1 ; Cl ; Cl] | 1-(4-{2-[4-(2-Trifluoromethylphenyl)piperazin-1-yl]ethyl}piperidin-1-yl)propan-2-one, dihydrochloride | 290 | IIIB |
| 668 | 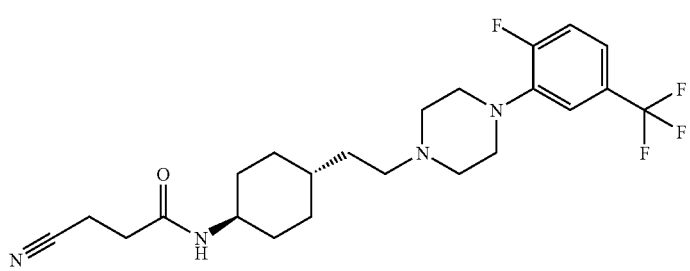 [SMILES: N#CCCC(=O)N[C@H]1CC[C@H](CCN2CCN(c3cc(C(F)(F)F)ccc3F)CC2)CC1] | 3-Cyano-N-(4-{2-[4-(2-fluoro-5-trifluoromethylphenyl)piperazin-1-yl]ethyl}cyclohexyl)propanamide | 164 | IIA |
| 669 | 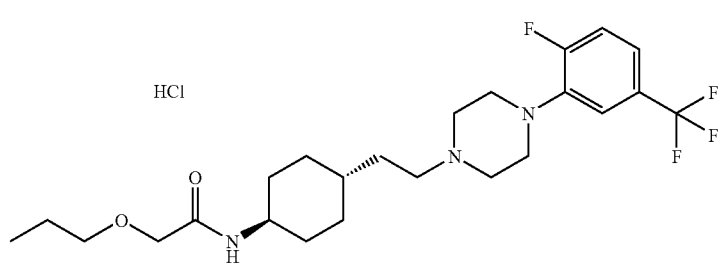 [SMILES: CCCOCC(=O)N[C@H]1CC[C@H](CCN2CCN(c3cc(C(F)(F)F)ccc3F)CC2)CC1 ; Cl] | N-(4-{2-[4-(2-Fluoro-5-trifluoromethylphenyl)piperazin-1-yl]ethyl}cyclohexyl)-2-propoxyacetamide, hydrochloride | 240 | IIA |
| 670 | 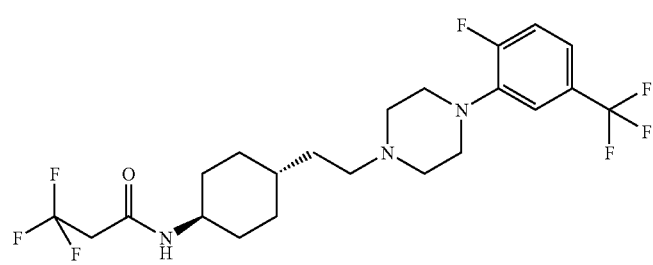 [SMILES: O=C(CC(F)(F)F)N[C@H]1CC[C@H](CCN2CCN(c3cc(C(F)(F)F)ccc3F)CC2)CC1] | 3,3,3-Trifluoro-N-(4-{2-[4-(2-fluoro-5-trifluoromethylphenyl)piperazin-1-yl]ethyl}cyclohexyl)propanamide | 177 | IIA |
| 671 | 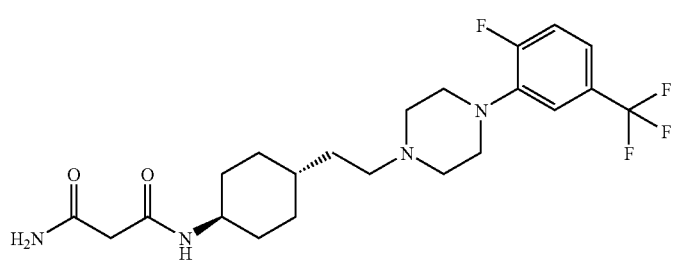 [SMILES: NC(=O)CC(=O)N[C@H]1CC[C@H](CCN2CCN(c3cc(C(F)(F)F)ccc3F)CC2)CC1] | N-(4-{2-[4-(2-Fluoro-5-trifluoromethylphenyl)piperazin-1-yl]ethyl}cyclohexyl)-malonamide | 185 | IIA |

-continued

| Ex | Structure | Name | M.P. (°C.) | Synthetic Path |
|---|---|---|---|---|
| 672 | HCl HCl | 1-(4-{2-[4-(3-Benzylphenyl)piperazin-1-yl]ethyl}piperidin-1-yl)propan-2-one, dihydrochloride | 253 | IIIB |
| 673 | 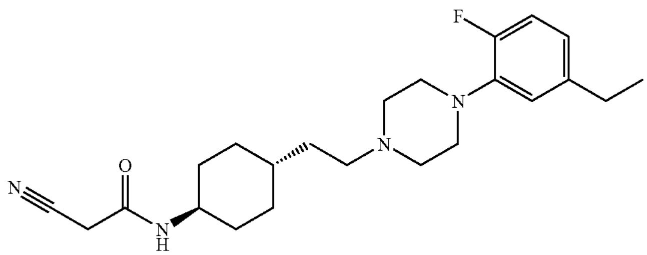 [SMILES: CCc1ccc(F)c(N2CCN(CC[C@H]3CC[C@H](NC(=O)CC#N)CC3)CC2)c1] | 2-Cyano-N-(4-{2-[4-(5-ethyl-2-fluorophenyl)piperazin-1-yl]ethyl}cyclohexyl)acetamide | 180 | IIA |
| 674 | 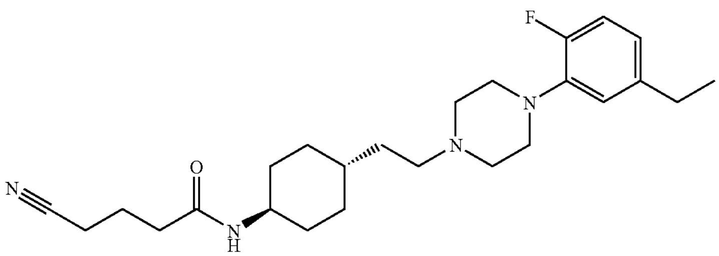 [SMILES: CCc1ccc(F)c(N2CCN(CC[C@H]3CC[C@H](NC(=O)CCCC#N)CC3)CC2)c1] | 4-Cyano-N-(4-{2-[4-(5-ethyl-2-fluorophenyl)piperazin-1-yl]ethyl}cyclohexyl)butanamide | 153 | IIA |
| 675 | 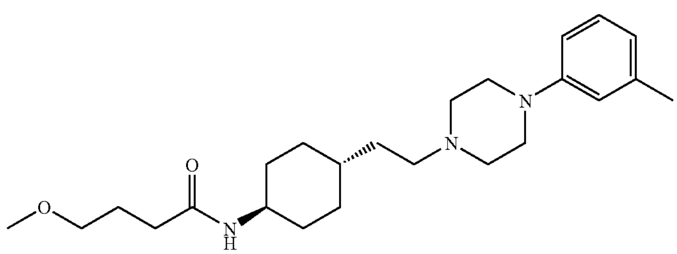 | 4-Methoxy-N-{4-[2-(4-m-tolylpiperazin-1-yl)ethyl]cyclohexyl}butanamide | 148 | IIA |
| 676 | HCl HCl | 1-(4-{2-[4-(3,4-Difluorophenyl)piperazin-1-yl]ethyl}piperidin-1-yl)propan-2-one, dihydrochloride | 249 | IIIB |
| 677 | HCl HCl | 1-(4-{2-[4-(4-Chlorophenyl)piperazin-1-yl]ethyl}piperidin-1-yl)propan-2-one, dihydrochloride | 277 | IIIB |

-continued

| Ex | Structure | Name | M.P. (° C.) | Synthetic Path |
|---|---|---|---|---|
| 678 | HCl HCl | 1-(4-{2-[4-(3-Isopropylphenyl)piperazin-1-yl]ethyl}piperidin-1-yl)propan-2-one, dihydrochloride | 252 | IIIB |
| 679 | HCl | 5-{4-[2-(4-Indan-4-ylpiperazin-1-yl)ethyl]piperidin-1-yl}-5-oxo-pentanenitrile, hydrochloride | 210 | IIIA |
| 680 | HCl | 2-Ethoxy-1-{4-[2-(4-indan-4-ylpiperazin-1-yl)ethyl]piperidin-1-yl}ethanone, hydrochloride | 270 | IIIA |
| 681 | 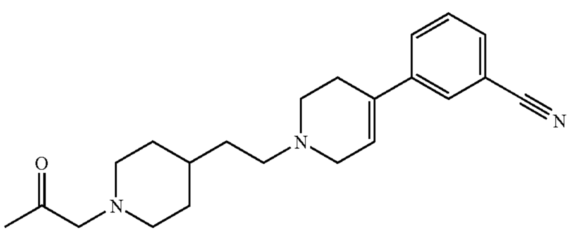 [SMILES: CC(=O)CN1CCC(CCN2CC=C(c3cccc(C#N)c3)CC2)CC1] | 3-(1-{2-[1-(2-Oxopropyl)piperidin-4-yl]ethyl}-1,2,3,6-tetrahydropyridin-4-yl)benzonitrile | 94 | IIIB |
| 682 | 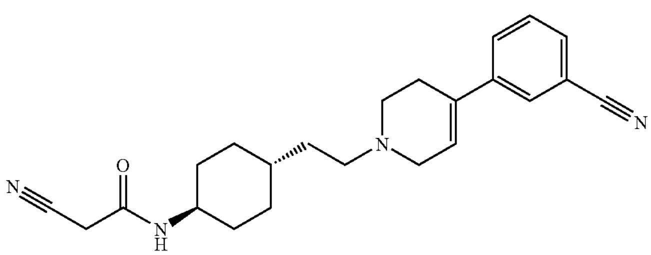 [SMILES: N#CCC(=O)N[C@H]1CC[C@H](CCN2CC=C(c3cccc(C#N)c3)CC2)CC1] | 2-Cyano-N-(4-{2-[4-(3-cyanophenyl)-3,6-dihydro-2H-pyridin-1-yl]ethyl}-cyclohexyl)acetamide | 185 | IIA |
| 683 | 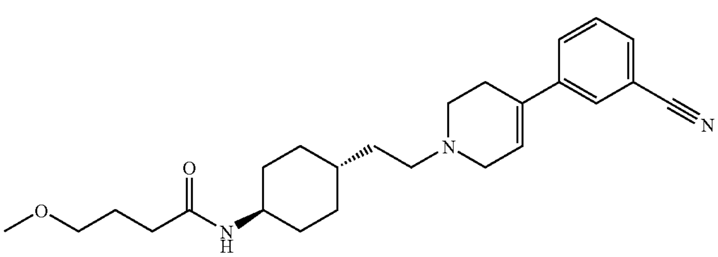 [SMILES: COCCCC(=O)N[C@H]1CC[C@H](CCN2CC=C(c3cccc(C#N)c3)CC2)CC1] | N-(4-{2-[4-(3-Cyanophenyl)-3,6-dihydro-2H-pyridin-1-yl]ethyl}cyclohexyl)-4-methoxybutanamide | 178 | IIA |

| Ex | Structure | Name | M.P. (° C.) | Synthetic Path |
|---|---|---|---|---|
| 684 | 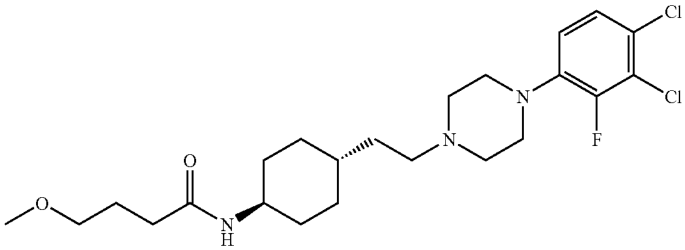 [SMILES: COCCCC(=O)N[C@H]1CC[C@H](CCN2CCN(c3ccc(Cl)c(Cl)c3F)CC2)CC1] | N-(4-{2-[4-(3,4-Dichloro-2-fluoro-phenyl)piperazin-1-yl]ethyl}cyclohexyl)-4-methoxybutanamide | 210 | IIA |
| 685 | 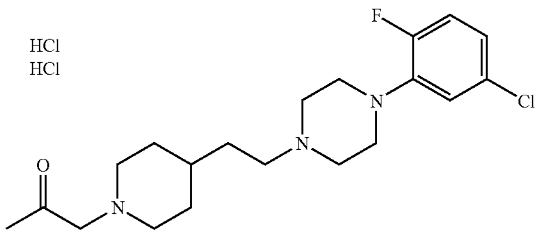 [SMILES: CC(=O)CN1CCC(CCN2CCN(c3cc(Cl)ccc3F)CC2)CC1 ; Cl ; Cl] | 1-(4-{2-[4-(5-Chloro-2-fluorophenyl)piperazin-1-yl]ethyl}piperidin-1-yl)propan-2-one, dihydrochloride | 270 | IIIB |
| 686 | 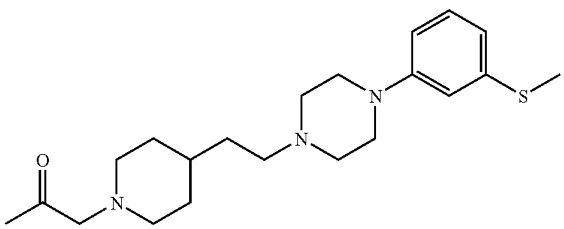 [SMILES: CSc1cccc(N2CCN(CCC3CCN(CC(C)=O)CC3)CC2)c1] | 1-(4-{2-[4-(3-Methylsulfanyl-phenyl)piperazin-1-yl]ethyl}-piperidin-1-yl)propan-2-one | 113 | IIIB |
| 687 | 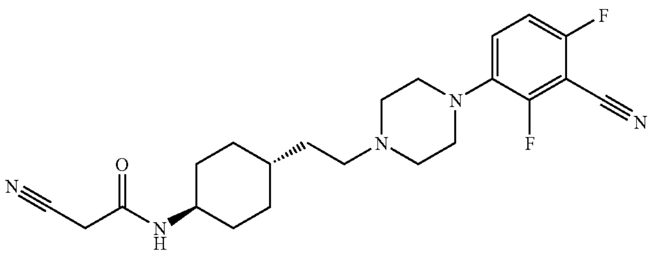 [SMILES: N#CCC(=O)N[C@H]1CC[C@H](CCN2CCN(c3ccc(F)c(C#N)c3F)CC2)CC1] | 2-Cyano-N-(4-{2-[4-(3-cyano-2,4-difluorophenyl)piperazin-1-yl]ethyl}cyclohexyl)acetamide | 210 | IIA |
| 688 | 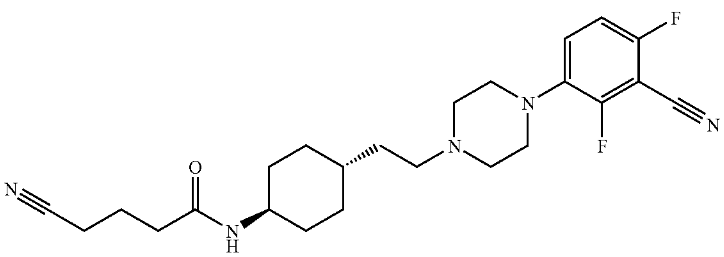 [SMILES: N#CCCCC(=O)N[C@H]1CC[C@H](CCN2CCN(c3ccc(F)c(C#N)c3F)CC2)CC1] | 4-Cyano-N-(4-{2-[4-(3-cyano-2,4-difluorophenyl)piperazin-1-yl]ethyl}cyclohexyl)butanamide | 203 | IIA |
| 689 | 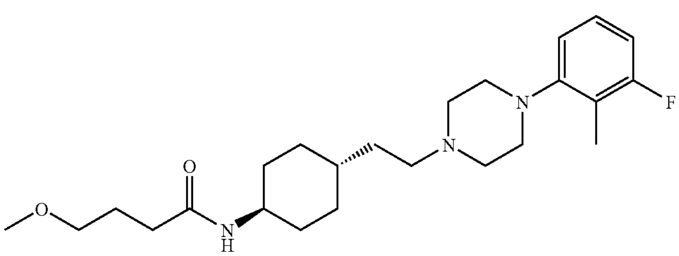 [SMILES: COCCCC(=O)N[C@H]1CC[C@H](CCN2CCN(c3cccc(F)c3C)CC2)CC1] | N-(4-{2-[4-(3-Fluoro-2-methylphenyl)piperazin-1-yl]ethyl}cyclohexyl)-4-methoxybutanamide | 172 | IIA |

| Ex | Structure | Name | M.P. (° C.) | Synthetic Path |
|---|---|---|---|---|
| 690 | 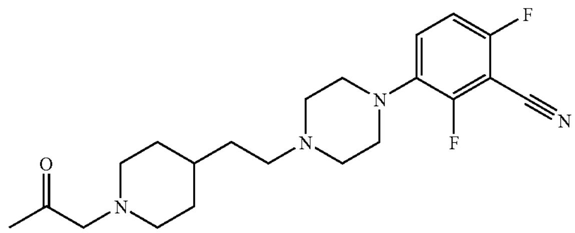 [SMILES: CC(=O)CN1CCC(CCN2CCN(c3ccc(F)c(C#N)c3F)CC2)CC1] | 2,6-Difluoro-3-(4-{2-[1-(2-oxo-propyl)piperidin-4-yl]ethyl}piperazin-1-yl)benzonitrile | 108 | IIIB |
| 691 | 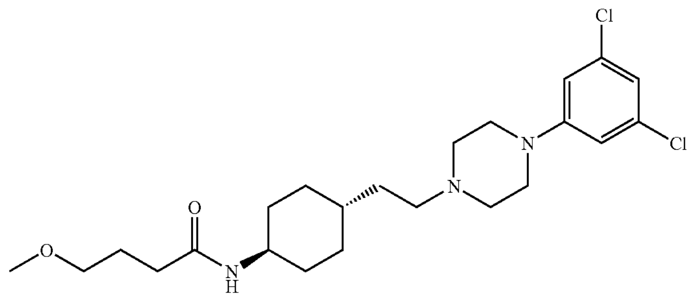 [SMILES: COCCCC(=O)N[C@H]1CC[C@H](CCN2CCN(c3cc(Cl)cc(Cl)c3)CC2)CC1] | N-(4-{2-[4-(3,5-Dichlorophenyl)piperazin-1-yl]ethyl}cyclohexyl)-4-methoxybutanamide | 184 | IIA |
| 692 | 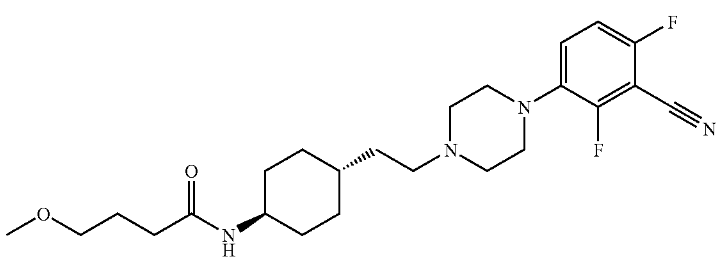 [SMILES: COCCCC(=O)N[C@H]1CC[C@H](CCN2CCN(c3ccc(F)c(C#N)c3F)CC2)CC1] | N-(4-{2-[4-(3-Cyano-2,4-difluorophenyl)piperazin-1-yl]ethyl}cyclohexyl)-4-methoxybutanamide | 211 | IIA |
| 693 | 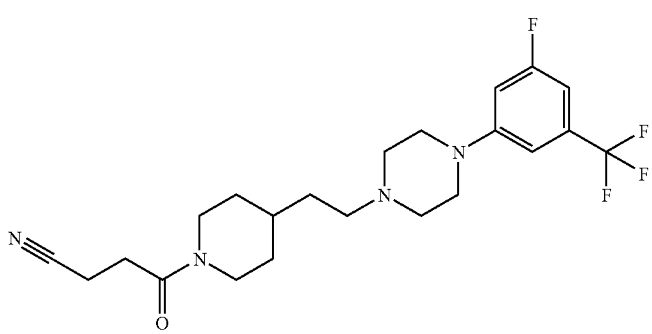 [SMILES: N#CCCC(=O)N1CCC(CCN2CCN(c3cc(F)cc(C(F)(F)F)c3)CC2)CC1] | 4-(4-{2-[4-(3-Fluoro-5-trifluoromethylphenyl)piperazin-1-yl]ethyl}piperidin-1-yl)-4-oxobutanonitrile | | IIIA |
| 694 | HCl HCl | 1-(4-{2-[4-(3-Methoxymethylphenyl)piperazin-1-yl]ethyl}piperidin-1-yl)propan-2-one, dihydrochloride | 255 | IIIB |

-continued

| Ex | Structure | Name | M.P. (° C.) | Synthetic Path |
|---|---|---|---|---|
| 695 | 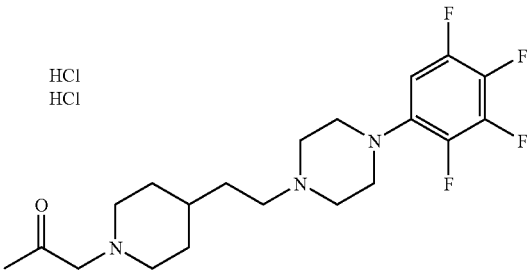 [SMILES: CC(=O)CN1CCC(CCN2CCN(c3cc(F)c(F)c(F)c3F)CC2)CC1 ; Cl ; Cl] | 1-(4-{2-[4-(2,3,4,5-Tetrafluorophenyl)piperazin-1-yl]ethyl}piperidin-1-yl)propan-2-one, dihydrochloride | 235 | IIIB |
| 696 | 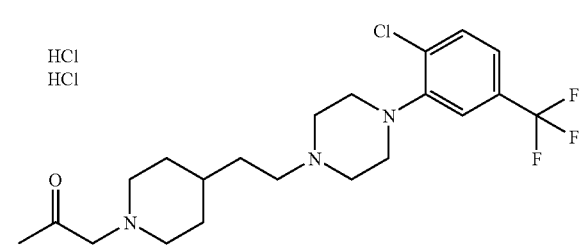 [SMILES: CC(=O)CN1CCC(CCN2CCN(c3cc(C(F)(F)F)ccc3Cl)CC2)CC1 ; Cl ; Cl] | 1-(4-{2-[4-(2-Chloro-5-trifluoromethylphenyl)piperazin-1-yl]ethyl}piperidin-1-yl)propan-2-one, dihydrochloride | 299 | IIIB |
| 697 | 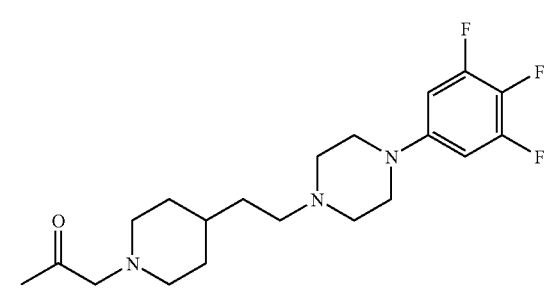 [SMILES: CC(=O)CN1CCC(CCN2CCN(c3cc(F)c(F)c(F)c3)CC2)CC1] | 1-(4-{2-[4-(3,4,5-Trifluoro-phenyl)-piperazin-1-yl]ethyl}piperidin-1-yl)propan-2-one | 86 | IIIB |
| 698 | 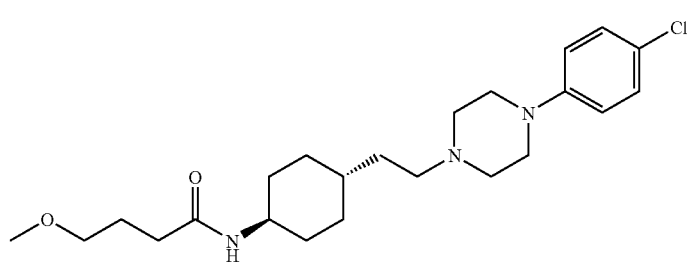 [SMILES: COCCCC(=O)N[C@H]1CC[C@H](CCN2CCN(c3ccc(Cl)cc3)CC2)CC1] | N-(4-{2-[4-(4-Chlorophenyl)-piperazin-1-yl]ethyl}cyclohexyl)-4-methoxybutanamide | 204 | IIA |
| 699 | 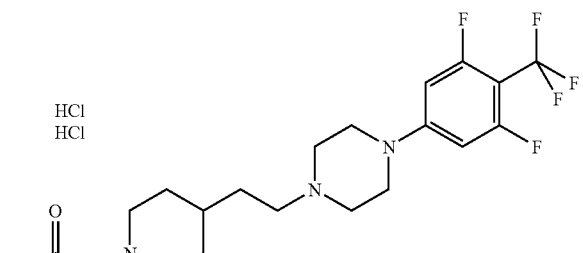 | 1-(4-{2-[4-(3,5-Difluoro-4-trifluoromethylphenyl)piperazin-1-yl]ethyl}piperidin-1-yl)propan-2-one | 80 | IIIB |

-continued

| Ex | Structure | Name | M.P. (° C.) | Synthetic Path |
|---|---|---|---|---|
| 700 | HCl HCl HCl 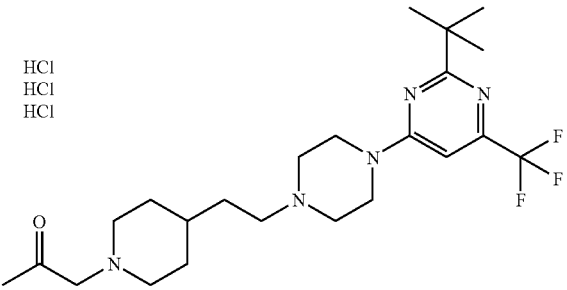 [SMILES: CC(=O)CN1CCC(CCN2CCN(c3cc(C(F)(F)F)nc(C(C)(C)C)n3)CC2)CC1 ; Cl ; Cl ; Cl] | 1-(4-{2-[4-(2-tert-Butyl-6-trifluoromethylpyrimidin-4-yl)piperazin-1-yl]ethyl}piperidin-1-yl)propan-2-one, trihydrochloride | 287 | IIIB |
| 701 | 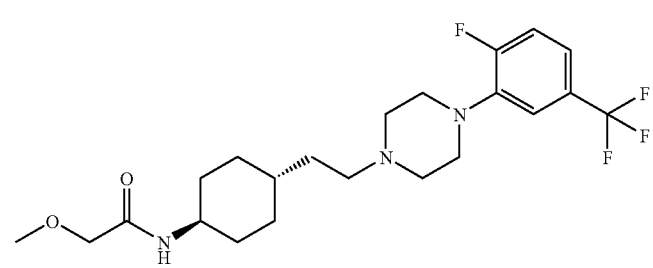 [SMILES: COCC(=O)N[C@H]1CC[C@H](CCN2CCN(c3cc(C(F)(F)F)ccc3F)CC2)CC1] | N-(4-{2-[4-(2-Fluoro-5-trifluoromethylphenyl)piperazin-1-yl]ethyl}cyclohexyl)-2-methoxyacetamide | 139 | IIA |
| 702 | HCl HCl 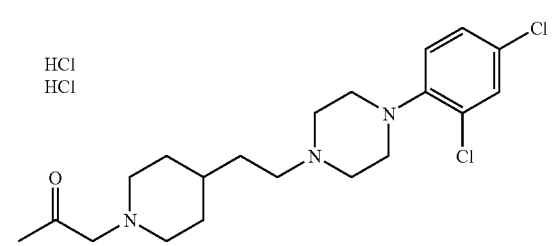 [SMILES: CC(=O)CN1CCC(CCN2CCN(c3ccc(Cl)cc3Cl)CC2)CC1 ; Cl ; Cl] | 1-(4-{2-[4-(2,4-Dichlorophenyl)piperazin-1-yl]ethyl}piperidin-1yl)propan-2-one, dihydrochloride | 283 | IIIB |
| 703 | HCl HCl 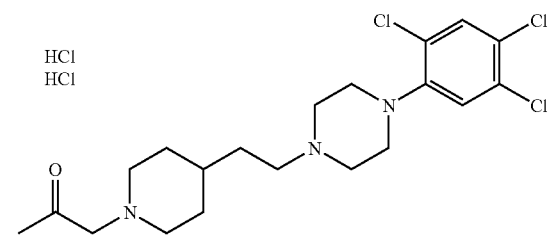 [SMILES: CC(=O)CN1CCC(CCN2CCN(c3cc(Cl)c(Cl)cc3Cl)CC2)CC1 ; Cl ; Cl] | 1-(4-{2-[4-(2,4,5-Trichlorophenyl)piperazin-1-yl]ethyl}piperidin-1-yl)propan-2-one, dihydrochloride | 261 | IIIB |
| 704 | HCl 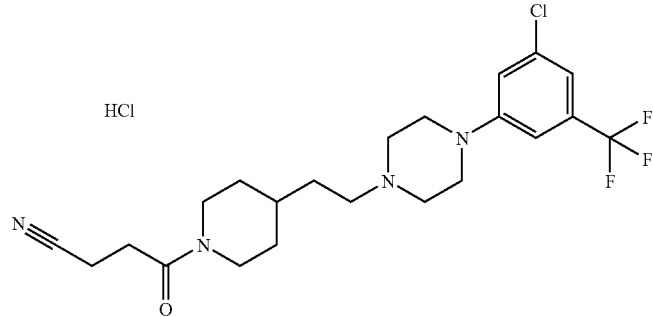 | 4-(4-{2-[4-(3-Chloro-5-trifluoromethylphenyl)piperazin-1-yl]ethyl}piperidin-1-yl)-4-oxobutanonitrile, hydrochloride | 128 | IIIA |

-continued

| Ex | Structure | Name | M.P. (° C.) | Synthetic Path |
|---|---|---|---|---|
| 705 | 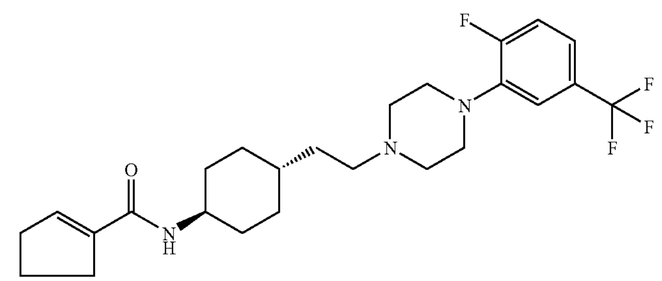 [SMILES: O=C(N[C@H]1CC[C@H](CCN2CCN(c3cc(C(F)(F)F)ccc3F)CC2)CC1)C1=CCCC1] | Cyclopent-1-enecarboxylic acid (4-{2-[4-(2-fluoro-5-trifluoromethylphenylpiperazin-1-yl]ethyl}cyclohexyl) amide | 199 | IIA |
| 706 | 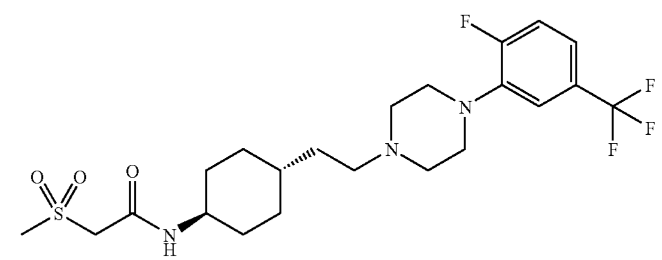 [SMILES: CS(=O)(=O)CC(=O)N[C@H]1CC[C@H](CCN2CCN(c3cc(C(F)(F)F)ccc3F)CC2)CC1] | N-(4-{2-[4-(2-Fluoro-5-trifluoromethylphenyl)piperazin-1-yl]ethyl}cyclohexyl)-2-methanesulfonylacetamide | 192 | IIA |
| 707 | 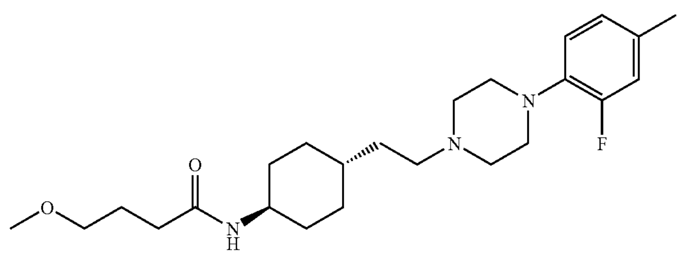 | N-(4-{2-[4-(2-Fluoro-4-methylphenyl)piperazin-1-yl]ethyl}cyclohexyl)-4-methoxybutanamide | | IIA |
| 708 | 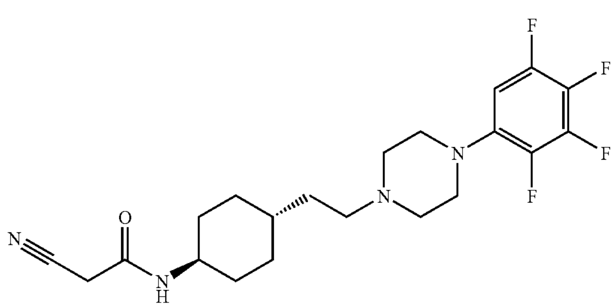 | 2-Cyano-N-(4-{2-[4-(2,3,4,5-tetrafluorophenyl)piperazin-1-yl]ethyl}cyclohexyl)acetamide | 214 | IIA |
| 709 | 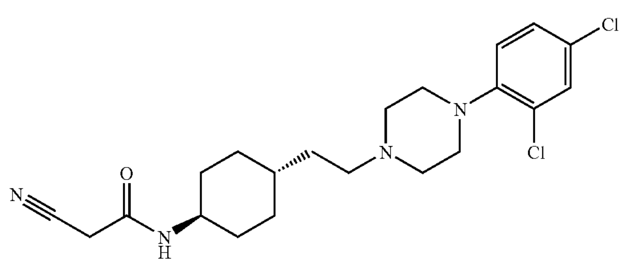 | 2-Cyano-N-(4-{2-[4-(2,4-dichlorophenyl)piperazin-1-yl]ethyl}cyclohexyl)acetamide | 189 | IIA |

-continued

| Ex | Structure | Name | M.P. (° C.) | Synthetic Path |
|---|---|---|---|---|
| 710 | 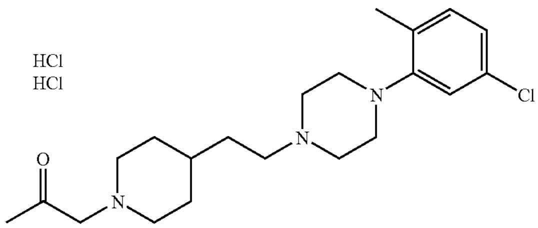 [SMILES: CC(=O)CN1CCC(CCN2CCN(c3cc(Cl)ccc3C)CC2)CC1 ; Cl ; Cl] | 1-(4-{2-[4-(5-Chloro-2-methylphenyl)piperazin-1-yl]ethyl}piperidin-1-yl)propan-2-one, dihydrochloride | 259 | IIIB |
| 711 | 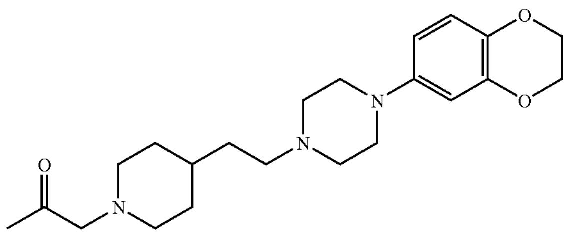 [SMILES: CC(=O)CN1CCC(CCN2CCN(c3ccc4c(c3)OCCO4)CC2)CC1] | 1-(4-{2-[4-(2,3-Dihydrobenzo[1,4]dioxin-6-yl)piperazin-1-yl]ethyl}piperidin-1-yl)propan-2-one | 126 | IIIB |
| 712 | 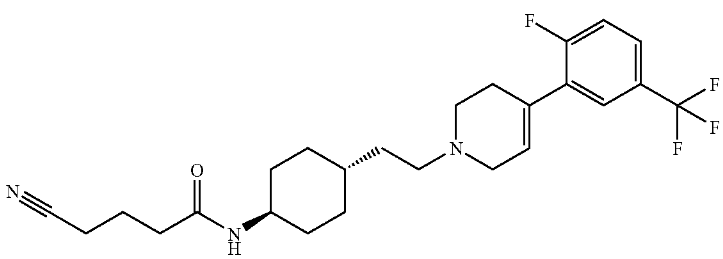 [SMILES: N#CCCCC(=O)N[C@H]1CC[C@H](CCN2CC=C(c3cc(C(F)(F)F)ccc3F)CC2)CC1] | 4-Cyano-N-(4-{2-[4-(2-fluoro-5-trifluoromethylphenyl)-3,6-dihydro-2H-pyridin-1-yl]ethyl}cyclohexyl)butanamide | 153 | IIA |
| 713 | 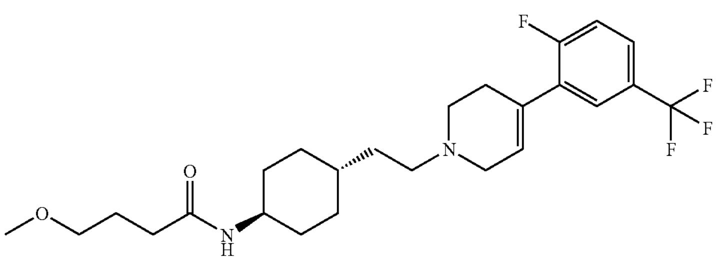 [SMILES: COCCCC(=O)N[C@H]1CC[C@H](CCN2CC=C(c3cc(C(F)(F)F)ccc3F)CC2)CC1] | N-(4-{2-[4-(2-Fluoro-5-trifluoromethylphenyl)-3,6-dihydro-2H-pyridin-1-yl]ethyl}cyclohexyl)-4-methoxybutanamide | 164 | IIA |
| 714 | 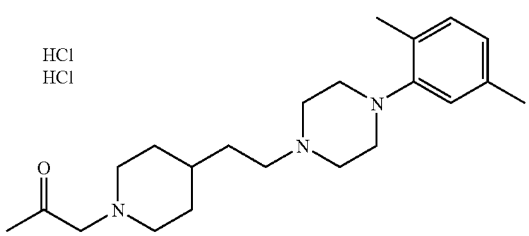 [SMILES: CC(=O)CN1CCC(CCN2CCN(c3cc(C)ccc3C)CC2)CC1 ; Cl ; Cl] | 1-(4-{2-[4-(2,5-Dimethylphenyl)-piperazin-1-yl]ethyl}piperidin-1-yl)propan-2-one, dihydrochloride | 350 | IIIB |
| 715 | 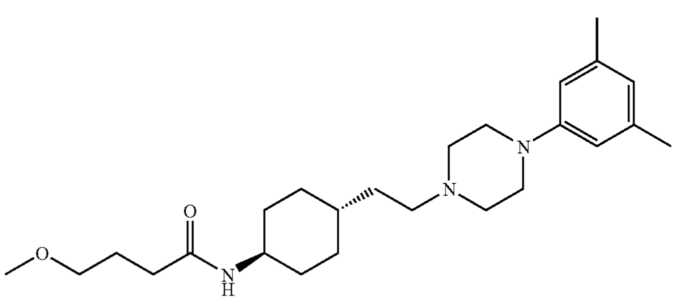 | N-(4-{2-[4-(3,5-Dimethylphenyl)-piperazin-1-yl]ethyl}cyclohexyl)-4-methoxybutanamide | 195 | IIA |

-continued

| Ex | Structure | Name | M.P. (°C.) | Synthetic Path |
|---|---|---|---|---|
| 716 | 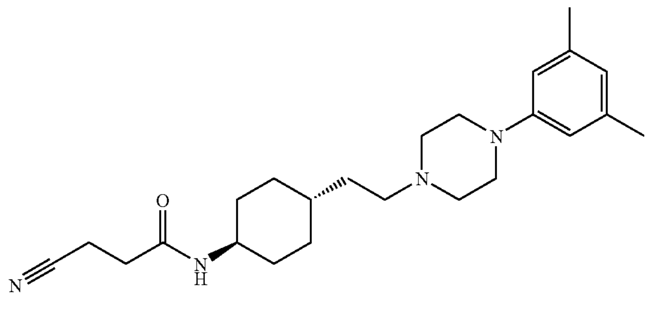 [SMILES: Cc1cc(C)cc(N2CCN(CC[C@H]3CC[C@H](NC(=O)CCC#N)CC3)CC2)c1] | 3-Cyano-N-(4-{2-[4-(3,5-dimethylphenyl)piperazin-1-yl]ethyl}cyclohexyl)propanamide | 175 | IIA |
| 717 | 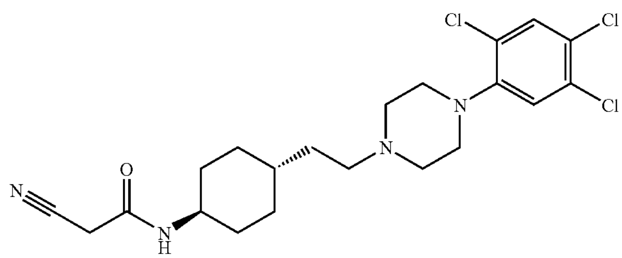 [SMILES: N#CCC(=O)N[C@H]1CC[C@H](CCN2CCN(c3cc(Cl)c(Cl)cc3Cl)CC2)CC1] | 2-Cyano-N-(4-{2-[4-(2,4,5-trichlorophenyl)piperazin-1-yl]ethyl}cyclohexyl)acetamide | 200 | IIA |
| 718 | 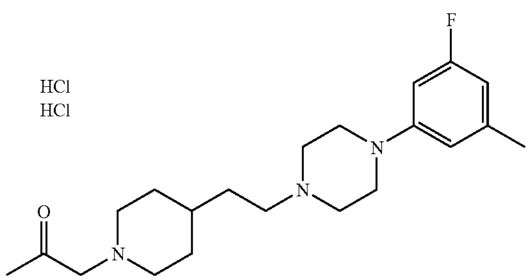 [SMILES: CC(=O)CN1CCC(CCN2CCN(c3cc(C)cc(F)c3)CC2)CC1 ; Cl ; Cl] | 1-(4-{2-[4-(3-Fluoro-5-methylphenyl)piperazin-1-yl]ethyl}piperidin-1-yl)propan-2-one, dihydrochloride | 273 | IIIB |
| 719 | 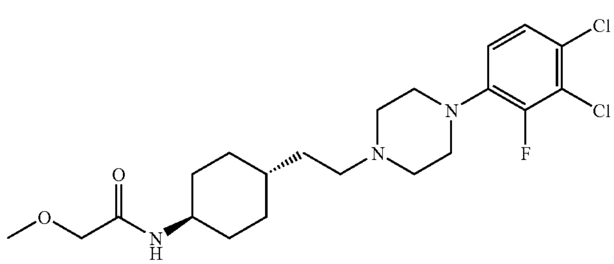 [SMILES: COCC(=O)N[C@H]1CC[C@H](CCN2CCN(c3ccc(Cl)c(Cl)c3F)CC2)CC1] | N-(4-{2-[4-(3,4-Dichloro-2-fluorophenyl)piperazin-1-yl]ethyl}cyclohexyl)-2-methoxyacetamide | 172 | IIIB |
| 720 | 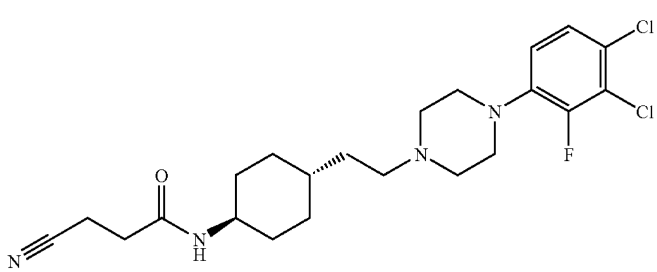 | 3-Cyano-N-(4-{2-[4-(3,4-dichloro-2-fluorophenyl)piperazin-1-yl]ethyl}cyclohexyl)propanamide | 210 | IIIB |

-continued

| Ex | Structure | Name | M.P. (° C.) | Synthetic Path |
|---|---|---|---|---|
| 721 | HCl HCl | 1-(4-{2-[4-(3-Fluoro-5-trifluoromethylphenyl)-3,6-dihydro-2H-pyridin-1-yl]ethyl}piperidin-1-yl)propan-2-one, dihydrochloride | 287 | IIIB |
| 722 | HCl | 4-(4-{2-[4-(2-Fluoro-5-trifluoromethylphenyl)-3,6-dihydro-2H-pyridin-1-yl]ethyl}piperidin-1-yl)-4-oxobutanonitrile, hydrochloride | 150 | IIIA |
| 723 | 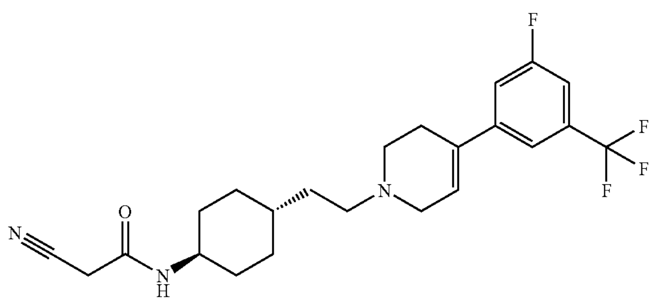 [SMILES: N#CCC(=O)N[C@H]1CC[C@H](CCN2CC=C(c3cc(F)cc(C(F)(F)F)c3)CC2)CC1] | 2-Cyano-N-(4-{2-[4-(3-fluoro-5-trifluoromethylphenyl)-3,6-dihydro-2H-pyridin-1-yl]ethyl}cyclohexyl)acetamide | 163 | IIA |
| 724 | 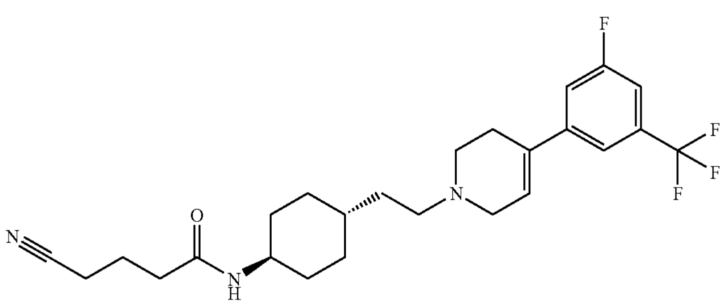 [SMILES: N#CCCCC(=O)N[C@H]1CC[C@H](CCN2CC=C(c3cc(F)cc(C(F)(F)F)c3)CC2)CC1] | 4-Cyano-N-(4-{2-[4-(3-fluoro-5-trifluoromethylphenyl)-3,6-dihydro-2H-pyridin-1-yl]ethyl}cyclohexyl)butanamide | 114 | IIA |
| 725 | 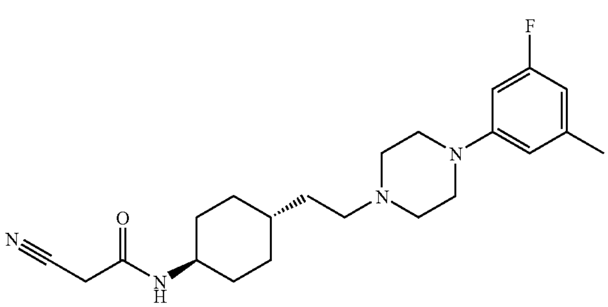 [SMILES: Cc1cc(F)cc(N2CCN(CC[C@H]3CC[C@H](NC(=O)CC#N)CC3)CC2)c1] | 2-Cyano-N-(4-{2-[4-(3-fluoro-5-methylphenyl)piperazin-1-yl]ethyl}cyclohexyl)acetamide | 180 | IIA |

-continued

| Ex | Structure | Name | M.P. (° C.) | Synthetic Path |
|---|---|---|---|---|
| 726 | 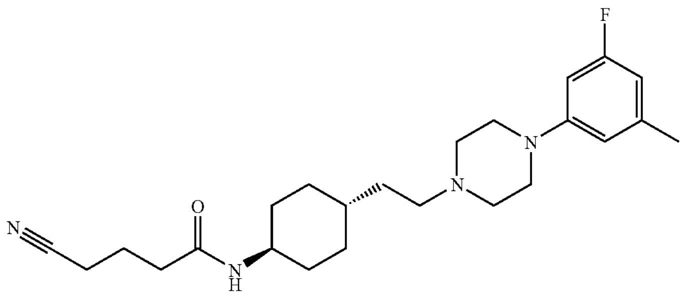 | 4-Cyano-N-(4-{2-[4-(3-fluoro-5-methylphenyl)piperazin-1-yl]ethyl}cyclohexyl)butanamide | 150 | IIA |
| 727 | HCl HCl | 1-(4-{2-[4-(2,3,4-Trichlorophenyl)piperazin-1-yl]ethyl}piperidin-1-yl)propan-2-one, dihydrochloride | 275 | IIIB |
| 728 | HCl HCl | 1-(4-{2-[4-(4-Fluoro-3-methylphenyl)piperazin-1-yl]ethyl}piperidin-1-yl)propan-2-one, dihydrochloride | 258 | IIIB |
| 729 | 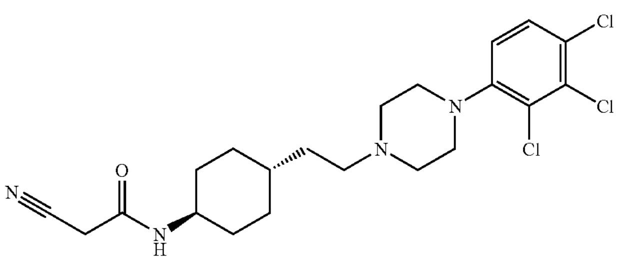 | 2-Cyano-N-(4-{2-[4-(2,3,4-trichlorophenyl)piperazin-1-yl]ethyl}cyclohexyl)acetamide | 217 | IIA |
| 730 | HCl HCl | 1-{4-[2-(4-Pentafluorophenyl-piperazin-1-yl)ethyl]piperidin-1-yl}propan-2-one, dihydrochloride | | IIIB |

| Ex | Structure | Name | M.P. (° C.) | Synthetic Path |
|---|---|---|---|---|
| 731 | 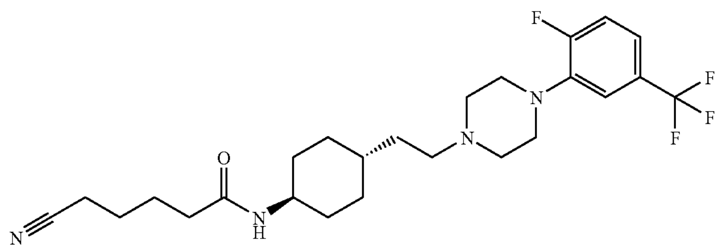 [SMILES: N#CCCCCC(=O)N[C@H]1CC[C@H](CCN2CCN(c3cc(C(F)(F)F)ccc3F)CC2)CC1] | 5-Cyano-pentanoic acid (4-{2-[4-(2-fluoro-5-trifluoromethyl-phenyl)piperazin-1-ylethyl}cyclohexyl)amide | 158 | IIA |
| 732 | 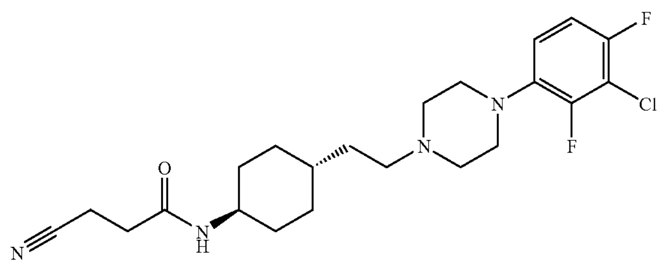 [SMILES: N#CCCC(=O)N[C@H]1CC[C@H](CCN2CCN(c3ccc(F)c(Cl)c3F)CC2)CC1] | N-(4-{2-[4-(3-Chloro-2,4-difluorophenyl)piperazin-1-yl]ethyl}cyclohexyl)-3-cyanopropanamide | 190 | IIA |
| 733 | 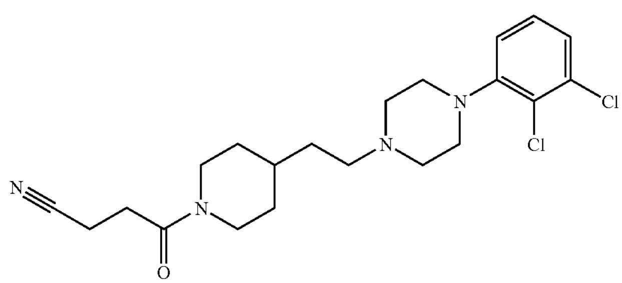 [SMILES: N#CCCC(=O)N1CCC(CCN2CCN(c3cccc(Cl)c3Cl)CC2)CC1] | 4-(4-{2-[4-(2,3-Dichlorophenyl)piperazin-1-yl]ethyl}piperidin-1-yl)-4-oxobutanonitrile | 94 | IIIA |
| 734 | 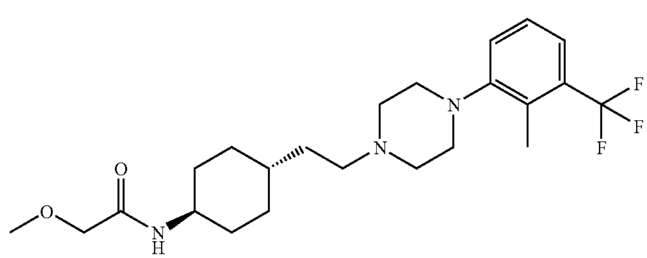 | 2-Methoxy-N-(4-{2-[4-(2-methyl-3-trifluoromethylphenyl)piperazin-1-yl]ethyl}cyclohexyl)acetamide | 159 | IIA |
| 735 | 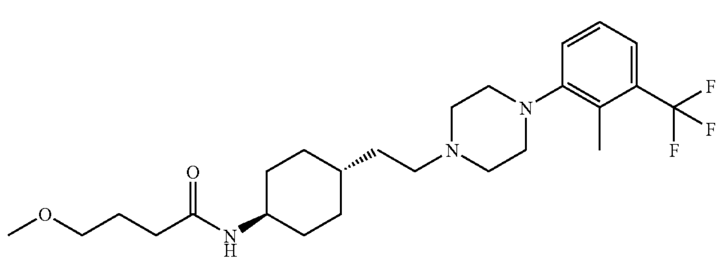 [SMILES: COCCCC(=O)N[C@H]1CC[C@H](CCN2CCN(c3cccc(C(F)(F)F)c3C)CC2)CC1] | 4-Methoxy-N-(4-{2-[4-(2-methyl-3-trifluoromethylphenyl)piperazin-1-yl]ethyl}cyclohexyl)butanamide | 173 | IIA |

-continued

| Ex | Structure | Name | M.P. (° C.) | Synthetic Path |
|---|---|---|---|---|
| 736 | 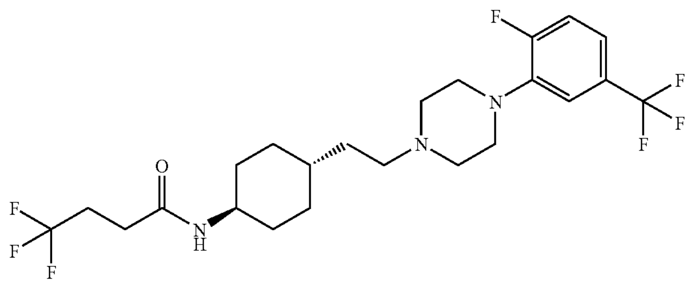 [SMILES: O=C(CCC(F)(F)F)N[C@H]1CC[C@H](CCN2CCN(c3cc(C(F)(F)F)ccc3F)CC2)CC1] | 4,4,4-Trifluoro-N-(4-{2-[4-(2-fluoro-5-trifluoromethyl-phenyl)piperazin-1-yl]ethyl}cyclohexyl)butanamide | 182 | IIA |
| 737 | 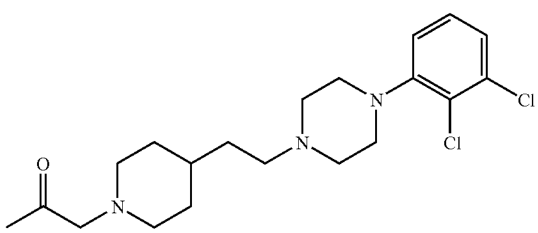 [SMILES: CC(=O)CN1CCC(CCN2CCN(c3cccc(Cl)c3Cl)CC2)CC1] | 1-(4-{2-[4-(2,3-Dichlorophenyl)piperazin-1-yl]ethyl}piperidin-1-yl)propan-2-one, dihydrochloride | 281 | IIIB |
| 738 | 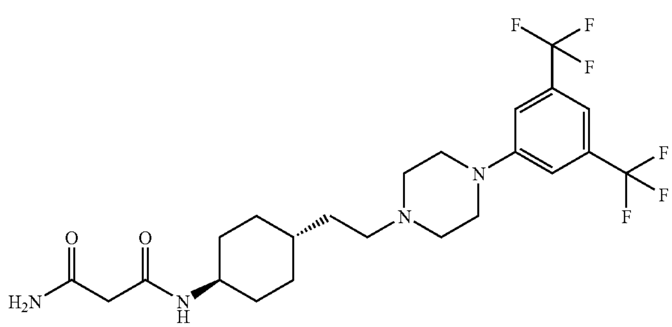 [SMILES: NC(=O)CC(=O)N[C@H]1CC[C@H](CCN2CCN(c3cc(C(F)(F)F)cc(C(F)(F)F)c3)CC2)CC1] | N-(4-{2-[4-(3,5-Bistrifluoro-methylphenyl)piperazin-1-yl]ethyl}cyclohexyl)malonamide | 165 | IIA |
| 739 | 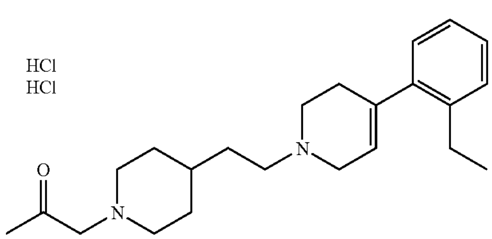 [SMILES: CCc1ccccc1C1=CCN(CCC2CCN(CC(C)=O)CC2)CC1 ; Cl ; Cl] | 1-(4-{2-[4-(2-Ethylphenyl)-3,6-dihydro-2H-pyridin-1-yl]ethyl}piperidin-1-yl)propan-2-one, dihydrochloride | 316 | IIIB |
| 740 | 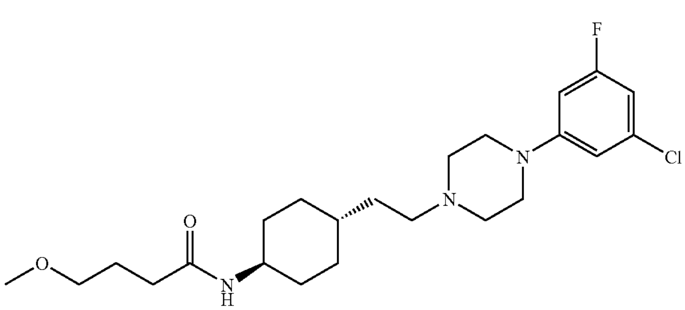 [SMILES: COCCCC(=O)N[C@H]1CC[C@H](CCN2CCN(c3cc(F)cc(Cl)c3)CC2)CC1] | N-(4-{2-[4-(3-Chloro-5-fluorophenyl)piperazin-1-yl]ethyl}cyclohexyl)-4-methoxybutanamide | 177 | IIA |

-continued

| Ex | Structure | Name | M.P. (° C.) | Synthetic Path |
|---|---|---|---|---|
| 741 | 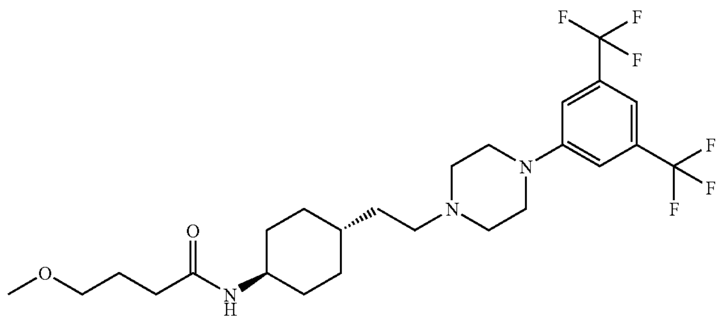 [SMILES: COCCCC(=O)N[C@H]1CC[C@H](CCN2CCN(c3cc(C(F)(F)F)cc(C(F)(F)F)c3)CC2)CC1] | N-(4-{2-[4-(3,5-Bistrifluoromethylphenyl)piperazin-1-yl]ethyl}cyclohexyl)-4-methoxybutanamide | 168 | IIA |
| 742 | 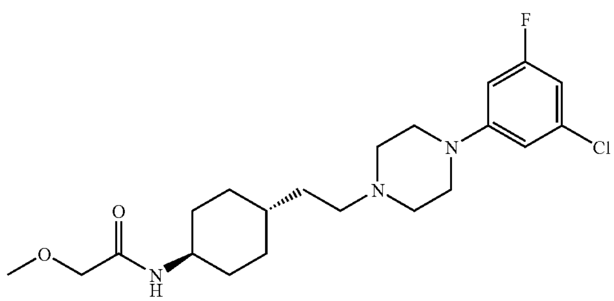 [SMILES: COCC(=O)N[C@H]1CC[C@H](CCN2CCN(c3cc(F)cc(Cl)c3)CC2)CC1] | N-(4-{2-[4-(3-Chloro-5-fluorophenyl)piperazin-1-yl]ethyl}cyclohexyl)-2-methoxyacetamide | 132 | IIA |
| 743 | 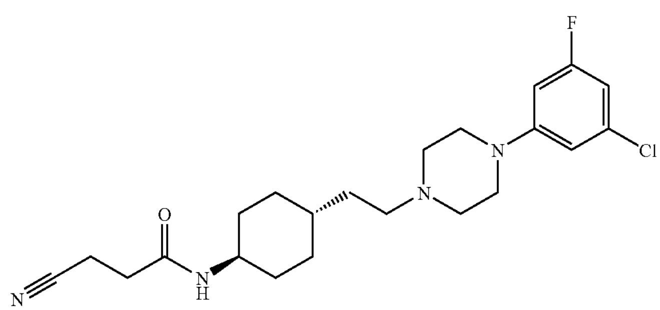 [SMILES: N#CCCC(=O)N[C@H]1CC[C@H](CCN2CCN(c3cc(F)cc(Cl)c3)CC2)CC1] | N-(4-{2-[4-(3-Chloro-5-fluorophenyl)piperazin-1-yl]ethyl}cyclohexyl)-3-cyanopropanamide | 148 | IIA |
| 744 | 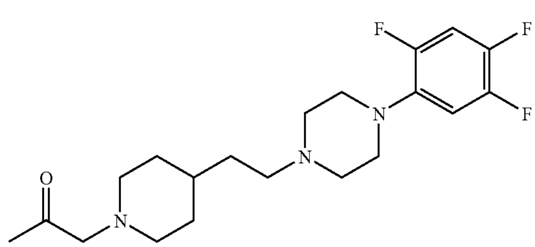 [SMILES: CC(=O)CN1CCC(CCN2CCN(c3cc(F)c(F)cc3F)CC2)CC1] | 1-(4-{2-[4-(2,4,5-Trifluorophenyl)-piperazin-1-yl]ethyl}piperidin-1-yl)propan-2-one | 68 | IIIB |
| 745 | 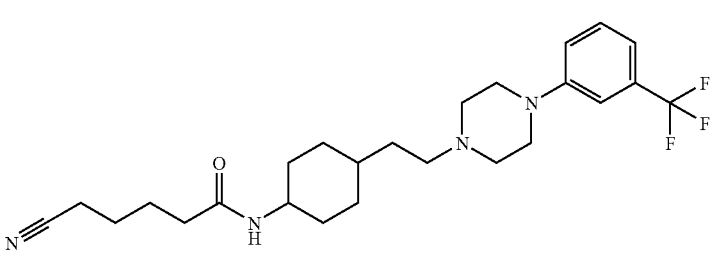 [SMILES: N#CCCCCC(=O)NC1CCC(CCN2CCN(c3cccc(C(F)(F)F)c3)CC2)CC1] | 5-Cyano-pentanoic acid (4-{2-[4-(3-trifluoromethylphenyl)-piperazin-1-yl]ethyl}cyclohexyl)amide | 90 | IIA |

| Ex | Structure | Name | M.P. (° C.) | Synthetic Path |
|---|---|---|---|---|
| 746 | 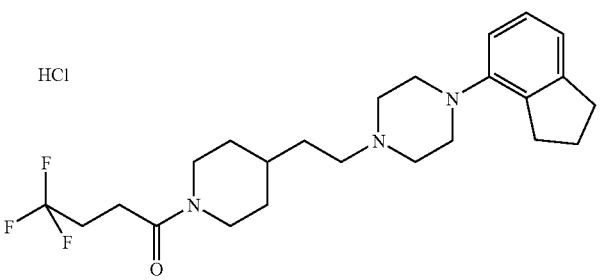 [SMILES: O=C(CCC(F)(F)F)N1CCC(CCN2CCN(c3cccc4c3CCC4)CC2)CC1 ; Cl] | 4,4,4-Trifluoro-1-{4-[2-(4-indan-4-ylpiperazin-1-yl)ethyl]piperidin-1-yl}butan-1-one, hydrochloride | 219 | IIIA |
| 747 | 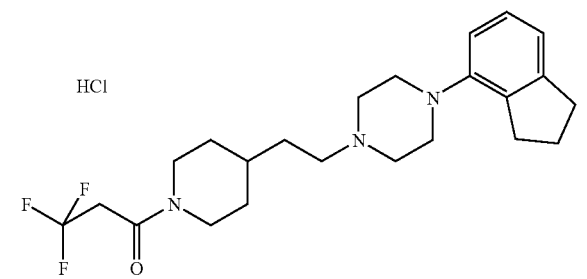 [SMILES: O=C(CC(F)(F)F)N1CCC(CCN2CCN(c3cccc4c3CCC4)CC2)CC1 ; Cl] | 3,3,3-Trifluoro-1-{4-[2-(4-indan-4-ylpiperazin-1-yl)ethyl]piperidin-1-yl}propan-1-one, hydrochloride | 206 | IIIA |
| 748 | 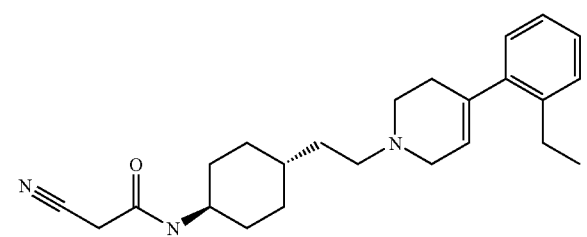 | 2-Cyano-N-(4-{2-[4-(2-ethylphenyl)-3,6-dihydro-2H-pyridin-1-yl]ethyl}cyclohexyl)acetamide | 158 | IIA |
| 749 | 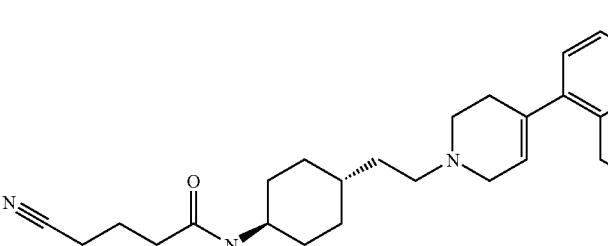 | 4-Cyano-N-(4-{2-[4-(2-ethylphenyl)-3,6-dihydro-2H-pyridin-1-yl]ethyl}cyclohexyl)butanamide | 120 | IIA |
| 750 | 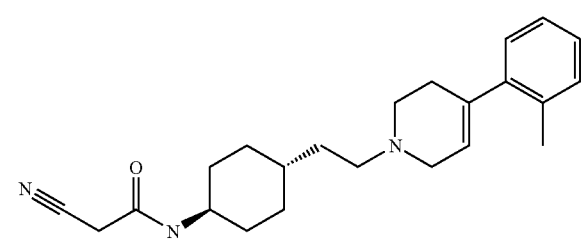 | 2-Cyano-N-{4-[2-(4-o-tolyl-3,6-dihydro-2H-pyridin-1-yl)ethyl]cyclohexyl}acetamide | 166 | IIA |

-continued

| Ex | Structure | Name | M.P. (°C.) | Synthetic Path |
|---|---|---|---|---|
| 751 | 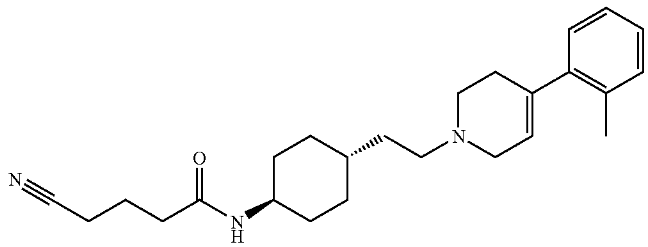 [SMILES: Cc1ccccc1C1=CCN(CC[C@H]2CC[C@H](NC(=O)CCCC#N)CC2)CC1] | 4-Cyano-N-{4-[2-(4-o-tolyl-3,6-dihydro-2H-pyridin-1-yl)ethyl]cyclohexyl}butanamide | 140 | IIA |
| 752 | HCl HCl | 1-{4-[2-(4-o-Tolyl-3,6-dihydro-2H-pyridin-1-yl)ethyl]piperidin-1-yl}propan-2-one, dihydrochloride | 292 | IIIB |
| 753 | 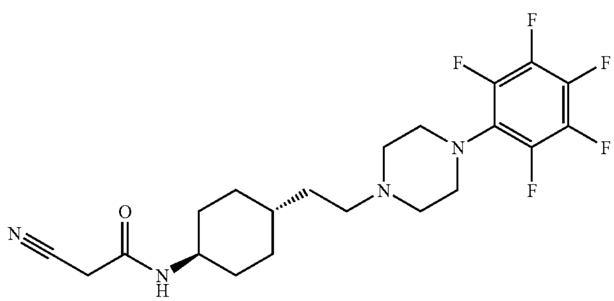 [SMILES: N#CCC(=O)N[C@H]1CC[C@H](CCN2CCN(c3c(F)c(F)c(F)c(F)c3F)CC2)CC1] | 2-Cyano-N-{4-[2-(4-pentafluorophenylpiperazin-1-yl)ethyl]cyclohexyl}acetamide | 202 | IIA |
| 754 | 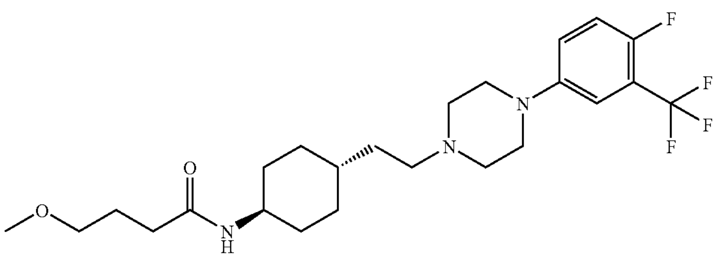 [SMILES: COCCCC(=O)N[C@H]1CC[C@H](CCN2CCN(c3ccc(F)c(C(F)(F)F)c3)CC2)CC1] | N-(4-{2-[4-(4-Fluoro-3-trifluoromethylphenyl)piperazin-1-yl]ethyl}cyclohexyl)-4-methoxybutanamide | 177 | IIA |
| 755 | 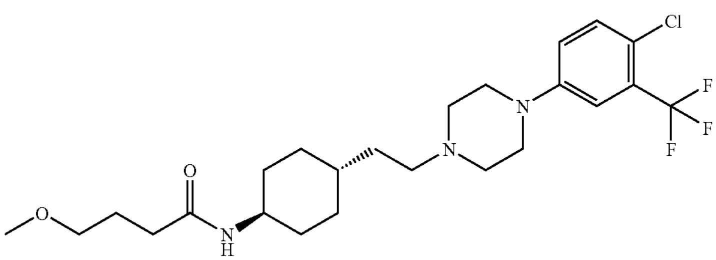 [SMILES: COCCCC(=O)N[C@H]1CC[C@H](CCN2CCN(c3ccc(Cl)c(C(F)(F)F)c3)CC2)CC1] | N-(4-{2-[4-(4-Chloro-3-trifluoromethylphenyl)piperazin-1-yl]ethyl}cyclohexyl)-4-methoxybutanamide | 171 | IIA |

-continued

| Ex | Structure | Name | M.P. (° C.) | Synthetic Path |
|---|---|---|---|---|
| 756 | 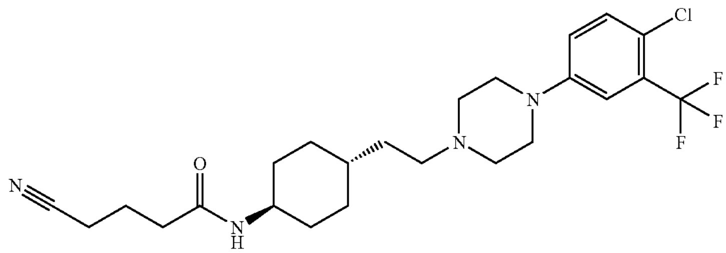 | N-(4-{2-[4-(4-Chloro-3-trifluoromethylphenyl)piperazin-1-yl]ethyl}cyclohexyl)-4-cyanobutanamide | 126 | IIA |
| 757 | 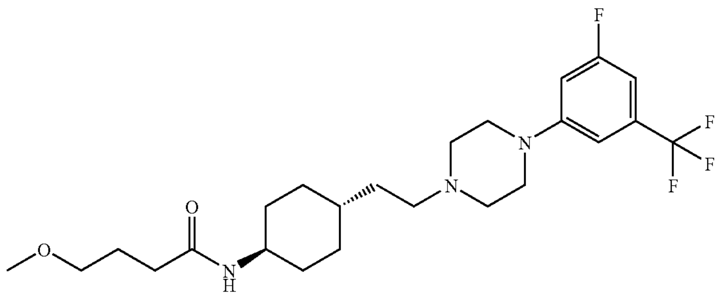 [SMILES: COCCCC(=O)N[C@H]1CC[C@H](CCN2CCN(c3cc(F)cc(C(F)(F)F)c3)CC2)CC1] | N-(4-{2-[4-(3-Fluoro-5-trifluoromethylphenyl)piperazin-1-yl]ethyl}cyclohexyl)-4-methoxybutanamide | 177 | IIA |
| 758 | HCl HCl | 1-(4-{2-[4-(2-Isobutylphenyl)piperazin-1-yl]ethyl}piperidin-1-yl)propan-2-one, dihydrochloride | 285 | IIIB |
| 759 | HCl HCl | 1-(4-{2-[4-(3-Isobutylphenyl)-piperazin-1-yl]ethyl}piperidin-1-yl)propan-2-one, dihydrochloride | 240 | IIIB |
| 760 | 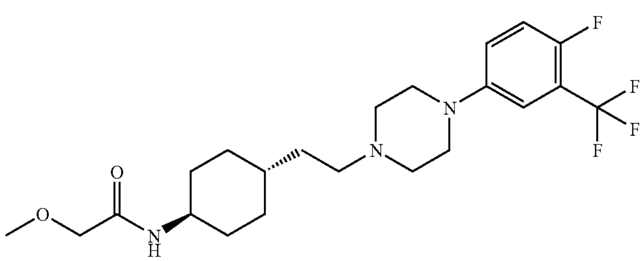 [SMILES: COCC(=O)N[C@H]1CC[C@H](CCN2CCN(c3ccc(F)c(C(F)(F)F)c3)CC2)CC1] | N-(4-{2-[4-(4-Fluoro-3-trifluoromethylphenyl)piperazin-1-yl]ethyl}cyclohexyl)-2-methoxyacetamide | 146 | IIA |
| 761 | 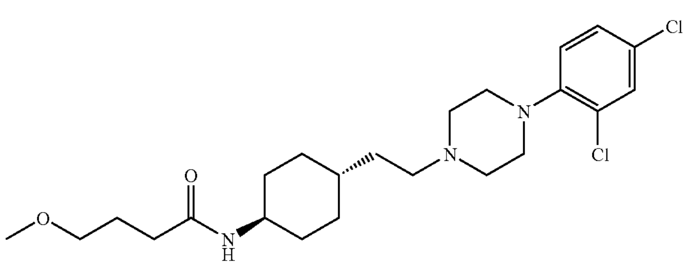 [SMILES: COCCCC(=O)N[C@H]1CC[C@H](CCN2CCN(c3ccc(Cl)cc3Cl)CC2)CC1] | N-(4-{2-[4-(2,4-Dichlorophenyl)piperazin-1-yl]ethyl}cyclohexyl)-4-methoxybutanamide | 171 | IIA |

-continued

| Ex | Structure | Name | M.P. (° C.) | Synthetic Path |
|---|---|---|---|---|
| 762 | 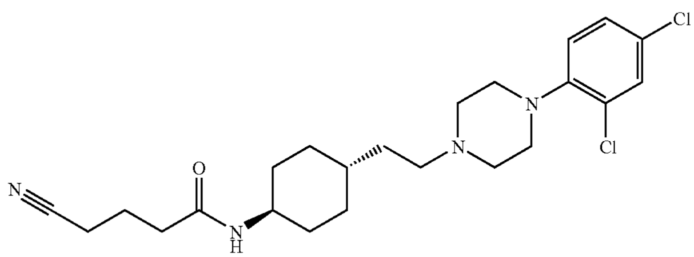 [SMILES: N#CCCCC(=O)N[C@H]1CC[C@H](CCN2CCN(c3ccc(Cl)cc3Cl)CC2)CC1] | 4-Cyano-N-(4-{2-[4-(2,4-dichlorophenyl)piperazin-1-yl]ethyl}cyclohexyl)butanamide | 162 | IIA |
| 763 | 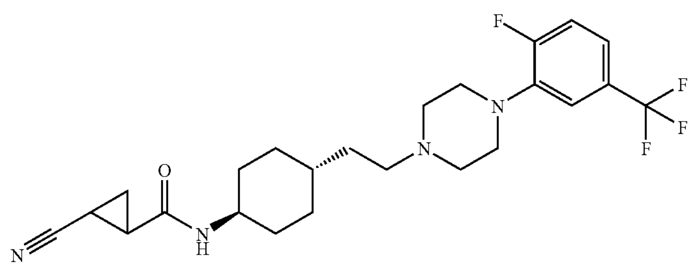 [SMILES: N#CC1CC1C(=O)N[C@H]1CC[C@H](CCN2CCN(c3cc(C(F)(F)F)ccc3F)CC2)CC1] | 2-Cyano-cyclopropanecarboxylic acid (4-{2-[4-(2-fluoro-5-trifluoromethylphenyl)piperazin-1-yl]ethyl}cyclohexyl) amide | 196 | IIA |
| 764 | 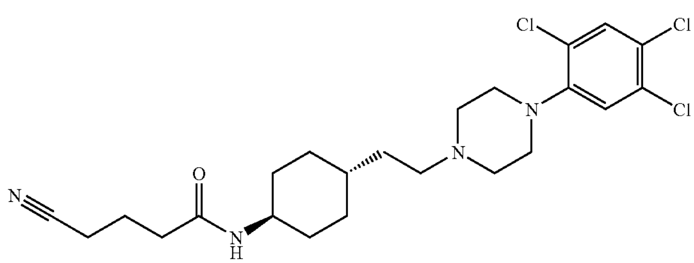 [SMILES: N#CCCCC(=O)N[C@H]1CC[C@H](CCN2CCN(c3cc(Cl)c(Cl)cc3Cl)CC2)CC1] | 4-Cyano-N-(4-{2-[4-(2,4,5-trichlorophenyl)piperazin-1-yl]ethyl}cyclohexyl)butanamide | 179 | IIA |
| 765 | 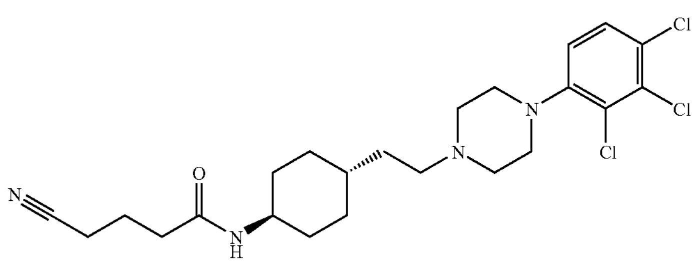 [SMILES: N#CCCCC(=O)N[C@H]1CC[C@H](CCN2CCN(c3ccc(Cl)c(Cl)c3Cl)CC2)CC1] | 4-Cyano-N-(4-{2-[4-(2,3,4-trichlorophenyl)piperazin-1-yl]ethyl}cyclohexyl)butanamide | 176 | IIA |
| 766 | 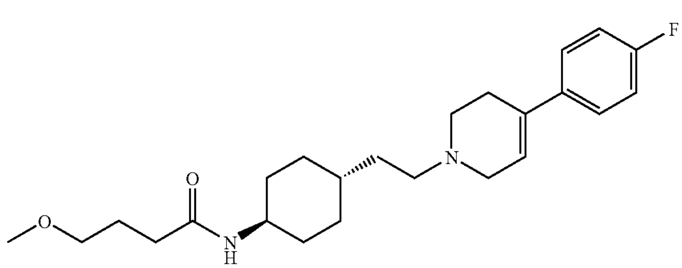 [SMILES: COCCCC(=O)N[C@H]1CC[C@H](CCN2CC=C(c3ccc(F)cc3)CC2)CC1] | N-(4-{2-[4-(4-Fluorophenyl)-3,6-dihydro-2H-pyridin-1-yl]ethyl}cyclohexyl)-4-methoxybutanamide | 201 | IIA |

-continued

| Ex | Structure | Name | M.P. (°C.) | Synthetic Path |
|---|---|---|---|---|
| 767 | 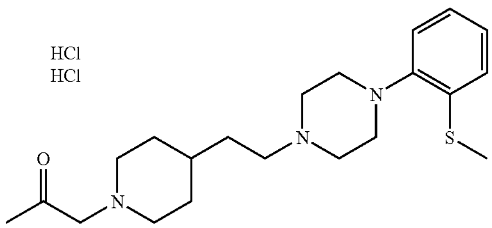 [SMILES: CSc1ccccc1N1CCN(CCC2CCN(CC(C)=O)CC2)CC1 ; Cl ; Cl] | 1-(4-{2-[4-(2-Methylsulfanylphenyl)piperazin-1-yl]ethyl}piperidin-1-yl)propan-2-one, dihydrochloride | 280 | IIIB |
| 768 | 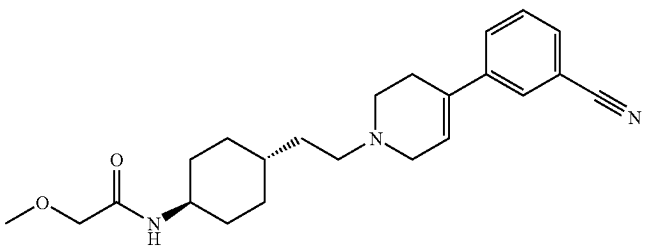 [SMILES: COCC(=O)N[C@H]1CC[C@H](CCN2CC=C(c3cccc(C#N)c3)CC2)CC1] | N-(4-{2-[4-(3-Cyanophenyl)-3,6-dihydro-2H-pyridin-1-yl]ethyl}cyclohexyl)-2-methoxyacetamide | 117 | IIA |
| 769 | 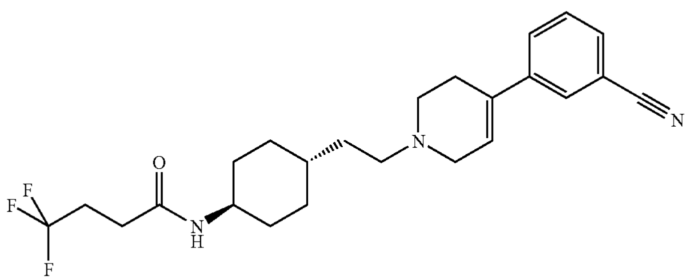 [SMILES: N#Cc1cccc(C2=CCN(CC[C@H]3CC[C@H](NC(=O)CCC(F)(F)F)CC3)CC2)c1] | N-(4-{2-[4-(3-Cyanophenyl)-3,6-dihydro-2H-pyridin-1-yl]ethyl}cyclohexyl)-4,4,4-trifluorobutanamide | 177 | IIA |
| 770 | 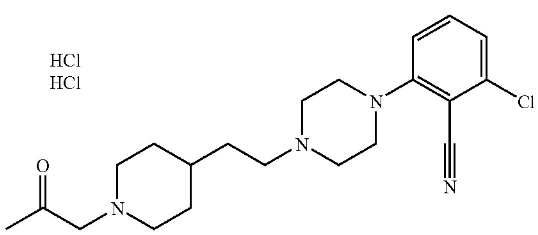 [SMILES: CC(=O)CN1CCC(CCN2CCN(c3cccc(Cl)c3C#N)CC2)CC1 ; Cl ; Cl] | 2-Chloro-6-(4-{2-[1-(2-oxopropyl)piperidin-4-yl]ethyl}piperazin-1-yl)benzonitrile, dihydrochloride | 284 | IIIB |
| 783 | 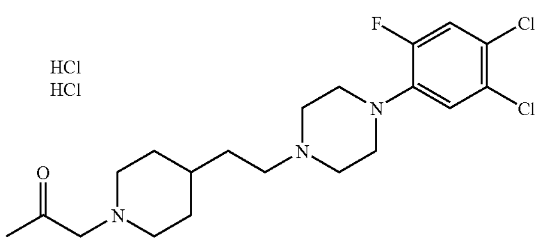 [SMILES: CC(=O)CN1CCC(CCN2CCN(c3cc(Cl)c(Cl)cc3F)CC2)CC1 ; Cl ; Cl] | 1-(4-{2-[4-(4,5-Dichloro-2-fluorophenyl)piperazin-1-yl]ethyl}piperidin-1-yl)propan-2-one | 309 (dec) | IIIB |
| 784 | 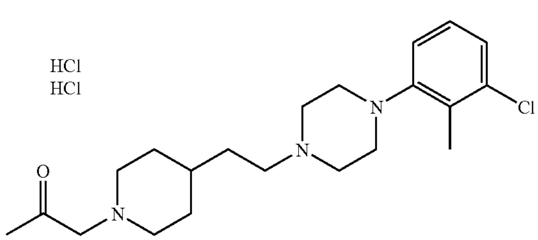 [SMILES: CC(=O)CN1CCC(CCN2CCN(c3cccc(Cl)c3C)CC2)CC1 ; Cl ; Cl] | 1-(4-{2-[4-(3-Chloro-2-methylphenyl)piperazin-1-yl]ethyl}piperidin-1-yl)propan-2-one, dihydrochloride | 320-325 | IIIB |

Further characterisation by ¹H NMR of some representative examples is given in the following table:
| Ex | Structure | ¹H NMR |
|---|---|---|
| 13 | 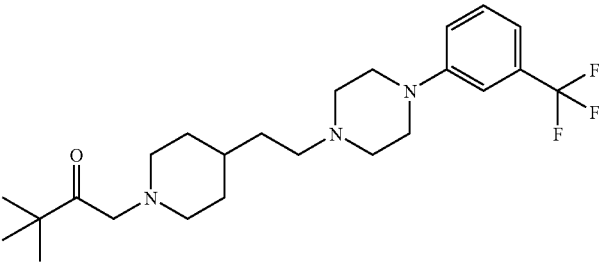 [SMILES: CC(C)(C)C(=O)CN1CCC(CCN2CCN(c3cccc(C(F)(F)F)c3)CC2)CC1] | 7.3 (t, 1H, J = 7.5); 7.15 to 7.0 (ms, 3H); 3.35 (s, 2H); 3.25 (m, 4H); 2.9 (m, 2H); 2.6 (m, 4H); 2.45 (m, 2H); 2.0 (m, 2H); 1.8 to 1.55 (ms, 2H); 1.55 to 1.2 (ms, 5H); 1.15 (s, 9H) |
| 37 | 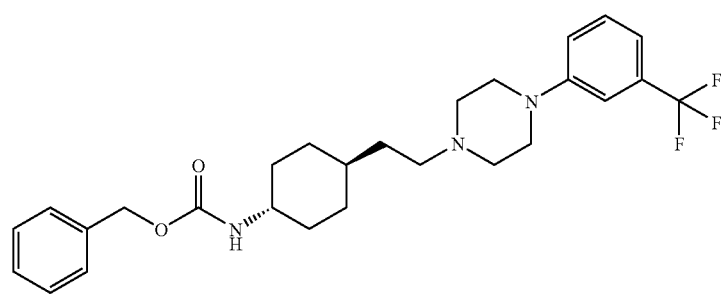 [SMILES: O=C(N[C@H]1CC[C@H](CCN2CCN(c3cccc(C(F)(F)F)c3)CC2)CC1)OCc1ccccc1] | 7.45 to 7.25 (ms, 6H); 7.2 to 7.0 (ms, 3H); 5.1 (s, 2H); 4.6 (broad d, 1H); 3.45 (m, 1H); 3.25 (m, 4H); 2.6 (m, 4H); 2.4 (m, 2H); 2.05 (m, 2H); 1.8 (m, 2H); 1.7 to 1.0 (ms, 7H) |
| 46 | 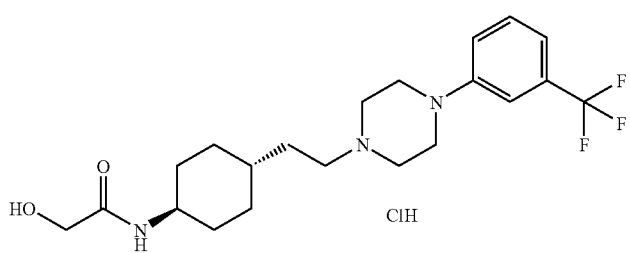 [SMILES: O=C(CO)N[C@H]1CC[C@H](CCN2CCN(c3cccc(C(F)(F)F)c3)CC2)CC1 ; Cl] | 7.5 (t, 1H, J = 7.5); 7.4 to 7.25 (ms, 3H); 4.05 (s, 2H); 4.0 to 3.8 (ms, 2H); 3.8 to 3.5 (ms, 3H); 3.35 to 3.05 (ms, 6H); 1.95 to 1.5 (ms, 7H); 1.5 to 1.0 (ms, 4H) (D₂O) |
| 59 | 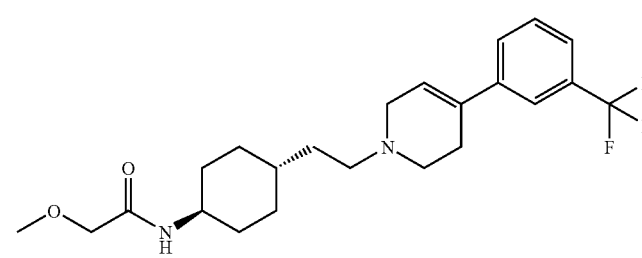 | 7.7 to 7.35 (ms, 4H); 6.35 (broad d, 1H); 6.15 (s, 1H); 3.9 (s, 2H); 3.8 (m, 1H); 3.4 (s, 3H); 3.2 (m, 2H); 2.7 (m, 2H); 2.6 (m, 2H), 2.5 (m, 2H); 2.0 (m, 2H); 1.8 (m, 2H); 1.75 to 1.4 (ms, 2H); 1.4 to 1.0 (ms, 5H) |
| 62 | 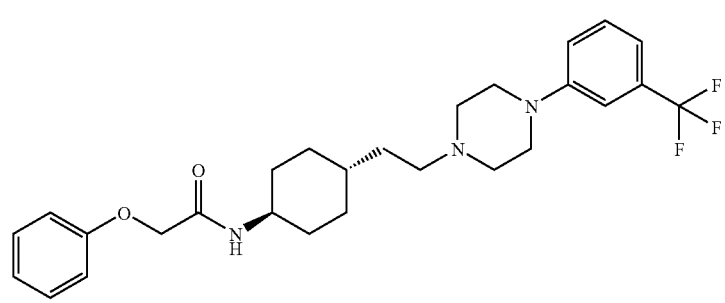 [SMILES: O=C(COc1ccccc1)N[C@H]1CC[C@H](CCN2CCN(c3cccc(C(F)(F)F)c3)CC2)CC1] | 7.45 to 7.25 (ms, 4H); 7.2 to 7.0 (ms, 3H); 7.0 to 6.85 (ms, 2H); 6.4 (broad d, 1H); 4.45 (s, 2H); 3.85 (m, 1H); 3.3 (m, 4H); 2.65 (m, 4H); 2.45 (m, 2H); 2.0 (m, 2H); 1.9 to 1.4 (ms, 4H); 1.4 to 1.0 (ms, 5H) |

-continued

| Ex | Structure | ¹H NMR |
|---|---|---|
| 79 | 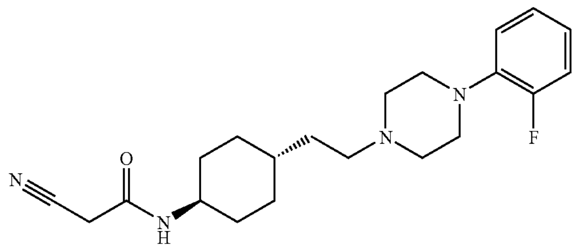 | 7.15 to 6.85 (ms, 4H); 5.85 (broad d, 1H); 3.75 (m, 1H), 3.4 (s, 2H); 3.15 (m, 4H); 2.65 (m, 4H); 2.45 (m, 2H); 2.0 (m, 2H); 1.85 (m, 2H); 1.8 to 1.4 (ms, 3H); 1.4 to 1.0 (ms, 4H) |
| 85 | 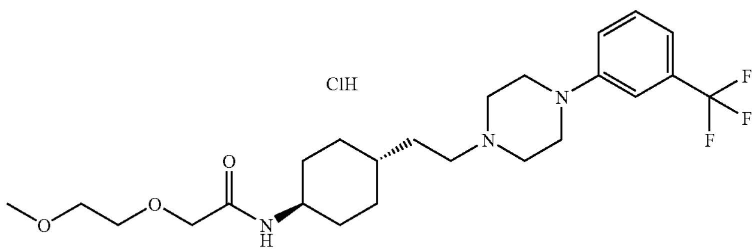 [SMILES: COCCOCC(=O)N[C@H]1CC[C@H](CCN2CCN(c3cccc(C(F)(F)F)c3)CC2)CC1 ; Cl] | 11.2 (broad s, 1H); 7.55 to 7.35 (ms, 2H); 7.3 (d, 1H, J = 5); 7.25 (s, 1H); 7.15 (d, 1H, J = 5); 4.0 to 3.7 (ms, 5H); 3.7 to 3.4 (ms, 4H); 3.4 to 2.95 (ms, 9H); 1.85 to 1.85 (ms, 13) (DMSO D₆) |
| 94 | 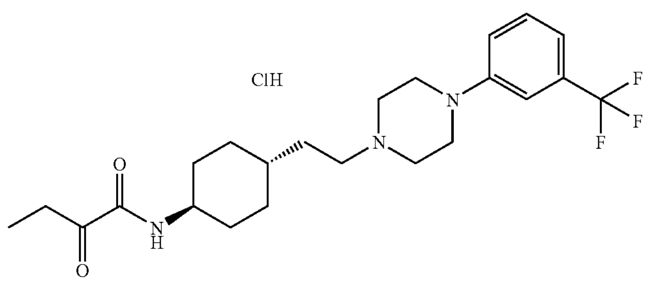 [SMILES: CCC(=O)C(=O)N[C@H]1CC[C@H](CCN2CCN(c3cccc(C(F)(F)F)c3)CC2)CC1 ; Cl] | 10.8 (broad s, 1H); 8.4 (d, 1H, J = 7.5); 7.35 to 7.2 (ms, 2H); 7.15 (d, 1H, J = 7.5); 3.9 (m, 2H); 3.5 (m, 2H); 3.4 to 3.05 (ms, 7H); 2.9 (q, 2H, J = 7.5); 1.85 to 1.55 (ms, 5H); 1.55 to 1.15 (ms, 4H); 1.15 to 1.85 (ms, 5H) (DMSO D₆) |
| 95 | 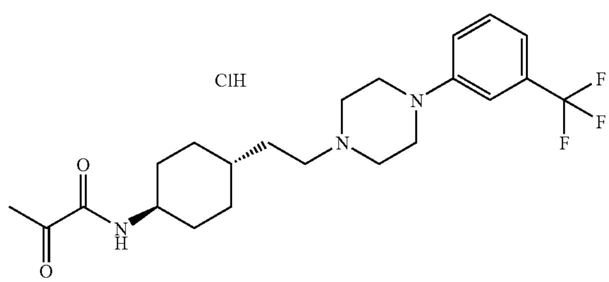 [SMILES: CC(=O)C(=O)N[C@H]1CC[C@H](CCN2CCN(c3cccc(C(F)(F)F)c3)CC2)CC1 ; Cl] | 11.05 (broad s, 1H); 8.35 (d, 1H, J = 7.5); 7.4 (t, 1H, J = 7.5); 7.35 to 7.2 (ms, 2H); 7.1 (d, 1H, J = 7.5); 3.9 (m, 2H); 3.75 to 3.4 (ms, 3H); 3.4 to 2.9 (ms, 6H); 2.3 (s, 3H); 1.9 to 1.15 (ms, 9H); 1.15 to 0.85 (ms, 2H) (DMSO D₆) |
| 96 | 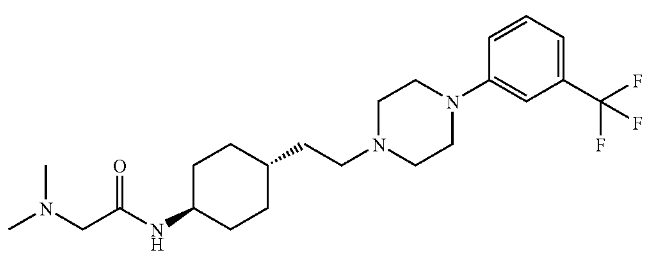 [SMILES: CN(C)CC(=O)N[C@H]1CC[C@H](CCN2CCN(c3cccc(C(F)(F)F)c3)CC2)CC1] | 7.35 (t, 1H, J = 7.5); 7.15 to 7.0 (ms, 3H); 6.95 (broad d, 1H); 3.75 (m, 1H); 3.25 (m, 4H); 2.9 (s, 2H); 2.65 (m, 4H); 2.45 (m, 2H); 2.25 (s, 6H); 2.0 (m, 2H); 1.8 (m, 2H); 1.5 (m, 2H); 1.4 to 1.0 (ms, 5H) |
| 100 | 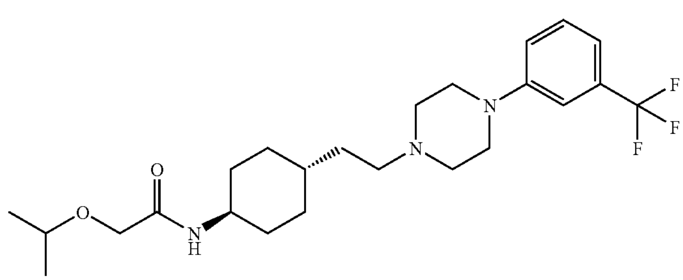 [SMILES: CC(C)OCC(=O)N[C@H]1CC[C@H](CCN2CCN(c3cccc(C(F)(F)F)c3)CC2)CC1] | 7.35 (t, 1H, J = 7.5); 7.2 to 7.0 (ms, 3H); 6.4 (broad d, 1H); 3.9 (s, 2H); 3.8 (m, 1H); 3.65 (m, 1H); 3.25 (m, 4H); 2.6 (m, 4H); 2.45 (m, 2H); 2.05 (m, 2H); 1.85 (m, 2H); 1.7 (m, 1H); 1.5 (m, 2H); 1.4 to 1.0 (ms, 10H) |

-continued

| Ex | Structure | ¹H NMR |
|---|---|---|
| 107 | 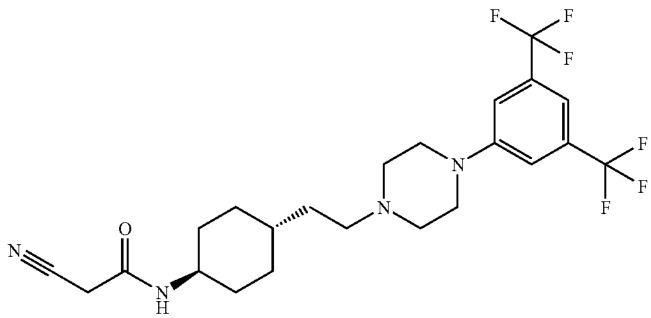 [SMILES: N#CCC(=O)N[C@H]1CC[C@H](CCN2CCN(c3cc(C(F)(F)F)cc(C(F)(F)F)c3)CC2)CC1] | 7.35 to 7.2 (ms, 2H); 5.85 (broad d, 1H); 3.75 (m, 1H); 3.4 (s, 2H); 3.3 (m, 4H); 2.6 (m, 4H); 2.45 (m, 2H); 2.05 (m, 2H); 1.85 (m, 2H); 1.6 (m, 1H); 1.5 (m, 2H); 1.4 to 1.0 (ms, 4H) |
| 109 | 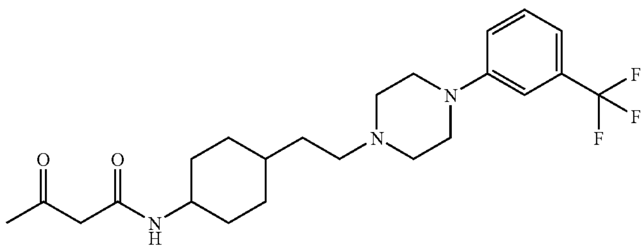 [SMILES: CC(=O)CC(=O)NC1CCC(CCN2CCN(c3cccc(C(F)(F)F)c3)CC2)CC1] | 7.35 (t, 1H, J = 7.5); 7.2 to 7.0 (ms, 3H); 6.75 (broad d, 1H); 3.7 (m, 1H); 3.4 (s, 2H); 3.25 (m, 4H); 2.6 (m, 4H); 2.45 (m, 2H); 2.3 (s, 3H); 2.05 (m, 2H); 1.85 (m, 2H); 1.75 to 1.4 (ms, 3H); 1.4 to 1.0 (ms, 4H) |
| 120 | 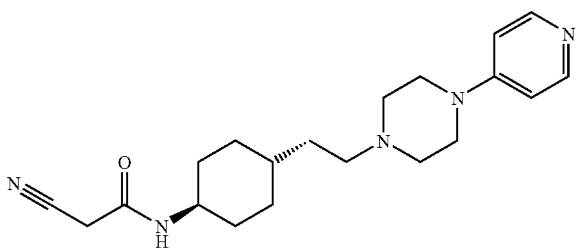 | 8.25 (d, 2H, J = 7.5); 6.65 (d, 2H, J = 7.5); 6.45 (broad s, 1H); 4.0 (0.35H equatorial); 3.7 (0.65H axial); 3.35 to 3.25 (ms, 6H); 2.55 (m, 4H); 2.4 (m, 2H); 2.3 (1.7H); 2.0 (m, 1.4H); 1.8 (m, 1.4H); 1.75 to 0.9 (ms, 7.5H) |
| 141 | 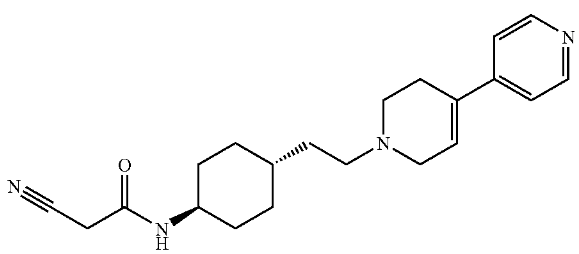 [SMILES: N#CCC(=O)N[C@H]1CC[C@H](CCN2CC=C(c3ccncc3)CC2)CC1] | 7.5 to 7.15 (ms, 5H); 6.1 (m, 1H); 5.85 (broad d, 1H); 3.75 (m, 1H); 3.35 (s, 2H); 3.2 (m, 2H); 2.7 (m, 2H); 2.6 (m, 2H); 2.5 (m, 2H); 2.05 (m, 2H); 1.9 (m, 2H); 1.5 (m, 2H); 1.4 to 1.0 (ms, 5H) |
| 149 | 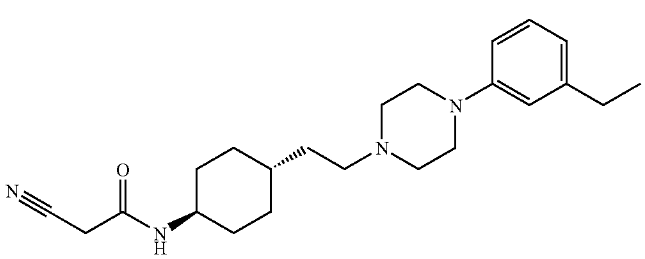 | 7.25 (t, 1H, J = 7.5); 6.85 to 6.65 (ms, 3H); 5.85 (broad d, 1H); 3.75 (m, 1H); 3.35 (s, 2H); 3.2 (m, 4H); 2.7 to 2.5 (ms, 6H); 2.4 (m, 2H); 2.05 (m, 2H); 1.85 (m, 2H); 1.45 (m, 2H); 1.4 to 1.0 (ms, 7H) |

-continued

| Ex | Structure | ¹H NMR |
|---|---|---|
| 154 | (structure) | 7.35 (t, 1H, J = 7.5); 7.2 to 7.0 (ms, 3H); 6.05 (broad s, 1H); 5.65 (broad d, 1H); 5.35 (broad s, 1H); 4.0 (m, 0.35H equatorial); 3.7 (m, 0.65H axial); 3.25 (m, 4H); 2.7 to 2.45 (ms, 8H); 2.4 (m, 2H); 2.0 (m, 2H); 1.8 (m, 2H); 1.55 (m, 1H); 2.5 (m, 2H); 2.4 to 1.0 (ms, 4H) |
| 172 | (structure) | 7.25 to 7.05 (ms, 3H); 5.3 (broad d, 1H); 3.7 (m, 1H); 3.15 (m, 4H); 2.65 (m, 4H); 2.55 to 2.4 (ms, 4H); 2.3 (t, 2H, J = 7.5); 2.0 (m, 4H); 1.8 (m, 2H); 1.45 (m, 2H); 1.4 to 1.0 (ms, 5H) |
| 175 | (structure) ClH | 10.4 (broad s, 1H); 8.2 (d, 1H, J = 7.5); 7.0 (t, 1H, J = 7.5); 6.4 (d, 1H, J = 7.5); 6.35 (s, 1H); 6.25 (d, 1H, J = 7.5); 3.7 (m, 2H); 3.65 (s, 2H); 3.6 to 3.3 (ms, 3H); 3.2 to 2.9 (ms, 6H); 1.9 to 1.5 (ms, 6H); 1.4 to 0.9 (ms, 5H) (DMSO D₆) |
| 290 | (structure) ClH | 10.3 (broad s, 1H); 7.4 (t, 1H, J = 7.5); 7.4 to 7.0 (ms, 7H); 4.8 (s, 2H); 4.6 (s, 2H); 3.9 (m, 2H); 3.5 (m, 2H); 3.3 to 2.8 (ms, 7H); 2.3 (d, 0.8H, J = 7.5); 2.2 (d, 1.2H, J = 7.5); 1.9 to 0.8 (ms, 11H) trans/cis 60/40 (DMSO D₆) |
| 293 | (structure) | 7.35 (t, 1H, J = 7.5); 7.2 to 7.0 (m, 3H); 3.25 (m, 4H); 3.2 (s, 3H); 2.95 (s, 3H); 2.45 (m, 4H); 2.2 (t, 2H, J = 7.5); 2.2 (d, 2H, J = 7.5); 1.9 to 1.6 (ms, 4H); 1.6 to 1.15 (ms, 5H); 1.15 to 0.75 (ms, 3H) |

| Ex | Structure | $^1$H NMR |
|---|---|---|
| 296 | 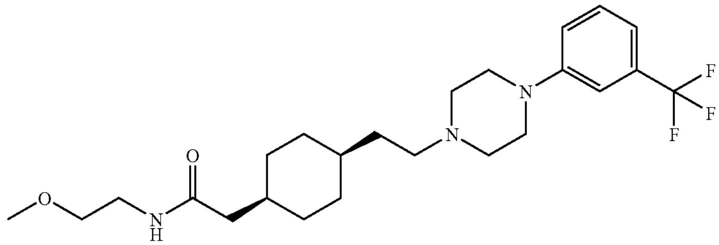 [SMILES: COCCNC(=O)C[C@H]1CC[C@@H](CCN2CCN(c3cccc(C(F)(F)F)c3)CC2)CC1] | 7.35 (t, 1H, J = 7.5); 7.15 to 7.0 (ms, 3H); 5.8 (broad t, 1H); 3.45 (m, 4H); 3.35 (s, 3H); 3.25 (m, 4H); 2.6 (m, 4H); 2.41 (t, 2H, J = 7.5); 2.05 (d, 2H, J = 7.5); 1.9 to 1.7 (ms, 5H); 1.6 to 1.1 (ms, 4H); 1.1 to 0.8 (ms, 3H) |
| 297 | 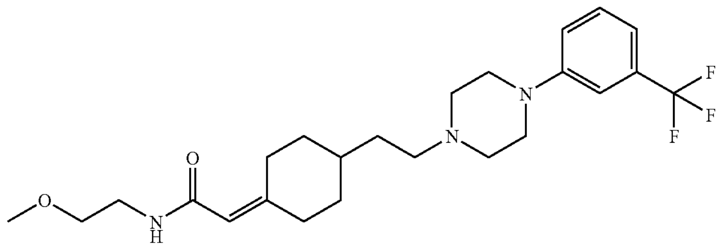 [SMILES: COCCNC(=O)C=C1CCC(CCN2CCN(c3cccc(C(F)(F)F)c3)CC2)CC1] | 7.35 (t, 1H); 7.15 to 7.0 (ms, 3H); 5.75 (broad t, 1H); 5.25 (s, 1H); 3.75 (m, 1H); 3.45 (m, 4H); 3.35 (s, 3H); 3.25 (m, 4H); 3.6 (m, 4H); 2.45 (t, 2H, J = 7.5); 2.3 to 1.85 (ms, 5H); 1.6 to 1.4 (ms, 2H); 1.3 to 1.0 (ms, 3H) |
| 352 | HCl HCl | 7.5 (t, 1H, J = 7.5); 7.4 to 7.2 (ms, 3H); 4.75 (2H); 3.9 (m, 2H); 3.7 (m, 2H); 3.55 (m, 2H); 3.45 to 3.05 (ms, 10H); 2.95 (m, 2H); 2.2 (s, 3H); 2.0 (m, 2H); 1.9 to 1.6 (3H); 1.5 (m, 2H) (D$_2$O) |
| 367 | HCl | 13.4 (broad s, 1H); 7.75 to 7.5 (ms, 2H); 7.1 (t, 1H, J = 7.5); 5.85 (d, 1H); 4.55 (m, 2H); 4.3 to 3.95 (ms, 3H); 3.7 (m, 4H); 3.15 (m, 2H); 2.6 to 2.15 (ms, 7H); 2.1 to 1.05 (ms, 13H) |
| 634 | HCl HCl | 7.35 to 7.2 (ms, 2H); 7.05 (t, 1H, J = 7.5); 4.85 (s, 2H); 4.25 (s, 2H); 3.65 (m, 2H); 3.5 (m, 2H); 3.35 to 2.85 (ms, 7H); 2.2 (s, 3H); 2.15 to 1.9 (ms, 6H); 1.9 to 1.5 (ms, 5H) |
| 649 | 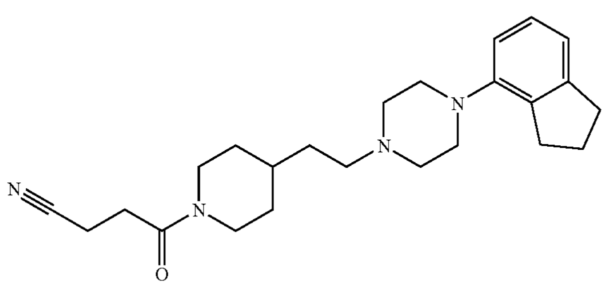 [SMILES: N#CCCC(=O)N1CCC(CCN2CCN(c3cccc4c3CCC4)CC2)CC1] | 7.15 (t, 1H, J = 7.5); 6.95 (d, 1H, J = 7.5); 6.75 (d, 1H, J = 7.5); 4.6 (m, 1H); 3.75 (m, 1H); 3.25 to 3.0 (ms, 5H); 2.9 (t, 2H, J = 7.5); 2.85 (t, 2H, J = 7.5); 2.8 to 2.5 (ms, 7H); 2.45 (m, 2H); 2.05 (m, 2H); 1.8 (m, 2H); 1.7 to 1.45 (ms, 5H); 2.15 (m, 2H) |

| Ex | Structure | ¹H NMR |
|---|---|---|
| 693 | 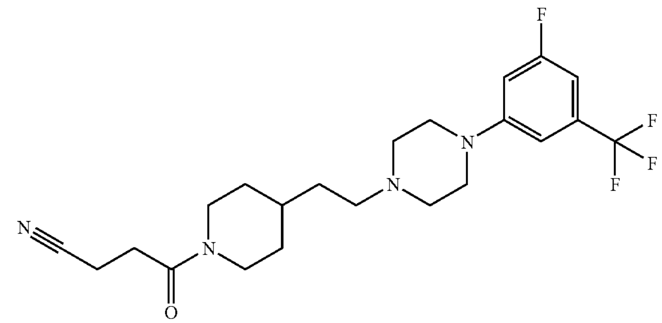 [SMILES: N#CCCC(=O)N1CCC(CCN2CCN(c3cc(F)cc(C(F)(F)F)c3)CC2)CC1] | 6.9 (s, s, 1H); 6.8 to 6.6 (m; 2H); 4.6 (m, 1H); 3.8 (m, 1H); 3.25 (m, 4H); 3.05 (m, 2H); 2.75 to 2.65 (ms, 3H); 2.5 to 2.35 (ms, 5H); 2.45 (m, 2H); 1.8 (m, 2H); 1.7 to 1.4 (ms, 3H); 1.2 (m, 2H) |
| 707 | 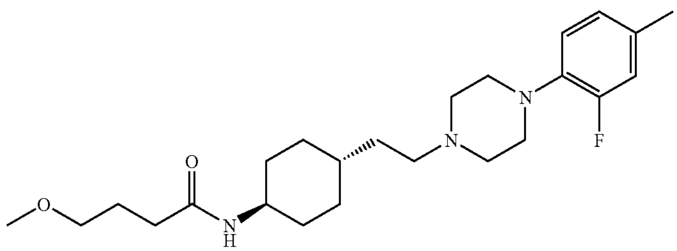 | 6.9 to 6.75 (ms, 3H); 5.45 (d, 1H, J = 7.5); 3.75 (m, 1H); 3.45 (t, 1H, J = 7.5); 3.4 (s, 3H); 3.1 (m, 4H); 2.65 (m, 4H); 2.45 (m, 2H); 2.3 (s, 3H); 2.25 (t, 2H, J = 7.5); 2.1 to 1.7 (ms, 6H); 1.45 (m, 2H); 1.35 to 1.0 (ms, 5H) |
| 730 | 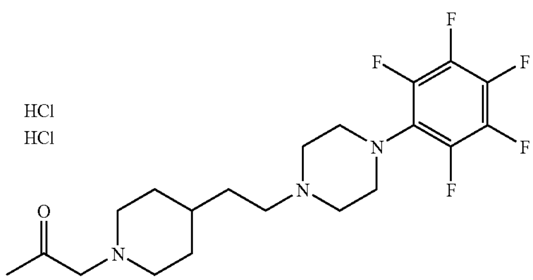 [SMILES: CC(=O)CN1CCC(CCN2CCN(c3c(F)c(F)c(F)c(F)c3F)CC2)CC1 ; Cl ; Cl] | 4.75 (s, 2H); 4.2 (s, 2H); 3.65 to 3.1 (ms, 12H); 3.0 (m, 2H); 2.2 (s, 3H); 2.0 (m, 2H); 1.85 to 1.4 (ms, 5H) (D₂O) |

Example 771

1-(4-{2-[4-(2,3-dichlorophenyl)piperazin-1-yl]ethyl}piperidin-1-yl)butan-2-one

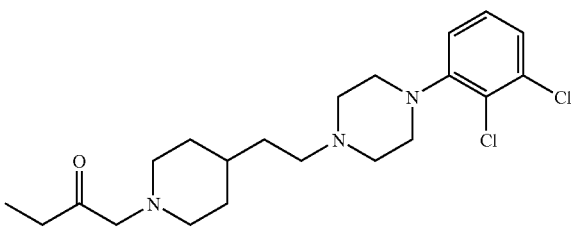 [SMILES: CCC(=O)CN1CCC(CCN2CCN(c3cccc(Cl)c3Cl)CC2)CC1]

Step a: 1-(4-{2-[4-(2,3-dichlorophenyl)piperazin-1-yl]ethyl}piperidin-1-yl)butan-2-ol

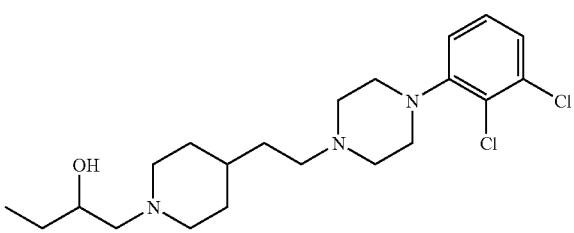 [SMILES: CCC(O)CN1CCC(CCN2CCN(c3cccc(Cl)c3Cl)CC2)CC1]

A suspension of 0.41 g (1 mmol) of 1-(2,3-dichlorophenyl)-4-(2-piperidin-4-ylethyl)piperazine, dihydrochloride in 25 mL of isopropanol and 0.29 g (2.1 mmol) of potassium carbonate is stirred for 30 minutes then 0.08 g (1.1 mmol of 2-ethyloxirane is added. The suspension is stirred to reflux overnight. The precipitate is filtered and the solution is concentrated under reduced pressure. The residue is dissolved in ethyl acetate, washed with water and with brine, dried over magnesium sulfate, filtered and concentrated under reduced pressure. The residue is purified over 10 g of silica gel (dichloromethane/methanol 90/10) to give 0.2 g (50%) of 1-(4-{2-[4-(2,3-dichlorophenyl)piperazin-1-yl]ethyl}piperidin-1-yl)butan-2-ol as an oil that crystallizes upon standing.

Melting point: 94° C.

¹H NMR: 7.2 to 7.05 (ms, 2H); 7.0 to 6.9 (m, 1H); 3.7 (m, 1H); 3.1 (m, 6H); 2.9 (m, 2H); 2.65 (m, 4H); 2.55 to 2.2 (ms, 4H); 2.05 (m, 1H); 1.7 (m, 2H); 1.65 to 1.25 (ms, 7H); 1.0 (t, 3H, J=7.5)

Step b: 1-(4-{2-[4-(2,3-dichlorophenyl)piperazin-1-yl]ethylpiperidin-1-yl)butan-2-one

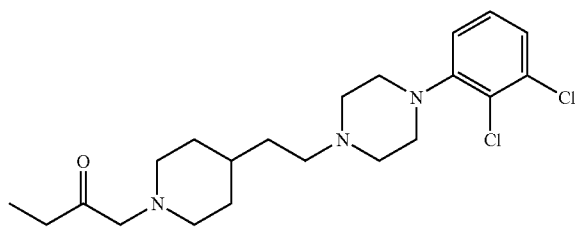 [SMILES: CCC(=O)CN1CCC(CCN2CCN(c3cccc(Cl)c3Cl)CC2)CC1]

The 1-(4-{2-[4-(2,3-dichlorophenyl)piperazin-1-yl]ethylpiperidin-1-yl)butan-2-one is obtained by Swern oxydation of 1-(4-{2-[4-(2,3-dichlorophenyl)piperazin-1-yl]ethyl} piperidin-1-yl)butan-2-ol according to the procedure described in example 7.

Melting point: 68° C.

$^1$H NMR: 7.2 to 7.1 (m, 2H); 6.95 (m, 1H); 3.2 (s, 2H); 3.15 (m, 4H); 2.85 (m, 2H); 2.7 (m, 4H); 2.6 to 2.4 (ms, 4H); 2.05 (m, 2H); 1.7 (m, 2H); 1.65 to 1.2 (ms, 5H); 1.1 (t, 3H, J=7.5)

Example 772

2-(4-{2-[4-(2,3-dimethylphenyl)piperazin-1-yl]ethyl}piperidin-1-yl)-N-methoxy-N-methylacetamide

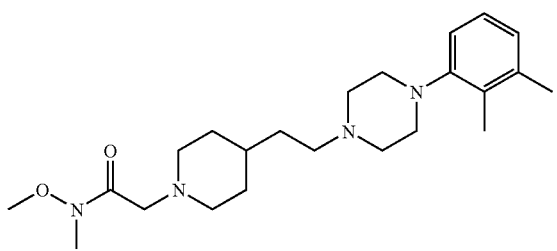

Step a: (4-{2-[4-(2,3-dimethylphenyl)piperazin-1-yl]ethyl}piperidin-1-yl)acetic acid

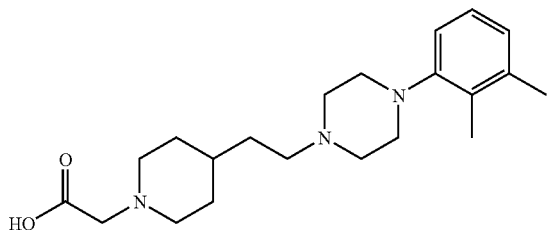 [SMILES: Cc1cccc(N2CCN(CCC3CCN(CC(=O)O)CC3)CC2)c1C]

The (4-{2-[4-(2,3-dimethylphenyl)piperazin-1-yl]ethyl}piperidin-1-yl)acetic acid is prepared from (4-{2-[4-(2,3-dimethylphenyl)piperazin-1-yl]ethyl}piperidin-1-yl)acetic acid ethyl ester using the procedure described in preparation F, step 1.

Step b: 2-(4-{2-[4-(2,3-dimethylphenyl)piperazin-1-yl]ethyl}piperidin-1-yl)-N-methoxy-N-methylacetamide

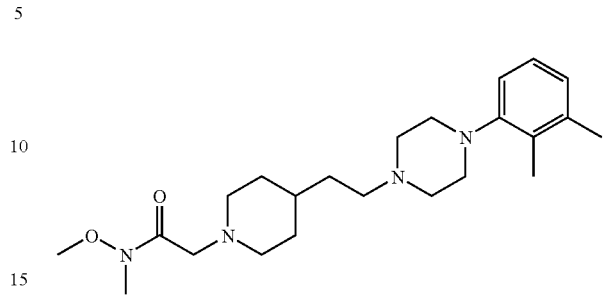

The 2-(4-{2-[4-(2,3-dimethylphenyl)piperazin-1-yl]ethyl} piperidin-1-yl)-N-methoxy-N-methylacetamide is prepared from 4-{2-[4-(2,3-dimethylphenyl)piperazin-1-yl]ethyl}piperidin-1-yl)acetic acid using the procedure described in preparation F, step 2.

Melting point: 66° C.

$^1$H NMR: 7.1 (t, 1H, J=7.5); 7.0 to 6.85 (ms, 2H); 3.7 (s, 3H); 3.35 (s, 2H); 3.3 to 2.6 (ms, 17H); 2.4 to 2.15 (ms, 8H); 1.9 to 1.65 (ms, 3H), 1.65 to 1.35 (ms, 2H)

Example 773

1-(4-{2-[4-(2,3-dimethylphenyl)piperazin-1-yl]ethyl}piperidin-1-yl)-3-methylbutan-2-one, hydrochloride

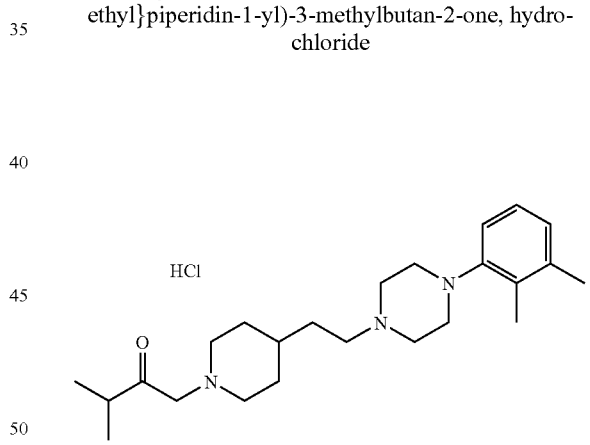

The 1-(4-{2-[4-(2,3-dimethylphenyl)piperazin-1-yl]ethyl}piperidin-1-yl)-3-methylbutan-2-one, hydrochloride is prepared by addition of a solution of isopropylmagnesium bromide on 2-(4-{2-[4-(2,3-dimethylphenyl)piperazin-1-yl]ethyl}piperidin-1-yl)-N-methoxy-N-methylacetamide using the procedure described in preparation F, step 3.

Melting point: 182° C.

$^1$H NMR: 7.1 (t, 1H, J=7.5); 7.0 to 6.85 (ms, 2H); 6.4 (broad s, 1H); 3.0 to 2.7 (ms, 8H); 2.7 to 2.5 (ms, 4H); 2.45 (m, 2H); 2.3 (s, 3H); 2.25 (s, 3H); 2.2 to 2.0 (ms, 3H); 1.7 (m, 2H); 1.5 (m, 2H); 1.4 to 1.1 (ms, 3H); 1.0 (d, 3H); 0.85 (d, 3H, J=7.5)

Example 774

1-(4-{2-[4-(2,3-dimethylphenyl)piperazin-1-yl]ethyl}piperidin-1-yl)butan-2-one, dihydrochloride

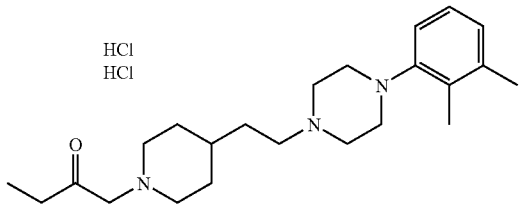 [SMILES: CCC(=O)CN1CCC(CCN2CCN(c3cccc(C)c3C)CC2)CC1 ; Cl ; Cl]

The 1-(4-{2-[4-(2,3-dimethylphenyl)piperazin-1-yl]ethyl}piperidin-1-yl)butan-2-one, dihydrochloride is prepared by addition of a solution of ethylmagnesium bromide on 2-(4-{2-[4-(2,3-dimethylphenyl)piperazin-1-yl]ethyl}piperidin-1-yl)-N-methoxy-N-methylacetamide using the procedure described in preparation F, step 3.

Melting point: 315° C.

Example 775

1-(4-{2-[4-(2,3-dimethylphenyl)piperazin-1-yl]ethyl}piperidin-1-yl)pentan-2-one

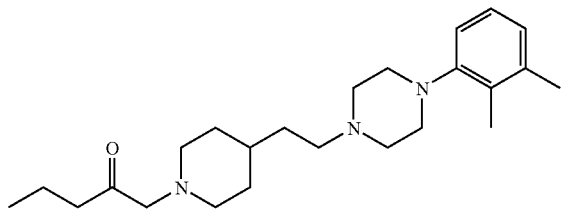 [SMILES: CCCC(=O)CN1CCC(CCN2CCN(c3cccc(C)c3C)CC2)CC1]

The 1-(4-{2-[4-(2,3-dimethylphenyl)piperazin-1-yl]ethyl}piperidin-1-yl)pentan-2-one is prepared by addition of a solution of propylmagnesium bromide on 2-(4-{2-[4-(2,3-dimethylphenyl)piperazin-1-yl]ethyl}piperidin-1-yl)-N-methoxy-N-methylacetamide using the procedure described in preparation F, step 3.

Melting point: 47° C.

Example 776

3-(4-{2-[4-(4-methoxybutanoylamino)cyclohexyl]ethyl}piperazin-1-yl)benzamide

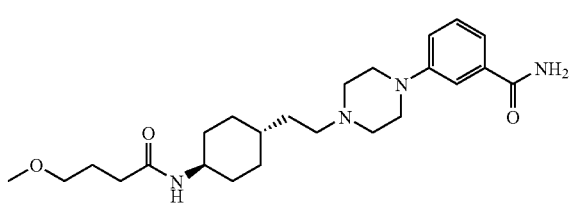 [SMILES: COCCCC(=O)N[C@H]1CC[C@H](CCN2CCN(c3cccc(C(N)=O)c3)CC2)CC1]

A mixture of 85 mg (0.2 mmol) of N-(4-{2-[4-(3-cyanophenyl)piperazin-1-yl]ethyl}cyclohexyl)-4-methoxybutanamide, 2 mL of dimethyl sulfoxide, 16.5 mg of potassium carbonate and 0.12 mL of an aqueous 30% hydrogen peroxyde solution is stirred for 2 hours at room temperature. The suspension is poured into 50 mL of water. The solid is filtered, washed with water, dried under reduced pressure to give 15 mg (17%) of 3-(4-{2-[4-(4-methoxybutanylamino)cyclohexyl]ethyl}piperazin-1-yl)benzamide as a white solid.

Melting point: 202° C.

$^1$H NMR (DMSO $D_6$): 7.85 (s, 1H); 7.6 (d, 1H, J=7.5); 7.35 (s, 1H); 7.3 to 7.15 (ms, 3H); 7.05 (m, 1H); 3.4 (m, 1H); 3.25 (t, 2H, J=7.5); 3.2 (s, 3H); 3.15 (m, 4H); 2.45 (m, 4H); 2.3 (m, 2H); 2.05 (m, 2H); 1.8 to 1.55 (ms, 6H); 1.35 (m, 2H); 1.25 to 0.8 (ms, 5H)

Example 777

[3-(4-{2-[1-(2-oxopropyl)piperidin-4-yl]ethyl}piperazin-1-yl)phenyl]carbamic acid ethyl ester

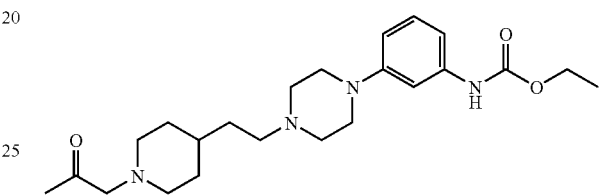

Step a: 1-(4-{2-[4-(3-aminophenyl)piperazin-1-yl]ethyl}piperidin-1-yl)propan-2-one

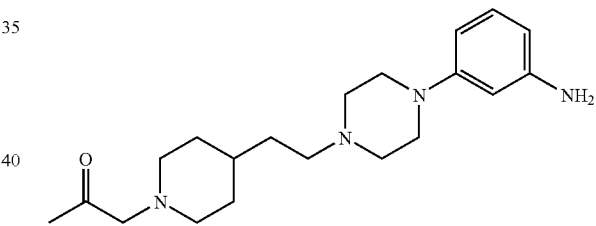

The 1-(4-{2-[4-(3-aminophenyl)piperazin-1-yl]ethyl}piperidin-1-yl)propan-2-one is prepared from 1-(4-{2-[4-(3-nitrophenyl)piperazin-1-yl]ethyl}piperidin-1-yl)propan-2-one using the procedure described in preparation D, step 2 to give the title compound in 49% crude yield, used without further purification.

Step b: [3-(4-{2-[1-(2-oxopropyl)piperidin-4-yl]ethyl}piperazin-1-yl)phenyl]carbamic acid ethyl ester

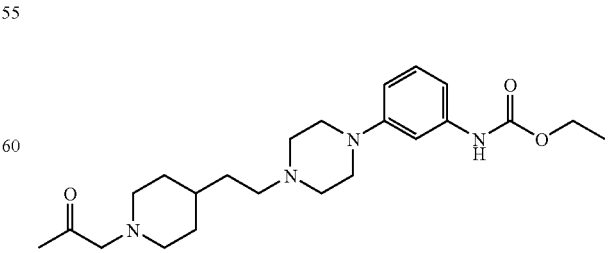

To a cooled solution of 0.1 g (0.3 mmol) of 1-(4-{2-[4-(3-aminophenyl)piperazin-1-yl]ethyl}piperidin-1-yl)propan-2- one in 5 mL of dichloromethane and 0.03 g (0.3 mmol) of triethylamine, is slowly added 0.032 g (0.3 mmol) of ethyl chloroformate. The mixture is stirred overnight at room temperature then concentrated under reduced pressure. The product is dissolved in ethyl acetate, washed twice with water, dried over magnesium sulfate, filtered and concentrated under reduced pressure. The oily residue is purified over 10 g of silica gel (eluant dichloromethane/methanol 95/5) to give 0.025 g (20%) of [3-(4-{2-[1-(2-oxopropyl)piperidin-4-yl]ethyl}piperazin-1-yl)phenyl]carbamic acid ethyl ester as a solid.

Melting point: 118° C.

$^1$H NMR: 7.25 to 7.1 (ms, 2H); 6.75 (d, 1H, J=7.5); 6.65 (d, 1H, J=7.5); 6.55 (s, 1H); 4.25 (q, 2H, J=7.5); 3.25 (m, 4H); 3.15 (s, 2H); 2.85 (m, 2H); 2.6 (m, 4H); 2.45 (m, 2H); 2.2 (s, 3H); 2.05 (m, 2H); 1.8 to 1.2 (ms, 10H)

Example 778

3-oxo-4-(4-{2[4-(3-trifluoromethylphenyl)piperazin-1-yl]ethyl}piperidin-1-yl)butanenitrile, dihydrochloride

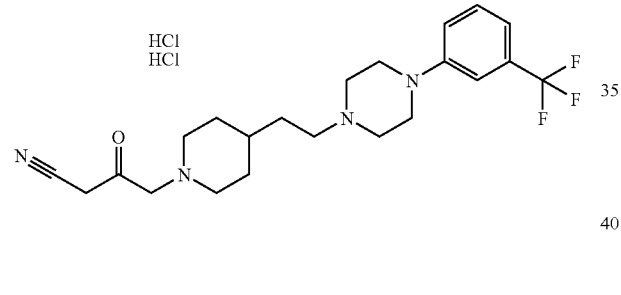

A solution of 0.77 mL (1.3 mmol) of potassium tert-pentoxyde solution (1.7M in toluene) is added dropwise at room temperature to a stirred solution of 52 mg (1.27 mmol) of acetonitrile in 2.5 mL of tetrahydrofuran followed by dropwise addition of 0.19 g (0.44 mmol) of (4-{2-[4-(3-trifluoromethylphenyl)piperazin-1-yl]ethyl}piperidin-1-yl)acetic acid ethyl ester in 1 mL of tetrahydrofuran. After 30 minutes at room temperature, the reaction mixture is diluted with 10 mL of an aqueous 0.2N aqueous hydrochloric acid solution and 50 mL of ethyl acetate forming an emulsion. The mixture is concentrated under reduced pressure and the product is purified over 10 g of silica gel (eluant dichloromethane/methanol 95/5). The oily product is dissolved in 2 mL of diethyl ether and acidified with a hydrochloric acid diethyl ether solution. The precipitate is filtered, washed with diethyl ether and dried under reduced pressure to give 30 mg (14%) of 3-oxo-4-(4-{2[4-(3-trifluoromethylphenyl)piperazin-1-yl]ethyl}piperidin-1-yl)butanenitrile, dihydrochloride.

Melting point: 160° C.

$^1$H NMR (DMSO D$_6$): 11.2 (broad s, 1H); 10.2 (broad s, 1H); 7.45 (t, 1H, J=7.5); 7.3 (d, 1H, J=7.5); 7.25 (s, 1H); 7.1 (d, 1H, J=7.5); 4.35 (s, 2H); 4.2 (s, 2H); 3.95 (m, 2H); 2.55 (m, 2H); 2.45 to 2.9 (ms, 10H); 2.0 to 2.45 (ms, 7H)

Example 779

N-(4-{2-[4-(3-acetylphenyl)piperazin-1-yl]ethyl}cyclohexyl)-3,3,3-trifluoropropanamide

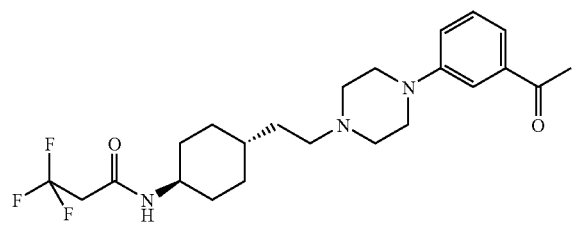 [SMILES: CC(=O)c1cccc(N2CCN(CC[C@H]3CC[C@H](NC(=O)CC(F)(F)F)CC3)CC2)c1]

The N-(4-{2-[4-(3-acetylphenyl)piperazin-1-yl]ethyl}cyclohexyl)-3,3,3-trifluoropropanamide is prepared by oxidation of 3,3,3-trifluoro-N-[4-(2-{4-[3-(1-hydroxyethyl)phenyl]piperazin-1-yl}ethyl)cyclohexyl]propanamide (example 477) using the procedure described in example 7 to give the title compound.

Melting point 165° C.

Example 780

2-cyano-N-(4-{2-[4-(3-propanoylphenyl)piperazin-1-yl]ethyl}cyclohexyl)acetamide

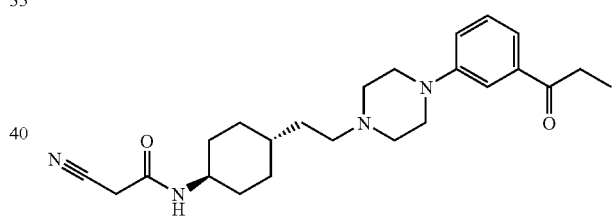

The 2-cyano-N-(4-{2-[4-(3-propanoylphenyl)piperazin-1-yl]ethyl}cyclohexyl)acetamide is prepared by oxidation of 2-cyano-N-[4-(2-{4-[3-(1-hydroxypropyl)phenyl]piperazin-1-yl}ethyl)cyclohexyl]acetamide (example 566) using the procedure described in example 7 to give the title compound.

Melting point 178° C.

Example 781

4-cyano-N-(4-{2-[4-(3-propanoylphenyl)piperazin-1-yl]ethyl}cyclohexyl)butanamide

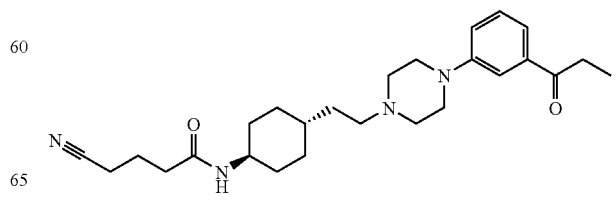

The 4-cyano-N-(4-{2-[4-(3-propanoylphenyl)piperazin-1-yl]ethyl}cyclohexyl)butanamide is prepared by oxidation of 4-cyano-N-[4-(2-{4-[3-(1-hydroxypropyl)phenyl]piperazin-1-yl}ethyl)cyclohexyl]butanamide (example 540) using the procedure described in example 7 to give the title compound.

Melting point 158° C.

Example 782

2-cyano-N-(4-{2-[4-(3-isobutanylphenyl)piperazin-1-yl]ethyl}cyclohexyl)acetamide, dihydrochloride

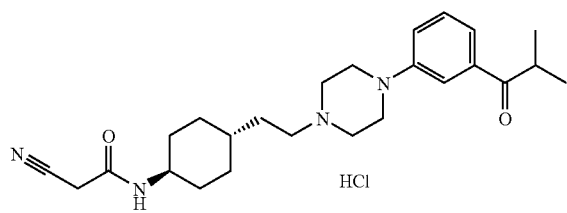 [SMILES: CC(C)C(=O)c1cccc(N2CCN(CC[C@H]3CC[C@H](NC(=O)CC#N)CC3)CC2)c1 ; Cl]

The 2-cyano-N-(4-{2-[4-(3-isobutanylphenyl)piperazin-1-yl]ethyl}cyclohexyl)acetamide, dihydrochloride is prepared by oxidation of 2-cyano-N-[4-(2-{4-[3-(1-hydroxy-2-methylpropyl)phenyl]piperazin-1-yl}ethyl)cyclohexyl]acetamide (example 575) using the procedure described in example 7 to give the title compound.

Melting point 185° C.

Affinity of compounds for the human $D_3$ receptor can be determined by [$^3$H] spiperone binding CHO cells have been transfected by the cDNA coding for the human $D_3$ receptor ($hD_3$). [$^3$H]Spiperone (0.5 à 2 nM) binding is performed in the presence of 2.5 to 5 μg of membrane proteins in a medium containing 120 mM NaCl, 5 mM KCl, and 50 mM Tris HCl pH 7.4; incubation for 60 minutes at room temperature is performed. Non specific binding is estimated in the presence of 10 μM haloperidol. Non transfected cells are devoid of any specific binding.

Exemplified compounds all display an inhibitory constant below 1 μM, most of them are below 50 nM.

Affinities for the human $D_3$ receptor of some representative examples are given in the following table:

| Ex | Structure | Ki (nM) |
|----|-----------|---------|
| 2  | 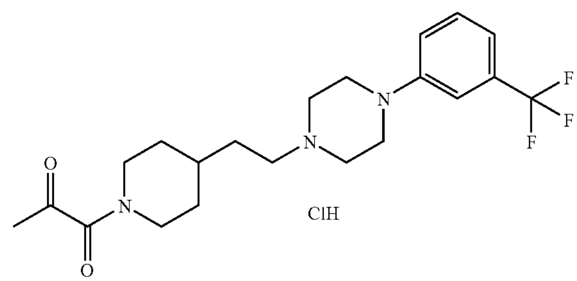 [SMILES: CC(=O)C(=O)N1CCC(CCN2CCN(c3cccc(C(F)(F)F)c3)CC2)CC1 ; Cl]          | 6.6     |
| 14 | 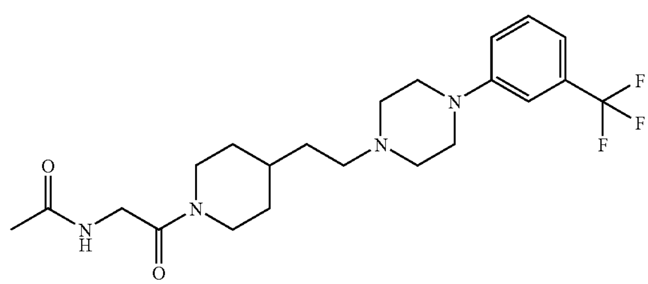 [SMILES: CC(=O)NCC(=O)N1CCC(CCN2CCN(c3cccc(C(F)(F)F)c3)CC2)CC1]          | 15.1    |
| 15 | 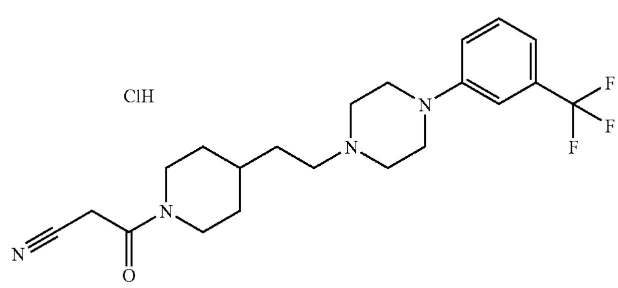 [SMILES: N#CCC(=O)N1CCC(CCN2CCN(c3cccc(C(F)(F)F)c3)CC2)CC1 ; Cl]          | 15.1    |

-continued

| Ex | Structure | Ki (nM) |
|---|---|---|
| 20 | 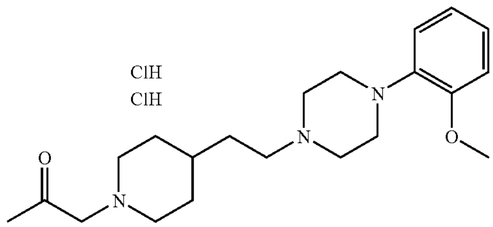 [SMILES: COc1ccccc1N1CCN(CCC2CCN(CC(C)=O)CC2)CC1 ; Cl ; Cl] | 9.5 |
| 36 | 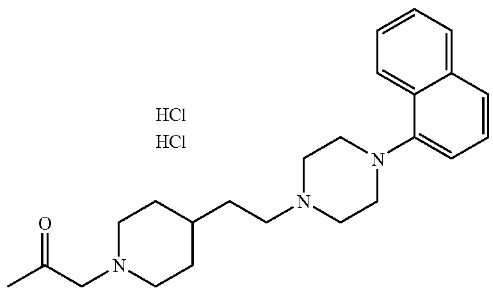 [SMILES: CC(=O)CN1CCC(CCN2CCN(c3cccc4ccccc34)CC2)CC1 ; Cl ; Cl] | 1.32 |
| 46 | 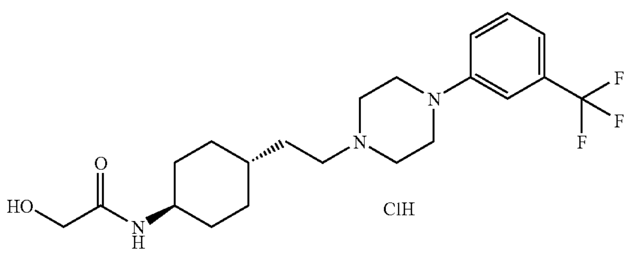 [SMILES: O=C(CO)N[C@H]1CC[C@H](CCN2CCN(c3cccc(C(F)(F)F)c3)CC2)CC1 ; Cl] | 12.0 |
| 54 | 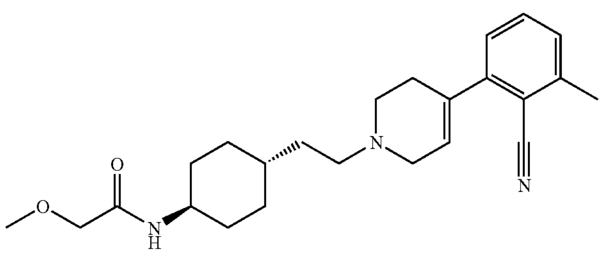 | 18.3 |
| 61 | 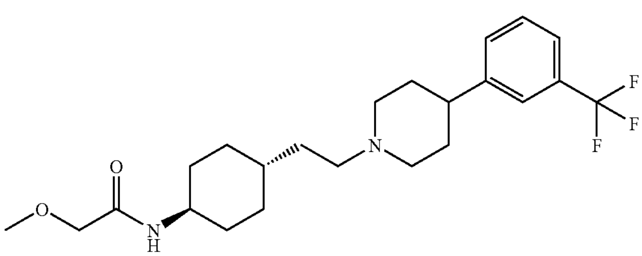 | 8.5 |
| 65 | 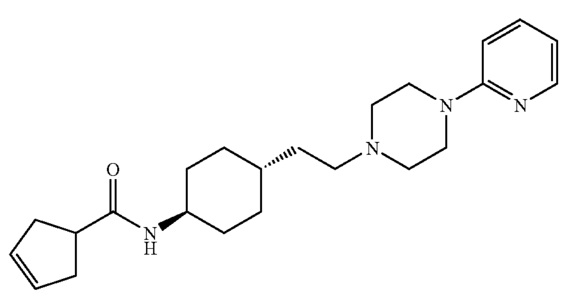 [SMILES: O=C(N[C@H]1CC[C@H](CCN2CCN(c3ccccn3)CC2)CC1)C1CC=CC1] | 31.6 |

-continued

| Ex | Structure | Ki (nM) |
|---|---|---|
| 110 | 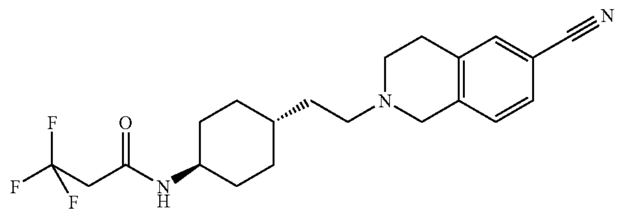 [SMILES: N#Cc1ccc2c(c1)CCN(CC[C@H]1CC[C@H](NC(=O)CC(F)(F)F)CC1)C2] | 10.6 |
| 187 | 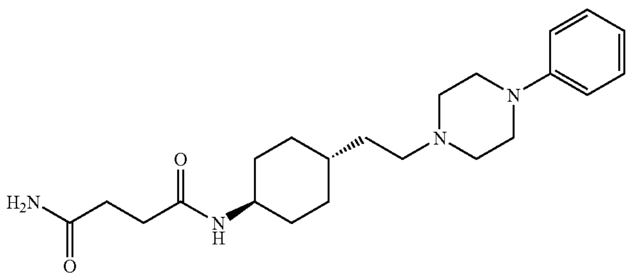 [SMILES: NC(=O)CCC(=O)N[C@H]1CC[C@H](CCN2CCN(c3ccccc3)CC2)CC1] | 3.9 |
| 288 | 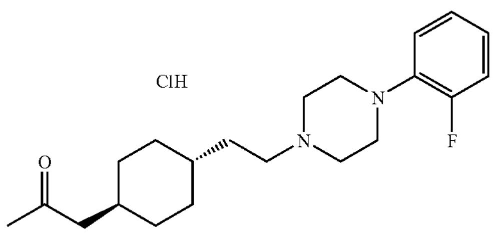 [SMILES: CC(=O)C[C@H]1CC[C@H](CCN2CCN(c3ccccc3F)CC2)CC1 ; Cl] | 2.1 |
| 291 | 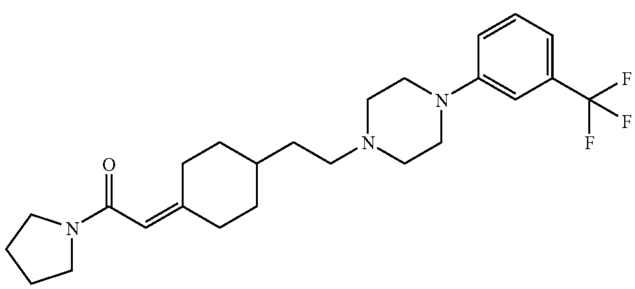 [SMILES: O=C(C=C1CCC(CCN2CCN(c3cccc(C(F)(F)F)c3)CC2)CC1)N1CCCC1] | 4.4 |
| 308 | 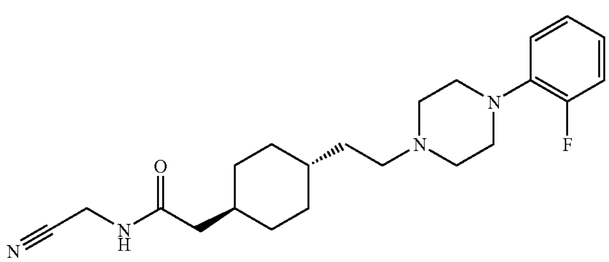 [SMILES: N#CCNC(=O)C[C@H]1CC[C@H](CCN2CCN(c3ccccc3F)CC2)CC1] | 3.5 |

The invention claimed is:
1. Compounds of the formula (I):

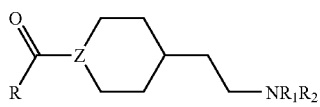

wherein NR$_1$R$_2$ is:

Z is:

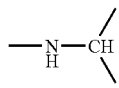

R representing; cyanoalkyl; monohalogenocyanoalkyl; polyhalogenocyanoalkyl; hydroxyalkyl; monohalogenoalkyl; polyhalogenoalkyl; monhalogenocycloalkyl; polyhalogenocycloalkyl; cyanocycloalkyl; monohalogenoalkoxy; polyhalogenoalkoxy; alkoxyalkyl; monohalogeno-alkoxyalkyl; polyhalogenoalkoxyalkyl; alkoxyalkoxyalkyl; monohalogenoalkoxyalkoxyalkyl; polyhalogenoalkoxyalkoxyalkyl; alkylcarbonyl; aryloxy; aryloxyalkyl; mono- or polyhalogenoaryloxyalkyl; arylalkoxy; alkenyl; cycloalkenyl; cycloalkenylalkyl; cycloalkenyl fused with benzene; alkynyl, dialkylaminoalkyl; halodialkylaminoalkyl; polyhalogenodialkylaminoalkyl;

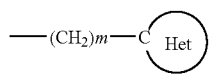

where

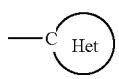

is a non aromatic heterocycle selected from the group consisting of pyrrolidinyl, tetrahydrofuranyl, piperidyl, dihydropyranyl, and 2,3-dihydrofuranyl, optionally substituted with one or more moieties selected from the group consisting of acyl, alkyl and halogen; arylaminoalkyl; alkoxyalkylamino; alkoxy(alkyl)amino; cyanoalkylamino; alkylcarbonylalkyl; acylaminoalkyl; aminocarbonylalkyl; alkylsulfanylalkyl; alkylsulfinylalkyl; alkylsulfonylalkyl;
n being an integer from 1 to 3;
m being an integer from 0 to 4;
Ar representing an aryl; an heteroaryl selected from the group consisting of pyridyl, pyrimidinyl, quinolinyl and benzothienyl or an aryl fused with a cycloalkyl or an heterocycle selected from the fused systems resulting from the condensation of a phenyl group with a dioxolanyl or a dioxanyl; Ar being optionally substituted with one or more alkyl; alkenyl; alkynyl; cyano; halogeno; alkoxy; monohalogenoalkoxy; polyhalogenoalkoxy; alkoxyalkyl; dialkylamino; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; oxazolyl; aryl; aralkyl; aryloxy; alkoxy-carbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;
with the proviso that:
when Z is NHCH and NR1R2 is

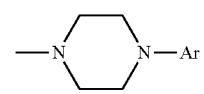

with Ar representing a phenyl substituted with two chlorine atoms or fused with a carbocycle, then R is not alkenyl;
or their pharmaceutically acceptable salts, or the polymorphic, crystalline structures of these compounds or their optical isomers, racemates, diastereomers or enantiomers.

2. Compounds according to claim 1, wherein R is cyanoalkyl, polyhalogenocyanoalkyl, hydroxyalkyl, polyhalogenoalkyl, cyanocycloalkyl, alkoxyalkyl, alkoxyalkoxyalkyl, alkylcarbonyl, aryloxyalkyl, mono- or polyhalogenoaryloxyalkyl, arylalkoxy, alkenyl, cycloalkenyl, non aromatic heterocyclyl(CH$_2$)m wherein the non aromatic heterocycle is selected from the group consisting of pyrrolidinyl, tetrahydrofuranyl, piperidyl, dihydropyranyl, and 2,3-dihydrofuranyl, optionally substituted with one or more moieties selected from the group consisting of acyl, alkyl and halogen, alkylcarbonylalkyl, acylaminoalkyl, aminocarbonylalkyl, alkylsulfanylalkyl, alkylsulfonylalkyl,
m being an integer from 0 to 4.

3. Compounds according to claim 1, wherein Ar represents an aryl.

4. Compounds according to claim 1, wherein Ar is substituted with one or more moieties selected from the group consisting of alkyl, cyano, halogeno, alkoxy, polyhalogenoalkoxy, alkanediyl, dialkylamino, alkylsulfanyl, aryl, aralkyl, aryloxy, alkoxycarbonylamino, acyl, alkylsulfonylamino, polyhalogenoalkyl, hydroxy, hydroxyalkyl, and oxoalkyl.

5. Compounds according to claim 1, wherein the compounds are those of formula (A):

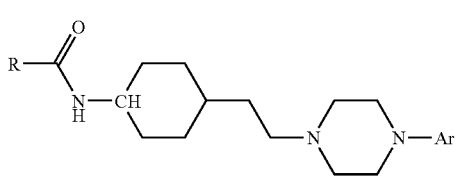

where
R is chosen from cyanoalkyl; monohalogenoalkyl; polyhalogenoalkyl; monohalogenocycloalkyl; polyhalogenocycloalkyl; monohalogenoalkoxy; polyhalogenoalkoxy; alkoxyalkyl; monohalogenoalkoxyalkyl; polyhalogenoalkoxyalkyl; alkoxyalkoxyalkyl; monohalogenoalkoxyalkoxyalkyl; polyhalogenoalkoxyalkoxyalkyl; monohalogenocyanoalkyl; polyhalogenocyanoalkyl; cyanocycloalkyl; aryloxy; aryloxyalkyl; arylalkoxy; cycloalkenyl; cycloalkenylalkyl; cycloalkenyl fused with benzene; alkynyl; dialkylaminoalkyl; hydroxyalkyl; polyhalogenodialkylaminoalkyl;

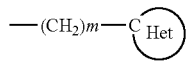

where

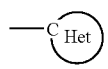

is a non aromatic heterocycle selected from the group consisting of pyrrolidinyl, tetrahydrofuranyl, piperidyl, dihydropyranyl, and 2,3-dihydrofuranyl, optionally substituted with one or more moieties selected from the group consisting of acyl, alkyl and halogen; arylaminoalkyl; alkoxyalkylamino; alkoxy(alkyl)amino; cyanoalkylamino; alkylcarbonylalkyl; acylaminoalkyl; aminocarbonylalkyl; alkylsulfanylalkyl; alkylsulfinylalkyl; alkylsulfonylalkyl; alkylcarbonyl; mono- or polyhalogenoaryl; mono- or polyhalogenoaryloxyalkyl;

m being an integer from 0 to 4,

Ar represents an aryl; an heteroaryl selected from the group consisting of pyridyl, pyrimidinyl, quinolinyl and benzothienyl or an aryl fused with a cycloalkyl or an heterocycle selected from the fused systems resulting from the condensation of a phenyl group with a dioxolanyl or a dioxanyl; Ar being optionally substituted with one or more alkyl; alkenyl; alkynyl; cyano; halogeno; alkoxy; monohalogenoalkoxy; polyhalogenoalkoxy; alkoxyalkyl; dialkylamino; alkylsulfanyl; alkylsulfinyl; alkylsulfonyl; monohalogenoalkylsulfanyl; monohalogenoalkylsulfinyl; monohalogenoalkylsulfonyl; polyhalogenoalkylsulfanyl; polyhalogenoalkylsulfinyl; polyhalogenoalkylsulfonyl; oxazolyl; aryl; aralkyl; aryloxy; alkoxy-carbonylamino; acyl; acylamino; aminocarbonyl; monoalkylaminocarbonyl; dialkylaminocarbonyl; alkylsulfonylamino; monohalogenoalkyl; polyhalogenoalkyl; hydroxyl; hydroxyalkyl; oxoalkyl;

or their pharmaceutically acceptable salts, or the polymorphic, crystalline structures of these compounds or their optical isomers, racemates, diastereomers or enantiomers.

6. Compounds according to claim 1 selected from among:
2-cyano-N-(4-{2-[4-(3-trifluoromethylphenyl)piperazin-1-yl]ethyl}cyclohexyl)acetamide,
N-(4-{2-[4-(3-acetylphenyl)piperazin-1-yl]ethyl}cyclohexyl)-2-cyanoacetamide,
(4-{2-[4-(3-Trifluoromethylphenyl)piperazin-1-yl]ethyl}cyclohexyl)carbamic acid benzyl ester,
2,2,2-Trifluoro-N-(4-{2-[4-(3-trifluoromethylphenyl)piperazin-1-yl]ethyl}cyclohexyl)acetamide,
Tetrahydrofuran-2-carboxylic acid (4-{2-[4-(3-trifluoromethyl-phenyl)piperazin-1-yl]ethyl}cyclohexyl)amide,
2-Methoxy-N-(4-{2-[4-(3-trifluoromethylphenyl)piperazin-1-yl]ethyl}cyclohexyl)acetamide,
2-Methoxy-N-(4-{2-[4-(3-trifluoromethylphenyl)piperazin-1-yl]ethyl}cyclohexyl)acetamide, hydrochloride,
2,2-Difluoro-N-(4-{2-[4-(3-trifluoromethylphenyl)piperazin-1-yl]ethyl}cyclohexyl)acetamide,
Cyclopent-1-enecarboxylic acid (4-{2-[4-(3-trifluoromethyl-phenyl)piperazin-1-yl]ethyl}cyclohexyl)amide,
2-Hydroxy-N-(4-{2-[4-(3-trifluoromethylphenyl)piperazin-1-yl]ethyl}cyclohexyl)acetamide, hydrochloride,
3-Methoxy-N-(4-{2-[4-(3-trifluoromethylphenyl)piperazin-1-yl]ethyl}cyclohexyl)propanamide,
N-(4-{2-[4-(2,4-Difluorophenyl)piperazin-1-yl]ethyl}cyclohexyl)-2-methoxyacetamide,
N-(4-{2-[4-(2-Cyano-3-methylphenyl)piperazin-1-yl]ethyl}cyclohexyl)-2-methoxyacetamide,
N-(4-{2-[4-(2-Fluorophenyl)piperazin-1-yl]ethyl}cyclohexyl)-2-methoxyacetamide,
2-Ethoxy-N-(4-{2-[4-(3-trifluoromethylphenyl)piperazin-1-yl]ethyl}cyclohexyl)acetamide, hydrochloride,
Cyclopent-3-enecarboxylic acid (4-{2-[4-(3-trifluoromethyl-phenyl)piperazin-1-yl]ethyl}cyclohexyl)amide,
Cyclohex-1-enecarboxylic acid (4-{2-[4-(3-trifluoromethyl-phenyl)piperazin-1-yl]ethyl}cyclohexyl)-amide,
2-Ethoxy-N-(4-{2-[4-(2-fluorophenyl)piperazin-1-yl]ethyl}cyclo-hexyl)acetamide,
Tetrahydrofuran-2-carboxylic acid (4-{2-[4-(2-fluorophenyl)piperazin-1-yl]ethyl}cyclohexyl)amide,
N-(4-{2-[4-(2-Cyanophenyl)piperazin-1-yl]ethyl}cyclohexyl)-2-methoxyacetamide,
2-Methoxy-N-{4-[2-(4-phenylpiperazin-1-yl)ethyl]cyclohexyl}acetamide,
2-Phenoxy-N-(4-{2-[4-(3-trifluoromethylphenyl)piperazin-1-yl]ethyl}cyclohexyl)acetamide,
3,3,3-Trifluoro-N-(4-{2-[4-(3-trifluoromethylphenyl)piperazin-1-yl]ethyl}cyclohexyl)propanamide,
4-Methoxy-N-(4-{2-[4-(3-trifluoromethylphenyl)piperazin-1-yl]ethyl}cyclohexyl)butanamide,
Cyclopent-3-enecarboxylic acid {4-[2-(4-pyridin-2-ylpiperazin-1-yl)ethyl]cyclohexyl}amide,
Cyclohex-1-enecarboxylic acid {4-[2-(4-phenylpiperazin-1-yl)ethyl]cyclohexyl}amide,
Cyclohex-1-enecarboxylic acid (4-{2-[4-(2-fluorophenyl)piperazin-1-yl]ethyl}cyclohexyl)amide,
Cyclopent-1-enecarboxylic acid (4-{2-[4-(2-fluorophenyl)piperazin-1-yl]ethyl}cyclohexyl)amide,
N-(4-{2-[4-(2-Fluorophenyl)piperazin-1-yl]ethyl}cyclohexyl)-2-methoxypropanamide,
Cyclopent-3-enecarboxylic acid (4-{2-[4-(2-fluorophenyl)piperazin-1-yl]ethyl}cyclohexyl)amide,
Cyclohex-1-enecarboxylic acid (4-{2-[4-(2,4-difluorophenyl)piperazin-1-yl]ethyl}cyclohexyl)amide,
N-(4-{2-[4-(2-Cyanophenyl)piperazin-1-yl]ethyl}cyclohexyl)-2-ethoxyacetamide,
Cyclopent-1-enecarboxylic acid (4-{2-[4-(2-cyanophenyl)piperazin-1-yl]ethyl}cyclohexyl)amide,
N-(4-{2-[4-(2-Fluorophenyl)piperazin-1-yl]ethyl}cyclohexyl)-2-methoxypropanamide,
N-(4-{2-[4-(2-Fluorophenyl)piperazin-1-yl]ethyl}cyclohexyl)-4-methoxybutanamide,
2-Methoxy-2-methyl-N-(4-{2-[4-(3-trifluoromethylphenyl)piperazin-1-yl]ethyl}cyclohexyl)propanamide,
N-(4-{2-[4-(3-Cyanophenyl)piperazin-1-yl]ethyl}cyclohexyl)-2-ethoxyacetamide,
2-Cyano-N-(4-{2-[4-(2-fluorophenyl)piperazin-1-yl]ethyl}cyclohexyl)acetamide,
2-Methylsulfanyl-N-(4-{2-[4-(3-trifluoromethylphenyl)piperazin-1-yl]ethyl}cyclohexyl)acetamide,
2-(2-Methoxyethoxy)-N-(4-{2-[4-(3-trifluoromethylphenyl)piperazin-1-yl]ethyl}cyclohexyl)acetamide, hydrochloride, N-(4-{2-[4-(3-Cyanophenyl)piperazin-1-yl]
ethyl}cyclohexyl)-2-methoxyacetamide,
3,3,3-Trifluoro-N-(4-{2-[4-(2-fluorophenyl)piperazin-1-yl]ethyl}cyclohexyl)propanamide,
N-(4-{2-[4-(2-Fluorophenyl)piperazin-1-yl]
ethyl}cyclohexyl)-2-phenoxyacetamide,
N-(4-{2-[4-(2-Fluorophenyl)piperazin-1-yl]
ethyl}cyclohexyl)-2-oxobutanamide,
2-Cyano-N-(4-{2-[4-(3-cyanophenyl)piperazin-1-yl]
ethyl}cyclohexyl)acetamide,
N-(4-{2-[4-(2,3-Difluorophenyl)piperazin-1-yl]
ethyl}cyclohexyl)-2-methoxyacetamide,
2-oxo-N-(4-{2-[4-(3-trifluoromethylphenyl)piperazin-1-yl]ethyl}cyclohexyl)butanamide,hydrochloride,
2-oxo-N-(4-{2-[4-(3-trifluoromethylphenyl)piperazin-1-yl]ethyl}cyclohexyl)propanamide, hydrochloride,
2-Dimethylamino-N-(4-{2-[4-(3-trifluoromethylphenyl)piperazin-1-yl]ethyl}cyclohexyl)acetamide,
N-(4-{2-[4-(2-Fluorophenyl)piperazin-1-yl]
ethyl}cyclohexyl)-2-isopropoxyacetamide,
4-Methoxy-N-{4-[2-(4-phenylpiperazin-1-yl)ethyl]
cyclohexyl}butanamide,
2-Isopropoxy-N-(4-{2-[4-(3-trifluoromethylphenyl)piperazin-1-yl]ethyl}cyclohexyl)acetamide,
N-(4-{2-[4-(2-Cyano-3-trifluoromethylphenyl)piperazin-1-yl]ethyl}cyclohexyl)-2-isopropoxyacetamide,
N-(4-{2-[4-(2-Cyano-3-trifluoromethylphenyl)piperazin-1-yl]ethyl}cyclohexyl)-2-ethoxyacetamide,
2-Cyano-N-(4-{2-[4-(2-cyano-3-trifluoromethylphenyl)piperazin-1-yl]ethyl}cyclohexyl)acetamide,
2-Cyano-N-{4-[2-(4-phenylpiperazin-1-yl)ethyl]
cyclohexyl}acetamide, hydrochloride,
2-Acetylamino-N-(4-{2-[4-(3-trifluoromethylphenyl)piperazin-1-yl]ethyl}cyclohexyl)acetamide,
N-(4-{2-[4-(3,5-Bistrifluoromethylphenyl)piperazin-1-yl]ethyl}cyclohexyl)-2-cyanoacetamide,
N-(4-{2-[4-(3,5-Bistrifluoromethylphenyl)piperazin-1-yl]ethyl}cyclohexyl)-2-ethoxyacetamide,
3-Oxo-N-(4-{2-[4-(3-trifluoromethylphenyl)piperazin-1-yl]ethyl}cyclohexyl)butanamide,
2-Cyano-N-(4-{2-[4-(2,6-di-tert-butylpyrimidin-4-yl)piperazin-1-yl]ethyl}cyclohexyl)acetamide,
N-(4-{2-[4-(2,3-Difluorophenyl)piperazin-1-yl]
ethyl}cyclohexyl)-2-ethoxyacetamide,
2-Cyano-N-(4-{2-[4-(2,3-difluorophenyl)piperazin-1-yl]
ethyl}cyclohexyl)acetamide,
2-Cyano-N-(4-{2-[4-(2-cyano-3-methylphenyl)piperazin-1-yl]ethyl}cyclohexyl)acetamide,
N-(4-{2-[4-(2-Cyano-3-methylphenyl)piperazin-1-yl]
ethyl}cyclohexyl)-3,3,3-trifluoropropanamide,
2-Cyano-N-(4-{2-[4-(5,6,7,8-tetrahydronaphthalen-1-yl)piperazin-1-yl]ethyl}cyclohexyl)acetamide,
2-Ethoxy-N-(4-{2-[4-(5,6,7,8-tetrahydronaphthalen-1-yl)piperazin-1-yl]ethyl}cyclohexyl)acetamide,
N-(4-{2-[4-(3,5-Bistrifluoromethylphenyl)piperazin-1-yl]ethyl}cyclohexyl)-2-methoxyacetamide,
N-(4-{2-[4-(2-Cyano-3-trifluoromethylphenyl)piperazin-1-yl]ethyl}cyclohexyl)-2-methoxyacetamide,
2-Cyano-N-{4-[2-(4-pyridin-4-ylpiperazin-1-yl)ethyl]
cyclohexyl}acetamide,
N-(4-{2-[4-(2,6-Di-tert-butylpyrimidin-4-yl)piperazin-1-yl]ethyl}cyclohexyl)-2-ethoxyacetamide,
N-(4-{2-[4-(2,6-Di-tert-butylpyrimidin-4-yl)piperazin-1-yl]ethyl}cyclohexyl)-2-methoxyacetamide,
2-Ethoxy-N-(4-{2-[4-(2-methoxyphenyl)piperazin-1-yl]
ethyl}cyclohexyl)acetamide,
2-Cyano-N-(4-{2-[4-(2-methoxyphenyl)piperazin-1-yl]
ethyl}cyclohexyl)acetamide,
2-Methoxy-N-(4-{2-[4-(2-methoxyphenyl)piperazin-1-yl]ethyl}cyclohexyl)acetamide,
2-Cyano-N-(4-{2-[4-(2-fluorophenyl)piperazin-1-yl]
ethyl}cyclohexyl)acetamide, hydrochloride,
2-Acetylamino-N-{4-[2-(4-phenylpiperazin-1-yl)ethyl]
cyclohexyl}acetamide,
N-(4-{2-[4-(2-Chlorophenyl)piperazin-1-yl]
ethyl}cyclohexyl)-2-methoxyacetamide,
2-Methoxy-N-(4-{2-[4-(5,6,7,8-tetrahydronaphthalen-1-yl)piperazin-1-yl]ethyl}cyclohexyl)acetamide,
N-(4-{2-[4-(2-Chlorophenyl)piperazin-1-yl]
ethyl}cyclohexyl)-2-cyanoacetamide,
N-(4-{2-[4-(2-Chlorophenyl)piperazin-1-yl]
ethyl}cyclohexyl)-2-ethoxyacetamide,
2-Cyano-N-(4-{2-[4-(3-fluorophenyl-piperazin-1-yl)
ethyl}cyclohexyl)acetamide,
2-Acetylamino-N-(4-{2-[4-(2-fluorophenyl)piperazin-1-yl]ethyl}cyclohexyl)acetamide,
2-tert-Butoxy-N-(4-{2-[4-(3-trifluoromethylphenyl)piperazin-1-yl]ethyl}cyclohexyl)acetamide,
N-(4-{2-[4-(3-Chloro-2-methylphenyl)piperazin-1-yl]
ethyl}cyclohexyl)-2-cyanoacetamide,
N-(4-{2-[4-(3-Chloro-2-methylphenyl)piperazin-1-yl]
ethyl}cyclohexyl)-2-ethoxyacetamide,
N-(4-{2-[4-(3-Cyano-5-trifluoromethylphenyl)piperazin-1-yl]ethyl}cyclohexyl)-2-methoxyacetamide,
N-(4-{2-[4-(3-Cyano-5-trifluoromethylphenyl)piperazin-1-yl]ethyl}cyclohexyl)-2-ethoxyacetamide,
N-(4-{2-[4-(2,3-Dichlorophenyl)piperazin-1-yl]
ethyl}cyclohexyl)-2-methoxyacetamide,
2-Cyano-N-(4-{2-[4-(2,3-dichlorophenyl)piperazin-1-yl]
ethyl}cyclohexyl)acetamide,
N-(4-{2-[4-(2,3-Dichlorophenyl)piperazin-1-yl]
ethyl}cyclohexyl)-2-ethoxyacetamide,
2-Acetylamino-N-(4-{2-[4-(2,3-difluorophenyl)piperazin-1-yl]ethyl}cyclohexyl)acetamide,
N-(4-{2-[4-(2,3-Difluorophenyl)piperazin-1-yl]
ethyl}cyclohexyl)-2-isopropoxyacetamide, hydrochloride,
2-Cyano-N-(4-{2-[4-(3,5-dimethylphenyl)piperazin-1-yl]
ethyl}cyclohexyl)acetamide,
2-Cyano-N-(4-{2-[4-(3-ethylphenyl)piperazin-1-yl]
ethyl}cyclohexyl)acetamide,
2-Cyano-N-(4-{2-[4-(3-dimethylaminophenyl)piperazin-1-yl]ethyl}cyclohexyl)acetamide,
2-Cyano-N-(4-{2-[4-(3,5-dichlorophenyl)piperazin-1-yl]
ethyl}cyclohexyl)acetamide,
2-Cyano-N-(4-{2-[4-(2,5-dimethylphenyl)piperazin-1-yl]
ethyl}cyclohexyl)acetamide,
1-Acetylpiperidine-4-carboxylic acid (4-{2-[4-(3-trifluoromethyl-phenyl)piperazin-1-yl]ethyl}cyclohexyl)
amide,
N-(4-{2-[4-(3-Trifluoromethylphenyl)piperazin-1-yl]
ethyl}cyclo-hexyl)succinamide,
N-(4-{2-[4-(5-Chloro-2-methylphenyl)piperazin-1-yl]
ethyl}cyclohexyl)-2-cyanoacetamide,
N-(4-{2-[4-(3-Chlorophenyl)piperazin-1-yl]
ethyl}cyclohexyl)-2-cyanoacetamide,
2-Cyano-N-(4-{2-[4-(3-trifluoromethoxyphenyl)piperazin-1-yl]ethyl}cyclohexyl)acetamide,
2-Cyano-N-(4-{2-[4-(2-fluoro-3-trifluoromethylphenyl)
piperazin-1-yl]ethyl}cyclohexyl)acetamide,
2-Cyano-N-(4-{2-[4-(3,5-difluorophenyl)piperazin-1-yl]
ethyl}cyclohexyl)acetamide, 2-Cyano-N-(4-{2-[4-(3-methoxy-5-trifluoromethylphenyl)piperazin-1-yl]ethyl}cyclohexyl)acetamide,
4-Cyano-N-(4-{2-[4-(3-trifluoromethylphenyl)piperazin-1-yl]ethyl}cyclohexyl)butanamide,
2-Cyano-N-(4-{2-[4-(2,4-difluorophenyl)piperazin-1-yl]ethyl}cyclohexyl)acetamide,
2-Cyano-N-(4-{2-[4-(3-isopropoxyphenyl)piperazin-1-yl]ethyl}cyclohexyl)acetamide, hydrochloride,
2-Cyano-N-(4-{2-[4-(3-methoxyphenyl)piperazin-1-yl]ethyl}cyclohexyl)acetamide, hydrochloride,
2-Cyano-N-(4-{2-[4-(2-methoxy-5-trifluoromethylphenyl)piperazin-1-yl]ethyl}cyclohexyl)acetamide,
2-Cyano-N-{4-[2-(4-m-tolylpiperazin-1-yl)ethyl]cyclohexyl}acetamide,
3-Diethylamino-N-(4-{2-[4-(3-trifluoromethylphenyl)piperazin-1-yl]ethyl}cyclohexyl)propanamide,
3-Cyano-N-(4-{2-[4-(3-trifluoromethylphenyl)piperazin-1-yl]ethyl}cyclohexyl)propanamide, hydrochloride,
N-(4-{2-[4-(3-tert-Butylphenyl)piperazin-1-yl]ethyl}cyclohexyl)-2-cyanoacetamide,
2-Cyano-N-(4-{2-[4-(3-ethoxyphenyl)piperazin-1-yl]ethyl}cyclohexyl)acetamide,
N-(4-{2-[4-(5-Chloro-2-fluorophenyl)piperazin-1-yl]ethyl}cyclohexyl)-2-cyanoacetamide,
4-Cyano-N-(4-{2-[4-(2-fluoro-3-trifluoromethylphenyl)piperazin-1-yl]ethyl}cyclohexyl)butanamide,
2-Cyano-N-(4-{2-[4-(6-trifluoromethylbenzo[b]thiophen-3-yl)piperazin-1-yl]ethyl}cyclohexyl)acetamide,
2-Cyano-N-(4-{2-[4-(2-fluoro-5-trifluoromethylphenyl)piperazin-1-yl]ethyl}cyclohexyl)acetamide,
2-Cyano-N-(4-{2-[4-(3-hydroxyphenyl)piperazin-1-yl]ethyl}cyclo-hexyl)acetamide, hydrochloride,
N-(4-{2-[4-(5-Chloro-2-methoxyphenyl)piperazin-1-yl]ethyl}cyclohexyl)-2-cyanoacetamide,
N-(4-{2-[4-(2-tert-Butyl-6-trifluoromethylpyrimidin-4-yl)piperazin-1-yl]ethyl}cyclohexyl)-2-cyanoacetamide,
2-Cyano-N-(4-{2-[4-(2-methyl-3-trifluoromethylphenyl)piperazin-1-yl]ethyl}cyclohexyl)acetamide,
N-(4-{2-[4-(5-Chloro-2-methylphenyl)piperazin-1-yl]ethyl}cyclohexyl)-3,3,3-trifluoropropanamide,
2-Cyano-N-(4-{2-[4-(3,5-dimethoxyphenyl)piperazin-1-yl]ethyl}cyclohexyl)acetamide,
N-(4-{2-[4-(3-Chloro-5-fluorophenyl)piperazin-1-yl]ethyl}cyclohexyl)-2-cyanoacetamide,
2-Cyano-N-(4-{2-[4-(3-methylsulfanylphenyl)piperazin-1-yl]ethyl}cyclohexyl)acetamide,
2-Cyano-N-{4-[2-(4-naphthalen-1-ylpiperazin-1-yl)ethyl]cyclohexyl}acetamide,
N-(4-{2-[4-(3,5-Bistrifluoromethylphenyl)piperazin-1-yl]ethyl}cyclohexyl)-4-cyanobutanamide,
N-(4-{2-[4-(3-Chloro-2-fluorophenyl)piperazin-1-yl]ethyl}cyclohexyl)-2-cyanoacetamide,
N-(4-{2-[4-(2-Fluorophenyl)piperazin-1-yl]ethyl}cyclohexyl)succinamide,
N-{4-[2-(4-Phenylpiperazin-1-yl)ethyl]cyclohexyl}succinamide,
3,3,3-Trifluoro-N-{4-[2-(4-phenylpiperazin-1-yl)ethyl]cyclohexyl} propanamide,
N-(4-{2-[4-(2-Chloro-5-trifluoromethylphenyl)piperazin-1-yl]ethyl}cyclohexyl)-2-cyanoacetamide,
N-(4-{2-[4-(5-Chloro-2-methylphenyl)piperazin-1-yl]ethyl}cyclohexyl)succinamide,
4-Oxopentanoic acid (4-{2-[4-(3-trifluoromethylphenyl)piperazin-1-yl]ethyl}cyclohexyl)amide,
2-Cyano-N-(4-{2-[4-(2-fluoro-5-methylphenyl)piperazin-1-yl]ethyl}cyclohexyl)acetamide,
N-(4-{2-[4-(2-Chloro-5-methoxyphenyl)piperazin-1-yl]ethyl}cyclohexyl)-2-cyanoacetamide,
2-Cyano-N-(4-{2-[4-(2-methylsulfanylphenyl)piperazin-1-yl]ethyl}cyclohexyl)acetamide,
2-Cyano-N-(4-{2-[4-(2-methoxy-5-methylphenyl)piperazin-1-yl]ethyl}cyclohexyl)acetamide,
2-Cyano-N-(4-{2-[4-(5-fluoro-2-methylphenyl)piperazin-1-yl]ethyl}cyclohexyl)acetamide,
N-(4-{2-[4-(5-tert-Butyl-2-methoxyphenyl)piperazin-1-yl]ethyl}cyclohexyl)-2-cyanoacetamide,
2-Cyano-N-(4-{2-[4-(5-methoxy-2-methylphenyl)piperazin-1-yl]ethyl}cyclohexyl)acetamide,
5-Oxohexanoic acid (4-{2-[4-(3-trifluoromethylphenyl)piperazin-1-yl]ethyl}cyclohexyl)amide,
4-Cyano-N-(4-{2-[4-(3-ethylphenyl)piperazin-1-yl]ethyl}cyclohexyl)butanamide, hydrochloride,
4-Cyano-N-(4-{2-[4-(2-fluorophenyl)piperazin-1-yl]ethyl}cyclohexyl)butanamide,
N-(4-{2-[4-(3-Chloro-2-fluorophenyl)piperazin-1-yl]ethyl}cyclohexyl)-4-cyanobutanamide,
4-Cyano-N-(4-{2-[4-(3-trifluoromethoxyphenyl)piperazin-1-yl]ethyl}cyclohexyl)butanamide,
4-Cyano-N-(4-{2-[4-(2-fluoro-5-trifluoromethylphenyl)piperazin-1-yl]ethyl}cyclohexyl)butanamide,
2-Cyano-N-(4-{2-[4-(2-cyano-3-fluorophenyl-piperazin-1-yl]ethyl}cyclohexyl)acetamide,
4-Cyano-N-(4-{2-[4-(5,6,7,8-tetrahydronaphthalen-1-yl)piperazin-1-yl]ethyl}cyclohexyl)butanamide,
4-Cyano-N-(4-{2-[4-(2,3-dichlorophenyl)piperazin-1-yl]ethyl}cyclohexyl)butanamide,
2-Cyano-N-(4-{2-[4-(5,6,7,8-tetrahydronaphthalen-2-yl)piperazin-1-yl]ethyl}cyclohexyl)acetamide,
2-Cyano-N-{4-[2-(4-indan-5-ylpiperazin-1-yl)ethyl]cyclohexyl}acetamide,
N-(4-{2-[4-(3,5-Bistrifluoromethylphenyl)piperazin-1-yl]ethyl}cyclohexyl)-3-cyanopropanamide,
3-Cyano-N-(4-{2-[4-(2-fluoro-3-trifluoromethylphenyl)piperazin-1-yl]ethyl}cyclohexyl)propanamide,
N-(4-{2-[4-(3-Chloro-2-methoxyphenyl)piperazin-1-yl]ethyl}cyclohexyl)-2-cyanoacetamide,
N-(4-{2-[4-(3-Benzylphenyl)piperazin-1-yl]ethyl}cyclohexyl)-2-cyanoacetamide,
[3-(4-{2-[4-(2-Cyanoacetylamino)cyclohexyl]ethyl}piperazin-1-yl)phenyl]carbamic acid ethyl ester,
2-Cyano-N-(4-{2-[4-(2,3-dimethylphenyl)piperazin-1-yl]ethyl}cyclohexyl)acetamide,
2-Cyano-N-{4-[2-(4-o-tolylpiperazin-1-yl)ethyl]cyclohexyl}acetamide,
2-Cyano-N-(4-{2-[4-(2,5-dimethoxyphenyl)piperazin-1-yl]ethyl}cyclohexyl)acetamide,
4-Oxopentanoic acid (4-{2-[4-(3,5-bis-trifluoromethylphenyl)piperazin-1-yl]ethyl}cyclohexyl)amide,
4-Dimethylamino-N-(4-{2-[4-(3-trifluoromethylphenyl)piperazin-1-yl]ethyl}cyclohexyl)butanamide,
2-(4-Fluorophenoxy)-N-(4-{2-[4-(3-trifluoromethylphenyl)piperazin-1-yl]ethyl}cyclohexyl)acetamide,
2-Cyano-N-(4-{2-[4-(2-trifluoromethylphenyl)piperazin-1-yl]ethyl}cyclohexyl)acetamide, hydrochloride,
2-Cyano-N-(4-{2-[4-(2,5-difluorophenyl)piperazin-1-yl]ethyl}cyclohexyl)acetamide,
N-(4-{2-[4-(2-Chloro-5-methylphenyl)piperazin-1-yl]ethyl}cyclohexyl)-2-cyanoacetamide,
2-Cyano-N-(4-{2-[4-(2,5-dichlorophenyl)piperazin-1-yl]ethyl}cyclohexyl)acetamide, N-(4-{2-[4-(3-Chlorophenyl)piperazin-1-yl]
ethyl}cyclohexyl)-4-cyanobutanamide,
4-Cyano-N-(4-{2-[4-(2-methyl-3-trifluoromethylphenyl)
piperazin-1-yl]ethyl}cyclohexyl)butanamide,
4-Oxopentanoic acid (4-{2-[4-(2-fluoro-3-trifluoromethylphenyl)piperazin-1-yl]ethyl}cyclohexyl)amide,
2-Cyano-N-(4-{2-[4-(3,5-di-tert-butylphenyl)piperazin-1-yl]ethyl}cyclohexyl)acetamide,
N-(4-{2-[4-(2-Chlorophenyl)piperazin-1-yl]
ethyl}cyclohexyl)-4-cyanobutanamide,
4-Cyano-N-{4-[2-(4-m-tolylpiperazin-1-yl)ethyl]
cyclohexyl}butanamide,
3,3,3-Trifluoro-N-{4-[2-(4-m-tolylpiperazin-1-yl)ethyl]
cyclohexyl}propanamide,
4-Cyano-N-(4-{2-[4-(2-methylsulfanylphenyl)piperazin-1-yl]ethyl}cyclohexyl)butanamide,
2-Cyano-N-{4-[2-(4-quinolin-8-ylpiperazin-1-yl)ethyl]
cyclohexyl}acetamide,
4-Cyano-N-(4-{2-[4-(3-methylsulfanylphenyl)piperazin-1-yl]ethyl}cyclohexyl)butanamide,
2-Cyano-N-{4-[2-(4-quinolin-5-ylpiperazin-1-yl)ethyl]
cyclohexyl}acetamide,
2-Cyano-N-(4-{2-[4-(3-methanesulfonylaminophenyl)
piperazin-1-yl]ethyl}cyclohexyl)acetamide,
2-Cyano-N-(4-{2-[4-(4-fluoro-phenyl)piperazin-1-yl]
ethyl}cyclohexyl)acetamide,
2-Cyano-N-{4-[2-(4-p-tolylpiperazin-1-yl)ethyl]
cyclohexyl}acetamide,
2-Cyano-N-(4-{2-[4-(2-ethoxyphenyl)piperazin-1-yl]
ethyl}cyclohexyl)acetamide,
N-(4-{2-[4-(2-tert-Butyl-6-trifluoromethylpyrimidin-4-yl)piperazin-1-yl]ethyl}cyclohexyl)-3-cyanopropanamide,
2-Cyano-N-(4-{2-[4-(2-phenoxyphenyl)piperazin-1-yl]
ethyl}cyclohexyl)acetamide,
N-(4-{2-[4-(3-Chloro-2-cyanophenyl)piperazin-1-yl]
ethyl}cyclohexyl)-2-cyanoacetamide,
2-Cyano-N-(4-{2-[4-(2-ethylphenyl)piperazin-1-yl]
ethyl}cyclohexyl)acetamide,
N-(4-{2-[4-(5-Chloro-2-methylphenyl)piperazin-1-yl]
ethyl}cyclohexyl)-4-cyanobutanamide,
4-Cyano-N-(4-{2-[4-(3,5-dimethylphenyl)piperazin-1-yl]
ethyl}cyclohexyl)butanamide,
N-(4-{2-[4-(3-Ethylphenyl)piperazin-1-yl]
ethyl}cyclohexyl)-3,3,3-trifluoropropanamide,
3-Cyano-N-(4-{2-[4-(3-ethylphenyl)piperazin-1-yl]
ethyl}cyclohexyl)propanamide,
4-Cyano-N-(4-{2-[4-(6-trifluoromethylbenzo[b]
thiophen-3-yl)piperazin-1-yl]ethyl}cyclohexyl)butanamide,
4-Cyano-N-(4-{2-[4-(3,5-difluorophenyl)piperazin-1-yl]
ethyl}cyclohexyl)butanamide,
2-Cyano-N-(4-{2-[4-(2,4-diethylphenyl)piperazin-1-yl]
ethyl}cyclohexyl)acetamide,
3,3,3-Trifluoro-N-(4-{2-[4-(2-fluoro-3-trifluoromethylphenyl)piperazin-1-yl]ethyl}cyclohexyl)propanamide,
N-(4-{2-[4-(5-Chloro-2-methylphenyl)piperazin-1-yl]
ethyl}cyclohexyl)-3-cyanopropanamide,
N-(4-{2-[4-(3-Chloro-2-methylphenyl)piperazin-1-yl]
ethyl}cyclohexyl)-4-cyanobutanamide,
N-(4-{2-[4-(3-Chloro-5-fluorophenyl)piperazin-1-yl]
ethyl}cyclohexyl)-4-cyanobutanamide,
N-(4-{2-[4-(2-Fluoro-3-trifluoromethylphenyl)piperazin-1-yl]ethyl}cyclohexyl)-2-methoxyacetamide,
4-Cyano-N-(4-{2-[4-(3,5-dichlorophenyl)piperazin-1-yl]
ethyl}cyclohexyl)butanamide,
4-Cyano-N-{4-[2-(4-quinolin-8-ylpiperazin-1-yl)ethyl]
cyclohexyl}butanamide,
4,4,4-Trifluoro-N-(4-{2-[4-(3-trifluoromethylphenyl)piperazin-1-yl]ethyl}cyclohexyl)butanamide,
3-Cyano-N-(4-{2-[4-(2-fluorophenyl)piperazin-1-yl]
ethyl}cyclohexyl)propanamide,
2-Cyano-N-(4-{2-[4-(2,6-dimethylphenyl)piperazin-1-yl]
ethyl}cyclohexyl)acetamide,
2-Cyano-N-(4-{2-[4-(3-hydroxymethylphenyl)piperazin-1-yl]ethyl}cyclohexyl)acetamide,
3-Cyano-N-(4-{2-[4-(3-methylsulfanylphenyl)piperazin-1-yl]ethyl}cyclohexyl)propanamide,
2-Cyano-N-(4-{2-[4-(3-methoxymethylphenyl)piperazin-1-yl]ethyl}cyclohexyl)acetamide,
2-Cyano-N-(4-{2-[4-(3-propylphenyl)piperazin-1-yl]
ethyl}cyclohexyl)acetamide,
2-Cyano-N-(4-{2-[4-(3,4-dichlorophenyl)piperazin-1-yl]
ethyl}cyclohexyl)acetamide,
2-Cyano-N-[4-(2-{4-[3-(1-hydroxyethyl)phenyl]piperazin-1-yl}ethyl)cyclohexyl]acetamide,
2-Cyano-N-(4-{2-[4-(4-trifluoromethylphenyl)piperazin-1-yl]ethyl}cyclohexyl)acetamide,
N-(4-{2-[4-(4-Chlorophenyl)piperazin-1-yl]
ethyl}cyclohexyl)-2-cyanoacetamide,
N-{4-[2-(4-Biphenyl-3-yl-piperazin-1-yl)ethyl]cyclohexyl}-2-cyanoacetamide,
2-Cyano-N-(4-{2-[4-(4-fluoro-3-trifluoromethylphenyl)
piperazin-1-yl]ethyl}cyclohexyl)acetamide,
3-Cyano-N-(4-{2-[4-(5-fluoro-2-methylphenyl)piperazin-1-yl]ethyl}cyclohexyl)propanamide,
4-Cyano-N-(4-{2-[4-(5-fluoro-2-methylphenyl)piperazin-1-yl]ethyl}cyclohexyl)butanamide,
N-(4-{2-[4-(3-Bromophenyl)piperazin-1-yl]
ethyl}cyclohexyl)-2-cyanoacetamide,
2-Cyano-N-[4-(2-{4-[3-(1,1-difluoroethyl)phenyl]piperazin-1-yl}ethyl)cyclohexyl]acetamide,
2-Cyano-2,2-dimethyl-N-(4-{2-[4-(3-trifluoromethylphenyl)piperazin-1-yl]ethyl}cyclohexyl)acetamide,
4-Cyano-N-(4-{2-[4-(4-fluorophenyl)piperazin-1-yl]
ethyl}cyclohexyl)butanamide,
3,3,3-Trifluoro-N-(4-{2-[4-(4-fluorophenyl)piperazin-1-yl]ethyl}cyclohexyl)propanamide,
2-Cyano-N-(4-{2-[4-(4-ethylphenyl)piperazin-1-yl]
ethyl}cyclohexyl)acetamide,
4-Cyano-N-(4-{2-[4-(2-ethylphenyl)piperazin-1-yl]
ethyl}cyclohexyl)butanamide,
N,N-Dimethyl-2-(4-{2-[4-(3-trifluoromethylphenyl)piperazin-1-yl]ethyl}cyclohexyl)acetamide,
N-(2-Methoxyethyl)-2-(4-{2-[4-(3-trifluoromethylphenyl)piperazin-1-yl]ethyl}cyclohexyl)acetamide,
N-(2-Methoxyethyl)-2-(4-{2-[4-(3-trifluoromethylphenyl)piperazin-1-yl]ethyl}cyclohexyl)acetamide, hydrochloride,
-2-(4-{2-[4-(2-Fluorophenyl)piperazin-1-yl]
ethyl}cyclohexyl)-N-methylacetamide,
4-cyano-N-(4-{2-[4-(3-propylphenyl)piperazin-1-yl]
ethyl}cyclohexyl)butanamide
2-cyano-N-(4-{2-[4-(3-fluoro-2-methylphenyl)piperazin-1-yl]ethyl}cyclohexyl)acetamide
4-cyano-N-[4-(2-{4-[3-(1,1-difluoroethyl)phenyl]piperazin-1-yl}ethyl)cyclohexyl]butanamide
N-{4-[2-(4-benzo[1,3]dioxol-5-ylpiperazin-1-yl)ethyl]
cyclohexyl}-2-cyanoacetamide
2-cyano-N-(4-{2-[4-(2,3-dihydrobenzo[1,4]dioxin-6-yl)
piperazin-1-yl]ethyl}cyclohexyl)acetamide
3,3,3-trifluoro-N-{4-[2-(4-quinolin-5-ylpiperazin-1-yl)
ethyl]cyclohexyl}propanami-de 4-cyano-N-{4-[2-(4-quinolin-5-ylpiperazin-1-yl)ethyl]
cyclohexyl}butanamide
2-cyano-N-(4-{2-[4-(4-fluoro-3-methylphenyl)piperazin-
1-yl]ethyl}cyclohexyl)acetamide
2-cyano-cyclopropanecarboxylic acid (4-{2-[4-(3-trifluo-
romethylphenyl)piperazin-1-yl]ethyl}cyclohexyl)
amide
2-cyano-N-(4-{2-[4-(3,4-difluorophenyl)piperazin-1-yl]
ethyl}cyclohexyl)acetamide
2-cyano-N-(4-{2-[4-(3-ethylphenyl)piperazin-1-yl]
ethyl}cyclohexyl)acetamide
2-methanesulfinyl-N-(4-{2-[4-(3-trifluoromethylphenyl)
piperazin-1-yl]ethyl}cyclohexyl)acetamide
2-cyano-N-(4-{2-[4-(3-isopropylphenyl)piperazin-1-yl]
ethyl}cyclohexyl)acetamide
2-cyano-N-(4-{2-[4-(3,5-dimethylphenyl)piperazin-1-yl]
ethyl}cyclohexyl)acetamide
2-methanesulfonyl-N-(4-{2-[4-(3-trifluoromethylphenyl)
piperazin-1-yl]ethyl}cyclohexyl)acetamide
2-cyano-N-(4-{2-[4-(3-fluoro-4-methylphenyl)piperazin-
1-yl]ethyl}cyclohexyl)acetamide
2-cyano-N-(4-{2-[4-(3,4-dimethylphenyl)piperazin-1-yl]
ethyl}cyclohexyl)acetamide
2-cyano-N-(4-{2-[4-(3,4,5-trifluorophenyl)piperazin-1-
yl]ethyl}cyclohexyl)acetamide
2-cyano-N-(4-{2-[4-(3-trifluoromethylsulfanylphenyl)
piperazin-1-yl]ethyl}cyclohexyl)acetamide
2-cyano-N-(4-{2-[4-(3-methanesulfonylphenyl)piper-
azin-1-yl]ethyl}cyclohexyl)acetamide
2-cyano-N-(4-{2-[4-(3-difluoromethylphenyl)piperazin-
1-yl]ethyl}cyclohexyl)acetamide
4-cyano-N-(4-{2-[4-(3-fluoro-2-methylphenyl)piperazin-
1-yl]ethyl}cyclohexyl)butanamide
4-cyano-N-(4-{2-[4-(3,4-difluorophenyl)piperazin-1-yl]
ethyl}cyclohexyl)butanamide
4-cyano-N-(4-{2-[4-(4-fluoro-3-methylphenyl)piperazin-
1-yl]ethyl}cyclohexylbutanamide
N-(4-{2-[4-(4-chloro-2-fluorophenyl)piperazin-1-yl]
ethyl}cyclohexyl)-2-cyanoacetamide
N-(4-{2-[4-(4-chloro-3-trifluoromethylphenyl)piperazin-
1-yl]ethyl}cyclohexyl)-2-cyanoacetamide
4-cyano-N-(4-{2-[4-(3-trifluoromethylsulfanylphenyl)
piperazin-1-yl]ethyl}cyclohexyl)butanamide
4-cyano-N-(4-{2-[4-(3-difluoromethylphenyl)piperazin-
1-yl]ethyl}cyclohexyl)butanamide
N-{4-[2-(4-benzo[1,3]dioxol-5-ylpiperazin-1-yl)ethyl]
cyclohexyl}-4-cyanobutanamide
4-cyano-N-(4-{2-[4-(2-fluoro-3-trifluoromethylphenyl)
piperazin-1-yl]ethyl}cyclohexyl)butanamide
4-cyano-N-(4-{2-[4-(4-fluoro-3-methylphenyl)piperazin-
1-yl]ethyl}cyclohexyl)butanamide, hydrochloride
4-cyano-N-(4-{2-[4-(3,4-dichlorophenyl)piperazin-1-yl]
ethyl}cyclohexyl)butanamide
N-(4-{2-[4-(3-chloro-4-methylphenyl)piperazin-1-yl]
ethyl}cyclohexyl)-2-cyanoacetamide
2-cyano-N-(4-{2-[4-(4-cyanophenyl)piperazin-1-yl]
ethyl}cyclohexyl)acetamide
4-cyano-N-(4-{2-[4-(2,5-dichlorophenyl)piperazin-1-yl]
ethyl}cyclohexyl)butanamide
cyclopent-3-enecarboxylic acid (4-{2-[4-(2-methoxyphe-
nyl)piperazin-1-yl]ethyl}cyclohexyl)amide
2-cyclopent-2-enyl-N-(4-{2-[4-(3-trifluoromethylphenyl)
piperazin-1-yl]ethyl}cyclohexyl)acetamide
4-cyano-N-(4-{2-[4-(3,4,5-trifluorophenyl)piperazin-1-
yl]ethyl}cyclohexyl)butanamide
N-(4-{2-[4-(3-acetylphenyl)piperazin-1-yl]ethylcyclo-
hexyl)-4-cyanobutanamide
2-cyano-N-(4-{2-[4-(2-cyanophenyl)piperazin-1-yl]
ethyl}cyclohexyl)acetamide
4-cyano-N-(4-{2-[4-(2-cyanophenyl)piperazin-1-yl]
ethyl}cyclohexyl)butanamide
cyclopent-3-enecarboxylic acid (4-{2-[4-(3-ethylphenyl)
piperazin-1-yl]ethyl}cyclohexyl)amide
cyclopent-3-enecarboxylic acid {4-[2-(4-m-tolylpiper-
azin-1-yl)ethyl]cyclohexyl}
cyclopent-1-enecarboxylic acid {4-[2-(4-m-tolylpiper-
azin-1-yl)ethyl]cyclohexyl} amide
N-(4-{2-[4-(3-chloro-4-methylphenyl)piperazin-1-yl]
ethyl}cyclohexyl)-4-cyanobutanamide
4-cyano-N-(4-{2-[4-(2-methoxyphenyl)piperazin-1-yl]
ethyl}cyclohexyl)butanamide
cyclopent-1-enecarboxylic acid (4-{2-[4-(2,4-difluo-
rophenyl)piperazin-1-yl]ethyl}cyclohexyl)amide
N-(4-{2-[4-(2,4-difluorophenyl)piperazin-1-yl]
ethyl}cyclohexyl)-2-(4-fluorophenoxy)acetamide
N-(4-{2-[4-(2,4-difluorophenyl)piperazin-1-yl]
ethyl}cyclohexyl)-3,3,3-trifluoropropanamide
2-cyclopent-3-enyl-N-(4-{2-[4-(2-fluorophenylpiperazin-
1-yl]ethyl}cyclohexyl)acetamide
N-(4-{2-[4-(2-chloro-4-fluoro-5-methylphenyl)piper-
azin-1-yl]ethyl}cyclohexyl)-2-cyanoacetamide
N-(4-{2-[4-(2-chloro-4-fluoro-5-methylphenylpiperazin-
1-yl]ethyl}cyclohexyl)-4-cyanobutanamide
4-cyano-N-(4-{2-[4-(5-methoxy-2-methylphenyl)piper-
azin-1-yl]ethyl}cyclohexyl)butanamide
4-cyano-N-(4-{2-[4-(3,5-dimethoxyphenyl)piperazin-1-
yl]ethyl}cyclohexyl)butanamide
N-(4-{2-[4-(3-chloro-2-cyanophenyl)piperazin-1-yl]
ethyl}cyclohexyl)-4-cyanobutanamide
cyclohex-1-enecarboxylic acid (4-{2-[4-(3-fluorophenyl)
piperazin-1-yl]ethyl}cyclohexylamide
4-cyano-N-(4-{2-[4-(3-fluorophenyl)piperazin-1-yl]
ethyl}cyclohexyl)butanamide
N-(4-{2-[4-(3-fluorophenyl)piperazin-1-yl]
ethyl}cyclohexyl)-2-phenoxyacetamide
N-(4-{2-[4-(3-fluorophenyl)piperazin-1-yl]
ethyl}cyclohexyl)succinamide
N-(4-{2-[4-(3-fluorophenyl)piperazin-1-yl]
ethyl}cyclohexyl)succinamide
cyclopent-1-enecarboxylic acid (4-{2-[4-(3-fluorophenyl)
piperazin-1-yl]ethyl}cyclohexyl)amide
4-cyano-N-(4-{2-[4-(2,4-difluorophenyl)piperazin-1-yl]
ethyl}cyclohexyl)butanamide
3-cyano-N-(4-{2-[4-(2,4-difluorophenyl)piperazin-1-yl]
ethyl}cyclohexyl)propanamide
N-(4-{2-[4-(2-chloro-5-trifluoromethylphenyl)piperazin-
1-yl]ethyl}cyclohexyl)-4-cyanobutanamide
4-cyano-N-(4-{2-[4-(2-methoxy-5-trifluoromethylphe-
nyl)piperazin-1-yl]ethyl}cyclohexyl)butanamide
1H-indene-2-carboxylic acid (4-{2-[4-(3-fluorophenyl)
piperazin-1-yl]ethyl}cyclohexyl)amide
cyclopent-3-enecarboxylic acid (4-{2-[4-(3-fluorophenyl)
piperazin-1-yl]ethyl}cyclohexyl)amide
3,3,3-trifluoro-N-(4-{2-[4-(3-fluorophenyl)piperazin-1-
yl]ethyl}cyclohexyl)propanamide
3-diethylamino-N-(4-{2-[4-(3-fluorophenyl)piperazin-1-
yl]ethyl}cyclohexyl)propanamide
3-cyano-N-(4-{2-[4-(3-fluorophenyl)piperazin-1-yl]
ethyl}cyclohexyl)propanamide
4-cyano-N-(4-{2-[4-(2,5-dimethylphenyl)piperazin-1-yl]
ethyl}cyclohexyl)butanamide
N-(4-{2-[4-(5-chloro-2-fluorophenyl)piperazin-1-yl]
ethyl}cyclohexyl)-4-cyanobutanamide N-(4-{2-[4-(5-chloro-2-methoxyphenyl)piperazin-1-yl]ethyl}cyclohexyl)-4-cyanobutanamide
4-cyano-N-(4-{2-[4-(3-methoxyphenyl)piperazin-1-yl]ethyl}cyclohexyl)butanamide
cyclopent-1-enecarboxylic acid (4-{2-[4-(3-methoxyphenyl)piperazin-1-yl]ethyl}cyclohexyl)amide
3-cyano-N-(4-{2-[4-(3-methoxyphenyl)piperazin-1-yl]ethyl}cyclohexyl)propanamide
N-(4-{2-[4-(3-fluorophenyl)piperazin-1-yl]ethyl}cyclohexyl)-4-methoxybutanamide
2-cyclopent-2-enyl-N-(4-{2-[4-(3-fluorophenyl)piperazin-1-yl]ethyl}cyclohexyl)acetamide
4-cyano-N-(4-{2-[4-(3-methoxy-5-trifluoromethylphenyl)piperazin-1-yl]ethyl}cyclohexyl)butanamide
N-(4-{2-[4-(2-ethylphenyl)piperazin-1-yl]ethyl}cyclohexyl)-3,3,3-trifluoropropanamide
2-cyano-N-(4-{2-[4-(2,4-dichloro-5-trifluoromethylphenyl)piperazin-1-yl]ethyl}cyclohexyl)acetamide
4-cyano-N-(4-{2-[4-(2,4-dichloro-5-trifluoromethylphenyl)piperazin-1-yl]ethyl}cyclohexyl)butanamide
N-(4-{2-[4-(3-ethylphenyl)piperazin-1-yl]ethyl}cyclohexyl)-2-methanesulfonylacetamide
N-(4-{2-[4-(2,3-difluorophenyl)piperazin-1-yl]ethyl}cyclohexyl)-2-methanesulfonylacetamide
N-(4-{2-[4-(4-chlorophenyl)piperazin-1-yl]ethyl}cyclohexyl)-2-methanesulfonylacetamide
4-cyano-N-{4-[2-(4-o-tolylpiperazin-1-yl)ethyl]cyclohexyl}butanamide
4-cyano-N-(4-{2-[4-(2,3-dimethylphenyl)piperazin-1-yl]ethyl}cyclohexyl)butanamide
4-cyano-N-(4-{2-[4-(4-fluoro-3-trifluoromethylphenyl)piperazin-1-yl]ethyl}cyclohexyl)butanamide
cyclopent-1-enecarboxylic acid (4-{2-[4-(4-fluorophenyl)piperazin-1-yl]ethyl}cyclohexyl)amide
4-cyano-N-(4-{2-[4-(3-cyano-5-trifluoromethylphenyl)piperazin-1-yl]ethyl}cyclohexyl)butanamide
4-cyano-N-(4-{2-[4-(2-trifluoromethylphenyl)piperazin-1-yl]ethylcyclohexyl)butanamide, hydrochloride
N-(4-{2-[4-(3-chloro-5-methylphenyl)piperazin-1-yl]ethyl}cyclohexyl)-2-cyanoacetamide
N-(4-{2-[4-(3-chloro-5-methylphenyl)piperazin-1-yl]ethyl}cyclohexyl)-4-cyanobutanamide
4-cyano-N-(4-{2-[4-(2-ethoxyphenyl)piperazin-1-yl]ethyl}cyclohexyl)butanamide
4-cyano-N-(4-{2-[4-(2-fluoro-5-methylphenyl)piperazin-1-yl]ethyl}cyclohexyl)butanamide
cyclopent-1-enecarboxylic acid (4-{2-[4-(2,5-difluorophenyl)piperazin-1-yl]ethyl}cyclohexyl)amide
4-cyano-N-(4-{2-[4-(2,5-difluorophenyl)piperazin-1-yl]ethyl}cyclohexyl)butanamide
2,2-difluoro-N-(4-{2-[4-(2-fluoro-3-trifluoromethylphenyl)piperazin-1-yl]ethyl}cyclohexyl)acetamide
4-cyano-N-(4-{2-[4-(2,3-difluorophenyl)piperazin-1-yl]ethyl}cyclohexyl)butanamide
N-(4-{2-[4-(2,3-difluorophenyl)piperazin-1-yl]ethyl}cyclohexyl)-3,3,3-trifluoropropanamide
cyclopent-1-enecarboxylic acid (4-{2-[4-(2,3-difluorophenyl)piperazin-1-yl]ethyl}cyclohexyl)amide
4-cyano-N-(4-{2-[4-(3-cyanophenyl)piperazin-1-yl]ethyl}cyclohexyl)butanamide
N-(4-{2-[4-(3-chloro-2-methoxyphenyl)piperazin-1-yl]ethyl}cyclohexyl)-4-cyanobutanamide
2-cyano-N-(4-{2-[4-(2,3,4-trifluorophenyl)piperazin-1-yl]ethyl}cyclohexyl)acetamide
4-cyano-N-(4-{2-[4-(2,3,4-trifluorophenyl)piperazin-1-yl]ethyl}cyclohexyl)butanamide
3,3,3-trifluoro-N-(4-{2-[4-(3-methanesulfonylphenyl)piperazin-1-yl]ethyl}cyclohexyl)propanamide
2-cyano-N-{4-[2-(4-indan-4-ylpiperazin-1-yl)ethyl]cyclohexyl}acetamide
4-cyano-N-{4-[2-(4-indan-4-ylpiperazin-1-yl)ethyl]cyclohexyl}butanamide
cyclopent-1-enecarboxylic acid (4-{2-[4-(2-fluoro-3-trifluoromethylphenyl)piperazin-1-yl]ethyl}cyclohexyl)amide
N-(4-{2-[4-(2-fluoro-3-trifluoromethylphenyl)piperazin-1-yl]ethyl}cyclohexyl)succinamide
4-cyano-2,2-difluoro-N-(4-{2-[4-(2-fluoro-3-trifluoromethylphenyl)piperazin-1-yl]ethyl}cyclohexyl)butanamide
2,2,2-trifluoro-N-(4-{2-[4-(3-methanesulfonylphenyl)piperazin-1-yl]ethyl}cyclohexyl)acetamide
N-{4-[2-(4-biphenyl-3-ylpiperazin-1-yl)ethyl]cyclohexyl}-4-cyanobutanamide
cyclopent-1-enecarboxylic acid (4-{2-[4-(3,4,5-trifluorophenyl)piperazin-1-yl]ethyl}cyclohexyl)amide
2-ethoxy-N-(4-{2-[4-(3,4,5-trifluorophenyl)piperazin-1-yl]ethyl}cyclohexyl)acetamide
cyclopent-3-enecarboxylic acid (4-{2-[4-(3,4,5-trifluorophenyl)piperazin-1-yl]ethyl}cyclohexyl)amide
4-cyano-N-{4-[2-(4-p-tolylpiperazin-1-yl)ethyl]cyclohexyl}butanamide
4,4,4-trifluoro-N-(4-{2-[4-(3-methanesulfonylphenyl)piperazin-1-yl]ethyl}cyclohexyl)butanamide
N-(4-{2-[4-(2-fluoro-3-trifluoromethylphenyl)piperazin-1-yl]ethyl}cyclohexyl)-4-methoxybutanamide
N-(4-{2-[4-(4-chloro-2-fluorophenyl)piperazin-1-yl]ethyl}cyclohexyl)-4-cyanobutanamide
2-cyano-N-(4-{2-[4-(2,4,5-trifluorophenyl)piperazin-1-yl]ethyl}cyclohexyl)acetamide
4-cyano-N-(4-{2-[4-(2,4,5-trifluorophenyl)piperazin-1-yl]ethyl}cyclohexyl)butanamide
2-ethoxy-N-{4-[2-(4-p-tolylpiperazin-1-yl)ethyl]cyclohexyl}acetamide
cyclopent-1-enecarboxylic acid {4-[2-(4-p-tolylpiperazin-1-yl)ethyl]cyclohexyl}amide
5,6-dihydro-4H-pyran-3-carboxylic acid (4-{2-[4-(2-fluoro-3-trifluoromethylphenyl)piperazin-1-yl]ethyl}cyclohexyl amide
3,3,3-trifluoro-N-[4-(2-{4-[3-(1-hydroxyethyl)phenyl]piperazin-1-yl}ethyl)cyclohexyl]propanamide
2-ethoxy-N-(4-{2-[4-(2-fluoro-3-trifluoromethylphenyl)piperazin-1-yl]ethyl}cyclohexyl)acetamide
N-(4-{2-[4-(4-chlorophenyl)piperazin-1-yl]ethyl}cyclohexyl)-4-cyanobutanamide
N-(4-{2-[4-(4-chlorophenyl)piperazin-1-yl]ethyl}cyclohexyl)-3,3,3-trifluoropropanamide
4-cyano-N-(4-{2-[4-(2-methoxy-5-methylphenyl)piperazin-1-yl]ethyl}cyclohexyl)butanamide
2-cyano-N-(4-{2-[4-(2-fluoro-4-methylphenyl)piperazin-1-yl]ethyl}cyclohexyl)acetamide
4-cyano-N-(4-{2-[4-(2-fluoro-4-methylphenyl)piperazin-1-yl]ethyl}cyclohexyl)butanamide
cyclopent-1-enecarboxylic acid (4-{2-[4-(3,4-dichlorophenyl)piperazin-1-yl]ethyl}cyclohexyl)amide
N-(4-{2-[4-(3,4-dichlorophenyl)piperazin-1-yl]ethyl}cyclohexyl)-2-ethoxyacetamide
cyclopent-1-enecarboxylic acid (4-{2-[4-(4-chlorophenyl)piperazin-1-yl]ethyl}cyclohexyl)amide
N-(4-{2-[4-(3-chloro-4-methylphenyl)piperazin-1-yl]ethyl}cyclohexyl)-2-ethoxyacetamide
cyclopent-1-enecarboxylic acid (4-{2-[4-(3-chloro-4-methylphenyl)piperazin-1-yl]ethyl}cyclohexyl)amide N-(4-{2-[4-(3-chloro-4-methylphenyl)piperazin-1-yl]ethyl}cyclohexyl)-3,3,3-trifluoropropanamide
3,3,3-trifluoro-N-{4-[2-(4-p-tolylpiperazin-1-yl)ethyl]cyclohexyl} propanamide
cyclopent-3-enecarboxylic acid (4-{2-[4-(2,4-difluorophenyl)piperazin-1-yl]ethyl}cyclohexyl)amide
4,5-dihydrofuran-3-carboxylic acid (4-{2-[4-(2-fluoro-3-trifluoromethylphenyl)piperazin-1-yl]ethyl}cyclohexyl)amide
pyrrolidine-2-carboxylic acid (4-{2-[4-(2-fluoro-3-trifluoromethylphenyl)piperazin-1-yl]ethyl}cyclohexyl)amide
N-(4-{2-[4-(3,4-dichlorophenyl)piperazin-1-yl]ethyl}cyclohexyl)-4-methoxybutanamide
N-(4-{2-[4-(2,4-difluorophenyl)piperazin-1-yl]ethyl}cyclohexyl)-2-ethoxyacetamide
N-(4-{2-[4-(2,4-difluorophenyl)piperazin-1-yl]ethyl}cyclohexyl)-4-methoxybutanamide
4-cyano-N-(4-{2-[4-(3,4-dimethylphenyl)piperazin-1-yl]ethyl}cyclohexyl)butanamide
N-(4-{2-[4-(3,4-dimethylphenyl)piperazin-1-yl]ethyl}cyclohexyl)-4-methoxybutanamide
cyclopent-1-enecarboxylic acid (4-{2-[4-(3,4-dimethylphenyl)piperazin-1-yl]ethyl}cyclohexyl)amide
N-(4-{2-[4-(3,4-dimethylphenyl)piperazin-1-yl]ethyl}cyclohexyl)-2-ethoxyacetamide
N-(4-{2-[4-(3,4-dimethylphenyl)piperazin-1-yl]ethyl}cyclohexyl)-3,3,3-trifluoropropanamide
4-cyano-N-(4-{2-[4-(5,6,7,8-tetrahydronaphthalen-2-yl)piperazin-1-yl]ethyl}cyclohexyl)butanamide
N-(4-{2-[4-(3-cyanophenyl)piperazin-1-yl]ethyl}cyclohexyl)-3,3,3-trifluoropropanamide
cyclopent-1-enecarboxylic acid (4-{2-[4-(3-cyanophenyl)piperazin-1-yl]ethyl}cyclohexyl)amide
N-(4-{2-[4-(3-cyanophenyl)piperazin-1-yl]ethyl}cyclohexyl)-4-methoxybutanamide
2-ethoxy-N-(4-{2-[4-(2-fluoro-5-trifluoromethylphenyl)piperazin-1-yl]ethyl}cyclohexyl)acetamide
N-(4-{2-[4-(4-chloro-phenyl)piperazin-1-yl]ethyl}-cyclohexyl)-2-ethoxyacetamide
N-(4-{2-[4-(2-fluoro-3-trifluoromethylphenyl)piperazin-1-yl]ethyl}cyclohexyl)-2-propoxyacetamide
cyclopent-1-enecarboxylic acid (4-{2-[4-(4-chloro-2-fluorophenyl)piperazin-1-yl]ethyl}cyclohexyl)amide
cyclopent-1-enecarboxylic acid (4-{2-[4-(2-fluoro-4-methylphenyl)piperazin-1-yl]ethyl}cyclohexyl)amide
2-cyano-N-(4-{2-[4-(3,4-dichloro-2-fluorophenyl)piperazin-1-yl]ethyl}cyclohexyl)acetamide
4-cyano-N-(4-{2-[4-(3,4-dichloro-2-fluorophenyl)piperazin-1-yl]ethyl}cyclohexyl)butanamide
N-(4-{2-[4-(2,5-dichlorophenyl)piperazin-1-yl]ethyl}cyclohexyl)-2-ethoxyacetamide
4-cyano-N-(4-{2-[4-(2-cyano-3-fluorophenyl)piperazin-1-yl]ethyl}cyclohexyl)butanamide
cyclopent-1-enecarboxylic acid (4-{2-[4-(2,4,5-trifluorophenyl)piperazin-1-yl]ethyl}cyclohexyl)amide
4,5-dihydrofuran-3-carboxylic acid (4-{2-[4-(3-cyanophenyl)piperazin-1-yl]ethyl}cyclohexyl)amide
cyclopent-1-enecarboxylic acid (4-{2-[4-(5-chloro-2-fluorophenyl)piperazin-1-yl]ethyl}cyclohexyl)amide
4-cyano-N-(4-{2-[4-(3-oxazol-2-ylphenyl)piperazin-1-yl]ethyl}cyclohexyl)butanamide
4,5-dihydrofuran-3-carboxylic acid (4-{2-[4-(2,4-difluorophenyl)piperazin-1-yl]ethyl}cyclohexyl)amide
N-(4-{2-[4-(3-chloro-5-trifluoromethylphenyl)piperazin-1-yl]ethyl}cyclohexyl)-2-cyanoacetamide
N-(4-{2-[4-(3-chloro-5-trifluoromethylphenyl)piperazin-1-yl]ethyl}cyclohexyl)-4-cyanobutanamide
2-cyano-N-(4-{2-[4-(3-oxazol-2-ylphenyl)piperazin-1-yl]ethyl}cyclohexyl)acetamide
4,5-dihydrofuran-3-carboxylic acid(4-{2-[4-(3-oxazol-2-ylphenyl)piperazin-1-yl]ethyl}cyclohexyl)amide
cyclopent-1-enecarboxylic acid (4-{2-[4-(2-fluoro-5-methylphenyl)piperazin-1-yl]ethyl}cyclohexyl)amide
4-cyano-N-(4-{2-[4-(3-ethoxyphenyl)piperazin-1-yl]ethyl}cyclohexyl)butanamide
cyclopent-1-enecarboxylic acid (4-{2-[4-(3-fluoro-4-methylphenyl)piperazin-1-yl]ethyl}cyclohexyl)amide
4-cyano-N-(4-{2-[4-(3-fluoro-4-methylphenyl)piperazin-1-yl]ethyl}cyclohexyl)butanamide
2-ethoxy-N-(4-{2-[4-(3-fluoro-4-methylphenyl)piperazin-1-yl]ethyl}cyclohexyl)acetamide
4-cyano-N-[4-(2-{4-[3-(1-hydroxypropyl)phenyl]piperazin-1-yl}ethyl)cyclohexyl]butanamide
pyrrolidine-2-carboxylic acid (4-{2-[4-(3-cyanophenyl)piperazin-1-yl]ethyl}cyclohexyl)amide, dihydrochloride
2-methoxy-N-(4-{2-[4-(3,4,5-trifluorophenyl)piperazin-1-yl]ethyl}cyclohexyl)acetamide
cyclopent-1-enecarboxylic acid (4-{2-[4-(2,3,4-trifluorophenylpiperazin-1-yl]ethyl}cyclohexyl)amide
4-cyano-N-(4-{2-[4-(4-trifluoromethylphenyl)piperazin-1-yl]ethyl}cyclohexyl)butanamide
N-(4-{2-[4-(2,5-dichlorophenyl)piperazin-1-yl]ethyl}cyclohexyl)-2-ethoxyacetamide
pyrrolidine-2-carboxylic acid (4-{2-[4-(2-fluoro-5-trifluoromethylphenyl)piperazin-1-yl]ethyl}cyclohexyl)amide
N-(4-{2-[4-(3-chloro-2-methylphenyl)piperazin-1-yl]ethyl}cyclohexyl)-4-methoxybutanamide
pyrrolidine-2-carboxylic acid (4-{2-[4-(2,4-difluorophenyl)piperazin-1-yl]ethyl}cyclohexyl)amide, dihydrochloride
N-(4-{2-[4-(3-chloro-2,4-difluorophenyl)piperazin-1-yl]ethyl}cyclohexyl)-2-cyanoacetamide
N-(4-{2-[4-(3-chloro-2,4-difluorophenyl)piperazin-1-yl]ethyl}cyclohexyl)-4-cyanobutanamide
cyclopent-1-enecarboxylic acid {4-[2-(4-o-tolylpiperazin-1-yl)ethyl]cyclohexyl}amide
2-ethoxy-N-{4-[2-(4-o-tolylpiperazin-1-ylethyl]cyclohexyl}acetamide
N-(4-{2-[4-(3-ethylphenyl)piperazin-1-yl]ethyl}cyclohexyl)-4-methoxybutanamide
5,6-dihydro-4H-pyran-2-carboxylic acid (4-{2-[4-(3-ethylphenyl)piperazin-1-yl]ethyl}cyclohexyl)amide
5,6-dihydro-4H-pyran-2-carboxylic acid (4-{2-[4-(3-trifluoromethylphenyl)piperazin-1-yl]ethyl}cyclohexyl)amide
2-ethoxy-N-(4-{2-[4-(3-ethylphenyl)piperazin-1-yl]ethyl}cyclohexyl)acetamide
4,5-dihydrofuran-3-carboxylic acid (4-{2-[4-(3-trifluoromethylphenyl)piperazin-1-yl]ethyl}cyclohexyl)amide
5,6-dihydro-4H-pyran-2-carboxylic acid (4-{2-[4-(2,4-difluorophenyl)piperazin-1-yl]ethyl}cyclohexyl)amide
2-cyano-N-[4-(2-{4-[3-(1-hydroxypropyl)phenyl]piperazin-1-yl}ethyl)cyclohexyl]acetamide
4-methoxy-N-(4-{2-[4-(3,4,5-trifluorophenyl)piperazin-1-yl]ethyl}cyclohexyl)butanamide
cyclopent-1-enecarboxylic acid (4-{2-[4-(4-methoxyphenyl)piperazin-1-yl]ethyl}cyclohexyl)amide
2-ethoxy-N-(4-{2-[4-(4-methoxyphenyl)piperazin-1-yl]ethyl}cyclohexyl)acetamide 2-cyano-N-(4-{2-[4-(4-methoxyphenyl)piperazin-1-yl]ethyl}cyclohexyl)acetamide
2-cyano-N-(4-{2-[4-(3,5-difluoro-4-trifluoromethylphenyl)piperazin-1-yl]ethyl}cyclohexyl)acetamide
2-cyano-N-[4-(2-{4-[3-(1-hydroxy-2-methylpropyl)phenyl]piperazin-1-yl}ethyl)cyclohexyl]acetamide
N-(4-{2-[4-(3-chloro-5-methylphenyl)piperazin-1-yl]ethyl}cyclohexyl)-2-ethoxyacetamide
N-(4-{2-[4-(3-chloro-5-methylphenyl)piperazin-1-yl]ethyl}cyclohexyl)-4-methoxybutanamide
N-(4-{2-[4-(2-chloro-4-fluoro-5-methylphenyl)piperazin-1-yl]ethyl}cyclohexyl)-2-ethoxyacetamide
N-(4-{2-[4-(2-chloro-4-fluoro-5-methylphenyl)piperazin-1-yl]ethyl}cyclohexyl)-4-methoxybutanamide
4-cyano-N-(4-{2-[4-(4-methoxyphenyl)piperazin-1-yl]ethyl}cyclohexyl)butanamide
2-cyano-N-(4-{2-[4-(2-fluoro-5-trifluoromethylphenyl)piperazin-1-yl]ethyl}cyclohexyl)acetamide
N-(4-{2-[4-(3-chloro-4-fluorophenyl)piperazin-1-yl]ethyl}cyclohexyl)-2-cyanoacetamide
N-(4-{2-[4-(3-chloro-4-fluorophenyl)piperazin-1-yl]ethyl}cyclohexyl)-4-cyanobutanamide
N-(4-{2-[4-(2-chloro-5-cyanophenyl)piperazin-1-yl]ethyl}cyclohexyl)-2-cyanoacetamide
N-(4-{2-[4-(2-chloro-5-cyanophenyl)piperazin-1-yl]ethyl}cyclohexyl)-4-cyanobutanamide
N-(4-{2-[4-(3-chloro-2,4-difluorophenyl)piperazin-1-yl]ethyl}cyclohexyl)succinamide
2-cyano-N-(4-{2-[4-(4-trifluoromethylphenyl)piperazin-1-yl]ethyl}cyclohexyl)acetamide
N-(4-{2-[4-(2-fluoro-5-trifluoromethylphenyl)piperazin-1-yl]ethyl}cyclohexyl)-4-methoxybutanamide
N-(4-{2-[4-(2-fluoro-5-trifluoromethylphenyl)piperazin-1-yl]ethyl}cyclohexyl)succinamide
3-cyano-N-(4-{2-[4-(4-trifluoromethylphenyl)piperazin-1-yl]ethyl}cyclohexyl)propanamide
3-cyano-N-(4-{2-[4-(3-cyanophenyl)piperazin-1-yl]ethyl}cyclohexyl)propanamide
2-cyano-N-(4-{2-[4-(2-fluoro-4-trifluoromethylphenyl)piperazin-1-yl]ethyl}cyclohexyl)acetamide
4-cyano-N-(4-{2-[4-(2-fluoro-4-trifluoromethylphenyl)piperazin-1-yl]ethyl}cyclohexyl)-butanamide
4-methoxy-N-(4-{2-[4-(2,3,4-trifluorophenyl)piperazin-1-yl]ethyl}cyclohexyl)butanamide
N-(4-{2-[4-(3-cyanophenyl)piperazin-1-yl]ethyl}cyclohexyl)-4,4,4-trifluorobutanamide
N-(4-{2-[4-(3-cyanophenyl)piperazin-1-yl]ethyl}cyclohexyl)-3-methoxypropanamide
2-cyano-N-(4-{2-[4-(3-cyano-4-fluorophenyl)piperazin-1-yl]ethyl}cyclohexyl)acetamide
N-(4-{2-[4-(3-cyano-4-fluorophenyl)piperazin-1-yl]ethyl}cyclohexyl)-4-methoxybutanamide
4-cyano-N-(4-{2-[4-(3-cyano-4-fluorophenyl)piperazin-1-yl]ethyl}cyclohexyl)butanamide
2-cyano-N-(4-{2-[4-(3-fluoro-5-trifluoromethylphenyl)piperazin-1-yl]ethyl}cyclohexyl)acetamide
4-cyano-N-(4-{2-[4-(3-fluoro-5-trifluoromethylphenyl)piperazin-1-yl]ethyl}cyclohexyl)butanamide
3-cyano-N-(4-{2-[4-(2-fluoro-5-trifluoromethylphenyl)piperazin-1-yl]ethyl}cyclohexyl)propanamide
N-(4-{2-[4-(2-fluoro-5-trifluoromethylphenyl)piperazin-1-yl]ethyl}cyclohexyl)-2-propoxyacetamide, hydrochloride
3,3,3-trifluoro-N-(4-{2-[4-(2-fluoro-5-trifluoromethylphenyl)piperazin-1-yl]ethyl}cyclohexyl)propanamide
N-(4-{2-[4-(2-fluoro-5-trifluoromethylphenyl)piperazin-1-yl]ethyl}cyclohexyl)-malonamide
2-cyano-N-(4-{2-[4-(5-ethyl-2-fluorophenyl)piperazin-1-yl]ethyl}cyclohexyl)acetamide
4-cyano-N-(4-{2-[4-(5-ethyl-2-fluorophenyl)piperazin-1-yl]ethyl}cyclohexyl)butanamide
4-methoxy-N-{4-[2-(4-m-tolylpiperazin-1-yl)ethyl]cyclohexyl}butanamide
N-(4-{2-[4-(3,4-dichloro-2-fluoro-phenyl)piperazin-1-yl]ethyl}cyclohexyl)-4-methoxybutanamide
2-cyano-N-(4-{2-[4-(3-cyano-2,4-difluorophenyl)piperazin-1-yl]ethyl}cyclohexyl)acetamide
4-cyano-N-(4-{2-[4-(3-cyano-2,4-difluorophenyl)piperazin-1-yl]ethyl}cyclohexyl)butanamide
N-(4-{2-[4-(3-fluoro-2-methylphenyl)piperazin-1-yl]ethyl}cyclohexyl)-4-methoxybutanamide
N-(4-{2-[4-(3,5-dichlorophenyl)piperazin-1-yl]ethyl}cyclohexyl)-4-methoxybutanamide
N-(4-{2-[4-(3-cyano-2,4-difluorophenyl)piperazin-1-yl]ethyl}cyclohexyl)-4-methoxybutanamide
N-(4-{2-[4-(4-chlorophenyl)piperazin-1-yl]ethyl}cyclohexyl)-4-methoxybutanamide
N-(4-{2-[4-(2-fluoro-5-trifluoromethylphenyl)piperazin-1-yl]ethyl}cyclohexyl)-2-methoxyacetamide
cyclopent-1-enecarboxylic acid (4-{2-[4-(2-fluoro-5-trifluoromethylphenylpiperazin-1-yl]ethyl}cyclohexyl)amide
N-(4-{2-[4-(2-fluoro-5-trifluoromethylphenyl)piperazin-1-yl]ethyl}cyclohexyl)-2-methanesulfonylacetamide
N-(4-{2-[4-(2-fluoro-4-methylphenyl)piperazin-1-yl]ethyl}cyclohexyl)-4-methoxybutanamide
2-cyano-N-(4-{2-[4-(2,3,4,5-tetrafluorophenyl)piperazin-1-yl]ethyl}cyclohexyl)acetamide
2-cyano-N-(4-{2-[4-(2,4-dichlorophenyl)piperazin-1-yl]ethyl}cyclohexyl)acetamide
N-(4-{2-[4-(3,5-dimethylphenyl)piperazin-1-yl]ethyl}cyclohexyl)-4-methoxybutanamide
3-cyano-N-(4-{2-[4-(3,5-dimethylphenyl)piperazin-1-yl]ethyl}cyclohexyl)propanamide
2-cyano-N-(4-{2-[4-(2,4,5-trichlorophenyl)piperazin-1-yl]ethyl}cyclohexyl)acetamide
N-(4-{2-[4-(3,4-dichloro-2-fluorophenyl)piperazin-1-yl]ethyl}cyclohexyl)-2-methoxyacetamide
3-cyano-N-(4-{2-[4-(3,4-dichloro-2-fluorophenyl)piperazin-1-yl]ethyl}cyclohexyl)propanamide
2-cyano-N-(4-{2-[4-(3-fluoro-5-methylphenyl)piperazin-1-yl]ethyl}cyclohexyl)acetamide
4-cyano-N-(4-{2-[4-(3-fluoro-5-methylphenyl)piperazin-1-yl]ethyl}cyclohexyl)butanamide
2-cyano-N-(4-{2-[4-(2,3,4-trichlorophenyl)piperazin-1-yl]ethyl}cyclohexyl)acetamide
5-cyano-pentanoic acid (4-{2-[4-(2-fluoro-5-trifluoromethylphenyl)piperazin-1-ylethyl}cyclohexyl)amide
N-(4-{2-[4-(3-chloro-2,4-difluorophenyl)piperazin-1-yl]ethyl}cyclohexyl)-3-cyanopropanamide
2-methoxy-N-(4-{2-[4-(2-methyl-3-trifluoromethylphenyl)piperazin-1-yl]ethyl}cyclohexyl)acetamide
4-methoxy-N-(4-{2-[4-(2-methyl-3-trifluoromethylphenyl)piperazin-1-yl]ethyl}cyclohexyl)butanamide
4,4,4-trifluoro-N-(4-{2-[4-(2-fluoro-5-trifluoromethylphenyl)piperazin-1-yl]ethyl}cyclohexyl)butanamide
N-(4-{2-[4-(3,5-bistrifluoromethylphenyl)piperazin-1-yl]ethyl}cyclohexyl)malonamide
N-(4-{2-[4-(3-chloro-5-fluorophenyl)piperazin-1-yl]ethyl}cyclohexyl)-4-methoxybutanamide
N-(4-{2-[4-(3,5-bistrifluoromethylphenyl)piperazin-1-yl]ethyl}cyclohexyl)-4-methoxybutanamide N-(4-{2-[4-(3-chloro-5-fluorophenyl)piperazin-1-yl]
ethyl}cyclohexyl)-2-methoxyacetamide
N-(4-{2-[4-(3-chloro-5-fluorophenyl)piperazin-1-yl]
ethyl}cyclohexyl)-3-cyanopropanamide
5-cyano-pentanoic acid (4-{2-[4-(3-trifluoromethylphenyl)piperazin-1-yl]ethyl}cyclohexyl)amide
2-cyano-N-{4-[2-(4-pentafluorophenylpiperazin-1-yl)
ethyl]cyclohexyl}acetamide
N-(4-{2-[4-(4-fluoro-3-trifluoromethylphenyl)piperazin-1-yl]ethyl}cyclohexyl)-4-methoxybutanamide
N-(4-{2-[4-(4-chloro-3-trifluoromethylphenyl)piperazin-1-yl]ethyl}cyclohexyl)-4-methoxybutanamide
N-(4-{2-[4-(4-chloro-3-trifluoromethylphenyl)piperazin-1-yl]ethyl}cyclohexyl)-4-cyanobutanamide
N-(4-{2-[4-(3-fluoro-5-trifluoromethylphenyl)piperazin-1-yl]ethyl}cyclohexyl)-4-methoxybutanamide
N-(4-{2-[4-(4-fluoro-3-trifluoromethylphenyl)piperazin-1-yl]ethyl}cyclohexyl)-2-methoxyacetamide
N-(4-{2-[4-(2,4-dichlorophenyl)piperazin-1-yl]
ethyl}cyclohexyl)-4-methoxybutanamide
4-cyano-N-(4-{2-[4-(2,4-dichlorophenyl)piperazin-1-yl]
ethyl}cyclohexyl)butanamide
2-cyano-cyclopropanecarboxylic acid (4-{2-[4-(2-fluoro-5-trifluoromethylphenyl)piperazin-1-yl]
ethyl}cyclohexyl)amide
4-cyano-N-(4-{2-[4-(2,4,5-trichlorophenyl)piperazin-1-yl]ethyl}cyclohexyl)butanamide
4-cyano-N-(4-{2-[4-(2,3,4-trichlorophenyl)piperazin-1-yl]ethyl}cyclohexyl)butanamide
3-(4-{2-[4-(4-methoxybutanoylamino)cyclohexyl]
ethyl}piperazin-1-yl)benzamide
N-(4-{2-[4-(3-acetylphenyl)piperazin-1-yl]
ethyl}cyclohexyl)-3,3,3-trifluoropropanamide
2-cyano-N-(4-{2-[4-(3-propanoylphenyl)piperazin-1-yl]
ethyl}cyclohexyl)acetamide
4-cyano-N-(4-{2-[4-(3-propanoylphenyl)piperazin-1-yl]
ethyl}cyclohexyl)butanamide
2-cyano-N-(4-{2-[4-(3-isobutanylphenyl)piperazin-1-yl]
ethyl}cyclohexyl)acetamide, dihydrochloride
4-Methoxy-N-(4-{2-[4-(2,3,4,5-tetrafluorophenyl)piperazin-1-yl]ethyl}cyclohexyl)butyramide
4-Cyano-N-(4-{2-[4-(2,3,4,5-tetrafluorophenyl)piperazin-1-yl]ethyl}cyclohexyl)butyramide
2-Cyano-N-(4-{2-[4-(2-methyl-5-trifluoromethylphenyl)
piperazin-1-yl]ethyl}cyclohexyl)acetamide
4-Cyano-N-(4-{2-[4-(2-methyl-5-trifluoromethylphenyl)
piperazin-1-yl]ethyl}cyclohexyl)butyramide
or their pharmaceutically acceptable salts, or the polymorphic, crystalline structures of these compounds or their optical isomers, racemates, diastereomers or enantiomers.

7. Compound according to claim 1 chosen from:
4-Methoxy-N-(4-{2-[4-(3-trifluoromethylphenyl)piperazin-1-yl]ethyl}cyclohexyl)butanamide
N-(4-{2-[4-(3-Cyanophenyl)piperazin-1-yl]
ethyl}cyclohexyl)-2-ethoxyacetamide
N-(4-{2-[4-(3-Cyanophenyl)piperazin-1-yl]
ethyl}cyclohexyl)-2-methoxyacetamide
N-(4-{2-[4-(3,5-Bistrifluoromethylphenyl)piperazin-1-yl]ethyl}cyclohexyl)-2-cyanoacetamide
N-(4-{2-[4-(3-Cyano-5-trifluoromethylphenyl)piperazin-1-yl]ethyl}cyclohexyl)-2-methoxyacetamide
N-(4-{2-[4-(3-Cyano-5-trifluoromethylphenyl)piperazin-1-yl]ethyl}cyclohexyl)-2-ethoxyacetamide
2-Cyano-N-(4-{2-[4-(3,5-dimethylphenyl)piperazin-1-yl]
ethyl}cyclohexyl)acetamide
2-Cyano-N-(4-{2-[4-(3-ethylphenyl)piperazin-1-yl]
ethyl}cyclohexyl)acetamide
4-Cyano-N-(4-{2-[4-(3-trifluoromethylphenyl)piperazin-1-yl]ethyl}cyclohexyl)butanamide
2-Cyano-N-(4-{2-[4-(2-fluoro-5-trifluoromethylphenyl)
piperazin-1-yl]ethyl}cyclohexyl)acetamide
N-(4-{2-[4-(3-Chloro-5-fluorophenyl)piperazin-1-yl]
ethyl}cyclohexyl)-2-cyanoacetamide
4-Cyano-N-(4-{2-[4-(2-fluoro-5-trifluoromethylphenyl)
piperazin-1-yl]ethyl}cyclohexyl)butanamide
N-(4-{2-[4-(5-Chloro-2-methylphenyl)piperazin-1-yl]
ethyl}cyclohexyl)-3-cyanopropanamide
2-Cyano-N-(4-{2-[4-(4-trifluoromethylphenyl)piperazin-1-yl]ethyl}cyclohexyl)acetamide
2-Cyano-N-(4-{2-[4-(4-fluoro-3-trifluoromethylphenyl)
piperazin-1-yl]ethyl}cyclohexyl)acetamide
4-Cyano-N-[4-(2-{4-[3-(1,1-difluoroethyl)phenyl]piperazin-1-yl}ethyl)cyclohexyl]butanamide
2-Cyano-N-(4-{2-[4-(3-methanesulfonylphenyl)piperazin-1-yl]ethyl}cyclohexyl)acetamide
2-Cyano-N-(4-{2-[4-(3-difluoromethylphenyl)piperazin-1-yl]ethyl}cyclohexyl)acetamide
N-(4-{2-[4-(3-Acetylphenyl)piperazin-1-yl]ethylcyclohexyl)-4-cyanobutanamide
Cyclopent-1-enecarboxylic acid (4-{2-[4-(2,4-difluorophenyl)piperazin-1-yl]ethyl}cyclohexyl)amide
4-Cyano-N-(4-{2-[4-(3,5-dimethoxyphenyl)piperazin-1-yl]ethyl}cyclohexyl)butanamide
3,3,3-Trifluoro-N-(4-{2-[4-(3-methanesulfonylphenyl)
piperazin-1-yl]ethyl}cyclohexyl)propanamide
N-(4-{2-[4-(3-Cyanophenyl)piperazin-1-yl]
ethyl}cyclohexyl)-4-methoxybutanamide
4-Cyano-N-[4-(2-{4-[3-(1-hydroxypropyl)phenyl]piperazin-1-yl}ethyl)cyclohexyl]butanamide
N-(4-{2-[4-(3-Chloro-2,4-difluorophenyl)piperazin-1-yl]
ethyl}cyclohexyl)-4-cyanobutanamide
2-Cyano-N-[4-(2-{4-[3-(1-hydroxypropyl)phenyl]piperazin-1-yl}ethyl)cyclohexyl]acetamide
N-(4-{2-[4-(3-Chloro-2,4-difluorophenyl)piperazin-1-yl]
ethyl}cyclohexyl)succinamide
N-(4-{2-[4-(2-Fluoro-5-trifluoromethylphenyl)piperazin-1-yl]ethyl}cyclohexyl)-4-methoxybutanamide
N-(4-{2-[4-(3-Cyanophenyl)piperazin-1-yl]
ethyl}cyclohexyl)-4,4,4-trifluorobutanamide
N-(4-{2-[4-(3-Cyanophenyl)piperazin-1-yl]
ethyl}cyclohexyl)-3-methoxypropanamide
or their pharmaceutically acceptable salts, free forms, or the polymorphic, crystalline structures of these compounds or their optical isomers, racemates, diastereomers or enantiomers.

8. Compound according to claim 1 chosen from:
N-(4-{2-[4-(3-Cyanophenyl)piperazin-1-yl]
ethyl}cyclohexyl)-2-methoxyacetamide
N-(4-{2-[4-(3,5-Bistrifluoromethylphenyl)piperazin-1-yl]ethyl}cyclohexyl)-2-cyanoacetamide
2-Cyano-N-(4-{2-[4-(3-methanesulfonylphenyl)piperazin-1-yl]ethyl}cyclohexyl)acetamide
2-Cyano-N-[4-(2-{4-[3-(1-hydroxypropyl)phenyl]piperazin-1-yl}ethyl)cyclohexyl]acetamide
N-(4-{2-[4-(3-Cyanophenyl)piperazin-1-yl]
ethyl}cyclohexyl)-4,4,4-trifluorobutanamide
N-(4-{2-[4-(3-Cyanophenyl)piperazin-1-yl]
ethyl}cyclohexyl)-3-methoxypropanamide
or their pharmaceutically acceptable salts, free forms, or the polymorphic, crystalline structures of these compounds or their optical isomers, racemates, diastereomers or enantiomers.

9. The process for preparing a compound according to claim 1, wherein the compounds of formula (I) in which Z is:

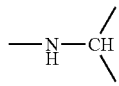

are prepared by coupling compounds of formula (III) with acid or acid derivatives of formulae R'COX or R'COCOX, wherein X is selected from the group consisting of: Cl, imidazol-1-yl, an hydroxysuccinimidoyl and 4-nitrophenoxy

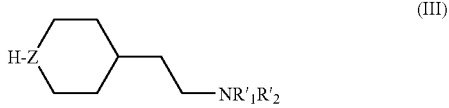

in which R' and $NR'_1R'_2$ respectively represent R and $NR_1R_2$ as defined in claim 1 and Z is:

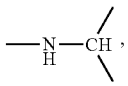

or wherein when a compound of formula (III) is coupled with R'COOH or R'COCOOH, the reaction is performed:
(a) in the presence of a reagent selected from the group consisting of a carbodiimide, carbonyldiimidazole and a chloroformate and a catalyst selected from the group consisting of DMAP and HOBt;
(b) in an inert solvent selected from the group consisting of dichloromethane, N,N-dimethylformamide, tetrahydrofuran and ethyl acetate; and
(c) at a temperature between 0° C. and 40° C.

10. A pharmaceutical composition, comprising a therapeutically effective amount of at least one derivative according to claim 1, with a pharmaceutically acceptable vehicle or excipient.

11. A method for treating illnesses involving the dopamine $D_3$ receptor comprising administering to a patient in need thereof an effective amount of a compound of the general formula (I) as defined in claim 1,
wherein said illness is a neuropsychiatric illness selected from the group consisting of Parkinson's disease, schizophrenia, dementia, dyskinesia, psychosis or psychotic states, depression, anxiety, and Gilles de la Tourette's disease;, and
wherein said compound according to claim 1 is combined with one or more of neuropsychiatric agent(s).

12. The method according to claim 11 wherein said neuropsychiatric agent is selected from anxiolytic, antipsychotic, antidepressant, procognitive or antidementia agents.

13. A method for treating illnesses involving the dopamine $D_3$ receptor comprising administering to a patient in need thereof an effective amount of a compound of the general formula (I) as defined in claim 1, wherein said illness is selected from the group consisting of:
a neuropsychiatric illness, said neuropsychiatric illness being selected from the group consisting of Parkinson's disease, schizophrenia, dementia, dyskinesia, psychosis or psychotic states, depression, anxiety, and Gilles de la Tourette's disease;
substance dependency;
sexual disorders;
motor disorders; and
renal insufficiency.

14. The method according to claim 13 wherein:
the substance dependency is associated with withdrawal, abstinence and/or detoxification of an individual dependent on an agent selected from the group consisting of opioids, amphetamines, cocaine, heroin, alcohol and nicotine;
the sexual disorder is male or female impotence;
the motor disorder is selected from the group consisting of essential or iatrogenic dyskinesia, essential or iatrogenic tremor; and restless leg syndrome.

* * * * *